United States Patent
Maloney et al.

(10) Patent No.: US 11,247,971 B2
(45) Date of Patent: *Feb. 15, 2022

(54) SMALL MOLECULE INHIBITORS OF LACTATE DEHYDROGENASE AND METHODS OF USE THEREOF

(71) Applicants: THE UNITED STATES OF AMERICA, AS REPRESENTED BY THE SECRETARY, DEPARTMENT OF HEALTH AND HUMAN SERVICES, Bethesda, MD (US); VANDERBILT UNIVERSITY, Nashville, TN (US); The UAB Research Foundation, Birmingham, AL (US); The Trustees of the University of Pennsylvania, Philadelphia, PA (US)

(72) Inventors: David J. Maloney, Point of Rocks, MD (US); Alex Gregory Waterson, Nashville, TN (US); Ganesh Rai Bantukallu, Arlington, VA (US); Kyle Ryan Brimacombe, Bethesda, MD (US); Plamen Christov, Nashville, TN (US); Chi V. Dang, Penn Valley, PA (US); Victor Darley-Usmar, Birmingham, AL (US); Xin Hu, Frederick, MD (US); Ajit Jadhav, Chantilly, VA (US); Somnath Jana, Nashville, TN (US); Kwangho Kim, Nashville, TN (US); Jennifer L. Kouznetsova, Silver Spring, MD (US); William J. Moore, Hagerstown, MD (US); Bryan T. Mott, College Park, MD (US); Leonard M. Neckers, Bethesda, MD (US); Anton Simeonov, Bethesda, MD (US); Gary Allen Sulikowski, Nashville, TN (US); Daniel Jason Urban, Rockville, MD (US); Shyh Ming Yang, Doylestown, PA (US)

(73) Assignees: THE TRUSTEES OF THE UNIVERSITY OF PENNSYLVANIA, Philadelphia, PA (US); THE UAB RESEARCH FOUNDATION, Birmingham, AL (US); VANDERBILT UNIVERSITY, Nashville, TN (US); THE UNITED STATES OF AMERICA, AS REPRESENTED BY THE SECRETARY, DEPARTMENT OF HEALTH AND HUMAN SERVICES, Bethesda, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 17/160,868

(22) Filed: Jan. 28, 2021

(65) Prior Publication Data

US 2021/0323928 A1 Oct. 21, 2021

Related U.S. Application Data

(63) Continuation of application No. 16/455,848, filed on Jun. 28, 2019, now Pat. No. 10,961,200, which is a (Continued)

(51) Int. Cl.
C07D 231/20 (2006.01)
C07D 231/38 (2006.01)
(Continued)

(52) U.S. Cl.
CPC .......... *C07D 231/20* (2013.01); *A61K 31/415* (2013.01); *A61K 31/4155* (2013.01); (Continued)

(58) Field of Classification Search
CPC .. C07D 231/20; C07D 231/38; C07D 401/04; C07D 403/04; C07D 403/06; (Continued)

(56) References Cited

U.S. PATENT DOCUMENTS

| 5,182,289 A | 1/1993 | Ting et al. |
| 5,342,851 A | 8/1994 | Sanfilippo et al. |

(Continued)

FOREIGN PATENT DOCUMENTS

| CN | 102089302 A | 6/2011 |
| CN | 102089303 A | 6/2011 |

(Continued)

OTHER PUBLICATIONS

Atobe et al., "Hit-to-Lead Optimization of 2-(1H-Pyrazol-1-yl)-Thiazole Derivatives as a Novel Class of EP1 Receptor Antagonists," Bioorganic and Medicinal Chemistry Letters, (2013), pp. 6064-6067.

(Continued)

*Primary Examiner* — Timothy R Rozof
(74) *Attorney, Agent, or Firm* — Cantor Colburn LLP

(57) ABSTRACT

Provided is a compound of formula (I),

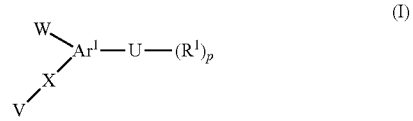

in which $Ar^1$, $R^1$, U, V, W, X, and p are as described herein. Also provided are methods of using a compound of formula (I), including a method of treating cancer, a method of treating a patient with cancer cells resistant to an anti-cancer agent, and a method of inhibiting lactate dehydrogenase A (LDHA) and/or lactate dehydrogenase B (LDHB) activity in a cell.

17 Claims, No Drawings

Related U.S. Application Data continuation of application No. 15/540,893, filed as application No. PCT/US2015/067895 on Dec. 29, 2015, now Pat. No. 10,351,532.

(60) Provisional application No. 62/097,226, filed on Dec. 29, 2014.

(51) Int. Cl.

| | | |
|---|---|---|
| *C07D 401/04* | (2006.01) | |
| *C07D 403/04* | (2006.01) | |
| *C07D 403/06* | (2006.01) | |
| *C07D 409/04* | (2006.01) | |
| *C07D 413/04* | (2006.01) | |
| *C07D 417/04* | (2006.01) | |
| *C07D 417/14* | (2006.01) | |
| *C07D 471/04* | (2006.01) | |
| *C07D 495/04* | (2006.01) | |
| *C07D 495/14* | (2006.01) | |
| *A61K 31/415* | (2006.01) | |
| *A61K 31/4155* | (2006.01) | |
| *A61K 31/4178* | (2006.01) | |
| *A61K 31/422* | (2006.01) | |
| *A61K 31/427* | (2006.01) | |
| *A61K 31/437* | (2006.01) | |
| *A61K 31/454* | (2006.01) | |
| *A61K 31/496* | (2006.01) | |
| *A61K 31/501* | (2006.01) | |
| *A61K 31/506* | (2006.01) | |
| *A61K 31/519* | (2006.01) | |
| *A61K 31/5355* | (2006.01) | |
| *A61K 31/4439* | (2006.01) | |
| *A61K 45/06* | (2006.01) | |

(52) U.S. Cl.
CPC ........ *A61K 31/4178* (2013.01); *A61K 31/422* (2013.01); *A61K 31/427* (2013.01); *A61K 31/437* (2013.01); *A61K 31/4439* (2013.01); *A61K 31/454* (2013.01); *A61K 31/496* (2013.01); *A61K 31/501* (2013.01); *A61K 31/506* (2013.01); *A61K 31/519* (2013.01); *A61K 31/5355* (2013.01); *A61K 45/06* (2013.01); *C07D 231/38* (2013.01); *C07D 401/04* (2013.01); *C07D 403/04* (2013.01); *C07D 403/06* (2013.01); *C07D 409/04* (2013.01); *C07D 413/04* (2013.01); *C07D 417/04* (2013.01); *C07D 417/14* (2013.01); *C07D 471/04* (2013.01); *C07D 495/04* (2013.01); *C07D 495/14* (2013.01)

(58) Field of Classification Search
CPC .. C07D 409/04; C07D 413/04; C07D 417/04; C07D 417/14; C07D 471/04; C07D 495/04; C07D 495/14; A61K 31/415; A61K 31/4155; A61K 31/4178; A61K 31/422; A61K 31/427; A61K 31/437; A61K 31/4399; A61K 31/454; A61K 31/496; A61K 31/501; A61K 31/506; A61K 31/519; A61K 31/5355; A61K 46/05

See application file for complete search history.

(56) References Cited

U.S. PATENT DOCUMENTS

| | | |
|---|---|---|
| 5,510,320 A | 4/1996 | Tseng |
| 5,602,113 A | 2/1997 | Hargrave et al. |
| 5,849,778 A | 12/1998 | Heil et al. |
| 6,136,079 A | 10/2000 | Evans et al. |
| 6,407,238 B1 | 6/2002 | Baron et al. |
| 6,436,965 B1 | 8/2002 | Labelle et al. |
| 6,682,590 B2 | 1/2004 | Omatsu et al. |
| 7,320,995 B2 | 1/2008 | Bonjouklian et al. |
| 7,358,267 B2 | 4/2008 | Amaral et al. |
| 7,456,292 B2 | 11/2008 | Neogi et al. |
| 7,544,835 B2 | 6/2009 | Matsuura et al. |
| 7,589,116 B2 | 9/2009 | Chakravarty et al. |
| 7,642,216 B2 | 1/2010 | Diamond et al. |
| 7,642,267 B2 | 1/2010 | Li et al. |
| 7,906,544 B2 | 6/2011 | Bartolini et al. |
| 7,968,530 B2 | 6/2011 | Filippini et al. |
| 7,994,202 B2 | 8/2011 | Atobe et al. |
| 8,063,080 B2 | 11/2011 | Fulp et al. |
| 8,178,538 B2 | 5/2012 | Alberati et al. |
| 8,222,280 B2 | 7/2012 | Liu et al. |
| 8,389,567 B2 | 3/2013 | Velicelebi et al. |
| 8,470,054 B2 | 6/2013 | Higashi et al. |
| 8,492,398 B2 | 7/2013 | Pierce et al. |
| 8,569,512 B2 | 10/2013 | Burgey et al. |
| 8,642,597 B2 | 2/2014 | Gross et al. |
| 8,722,709 B2 | 5/2014 | Guo et al. |
| 8,729,083 B2 | 5/2014 | Grob et al. |
| 8,742,106 B2 | 6/2014 | Badiger et al. |
| 8,742,119 B2 | 6/2014 | Salituro et al. |
| 8,871,778 B2 | 10/2014 | Choi et al. |
| 2004/0116425 A1 | 6/2004 | Li et al. |
| 2004/0166137 A1 | 8/2004 | Lackey |
| 2004/0167158 A1 | 8/2004 | Edwards et al. |
| 2006/0014746 A1 | 1/2006 | Hutchison et al. |
| 2007/0072911 A1 | 3/2007 | Avolio et al. |
| 2008/0004269 A1 | 1/2008 | Xu et al. |
| 2008/0090834 A1 | 4/2008 | Hoover et al. |
| 2008/0132510 A1 | 6/2008 | Han et al. |
| 2008/0312444 A1 | 12/2008 | Bacchi et al. |
| 2009/0069565 A1 | 3/2009 | Nazare et al. |
| 2009/0105238 A1 | 4/2009 | Filippini et al. |
| 2009/0306169 A1 | 12/2009 | Brandish et al. |
| 2010/0029690 A1 | 2/2010 | Atobe et al. |
| 2010/0029733 A1 | 2/2010 | Atobe et al. |
| 2014/0171446 A1 | 6/2014 | Chen et al. |
| 2014/0179694 A1 | 6/2014 | Su |
| 2014/0213601 A1 | 7/2014 | Degoey et al. |
| 2014/0213623 A1 | 7/2014 | Miller et al. |
| 2014/0228363 A1 | 8/2014 | Burger et al. |
| 2014/0296537 A1 | 10/2014 | Shimizu et al. |
| 2014/0315954 A1 | 10/2014 | Winters et al. |
| 2014/0323720 A1 | 10/2014 | Yar |

FOREIGN PATENT DOCUMENTS

| | | |
|---|---|---|
| CN | 102281816 A | 12/2011 |
| WO | 9405290 A1 | 3/1994 |
| WO | 2006077364 A1 | 7/2006 |
| WO | 2006077365 A1 | 7/2006 |
| WO | 2006077366 A1 | 7/2006 |
| WO | 2006077367 A1 | 7/2006 |
| WO | 2006077401 A1 | 7/2006 |
| WO | 2007018508 A1 | 2/2007 |
| WO | 2007018514 A1 | 2/2007 |
| WO | 2007038571 A2 | 4/2007 |
| WO | 2007048732 A1 | 5/2007 |
| WO | 2008006790 A1 | 1/2008 |
| WO | 2008009924 A2 | 1/2008 |
| WO | 2008121861 A2 | 10/2008 |
| WO | 2009076454 A2 | 6/2009 |
| WO | 2009108551 A2 | 9/2009 |
| WO | 2010010186 A1 | 1/2010 |
| WO | 2010059241 A2 | 5/2010 |
| WO | 2011057942 A1 | 5/2011 |
| WO | 2011091410 A1 | 7/2011 |
| WO | 2012074022 A1 | 6/2012 |
| WO | 2012085167 A1 | 6/2012 |
| WO | 2012154880 A1 | 11/2012 |
| WO | 2013092753 A1 | 6/2013 |
| WO | 2014021281 A1 | 2/2014 |
| WO | 2014062938 A1 | 4/2014 |

(56) References Cited

FOREIGN PATENT DOCUMENTS

| | | |
|---|---|---|
| WO | 2014099696 A1 | 6/2014 |
| WO | 2014099697 A1 | 6/2014 |
| WO | 2014099698 A1 | 6/2014 |
| WO | 2014115071 A1 | 7/2014 |
| WO | 2014156922 A1 | 10/2014 |
| WO | 2014173880 A1 | 10/2014 |
| WO | 2014176475 A2 | 10/2014 |

OTHER PUBLICATIONS

Atobe et al. "Discovery of 2-(1H-indazol-1-yl)-thiazole derivatives as selective EP1 receptor antagonists for treatment of overactive bladder by core structure replacement", Bioorganic & Medicinal Chemistry Letters, vol. 24, No. 5, pp. 1327-1333 (2014).

Hall et al. "Discovery of a novel indole series of EP1 receptor antagonists by scaffold hopping", Bioorganic & Medicinal Chemistry Letters vol. 18, No. 8, pp. 2684-2690 (2008).

International Search Report dated Jul. 20, 2016; International Application No. PCT/US2015/067895 International Filing Date Dec. 29, 2015 (8 pages).

Written Opinion dated Jul. 20, 2016; International Application No. PCT/US2015/067895; International Filing Date Dec. 29, 2015 (10 pages).

Wu, Peng et al. "Separation and analysis of nitrogen compounds in CS2-NMP extracts from oil shale", Journal of Heilongjiang Institute of Science & Technology, vol. 21, No. 6, pp. 429-432 (2011).

Kawamori, et al., "Chemopreventive Effects of ONO-8711, a Selective Prostaglandin E Receptor EP1, Antagonist, on Breast Cancer Development," Carcinogenesis, vol. 22, No. 12, (2001), pp. 2001-2004.

Kawamori, et al., "Evaluation of a Selective Prostaglandin E Receptor EP1 Antagonist for Potential Properties in Colon Carcinogenesis," Anticancer Research No. 21, (2001), pp. 3865-3869.

Matsuo, et al., "Inhibition of Human Glioma Cell Growth by a PHS-2 Inhibitor, NS398, and a Prostaglandin E Receptor Subtype EP1-Selective Antagonist, SC51089," Journal of Neuro-Oncology, No. 66, (2004), pp. 285-292.

Niho, et al., "Suppression of Azoxymethane-Induced Colon Cancer Development in Rats by a Prostaglandin E Receptor EP1—Selective Antagonist," Cancer Science, vol. 96, No. 5, (2005), pp. 260-264.

Tober, et al., "Importance of the EP1 Receptor in Cutaneous UVB-Induced Inflammation and Tumor Development," The Society of Investigative Dermatology, (2006), pp. 205-211.

SMALL MOLECULE INHIBITORS OF LACTATE DEHYDROGENASE AND METHODS OF USE THEREOF

CROSS REFERENCE TO RELATED APPLICATIONS

This application is a Continuation Application No. of application Ser. No. 16/455,848 filed Jun. 28, 2019, which claims priority to application Ser. No. 15/540,893 filed on Jun. 29, 2017, now U.S. Pat. No. 10,351,352, which is a US National Stage Application of PCT/US2015/067895 filed on Dec. 29, 2015, which claims the benefit of Provisional Application No. 62/097,226 filed on Dec. 29, 2014, and all the benefits accruing therefrom under 35 U.S.C. § 119, the contents of which are incorporated by reference in their entirety.

BACKGROUND

Agents that target enzymes involved in cancer cell metabolism offer an attractive therapeutic route in view of the potential to preferentially target cancer tissue over normal tissue. While normal tissue typically uses glycolysis only when the oxygen supply is low, cancer tissue relies heavily on aerobic glycolysis regardless of the oxygen supply level. This property is known as the Warburg effect (Vander Heiden et al., *Science,* 2009, 324(5930): 1029-1033). Lactate dehydrogenase (LDH) is involved in the final step of glycolysis, in which pyruvate is converted to lactate. The decrease in the rate of pyruvate entering the TCA (tricarboxylic acid) cycle and the concurrent increase in lactate production is vital for the growth and survival of tumors. There are two different subunits of LDH, LDHA and LDHB, but both subunits have the same active site and catalyze the conversion of pyruvate to lactate. In cancer patients, serum total lactate dehydrogenase (LDH5, a tetramer of LDHA sub-units; the major LDH isoenzyme involved in glycolysis) levels are often increased, and the gene for LDHA, is up-regulated. Tumor cells can then metabolize lactate as an energy source. Inhibition of LDH results in the stimulation of mitochondrial respiration as a compensatory mechanism. LDH inhibition is expected to reduce the ability of the cell to effectively metabolize glucose and reduce tumor cell proliferation and tumor growth. Thus, compounds that inhibit LDH activity have potential for the development of anti-cancer therapeutics.

LDHA inhibitors have been known previously. For example, gossypol is a nonselective inhibitor of LDH that blocks the binding of NADH, with a K, for LDHA and lactate dehydrogenase B (LDHB) of 1.9 and 1.4 µM, respectively (Doherty et al., *J. Clin. Invest.,* 2013, 123(9): 3685-3692). Billiard et al. (*Cancer and Metabolism,* 2013, 1(19): 1-17) reports that certain derivatives of 3-((3-carbamoyl-7-(3,5-dimethylisoxazol-4-yl)-6-methoxyquinolin-4-yl) amino) benzoic acid are potent inhibitors of LDH and were 10- to 80-fold more selective for LDHA inhibition than LDHB inhibition. However, the in vivo bioavailability of the inhibitors was found to be poor.

In view of the foregoing, there remains a need to provide novel LDH inhibitors with improved potency, selectivity, and/or bioavailability for the treatment of cancer.

SUMMARY

The present invention provides a compound of formula (I)

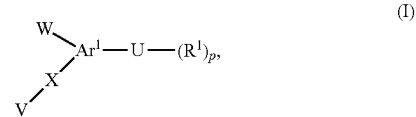

(I)

in which $Ar^1$, $R^1$, U, V, W, X, and p are as described herein. It has been discovered that a compound defined by formula (I) is effective in inhibiting lactate dehydrogenase A (LDHA) and/or lactate dehydrogenase B (LDHB) activity, thereby making the compound effective in treating cancer. It has also been discovered that inhibitors of LDHA and/or LDHB are useful for treating fibrosis, including idiopathic pulmonary fibrosis. It is envisioned that a compound of formula (I) is desirable for treating cancer because the compound tends to be selective for LDHA and/or LDHB relative to other dehydrogenases (e.g., GAPDH and PHGDH) and/or have a desired solubility, permeability, and/or pharmacokinetics profile (e.g., ADME) for an anti-cancer agent.

Thus, the disclosure further provides a method of treating cancer in a patient comprising administering to the patient an effective amount of the compound of formula (I) or a prodrug or a pharmaceutically acceptable salt thereof.

In another embodiment the disclosure provides a method of treating fibrosis, including idiopathic pulmonary fibrosis, in a patient comprising administering to the patient an effective amount of the compound of formula (I) or a prodrug or a pharmaceutically acceptable salt thereof.

Also provided is a method of treating a patient with cancer cells resistant to an anti-cancer agent, comprising administering to the patient an effective amount of the compound of formula (I) or a prodrug or a pharmaceutically acceptable salt thereof, and the anti-cancer agent, whereby the compound, prodrug, or pharmaceutically acceptable salt thereof re-sensitizes the cancer cells to the anti-cancer agent.

The invention provides a method of inhibiting lactate dehydrogenase A (LDHA) and/or lactate dehydrogenase B activity in a cell comprising administering a compound of formula (I) or a prodrug or a pharmaceutically acceptable salt thereof to a cell.

DETAILED DESCRIPTION OF THE INVENTION

The present invention provides a compound of formula (I)

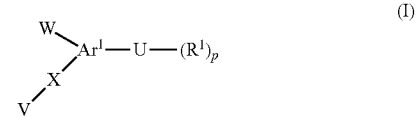

(I)

wherein $Ar^1$ is an optionally substituted moiety comprising at least one 5- or 6-membered monocyclic heteroaryl that contains one, two, or three heteroatoms selected from nitrogen, oxygen, and sulfur;

U is aryl, —C(O)aryl, Het, or —C(O)Het, each of which is optionally substituted, wherein Het is a monocyclic or bicyclic moiety comprising a heterocycloalkyl that contains at least two double bonds and one, two, or three heteroatoms selected from nitrogen, oxygen, and sulfur;

$R^1$ is independently chosen from halo, —$CO_2R^4$, —$C(O)NR^5R^6$, —($C_1$-$C_8$hydrocarbyl), —C(O)NHOH, —($C_0$-$C_4$hydrocarbyl)((mono- or bicyclic heterocycle having 1 to 4 heteroatoms independently chosen from N, O, and S), —C(O)O—($C_0$-$C_4$hydrocarbyl)(mono- or bicyclic heterocycle having 1 to 4 heteroatoms independently chosen from N, O, and S), —$P(O)(OH)_2$, —$SO_2(OH)$, —$B(OR^3)(OR^4)$, —$C(O)NHS(O)_2Me$ and —$SO_2NR^5R^6$, each of which $R^1$ except halo is substituted or unsubstituted;

$R^2$ is independently chosen from hydroxyl, halo, —CN, —$NO_2$, $C_1$-$C_8$hydrocarbyl, —O($C_1$-$C_8$hydrocarbyl), —($C_0$-$C_4$hydrocarbyl)$C_3$-$C_8$cycloalkyl, —O($C_0$-$C_4$hydrocarbyl)$C_3$-$C_8$ cycloalkyl, —($C_0$-$C_4$hydrocarbyl)$C_3$-$C_8$cycloalkenyl, —O($C_0$-$C_4$hydrocarbyl)$C_3$-$C_8$cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —$P(O)(OH)_2$, —$B(OR^{13})(OR^{14})$, —$SO_2(OH)$, —$C(O)NHS(O)_2Me$ and —$SO_2NR^5R^6$, each of which $R^1$ except halo is substituted or unsubstituted;

V is aryl, heteroaryl, or heterocycloalkyl, each of which is substituted with —$(R^2)_n$, wherein the heteroaryl or heterocycloalkyl is a 5- or 6-membered monocyclic moiety that contains one, two, or three heteroatoms selected from nitrogen, oxygen, and sulfur;

W is —$(R^3)_m$ or

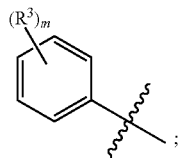

$R^2$ is independently chosen from hydroxyl, halo, —CN, —$NO_2$, $C_1$-$C_8$hydrocarbyl, —O($C_1$-$C_8$hydrocarbyl), —($C_0$-$C_4$hydrocarbyl)$C_3$-$C_8$cycloalkyl, —O($C_0$-$C_4$hydrocarbyl)$C_3$-$C_8$ cycloalkyl, —($C_0$-$C_4$hydrocarbyl)$C_3$-$C_8$cycloalkenyl, —O($C_0$-$C_4$hydrocarbyl)$C_3$-$C_8$cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —$C(O)R^4$, —$CO_2R^4$, —$C(O)NR^5R^6$, —$NR^5C(O)R^4$, —$(CH_2)_qNR^5(SO_2)R^4$, —$(CH_2)_qNR^5C(O)R^4$, —$(CH_2)_qNR^7C(O)NR^5R^6$, —$(CH_2)_qNR^5R^6$, —$(CH_2)_qSO_2NR^5R^6$, —$(CH_2)_qSO_2R^4$, each of which $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl) (mono- and bicyclic heterocycle having 1 to 4 heteroatoms independently chosen from N, O, and S) is substituted or unsubstituted;

$R^3$ is independently chosen from hydroxyl, halo, —CN, —$NO_2$, —$SF_5$, $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl) (mono- and bicyclic heterocycle having 1 to 4 heteroatoms independently chosen from N, O, and S), —$C(O)R^4$, —$CO_2R^4$, —$C(O)NR^5R^6$, —$NR^5C(O)R^4$, —$(CH_2)_qNR^5(SO_2)R^4$, —$(CH_2)_qNR^5C(O)R^4$, —$(CH_2)_qNR^7C(O)NR^5R^6$, —$(CH_2)_qNR^5R^6$, —$(CH_2)_qSO_2NR^5R^6$, —$(CH_2)_qSO_2R^4$, each of which $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl) (mono- and bicyclic heterocycle having 1 to 4 heteroatoms independently chosen from N, O, and S) is substituted or unsubstituted; or when W is phenyl, then two $R^3$ moieties and the phenyl group to which they are attached form a naphthyl group that is optionally substituted with at least one additional $R^3$ moiety;

each $R^4$, $R^5$, $R^6$, $R^7$, $R^8$, and $R^9$ is the same or different and each is hydrogen, $C_1$-$C_8$ alkyl, $C_2$-$C_8$ alkenyl, $C_3$-$C_6$ cycloalkyl, $C_6$-$C_{12}$aryl, heteroaryl, or heterocycloalkyl;

each $R^{13}$ and $R^{14}$ is the same or different and each is hydrogen, $C_1$-$C_8$ alkyl, $C_2$-$C_8$ alkenyl, $C_3$-$C_6$ cycloalkyl, $C_6$-$C_{12}$aryl, wherein $R^{13}$ and $R^{14}$ are optionally connected to each other to form a ring;

X is a bond, —$CR^8R^9$—, —$NR^5$—, —$CR^8NR^5$—, —$NR^5CR^8$—, —$NR^5C(O)$, —O—, —SO—, —$SO_2$—, or —S—;

m, n, and q are the same or different and each is 0 or an integer from 1-5; and p is 0, 1, or 2;

provided when $Ar^1$ is quinolinyl, then U is not pyrimidinyl;

when $Ar^1$—U is 2-(1H-indol-1-yl)thiazolyl, then X at the 3-position on the indolyl group is not a bond or —$CH_2$—, or W at the 3-position on the indolyl group is not phenyl, or $R^3$ at the 3-position on the indolyl group is not benzyl; and when $Ar^1$—U is 2-(1H-pyrazol-1-yl)thiazolyl, then W at the 3-position on the pyrazolyl group is not 4-trifluoromethylphenyl or 4-nitrophenyl, or X at the 4-position on the pyrazolyl group is not a bond, or a prodrug or pharmaceutically acceptable salt thereof.

In an aspect, $Ar^1$ is indolyl, pyrrolo[2,3-b]pyridinyl, pyrrolo[3,2-c]pyridinyl, pyrazolo[3,4-b]pyridinyl, quinolinyl, indazolyl, imidazolyl, oxazolyl, thiazolyl, furanyl, thiofuranyl, pyrrolyl, pyrazolyl, pyridinyl, pyrazinyl, or pyrimidinyl, each of which is optionally substituted. When $Ar^1$ is substituted, there can be 1 to 3 substituents (e.g., 1, 2, or 3 substituents) that are the same or different. Suitable substituents include, e.g., $C_1$-$C_8$alkyl, $C_2$-$C_8$alkenyl, $C_2$-$C_8$alkynyl, $C_3$-$C_6$cycloalkyl, $C_3$-$C_6$cycloalkylalkyl, hydroxyl, $C_1$-$C_8$ alkoxy, $C_3$-$C_6$cycloalkyloxy, $C_1$-$C_8$haloalkoxy, $C_1$-$C_8$haloalkyl, halo, —CN, cyanoalkyl, —$NO_2$, —$CO_2R^4$, —$C(O)NR^5R^6$, —$NR^5(SO_2)R^4$, —$NR^5C(O)R^4$, —$NR^7C(O)NR^5R^6$, —$NR^5R^6$, —$SO_2NR^5R^6$, —$SO_2R^4$, aryl, heteroaryl, and/or heterocycloalkyl.

In certain compounds, $Ar^1$ is pyrazolyl, indolyl, or pyrrolo[2,3-b]pyridinyl, each of which is optionally substituted. For example, $Ar^1$ can be pyrazolyl or indolyl substituted with a substituent, such as, $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, hydroxyl, $C_1$-$C_8$ alkoxy, $C_3$-$C_6$ cycloalkyloxy, $C_1$-$C_8$ haloalkoxy, $C_1$-$C_8$ haloalkyl, halo, —CN, cyanoalkyl, —$NO_2$, —$CO_2R^4$, —C(O)$NR^5R^6$, —$NR^5(SO_2)R^4$, —$NR^5C(O)R^4$, —$NR^7C(O)NR^5R^6$, —$NR^5R^6$, —$SO_2NR^5R^6$, —$SO_2R^4$, aryl, arylalkyl, heteroaryl, heteroarylalkyl, or heterocycloalkyl. The pyrazolyl can be substituted with $C_1$-$C_8$ alkyl, cyclopropyl, —$CH_2$-cyclopropyl, —CH=$CH_2$, —C≡C-cyclopropyl, —OH, —$CO_2H$, $C_1$-$C_8$ alkoxy, $CF_3$, Cl, F, I, —CN, —$CH_2CN$, $NH_2$, —C(O)$NH_2$, —NH-pyridinyl, —$CH_2$-tetrazolyl, phenyl, benzyl, or —$SO_2Me$.

In any of the foregoing embodiments, U is phenyl, —C(O)phenyl, indolyl, imidazolyl, oxazolyl, thiazolyl, furanyl, thiofuranyl, pyrrolyl, pyrazolyl, pyridinyl, pyrazinyl, pyrimidinyl, or 6-oxo-1,6-dihydropyridazin-3-yl, each of which is optionally substituted.

In other aspects, U is Het or —C(O)Het, and Het is

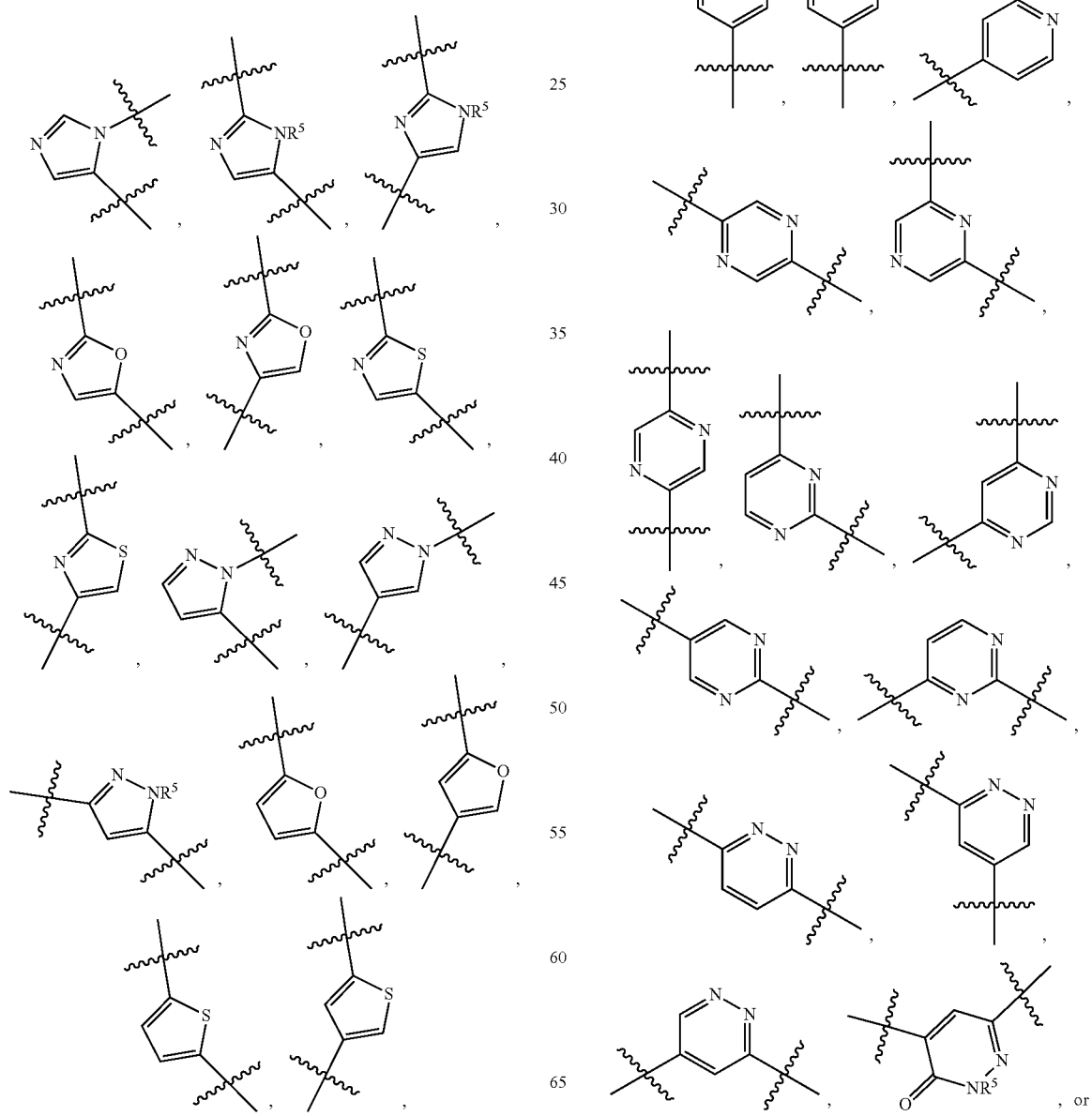

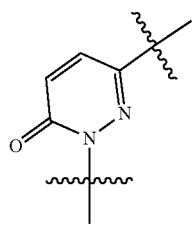

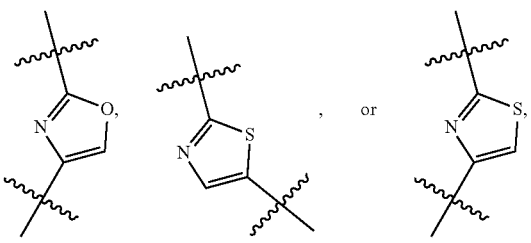

wherein $R^5$ is hydrogen, $C_1$-$C_8$ alkyl, $C_2$-$C_8$ alkenyl, $C_3$-$C_6$ cycloalkyl, aryl, heteroaryl, or heterocycloalkyl, each of these Het moieties is optionally substituted, and each point of attachment can be either $Ar^1$ or $R^1$.

In an embodiment, U is

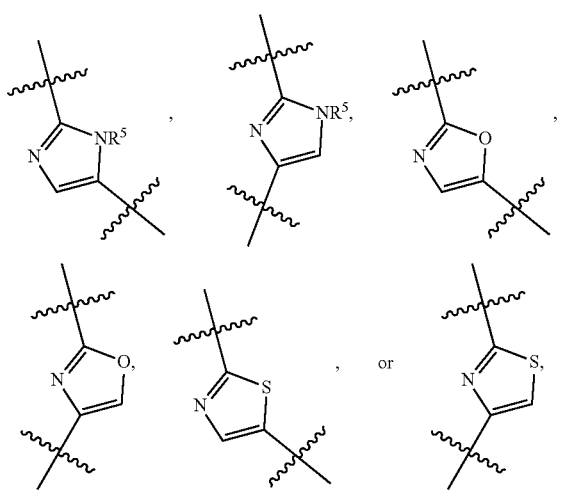

each of which is optionally substituted, and wherein each point of attachment can be either $Ar^1$ or $R^1$.

When U is substituted, there can be 1 or 2 substituents that are the same or different. Suitable substituents include, e.g., $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, hydroxyl, $C_1$-$C_8$ alkoxy, $C_3$-$C_6$ cycloalkyloxy, $C_1$-$C_8$ haloalkoxy, $C_1$-$C_8$ haloalkyl, halo, —CN, cyanoalkyl, —$NO_2$, $CO_2R^4$, $C(O)NR^5R^6$, $NR^5(SO_2)R^4$, $NR^5C(O)R^4$, $NR^7C(O)NR^5R^6$, —$NR^5R^6$, —$SO_2NR^5R^6$, —$SO^2R^4$, aryl, arylalkyl, heteroaryl, and/or heterocycloalkyl.

In a certain embodiment of a compound of formula (I), $Ar^1$ is pyrazolyl, indolyl, or pyrrolo[2,3-b]pyridinyl, each of which is optionally substituted, and U is

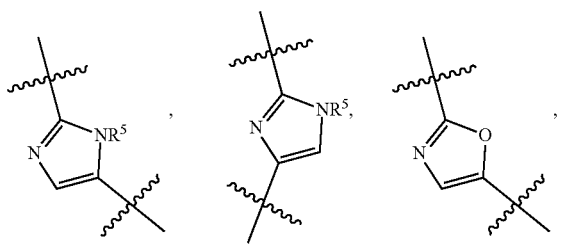

each of which is optionally substituted. In this embodiment, the following core structures of formula (I) can be formed:

in which $X^2$ is —$NR^5$—, —O—, or —S—; p is 0; 1 or 2; and $R^1$ is halo, —$CO_2R^4$, —$C(O)NR^5R^6$, —$CH_2OH$, —$CHCF_3OH$, —$C(CF_3)_2OH$, —$C(O)NHOH$—$C(O)OCR^5R^6OC(O)OR^4$, —C(O)O-2,3-dihydro-1H-indenyl, —C(O)O-(5-methyl-2-oxo-1,3-dioxol-4-yl)methyl, 1,3,4-oxadiazol-2(3H)-one, isoxazol-3(2H)-one, —$P(O)(OH)_2$, —$B(OR^{13})(OR^4)$, —$SO_2(OH)$, —$SO_2NR^5R^6$, or tetrazolyl.

In any of the foregoing embodiments, $R^1$ is —$CO_2H$ or —$CO_2(C_1$-$C_8$ alkyl), wherein the $C_1$-$C_8$ alkyl is substituted or unsubstituted, or a prodrug or a pharmaceutically acceptable salt thereof.

In any of the foregoing embodiments, V is phenyl, piperazinyl, pyrrolinyl, pyranyl, piperidyl, tetrahydrofuranyl, tetrahydrothiophenyl, morpholinyl, pyridinyl, pyridazinyl, pyrimidyl, or pyrazinyl, each of which is substituted with —$(R^2)_n$. In some aspects, V is phenyl substituted with —$(R^2)_n$.

In any of the foregoing embodiments, $R^2$ is —$SO_2NR^5R^6$; and $R^5$ and $R^6$ are the same or different and each is H or $C_1$-$C_8$ alkyl (e.g., methyl, ethyl, n-propyl, i-propyl, n-butyl, sec-butyl, or tert-butyl). In some aspects, $R^2$ is —$SO_2NH_2$.

In any of the foregoing embodiments, n is 1, so that V is monosubstituted.

In any of the foregoing embodiments, W is

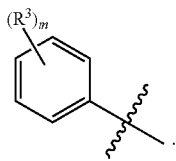

In any of the foregoing embodiments, $R^3$ is independently halo, $C_1$-$C_8$haloalkyl, $C_1$-$C_8$haloalkoxy, substituted or unsubstituted $C_1$-$C_4$alkyl, or substituted or unsubstituted phenyl.

In any of the foregoing embodiments, m is 1 or 2.

In any of the foregoing embodiments, X is —$CR^8R^9$— (e.g., —$CH_2$—), —O—, or —NH—, in which $R^8$ and $R^9$ are the same or different and each is hydrogen, $C_1$-$C_8$alkyl, $C_2$-$C_8$alkenyl, $C_3$-$C_6$cycloalkyl, or aryl.

In some aspects, the compound of formula (I) is a compound, prodrug, or pharmaceutically acceptable salt of formula (Ia)

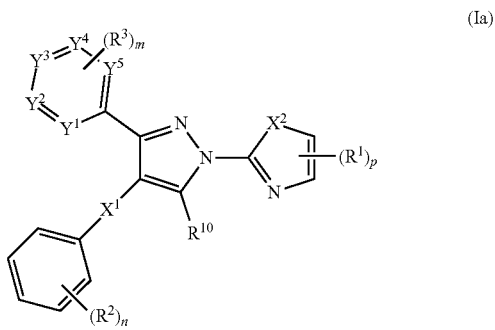

(Ia)

wherein $Y^1$, $Y^2$, $Y^3$, $Y^4$, and $Y^5$ are each independently CH or N;

$R^1$ is independently chosen from halo, —C(O)$R^4$, —$CH_2OH$, —C(O)NHCN, —C(O)NHSO$_2$H, —C(S)$R^4$, —CO$_2R^4$, —C(O)N$R^5R^6$, —($C_1$-$C_8$hydrocarbyl), —C(O)NHOH, —C(O)OC$R^5R^6$OC(O)O$R^4$, —($C_0$-$C_4$hydrocarbyl)((mono- or bicyclic heterocycle having 1 to 4 heteroatoms independently chosen from N, O, and S), —C(O)O—($C_0$-$C_4$hydrocarbyl)(mono- or bicyclic heterocycle having 1 to 4 heteroatoms independently chosen from N, O, and S), —P(O)(OH)$_2$, —B(O$R^{13}$)(O$R^{14}$), —SO$_2$(OH), —C(O)NHS(O)$_2$Me and —SO$_2$N$R^5R^6$, each of which R except halo is substituted or unsubstituted;

$R^2$ is independently chosen from hydroxyl, halo, —CN, —NO$_2$, $C_1$-$C_8$hydrocarbyl, —O($C_1$-$C_8$hydrocarbyl), —($C_0$-$C_4$hydrocarbyl)$C_3$-$C_8$cycloalkyl, —O($C_0$-$C_4$hydrocarbyl)$C_3$-$C_8$ cycloalkyl, —($C_0$-$C_4$hydrocarbyl)$C_3$-$C_8$cycloalkenyl, —O($C_0$-$C_4$hydrocarbyl)$C_3$-$C_8$cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —C(O)$R^4$, —CO$_2R^4$, —C(O)N$R^5R^6$, —N$R^5$C(O)$R^4$, —(CH$_2$)$_q$N$R^5$(SO$_2$)$R^4$, —(CH$_2$)$_q$N$R^5$C(O)$R^4$, —(CH$_2$)$_q$N$R^7$C(O)N$R^5R^6$, —(CH$_2$)$_q$SO$_2$N$R^5R^6$, —(CH$_2$)$_q$SO$_2R^4$, each of which $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S) is substituted or unsubstituted;

$R^3$ is independently chosen from hydroxyl, halo, —CN, —NO$_2$, —SF$_5$, $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —C(O)$R^4$, —CO$_2R^4$, —C(O)N$R^5R^6$, —N$R^5$C(O)$R^4$, —(CH$_2$)$_q$N$R^5$(SO$_2$)$R^4$, —(CH$_2$)$_q$N$R^5$C(O)$R^4$, —(CH$_2$)$_q$N$R^7$C(O)N$R^5R^6$, —(CH$_2$)$_q$N$R^5R^6$, —(CH$_2$)$_q$SO$_2$N$R^5R^6$, —(CH$_2$)$_q$SO$_2R^4$, each of which $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$cycloalkyl, —($C_0$-$C_4$hydrocarbyl)$C_3$-$C_8$cycloalkenyl, —O($C_0$-$C_4$hydrocarbyl)$C_3$-$C_8$cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S) is substituted or unsubstituted; or two $R^3$ moieties and the phenyl group to which they are attached form a naphthyl group or its heterocyclic analog that is optionally substituted;

each $R^4$, $R^5$, $R^6$, $R^7$, $R^8$, and $R^9$ is the same or different and each is hydrogen, $C_1$-$C_8$ alkyl, $C_2$-$C_8$ alkenyl, $C_3$-$C_6$ cycloalkyl, aryl, heteroaryl, or heterocycloalkyl;

$R^{10}$ is hydrogen, halo, —CN, —NO$_2$, —CO$_2R^4$, —C(O)N$R^5R^6$, —N$R^5$(SO$_2$)$R^4$, —N$R^5$C(O)$R^4$, —N$R^7$C(O)N$R^5R^6$, —N$R^5R^6$, —SO$_2$N$R^5R^6$, —SO$_2R^4$, $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), each of which $R^{10}$ except hydrogen, halo, —CN, and —NO$_2$ is substituted or unsubstituted;

each $R^{13}$ and $R^{14}$ is the same or different and each is hydrogen, $C_1$-$C_8$ alkyl, $C_2$-$C_8$ alkenyl, $C_3$-$C_6$ cycloalkyl, $C_6$-$C_{12}$aryl, wherein $R^{13}$ and $R^{14}$ are optionally connected to each other to form a ring;

$X^1$ is a bond, —$CR^8R^9$—, —N$R^5$—, —$CR^8NR^5$—, —N$R^5CR^8$—, —N$R^5$C(O)—, —O—, or —S—;

$X^2$ is —N$R^5$—, —O—, —CO—, —SO$_2$—, or —S—;

m, n, and q are the same or different and each is 0 or an integer from 1-5; and p is 1 or 2.

In an embodiment of formula (Ia), $R^1$ is independently chosen from halo, —CO$_2R^4$, —CONH$_2$, —C(O)NHOH, —P(O)(OH)$_2$, —B(O$R^{13}$)(O$R^4$), —SO$_2$(OH), —SO$_2$N$R^5R^6$, —($C_1$-$C_8$alkylene)OH, $C_1$-$C_4$alkyl, $C_1$-$C_4$alkoxy, $C_1$-$C_2$haloalkyl, $C_1$-$C_2$haloalkoxy, heteroaryl, and —C(O)O— heteroaryl, each of which $R^1$ except hydrogen, halo, —P(O)(OH)$_2$, —CONH$_2$, and —SO$_2$(OH), is substituted or unsubstituted;

each $R^4$, $R^5$, and $R^6$ is the same or different and each is hydrogen, $C_1$-$C_8$ alkyl, $C_2$-$C_8$ alkenyl, $C_3$-$C_6$ cycloalkyl, $C_6$-$C_{12}$ aryl, heteroaryl, or heterocycloalkyl, each of which $R^4$, $R^5$, and $R^6$ except H is substituted or unsubstituted;

$R^2$ is independently chosen from hydroxyl, halo, —CN, —NO$_2$, $C_1$-$C_8$ alkyl, $C_2$-$C_8$ alkenyl, $C_3$-$C_6$ cycloalkyl, $C_1$-$C_8$ alkoxy, —O—$C_3$-$C_6$cycloalkyl, $C_6$-$C_{12}$ aryl, —O—$C_6$-$C_{12}$ aryloxy, —(CH$_2$)$_q$aryl, —(CH$_2$)$_q$heteroaryl, —(CH$_2$)$_q$heterocycloalkyl, —C(O)R$^4$, —CO$_2$R$^4$, —C(O)NR$^5$R$^6$, —NR$^5$C(O)R$^4$, —(CH$_2$)$_q$NR$^5$(SO$_2$)R$^4$, —(CH$_2$)$_q$NR$^5$C(O)R$^4$, —(CH$_2$)$_q$NR$^7$C(O)NR$^5$R$^6$, —(CH$_2$)$_q$NR$^5$R$^6$, —(CH$_2$)$_q$SO$_2$NR$^5$R$^6$, and —(CH$_2$)$_q$SO$_2$R$^4$, each of which $R^2$ except hydrogen, hydroxyl, halo, —CN, —NO$_2$, SF$_5$, is substituted or unsubstituted;

$R^3$ is independently chosen from hydroxyl, halo, —CN, —NO$_2$, SF$_5$, $C_1$-$C_8$ alkyl, $C_2$-$C_8$ alkenyl, $C_2$-$C_8$ alkynyl, $C_3$-$C_6$ alkenynyl, $C_1$-$C_8$alkoxy, —(CH$_2$)$_q$$C_3$-$C_8$cycloalkyl, —O(CH$_2$)$_q$$C_3$-$C_8$cycloalkyl, —(CH$_2$)$_q$$C_3$-$C_8$cycloalkenyl, —(C$_2$-C$_4$alkynyl)(C$_3$-C$_6$cycloalkenyl), —(CH$_2$)$_q$$C_6$-$C_{12}$aryl, —O(CH$_2$)$_q$$C_6$-$C_{12}$aryl, —(CH$_2$)$_q$heteroaryl, —O(CH$_2$)$_q$heteroaryl, —(C$_2$-C$_4$alkenyl)heteroaryl, —(C$_2$-C$_4$alkynyl)heteroaryl, —(CH$_2$)$_q$heterocycloalkenyl, —O(CH$_2$)$_q$(heterocyloalkenyl, —(C$_2$-C$_4$alkenyl)heterocycloalkenyl, —(C$_2$-C$_4$alkynyl)heterocycloalkenyl, —(CH$_2$)$_q$heterocycloalkyl, —O(CH$_2$)$_q$heterocycloalkyl, —(C$_2$-C$_4$alkenyl)heterocycloalkyl, and —(C$_2$-C$_4$alkynyl)heterocycloalkyl, each of which $R^3$ except hydrogen, hydroxyl, halo, —CN, —NO$_2$, and SF$_5$ is substituted or unsubstituted;

$R^{10}$ is hydrogen, —CN, hydroxyl, halo, $C_1$-$C_8$alkyl, $C_2$-$C_8$alkenyl, $C_2$-$C_8$alkynyl, $C_1$-$C_6$alkoxy, —(C$_0$-C$_2$alkyl)NR$^5$R$^6$, —(C$_0$-C$_2$alkyl)C$_3$-C$_6$cycloalkyl, —C≡C(C$_3$-C$_6$cycloalkyl) —(C$_0$-C$_2$alkyl)C$_6$-C$_{12}$ aryl, —(C$_0$-C$_2$alkyl)heterocycloalkyl, or —(C$_0$-C$_2$alkyl)heteroaryl, each of which $R^{10}$ except hydrogen, hydroxyl, and halo is substituted or unsubstituted; and each $R^{13}$ and $R^{14}$ is the same or different and each is hydrogen, $C_1$-$C_8$ alkyl, $C_2$-$C_8$ alkenyl, $C_3$-$C_6$ cycloalkyl, $C_6$-$C_{12}$aryl, wherein $R^{13}$ and $R^{14}$ are optionally connected to each other to form a ring.

In another embodiment of formula (Ia), $R^1$ is independently chosen from halo, hydroxyl, —CONH$_2$, $C_1$-$C_4$alkyl, $C_1$-$C_4$alkoxy, —CO$_2$R$^4$, —CH$_2$OH, —CHCF$_3$OH, —C(CF$_3$)$_2$OH, —C(O)NHOH, —P(O)(OH)$_2$, —B(OR$^3$)(OR$^4$), —SO$_2$(OH), —SO$_2$NR$^5$R$^6$, —C(O)O-2,3-dihydro-1H-indenyl, —C(O)O-(5-methyl-2-oxo-1,3-dioxol-4-yl)methyl, 1,3,4-oxadiazol-2(3H)-one, isoxazol-3(2H)-one, and tetrazolyl, each of which $R^1$ except hydrogen, halo is substituted or unsubstituted;

$R^2$ is independently chosen from halo and —(CH$_2$)$_q$SO$_2$NR$^5$R$^6$, where one of $R^2$ is —(CH$_2$)$_q$SO$_2$NR$^5$R$^6$;

$R^3$ is independently chosen from hydroxyl, halo, —CN, —NO$_2$, SF$_5$, $C_1$-$C_8$ alkyl, $C_2$-$C_8$ alkenyl, $C_2$-$C_8$ alkynyl, $C_3$-$C_6$ alkenynyl, $C_1$-$C_8$alkoxy, —(CH$_2$)$_q$C$_3$-C$_8$cycloalkyl, —O(CH$_2$)$_q$C$_3$-C$_6$cycloalkyl, —(CH$_2$)$_q$C$_3$-C$_6$cycloalkenyl, —(C$_2$-C$_4$alkynyl)(C$_3$-C$_6$cycloalkenyl), —(CH$_2$)$_q$C$_6$-C$_{12}$phenyl, —O(CH$_2$)$_q$C$_6$-C$_{12}$phenyl, —(CH$_2$)$_q$heteroaryl, —O(CH$_2$)$_q$heteroaryl, —(C$_2$-C$_4$alkenyl)heteroaryl, and —(C$_2$-C$_4$alkynyl)heteroaryl, where the heteroaryl group is a oxazolyl, thienyl, thiazolyl, furanyl, pyrazolyl, and imidazolyl group;

—(CH$_2$)$_q$heterocycloalkenyl, —O(CH$_2$)$_q$(heterocyloalkenyl, —(C$_2$-C$_4$alkenyl)heterocycloalkenyl, —(C$_2$-C$_4$alkynyl)heterocycloalkenyl, where the heterocycloalkenyl is dihydropyranyl, dihydrofuranyl, dihydrothiopyranyl, and dihydropyridinyl, —(CH$_2$)$_q$heterocycloalkyl, —O(CH$_2$)$_q$heterocycloalkyl, —(C$_2$-C$_4$alkenyl)heterocycloalkyl, —(C$_2$-C$_4$alkynyl)heterocycloalkyl, where the heterocycloalkyl is tetrahydropyranyl, tetrahydrofuranyl, piperazinyl, piperidinyl, and pyrrolidinyl, each of which $R^3$ except hydrogen, hydroxyl, halo, —CN, —NO$_2$, and SF$_5$ is substituted or unsubstituted;

each $R^4$, $R^5$, and $R^6$ is the same or different and each is H or $C_1$-$C_8$ alkyl, wherein $C_1$-$C_8$ alkyl is substituted or unsubstituted;

$R^{10}$ is hydrogen, —OH, halo, —CH$_2$OH, —CN, —CH$_2$CN, —NH$_2$, $C_1$-$C_4$alkyl, $C_2$-$C_4$alkenyl, $C_1$-$C_4$alkoxy, $C_1$-$C_2$haloalkyl, $C_1$-$C_2$haloalkoxy, —(C$_0$-C$_3$ alkyl)-cyclopropyl, —(C$_0$-C$_3$ alkyl)-cyclobutyl, —C≡C-cyclopropyl, —C≡C-cyclobutyl phenyl, benzyl, or —CH$_2$-tetrazolyl, each of which cyclopropyl, —(C$_1$-C$_3$ alkyl)-cyclopropyl, —CH═CH$_2$, —C≡C-cyclopropyl, phenyl, or benzyl is substituted or unsubstituted; and each $R^{13}$ and $R^{14}$ is the same or different and each is hydrogen, $C_1$-$C_8$ alkyl, $C_2$-$C_8$ alkenyl, $C_3$-$C_6$ cycloalkyl, $C_6$-$C_{12}$aryl, wherein $R^{13}$ and $R^{14}$ are optionally connected to each other to form a ring.

In yet another embodiment of formula (Ia), $R^1$ is independently chosen from hydroxyl, halo, —CO$_2$H, —SO$_2$NH$_2$, $C_1$-$C_4$alkyl, $C_1$-$C_4$alkoxy, $C_1$-$C_2$haloalkyl optionally substituted with halo, $C_1$-$C_2$haloalkoxy, and —CO$_2$(C$_1$-C$_6$ alkyl), $R^2$ is chosen from F and —SO$_2$NH$_2$, where one of $R^2$ is —SO$_2$NH$_2$;

$R^3$ is independently chosen from (a) halogen, hydroxyl, SF$_5$;

(b) $C_1$-$C_6$hydrocarbyl where any alkylene (CH$_2$) group in the hydrocarbyl chain is optionally replaced with NH, O, or S;

(c) —C$_0$-C$_2$hydrocarbyl (phenyl), —C$_0$-C$_2$hydrocarbyl (phenyl), —C$_0$-C$_2$hydrocarbyl (thiophenyl), —C$_0$-C$_2$hydrocarbyl (oxazolyl), —C$_0$-C$_2$hydrocarbyl(thiazolyl), —C$_0$-C$_2$hydrocarbyl (tetrahydrofuranyl), —C$_0$-C$_2$hydrocarbyl(C$_3$-C$_6$cycloalkyl), —C$_0$-C$_2$hydrocarbyl(C$_3$-C$_6$cycloalkyl), —C$_0$-C$_2$hydrocarbyl(C$_3$-C$_6$cycloalkanyl), —C$_0$-C$_2$hydrocarbyl(C$_3$-C$_6$cycloalkenyl), —C$_0$-C$_2$hydrocarbyl (tetrahydropyrenyl), —C$_0$-C$_2$hydrocarbyl (imidazolyl), —C$_0$-C$_2$hydrocarbyl(thiophenyl), where any alkylene (CH$_2$) group in the C$_0$-C$_2$hydrocarbyl chain is optionally replaced with NH, O, or S;

where each of (b) is unsubstituted or substituted with 1 or more substituents independently chosen from halogen, hydroxyl, cyano, amino, $C_1$-$C_2$haloalkyl, and $C_1$-$C_2$haloalkoxy;

where each of (c) is unsubstituted or substituted with 1 or more substituents independently chosen from halogen, hydroxyl, cyano, amino, $C_1$-$C_4$alkyl, $C_1$-$C_6$cycloalkyl, mono- or di-$C_1$-$C_4$alkylamino, $C_1$-$C_4$alkoxy, $C_1$-$C_2$haloalkyl, and $C_1$-$C_2$haloalkoxy In some aspects, the compound of formula (I) is a compound, prodrug, or pharmaceutically acceptable salt of formula (Ib)

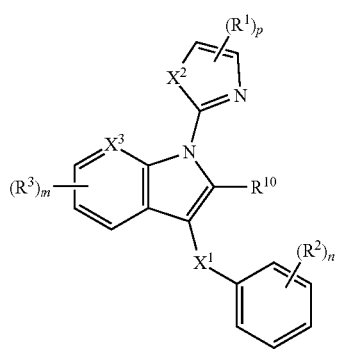

(Ib)

wherein $R^1$ is independently chosen from halo, —$CO_2R^4$, —C(O)$NR^5R^6$, —($C_1$-$C_8$hydrocarbyl), —C(O)NHOH, —C(O)OC$R^5R^6$OC(O)O$R^4$, —P(O)(OH)$_2$, —B(O$R^{13}$)(O$R^{14}$), —$SO_2$(OH), —C(O)NHS(O)$_2$Me and —$SO_2NR^5R^6$, each of which $R^1$ except halo is substituted or unsubstituted;

$R^2$ is independently chosen from hydroxyl, halo, —CN, —$NO_2$, $C_1$-$C_8$hydrocarbyl, —O($C_1$-$C_8$hydrocarbyl), —($C_0$-$C_4$hydrocarbyl)$C_3$-$C_8$cycloalkyl, —O($C_0$-$C_4$hydrocarbyl)$C_3$-$C_8$ cycloalkyl, —($C_0$-$C_4$hydrocarbyl)$C_3$-$C_8$cycloalkenyl, —O($C_0$-$C_4$hydrocarbyl)$C_3$-$C_8$cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —C(O)$R^4$, —$CO_2R^4$, —C(O)$NR^5R^6$, —$NR^5$C(O)$R^4$, —(CH$_2$)$_q$$NR^5$(SO$_2$)$R^4$, —(CH$_2$)$_q$$NR^5$C(O)$R^4$, —(CH$_2$)$_q$$NR^7$C(O)$NR^5R^6$, —(CH$_2$)$_q$$NR^5R^6$, —(CH$_2$)$_q$$SO_2NR^5R^6$, —(CH$_2$)$_q$$SO_2R^4$, —(CH$_2$)$_q$aryl, —(CH$_2$)$_q$heteroaryl, or —(CH$_2$)$_q$heterocycloalkyl, each of which $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S) is substituted or unsubstituted;

$R^3$ is independently chosen from hydroxyl, halo, —CN, —$NO_2$, —$SF_5$, $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —C(O)$R^4$, —$CO_2R^4$, —C(O)$NR^5R^6$, —$NR^5$C(O)$R^4$, —(CH$_2$)$_q$$NR^5$(SO$_2$)$R^4$, —(CH$_2$)$_q$$NR^5$C(O)$R^4$, —(CH$_2$)$_q$$NR^7$C(O)$NR^5R^6$, —(CH$_2$)$_q$$NR^5R^6$, —(CH$_2$)$_q$$SO_2NR^5R^6$, —(CH$_2$)$_q$$SO_2R^4$, each of which $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S) is substituted or unsubstituted; or each $R^4$, $R^5$, $R^6$, $R^7$, $R^8$, and $R^9$ is the same or different and each is hydrogen, $C_1$-$C_8$ alkyl, $C_2$-$C_8$ alkenyl, $C_3$-$C_6$ cycloalkyl, aryl, heteroaryl, or heterocycloalkyl, each of which $C_1$-$C_8$ alkyl, $C_2$-$C_8$ alkenyl, $C_3$-$C_6$ cycloalkyl, aryl, heteroaryl, or heterocycloalkyl is substituted or unsubstituted;

$R^{10}$ is hydrogen, halo, —CN, —$NO_2$, —$CO_2R^4$, —C(O)$NR^5R^6$, —$NR^5$(SO$_2$)$R^4$, —$NR^5$C(O)$R^4$, —$NR^7$C(O)$NR^5R^6$, —$NR^5R^6$, —$SO_2NR^5R^6$, —$SO_2R^4$, $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), each of which $R^{10}$ except hydrogen, halo, —CN, and —$NO_2$ is substituted or unsubstituted;

each $R^{13}$ and $R^{14}$ is the same or different and each is hydrogen, $C_1$-$C_8$ alkyl, $C_2$-$C_8$ alkenyl, $C_3$-$C_6$ cycloalkyl, $C_6$-$C_{12}$aryl, wherein $R^{13}$ and $R^{14}$ are optionally connected to each other to form a ring;

$X^1$ is a bond, —C$R^8R^9$—, —$NR^5$—, —C$R^8NR^5$—, —$NR^5$C$R^8$—, —$NR^5$C(O)—, —O—, —CO—, —$SO_2$—, or —S—;

$X^2$ is —$NR^5$—, —O—, —SO—, or —$SO_2$—, or —S—;

$X^3$ is CH or N;

m, n, and q are the same or different and each is 0 or an integer from 1-5; and p is 1 or 2.

In some aspects, the compound of formula (I) is a compound, prodrug, or pharmaceutically acceptable salt of formula (Ic)

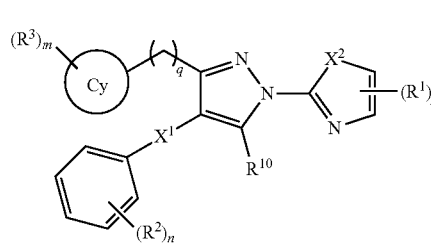

(Ic)

wherein $R^1$ is independently chosen from halo, —$CO_2R^4$, —C(O)$NR^5R^6$, —($C_1$-$C_8$hydrocarbyl), —C(O)NHOH, —P(O)(OH)$_2$, —B(O$R^3$)(O$R^4$), —$SO_2$(OH), —C(O)NHS(O)$_2$Me and —$SO_2NR^5R^6$, each of which $R^1$ except halo is substituted or unsubstituted;

$R^2$ is independently chosen from hydroxyl, halo, —CN, —$NO_2$, $C_1$-$C_8$hydrocarbyl, —O($C_1$-$C_8$hydrocarbyl), —($C_0$-$C_4$hydrocarbyl)$C_3$-$C_8$cycloalkyl, —O($C_0$-$C_4$hydrocarbyl)$C_3$-$C_8$ cycloalkyl, —($C_0$-$C_4$hydrocarbyl)$C_3$-$C_8$cycloalkenyl, —O($C_0$-$C_4$hydrocarbyl)$C_3$-$C_8$cycloalkenyl, —O($C_0$-$C_4$hydrocarbyl)$C_6$-$C_{12}$aryl, —($C_0$-$C_4$hydrocarbyl)$C_6$-

$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —C(O)$R^4$, —$CO_2R^4$, —C(O)$NR^5R^6$, —$NR^5$C(O)$R^4$, —$(CH_2)_qNR^5(SO_2)R^4$, —$(CH_2)_qNR^5$C(O)$R^4$, —$(CH_2)_qNR^7$C(O)$NR^5R^6$, —$(CH_2)_qNR^5R^6$, —$(CH_2)_qSO_2NR^5R^6$, —$(CH_2)_qSO_2R^4$, each of which $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)((mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S) is substituted or unsubstituted;

$R^3$ is independently chosen from hydroxyl, halo, —CN, —$NO_2$, —$SF_5$, $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —C(O)$R^4$, —$CO_2R^4$, —C(O)$NR^5R^6$, —$NR^5$C(O)$R^4$, —$(CH_2)_qNR^5(SO_2)R^4$, —$(CH_2)_qNR^5$C(O)$R^4$, —$(CH_2)_qNR^7$C(O)$NR^5R^6$, —$(CH_2)_qNR^5R^6$, —$(CH_2)_qSO_2NR^5R^6$, —$(CH_2)_qSO_2R^4$, each of which $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S) is substituted or unsubstituted;

each $R^4$, $R^5$, $R^6$, $R^7$, $R^8$, and $R^9$ is the same or different and each is hydrogen, $C_1$-$C_8$ alkyl, $C_2$-$C_8$ alkenyl, $C_3$-$C_6$ cycloalkyl, aryl, heteroaryl, or heterocycloalkyl;

$R^{10}$ is hydrogen, halo, —CN, —$NO_2$, —$CO_2R^4$, —C(O)$NR^5R^6$, —$NR^5(SO_2)R^4$, —$NR^5$C(O)$R^4$, —$NR^7$C(O)$NR^5R^6$, —$NR^5R^6$, —$SO_2NR^5R^6$, —$SO_2R^4$, $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), each of which $R^{10}$ except hydrogen, halo, —CN, and —$NO_2$ is substituted or unsubstituted;

each $R^{13}$ and $R^{14}$ is the same or different and each is hydrogen, $C_1$-$C_8$ alkyl, $C_2$-$C_8$ alkenyl, $C_3$-$C_6$ cycloalkyl, $C_6$-$C_{12}$aryl, wherein $R^3$ and $R^{14}$ are optionally connected to each other to form a ring;

ring Cy is substituted or unsubstituted $C_3$-$C_6$ cycloalkyl,
$X^1$ is a bond, —$CR^8R^9$—, —$NR^5$—, —$CR^8NR^5$—, —$NR^5CR^8$—, —$NR^5$C(O)—, —O—, —CO—, —SO—, —$SO_2$—, or —S—;
$X^2$ is —$NR^5$—, —O—, —$SO_2$—, or —S—;
m, n, and q are the same or different and each is 0 or an integer from 1-5; and
p is 1 or 2.

In some aspects, the compound of formula (I) is a compound, prodrug, or pharmaceutically acceptable salt of formula (Id)

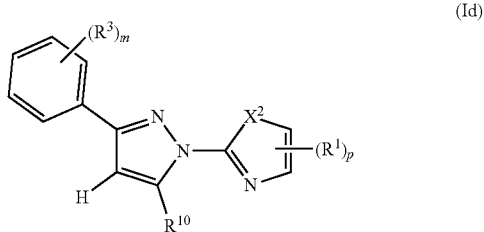

(Id)

wherein $R^1$ is independently chosen from halo, —$CO_2R^4$, —C(O)$NR^5R^6$, —($C_1$-$C_8$hydrocarbyl), —C(O)NHOH, —($C_0$-$C_4$hydrocarbyl)((mono- or bicyclic heterocycle having 1 to 4 heteroatoms independently chosen from N, O, and S), —C(O)O—($C_0$-$C_4$hydrocarbyl)(mono- or bicyclic heterocycle having 1 to 4 heteroatoms independently chosen from N, O, and S), —P(O)(OH)$_2$, —B(O$R^3$)(O$R^4$), —$SO_2$(OH), —$SO_2NR^5R^6$, each of which $R^1$ except halo is substituted or unsubstituted;

$R^3$ is independently chosen from hydroxyl, halo, —CN, —$NO_2$, —$SF_5$, $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S), —C(O)$R^4$, —$CO_2R^4$, —C(O)$NR^5R^6$, —$NR^5$C(O)$R^4$, —$(CH_2)_qNR^5(SO_2)R^4$, —$(CH_2)_qNR^5$C(O)$R^4$, —$(CH_2)_qNR^7$C(O)$NR^5R^6$, —$(CH_2)_qNR^5R^6$, —$(CH_2)_qSO_2NR^5R^6$, —$(CH_2)_qSO_2R^4$, each of which $C_1$-$C_8$hydrocarbyl, —O($C_1$-$C_8$hydrocarbyl), —($C_0$-$C_4$hydrocarbyl)$C_3$-$C_8$ cycloalkyl, —O($C_0$-$C_4$hydrocarbyl)$C_3$-$C_8$ cycloalkyl, —($C_0$-$C_4$hydrocarbyl)$C_3$-$C_8$ cycloalkenyl, —O($C_0$-$C_4$hydrocarbyl)$C_3$-$C_8$ cycloalkenyl, —O($C_0$-$C_4$hydrocarbyl)$C_6$-$C_{12}$aryl, —($C_0$-$C_4$hydrocarbyl)$C_6$-$C_{12}$aryl, —O($C_0$-$C_4$hydrocarbyl)(mono- and bicyclic heterocycle having 1 to 4 heteroatoms independently chosen from N, O, and S), —($C_0$-$C_4$hydrocarbyl)(mono- and bicyclic heterocycle having 1 to 4 heteroatoms independently chosen from N, O, and S) is substituted or unsubstituted; or two $R^3$ moieties and the phenyl group to which they are attached form a naphthyl group or its heterocyclic analog that is optionally substituted;

each $R^4$, $R^5$, $R^6$, and $R^7$ is the same or different and each is hydrogen, $C_1$-$C_8$ alkyl, $C_2$-$C_8$ alkenyl, $C_3$-$C_6$ cycloalkyl, $C_6$-$C_{12}$aryl, $C_1$-$C_{12}$heteroaryl, or $C_1$-$C_{12}$heterocycloalkyl, each of which $C_1$-$C_8$ alkyl, $C_2$-$C_8$ alkenyl, $C_3$-$C_6$ cycloalkyl, $C_6$-$C_{12}$aryl, $C_1$-$C_{12}$heteroaryl, or $C_1$-$C_{12}$heterocycloalkyl is substituted or unsubstituted;

$R^{10}$ is hydrogen, halo, —CN, —NO$_2$, —CO$_2$R$^4$, —C(O)NR$^5$R$^6$, —NR$^5$(SO$_2$)R$^4$, —NR$^5$C(O)R$^4$, —NR$^7$C(O)NR$^5$R$^6$, —NR$^5$R$^6$, —SO$_2$NR$^5$R$^6$, —SO$_2$R$^4$, C$_1$-C$_8$hydrocarbyl, —O(C$_1$-C$_8$hydrocarbyl), —(C$_0$-C$_4$hydrocarbyl)C$_3$-C$_8$ cycloalkyl, —O(C$_0$-C$_4$hydrocarbyl)C$_3$-C$_8$ cycloalkyl, —(C$_0$-C$_4$hydrocarbyl)C$_3$-C$_8$ cycloalkenyl, —O(C$_0$-C$_4$hydrocarbyl)C$_3$-C$_8$ cycloalkenyl, —O(C$_0$-C$_4$hydrocarbyl)C$_6$-C$_{12}$aryl, —(C$_0$-C$_4$hydrocarbyl)C$_6$-C$_{12}$aryl, —O(C$_0$-C$_4$hydrocarbyl)(mono- and bicyclic heterocycle having 1 to 4 heteroatoms independently chosen from N, O, and S), —(C$_0$-C$_4$hydrocarbyl)(mono- and bicyclic heterocycle having 1 to 4 heteroatoms independently chosen from N, O, and S), each of which R$^{10}$ except hydrogen, halo, —CN, and —NO$_2$ is substituted or unsubstituted;

each R$^{13}$ and R$^{14}$ is the same or different and each is hydrogen, C$_1$-C$_8$ alkyl, C$_2$-C$_8$ alkenyl, C$_3$-C$_6$ cycloalkyl, C$_6$-C$_{12}$aryl, wherein R$^{13}$ and R$^{14}$ are optionally connected to each other to form a ring;

X$^2$ is —NR$^5$—, —O—, —SO—, —SO$_2$—, or —S—;

m and q are the same or different and each is 0 or an integer from 1-5; and p is 1 or 2.

In any of the foregoing embodiments of formula (Ia)-(Id), R$^{10}$ is hydrogen, C$_1$-C$_8$ alkyl, C$_2$-C$_8$ alkenyl, C$_2$-C$_8$ alkynyl, C$_3$-C$_6$ cycloalkyl, C$_3$-C$_6$ cycloalkylalkyl, aryl, arylalkyl, hydroxyl, hydroxyalkyl, halo, C$_1$-C$_8$ haloalkyl, —CN, cyanoalkyl, —NR$^5$R$^6$, or heteroarylalkyl. In an aspect, R$^{10}$ is hydrogen, C$_1$-C$_8$ alkyl, —CH=CH$_2$, cyclopropyl, —C≡C— cyclopropyl, —OH, —CH$_2$OH, —CF$_3$, —CF$_2$CF$_3$, —Cl, —F, —I, —CN, —CH$_2$CN, —NH$_2$, phenyl, benzyl, or —CH$_2$-tetrazolyl.

In any of the foregoing embodiments of formula (Ia)-(Id), R$^1$ is —CO$_2$H or substituted or unsubstituted —CO$_2$(C$_1$-C$_8$ alkyl) or a prodrug or a pharmaceutically acceptable salt thereof. In an aspect of this embodiment, p is 1.

In any of the foregoing embodiments of formula (Ia)-(Ic), R$^2$ is —SO$_2$NR$^5$R$^6$; and R$^5$ and R$^6$ are the same or different and each is hydrogen or substituted or unsubstituted C$_1$-C$_8$ alkyl.

In any of the foregoing embodiments of formula (Ia)-(Ic), n is 1.

In any of the foregoing embodiments of formula (Ia)-(Id), R$^3$ is hydrogen, halo, substituted or unsubstituted C$_1$-C$_8$ haloalkyl, substituted or unsubstituted C$_1$-C$_8$ haloalkoxy, or substituted or unsubstituted aryl.

In any of the foregoing embodiments of formula (Ia)-(Id), m is 1 or 2.

In any of the foregoing embodiments of formula (Ia)-(Ic), X$^1$ is —CR$^8$R$^9$— (e.g., —CH$_2$—), —O—, or —NH—, in which R$^8$ and R$^9$ are the same or different and each is hydrogen, substituted or unsubstituted C$_1$-C$_8$ alkyl, substituted or unsubstituted C$_2$-C$_8$ alkenyl, substituted or unsubstituted C$_3$-C$_6$ cycloalkyl, or substituted or unsubstituted aryl.

In any of the foregoing embodiments of formula (Ia)-(Id), X$^2$ is —S—.

In any of the foregoing embodiments of the compound of formula (Ib), X$^3$ is —CH—.

In an aspect, the compound of formula (Ia) is a compound, prodrug, or pharmaceutically acceptable salt of formula (Ia-1):

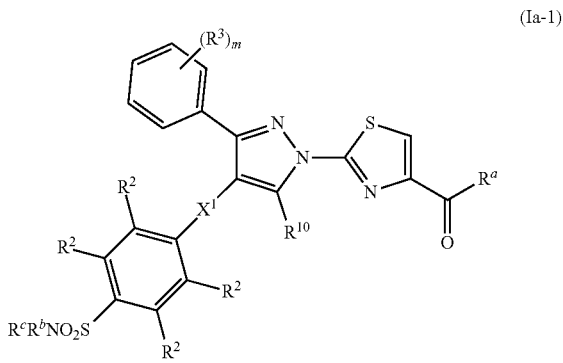

(Ia-1)

wherein

R$^a$ is —R$^4$, —OR$^4$, or —NR$^5$R$^6$, each of which is substituted or unsubstituted;

R$^b$ and R$^c$ are the same or different and each is H or substituted or unsubstituted C$_1$-C$_8$ alkyl;

each R$^2$ is the same or different and is independently chosen from hydroxyl, C$_1$-C$_8$ alkyl, C$_2$-C$_8$ alkenyl, C$_3$-C$_6$ cycloalkyl, C$_1$-C$_8$ alkoxy, C$_3$-C$_6$ cycloalkyloxy, aryloxy, halo, C$_1$-C$_8$ haloalkoxy, C$_1$-C$_8$ haloalkyl, haloaryl, haloaryloxy, —CN, —NO$_2$, —C(O)R$^4$, —CO$_2$R$^4$, —C(O)NR$^5$R$^6$, —NR$^5$C(O)R$^4$, —(CH$_2$)$_q$NR$^5$(SO$_2$)R$^4$, —(CH$_2$)$_q$NR$^5$C(O)R$^4$, —(CH$_2$)$_q$NR$^7$C(O)NR$^5$R$^6$, —(CH$_2$)$_q$NR$^5$R$^6$, —(CH$_2$)$_q$SO$_2$NR$^5$R$^6$, —(CH$_2$)$_q$SO$_2$R$^4$, —(CH$_2$)$_q$aryl, —(CH$_2$)$_q$heteroaryl, and —(CH$_2$)$_q$heterocycloalkyl, each of which R$^2$ except hydroxyl and halo is substituted or unsubstituted;

R$^3$ is independently chosen from hydroxyl, C$_1$-C$_8$ alkyl, C$_2$-C$_8$ alkenyl, C$_2$-C$_8$ alkynyl, C$_3$-C$_6$ cycloalkyl, —(C$_1$-C$_4$hydrocarbyl)C$_3$-C$_6$ cycloalkyl, C$_1$-C$_8$ alkoxy, —(C$_0$-C$_4$alkoxy)C$_3$-C$_6$cycloalkyl, —(C$_0$-C$_4$alkoxy)aryl, halo, C$_1$-C$_8$ haloalkoxy, C$_1$-C$_8$ haloalkyl, haloaryl, haloaryloxy, —CN, —NO$_2$, —C(O)R$^4$, —CO$_2$R$^4$, —C(O)NR$^5$R$^6$, —NR$^5$C(O)R$^4$, —(CH$_2$)$_q$NR$^5$(SO$_2$)R$^4$, —(CH$_2$)$_q$NR$^5$C(O)R$^4$, —(CH$_2$)$_q$NR$^7$C(O)NR$^5$R$^6$, —(CH$_2$)$_q$NR$^5$R$^6$, —(CH$_2$)$_q$SO$_2$NR$^5$R$^6$, —(CH$_2$)$_q$SO$_2$R$^4$, —(C$_0$-C$_4$hydrocarbyl)aryl, —(C$_0$-C$_4$hydrocarbyl)heteroaryl, —(C$_0$-C$_4$alkoxy)heteroaryl, —(C$_0$-C$_4$alkoxy)heterocycloalkyl, and —(C$_0$-C$_4$hydrocarbyl) heterocycloalkyl, each of which R$^3$ except hydroxyl and halo is substituted or unsubstituted; or two R$^3$ moieties and the phenyl group to which they are attached form a naphthyl group that is optionally substituted;

each R$^4$, R$^5$, R$^6$, and R$^7$ is the same or different and each is hydrogen, C$_1$-C$_8$ alkyl, or C$_3$-C$_6$ cycloalkyl, each of which C$_1$-C$_8$ alkyl and C$_3$-C$_6$ cycloalkyl is substituted or unsubstituted;

R$^{10}$ is hydrogen, C$_1$-C$_8$ alkyl, C$_2$-C$_8$ alkenyl, C$_2$-C$_8$ alkynyl, C$_3$-C$_6$ cycloalkyl, C$_3$-C$_6$ cycloalkylalkyl, hydroxyl, hydroxyalkyl, C$_1$-C$_8$ alkoxy, halo, C$_1$-C$_8$ haloalkyl, —CN, —CO$_2$R$^4$, —NR$^5$R$^6$, aryl, arylalkyl, heteroarylalkyl, or —SO$_2$R$^4$, each of which R$^{10}$ except hydrogen, hydroxyl and halo is substituted or unsubstituted;

X is a bond, —CR$^8$R$^9$—, —NR$^5$—, —O—, —S(O)—, or —S(O)$_2$—, or —S—;

n is an integer from 0 to 4; and m and q are the same or different and each is 0 or an integer from 1-5.

In an embodiment, compound of formula (Ia-1) comprise R$^a$ is hydroxyl or —O(C$_1$-C$_8$ alkyl); R$^b$ and R$^c$ are H; R$^2$ is hydrogen; R$^3$ is halo, aryl, or haloaryl (e.g., halo or phenyl); or two R$^3$ moieties and the phenyl group to which they are attached form a naphthyl group that is optionally substituted; R$^{10}$ is hydrogen, C$_1$-C$_8$ alkyl, cyclopropyl, —CH$_2$-cyclopropyl, —CH₂CH₂cyclopropyl, cyclobutyl, —CH₂-cyclobutyl, —CH=CH₂, —C≡C-cyclopropyl, phenyl, benzyl, —I, —CF₃, —NH₂, or —CN; and X¹ is —CH₂— or —NH—; and m is 0, 1, or 2.

In an embodiment, the disclosure includes compounds and salts of formula (Ia-1), wherein
R$^a$ is R⁴, —OR⁴, or —NR⁵R⁶;
R² is one or more substituents independently chosen from halo, hydroxyl, —CN, —NO₂, amino, —C(O)R⁴, —CO₂R⁴, —C(O)NR⁵R⁶, —NR⁵C(O)R⁴, C₁-C₂ alkyl, C₁-C₂ alkoxy, C₁-C₂ haloalkyl, and C₁-C₂haloalkoxy;
each R⁴, R⁵, and R⁶, is the same or different and each is hydrogen or C₁-C₂ alkyl; and
R¹⁰ is hydrogen, hydroxyl, halo, —CN, C₁-C₄ alkyl, hydroxylC₁-C₄alkyl, C₁-C₄ alkoxy, C₂-C₄ alkenyl, (C₃-C₆ cycloalkyl)C₀-C₂alkyl, C₁-C₂ haloalkyl, C₁-C₂haloalkoxy, —CO₂R⁴, —NR⁵R⁶, or —SO₂R⁴.

In an embodiment the disclosure also includes compounds and salts of formula (Ia-1) wherein:
one of R³ is selected from C₂-C₆alkynyl, —(C₀-C₂alkyl)C₃-C₆cycloalkyl, —(C₂-C₄alkenyl)C₃-C₆cycloalkyl, —(C₂-C₄alkynyl)C₃-C₆cycloalkyl, —(C₀-C₂alkoxy)C₃-C₆cycloalkyl, dihydropyranyl, —(C₀-C₄alkoxy)phenyl, —(C₀-C₄alkyl)phenyl, —(C₂-C₄alkenyl)phenyl, —(C₂-C₄alkynyl)phenyl, —(C₀-C₄alkoxy)heteroaryl, —(C₀-C₄alkyl)heteroaryl, —(C₂-C₄alkenyl)heteroaryl, and —(C₂-C₄alkynyl)heteroaryl, where heteroaryl is chosen from thienyl, furanyl, thiazolyl, pyrazolyl, imidazolyl; each of which one or more substituents selected from hydroxyl, halo, —CN, C₁-C₄ alkyl, C₂-C₄ alkenyl, C₁-C₄ alkynyl, C₁-C₄ alkoxy, (C₃-C₆ cycloalkyl)C₀-C₂alkyl, C₁-C₂ haloalkyl, and C₁-C₂haloalkoxy; and 0 or 1 or more R³ is selected from hydroxyl, halo, —CN, C₁-C₄ alkyl, C₁-C₄ alkoxy, C₁-C₂ haloalkyl, and C₁-C₂haloalkoxy.

In an aspect, a compound of formula (Ia-1) is a compound, prodrug, or pharmaceutically acceptable salt of formula (Ia-2):

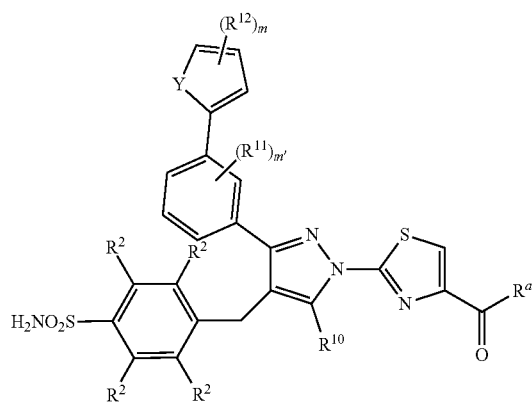

(Ia-2)

Wherein
Y=—CH=CH—, O, S, NH;
R$^a$ is —R⁴, —OR⁴, or —NR⁵R⁶, each of which R⁴' R⁵, and R⁶ is substituted or unsubstituted;
each R² is the same or different and each is hydrogen, hydroxyl, C₁-C₈ alkyl, C₂-C₈ alkenyl, C₃-C₆ cycloalkyl, C₃-C₆ cycloalkylalkyl, C₁-C₈ alkoxy, C₃-C₆ cycloalkyloxy, aryloxy, halo, C₁-C₈ haloalkoxy, C₁-C₈ haloalkyl, haloaryl, haloaryloxy, —CN, —NO₂, —C(O)R⁴, —CO₂R⁴, —C(O)NR⁵R⁶, —NR⁵C(O)R⁴, —(CH₂)$_q$NR⁵(SO₂)R⁴, —(CH₂)$_q$NR⁵C(O)R⁴, —(CH₂)$_q$NR⁷C(O)NR⁵R⁶, —(CH₂)$_q$NR⁵R⁶, —(CH₂)$_q$SO₂NR⁵R⁶, —(CH₂)$_q$SO₂R⁴, —(CH₂)$_q$aryl, —(CH₂)$_q$heteroaryl, or —(CH₂)$_q$heterocycloalkyl, each of which R² except hydrogen, hydroxyl and halo is substituted or unsubstituted;

Each R¹¹ and R¹² are independently selected from hydroxyl, halo, —CN, NO₂, C₁-C₈ alkyl, C₂-C₈ alkenylC₁-C₈ alkoxy, C₁-C₂ haloalkoxy, C₁-C₂ haloalkyl, —C(O)R⁴, —CO₂R⁴, —C(O)NR⁵R⁶, —NR⁵C(O)R⁴, —(CH₂)$_q$NR⁵(SO₂)R⁴, —(CH₂)$_q$NR⁵C(O)R⁴, —(CH₂)$_q$NR⁷C(O)NR⁵R⁶, —(CH₂)$_q$NR⁵R⁶, —(CH₂)$_q$SO₂NR⁵R⁶, and —(CH₂)$_q$SO₂R⁴, each of which R¹ and R¹² other than hydroxyl, halo, —CN, NO₂, is substituted or unsubstituted;
each R⁴, R⁵, R⁶, and R⁷ is the same or different and each is hydrogen, C₁-C₈ alkyl, or C₃-C₆ cycloalkyl, each of which C₁-C₈ alkyl and C₃-C₆ cycloalkyl is substituted or unsubstituted;
R¹⁰ is hydrogen, C₁-C₈ alkyl, C₂-C₈ alkenyl, C₂-C₈ alkynyl, C₃-C₆ cycloalkyl, C₃-C₆ cycloalkylalkyl, hydroxyl, hydroxyalkyl, C₁-C₈ alkoxy, halo, C₁-C₈ haloalkyl, aryl, arylalkyl, heteroarylalkyl, —CN, —CO₂R⁴, —NR⁵R⁶, or —SO₂R⁴, each of which R¹⁰ except hydrogen and halo is substituted or unsubstituted;
m and q are the same or different and each; and
m' is 0 or an integer from 1-4.

In an aspect, a compound of formula (Ia-1) is a compound, prodrug, or pharmaceutically acceptable salt of formula (Ia-3):

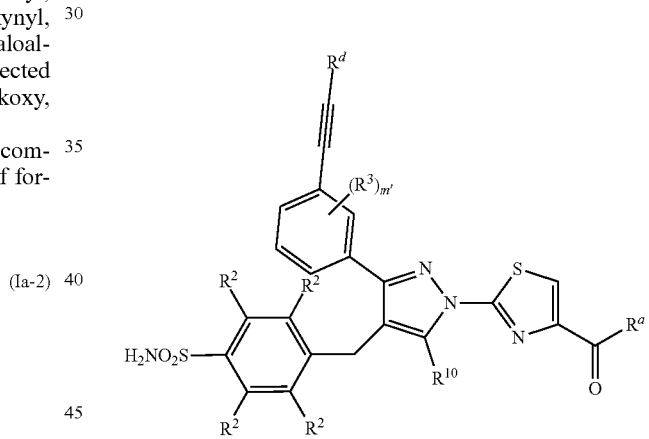

wherein
R$^a$ is —R⁴, —OR⁴, or —NR⁵R⁶, each of which R⁴' R⁵, and R⁶ is substituted or unsubstituted;
each R² is the same or different and each is hydrogen, hydroxyl, C₁-C₈ alkyl, C₂-C₈ alkenyl, C₃-C₆ cycloalkyl, C₃-C₆ cycloalkylalkyl, C₁-C₈ alkoxy, C₃-C₆ cycloalkyloxy, aryloxy, halo, C₁-C₈ haloalkoxy, C₁-C₈ haloalkyl, haloaryl, haloaryloxy, —CN, —NO₂, —C(O)R⁴, —CO₂R⁴, —C(O)NR⁵R⁶, —NR⁵C(O)R⁴, —(CH₂)$_q$NR⁵(SO₂)R⁴, —(CH₂)$_q$NR⁵C(O)R⁴, —(CH₂)$_q$NR⁷C(O)NR⁵R⁶, —(CH₂)$_q$NR⁵R⁶, —(CH₂)$_q$SO₂NR⁵R⁶, —(CH₂)$_q$SO₂R⁴, —(CH₂)$_q$aryl, —(CH₂)$_q$heteroaryl, or —(CH₂)$_q$heterocycloalkyl, each of which R² except hydrogen, hydroxyl and halo is substituted or unsubstituted;
R³ is hydroxyl, C₁-C₈ alkyl, C₂-C₈ alkenyl, C₃-C₆ cycloalkyl, C₃-C₆ cycloalkylalkyl, C₁-C₈ alkoxy, C₃-C₆ cycloalkyloxy, aryloxy, halo, C₁-C₈ haloalkoxy, C₁-C₈ haloalkyl, haloaryl, haloaryloxy, —CN, —NO₂, —C(O)R⁴, —CO₂R⁴, —C(O)NR⁵R⁶, —NR⁵C(O)R⁴, —(CH₂)$_q$NR⁵(SO₂)R⁴, —(CH₂)$_q$NR⁵C(O)R⁴, —(CH₂)$_q$NR⁷C(O)NR⁵R⁶, —$(CH_2)_qNR^5R^6$, —$(CH_2)_qSO_2NR^5R^6$, —$(CH_2)_qSO_2R^4$, —$(CH_2)_q$aryl, —$(CH_2)_q$heteroaryl, or —$(CH_2)_q$heterocycloalkyl, each of which $R^3$ except hydroxyl and halo is substituted or unsubstituted;

each $R^4$, $R^5$, $R^6$, and $R^7$ is the same or different and each is hydrogen, $C_1$-$C_8$ alkyl, or $C_3$-$C_6$ cycloalkyl, each of which $C_1$-$C_8$ alkyl and $C_3$-$C_6$ cycloalkyl is substituted or unsubstituted;

$R^4$ is hydrogen, $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, hydroxyl, hydroxyalkyl, $C_1$-$C_8$ alkoxy, halo, $C_1$-$C_8$ haloalkyl, aryl, arylalkyl, heteroarylalkyl, —CN, —$CO_2R^4$, —$NR^5R^6$, or —$SO_2R^4$;

q are the same or different and each; and m' is 0 or an integer from 1-4

$R^{10}$ is hydrogen, $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, hydroxyl, hydroxyalkyl, $C_1$-$C_8$ alkoxy, halo, $C_1$-$C_8$ haloalkyl, aryl, arylalkyl, heteroarylalkyl, —CN, —$CO_2R^4$, —$NR^5R^6$, or —$SO_2R^4$, each of which $R^{10}$ except hydrogen and halo is substituted or unsubstituted; and $R^d$ is hydrogen, $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, hydroxyl, hydroxyalkyl, $C_1$-$C_8$ alkoxy, halo, $C_1$-$C_8$ haloalkyl, aryl, arylalkyl, heteroaryl, heteroarylalkyl, —CN, —$CO_2R^4$, —$NR^5R^6$, or —$SO_2R^4$; each of which $R^{11}$ other than hydrogen and —CN is optionally substituted.

In certain embodiments $R^d$ is phenyl, thienyl, thiazolyl, furanyl, oxazolyl, pyrazolyl, oxadiazolyl, or imidazolyl, each of which is substituted or unsubstituted. In certain embodiments $R^d$ is phenyl, thienyl, thiazolyl, furanyl, oxazolyl, pyrazolyl, oxadiazolyl, or imidazolyl, each of which is unsubstituted or substituted with 1 or more substituents independently chosen from hydroxyl, cyano, amino, $C_1$-$C_2$alkyl, $C_1$-$C_2$alkoxy, mono- or di-$C_1$-$C_2$alkylamino, $C_1$-$C_2$haloalkyl, and $C_1$-$C_2$haloalkoxy. In certain embodiments $R^d$ is thienyl substituted with methyl.

In certain embodiments, the disclosure includes compounds and salts of formula (Ia-3) wherein:

$R^a$ is hydrogen, hydroxyl, amino, $C_1$-$C_2$alkyl, $C_1$-$C_2$alkoxy, and mono- or di-$C_1$-$C_2$alkylamino-;

each $R^2$ is the same or different and is independently selected from hydrogen, halo, hydroxyl, —CN, —$NO_2$, amino, —C(O)$R^4$, —$CO_2R^4$, —C(O)$NR^5R^6$, —$NR^5$C(O) $R^4$, $C_1$-$C_2$ alkyl, $C_1$-$C_2$ alkoxy, $C_1$-$C_2$ haloalkyl, and $C_1$-$C_2$haloalkoxy;

each $R^3$ is independently chosen from hydroxyl, halo, —CN, $NO_2$, $C_1$-$C_2$ alkyl, $C_1$-$C_2$ alkoxy, $C_1$-$C_2$ haloalkoxy, and $C_1$-$C_2$ haloalkyl;

each $R^4$, $R^5$, $R^6$, and $R^7$ is the same or different and each is hydrogen or $C_1$-$C_2$ alkyl;

m' is 0 or an integer from 1-4; and $R^{10}$ is hydrogen, hydroxyl, halo, —CN, $C_1$-$C_4$ alkyl, hydroxyl$C_1$-$C_4$alkyl, $C_1$-$C_4$ alkoxy, $C_2$-$C_4$ alkenyl, ($C_3$-$C_6$ cycloalkyl)$C_0$-$C_2$alkyl, $C_1$-$C_2$ haloalkyl, $C_1$-$C_2$haloalkoxy, —$CO_2R^4$, —$NR^5R^6$, or —$SO_2R^4$.

$R^d$ in this embodiments can be thienyl substituted with methyl.

In an embodiment of the compound of formula (Ia-2): $R^a$ is hydroxyl or substituted or unsubstituted —O($C_1$-$C_8$ alkyl); $R^2$ is hydrogen, substituted or unsubstituted $C_1$-$C_8$ alkyl, substituted or unsubstituted $C_1$-$C_8$ alkoxy, or halo; $R^{11}$ and $R^{12}$ are each independently chosen from substituted or unsubstituted $C_1$-$C_8$ alkyl (e.g., $C_{1-4}$ alkyl, such methyl, ethyl, propyl, or butyl), substituted or unsubstituted $C_1$-$C_8$ alkoxy, or halo (e.g., —F, —I, —Cl, or —Br); $R^{10}$ is hydrogen, substituted or unsubstituted $C_1$-$C_8$ alkyl, cyclopropyl, —$CH_2$-cyclopropyl, cyclobutyl, —$CH_2$-cyclobutyl, —CH=$CH_2$, —C≡C-cyclopropyl, —C≡C-cyclobutyl, phenyl, benzyl, —I, —$CF_3$, —$NH_2$, or —CN; m is 0, 1, or 2; and m' is 0.

The disclosure also includes a compound or salt of formula (Ia-4):

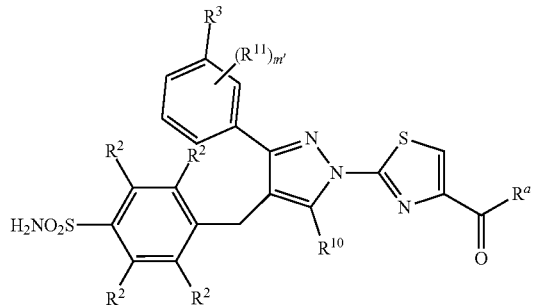

(Ia-4)

Within formula (Ia-4):

$R^a$ is —$R^4$, —$OR^4$, or —$NR^5R^6$, each of which $R^{4'}$ $R^5$, and $R^6$ is substituted or unsubstituted;

Each $R^2$ is the same or different and is hydrogen, hydroxyl, $C_1$-$C_8$ alkyl, $C_2$-$C_8$ alkenyl, $C_3$-$C_6$ cycloalkyl, $C_3$-$C_6$ cycloalkylalkyl, $C_1$-$C_8$ alkoxy, $C_3$-$C_6$ cycloalkyloxy, aryloxy, halo, $C_1$-$C_8$ haloalkoxy, $C_1$-$C_8$ haloalkyl, haloaryl, haloaryloxy, —CN, —$NO_2$, —C(O)$R^4$, —$CO_2R^4$, —C(O) $NR^5R^6$, —$NR^5$C(O)$R^4$, —$(CH_2)_qNR^5(SO_2)R^4$, —$(CH_2)_qNR^5C(O)R^4$, —$(CH_2)_qNR^7C(O)NR^5R^6$, —$(CH_2)_qNR^5R^6$, —$(CH_2)_qSO_2NR^5R^6$, —$(CH_2)_qSO_2R^4$, —$(CH_2)_q$aryl, —$(CH_2)_q$heteroaryl, or —$(CH_2)_q$heterocycloalkyl, each of which $R^2$ except hydrogen, hydroxyl and halo is substituted or unsubstituted;

$R^3$ is selected from $C_2$-$C_6$alkynyl, —($C_0$-$C_2$alkyl)$C_3$-$C_6$cycloalkyl, —($C_2$-$C_4$alkenyl)$C_3$-$C_6$cycloalkyl, —($C_2$-$C_4$alkynyl)$C_3$-$C_6$cycloalkyl, —($C_0$-$C_2$alkoxy)$C_3$-$C_6$cycloalkyl, dihydropyranyl, —($C_0$-$C_4$alkoxy)phenyl, —($C_0$-$C_4$alkyl)phenyl, —($C_2$-$C_4$alkenyl)phenyl, —($C_2$-$C_4$alkynyl)phenyl, —($C_0$-$C_4$alkoxy)heteroaryl, —($C_0$-$C_4$alkyl)heteroaryl, —($C_2$-$C_4$alkenyl)heteroaryl, and —($C_2$-$C_4$alkynyl)heteroaryl, where heteroaryl is a 5- or 6-membered heteroaryl having 1, 2, 3, or 4 heteroatoms independently chosen from N, O, and S, and where each $R^3$ is unsubstituted or substituted with one or more substituents selected from hydroxyl, halo, —CN, $C_1$-$C_4$ alkyl, $C_2$-$C_4$ alkenyl, $C_1$-$C_4$ alkynyl, $C_1$-$C_4$ alkoxy, ($C_3$-$C_6$ cycloalkyl)$C_0$-$C_2$alkyl, $C_1$-$C_2$ haloalkyl, and $C_1$-$C_2$haloalkoxy;

each $R^{11}$ is independently selected from hydroxyl, halo, —CN, $NO_2$, $C_1$-$C_8$ alkyl, $C_2$-$C_8$ alkenyl$C_1$-$C_5$ alkoxy, $C_1$-$C_2$ haloalkoxy, $C_1$-$C_2$ haloalkyl, —C(O)$R^4$, —$CO_2R^4$, —C(O) $NR^5R^6$, —$NR^5$C(O)$R^4$, —$(CH_2)_qNR^5(SO_2)R^4$, —$(CH_2)_qNR^5C(O)R^4$, —$(CH_2)_qNR^7C(O)NR^5R^6$, —$(CH_2)_qNR^5R^6$, —$(CH_2)_qSO_2NR^5R^6$, and —$(CH_2)_qSO_2R^4$, each of which $R^{11}$ and $R^{12}$ other than hydroxyl, halo, —CN, $NO_2$, is substituted or unsubstituted;

each $R^4$, $R^5$, $R^6$, and $R^7$ is the same or different and each is hydrogen, $C_1$-$C_8$ alkyl, or $C_3$-$C_6$ cycloalkyl, each of which $C_1$-$C_8$ alkyl and $C_3$-$C_6$ cycloalkyl is substituted or unsubstituted;

$R^{10}$ is hydrogen, $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, hydroxyl, hydroxyalkyl, $C_1$-$C_8$ alkoxy, halo, $C_1$-$C_8$ haloalkyl, aryl, arylalkyl, —CN, —CO$_2$R$^4$, —NR$^5$R$^6$, or —SO$_2$R$^4$, each of which R$^{10}$ except hydrogen and halo is substituted or unsubstituted;

m is 0 or 1, 2, 3, 4, or 5; and m' is 0 or an integer from 1-4.

In an embodiment the disclosure includes a compound or salt of formula (Ia-4) wherein R$^a$ is hydrogen, hydroxyl, amino, C$_1$-C$_2$alkyl, C$_1$-C$_2$alkoxy, and mono- or di-C$_1$-C$_2$alkylamino-;

each R$^2$ is the same or different and is independently selected from hydrogen, halo, hydroxyl, —CN, —NO$_2$, amino, —C(O)R$^4$, —CO$_2$R$^4$, —C(O)NR$^5$R$^6$, —NR$^5$C(O)R$^4$, C$_1$-C$_2$ alkyl, C$_1$-C$_2$ alkoxy, C$_1$-C$_2$ haloalkyl, and C$_1$-C$_2$haloalkoxy;

R$^3$ is selected from C$_2$-C$_6$alkynyl, —(C$_0$-C$_2$alkyl)C$_3$-C$_6$cycloalkyl, —(C$_2$-C$_4$alkenyl)C$_3$-C$_6$cycloalkyl, —(C$_2$-C$_4$alkynyl)C$_3$-C$_6$cycloalkyl, —(C$_0$-C$_2$alkoxy)C$_3$-C$_6$cycloalkyl, dihydropyranyl, —(C$_0$-C$_4$alkoxy)phenyl, —(C$_0$-C$_4$alkyl)phenyl, —(C$_2$-C$_4$alkenyl)phenyl, —(C$_2$-C$_4$alkynyl)phenyl, —(C$_0$-C$_4$alkoxy)heteroaryl, —(C$_0$-C$_4$alkyl)heteroaryl, —(C$_2$-C$_4$alkenyl)heteroaryl, and —(C$_2$-C$_4$alkynyl)heteroaryl, where heteroaryl is chosen from thienyl, furanyl, thiazolyl, pyrazolyl, imidazolyl; each of which one or more substituents selected from hydroxyl, halo, —CN, C$_1$-C$_4$ alkyl, C$_2$-C$_4$ alkenyl, C$_1$-C$_4$ alkynyl, C$_1$-C$_4$ alkoxy, (C$_3$-C$_6$ cycloalkyl)C$_0$-C$_2$alkyl, C$_1$-C$_2$ haloalkyl, and C$_1$-C$_2$haloalkoxy;

Each R$^{11}$ is independently selected from hydroxyl, halo, —CN, C$_1$-C$_4$ alkyl, C$_1$-C$_4$ alkoxy, C$_1$-C$_2$ haloalkyl, and C$_1$-C$_2$haloalkoxy;

Each R$^4$, R$^5$, and R$^6$ is the same or different and each is hydrogen or C$_1$-C$_2$ alkyl;

m' is 0 or an integer from 1-4; and

R$^{10}$ is hydrogen, hydroxyl, halo, —CN, C$_1$-C$_4$ alkyl, hydroxylC$_1$-C$_4$alkyl, C$_1$-C$_4$ alkoxy, C$_2$-C$_4$ alkenyl, (C$_3$-C$_6$ cycloalkyl)C$_0$-C$_2$alkyl, C$_1$-C$_2$ haloalkyl, C$_1$-C$_2$haloalkoxy, —CO$_2$R$^4$, —NR$^5$R$^6$, or —SO$_2$R$^4$.

In certain embodiments, the disclosure includes a compound or salt of formula (Ia-4) in which:

R$^a$ is hydrogen, hydroxyl, C$_1$-C$_2$alkyl, or C$_1$-C$_2$alkoxy;

each R$^2$ is the same or different and is independently selected from hydrogen, halo, hydroxyl, C$_1$-C$_2$ alkyl, C$_1$-C$_2$ alkoxy, C$_1$-C$_2$ haloalkyl, and C$_1$-C$_2$haloalkoxy;

R$^3$ is selected from C$_2$-C$_6$alkynyl, —(C$_0$-C$_2$alkyl)C$_3$-C$_6$cycloalkyl, —(C$_2$-C$_4$alkenyl)C$_3$-C$_6$cycloalkyl, —(C$_2$-C$_4$alkynyl)C$_3$-C$_6$cycloalkyl, —(C$_0$-C$_2$alkoxy)C$_3$-C$_6$cycloalkyl, dihydropyranyl, —(C$_0$-C$_4$alkoxy)phenyl, —(C$_0$-C$_4$alkyl)phenyl, —(C$_2$-C$_4$alkenyl)phenyl, —(C$_2$-C$_4$alkynyl)phenyl, —(C$_0$-C$_4$alkoxy)heteroaryl, —(C$_0$-C$_4$alkyl)heteroaryl, —(C$_2$-C$_4$alkenyl)heteroaryl, and —(C$_2$-C$_4$alkynyl)heteroaryl, where heteroaryl is chosen from thienyl, furanyl, thiazolyl, pyrazolyl, imidazolyl; each of which one or more substituents selected from hydroxyl, halo, —CN, C$_1$-C$_4$ alkyl, C$_2$-C$_4$ alkenyl, C$_1$-C$_4$ alkynyl, C$_1$-C$_4$ alkoxy, (C$_3$-C$_6$ cycloalkyl)C$_0$-C$_2$alkyl, C$_1$-C$_2$ haloalkyl, and C$_1$-C$_2$haloalkoxy;

Each R$^{11}$ is independently selected from hydroxyl, halo, —CN, C$_1$-C$_4$ alkyl, C$_1$-C$_4$ alkoxy, C$_1$-C$_2$ haloalkyl, and C$_1$-C$_2$haloalkoxy;

m' is 0 or an integer from 1-4; and

R$^{10}$ is hydrogen, hydroxyl, halo, —CN, C$_1$-C$_4$ alkyl, hydroxylC$_1$-C$_4$alkyl, C$_1$-C$_4$ alkoxy, C$_2$-C$_4$ alkenyl, (C$_3$-C$_6$ cycloalkyl)C$_0$-C$_2$alkyl, C$_1$-C$_2$ haloalkyl, or C$_1$-C$_2$haloalkoxy.

The disclosure further includes compounds and salts of formula (Ia-4) in which

R$^a$ is hydroxyl; and

Each R$^2$ is independently chosen from hydrogen and halogen.

In any of embodiments of formula (Ia-1 to Ia-4) the group

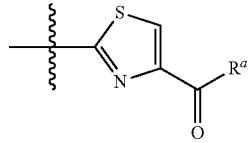

can be a group in which R$^a$ is hydroxyl, NHCN, or NHSO$_2$H, —NHSO$_2$alkyl, CH$_2$SO$_2$phenyl, —NHOH or —NHOalkyl, or can be a group in which —C(O)R$^a$ is replaced by —CH$_2$OH, —P(O)(OH)$_2$, —P(O)(OH)alkyl, or —SO$_2$OH.

In some aspects, the compound of formula (Ib) is a compound, prodrug, or pharmaceutically acceptable salt of formula (Ib-1):

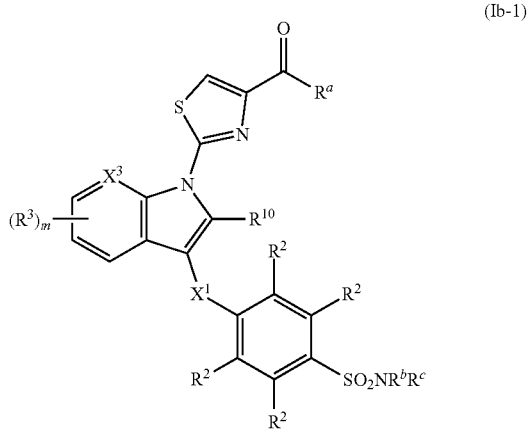

(Ib-1)

wherein

R$^a$ is —R$^4$, —OR$^4$, or —NR$^5$R$^6$, each of which R$^4$, R$^5$, and R$^6$ is substituted or unsubstituted;

R$^b$ and R$^c$ are the same or different and each is H or substituted or unsubstituted C$_1$-C$_8$ alkyl;

each R$^2$ is the same of different and each is hydrogen, hydroxyl, C$_1$-C$_8$ alkyl, C$_2$-C$_8$ alkenyl, C$_3$-C$_6$ cycloalkyl, C$_1$-C$_8$ alkoxy, C$_3$-C$_6$ cycloalkyloxy, aryloxy, halo, C$_1$-C$_8$ haloalkoxy, C$_1$-C$_8$ haloalkyl, haloaryl, haloaryloxy, —CN, —NO$_2$, —C(O)R$^4$, —CO$_2$R$^4$, —C(O)NR$^5$R$^6$, —NR$^5$C(O)R$^4$, —(CH$_2$)$_q$NR$^5$(SO$_2$)R$^4$, —(CH$_2$)$_q$NR$^5$C(O)R$^4$, —(CH$_2$)$_q$NR$^7$C(O)NR$^5$R$^6$, —(CH$_2$)$_q$NR$^5$R$^6$, —(CH$_2$)$_q$SO$_2$NR$^5$R$^6$, —(CH$_2$)$_q$SO$_2$R$^4$, —(CH$_2$)$_q$aryl, —(CH$_2$)$_q$heteroaryl, or —(CH$_2$)$_q$heterocycloalkyl, each of which R$^2$ except hydrogen, hydroxyl, halo, —CN, and —NO$_2$ is substituted or unsubstituted;

R$^3$ is halo, —C(O)R$_4$, C$_2$-C$_8$ alkynyl, haloaryl, —(CH$_2$)$_q$aryl, —(CH$_2$)$_q$heteroaryl, or —(CH$_2$)$_q$heterocycloalkyl, each of which R$^3$ is substituted or unsubstituted;

each R$^4$, R$^5$, R$^6$, R$^7$, R$^8$, and R$^9$ is the same or different and each is hydrogen, C$_1$-C$_8$ alkyl, C$_2$-C$_8$ alkenyl, C$_3$-C$_6$ cycloalkyl, aryl, heteroaryl, or heterocycloalkyl, each of which C$_1$-C$_8$ alkyl, C$_2$-C$_8$ alkenyl, C$_3$-C$_6$ cycloalkyl, aryl, heteroaryl, or heterocycloalkyl is substituted or unsubstituted;

R$^{10}$ is hydrogen, C$_1$-C$_8$ alkyl, C$_2$-C$_8$ alkenyl, C$_2$-C$_8$ alkynyl, C$_3$-C$_6$ cycloalkyl, C$_3$-C$_6$ cycloalkylalkyl, hydroxyl, hydroxyalkyl, $C_1$-$C_8$ alkoxy, $C_1$-$C_8$ haloalkyl, halo, aryl, arylalkyl, heteroarylalkyl, —CN, —$CO_2R^4$, —$NR^5R^6$, or —$SO_2R^4$, each of which $R^{10}$ except hydrogen, hydroxyl, halo, and —CN is substituted or unsubstituted;

$X^1$ is a bond, —$CR^8R^9$—, —$NR^5$—, —O—, —SO—, or —$SO_2$—, or —S—, each of which $R^5$, $R^8$, and $R^9$ is substituted or unsubstituted;

$X^3$ is CH or N; and m and q are the same or different and each is 0 or an integer from 1-5.

In an embodiment, the compound of formula (Ib-1) comprises $R^a$ is hydroxyl or substituted or unsubstituted —O($C_1$-$C_8$ alkyl); $R^b$ and $R^c$ are each hydrogen; $R^2$ is hydrogen; $R^3$ is halo, substituted or unsubstituted —C(O)morpholinyl, or substituted or unsubstituted 2-fluorophenyl; $R^0$ is hydrogen, substituted or unsubstituted $C_1$-$C_8$ alkyl, substituted or unsubstituted —CH=$CH_2$, substituted or unsubstituted cyclopropyl, substituted or unsubstituted —C≡C-cyclopropyl, substituted or unsubstituted cyclobutyl, substituted or unsubstituted —C≡C— cyclobutyl, —OH, —$CH_2OH$, —$CF_3$, —$CF_2CF_3$, —Cl, —F, —I, —CN, —$CH_2CN$, —$NH_2$, substituted or unsubstituted phenyl, substituted or unsubstituted benzyl, or substituted or unsubstituted —$CH_2$-tetrazolyl; $X^1$ is —$CH_2$— or —NH—; and m is 0, 1, or 2.

Compounds of formula (I), including compounds of formulas (Ia), (Ib), (Ic), and (Id), are set forth below in Table 6 as representative examples. Prodrugs and pharmaceutically acceptable salts of the exemplified compounds are also included in the disclosure.

Terminology

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or language denoting examples (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The term "substituted", as used herein, means that any one or more hydrogens on the designated atom or group is replaced with a selection from the indicated group, provided that the designated atom's normal valence is not exceeded. When the substituent is oxo (i.e., =O) then 2 hydrogens on the atom are replaced. When an oxo group substitutes a heteroaromatic moiety, the resulting molecule can sometimes adopt tautomeric forms. For example a pyridyl group substituted by oxo at the 2- or 4-position can sometimes be written as a pyridine or hydroxypyridine. Combinations of substituents and/or variables are permissible only if such combinations result in stable compounds or useful synthetic intermediates. A stable compound or stable structure is meant to imply a compound that is sufficiently robust to survive isolation from a reaction mixture and subsequent formulation into an effective therapeutic agent. Unless otherwise specified, substituents are named into the core structure. For example, it is to be understood that aminoalkyl means the point of attachment of this substituent to the core structure is in the alkyl portion and alkylamino means the point of attachment is a bond to the nitrogen of the amino group.

Suitable groups that may be present on a "substituted" or "optionally substituted" position include, but are not limited to, halogen; cyano; —OH; nitro; alkyl groups (including cycloalkyl and (cycloalkyl)alkyl groups) having 1 to about 8 carbon atoms, or 1 to about 6 carbon atoms; alkenyl and alkynyl groups including groups having one or more unsaturated linkages and from 2 to about 8, or 2 to about 6 carbon atoms; alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms. For example, suitable groups that may be present on a "substituted" or "optionally substituted" position include hydroxyl, halogen, cyano, alkyl groups, and alkoxy groups.

In any of the embodiments above, the term "alkyl" implies a straight-chain or branched alkyl substituent containing from, for example, from about 1 to about 8 carbon atoms, e.g., from about 1 to about 6 carbon atoms. Examples of alkyl group include methyl, ethyl, n-propyl, isopropyl, n-butyl, sec-butyl, isobutyl, tert-butyl, n-pentyl, isopentyl, n-hexyl, and the like. This definition also applies wherever "alkyl" occurs as part of a group, such as, e.g., in $C_3$-$C_6$ cycloalkylalkyl, hydroxyalkyl, haloalkyl (e.g., monohaloalkyl, dihaloalkyl, and trihaloalkyl), cyanoalkyl, aminoalkyl, alkylamino, dialkylamino, arylalkyl, etc. The alkyl can be substituted or unsubstituted, as described herein. Even in instances in which the alkyl is an alkylene chain (e.g., —$(CH_2)_n$—), the alkyl group can be substituted or unsubstituted. An example of a substituted alkylene chain includes —$CF_2$-cyclopropyl.

In any of the embodiments above, the term "alkenyl," as used herein, means a linear alkenyl substituent containing from, for example, about 2 to about 8 carbon atoms (branched alkenyls are about 3 to about 8 carbons atoms), e.g., from about 3 to about 6 carbon atoms (branched alkenyls are about 3 to about 6 carbons atoms). In accordance with an embodiment, the alkenyl group is a $C_2$-$C_4$ alkenyl. Examples of alkenyl group include ethenyl, allyl, 2-propenyl, 1-butenyl, 2-butenyl, 1-pentenyl, 2-pentenyl, 3-pentenyl, 1-hexenyl, and the like. The alkenyl can be substituted or unsubstituted, as described herein.

In any of the embodiments above, the term "alkynyl," as used herein, means a linear alkynyl substituent containing at least one carbon-carbon triple bond and from, for example, about 2 to about 8 carbon atoms (branched alkynyls are about 4 to about 12 carbons atoms), e.g., from about 2 to about 6 carbon atoms (branched alkynyls can be from about 4 to about 8 carbon atoms), e.g., from about 2 to about 4 carbon atoms. Examples of such substituents include propynyl, propargyl, n-butynyl, pentynyl, isopentynyl, hexynyl, octynyl, and the like. The alkynyl can be substituted or unsubstituted, as described herein.

In any of the embodiments above, the term "cycloalkyl," as used herein, means a cyclic alkyl moiety containing from, for example, 3 to 6 carbon atoms or from 5 to 6 carbon atoms. Examples of such moieties include cyclopropyl, cyclobutyl, cyclopentyl, cyclohexyl, and the like. The cycloalkyl can be substituted or unsubstituted, as described herein. For example, a substituted cycloalkyl includes a halo- or haloalkyl-substituted cyclopropyl, such as 2-fluorocyclopropyl, 2,2-difluorocyclopropyl, 1-(trifluoromethyl) cyclopropyl, and 2-(trifluoromethyl)cyclopropyl.

In any of the embodiments above, the term "hydrocarbyl" means an aliphatic group having the specified number of carbon atoms and the appropriate valence in view of the number of substitutions shown in the structure. Hydrocarbyl groups contain at least carbon and hydrogen, and can contain single, double, and triple carbon-carbon bonds. In certain embodiments hydrocarbyl groups optionally contain 1 or more (e.g., 1-8) heteroatoms selected from N, O, S, Si, P, or a combination thereof. Hydrocarbyl groups can be unsubstituted or substituted with one or more substituent groups up to the valence allowed by the hydrocarbyl group. For example the hydrocarbyl group may be substituted with hydroxyl, cyano, amino, halogen, oxo, cycloalkyl, 5- to 7-membered heterocycloalkyl containing 1 to 3 heteroatoms selected from N, O, and S, 5- or 6-membered heteroaryl selected with 1 to 5 heteroatoms selected from N, O, and S, and phenyl.

In any of the embodiments above, the term "hydroxy" refers to the group —OH.

In any of the embodiments above, the terms "alkoxy" and "cycloalkyloxy" embrace linear or branched alkyl and cycloalkyl groups, respectively, that are attached to a divalent oxygen. The alkyl and cycloalkyl groups are the same as described herein. The term "aryloxy" refers to substituents that have an aryl group attached to divalent oxygen. The aryl group is the same as described herein.

In any of the embodiments above, the term "halo" refers to a halogen selected from fluorine, chlorine, bromine, and iodine.

In any of the embodiments above, the term "aryl" refers to a mono, bi, or tricyclic carbocyclic ring system having one, two, or three aromatic rings, for example, phenyl, naphthyl, anthracenyl, or biphenyl. The term "aryl" refers to an unsubstituted or substituted aromatic carbocyclic moiety, as commonly understood in the art, and includes monocyclic and polycyclic aromatics such as, for example, phenyl, biphenyl, naphthyl, anthracenyl, pyrenyl, and the like. An aryl moiety generally contains from, for example, 6 to 30 carbon atoms, from 6 to 18 carbon atoms, from 6 to 14 carbon atoms, or from 6 to 10 carbon atoms. It is understood that the term aryl includes carbocyclic moieties that are planar and comprise 4n+2 π electrons, according to Hückel's Rule, wherein n=1, 2, or 3. This definition also applies wherever "aryl" occurs as part of a group, such as, e.g., in haloaryl (e.g., monohaloaryl, dihaloaryl, and trihaloaryl), arylalkyl, etc. The aryl can be substituted or unsubstituted, as described herein.

In any of the embodiments above, the term "heteroaryl" refers to aromatic 5 or 6 membered monocyclic groups, 9 or 10 membered bicyclic groups, and 11 to 14 membered tricyclic groups which have at least one heteroatom (O, S, or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized, and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. Illustrative examples of heteroaryl groups are pyridinyl, pyridazinyl, pyrimidyl, pyrazinyl, benzimidazolyl, triazinyl, imidazolyl, (1,2,3)- and (1,2,4)-triazolyl, pyrazinyl, tetrazolyl, furyl, pyrrolyl, thienyl, isothiazolyl, thiazolyl, isoxazolyl, and oxadiazolyl. The heteroaryl can be substituted or unsubstituted, as described herein.

The term "Het" means a "heterocycloalkyl," which is a stable, monocyclic or bicyclic system containing at least two double bonds, 3 to 7 ring members of carbon atoms and one, two, or three heteroatoms selected from nitrogen, sulfur, and/or oxygen. In an aspect, "Het" is a 5, 6, or 7-membered monocyclic ring and contains one, two, or three heteroatoms selected from nitrogen, oxygen, and sulfur. In some instances, "Het" is a heteroaryl, as described herein.

The term "heterocycloalkyl" means a stable, saturated, or partially unsaturated monocyclic, bicyclic, and spiro ring system containing 3 to 7 ring members of carbon atoms and other atoms selected from nitrogen, sulfur, and/or oxygen. In an aspect, a heterocycloalkyl is a 5, 6, or 7-membered monocyclic ring and contains one, two, or three heteroatoms selected from nitrogen, oxygen, and sulfur. The heterocycloalkyl may be attached to the parent structure through a carbon atom or through any heteroatom of the heterocycloalkyl that results in a stable structure. Examples of such heterocycloalkyl rings are isoxazolyl, thiazolinyl, imidazolidinyl, piperazinyl, homopiperazinyl, pyrrolyl, pyrrolinyl, pyrazolyl, pyranyl, piperidyl, oxazolyl, and morpholinyl. The heterocycloalkyl can be substituted or unsubstituted, as described herein.

In any of the embodiments above, the alkyl, alkoxy, and alkylamino groups can be linear or branched.

In other aspects, any substituent that is not hydrogen (e.g., $C_1$-$C_8$ alkyl, $C_2$-$C_8$ alkenyl, $C_2$-$C_8$ alkynyl, $C_3$-$C_6$ cycloalkyl, $C_3$-$C_6$ cycloalkylalkyl, aryl, arylalkyl, heteroaryl, heteroarylalkyl, heterocycloalkyl, or heterocycloalkylalkyl) can be an optionally substituted moiety. The substituted moiety typically comprises at least one substituent (e.g., 1, 2, 3, 4, 5, 6, etc.) in any suitable position (e.g., 1-, 2-, 3-, 4-, 5-, or 6-position, etc.). When an aryl group is substituted with a substituent, e.g., halo, amino, alkyl, OH, alkoxy, and others, the aromatic ring hydrogen is replaced with the substituent and this can take place in any of the available hydrogens, e.g., 2, 3, 4, 5, and/or 6-position wherein the 1-position is the point of attachment of the aryl group in the compound of the present invention. Suitable substituents include, e.g., halo, alkyl, alkenyl, alkynyl, hydroxy, nitro, cyano, amino, alkylamino, alkoxy, aryloxy, aralkoxy, carboxyl, carboxyalkyl, carboxyalkyloxy, amido, alkylamido, haloalkylamido, aryl, heteroaryl, and heterocycloalkyl, each of which is described herein. In some instances, the substituent is at least one alkyl, halo, and/or haloalkyl (e.g., 1 or 2).

In any of the embodiments above, whenever a range of the number of atoms in a structure is indicated (e.g., a $C_{1-12}$, $C_{1-8}$, $C_{1-6}$, or $C_{1-4}$ alkyl, cycloalkyl, etc.), it is specifically contemplated that any sub-range or individual number of carbon atoms falling within the indicated range also can be used. Thus, for instance, the recitation of a range of 1-8 carbon atoms (e.g., $C_1$-$C_8$), 1-6 carbon atoms (e.g., $C_1$-$C_6$), 1-4 carbon atoms (e.g., $C_1$-$C_4$), 1-3 carbon atoms (e.g., $C_1$-$C_3$), or 2-8 carbon atoms (e.g., $C_2$-$C_8$) as used with respect to any chemical group (e.g., alkyl, cycloalkyl, etc.) referenced herein encompasses and specifically describes 1, 2, 3, 4, 5, 6, 7, and/or 8 carbon atoms, as appropriate, as well as any sub-range thereof (e.g., 1-2 carbon atoms, 1-3 carbon atoms, 1-4 carbon atoms, 1-5 carbon atoms, 1-6 carbon atoms, 1-7 carbon atoms, 1-8 carbon atoms, 2-3 carbon atoms, 2-4 carbon atoms, 2-5 carbon atoms, 2-6 carbon atoms, 2-7 carbon atoms, 2-8 carbon atoms, 3-4 carbon atoms, 3-5 carbon atoms, 3-6 carbon atoms, 3-7 carbon atoms, 3-8 carbon atoms, 4-5 carbon atoms, 4-6 carbon atoms, 4-7 carbon atoms, 4-8 carbon atoms, etc., as appropriate).

The subscripts "m" and "n" represent the number of substituents, e.g., $R^2$ or $R^3$, in which each substituent, e.g., $R^2$ or $R^3$, can be the same or different. The subscripts m and n can be the same or different and each is either 0 or an integer from 1-5 (i.e., 1, 2, 3, 4, or 5). When m or n is 0, then the corresponding substituent, i.e., $R^2$ or $R^3$, is not present in the compound of formula (I). The subscripts "o" and "q" represent the number of methylene repeat units. The subscripts o and q are either 0 or an integer from 1-5 (i.e., 1, 2, 3, 4, or 5). When o or q is 0, then the respective moiety does not contain any methylene repeat units.

In any of the embodiments described herein, a compound of the present invention can also be provided as a prodrug, which is a drug derivative or drug precursor compound that typically is inactive or less than fully active until it is converted in the body through a normal metabolic process such as, for example, hydrolysis of an ester or amide form of the drug, to the active drug. A prodrug may be selected and used instead of the parent drug because, for example, in its prodrug form it is less toxic, and/or may have better absorption, distribution, metabolism and excretion (ADME) characteristics, and the like, than the parent drug. A prodrug might also be used to improve how selectively the drug interacts with cells or processes that are not its intended target. This approach may be employed particularly, for example, to prevent or decrease adverse effects, especially in cancer treatments, which may be especially prone to having severe unintended and undesirable side effects.

The term "prodrug" denotes a derivative of a compound, which derivative, when administered to warm-blooded animals, e.g., humans, is converted into the compound (drug). For example, the enzymatic and/or chemical hydrolytic cleavage of a derivative compound of the present invention occurs in such a manner that the proven drug form is released, and the moiety or moieties split off remain nontoxic or are metabolized so that nontoxic metabolites are produced. For example, a carboxylic acid group can be esterified, e.g., with a methyl group or ethyl group to yield an ester. When an ester is administered to a subject, the ester is cleaved, enzymatically or non-enzymatically, reductively, oxidatively, or hydrolytically, to reveal the anionic group. An anionic group can be esterified with moieties (e.g., acyloxymethyl esters) which are cleaved to reveal an intermediate compound which subsequently decomposes to yield the active compound.

The prodrug can be prepared in situ during the isolation and purification of the compound of formula (I), including a compound of formula (Ia), (Ib), (Ic), or (Id), or by separately reacting the purified compound with a suitable derivatizing agent. For example, hydroxy groups can be converted into esters via treatment with a carboxylic acid in the presence of a catalyst. Examples of cleavable alcohol prodrug moieties include substituted or unsubstituted, branched or unbranched alkyl ester moieties, e.g., ethyl esters, alkenyl esters, di-alkylamino alkyl esters, e.g., dimethylaminoethyl ester, acylamino alkyl esters, acyloxy alkyl esters (e.g., pivaloyloxymethyl ester), aryl esters, e.g., phenyl ester, aryl-alkyl esters, e.g., benzyl ester, optionally substituted, e.g., with methyl, halo, or methoxy substituents aryl and aryl-alkyl esters, amides, alkyl amides, di-alkyl amides, and hydroxy amides.

Knowing the disclosures herein, it will be appreciated also that a compound of the present invention can be in the form of a prodrug, and that such prodrugs can be prepared using reagents and synthetic transformations that are well-known to those having ordinary skill in the art. The effectiveness of a particular prodrug can be determined using one or more analytical methods (e.g. pharmacokinetics, bioassays, in vivo efficacy studies, and the like) that are well-known to those of ordinary skill in the art.

More specifically, a prodrug of a compound of formula (I), including a compound of formula (Ia), (Ib), (Ic), or (Id), may be prepared using routine chemical procedures. For example, a hydroxyl substituent on a compound of formula (I) can be substituted with —CO-alkyl, —$CO_2$alkyl, —CONH-alkyl, —CO-alkenyl, —$CO_2$-alkenyl, —CONH— alkenyl, —CO-aryl, —$CO_2$-aryl, —CONH-aryl, —CO-heterocycle, —$CO_2$-heterocycle, —CONH-heterocycle, or —$PO_3H_2$. Specific modifying groups of hydroxyl include, for example, acetyl, propionyl, isobutyryl, pivaloyl, palmitoyl, benzoyl, 4-methylbenzoyl, dimethylcarbamoyl, dimethylaminomethylcarbonyl, sulfo, alanyl, and fumaryl group.

An amino group can be substituted with —CO-alkyl, —$CO_2$-alkyl, —CO— alkenyl, —$CO_2$-alkenyl, —$CO_2$-aryl, —CO-aryl, —CO-heterocycle, —$CO_2$-heterocycle, or —$PO_3H_2$. The alkyl, alkenyl, aryl, and heterocycle moieties are optionally substituted by halogen, alkyl, hydroxyl, alkoxy, carboxy, amino, an amino acid residue, —$PO_3H_2$, —$SO_3H$, —$OPO_3H_2$, and —$OSO_3H$. Specific modifying groups of amino include, for example, tert-butyl, docosanoyl, pivaloylmethyloxy, alanyl, hexylcarbamoyl, pentylcarbamoyl, 3-methylthio-1-(acetylamino)propylcarbonyl, 1-sulfo-1-(3-ethoxy-4-hydroxyphenyl)methyl, (5-methyl-2-oxo-1,3-dioxol-4-yl)methyl, (5-methyl-2-oxo-1,3-dioxol-4-yl)methoxycarbonyl, tetrahydrofuranyl, and pyrrolidylmethyl.

Suitable modifying groups of carboxyl include, for example, methyl, ethyl, propyl, isopropyl, butyl, isobutyl, tert-butyl, pivaloyloxymethyl, carboxymethyl, dimethylaminomethyl, 1-(acetyloxy)ethyl, 1-(ethoxycarbonyloxy)ethyl, 1-(isopropyloxycarbonyloxy)ethyl, 1-(cyclohexyloxycarbonyloxy)ethyl, carboxylmethyl, (5-methyl-2-oxo-1, 3-dioxol-4-yl)methyl, benzyl, phenyl, o-tolyl, morpholinoethyl, N,N-diethylcarbamoylmethyl, and phthalidyl.

In any of the embodiments above, the phrase "salt" or "pharmaceutically acceptable salt" is intended to include nontoxic salts synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. For example, an inorganic acid (e.g., hydrochloric acid, sulfuric acid, phosphoric acid, or hydrobromic acid), an organic acid (e.g., oxalic acid, malonic acid, citric acid, fumaric acid, lactic acid, malic acid, succinic acid, tartaric acid, acetic acid, trifluoroacetic acid, gluconic acid, ascorbic acid, methylsulfonic acid, or benzylsulfonic acid), an inorganic base (e.g., sodium hydroxide, potassium hydroxide, calcium hydroxide, magnesium hydroxide, or ammonium hydroxide), an organic base (e.g., methylamine, diethylamine, triethylamine, triethanolamine, ethylenediamine, tris(hydroxymethyl)methylamine, guanidine, choline, or cinchonine), or an amino acid (e.g., lysine, arginine, or alanine) can be used. Generally, non-aqueous media such as ether, ethyl acetate, ethanol, isopropanol, or acetonitrile are typical. Lists of suitable salts are found in *Remington's Pharmaceutical Sciences,* 18th ed., Mack Publishing Company, Easton, Pa., 1990, p. 1445, and *Journal of Pharmaceutical Science,* 66, 2-19 (1977). For example, they can be a salt of an alkali metal (e.g., sodium or potassium), alkaline earth metal (e.g., calcium), or ammonium of salt.

The methods described herein comprise administering a compound of formula (I) or a prodrug or a pharmaceutically acceptable salt thereof in the form of a pharmaceutical composition. In particular, a pharmaceutical composition will comprise at least one compound of formula (I) or a prodrug or a pharmaceutically acceptable salt thereof and a pharmaceutically acceptable carrier. The pharmaceutically acceptable excipients described herein, for example, vehicles, adjuvants, carriers or diluents, are well-known to those who are skilled in the art and are readily available to the public. Typically, the pharmaceutically acceptable carrier is one that is chemically inert to the active compounds and one that has no detrimental side effects or toxicity under the conditions of use.

The pharmaceutical compositions can be administered as oral, sublingual, transdermal, subcutaneous, topical, absorption through epithelial or mucocutaneous linings, intravenous, intranasal, intraarterial, intramuscular, intratumoral, peritumoral, interperitoneal, intrathecal, rectal, vaginal, or aerosol formulations. In some aspects, the pharmaceutical composition is administered orally or intravenously.

In accordance with any of the embodiments, the compound of formula (I) or a prodrug or a pharmaceutically acceptable salt thereof can be administered orally to a subject in need thereof. Formulations suitable for oral administration can consist of (a) liquid solutions, such as an effective amount of the compound dissolved in diluents, such as water, saline, or orange juice and include an additive, such as cyclodextrin (e.g., α-, β-, or γ-cyclodextrin, hydroxypropyl cyclodextrin) or polyethylene glycol (e.g., PEG400); (b) capsules, sachets, tablets, lozenges, and troches, each containing a predetermined amount of the active ingredient, as solids or granules; (c) powders; (d) suspensions in an appropriate liquid; and (e) suitable emulsions and gels. Liquid formulations may include diluents, such as water and alcohols, for example, ethanol, benzyl alcohol, and the polyethylene alcohols, either with or without the addition of a pharmaceutically acceptable surfactant, suspending agent, or emulsifying agent. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound of formula (I) or a salt thereof can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters. Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylene-polypropylene copolymers, (d) amphoteric detergents such as, for example, alkyl-beta-aminopropionates, and 2-alkyl-imidazoline quaternary ammonium salts, and (3) mixtures thereof.

The parenteral formulations will typically contain from about 0.5 to about 25% by weight of the inhibitors in solution. Suitable preservatives and buffers can be used in such formulations. In order to minimize or eliminate irritation at the site of injection, such compositions may contain one or more nonionic surfactants having a hydrophile-lipophile balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use.

Extemporaneous injection solutions and suspensions can be prepared from sterile powders, granules, and tablets of the kind previously described.

The inhibitors may be made into injectable formulations. The requirements for effective pharmaceutical carriers for injectable compositions are well known to those of ordinary skill in the art. See *Pharmaceutics and Pharmacy Practice*, J. B. Lippincott Co., Philadelphia, Pa., Banker and Chalmers, eds., pages 238-250 (1982), and *ASHP Handbook on Injectable Drugs*, Toissel, 4th ed., pages 622-630 (1986).

Topically applied compositions are generally in the form of liquids (e.g., mouthwash), creams, pastes, lotions and gels. Topical administration includes application to the oral mucosa, which includes the oral cavity, oral epithelium, palate, gingival, and the nasal mucosa. In some embodiments, the composition contains at least one active component and a suitable vehicle or carrier. It may also contain other components, such as an anti-irritant. The carrier can be a liquid, solid or semi-solid. In embodiments, the composition is an aqueous solution, such as a mouthwash. Alternatively, the composition can be a dispersion, emulsion, gel, lotion or cream vehicle for the various components. In one embodiment, the primary vehicle is water or a biocompatible solvent that is substantially neutral or that has been rendered substantially neutral. The liquid vehicle can include other materials, such as buffers, alcohols, glycerin, and mineral oils with various emulsifiers or dispersing agents as known in the art to obtain the desired pH, consistency and viscosity. It is possible that the compositions can be produced as solids, such as powders or granules. The solids can be applied directly or dissolved in water or a biocompatible solvent prior to use to form a solution that is substantially neutral or that has been rendered substantially neutral and that can then be applied to the target site. In embodiments of the invention, the vehicle for topical application to the skin can include water, buffered solutions, various alcohols, glycols such as glycerin, lipid materials such as fatty acids, mineral oils, phosphoglycerides, collagen, gelatin and silicone based materials.

The compound of formula (I) or a prodrug or a pharmaceutically acceptable salt thereof, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer.

The dose administered to the mammal, particularly human and other mammals, in accordance with the present invention should be sufficient to affect the desired response. One skilled in the art will recognize that dosage will depend upon a variety of factors, including the age, condition or disease state, predisposition to disease, genetic defect or defects, and body weight of the mammal. The size of the dose will also be determined by the route, timing and frequency of administration as well as the existence, nature, and extent of any adverse side-effects that might accompany the administration of a particular inhibitor and the desired effect. It will be appreciated by one of skill in the art that various conditions or disease states may require prolonged treatment involving multiple administrations.

The inventive methods comprise administering an effective amount of a compound of formula (I) or a prodrug or a pharmaceutically acceptable salt thereof. An "effective amount" means an amount sufficient to show a meaningful benefit in an individual, e.g., promoting at least one aspect of tumor cell cytotoxicity (e.g., inhibition of growth, inhibiting survival of a cancer cell, reducing proliferation, reducing size and/or mass of a tumor (e.g., solid tumor)), or treatment, healing, prevention, delay of onset, halting, or amelioration of other relevant medical condition(s) associated with a particular cancer. The meaningful benefit observed in the patient can be to any suitable degree (10, 20, 30, 40, 50, 60, 70, 80, 90% or more). In some aspects, one or more symptoms of the cancer are prevented, reduced, halted, or eliminated subsequent to administration of a compound of formula (I), including a compound of formula (Ia), (Ib), (Ic), or (Id), or a prodrug or a pharmaceutically acceptable salt thereof, thereby effectively treating the cancer to at least some degree.

Effective amounts may vary depending upon the biological effect desired in the individual, condition to be treated, and/or the specific characteristics of the compound of formula (I)), including a compound of formula (Ia), (Ib), (Ic), or (Id), or a prodrug or a pharmaceutically acceptable salt thereof, and the individual. In this respect, any suitable dose of the compound of formula (I) or a prodrug or a pharmaceutically acceptable salt thereof can be administered to the patient (e.g., human), according to the type of cancer to be treated. Various general considerations taken into account in determining the "effective amount" are known to those of skill in the art and are described, e.g., in Gilman et al., eds., Goodman And Gilman's: *The Pharmacological Bases of Therapeutics*, 8th ed., Pergamon Press, 1990; and Remington's Pharmaceutical Sciences, 17th Ed., Mack Publishing Co., Easton, Pa., 1990, each of which is herein incorporated by reference. The dose of the compound of formula (I), including a compound of formula (Ia), (Ib), (Ic), or (Id), or a prodrug or a pharmaceutically acceptable salt thereof desirably comprises about 0.1 mg per kilogram (kg) of the body weight of the mammal (mg/kg) to about 400 mg/kg (e.g., about 0.75 mg/kg, about 5 mg/kg, about 30 mg/kg, about 75 mg/kg, about 100 mg/kg, about 200 mg/kg, or about 300 mg/kg). In another embodiment, the dose of the compound of formula (I), including a compound of formula (Ia), (Ib), (Ic), or (Id), comprises about 0.5 mg/kg to about 300 mg/kg (e.g., about 0.75 mg/kg, about 5 mg/kg, about 50 mg/kg, about 100 mg/kg, or about 200 mg/kg), about 10 mg/kg to about 200 mg/kg (e.g., about 25 mg/kg, about 75 mg/kg, or about 150 mg/kg), or about 50 mg/kg to about 100 mg/kg (e.g., about 60 mg/kg, about 70 mg/kg, or about 90 mg/kg).

In an aspect, a compound formula (I) inhibits LDHA and/or LDHB. In an embodiment, a compound of formula (I) is selective for LDHA and/or LDHB relative to other dehydrogenases (e.g., GAPDH and PHGDH). For example, the compound can be at least 2 times (e.g., at least 5 times, at least 10 times, at least 20 times, at least 50 times, or at least 100 times) more selective for LDHA and/or LDHB compared to one or more other dehydrogenases.

While elevated levels of LDHA are a marker for many types of cancer, the majority of which are glycolytic and/or hypoxic, LDHB can be overexpressed in some cancers (e.g., lung adenocarcinoma, prostate cancer). See, e.g., McCleland et al., *Clin Cancer Res*, 2013; 19(4): 773-784 and Leiblich et al., *Oncogene*, 2006; 25(20): 2953-2960. Thus, in some aspects of the invention, it is envisioned to provide a compound that can selectively inhibit LDHB or inhibit both LDHA and LDHA. In an embodiment, a compound of formula (I) can effectively inhibit LDHB. In such embodiments, the compound may or may not have selectivity for LDHA, such that the inhibition is more selective for LDHA compared to LDHB or the inhibition of LDHA is about equal to the inhibition of LDHB or the inhibition is more selective for LDHB relative to LDHA.

Inhibition of LDHA and/or LDHB has been described in the art as a viable treatment of cancer. See, e.g., Billiard et al. (*Cancer and Metabolism*, 2013, 1(19): 1-17). Thus, certain invention compounds of formula (I), which includes compounds of formulas (Ia), (Ib), (Ic), and (Id), or a prodrug or pharmaceutically acceptable salt thereof, can be administered to a patient in need thereof to treat cancer. While not wishing to be bound by any particular theory, it is believed that inhibition of LDH stimulates mitochondrial respiration and reduces cellular proliferative and tumorigenic potential. Anti-cancer activity can be measured by any suitable method, including the assays described herein. In general, activity will be measured as a function of lactate output, % ECAR (extracellular acidification rate), which quantifies glycolysis, and/or % OCR (oxygen consumption rate), which is a measure of mitochondrial respiration.

The type of cancer is not particularly limited, but in certain aspects, the cancer is characterized as hypoxic and/or highly glycolytic relative to normal tissue of the same type. "Hypoxic" cells as used herein relates to one or more cells that are exposed, transiently or permanently, to an oxygen partial pressure (pO2) that is lower than the typical pO2 in cells in tissue that is considered as normal or healthy. Hypoxic cells can include, for example, cells with reduced or no access to vasculature, such as in a solid tumor.

Examples of cancer treatable with the inventive method include cancers of the head and neck, eye, skin, mouth, throat, esophagus, chest, bone, lung, colon, sigmoid, rectum, stomach, prostate, breast, ovaries, kidney, liver, pancreas, brain, intestine, heart, or adrenals. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-borne tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocyctic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., eds., pp. 491 762 (15th ed. 2001). In some aspects, the cancer is a solid tumor. In accordance with an embodiment, the cancer is selected from leukemia, melanoma, liver cancer, pancreatic cancer, lung cancer, colon cancer, brain cancer, ovarian cancer, breast cancer, prostate cancer, and renal cancer. In another embodiment, the cancer is liver cancer, pancreatic cancer, non-small cell lung cancer, breast cancer, or renal cancer.

The invention provides a method of treating a patient with cancer cells resistant to an anti-cancer agent, comprising administering to the patient an effective amount of the compound of formula (I), including a compound of formula (Ia), (Ib), (Ic), or (Id), or a prodrug or a pharmaceutically acceptable salt thereof, and the anti-cancer agent, whereby the compound, prodrug, or pharmaceutically acceptable salt thereof re-sensitizes the cancer cells to the anti-cancer agent. The cancer cell is the same as described herein. In accordance with an embodiment, the cancer cells are selected from leukemia, melanoma, liver cancer, pancreatic cancer, lung cancer, colon cancer, brain cancer, ovarian cancer, breast cancer, prostate cancer, and renal cancer. In another embodiment, the cancer cells are liver cancer, pancreatic cancer, non-small cell lung cancer, breast cancer, or renal cancer.

In certain embodiments of this method, the compound of formula (I), including a compound of formula (Ia), (Ib), (Ic), or (Id), or a prodrug or a pharmaceutically acceptable salt thereof can be co-administered with an anti-cancer agent (e.g., a chemotherapeutic agent) and/or radiation therapy. In an aspect, the method comprises administering an amount of a compound, prodrug, or salt that is effective to sensitize the cancer cells to one or more therapeutic regimens (e.g., chemotherapy or radiation therapy). The terms "co-administered" or "co-administration" refer to simultaneous or sequential administration. A compound may be administered before, concurrently with, or after administration of another compound.

One or more than one, e.g., two, three, or more anti-cancer agents can be administered. In this regard, the present invention is directed a pharmaceutical composition comprising a pharmaceutically acceptable carrier and a combination of the compound of formula (I), including a compound of formula (Ia), (Ib), (Ic), or (Id), or a prodrug or a pharmaceutically acceptable salt thereof and at least one anti-cancer agent (e.g., chemotherapeutic agent).

Examples of anti-cancer agents include platinum compounds (e.g., cisplatin, carboplatin, oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, bendamustine), antitumor antibiotics (e.g., daunorubicin, doxorubicin, idarubicin, epirubicin, mitoxantrone, bleomycin, mytomycin C, plicamycin, dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), *vinca* alkaloids (e.g., vicristine, vindesine, vinorelbine, and vinblastine), tyrosine kinase inhibitors (e.g., imatinib, dasatinib, nilotinib, sorafenib, sunitinib), monoclonal antibodies (e.g., rituximab, cetuximab, panetumumab, tositumomab, trastuzumab, alemtuzumab, gemtuzumab ozogamicin, bevacizumab), nitrosoureas (e.g., carmustine, fotemustine, and lomustine), enzymes (e.g., L-Asparaginase), biological agents (e.g., interferons and interleukins), hexamethylmelamine, mitotane, angiogenesis inhibitors (e.g., thalidomide, lenalidomide), steroids (e.g., prednisone, dexamethasone, and prednisolone), hormonal agents (e.g., tamoxifen, raloxifene, leuprolide, bicaluatmide, granisetron, flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, oxaprozin), selective cyclooxygenase-2 (COX-2) inhibitors, or any combination thereof.

For purposes of the present invention, the term "patient" typically is directed to a mammal. For example, the subject can be any patient with a disease that requires chemotherapy and/or radiation therapy. Mammals include, but are not limited to, the order Rodentia, such as mice, and the order Logomorpha, such as rabbits. In some aspects, the mammals are from the order Carnivora, including Felines (cats) and Canines (dogs), Artiodactyla, including Bovines (cows) and Swines (pigs) or of the order Perssodactyla, including Equines (horses). In some aspects, the mammals are of the order Primates, Ceboids, or Simioids (monkeys) or of the order Anthropoids (humans and apes). In embodiments of the invention, the patient is a human.

The invention is further directed to a method of inhibiting lactate dehydrogenase A (LDHA) and/or lactate dehydrogenase b (LDHB) activity in a cell comprising administering a compound of formula (I), including a compound of formula (Ia), (Ib), (Ic), or (Id), or a prodrug or a pharmaceutically acceptable salt thereof to a cell, whereby activity of LDHA and/or LDHB is inhibited. LDHA and LDHB activity can be measured by any method known in the art for measuring enzyme inhibitions, including by the assays described herein. Typically, inhibition of LDHA and LDHB activity will be demonstrated by a decrease in lactate accumulation and/or an increase in pyruvate relative to a control sample.

The following examples are provided for further illustration, and should not be construed as limiting in any way.

EXAMPLES

Example 1

This example describes a human LDHA primary biochemical assay employed in the characterization of a compound of formula (I) in an embodiment of the invention.

Test compounds were placed in a Greiner Bio-One (Monroe, N.C.) 1536-well black solid bottom assay plate. 200 millimolar (mM) Tris HCl, pH 7.4, 100 micromolar (μM) EDTA and 0.01% TWEEN-20™, final concentration, was used as the assay buffer. The LDHA reagent was 2 nanomolar (nM) Human LDHA (Meridian Life Science, Inc., Memphis, Tenn.), final concentration, in assay buffer. The substrate reagent was 0.06 mM NADH and 0.2 mM sodium pyruvate, final concentration, in assay buffer. The resazurin/diaphorase coupling reagent was 0.037 mM resazurin and 0.133 milligrams per milliliter (mg/mL) diaphorase, final concentration, in assay buffer. The sequence of steps, amount and types of reagents, and time required for each step are set forth in Table 1. The inhibition of LDHA activity was measured by fluorescence emission.

TABLE 1

| Sequence | Parameter | Value | Notes |
| --- | --- | --- | --- |
| 1 | Reagent | 3 μL | LDHA reagent |
| 2 | Compound | 23 nL | Compound of formula (I) |
| 3 | Time | 15 min | RT incubation |
| 4 | Reagent | 1 μL | Substrate reagent |
| 5 | Time | 7 min | RT incubation |

TABLE 1-continued

| Sequence | Parameter | Value | Notes |
| --- | --- | --- | --- |
| 6 | Reagent | 1 μL | Resazurin/diaphorase coupling reagent |
| 7 | Detector | Fluorescence (ex 525 nm/ em 598 nm) | VIEWLUX ™ in end-point mode: 2 sec exp., 5000 excitation energy |

Example 2

This example describes a human LDHB counterscreen biochemical assay employed in the characterization of a compound of formula (I) in an embodiment of the invention.

Test compounds were placed in a Greiner Bio-One (Monroe, N.C.) 1536-well black solid bottom assay plate. 200 mM Tris HCl, pH 7.4, 100 μM EDTA and 0.01% TWEEN-20™, final concentration, was used as the assay buffer. The LDHB reagent was 2 nM Human LDHB (Meridian Life Science, Inc., Memphis, Tenn.), final concentration, in assay buffer. The substrate reagent was 0.13 mM NADH and 0.16 mM sodium pyruvate, final concentration, in assay buffer. The resazurin/diaphorase coupling reagent was 0.037 mM resazurin and 0.133 mg/mL diaphorase, final concentration, in assay buffer. The sequence of steps, amount and types of reagents, and time required for each step are set forth in Table 2. The inhibition of LDHB activity was measured by fluorescence emission.

TABLE 2

| Sequence | Parameter | Value | Notes |
| --- | --- | --- | --- |
| 1 | Reagent | 3 μL | LDHB reagent |
| 2 | Compound | 23 nL | Compound of formula (I) |
| 3 | Time | 15 min | RT incubation |
| 4 | Reagent | 1 μL | Substrate reagent |
| 5 | Time | 7 min | RT incubation |
| 6 | Reagent | 1 μL | Resazurin/diaphorase coupling reagent |
| 7 | Detector | Fluorescence (ex 525 nm/ em 598 nm) | VIEWLUX ™ in end-point mode: 2 sec exp., 5000 excitation energy |

Example 3

This example describes a human PHGDH counterscreen biochemical assay employed in the characterization of a compound of formula (I) in an embodiment of the invention.

Test compounds were placed in a Greiner Bio-One (Monroe, N.C.) 1536-well black solid bottom assay plate. 50 mM TEA, pH 8.0, 10 mM $MgCl_2$, 0.05% BSA, and 0.01% TWEEN-20™, final concentration, was used as the assay buffer. The substrate reagent was 10 μM EDTA, 0.625 mM glutamate, 500 nM human PSAT1, 500 nM human PSPH, 0.05 mM 3-phosphoglycerate, 0.1 mM resazurin, and 0.1 mg/mL diaphorase, final concentration, in assay buffer. The PHGDH reagent was 0.15 mM $NAD^+$ and 10 nM human PHGDH, final concentration, in assay buffer. The sequence of steps, amount and types of reagents, and time required for each step are set forth in Table 3. The inhibition of PHGDH activity was measured by fluorescence emission.

TABLE 3

| Sequence | Parameter | Value | Notes |
| --- | --- | --- | --- |
| 1 | Reagent | 3 μL | Substrate reagent |
| 2 | Compound | 23 nL | Compound of formula (I) |
| 3 | Reagent | 1 μL | PHGDH reagent |
| 4 | Detector | Fluorescence (ex 525 nm/ em 598 nm) | VIEWLUX ™ in end-point mode: 2 sec exp., 5000 excitation energy, use Δ between 0 and 30 min |

Example 4

This example describes a human GAPDH counterscreen biochemical assay employed in the characterization of a compound of formula (I) in an embodiment of the invention.

Test compounds were placed in a Greiner Bio-One (Monroe, N.C.) 1536-well black solid bottom assay plate. 105 mM Tris HCl, pH 7.4, 10 μM EDTA, 1.27 mM $KH_2PO_4$, 0.875 mM $MgCl_2$, 0.0875% BSA, 0.01 mM DTT, and 0.01% TWEEN-20™, final concentration, was used as the assay buffer. The substrate reagent was 0.48 mM glyceraldehyde 3-phosphate, 0.06 mM resazurin, and 0.21 mg/mL diaphorase, final concentration, in assay buffer. The GAPDH reagent was 0.007 mM $NAD^+$ and 2.5 nM human GAPDH, final concentration, in assay buffer. The sequence of steps, amount and types of reagents, and time required for each step are set forth in Table 4. The inhibition of GAPDH activity was measured by fluorescence emission.

TABLE 4

| Sequence | Parameter | Value | Notes |
| --- | --- | --- | --- |
| 1 | Reagent | 3 μL | Substrate reagent |
| 2 | Compound | 23 nL | Compound of formula (I) |
| 3 | Reagent | 1 μL | GAPDH reagent |
| 4 | Detector | Fluorescence (ex 525 nm/ em 598 nm) | VIEWLUX ™ in kinetic mode: 1 sec exp., 5000 excitation energy, use Δ between 0 and 20 min |

Example 5

This example describes cell-based metabolite assay by mass spectrometry (MS) employed in the characterization of a compound of formula (I) in an embodiment of the invention.

The sequence of steps, amount and types of reagents, and time required for each step are set forth in Table 5.

TABLE 5

| Sequence | Parameter | Value | Notes |
| --- | --- | --- | --- |
| 1 | Reagent | Snu398 cells | 100k/well in 100 μL RPMI 10% FBS-phenol red |
| 2 | Time | 24 h | 37° C., 5% $CO_2$ incubation |
| 3 | Reagent | Wash | Aspirate media and replace with fresh |
| 4 | Reagent | Compound | Dose LDHA inhibitors/controls in media |
| 5 | Time | 48 h | 37° C., 5% $CO_2$ incubation |
| 6 | Reagent | Media | Aspirate 75 μL of media and collect in separate plate. Snap freeze and store at −80° C. Pyruvate/lactate/NADH ion counts collected by Quintara Discovery, Inc. using MS-MS. |

Example 6

This example describes a cell-based metabolite assay by colorimetric/fluorometric detection employed in the characterization of a compound of formula (I) in an embodiment of the invention.

Cell-based HT Lactate assay is a miniaturized Biovision Lactate Colorimetric/Fluorometric Assay Kit (Cat #K607-100). The assay is roughly a 3.5 hour assay run in a 1536 plate format. Cell number optimization should be run for each cell line to achieve an optimal number in which lactate production equals roughly 90% of the standard curve range. Cell number per well optimization has been performed with the following cell lines: MiaPaCa2—500 cells/well, SNU398—500 cells/well, and P493—500 cells/well. The sequence of steps, amount and types of reagents, and time required for each step are set forth in Table 6.

TABLE 6

| Sequence | Parameter | Value | Notes |
| --- | --- | --- | --- |
| 1 | Reagent | MiaPaCa2 cells | 500/well in 4 μL in DMEM 4.5 g/L Glucose, -Glutamate, -FBS, -Phenol Red |
| 2 | Reagent | Compound | Dose LDHA inhibitors with pin tool |
| 3 | Time | 2.5 hr | 37° C., 5% CO2 incubation |
| 4 | Reagent | Compound | 2 μL/well |
| 5 | Time | 48 h | RT |
| 6 | Read | Media | Absorbance (570 nm) and Fluorescence (Ex/Em = 535/590 nm) |

Example 7

This example describes the preparation of tert-butyl 2-bromothiazole-4-carboxylate 1 in an embodiment of the invention.

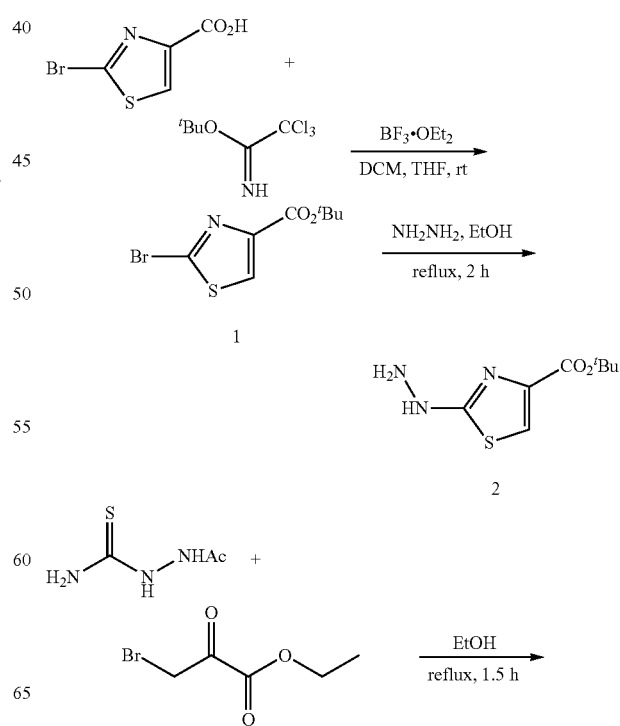

SCHEME 1

-continued

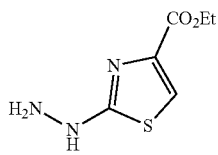

3

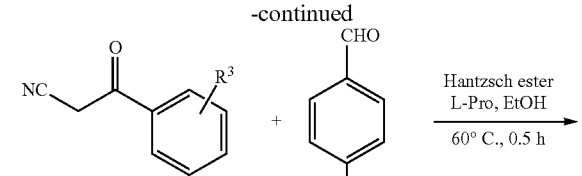

Tert-butyl 2,2,2-trichloroacetimidate (17.20 ml, 96 mmol, 2 eq) was added to a stirred suspension of 2-bromothiazole-4-carboxylic acid (10 g, 48.1 mmol, 1 eq) in dichloromethane (DCM) (100 mL) and tetrahydrofuran (THF) (50 mL), followed by dropwise addition of $BF_3 \cdot OEt_2$ (0.938 ml, 7.40 mmol, 10 mol %). The mixture was stirred at room temperature for 16 h, concentrated, quenched slowly with a saturated bicarbonate solution, and extracted with ethyl acetate. The organic layer was washed with saturated bicarbonate and brine, then dried, and the crude product was purified in a Biotage (Charlotte, N.C.) flash system eluting with 5-30% ethyl acetate in hexanes over 12 column volumes. The product fraction was concentrated to provide tert-butyl 2-bromothiazole-4-carboxylate 1 as a white solid (10.4 g, 82%).

Example 8

This example describes the preparation of tert-butyl 2-hydrazinylthiazole-4-carboxylate 2 in an embodiment of the invention. See Scheme 1.

A solution of tert-butyl 2-bromothiazole-4-carboxylate 1 (10.96 g, 41.5 mmol, 1 eq) from Example 1 and hydrazine hydrate (13 ml, 415 mmol, 10 eq) in EtOH (80 mL) was refluxed for 2 hr. After completion of the reaction, the solvent was removed and ice water was added. The precipitate formed was collected by filtration, washed with cold water, and dried under air. The crude product (tert-butyl 2-hydrazinylthiazole-4-carboxylate 2) was pure enough to be used for the following reaction.

Example 9

This example describes the preparation of ethyl 2-hydrazinylthiazole-4-carboxylate 3 in an embodiment of the invention. See Scheme 1.

Ethyl bromopyruvate (15.71 ml, 113 mmol) was added to a suspension of 2-acetylhydrazinecarbothioamide (15 g, 113 mmol) in ethanol (200 mL) and stirred at room temperature for 30 minutes until the solution became clear, then refluxed for 1.5 h. The solution was then concentrated and agitated with 20 mL of MeOH and 300 mL of ether. The yellow precipitate was collected by filtration, washed with ether, and dried to obtain a yellow solid (ethyl 2-hydrazinylthiazole-4-carboxylate 3) as HBr salt.

Example 10

This example describes a general procedure for the synthesis of substituted benzoyl acetonitriles 4 in an embodiment of the invention.

SCHEME 2

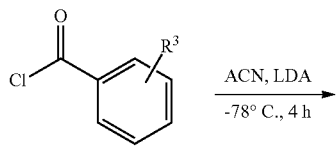

-continued

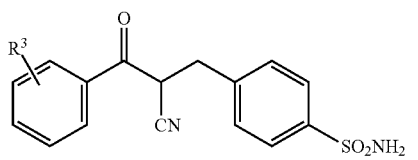

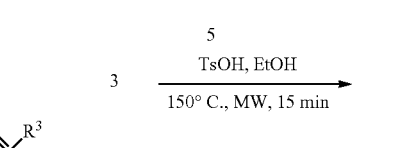

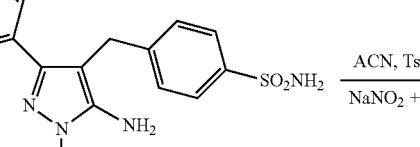

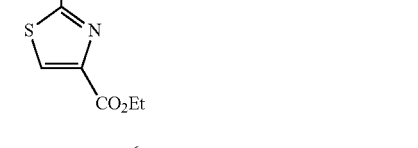

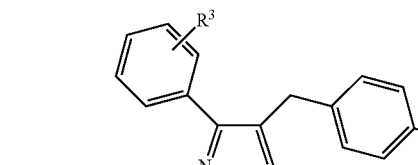

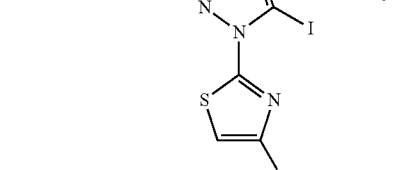

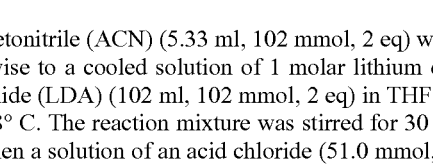

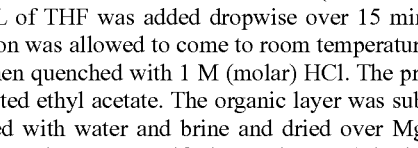

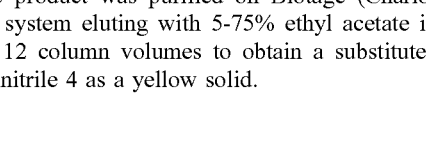

Acetonitrile (ACN) (5.33 ml, 102 mmol, 2 eq) was added dropwise to a cooled solution of 1 molar lithium diisopropylamide (LDA) (102 ml, 102 mmol, 2 eq) in THF (40 mL) at −78° C. The reaction mixture was stirred for 30 minutes, and then a solution of an acid chloride (51.0 mmol, 1 eq) in 20 mL of THF was added dropwise over 15 minutes. The reaction was allowed to come to room temperature over 4 h and then quenched with 1 M (molar) HCl. The product was extracted ethyl acetate. The organic layer was subsequently washed with water and brine and dried over $MgSO_4$. The crude product was purified on Biotage (Charlotte, N.C.) flash system eluting with 5-75% ethyl acetate in hexanes over 12 column volumes to obtain a substituted benzoyl acetonitrile 4 as a yellow solid.

Example 11

This example describes a general procedure for the synthesis of 4-(2-cyano-3-oxo-3-arylpropyl)benzenesulfonamide 5 in an embodiment of the invention. See Scheme 2.

2,6-Dimethyl-1,4-dihydro-pyridine-3,5-dicarboxylic acid diethyl ester (Hantzsch ester) (12.21 g, 48.2 mmol, 1.4 eq) and L-proline (0.793 g, 6.89 mmol, 20 mol %) were added to a solution of 3-oxo-3-phenyl-propanenitrile 4 (34.4 mmol, 1 eq) and 4-formylbenzenesulfonamide (7.02 g, 37.9 mmol, 1.1 eq) in ethanol (150 mL). The mixture was stirred at 60° C. for 30 minutes. The mixture was then cooled, mixed with silica gel, concentrated, and purified on a Biotage (Charlotte, N.C.) flash system with 20-100% ethyl acetate in hexanes over 6 column volumes then with 100% ethyl acetate over 8 column volumes to obtain 4-(2-cyano-3-oxo-3-arylpropyl) benzenesulfonamide 5 as a white solid.

Example 12

This example describes a general procedure for the synthesis of 2-(5-amino-3-aryl-4-(4-sulfamoylbenzyl)-1H-pyrazol-1-yl)thiazole-4-carboxylate 6 in an embodiment of the invention. See Scheme 2.

A mixture of ethyl 2-hydrazinylthiazole-4-carboxylate hydrogen bromide salt (3, 1.5 g, 5.59 mmol, 1 eq), 4-(2-cyano-3-oxo-3-arylpropyl)benzenesulfonamide (5.59 mmol, 1 eq) and tosic acid (2.128 g, 11.19 mmol, 2 eq) in ethanol (15 mL) was heated in a microwave for 15 minutes. The precipitate formed was collected by filtration and washed with cold ethanol to obtain pure product (ethyl 2-(5-amino-3-aryl-4-(4-sulfamoylbenzyl)-1H-pyrazol-1-yl)thiazole-4-carboxylate 6) as a yellow solid.

Example 13

This example describes a general procedure for the synthesis of ethyl 2-(5-iodo-3-aryl-4-(4-sulfamoylbenzyl)-1H-pyrazol-1-yl)thiazole-4-carboxylate 7 in an embodiment of the invention. See Scheme 2.

Tosic acid (5.37 g, 28.2 mmol, 3.5 eq) was added to a suspension of ethyl 2-(5-amino-3-aryl-4-(4-sulfamoylbenzyl)-1H-pyrazol-1-yl)thiazole-4-carboxylate 6 (8.07 mmol, 1 eq) in ACN (100 mL) and stirred for 10 minutes. During this period, the solution became clear, then a premixed solution of $NaNO_2$ (1.113 g, 16.13 mmol, 2 eq) and KI (4.02 g, 24.20 mmol, 3 eq) in 10 mL water was added dropwise over a period of 10-15 minutes at room temperature. The reaction mixture was allowed to stir at room temperature overnight. After completion of the reaction, the excess solvent was removed under reduce pressure, and the crude product was extracted with ethyl acetate. The organic layer was subsequently washed with saturated sodium thiosulfate solution, water, and brine. The crude product was purified on a Biotage (Charlotte, N.C.) flash system using a high performance column eluting with either 1-15% acetone in dichloromethane or 1-100% ethyl acetate in hexanes over 20 column volumes to obtain pure products.

Example 14

This example describes a general procedure for the trifluoromethylation of ethyl 2-(5-iodo-3-aryl-4-(4-sulfamoylbenzyl)-1H-pyrazol-1-yl)thiazole-4-carboxylates 7 in an embodiment of the invention.

SCHEME 3

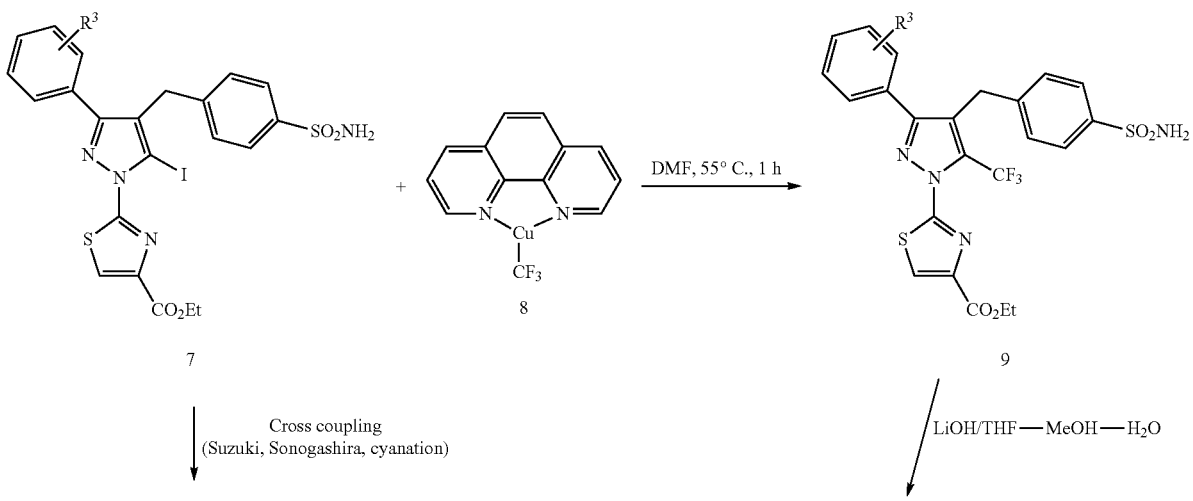

-continued

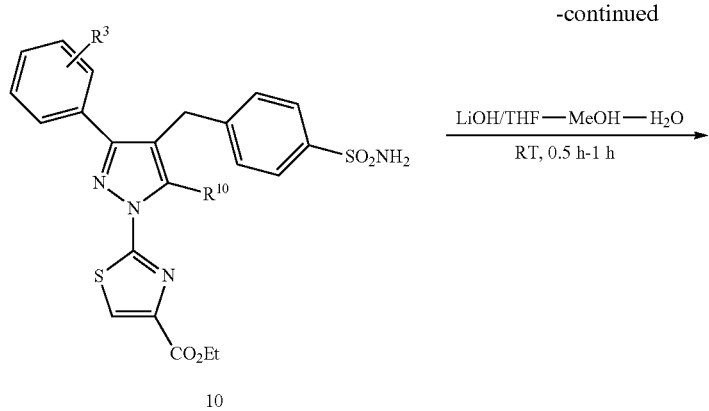

10

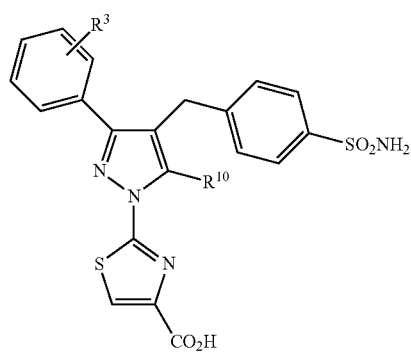

11

A mixture of ethyl 2-(5-iodo-3-aryl-4-(4-sulfamoylbenzyl)-1H-pyrazol-1-yl)thiazole-4-carboxylate 7 (0.4 g, 0.673 mmol) 7 and 1,10-phenanthroline)(trifluoromethyl)copper (I) 8 (0.316 g, 1.009 mmol, 1.5 eq) was degassed with argon, then DMF (2 mL) was added and stirred at 55° C. for 1 h. The reaction mixture was diluted with ethyl acetate and washed with 1 molar HCl, water, and brine. The organic layer was dried with $MgSO_4$, concentrated, and purified on a Biotage (Charlotte, N.C.) flash system eluting with 20-100% ethyl acetate in hexanes over 12 column volumes to obtain an ethyl 2-(5-trifluoromethyl-3-aryl-4-(4-sulfamoylbenzyl)-1H-pyrazol-1-yl)thiazole-4-carboxylate 9 as a white solid.

Example 15

This example describes a general procedure for the Suzuki coupling of ethyl 2-(5-iodo-3-aryl-4-(4-sulfamoylbenzyl)-1H-pyrazol-1-yl)thiazole-4-carboxylates 7 in an embodiment of the invention. See Scheme 3.

In a sealed microwave vial, 2 molar $Na_2CO_3$ (0.17 mL, 0.336 mmol, 2 eq) was added to a mixture of ethyl 2-(5-iodo-3-aryl-4-(4-sulfamoylbenzyl)-1H-pyrazol-1-yl)thiazole-4-carboxylate 7 (0.168 mmol, 1 eq), SILIACAT™ DPP-Pd (0.1 g), boronic acid (0.336 mmol, 2 eq) in dimethyl ether (DME) (2 mL), then heated in a microwave for 30 minutes at 130° C. The reaction mixture was concentrated by blowing forced air. The residue was taken up in DMF (2 mL) and stirred with a silica-bound DMT, followed by filtering through a thiol resin cartridge to remove any leached palladium. Finally the compounds were purified on a preparative HPLC to obtain pure coupling products 10.

Example 16

This example describes a general procedure for the Sonogashira coupling of ethyl 2-(5-iodo-3-aryl-4-(4-sulfamoylbenzyl)-1H-pyrazol-1-yl)thiazole-4-carboxylates (7) in an embodiment of the invention. See Scheme 3.

A mixture of ethyl 2-(5-iodo-3-aryl-4-(4-sulfamoylbenzyl)-1H-pyrazol-1-yl)thiazole-4-carboxylate 7 (0.202 mmol, 1 eq), bis(triphenylphosphine)palladium(II) chloride (0.014 g, 0.020 mmol, 10 mol %), and CuI (3.84 mg, 0.020 mmol, 10 mol %) in THF (1 mL) was added triethylamine (TEA) (0.169 ml, 1.211 mmol, 6 eq) followed by the alkyne (0.404 mmol, 2 eq) under a nitrogen atmosphere. The vial was sealed and stirred at 80° C. for 4 h. After completion of the reaction, the product was extracted with ethyl acetate and the organic layer was washed with 1 molar HCl and brine. The crude product was purified on a Biotage (Charlotte, N.C.) flash system eluting with 20-100% ethyl acetate or in preparative HPLC to obtain pure coupling products 10.

Example 17

This example describes a general procedure for the cyanation of ethyl 2-(5-iodo-3-aryl-4-(4-sulfamoylbenzyl)-1H-pyrazol-1-yl)thiazole-4-carboxylates 7 in an embodiment of the invention. See Scheme 3.

A mixture of ethyl 2-(5-iodo-3-aryl-4-(4-sulfamoylbenzyl)-1H-pyrazol-1-yl)thiazole-4-carboxylate 7 (0.168 mmol, 1 eq) and CuCN (0.023 g, 0.252 mmol, 1.5 eq) in dimethylsulfoxide (DMSO) (0.5 ml) was heated in a microwave for 0.5 h at 160° C. The product was extracted with ethyl acetate. The organic layer was washed with a saturated bicarbonate solution, water, and brine. The crude product was purified on a Biotage (Charlotte, N.C.) flash system eluting with 30-100% ethyl acetate in hexanes over 15 column volumes to obtain pure products 10.

Example 18

This example describes a general procedure for the hydrolysis of the ethyl and methyl esters 10 in an embodiment of the invention. See Scheme 3.

A 1.5 molar solution of LiOH in water was added to a solution of ethyl 2-(3-aryl-4-(4-sulfamoylbenzyl)-1H-pyrazol-1-yl)thiazole-4-carboxylate 10 (0.252 mmol, 1 eq) in THF/MeOH (3 mL/1.5 mL) and stirred at room temperature for 0.5-1 h. After completion of the reaction, the solvent was evaporated under reduced pressure, and the residue was taken up in DMSO. Finally the compounds 11 were purified on preparative HPLC.

Example 19

This example describes a general procedure for the ethyl 2-(5-(cyanomethyl)-3-aryl-4-(4-sulfamoylbenzyl)-1H-pyrazol-1-yl)thiazole-4-carboxylate 12a in an embodiment of the invention (Scheme 4, Step a).

SCHEME 4

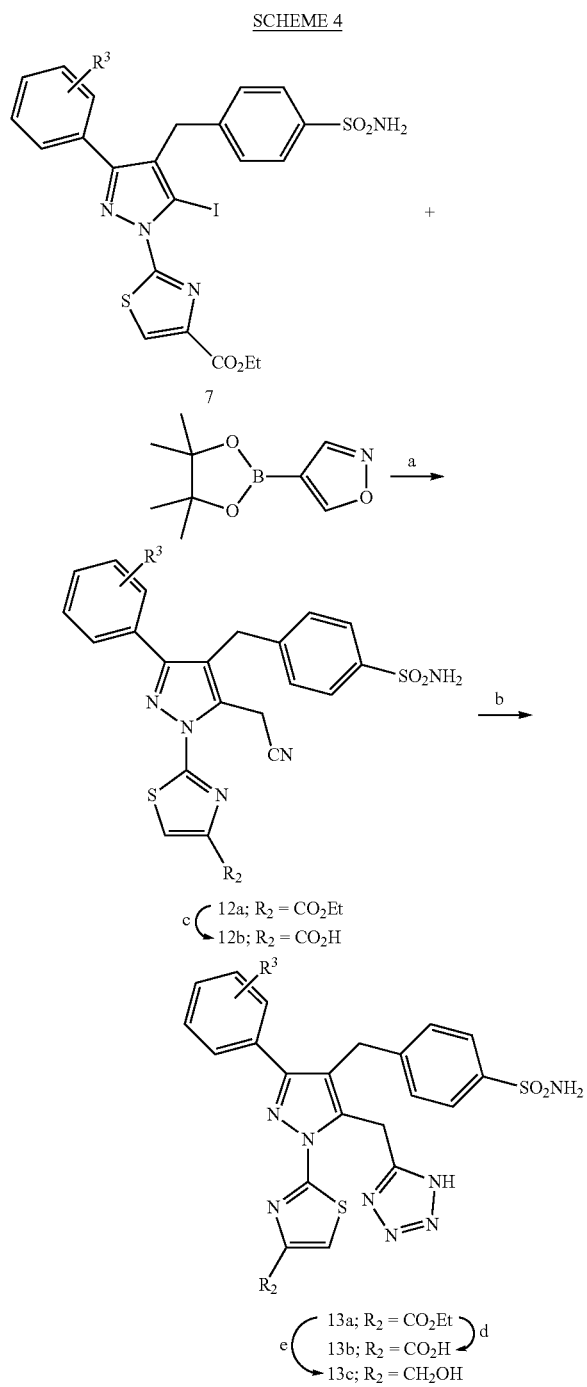

Reactants and Conditions:
a) PdCl$_2$(dppf), KF, DMSO, 130° C., 24 h
b) NaN$_3$, NH$_4$Cl, DMF, 125° C., MW, 2 h
c) Me$_3$SnOH, DCE, 80° C., 24 h
d) LiOH, THF, MeOH, H$_2$O, RT, 1 h
e) LiAlH$_4$, THF, RT, 2 h DMSO (2.5 mL) was added to a solution of KF (0.147 g, 2.52 mmol, 3 eq) in 0.9 mL water, followed by ethyl 2-(5-iodo-3-aryl-4-(4-sulfamoylbenzyl)-1H-pyrazol-1-yl)thiazole-4-carboxylate 7 (0.841 mmol, 1 eq), PdCl$_2$(dppf)-CH$_2$Cl$_2$ adduct (0.137 g, 0.168 mmol, 20 mol %), and 4-(4,4,5,5-tetramethyl-1,3,2-dioxaborolan-2-yl)isoxazole (0.246 g, 1.262 mmol, 1.5 eq). The mixture was bubbled with argon for 2 minutes. Next, the vial was sealed and stirred on a preheated heating block at 130° C. for 3 h, then another portion of 0.9 mL of water was added, and the mixture was stirred at 130° C. for another 21 h. After completion of the reaction, a silica-bound metal scavenger was added and stirred for 30 minutes. The reaction mixture was diluted with ethyl acetate and filtered through a silica plug. The filtrate was washed with water, saturated ammonium chloride, and brine. The crude product was purified on a Biotage (Charlotte, N.C.) flash system eluting with 20-100% ethyl acetate in hexanes to obtain pure product ethyl 2-(5-(cyanomethyl)-3-aryl-4-(4-sulfamoylbenzyl)-1H-pyrazol-1-yl)thiazole-4-carboxylate 12a as a white solid.

Example 20

This example describes a general procedure for the 2-(5-(cyanomethyl)-3-aryl-4-(4-sulfamoylbenzyl)-1H-pyrazol-1-yl)thiazole-4-carboxylic acid 12b in an embodiment of the invention. See Scheme 4, Step c.

A mixture of ethyl 2-(5-(cyanomethyl)-3-phenyl-4-(4-sulfamoylbenzyl)-1H-pyrazol-1-yl)thiazole-4-carboxylate 12a (0.049 mmol) and hydroxytrimethylstannane (0.018 g, 0.099 mmol, 2 eq) in dichloroethane (DCE) was stirred at 80° C. for 24 h. The solvent was removed by forced air. The residue was taken up DMSO and passed through a sulfonic acid cartridge to remove the trimethyl tin hydroxide. The crude product 2-(5-(cyanomethyl)-3-aryl-4-(4-sulfamoylbenzyl)-1H-pyrazol-1-yl)thiazole-4-carboxylic acid 12b was purified on HPLC.

Example 21

This example describes a general procedure for the synthesis of tetrazoles 13a in an embodiment of the invention. See Scheme 4, Step b.

A mixture of ethyl 2-(5-(cyanomethyl)-3-aryl-4-(4-sulfamoylbenzyl)-1H-pyrazol-1-yl)thiazole-4-carboxylate 12a (0.414 mmol, 1 eq), NH$_4$C$_1$ (0.066 g, 1.241 mmol, 3 eq), and NaN$_3$ (0.081 g, 1.241 mmol, 3 eq) in DMF (2 ml) was heated in a microwave for 2 h at 125° C. The product was purified on a reverse phase flash system to obtain pure products 13a.

Example 22

This example describes a general procedure for the synthesis of tetrazole derivatives 13c in an embodiment of the invention. See Scheme 4, Step e.

A solution of ethyl 2-(5-((1H-tetrazol-5-yl)methyl)-3-aryl-4-(4-sulfamoylbenzyl)-1H-pyrazol-1-yl)thiazole-4-carboxylate 13a (0.091 mmol, 1 eq) in THF (3 ml) was added LiAlH$_4$ (0.363 ml, 0.363 mmol, 4 eq) upon cooling. The reaction mixture was stirred at room temperature for 1 and then quenched with water. The residue was suspended in a DCM/MeOH mixture and filtered through a silica plug. The crude product 13c obtained after evaporating the solvent was purified on a preparative HPLC.

Example 23

This example describes the preparation of N,N-bis(3,4-dimethoxybenzyl)-4-nitrobenzenesulfonamide 14 in an embodiment of the invention. See Scheme 5, first step.

SCHEME 5

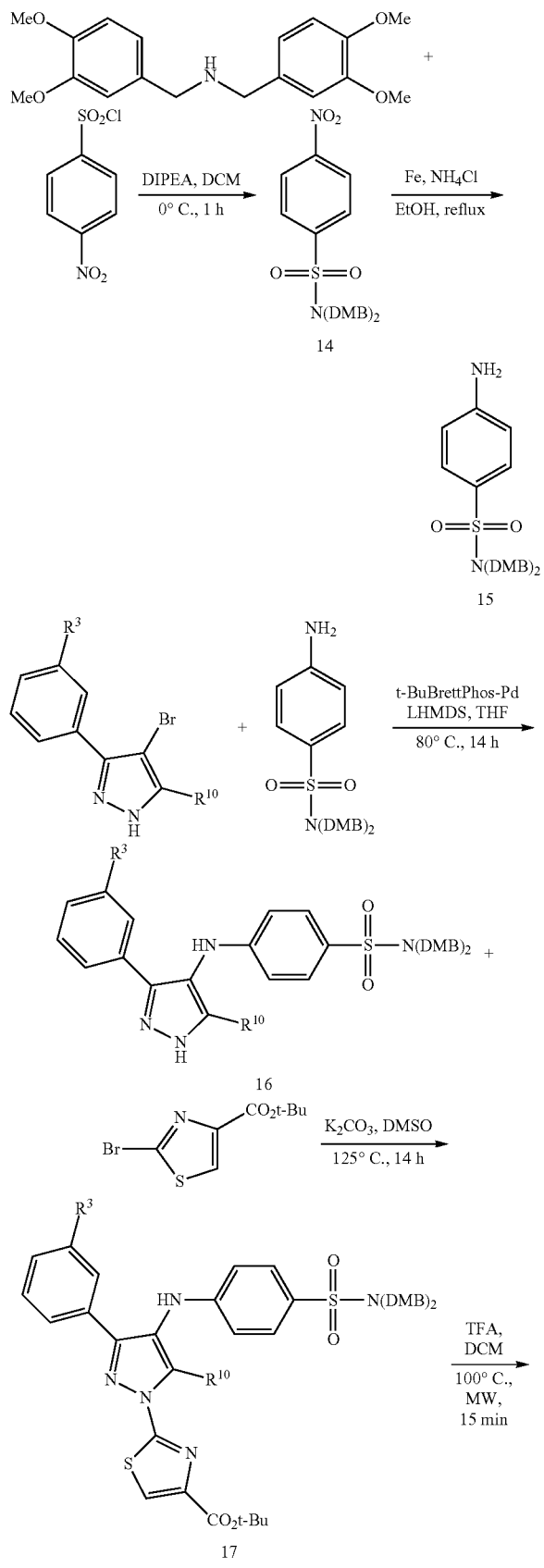

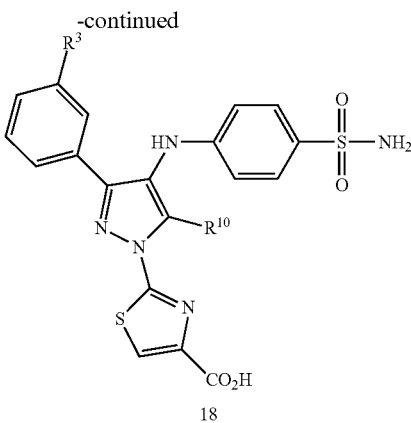

4-Nitrobenzene-1-sulfonyl chloride (1.746 g, 7.88 mmol, 1 eq) was added to a solution of bis(3,4-dimethoxybenzyl)amine (2.5 g, 7.88 mmol, 1 eq) and Hünig's base (2.75 ml, 15.75 mmol, 2 eq) in DCM (15 ml) upon cooling. The reaction mixture was stirred at room temperature for 1 h. The crude product obtained after evaporating the solvent was purified on a Biotage (Charlotte, N.C.) flash system eluting with 25-100% ethyl acetate in hexanes to obtain N,N-bis(3,4-dimethoxybenzyl)-4-nitrobenzenesulfonamide 14 as a yellow solid. Yield (2.85 g, 72%).

Example 24

This example describes the preparation of 4-amino-N,N-bis(3,4-dimethoxybenzyl)benzenesulfonamide 15 in an embodiment of the invention. See Scheme 5, second step.

A solution of ammonium chloride (0.8 g, 14.92 mmol) in 10 mL water and iron powder (1.389 g, 24.87 mmol) was added to a suspension of N,N-bis(3,4-dimethoxybenzyl)-4-nitrobenzenesulfonamide 14 (2.5 g, 4.97 mmol, 1 eq) in ethanol (50 mL). The reaction mixture was stirred overnight at 85° C. The reaction mixture was diluted with methanol and filtered through a pad of CELITE™. The filtrate was concentrated, neutralized with bicarbonate, and extracted with DCM. The DCM layer was washed with bicarbonate and brine. The crude product was purified on a Biotage (Charlotte, N.C.) flash system eluting with 1-15% MeOH (ammoniated) in DCM to obtain 4-amino-N,N-bis(3,4-dimethoxybenzyl)benzenesulfonamide 15 as a white solid. Yield (2.2 g, 94%).

Example 25

This example describes a general preparation of N,N-bis(3,4-dimethoxybenzyl)-4-((3-aryl-1H-pyrazol-4-yl)amino)-benzenesulfonamide 16 in an embodiment of the invention. See Scheme 5, third step.

A mixture of 4-bromo-3-aryl-1H-pyrazole (1.569 mmol, 1 eq), 4-amino-N,N-bis(3,4-dimethoxybenzyl)benzenesulfonamide 15 (1.038 g, 2.197 mmol, 1.4 eq), t-butyl BrettPhos (CAS #1160861-53-9) (Stem Chemicals, Newburyport, Mass., Catalog #15-1164) (0.038 g, 0.078 mmol, 5 mol %) and t-butyl BrettPhos Palladacycle (CAS #1148148-01-9) (Stem Chemicals, Newburyport, Mass., Catalog #46-0325) (0.067 g, 0.078 mmol, 5 mol %) in a microwave (MW) vial was purged with argon, and then THF (4 ml) was added, followed by lithium hexamethyldisilazide (LHMDS) (2.62 ml, 3.92 mmol, 2.5 eq). The mixture was stirred in a preheated block at 80° C. for 14 h. The reaction mixture was poured into acidified water (1 molar HCl) and extracted with ethyl acetate. The organic layer was washed with water and brine. The crude product N,N-bis(3,4-dimethoxybenzyl)-4-((3-aryl-1H-pyrazol-4-yl)amino)-benzenesulfonamide 16 was purified on a Biotage (Charlotte, N.C.) flash system eluting with 30-100% ethyl acetate in hexanes.

Example 26

This example describes a general preparation of tert-butyl 2-(4-((4-(N,N-bis(3,4-dimethoxybenzyl)sulfamoyl)phenyl)-amino)-3-aryl-1H-pyrazol-1-yl)thiazole-4-carboxylate 17 in an embodiment of the invention. See Scheme 5, fourth step.

A mixture of N,N-bis(3,4-dimethoxybenzyl)-4-((3-aryl-1H-pyrazol-4-yl)amino)benzenesulfon-amide 16 (0.732 mmol, 1 eq), $K_2CO_3$ (0.202 g, 1.464 mmol), and tert-butyl 2-bromothiazole-4-carboxylate (0.213 g, 0.805 mmol, 1.1 eq) in DMSO (1.5 mL) was stirred for 12 h at 125° C. The reaction mixture was diluted with ethyl acetate and filtered through a pad of CELITE™. The filtrate was washed with saturated ammonium chloride and brine. The crude product tert-butyl 2-(4-((4-(N,N-bis(3,4-dimethoxybenzyl)sulfamoyl)phenyl)-amino)-3-aryl-1H-pyrazol-1-yl)thiazole-4-carboxylate 17 was purified on a Biotage (Charlotte, N.C.) flash system eluting with 40-100% ethyl acetate in hexanes.

Example 27

This example describes a general procedure for the deprotection of (N,N-bis(3,4-dimethoxybenzyl) and t-butyl groups and synthesis of compounds 18 in an embodiment of the invention. See Scheme 5, fifth step.

Tert-butyl 2-(4-((4-(N,N-bis(3,4-dimethoxybenzyl)sulfamoyl)-phenyl)amino)-3-aryl-1H-pyrazol-1-yl)thiazole-4-carboxylate (0.251 mmol) 17 in a mixture of DCM (1.5 mL) and trifluoroacetic acid (TFA) (1.5 mL) was heated in microwave at 100° C. for 15 min at normal absorption. The solvent was removed by forced air, the crude product 18 was dissolved in DMSO, and then purified using preparative HPLC.

Example 28

This example describes the synthesis of 2-(3-phenyl-4-(4-sulfamoylbenzyl)-1H-pyrazol-1-yl)thiazole-4-carboxylic acid 19 in an embodiment of the invention.

SCHEME 6

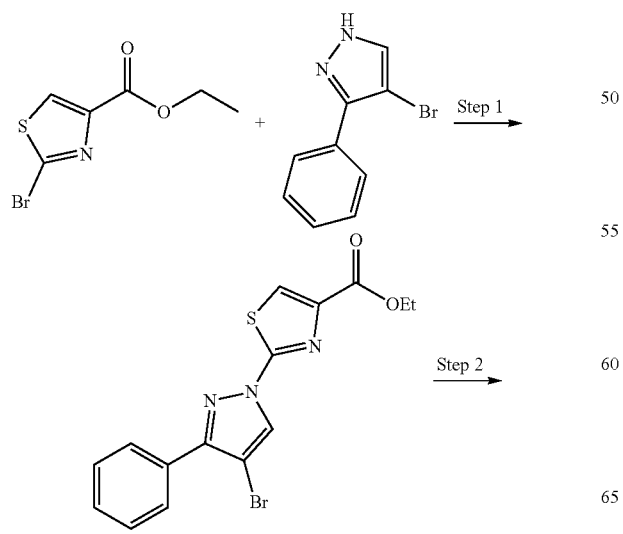

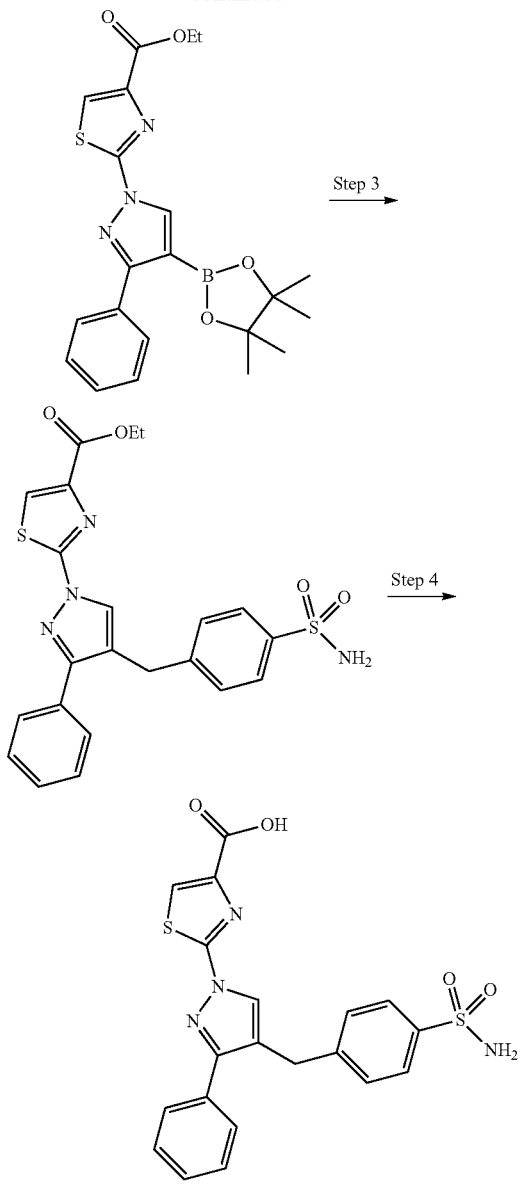

Step 1: Synthesis of ethyl 2-(4-bromo-3-phenyl-1H-pyrazol-1-yl)thiazole-4-carboxylate In a microwave tube was placed ethyl 2-bromothiazole-4-carboxylate (1058 mg, 4.48 mmol), 3-bromo-4-phenyl-1H-pyrrole (995 mg, 4.48 mmol), and $K_2CO_3$ (929 mg, 6.72 mmol). The tube was sealed and DMSO (4 ml) was added. The mixture was heated at 120° C. for 4 h. The mixture was poured into vigorously stirred $H_2O$ (100 mL), and the solid was filtered, triturated with $H_2O$, and dried. The solid was re-dissolved in EtOAc and filtered. Some undissolved material was the hydrolized acid. The filtrate was concentrated and triturated with ca. 3% EtOAc/hexane to give ethyl 2-(4-bromo-3-phenyl-1H-pyrazol-1-yl)thiazole-4-carboxylate (1329 mg, 3.51 mmol, 78% yield).

Step 2: Synthesis of ethyl 2-(3-phenyl-4-(4,4,5,5-tetramethyl-1,3,2-dioxaborolan-2-yl)-1H-pyrazol-1-yl)thiazole-4-carboxylate In a microwave tube was placed ethyl 2-(4-bromo-3-phenyl-1H-pyrazol-1-yl)thiazole-4-carboxylate (378 mg, 1 mmol), 4,4,4',4',5,5,5',5'-octamethyl-2,2'-bi(1,3,2-dioxaborolane) (330 mg, 1.300 mmol), PdCl$_2$(dppf) (73.2 mg, 0.100 mmol), and potassium acetate (294 mg, 3.00 mmol). The tube was sealed and air was removed and re-filled with N$_2$ (2-3 times). Then, 1,4-dioxane (4 ml) was added and stirred at 95° C. (pre-heated) for overnight. The mixture was diluted with EtOAc and filtered through CELITE™ and eluted with EtOAc. After removal of the solvent, the product was purified by silica gel chromatography using 10-25% EtOAc/hexane as the eluent to give product, which was triturated with a small amount of hexane and then dried to give ethyl 2-(3-phenyl-4-(4,4,5,5-tetramethyl-1,3,2-dioxaborolan-2-yl)-1H-pyrazol-1-yl)thiazole-4-carboxylate (540 mg, 0.762 mmol, 76% yield) as solid. The product contained about 40% of reduction (de-Br) product, which was used for the next step without further purification.

Step 3: Synthesis of ethyl 2-(3-phenyl-4-(4-sulfamoylbenzyl)-1H-pyrazol-1-yl)thiazole-4-carboxylate In a microwave tube was placed ethyl 2-(3-phenyl-4-(4,4,5,5-tetramethyl-1,3,2-dioxaborolan-2-yl)-1H-pyrazol-1-yl)thiazole-4-carboxylate (70.9 mg, 0.1 mmol), 4-(bromomethyl)benzenesulfonamide (25.01 mg, 0.100 mmol), and Pd(Ph$_3$P)$_4$ (11.56 mg, 10.00 μmol). The tube was sealed and air was removed and re-filled with N$_2$ (2-3 times). A mixture of toluene (0.75 ml, ratio: 2.500)/EtOH (0.3 ml, ratio: 1.000) was added, and then 2N Na$_2$CO$_{3(aq)}$ (0.3 mL, 0.6 mmol, 6 equiv) was added. The mixture was stirred at 80° C. (pre-heated) for 2 h. The organic layer was separated, and the aqueous layer was extracted with EtOAc (2 mL×3). The combined organic layer was dried (Na$_2$SO$_4$) and filtered. After removal of the solvent, the product was purified by silica gel chromatography using 30-60% EtOAc/hexane as the eluent to give ethyl 2-(3-phenyl-4-(4-sulfamoylbenzyl)-1H-pyrazol-1-yl)thiazole-4-carboxylate (29 mg, 0.062 mmol, 61.9% yield) as a white solid.

Step 4: Synthesis of 2-(3-phenyl-4-(4-sulfamoylbenzyl)-1H-pyrazol-1-yl)thiazole-4-carboxylic acid (19)

To a solution of ethyl 2-(3-phenyl-4-(4-sulfamoylbenzyl)-1H-pyrazol-1-yl)thiazole-4-carboxylate (26 mg, 0.055 mmol) in THF (1 ml) was added LiOH$_{(aq)}$ (1.5 N in H$_2$O, 0.4 mL, 0.6 mmol). The mixture was stirred at room temperature for 2 h. Then, 1N HCl$_{(aq)}$ (ca.0.6-0.65 mL) was added and until the pH of aqueous layer was around 4. Then, hexane (5 mL) was added and the resulting solid was filtered, triturated with H$_2$O (1 ml×2), hexane (2 mL×2), and dried to give 2-(3-phenyl-4-(4-sulfamoylbenzyl)-1H-pyrazol-1-yl)thiazole-4-carboxylic acid 19 (21 mg, 0.048 mmol, 86% yield).

The compound was pure enough and was submitted (19 mg) to system directly. $^1$H NMR (400 MHz, DMSO-d6) δ 13.18 (s, 1H), 8.21 (s, 2H), 7.80-7.71 (m, 2H), 7.72-7.63 (m, 2H), 7.52-7.37 (m, 5H), 7.28 (s, 2H), 4.15 (s. 2H); MS (M+H)$^+$=441.

Example 29

This example describes the synthesis of 2-(3-([1,1'-biphenyl]-3-yl)-4-(4-sulfamoylbenzyl)-1H-pyrazol-1-yl)thiazole-4-carboxylic acid 20 in an embodiment of the invention.

SCHEME 7

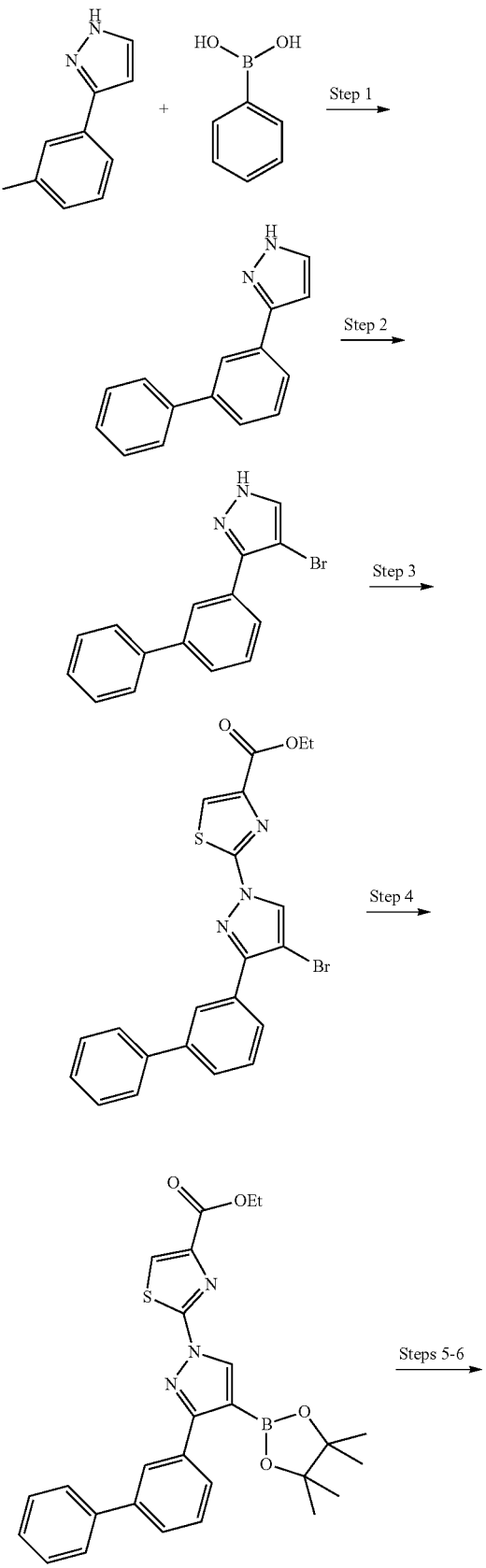

-continued

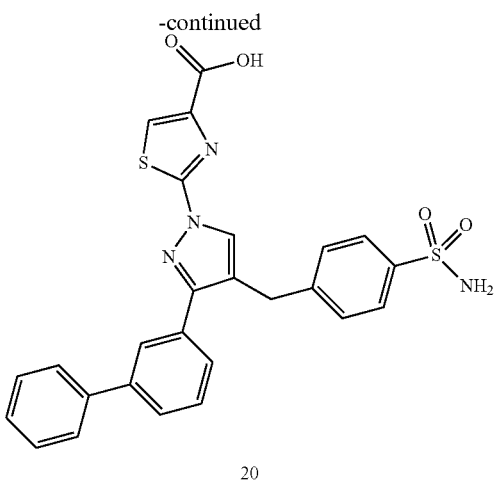

Step 1: Synthesis of 3-([1,1'-biphenyl]-3-yl)-1H-pyrazole

In a 2-neck flask was placed 3-(3-bromophenyl)-1H-pyrazole (1115 mg, 5 mmol), phenylboronic acid (914 mg, 7.50 mmol), PdCl$_2$(dppf) (366 mg, 0.500 mmol), and K$_2$CO$_3$ (2073 mg, 15.00 mmol). The air was removed and re-filled with N$_2$ (2-3 times). Then a mixture of 1,4-dioxane (12 ml, ratio: 2.000) and water (6 ml, ratio: 1.000) was added and stirred at 95° C. (pre-heated) for 5 h. The organic layer was separated, and the aqueous layer was extracted with EtOAc (5 mL×2). The combined organic layer was dried (Na$_2$SO$_4$) and filtered. After removal of the solvent, the product was purified by silica gel chromatography using 30-40-50% EtOAc/hexane as the eluent to give 3-([1,1'-biphenyl]-3-yl)-1H-pyrazole (1050 mg, 4.77 mmol, 95% yield).

Step 2: Synthesis of 3-([1,1'-biphenyl]-3-yl)-4-bromo-1H-pyrazole

To a solution of 3-([1,1'-biphenyl]-3-yl)-1H-pyrazole (1050 mg, 4.77 mmol) in DMF (7.5 ml) was added NBS (891 mg, 5.01 mmol). The mixture was stirred at room temperature for 1 h. The mixture was poured into EtOAc/H$_2$O/sat. Na$_2$CO$_{3(aq)}$ (50 mL/30 mL/20 mL). The organic layer was washed with H$_2$O (50 mL), dried (Na$_2$SO$_4$), and filtered. After removal of the solvent, the product was purified by silica gel chromatography using 20-30% EtOAc/hexane as the eluent to give 3-([1,1'-biphenyl]-3-yl)-4-bromo-1H-pyrazole (1200 mg, 4.01 mmol, 84% yield).

Step 3: Synthesis of ethyl 2-(3-([1,1'-biphenyl]-3-yl)-4-bromo-1H-pyrazol-1-yl)thiazole-4-carboxylate In a microwave tube was placed ethyl 2-bromothiazole-4-carboxylate (472 mg, 2 mmol), 3-([1,1'-biphenyl]-3-yl)-4-bromo-1H-pyrrole (596 mg, 2.000 mmol), and K$_2$CO$_3$ (415 mg, 3.00 mmol). The tube was sealed and DMSO (4 ml) was added. The mixture was heated at 130° C. for 4 h. The mixture was poured into H$_2$O (100 mL), and the solid was filtered, triturated with H$_2$O, and dried. The solid was dissolved in EtOAc and filtered. The undissolved material was the hydrolized acid (21, ca. 110 mg with a small amount of impurity). The filtrate was concentrated and triturated with ca. 5% EtOAc/hexane to give 420 mg of pure product. The solution was concentrated and combined with the extraction from the original aqueous layer and then purified by silica gel chromatography using 20-30% EtOAc/hexane as the eluent to give another 210 mg of product. Total 630 mg of ethyl 2-(3-([1,1'-biphenyl]-3-yl)-4-bromo-1H-pyrazol-1-yl)thiazole-4-carboxylate (630 mg, 1.387 mmol, 69.3% yield) was obtained.

Step 4: Synthesis of ethyl 2-(3-([1,1'-biphenyl]-3-yl)-4-(4,4,5,5-tetramethyl-1,3,2-dioxaborolan-2-yl)-1H-pyrazol-1-yl)thiazole-4-carboxylate In a microwave tube was placed ethyl 2-(3-([1,1'-biphenyl]-3-yl)-4-bromo-1H-pyrazol-1-yl)thiazole-4-carboxylate (454 mg, 1 mmol), 4,4,4',4',5,5,5',5'-octamethyl-2,2'-bi(1,3,2-dioxaborolane) (381 mg, 1.500 mmol), PdCl$_2$(dppf) (73.2 mg, 0.100 mmol), and potassium acetate (294 mg, 3.00 mmol). The tube was sealed and air was removed and re-filled with N$_2$ (2-3 times). Then, 1,4-dioxane (4 ml) was added and stirred at 95° C. (pre-heated) for overnight. The mixture was diluted with EtOAc and filtered through CELITE™ and eluted with EtOAc. After removal of the solvent, the product was purified by silica gel chromatography using 10-25% EtOAc/hexane as the eluent to give product, which was triturated with a small amount of hexane and then dried to give ethyl 2-(3-([1,1'-biphenyl]-3-yl)-4-(4,4,5,5-tetramethyl-1,3,2-dioxaborolan-2-yl)-1H-pyrazol-1-yl)thiazole-4-carboxylate (450 mg, 0.494 mmol, 49.4% yield) as solid. The product contained about 45% of reduction (de-Br) product.

Step 5: Synthesis of ethyl 2-(3-([1,1'-biphenyl]-3-yl)-4-(4-sulfamoylbenzyl)-1H-pyrazol-1-yl)thiazole-4-carboxylate In a microwave tube was placed ethyl 2-(3-([1,1'-biphenyl]-3-yl)-4-(4,4,5,5-tetramethyl-1,3,2-dioxaborolan-2-yl)-1H-pyrazol-1-yl)thiazole-4-carboxylate (91 mg, 0.1 mmol), 4-(bromomethyl)benzenesulfonamide (25.01 mg, 0.100 mmol), and Pd(Ph$_3$P)$_4$ (11.56 mg, 10.00 µmol). The tube was sealed and air was removed and re-filled with N$_2$ (2-3 times). A mixture of toluene (0.75 ml, ratio: 2.500)/EtOH (0.3 ml, ratio: 1.000) was added, and then 2N Na$_2$CO$_{3(aq)}$ (0.3 mL, 0.6 mmol, 6 equiv) was added. The mixture was stirred at 80° C. (pre-heated) for 2 h. The organic layer was separated, and the aqueous layer was extracted with EtOAc (2 mL×3). The combined organic layer was dried (Na$_2$SO$_4$) and filtered. After removal of the solvent, the product was purified by silica gel chromatography using 30-60% EtOAc/hexane as the eluent to give ethyl 2-(3-([1,1'-biphenyl]-3-yl)-4-(4-sulfamoylbenzyl)-1H-pyrazol-1-yl)thiazole-4-carboxylate 20 (35 mg, 0.064 mmol, 64.3% yield) as a white solid. Some of the reduction product (ca. 30 mg) from either the reaction and/or from a previous step was collected and subjected to hydrolysis to give 22 (see Example 31, Scheme 7A).

Step 6: Synthesis of 2-(3-([1,1'-biphenyl]-3-yl)-4-(4-sulfamoylbenzyl)-1H-pyrazol-1-yl)thiazole-4-carboxylic acid (20)

To a solution of ethyl 2-(3-([1,1'-biphenyl]-3-yl)-4-(4-sulfamoylbenzyl)-1H-pyrazol-1-yl)thiazole-4-carboxylate (35 mg, 0.064 mmol) in THF (1 ml) was added LiOH(aq) (1.5 N in H$_2$O, 0.4 mL, 0.6 mmol). The mixture was stirred at room temperature for 2 h. Then, 1N HCl$_{(aq)}$ (ca.0.6-0.65 mL) was added and the pH of aqueous layer was around 4. Then, hexane (5 mL) was added and the resulting solid was filtered, triturated with H$_2$O (1 mL×2) and then hexane (2 mL×2) and dried to give 2-(3-([1,1'-biphenyl]-3-yl)-4-(4-sulfamoylbenzyl)-1H-pyrazol-1-yl)thiazole-4-carboxylic acid 20 (28 mg, 0.054 mmol, 84% yield).

The compound was pure enough and was submitted (24 mg) to system directly. $^1$H NMR (400 MHz, DMSO-d$_6$) δ 13.20 (s, 1H), 8.29 (s, 1H), 8.24 (s, 1H), 7.81 (d, J=1.8 Hz, 1H), 7.80-7.74 (m, 2H), 7.74-7.67 (m, 2H), 7.57 (d, J=7.6 Hz, 3H), 7.50-7.42 (m, 4H), 7.37 (dd, J=8.4, 6.3 Hz, 1H), 7.30 (s, 2H), 4.21 (s, 2H); MS (M+H)$^+$=517.

Example 30

This example describes the synthesis of 2-(3-([1,1'-biphenyl]-3-yl)-4-bromo-1H-pyrazol-1-yl)thiazole-4-carboxylic acid, TFA 21 in an embodiment of the invention.

The side product of step 3 in Example 28 was re-purified by reverse phase chromatography to give 2-(3-([1,1'-biphenyl]-3-yl)-4-bromo-1H-pyrazol-1-yl)thiazole-4-carboxylic acid, TFA 21. $^1$H NMR (400 MHz, DMSO-d$_6$) δ 13.25 (s, 1H), 8.93 (s, 1H), 8.28 (s, 1H), 8.12 (d, J=1.8 Hz, 1H), 7.85 (dd, J=7.7, 1.5 Hz, 1H), 7.79 (dd, J=7.9, 1.5 Hz, 1H), 7.72 (dd, J=7.5, 1.7 Hz, 2H), 7.63 (t, J=7.8 Hz, 1H), 7.50 (t, J=7.6 Hz, 2H), 7.40 (t, J=7.4 Hz, 1H); MS (M+H)$^+$=427

Example 31

This example describes the synthesis of 2-(3-([1,1'-biphenyl]-3-yl)-1H-pyrazol-1-yl)thiazole-4-carboxylic acid, TFA 22 in an embodiment of the invention. See Scheme 7A.

To a solution of ethyl 2-(3-([1,1'-biphenyl]-3-yl)-1H-pyrazol-1-yl)thiazole-4-carboxylate (30 mg, 0.080 mmol) in THF (1 ml) was added LiOH$_{(aq)}$ (1.5 N in H$_2$O, 0.4 mL, 0.6 mmol). The mixture was stirred at room temperature for 2 h. Then, 1N HCl$_{(aq)}$ (ca.0.6-0.65 mL) was added and the pH of aqueous layer was around 4. Then, hexane (5 mL) was added, and the resulting solid was filtered, triturated with H$_2$O (1 mL×2) and then hexane (2 mL×2), and dried. The product still contained a small amount of impurity, which was dissolved in DMF, filtered through a filter, and submitted for purification to give 2-(3-([1,1'-biphenyl]-3-yl)-1H-pyrazol-1-yl)thiazole-4-carboxylic acid, TFA 22 (0.8 mg, 1.734 μmol, 2.170% yield). MS (M+H)$^+$=348.

Example 32

This example describes the synthesis of 2-(3-(3,4-difluorophenyl)-1H-pyrrolo[2,3-b]pyridin-1-yl)thiazole-4-carboxylic acid, TFA 23 in an embodiment of the invention.

SCHEME 7A

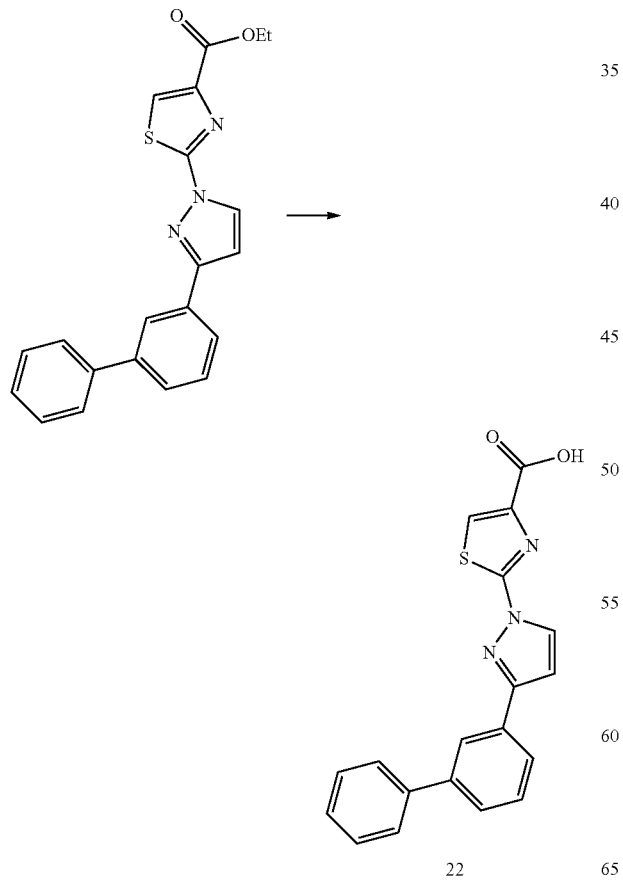

SCHEME 8

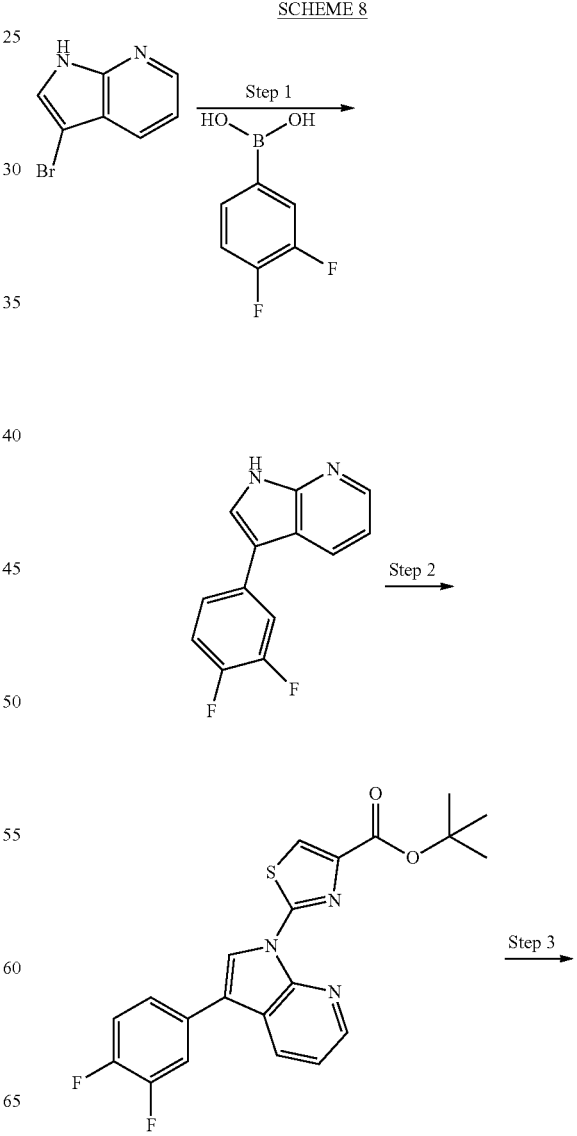

-continued

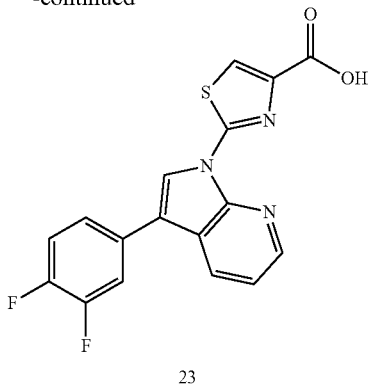

23

Step 1: Synthesis of 3-(3,4-difluorophenyl)-1H-pyrrolo[2,3-b]pyridine

In a 2-neck flask was placed 3-bromo-1H-pyrrolo[2,3-b]pyridine (788 mg, 4 mmol), (3,4-difluorophenyl)boronic acid (758 mg, 4.80 mmol), PdCl$_2$(dppf) (146 mg, 0.200 mmol), and K$_2$CO$_3$ (1658 mg, 12.00 mmol). The air was removed and re-filled with N$_2$ (2-3 times). Then a mixture of 1,4-dioxane (12 ml, ratio: 2.000) and water (6 ml, ratio: 1.000) was added and stirred at 95° C. (pre-heated) for 3 h. The organic layer was separated, and the aqueous layer was extracted with EtOAc (5 mL×2). The combined organic was dried (Na$_2$SO$_4$) and filtered. After removal of the solvent, the product was purified by silica gel chromatography using 30-40% EtOAc/hexane as the eluent to give 3-(3,4-difluorophenyl)-1H-pyrrolo[2,3-b]pyridine (260 mg, 1.129 mmol, 28.2% yield).

Step 2: Synthesis of tert-butyl 2-(3-(3,4-difluorophenyl-1H-pyrrolo[2,3-b]pyridin-1-yl)thiazole-4-carboxylate In a microwave tube was placed 3-(3,4-difluorophenyl)-1H-pyrrolo[2,3-b]pyridine (50.6 mg, 0.220 mmol), tert-butyl 2-bromothiazole-4-carboxylate (52.8 mg, 0.2 mmol), (1S,2S)—N$^1$,N$^2$-dimethylcyclohexane-1,2-diamine (5.69 mg, 0.040 mmol), CuI (3.81 mg, 0.020 mmol), and K$_3$PO$_4$ (127 mg, 0.600 mmol). The air was removed and re-filled with N$_2$ (3 times). Then toluene (2 ml) was added and the mixture was stirred at 110° C. for overnight. After cooling to room temperature, the mixture was diluted with EtOAc (3 mL) and filtered through celite and eluted with EtOAc. The filtrate was concentrated and the mixture was purified by silica gel chromatography using 10-30% EtOAc/hexane as the eluent to give tert-butyl 2-(3-(3,4-difluorophenyl)-1H-pyrrolo[2,3-b]pyridin-1-yl)thiazole-4-carboxylate (75 mg, 0.181 mmol, 91% yield). This material contained some Br-starting material and impurity was used for de-protection and purified in the next step.

Step 3: Synthesis of 2-(3-(3,4-difluorophenyl)-1H-pyrrolo[2,3-b]pyridin-1-yl)thiazole-4-carboxylic acid, TFA (23)

To a solution of tert-butyl 2-(3-(3,4-difluorophenyl)-1H-pyrrolo[2,3-b]pyridin-1-yl)thiazole-4-carboxylate (75 mg, 0.181 mmol) in 1,4-dioxane (1 ml) was added HCl (4M in dioxane, 1 mL, 4 mmol). The mixture was stirred at room temperature for 2 h. The mixture was concentrated and the crude material was dissolved in DMF, filtered through a filter, and submitted for purification to give 2-(3-(3,4-difluorophenyl)-1H-pyrrolo[2,3-b]pyridin-1-yl)thiazole-4-carboxylic acid, TFA 23 (1.6 mg, 3.39 µmol, 1.871% yield). MS (M+H)$^+$=358.

Example 33

This example describes the synthesis of 2-(5-hydroxy-3-phenyl-4-(4-sulfamoylphenoxy)-1H-pyrazol-1-yl)thiazole-4-carboxylic acid, TFA 24 in an embodiment of the invention.

SCHEME 9

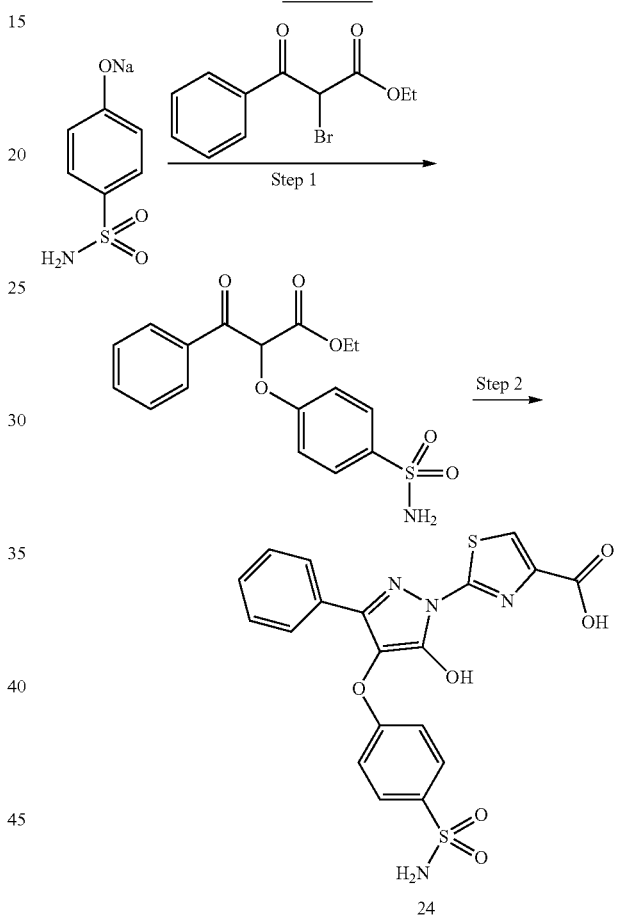

24

Step 1: Synthesis of ethyl 3-oxo-3-phenyl-2-(4-sulfamoylphenoxy)propanoate

To a mixture of sodium 4-sulfamoylphenolate (195 mg, 1 mmol) and ethyl 2-bromo-3-oxo-3-phenylpropanoate (298 mg, 1.100 mmol) was added EtOH (1 ml). The mixture was stirred at room temperature for 30 min. The mixture was concentrated and purified by silica gel chromatography using 30-50% EtOAc/hexane as the eluent to give ethyl 3-oxo-3-phenyl-2-(4-sulfamoylphenoxy)propanoate (66 mg, 0.182 mmol, 18.16% yield).

Step 2: Synthesis of give 2-(5-hydroxy-3-phenyl-4-(4-sulfamoylphenoxy)-1H-pyrazol-1-yl)thiazole-4-carboxylic acid, TFA (24)

In a microwave tube was placed ethyl 3-oxo-3-phenyl-2-(4-sulfamoylphenoxy)propanoate (66 mg, 0.182 mmol), ethyl 2-hydrazinylthiazole-4-carboxylate (34.0 mg, 0.182 mmol), and p-TsOH (34.5 mg, 0.182 mmol) and added EtOH (2 ml). The tube was sealed and heated at 150° C. for 20 min. The solvent was removed via air blow-down and then added THF (1 mL) and 1.5 N LiOH$_{(aq)}$ (1 mL, 1.5 mmol). The mixture was stirred at room temperature for 1 h. Then 1 N HCl$_{(aq)}$ (ca. 1.5-1.55 mL) was added (pH of aqueous layer is ca. 3), and the aqueous layer was extracted with EtOAc (3 mL×4). The combined organic layer was dried (Na$_2$SO$_4$), filtered, and concentrated. The crude product was dissolved in DMF and submitted for purification to give 2-(5-hydroxy-3-phenyl-4-(4-sulfamoylphenoxy)-1H-pyrazol-1-yl)thiazole-4-carboxylic acid, TFA 24 (20.8 mg, 0.036 mmol, 20.00% yield). MS (M+H)$^+$=459

Example 34

This example describes the synthesis of 2-(3-(3,4-difluorophenyl)-1H-pyrazolo[3,4-b]pyridin-1-yl)thiazole-4-carboxylic acid 25 in an embodiment of the invention.

SCHEME 10

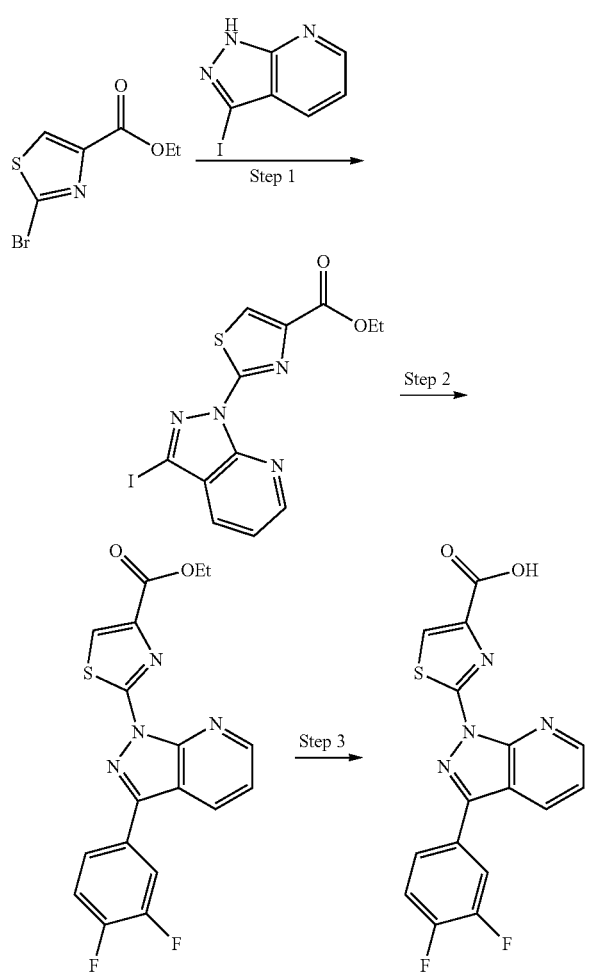

Step 1: Synthesis of ethyl 2-(3-iodo-1H-pyrazolo[3,4-b]pyridin-1-yl)thiazole-4-carboxylate In a microwave tube was placed ethyl 2-bromothiazole-4-carboxylate (472 mg, 2 mmol), 3-iodo-1H-pyrazolo[3,4-b]pyridine (515 mg, 2.100 mmol), and K$_2$CO$_3$ (304 mg, 2.200 mmol). The tube was sealed and DMSO (2 ml) was added. The mixture was heated at 140° C. for 2 h. The mixture was poured into EtOAc/H$_2$O (30 mL/30 mL). The organic layer was dried (Na$_2$SO$_4$) and filtered. After removal of the solvent, the product was purified by silica gel chromatography using 30-50-80% EtOAc/hexane as the eluent to give ethyl 2-(3-iodo-1H-pyrazolo[3,4-b]pyridin-1-yl)thiazole-4-carboxylate (328 mg, 0.820 mmol, 41.0% yield).

Step 2: Synthesis of ethyl 2-(3-(3,4-difluorophenyl)-1H-pyrazolo[3,4-b]pyridin-1-yl)thiazole-4-carboxylate In a 2-neck flask was placed ethyl 2-(3-iodo-1H-pyrazolo[3,4-b]pyridin-1-yl)thiazole-4-carboxylate (40.0 mg, 0.1 mmol), (3,4-difluorophenyl)boronic acid (31.6 mg, 0.200 mmol), PdCl$_2$(dppf) (7.32 mg, 10.00 µmol), and K$_2$CO$_3$ (69.1 mg, 0.500 mmol). The air was removed and re-filled with N$_2$ (2-3 times). Then a mixture of 1,4-dioxane (1 mL, ratio: 2.000) and water (0.5 ml, ratio: 1.000) was added and stirred at 95° C. (pre-heated) for 3 h. The organic layer was separated, and the aqueous layer was extracted with EtOAc (5 mL×3). The combined organic layer was dried (Na$_2$SO$_4$) and filtered. After removal of the solvent, the product was purified by silica gel chromatography using 40-70% EtOAc/hexane as the eluent to give ethyl 2-(3-(3,4-difluorophenyl)-1H-pyrazolo[3,4-b]pyridin-1-yl)thiazole-4-carboxylate (11 mg, 0.028 mmol, 28.5% yield).

Step 3: Synthesis of 2-(3-(3,4-difluorophenyl)-1H-pyrazolo[3,4-b]pyridin-1-yl)thiazole-4-carboxylic acid (25)

To a solution of ethyl 2-(3-(3,4-difluorophenyl)-1H-pyrazolo[3,4-b]pyridin-1-yl)thiazole-4-carboxylate (10 mg, 0.026 mmol) in THF (1 ml) was added LiOH$_{(aq)}$ (1.5 N in H$_2$O, 0.4 mL, 0.6 mmol). The mixture was stirred at room temperature for 2 h. Then, 1 N HCl(aq) (ca.0.6-0.65 mL) was added and the pH of aqueous layer was around 4. Then, hexane (5 mL) was added, and the resulting solid was filtered, triturated with hexane (2 mL×2), and dried to give 2-(3-(3,4-difluorophenyl)-1H-pyrazolo[3,4-b]pyridin-1-yl)thiazole-4-carboxylic acid 25 (6 mg, 0.017 mmol, 64.7% yield). $^1$H NMR (400 MHz, DMSO-d$_6$) δ 13.16 (s, 1H), 8.88-8.78 (m, 2H), 8.33 (s, 1H), 8.15 (ddd, J=11.7, 7.7, 2.2 Hz, 1H), 8.05-7.97 (m, 1H), 7.68 (dt, J=10.8, 8.5 Hz, 1H), 7.60 (dd, J=8.1, 4.6 Hz, 1H); MS (M+H)$^+$=359.

Example 35

This example describes the synthesis of 2-(3-(4-sulfamoylbenzyl)-1H-pyrrolo[2,3-b]pyridin-1-yl)thiazole-4-carboxylic acid 26 in an embodiment of the invention.

SCHEME 11

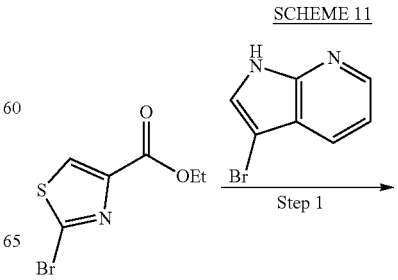

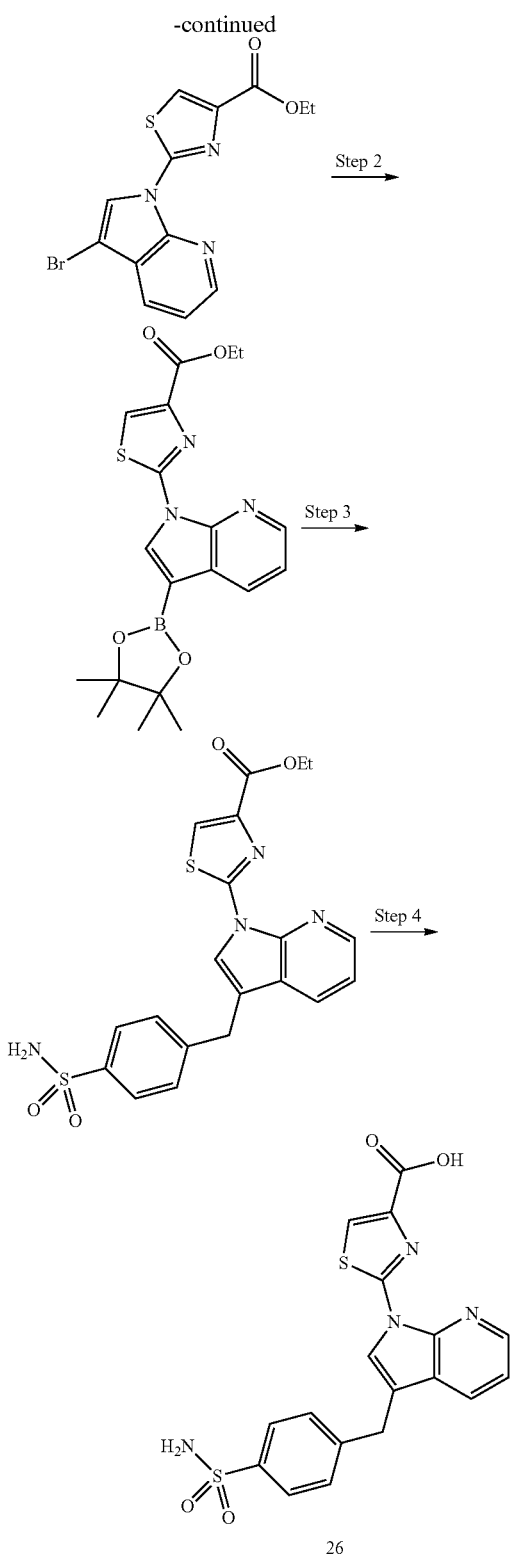

Step 1: Synthesis of ethyl 2-(3-bromo-1H-pyrrolo[2,3-b]pyridin-1-yl)thiazole-4-carboxylate In a microwave tube was placed ethyl 2-bromothiazole-4-carboxylate (944 mg, 4 mmol), 3-bromo-1H-pyrrolo[2,3-b]pyridine (867 mg, 4.40 mmol), and $K_2CO_3$ (663 mg, 4.80 mmol). The tube was sealed and DMSO (7.5 ml) was added. The mixture was heated at 150° C. for 3 h. The mixture was poured into EtOAc/$H_2O$ (30 mL/30 mL). The organic was dried ($Na_2SO_4$) and filtered. After removal of the solvent, the product was purified (twice) by silica gel chromatography using 10-20% EtOAc/hexane as the eluent to give ethyl 2-(3-bromo-1H-pyrrolo[2,3-b]pyridin-1-yl)thiazole-4-carboxylate (587 mg, 1.667 mmol, 41.7% yield).

Step 2: Synthesis of ethyl 2-(3-(4,4,5,5-tetramethyl-1,3,2-dioxaborolan-2-yl)-1H-pyrrolo[2,3-b]pyridin-1-yl)thiazole-4-carboxylate In a microwave tube was placed ethyl 2-(3-bromo-1H-pyrrolo[2,3-b]pyridin-1-yl)thiazole-4-carboxylate (352 mg, 1 mmol), 4,4,4',4',5,5,5',5'-octamethyl-2,2'-bi(1,3,2-dioxaborolane) (330 mg, 1.300 mmol), $PdCl_2$(dppf) (73.2 mg, 0.100 mmol), and AcOK (294 mg, 3.00 mmol). The tube was sealed and air was removed and re-filled with $N_2$ (2-3 times). Then, 1,4-dioxane (3 ml) was added and stirred at 95° C. (pre-heated) for overnight. The mixture was diluted with EtOAc and filtered through CELITE™ and eluted with EtOAc. After removal of the solvent, the product was purified by silica gel chromatography using 10-25% EtOAc/hexane as the eluent to give product, which was triturated with a small amount of hexane to give ethyl 2-(3-(4,4,5,5-tetramethyl-1,3,2-dioxaborolan-2-yl)-1H-pyrrolo[2,3-b]pyridin-1-yl)thiazole-4-carboxylate (293 mg, 0.734 mmol, 73.4% yield) as solid.

Step 3: Synthesis of ethyl 2-(3-(4-sulfamoylbenzyl)-1H-pyrrolo[2,3-b]pyridin-1-yl)thiazole-4-carboxylate In a microwave tube was placed ethyl 2-(3-(4,4,5,5-tetramethyl-1,3,2-dioxaborolan-2-yl)-1H-pyrrolo[2,3-b]pyridin-1-yl)thiazole-4-carboxylate (39.9 mg, 0.1 mmol), 4-(bromomethyl)benzenesulfonamide (25.01 mg, 0.100 mmol), and Pd($Ph_3P$)$_4$ (11.56 mg, 10.00 µmol). The tube was sealed and air was removed and re-filled with $N_2$ (2-3 times). A mixture of toluene (0.75 ml, ratio: 2.500)/EtOH (0.3 ml, ratio: 1.000) was added, and then 2N $Na_2CO_{3(aq)}$ (0.3 mL, 0.6 mmol, 6 equiv) was added. The mixture was stirred at 80° C. (pre-heated) for 2 h. The organic layer was separated, and the aqueous layer was extracted with EtOAc (2 mL×3). The combined organic layer was dried ($Na_2SO_4$) and filtered. After removal of the solvent, the product was purified by silica gel chromatography using 30-80% EtOAc/hexane as the eluent to give ethyl 2-(3-(4-sulfamoylbenzyl)-1H-pyrrolo[2,3-b]pyridin-1-yl)thiazole-4-carboxylate (28 mg, 0.063 mmol, 63.3% yield) as a white solid.

Step 4: Synthesis of 2-(3-(4-sulfamoylbenzyl)-1H-pyrrolo[2,3-b]pyridin-1-yl)thiazole-4-carboxylic acid (26)

To a solution of ethyl 2-(3-(4-sulfamoylbenzyl)-1H-pyrrolo[2,3-b]pyridin-1-yl)thiazole-4-carboxylate (28 mg, 0.063 mmol) in THF (1 ml) was added LiOH$_{(aq)}$ (1.5 N in $H_2O$, 0.4 mL, 0.6 mmol). The mixture was stirred at room temperature for 2 h. Then, 1N HCl$_{(aq)}$ (ca.0.6-0.65 mL) was added and the pH of aqueous layer was around 4. Then, hexane (5 mL) was added and the resulting solid was filtered, triturated with $H_2O$ (1 ml×2) and then hexane (2 mL×2), and dried to give 2-(3-(4-sulfamoylbenzyl)-1H-pyrrolo[2,3-b]pyridin-1-yl)thiazole-4-carboxylic acid 26 (21 mg, 0.051 mmol, 80% yield). $^1$H NMR (400 MHz, DMSO-d$_6$) δ 13.04 (s, 1H), 8.46 (dd, J=4.8, 1.5 Hz, 1H), 8.19 (s, 1H), 8.09 (dd, J=7.8, 1.5 Hz, 1H), 8.07 (s, 1H), 7.80-7.72 (m, 2H), 7.58 (d, J=8.2 Hz, 2H), 7.32 (dd, J=7.9, 4.8 Hz, 1H), 7.27 (s, 2H), 4.23 (s, 2H); MS (M+H)$^+$=415.

Example 36

This example describes the synthesis of 2-(4-(4-(methylsulfonyl)benzyl)-3-phenyl-1H-pyrazol-1-yl)thiazole-4-carboxylic acid 27 in an embodiment of the invention.

SCHEME 12

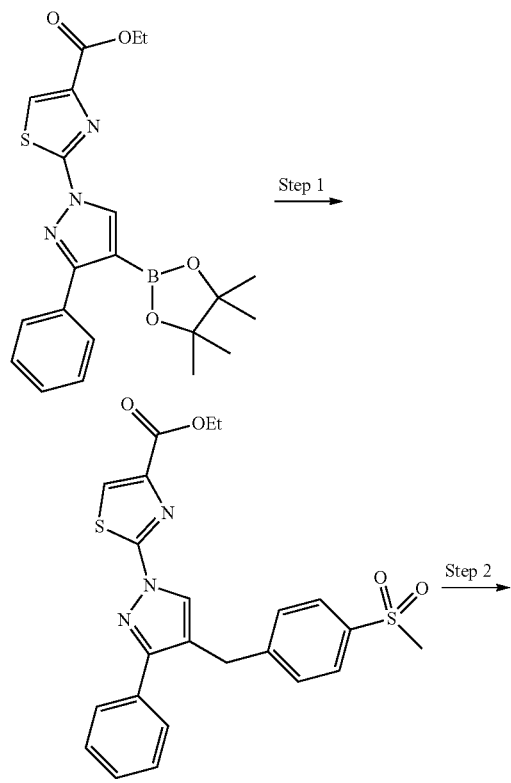

Step 1: Synthesis of ethyl 2-(4-(4-(methylsulfonyl)benzyl-3-phenyl-1H-pyrazol-1-yl)thiazole-4-carboxylate In a microwave tube was placed ethyl 2-(3-phenyl-4-(4,4,5,5-tetramethyl-1,3,2-dioxaborolan-2-yl)-1H-pyrazol-1-yl)thiazole-4-carboxylate (70.9 mg, 0.1 mmol), 1-(bromomethyl)-4-(methylsulfonyl)benzene (24.91 mg, 0.100 mmol), and Pd(Ph$_3$P)$_4$ (11.56 mg, 10.00 μmol). The tube was sealed and air was removed and re-filled with N$_2$ (2-3 times). A mixture of toluene (0.75 ml, ratio: 2.500)/EtOH (0.3 ml, ratio: 1.000) was added, and then 2N Na$_2$CO$_{3(aq)}$ (0.3 mL, 0.6 mmol, 6 equiv) was added. The mixture was stirred at 80° C. (pre-heated) for 2 h. The organic layer was separated, and the aqueous layer was extracted with EtOAc (2 mL×3). The combined organic layer was dried (Na$_2$SO$_4$) and filtered. After removal of the solvent, the product was purified by silica gel chromatography using 25-50% EtOAc/hexane as the eluent to give ethyl 2-(4-(4-(methylsulfonyl)benzyl)-3-phenyl-1H-pyrazol-1-yl)thiazole-4-carboxylate (35 mg, 0.075 mmol, 74.9% yield) as a white solid.

Step 2: Synthesis of 2-(4-(4-(methylsulfonyl)benzyl)-3-phenyl-1H-pyrazol-1-yl)thiazole-4-carboxylic acid (27)

To a solution of ethyl 2-(4-(4-(methylsulfonyl)benzyl)-3-phenyl-1H-pyrazol-1-yl)thiazole-4-carboxylate (35 mg, 0.075 mmol) in THF (1 ml) was added LiOH$_{(aq)}$ (1.5 N in H$_2$O, 0.4 mL, 0.6 mmol). The mixture was stirred at room temperature for 2 h. Then, 1 N HCl$_{(aq)}$ (ca.0.6-0.65 mL) was added and the pH of aqueous layer was around 4. Then, hexane (5 mL) was added and the resulting solid was filtered, triturated with H$_2$O (1 ml×2) and then hexane (2 mL×2), and dried to give 2-(4-(4-(methylsulfonyl)benzyl)-3-phenyl-1H-pyrazol-1-yl)thiazole-4-carboxylic acid 27 (30 mg, 0.068 mmol, 91% yield). $^1$H NMR (400 MHz, DMSO-d$_6$) δ 13.17 (s, 1H), 8.34 (s, 1H), 8.23 (d, J=1.7 Hz, 1H), 7.86-7.79 (m, 2H), 7.70-7.62 (m, 2H), 7.53-7.37 (m, 5H), 4.19 (s, 2H), 3.17 (s, 3H); MS (M+H)$^+$=440.

Example 37

This example describes the synthesis of 2-(3-phenyl-4-(4-(trifluoromethyl)benzyl)-1H-pyrazol-1-yl)thiazole-4-carboxylic acid, TFA 28 in an embodiment of the invention.

SCHEME 13

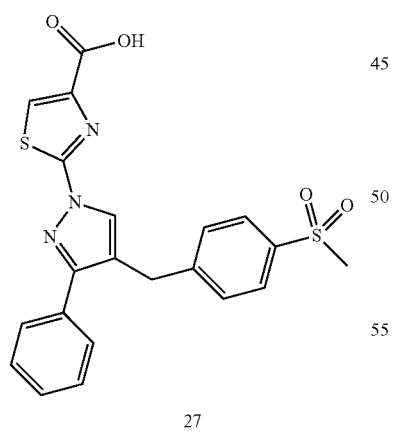

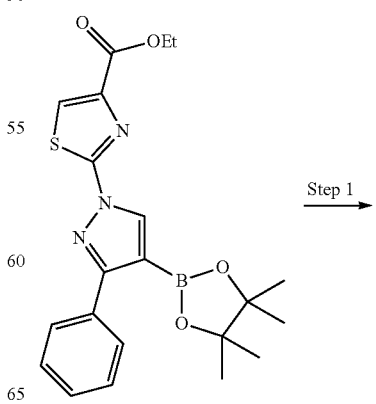

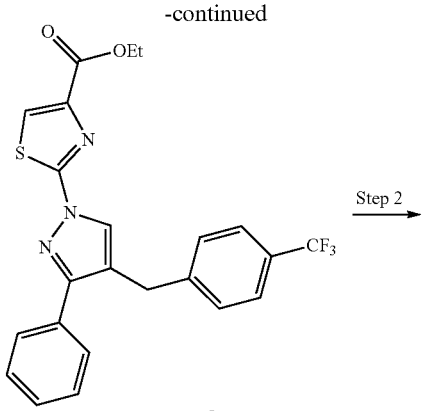

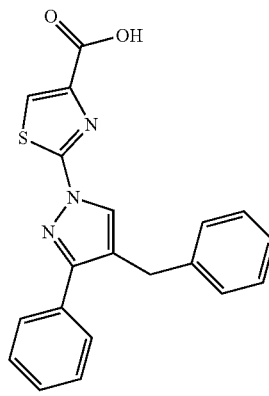

28

Step 1: Synthesis of ethyl 2-(3-phenyl-4-(4-(trifluoromethyl)benzyl)-1H-pyrazol-1-yl)thiazole-4-carboxylate In a microwave tube was placed ethyl 2-(3-phenyl-4-(4,4,5,5-tetramethyl-1,3,2-dioxaborolan-2-yl)-1H-pyrazol-1-yl)thiazole-4-carboxylate (70.9 mg, 0.1 mmol), 1-(bromomethyl)-4-(trifluoromethyl)benzene (23.90 mg, 0.100 mmol), and Pd(Ph$_3$P)$_4$ (11.56 mg, 10.00 μmol). The tube was sealed and air was removed and re-filled with N2 (2-3 times). A mixture of toluene (0.75 ml, ratio: 2.500)/EtOH (0.3 ml, ratio: 1.000) was added, and then 2 N Na$_2$CO$_{3(aq)}$ (0.3 mL, 0.6 mmol, 6 equiv) was added. The mixture was stirred at 80° C. (pre-heated) for 2 h. The organic layer was separated, and the aqueous layer was extracted with EtOAc (2 mL×3). The combined organic layer was dried (Na$_2$SO$_4$) and filtered. After removal of the solvent, the product was purified by silica gel chromatography using 10-25% EtOAc/hexane as the eluent to give ethyl 2-(3-phenyl-4-(4-(trifluoromethyl)benzyl)-1H-pyrazol-1-yl)thiazole-4-carboxylate (58 mg, 0.070 mmol, 69.7% yield) as a white solid. This material was mixed with the reduction product and was used for hydrolysis directly and purified at the next step.

Step 2: Synthesis of 2-(3-phenyl-4-(4-(trifluoromethyl)benzyl)-1H-pyrazol-1-yl)thiazole-4-carboxylic acid, TFA (28)

To a solution of ethyl 2-(3-phenyl-4-(4-(trifluoromethyl)benzyl)-1H-pyrazol-1-yl)thiazole-4-carboxylate (58 mg, 0.070 mmol) in THF (1 ml) was added LiOH$_{(aq)}$ (1.5 N in H$_2$O, 0.4 mL, 0.6 mmol). The mixture was stirred at room temperature for 2 h. Then, 1 N HCl$_{aq}$ (ca.0.6-0.65 mL) was added, and the pH of aqueous layer was around 4. Then, the mixture was concentrated and the residue was dissolved in DMF, filtered through a filter and submitted for purification to give 2-(3-phenyl-4-(4-(trifluoromethyl)benzyl)-1H-pyrazol-1-yl)thiazole-4-carboxylic acid, TFA 28 (13 mg, 0.024 mmol, 34.3% yield). $^1$H NMR (400 MHz, DMSO-d$_6$) δ 13.17 (s, 1H), 8.33 (s, 1H), 8.23 (s, 1H), 7.69-7.59 (m, 4H), 7.50-7.36 (m, 5H), 4.18 (s, 2H); MS (M+H)$^+$=430.

Example 38

This example describes the synthesis of 2-(3-([1,1'-biphenyl]-3-yl)-1H-pyrrolo[2,3-b]pyridin-1-yl)thiazole-4-carboxylic acid, TFA 29 in an embodiment of the invention.

SCHEME 14

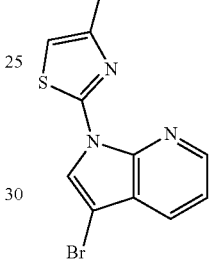

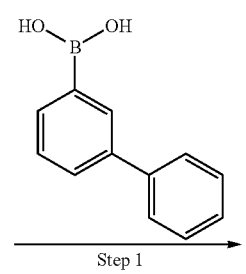

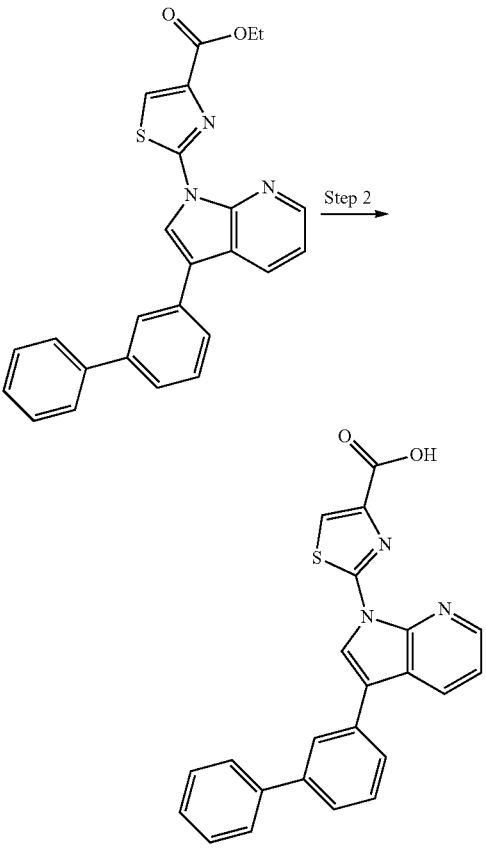

29

Step 1: Synthesis of ethyl 2-(3-([1,1'-biphenyl]-3-yl)-1H-pyrrolo[2,3-b]pyridin-1-yl)thiazole-4-carboxylate In a 2-neck flask was placed ethyl 2-(3-bromo-1H-pyrrolo[2,3-b]pyridin-1-yl)thiazole-4-carboxylate (35.2 mg, 0.1 mmol), [1,1'-biphenyl]-3-ylboronic acid (39.6 mg, 0.200 mmol), PdCl$_2$(dppf) (7.32 mg, 10.00 μmol), and K$_2$CO$_3$ (69.1 mg, 0.500 mmol). The air was removed and re-filled with N$_2$ (2-3 times). Then a mixture of 1,4-dioxane (1 mL, ratio: 2.000) and water (0.5 ml, ratio: 1.000) was added and stirred at 95° C. (pre-heated) for 3 h. The organic layer was separated, and the aqueous layer was extracted with EtOAc (5 mL×3). The combined organic layer was dried (Na$_2$SO$_4$) and filtered. After removal of the solvent, the product was purified by silica gel chromatography using 40-70% EtOAc/hexane as the eluent to give ethyl 2-(3-([1,1'-biphenyl]-3-yl)-1H-pyrrolo[2,3-b]pyridin-1-yl)thiazole-4-carboxylate (30 mg, 0.053 mmol, 52.9% yield). This product contained some impurity and was used for the next step without further purification.

Step 2: Synthesis of 2-(3-([1,1'-biphenyl]-3-yl)-1H-pyrrolo[2,3-b]pyridin-1-yl)thiazole-4-carboxylic acid, TFA (29)

To a solution of ethyl 2-(3-([1,1'-biphenyl]-3-yl)-1H-pyrrolo[2,3-b]pyridin-1-yl)thiazole-4-carboxylate (30 mg, 0.071 mmol) in THF (1 ml) was added LiOH$_{(aq)}$ (1.5 N in H2O, 0.4 mL, 0.6 mmol). The mixture was stirred at room temperature for 3 h. Then, 1 N HCl$_{(aq)}$ (ca.0.6-0.65 mL) was added and the pH of aqueous layer was around 4. The mixture was concentrated and the residue was dissolved in DMF, filtered through a filter, and submitted for purification to give 2-(3-([1,1'-biphenyl]-3-yl)-1H-pyrrolo[2,3-b]pyridin-1-yl)thiazole-4-carboxylic acid, TFA 29 (2.1 mg, 4.11 μmol, 5.82% yield). $^1$H NMR (400 MHz, DMSO-d$_6$) δ 13.08 (s, 1H), 8.68 (s, 1H), 8.57 (d, J=4.7 Hz, 1H), 8.55-8.50 (m, 1H), 8.28 (s, 1H), 8.07 (d, J=2.0 Hz, 1H), 7.83 (m, 3H), 7.68 (d, J=7.7 Hz, 1H), 7.61 (t, J=7.6 Hz, 1H), 7.54-7.44 (m, 3H), 7.43-7.35 (m, 1H); MS (M+H)$^+$=398.

Example 39

This example describes the synthesis of 2-(5-(morpholine-4-carbonyl)-3-(4-sulfamoylbenzyl)-1H-indol-1-yl)thiazole-4-carboxylic acid 30 in an embodiment of the invention.

SCHEME 15

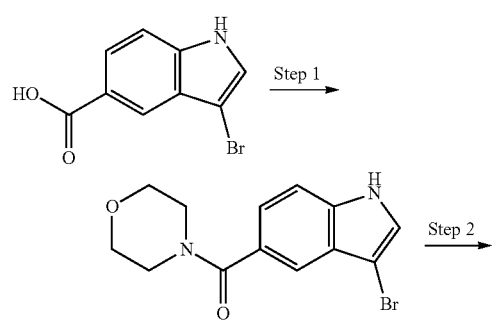

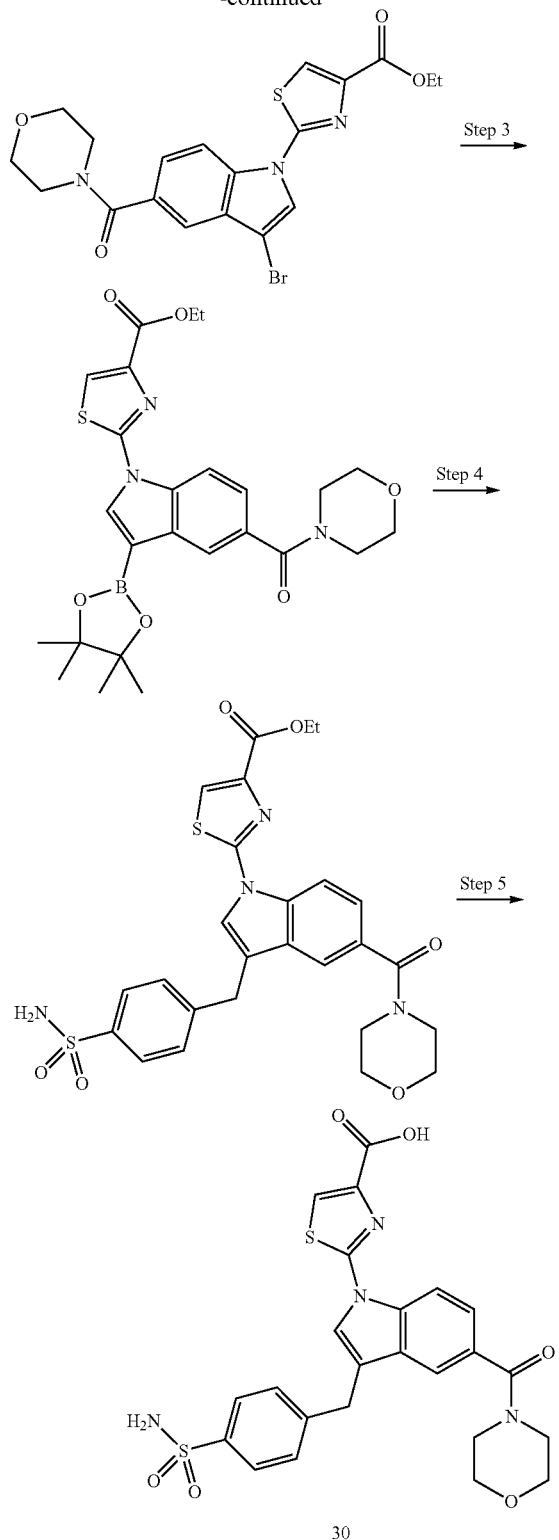

30

Step 1: Synthesis of (3-bromo-1H-indol-5-yl)(morpholino)methanone

To a mixture of 3-bromo-1H-indole-5-carboxylic acid (960 mg, 4 mmol) and HATU (2281 mg, 6.00 mmol) was added DMF (5 ml) and then morpholine (697 mg, 8.00 mmol) and Hünig's base (1.048 ml, 6.00 mmol). The mixture was stirred at room temperature for 1.5 h. The mixture was poured into EtOAc/H₂O (60 mL/60 mL). The organic layer was dried (Na₂SO₄) and filtered. After removal of the solvent, the product was purified by silica gel chromatography using 50-100% EtOAc/hexane as the eluent to give (3-bromo-1H-indol-5-yl)(morpholino)methanone (1204 mg, 3.89 mmol, 97% yield).

Step 2: Synthesis of ethyl 2-(3-bromo-5-(morpholine-4-carbonyl)-1H-indol-1-yl)thiazole-4-carboxylate In a microwave tube was placed ethyl 2-bromothiazole-4-carboxylate (425 mg, 1.800 mmol), (3-bromo-1H-indol-5-yl)(morpholino)methanone (464 mg, 1.5 mmol), and K₂CO₃ (415 mg, 3.00 mmol). The tube was sealed and DMSO (3 ml) was added. The mixture was heated at 125° C. for overnight. The mixture was poured into vigorously stirred H₂O (100 mL) and the solid was filtered, triturated with H₂O, and dried. To the solid was added hexane (30 mL), and the mixture was sonicated and filtered. The solid was dried to give ethyl 2-(3-bromo-5-(morpholine-4-carbonyl)-1H-indol-1-yl)thiazole-4-carboxylate (485 mg, 1.045 mmol, 69.6% yield).

Step 3: Synthesis of ethyl 2-(5-(morpholine-4-carbonyl)-3-(4,4,5,5-tetramethyl-1,3,2-dioxaborolan-2-yl)-1H-indol-1-yl)thiazole-4-carboxylate In a microwave tube was placed ethyl 2-(3-bromo-5-(morpholine-4-carbonyl)-1H-indol-1-yl)thiazole-4-carboxylate (464 mg, 1 mmol), 4,4,4',4',5,5,5',5'-octamethyl-2,2'-bi(1,3,2-dioxaborolane) (381 mg, 1.500 mmol), PdCl₂(dppf) (73.2 mg, 0.100 mmol), and potassium, acetate (294 mg, 3.00 mmol). The tube was sealed and air was removed and re-filled with N₂ (2-3 times). Then, 1,4-dioxane (3 ml) was added and stirred at 95° C. (pre-heated) for overnight. The mixture was diluted with EtOAc and filtered through CELITE™ and eluted with EtOAc. After removal of the solvent, the product was purified by silica gel chromatography using 40-100% EtOAc/hexane as the eluent to give product, which was triturated with a small amount of hexane to give ethyl 2-(5-(morpholine-4-carbonyl)-3-(4,4,5,5-tetramethyl-1,3,2-dioxaborolan-2-yl)-1H-indol-1-yl)thiazole-4-carboxylate (360 mg, 0.669 mmol, 66.9% yield) as solid. This material contained a very small amount of reduction (de-Br) product, ~5%, and was used without further purification.

Step 4: Synthesis of ethyl 2-(5-(morpholine-4-carbonyl)-3-(4-sulfamoylbenzyl)-1H-indol-1-yl)thiazole-4-carboxylate In a microwave tube was placed ethyl 2-(5-(morpholine-4-carbonyl)-3-(4,4,5,5-tetramethyl-1,3,2-dioxaborolan-2-yl)-1H-indol-1-yl)thiazole-4-carboxylate (77 mg, 0.15 mmol), 4-(bromomethyl)benzenesulfonamide (49.9 mg, 0.200 mmol), and Pd(Ph₃P)₄ (17.33 mg, 0.015 mmol). The tube was sealed and air was removed and re-filled with N₂ (2-3 times). A mixture of toluene (0.75 ml, ratio: 2.500)/EtOH (0.3 ml, ratio: 1.000) was added, and then 2 N Na₂CO₃$_{(aq)}$ (0.3 mL, 0.6 mmol, 4 equiv) was added. The mixture was stirred at 80° C. (pre-heated) for 2 h. The organic layer was separated, and the aqueous layer was extracted with EtOAc (2 mL×3). The combined organic layer was dried (Na₂SO₄) and filtered. After removal of the solvent, the product was purified by silica gel chromatography using 90-100% EtOAc/hexane as the eluent to give ethyl 2-(5-(morpholine-4-carbonyl)-3-(4-sulfamoylbenzyl)-1H-indol-1-yl)thiazole-4-carboxylate (70 mg, 0.126 mmol, 84% yield) as a white solid.

Step 5: Synthesis of 2-(5-(morpholine-4-carbonyl)-3-(4-sulfamoylbenzyl)-1H-indol-1-yl)thiazole-4-carboxylic acid (30)

To a solution of ethyl 2-(5-(morpholine-4-carbonyl)-3-(4-sulfamoylbenzyl)-1H-indol-1-yl)thiazole-4-carboxylate (65 mg, 0.117 mmol) in THF (1 ml) was added LiOH$_{(aq)}$ (1.5 N in H₂O, 0.4 mL, 0.6 mmol). The mixture was stirred at room temperature for 2 h. Then, 1 N HCl$_{(aq)}$ (ca.0.6-0.65 mL) was added and the pH of aqueous layer was around 4. Then, hexane (5 mL) was added, and the resulting solid was filtered, triturated with H₂O (1 ml×2) and then hexane (2 mL×2), and dried. The solid was collected and 10% CH₂Cl₂/hexane (15 mL) was added, and the mixture was sonicated and filtered. The solid was dried to give 2-(5-(morpholine-4-carbonyl)-3-(4-sulfamoylbenzyl)-1H-indol-1-yl)thiazole-4-carboxylic acid 30 (19 mg, 0.036 mmol, 30.8% yield). ¹H NMR (400 MHz, DMSO-d₆) δ 13.20 (s, 1H), 8.40 (d, J=8.5 Hz, 1H), 8.20 (s, 1H), 7.95 (s, 1H), 7.73 (d, J=8.0 Hz, 2H), 7.61 (s, 1H), 7.55 (d, J=8.0 Hz, 2H), 7.43 (d, J=8.6 Hz, 1H), 7.25 (s, 2H), 4.21 (s, 2H), 3.76-3.34 (m, 8H); MS (M+H)⁺ =527.

Example 40

This example describes the synthesis of 2-(5-fluoro-3-(4-sulfamoylbenzyl)-1H-indol-1-yl)thiazole-4-carboxylic acid 31 in an embodiment of the invention.

SCHEME 16

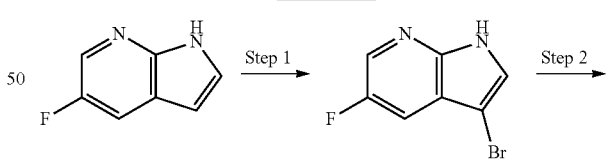

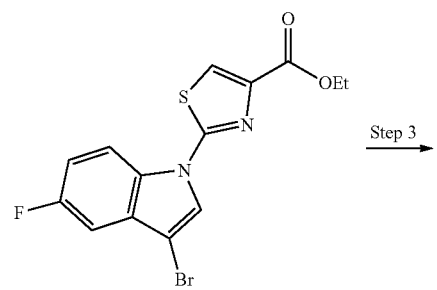

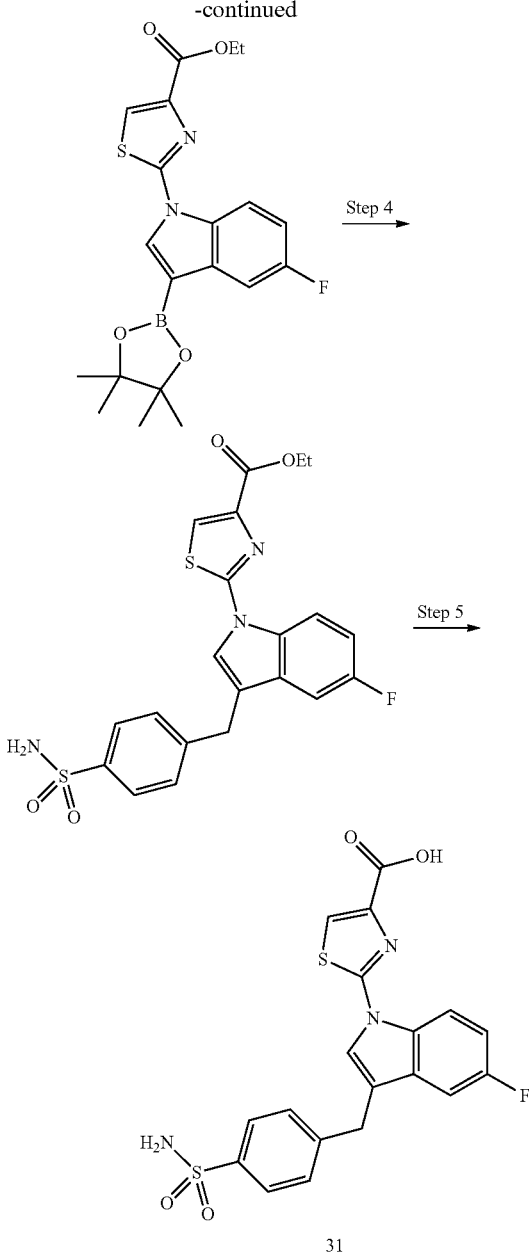

Step 1: Synthesis of 3-bromo-5-fluoro-1H-indole

To a solution of 5-fluoro-1H-indole (1351 mg, 10 mmol) in CHCl₃ (10 ml) and pyridine (1.779 ml, 22.00 mmol) at 0° C. was added NBS (1958 mg, 11.00 mmol). The mixture was stirred at 0° C. for 2 h. The mixture was concentrated to remove most of the solvent. The residue was dissolved in EtOAc (50 mL) and the organic layer washed 0.5 N $HCl_{(aq)}$ (50 mL), $H_2O$ (50 mL), 2 N $Na_2CO_{3(aq)}$ (50 mL), $H_2O$ (50 mL), dried ($Na_2SO_4$), and filtered. The product was checked by LCMS and was dried to give 3-bromo-5-fluoro-1H-indole (1945 mg, 9.09 mmol, 91% yield). This material was used for the next step without further purification.

Step 2: Synthesis of ethyl 2-(3-bromo-5-fluoro-1H-indol-1-yl)thiazole-4-carboxylate In a microwave tube was placed ethyl 2-bromothiazole-4-carboxylate (708 mg, 3 mmol), 3-bromo-5-fluoro-1H-indole (642 mg, 3.00 mmol), and $K_2CO_3$ (829 mg, 6.00 mmol). The tube was sealed and DMSO (4 ml) was added. The mixture was heated at 125° C. for 5 h. The mixture was poured into vigorously stirred $H_2O$ (100 mL) and the solid was filtered, triturated with $H_2O$ and then hexane, and dried to give ethyl 2-(3-bromo-5-fluoro-1H-indol-1-yl)thiazole-4-carboxylate (800 mg, 2.167 mmol, 72.2% yield).

Step 3: Synthesis of ethyl 2-(5-fluoro-3-(4,4,5,5-tetramethyl-1,3,2-dioxaborolan-2-yl)-1H-indol-1-yl)thiazole-4-carboxylate In a microwave tube was placed ethyl 2-(3-bromo-5-fluoro-1H-indol-1-yl)thiazole-4-carboxylate (554 mg, 1.5 mmol), 4,4,4',4',5,5,5',5'-octamethyl-2,2'-bi(1,3,2-dioxaborolane) (571 mg, 2.250 mmol), $PdCl_2(dppf)$ (110 mg, 0.150 mmol), and potassium acetate (442 mg, 4.50 mmol). The tube was sealed and air was removed and re-filled with $N_2$ (2-3 times). Then, 1,4-dioxane (4 ml) was added and stirred at 95° C. (pre-heated) for overnight. The mixture was diluted with EtOAc and filtered through CELITE™ and eluted with EtOAc. After removal of the solvent, the product was purified by silica gel chromatography using 5-20% EtOAc/hexane as the eluent to give product, which was triturated with a small amount of hexane to give ethyl 2-(5-fluoro-3-(4,4,5,5-tetramethyl-1,3,2-dioxaborolan-2-yl)-1H-indol-1-yl)thiazole-4-carboxylate (730 mg, ca. 55% purity, 0.965 mmol, 64.3% yield) as solid. This material contained reduction (de-Br) product, ~45%.

Step 4: Synthesis of ethyl 2-(5-fluoro-3-(4-sulfamoylbenzyl)-1H-indol-1-yl)thiazole-4-carboxylate In a microwave tube was placed ethyl 2-(5-fluoro-3-(4,4,5,5-tetramethyl-1,3,2-dioxaborolan-2-yl)-1H-indol-1-yl)thiazole-4-carboxylate (114 mg, 0.15 mmol, ~55% purity), 4-(bromomethyl)benzenesulfonamide (49.9 mg, 0.200 mmol), and $Pd(Ph_3P)_4$ (17.33 mg, 0.015 mmol). The tube was sealed and air was removed and re-filled with $N_2$ (2-3 times). A mixture of toluene (0.75 ml, ratio: 2.500)/EtOH (0.3 ml, ratio: 1.000) was added, and then 2 N $Na_2CO_{3(aq)}$ (0.3 mL, 0.6 mmol, 4 equiv) was added. The mixture was stirred at 80° C. (pre-heated) for 2 h. The organic layer was separated, and the aqueous layer was extracted with EtOAc (2 mL×3). The combined organic layer was dried ($Na_2SO_4$) and filtered. After removal of the solvent, the product was purified by silica gel chromatography using 20-50% EtOAc/hexane as the eluent to give ethyl 2-(5-fluoro-3-(4-sulfamoylbenzyl)-1H-indol-1-yl)thiazole-4-carboxylate (47 mg, 0.102 mmol, 68.2% yield) as a white solid.

Step 5: Synthesis of 2-(5-fluoro-3-(4-sulfamoylbenzyl)-1H-indol-1-yl)thiazole-4-carboxylic acid (31)

To a solution of ethyl 2-(5-fluoro-3-(4-sulfamoylbenzyl)-1H-indol-1-yl)thiazole-4-carboxylate (47 mg, 0.102 mmol) in THF (1 ml) was added $LiOH_{(aq)}$ (1.5 N in $H_2O$, 0.4 mL, 0.6 mmol). The mixture was stirred at room temperature for 2 h. Then, 1 N $HCl_{(aq)}$ (ca.0.6-0.65 mL) was added and the pH of aqueous layer was around 4. Then, hexane (5 mL) was added and the resulting solid was filtered, triturated with $H_2O$ (1 ml×2) and then hexane (2 mL×2) and dried to give 2-(5-fluoro-3-(4-sulfamoylbenzyl)-1H-indol-1-yl)thiazole-4-carboxylic acid 31 (37 mg, 0.086 mmol, 84% yield). $^1$H NMR (400 MHz, DMSO-d$_6$) δ 13.17 (s, 1H), 8.40 (dd, J=9.2, 4.5 Hz, 1H), 8.19 (d, J=1.0 Hz, 1H), 7.93 (s, 1H), 7.73 (d, J=8.0 Hz, 2H), 7.56 (d, J=8.0 Hz, 2H), 7.37 (dd, J=9.2, 2.6 Hz, 1H), 7.27-7.18 (m, 3H), 4.16 (s, 2H); MS (M+H)$^+$=432.

Example 41

This example describes the synthesis of 2-(5-(morpholinomethyl)-3-(4-sulfamoylbenzyl)-1H-indol-1-yl)thiazole-4-carboxylic acid 32 in an embodiment of the invention.

SCHEME 17

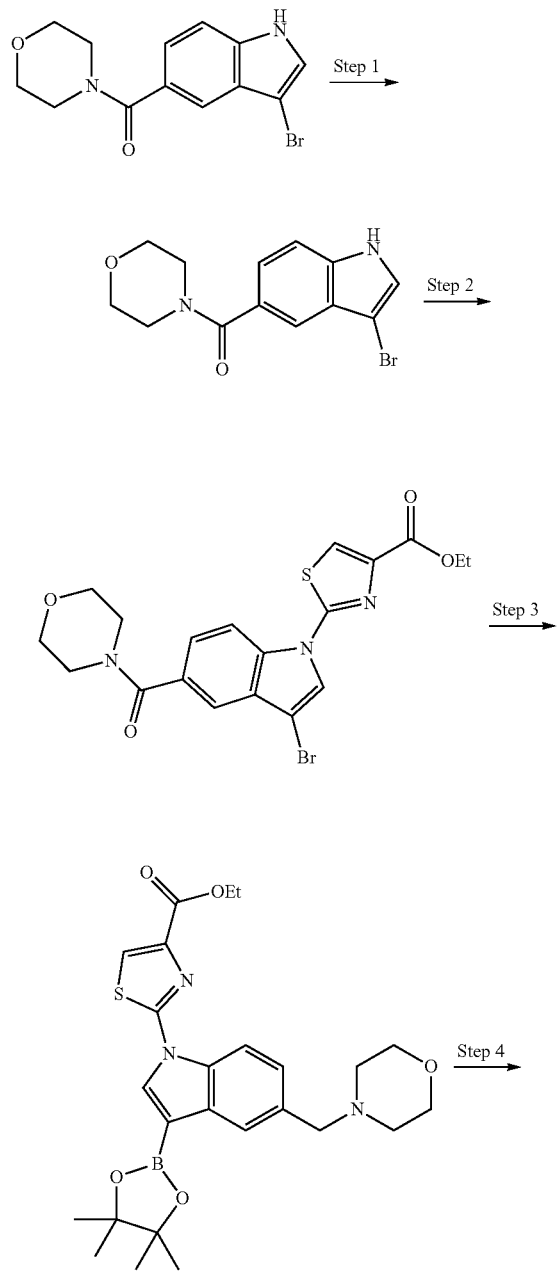

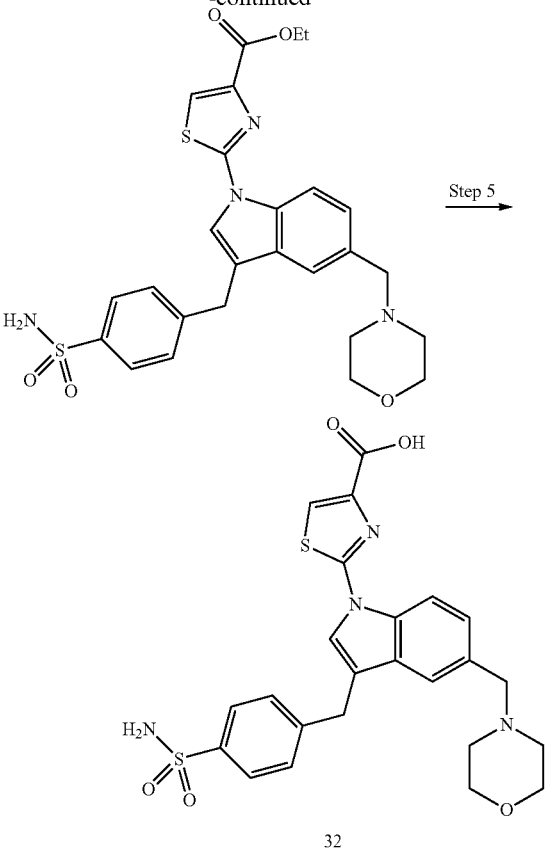

Step 1: Synthesis of 4-((3-bromo-1H-indol-5-yl)methyl)morpholine

To a solution of (3-bromo-1H-indol-5-yl)(morpholino)methanone (711 mg, 2.3 mmol) in CH$_2$Cl$_2$ (5 ml) under N$_2$ at 0° C. was added DIBAL-H (1636 mg, 11.50 mmol) (1 M in THF, 11.5 mL). After addition of DIBAL-H, the mixture was allowed to warm to room temperature for 2 h. The mixture was slowly poured into vigorously stirred sat. Rochelle salt solution (aq.) (15 mL) was added, and the mixture was stirred for 30 min. The aqueous layer was extracted with CH$_2$Cl$_2$ (10 mL×2). The combined organic layer was dried (Na$_2$SO$_4$) and filtered. After removal of the solvent, the product was purified by silica gel chromatography using 50-100% EtOAc/hexane as the eluent to give 4-((3-bromo-1H-indol-5-yl)methyl)morpholine (477 mg, 1.616 mmol, 70.3% yield).

Step 2: Synthesis of ethyl 2-(3-bromo-5-(morpholinomethyl)-1H-indol-1-yl)thiazole-4-carboxylate In a microwave tube was placed ethyl 2-bromothiazole-4-carboxylate (443 mg, 1.875 mmol), 4-((3-bromo-1H-indol-5-yl)methyl)morpholine (443 mg, 1.5 mmol), and K$_2$CO$_3$ (311 mg, 2.250 mmol). The tube was sealed and DMSO (2 ml) was added. The mixture was heated at 125° C. for 3 h. The mixture was poured into EtOAc/H$_2$O (50 mL/50 mL). The aqueous layer was extracted with EtOAc (50 mL×2). The combined organic layer was dried (Na$_2$SO$_4$) and filtered. After removal of the solvent, the product was purified by silica gel chromatography using 40-100%

EtOAc/hexane as the eluent to give ethyl 2-(3-bromo-5-(morpholinomethyl)-1H-indol-1-yl)thiazole-4-carboxylate (426 mg, 0.946 mmol, 63.1% yield).

Step 3: Synthesis of ethyl 2-(5-(morpholinomethyl)-3-(4,4,5,5-tetramethyl-1,3,2-dioxaborolan-2-yl)-1H-indol-1-yl)thiazole-4-carboxylate In a microwave tube was placed ethyl 2-(3-bromo-5-(morpholinomethyl)-1H-indol-1-yl)thiazole-4-carboxylate (426 mg, 0.946 mmol), 4,4,4',4',5,5,5',5'-octamethyl-2,2'-bi(1,3,2-dioxaborolane) (480 mg, 1.892 mmol), PdCl$_2$(dppf) (69.2 mg, 0.095 mmol), and potassium acetate (371 mg, 3.78 mmol). The tube was sealed and air was removed and re-filled with N$_2$ (2-3 times). Then, 1,4-dioxane (2 ml) was added and stirred at 95° C. (pre-heated) for 5 h. The mixture was diluted with EtOAc and filtered through celite and eluted with EtOAc. After removal of the solvent, the product was purified by silica gel chromatography using 50-100% EtOAc/hexane as the eluent to give ethyl 2-(5-(morpholinomethyl)-3-(4,4,5,5-tetramethyl-1,3,2-dioxaborolan-2-yl)-1H-indol-1-yl)thiazole-4-carboxylate as solid.

Step 4: Synthesis of ethyl 2-(5-(morpholinomethyl)-3-(4-sulfamoylbenzyl)-1H-indol-1-yl)thiazole-4-carboxylate In a microwave tube was placed ethyl 2-(5-(morpholinomethyl)-3-(4,4,5,5-tetramethyl-1,3,2-dioxaborolan-2-yl)-1H-indol-1-yl)thiazole-4-carboxylate (99 mg, 0.2 mmol), 4-(bromomethyl)benzenesulfonamide (50.0 mg, 0.2 mmol), and Pd(Ph$_3$P)$_4$ (23.11 mg, 0.020 mmol). The tube was sealed and air was removed and re-filled with N$_2$ (2-3 times). A mixture of toluene (0.75 ml, ratio: 2.500)/EtOH (0.3 ml, ratio: 1.000) was added, and then 2 N Na$_2$CO$_{3(aq)}$ (0.3 mL, 0.6 mmol, 6 equiv) was added. The mixture was stirred at 80° C. (pre-heated) for 2 h. The organic layer was separated, and the aqueous layer was extracted with EtOAc (2 mL×3). The combined organic layer was dried (Na$_2$SO$_4$) and filtered. After removal of the solvent, the product was purified by silica gel chromatography using 60-100% EtOAc/hexane as the eluent to give ethyl 2-(5-(morpholinomethyl)-3-(4-sulfamoylbenzyl)-1H-indol-1-yl)thiazole-4-carboxylate (37 mg, 0.068 mmol, 34.2% yield).

Step 5: Synthesis of 2-(5-(morpholinomethyl)-3-(4-sulfamoylbenzyl)-1H-indol-1-yl)thiazole-4-carboxylic acid (32)

To a solution of ethyl 2-(5-(morpholinomethyl)-3-(4-sulfamoylbenzyl)-1H-indol-1-yl)thiazole-4-carboxylate (37 mg, 0.068 mmol) in THF (1 ml) was added LiOH$_{(aq)}$ (1.5 N in H$_2$O, 0.4 mL, 0.6 mmol). The mixture was stirred at room temperature for 2 h. Then, 1 N HCl$_{(aq)}$ (ca.0.6 mL) was added and the pH of aqueous layer was around 6. Then, hexane (5 mL) was added and the solid was filtered, triturated with H$_2$O (1 ml×2) and then hexane (2 mL×2), and dried to give 2-(5-(morpholinomethyl)-3-(4-sulfamoylbenzyl)-1H-indol-1-yl)thiazole-4-carboxylic acid 32 (23 mg, 0.045 mmol, 65.6% yield). MS (M+H)$^+$=513.

Example 42

This example describes the synthesis of 2-(3-phenyl-4-(4-sulfamoylphenoxy)-1H-pyrazol-1-yl)thiazole-4-carboxylic acid 33 in an embodiment of the invention.

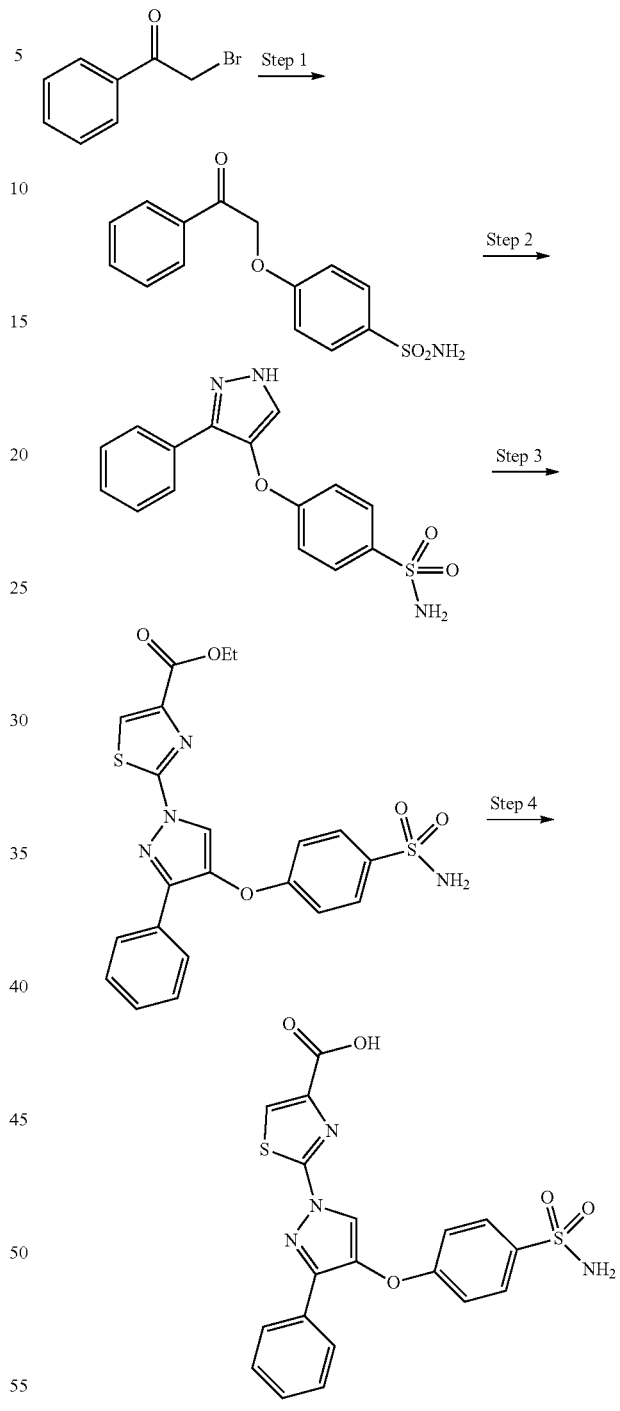

SCHEME 18

Step 1: Synthesis of 4-(2-oxo-2-phenylethoxy)benzenesulfonamide

To a mixture of 4-hydroxybenzenesulfonamide (520 mg, 3.00 mmol) and K$_2$CO$_3$ (551 mg, 3.99 mmol) was added acetone (10 mL) and stirred at room temperature for 30 min. Then 2-bromo-1-phenylethanone (597 mg, 3 mmol) in acetone (5 mL) was added. The mixture was stirred at room temperature for 20 h. Then, H₂O (15 mL) and hexane (20 mL) were added to the reaction mixture. The solid was filtered and washed with H₂O (2 mL×2) and then 5% EtOAc/hexane (5 mL×3). The solid was dried to give 4-(2-oxo-2-phenylethoxy)benzenesulfonamide (804 mg, 2.76 mmol, 92% yield) as a white solid.

Step 2: Synthesis of 4-((3-phenyl-1H-pyrazol-4-yl)oxy)benzenesulfonamide

In a microwave tube was placed 4-(2-oxo-2-phenylethoxy)benzenesulfonamide (291 mg, 1 mmol) and 1,1-dimethoxy-N,N-dimethylmethanamine (1.5 ml, 11.29 mmol) (neat). The tube was sealed and heated at 90° C. for overnight. The mixture was concentrated by blowing air and the residue was dried in vacuo for hours to give crude mixture of 4-((1-(dimethylamino)-3-oxo-3-phenylprop-1-en-2-yl)oxy)benzenesulfonamide (maybe some isomer or aldehyde). To the crude intermediate was added EtOH (4 mL) and N₂H₄ monohydrate (MW=50, d=1.032, 0.145 mL, 3 mmol). The mixture was sealed and heated at 60° C. for 4 h. After cooling to room temperature, the solvent was removed by blowing air, and the residue was purified by silica gel chromatography using 40-80% EtOAc/hexane as the eluent to give 4-((3-phenyl-1H-pyrazol-4-yl)oxy)benzenesulfonamide (85 mg, 0.270 mmol, 27.0% yield) (2 steps). This material contained some impurity and was used for the next step without further purification.

Step 3: Synthesis of ethyl 2-(3-phenyl-4-(4-sulfamoylphenoxy)-1H-pyrazol-1-yl)thiazole-4-carboxylate In a microwave tube was placed ethyl 2-bromothiazole-4-carboxylate (70.0 mg, 0.296 mmol), 4-((3-phenyl-1H-pyrazol-4-yl)oxy)benzenesulfonamide (85 mg, 0.270 mmol), and potassium carbonate (55.9 mg, 0.404 mmol). The tube was sealed and DMSO (1.5 ml) was added. The mixture was heated at 120° C. for 3 h. The mixture was poured into EtOAc/H₂O (30 mL/30 mL). The aqueous layer was extracted with EtOAc (30 mL). The combined organic layer was dried (Na₂SO₄) and filtered. After removal of the solvent, the product was purified by silica gel chromatography using 30-50-60% EtOAc/hexane as the eluent to give ethyl 2-(3-phenyl-4-(4-sulfamoylphenoxy)-1H-pyrazol-1-yl)thiazole-4-carboxylate (35 mg, 0.074 mmol, 27.6% yield).

Step 4: Synthesis of 2-(3-phenyl-4-(4-sulfamoylphenoxy)-1H-pyrazol-1-yl)thiazole-4-carboxylic acid (33)

To a solution of ethyl 2-(3-phenyl-4-(4-sulfamoylphenoxy)-1H-pyrazol-1-yl)thiazole-4-carboxylate (32 mg, 0.068 mmol) in THF (1 ml) was added LiOH$_{(aq)}$ (1.5 N in H₂O, 0.4 mL, 0.6 mmol). The mixture was stirred at room temperature for 2 h. Then, 1N HCl(aq) (ca.0.6-0.65 mL) was added and the pH of aqueous layer was around 4. Then, hexane (5 mL) was added and the resulting solid was filtered, triturated with H₂O (1 ml×2) and then hexane (2 mL×2), and dried to give 2-(3-phenyl-4-(4-sulfamoylphenoxy)-1H-pyrazol-1-yl)thiazole-4-carboxylic acid 33 (21 mg, 0.047 mmol, 69.8% yield).

Example 43

This example describes the synthesis of 2-(3-(4-sulfamoylbenzyl)-1H-pyrrolo[3,2-c]pyridin-1-yl)thiazole-4-carboxylic acid, NH₃ 34 in an embodiment of the invention.

SCHEME 19

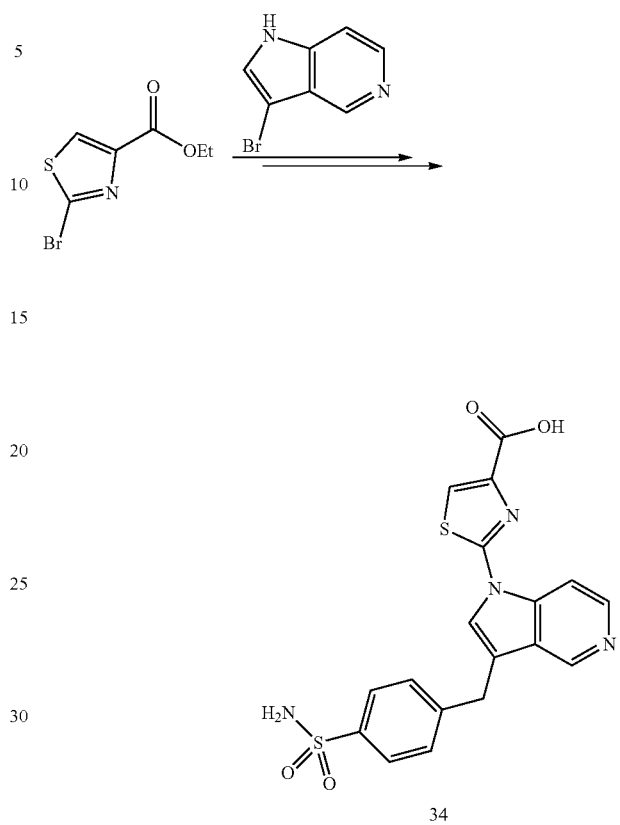

34

According to similar procedures described above for 26, the title compound was prepared starting from 3-bromo-1H-pyrrolo[3,2-c]pyridine, and the final product was purified by reverse phase HPLC chromatography under basic conditions to give 2-(3-(4-sulfamoylbenzyl)-1H-pyrrolo[3,2-c]pyridin-1-yl)thiazole-4-carboxylic acid, NH₃ 34 (NH₃ salt). MS (M+H)⁺=415.

Example 44

This example describes the synthesis of 2-(3-(4-sulfamoylbenzyl)-1H-indazol-1-yl)thiazole-4-carboxylic acid (35) in an embodiment of the invention.

SCHEME 20

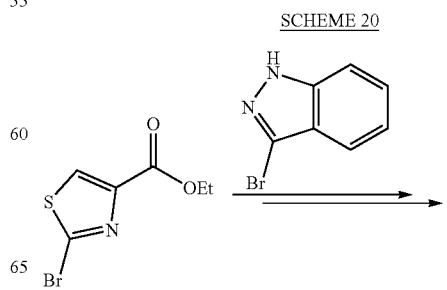

-continued

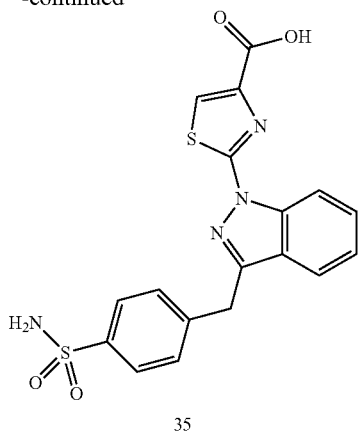

35

According to similar procedures described above for 26, the title compound was prepared starting from 3-bromoindazole to give 2-(3-(4-sulfamoylbenzyl)-1H-indazol-1-yl)thiazole-4-carboxylic acid 35. $^1$H NMR (400 MHz, DMSO-d6) δ 13.15 (s, 1H), 8.51 (d, J=8.4 Hz, 1H), 8.18 (s, 1H), 7.80 (dd, J=8.0, 1.0 Hz, 1H), 7.77-7.72 (m, 2H), 7.67 (ddd, J=8.3, 7.0, 1.1 Hz, 1H), 7.59-7.51 (m, 2H), 7.35 (ddd, J=8.1, 7.0, 0.9 Hz, 1H), 7.27 (s, 2H), 4.49 (s, 2H); MS (M+H)$^+$=415.

Example 45

This example describes the synthesis of 2-(3-(4-sulfamoylbenzyl)-5-((tetrahydro-2H-pyran-4-yl)oxy)-1H-indol-1-yl)thiazole-4-carboxylic acid, NH$_3$ 36 in an embodiment of the invention.

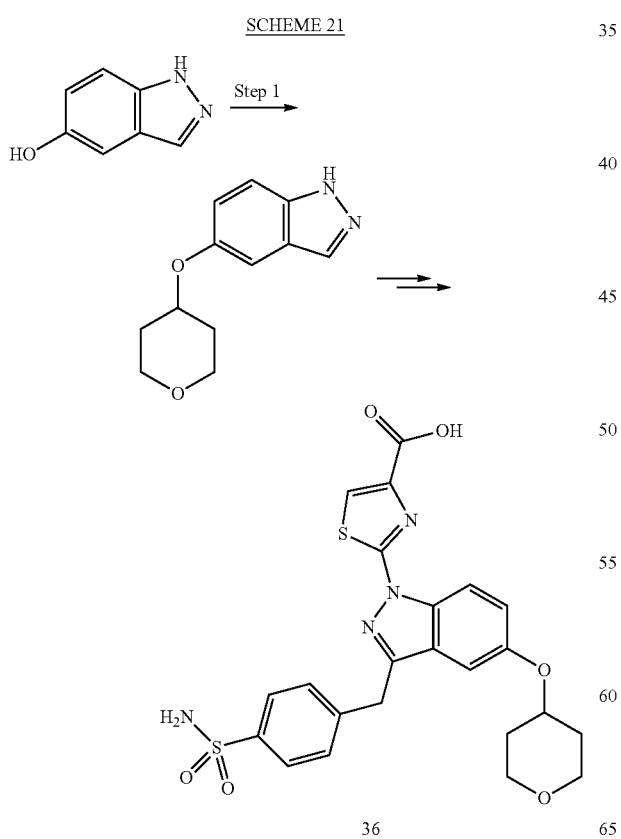

SCHEME 21

Step 1: Synthesis of 5-((tetrahydro-2H-pyran-4-yl)oxy)-1H-indole

To a mixture of 1H-indol-5-ol (0.799 g, 6 mmol), tetrahydro-2H-pyran-4-ol (0.919 g, 9.00 mmol), and PPh$_3$ (2.361 g, 9.00 mmol) in THF (10 ml) under N$_2$ was added a solution of (E)-di-tert-butyl diazene-1,2-dicarboxylate (2.072 g, 9.00 mmol) in THF (6 mL). The mixture was then stirred at 50° C. for 3 h. Tetrahydropyran-4-ol (3 mmol) was added and then a solution of PPh$_3$ (3 mmol) and (E)-di-tert-butyl diazene-1,2-dicarboxylate (3 mmol) in THF (5 mL) was added. The mixture was stirred at 50° C. for another 3 h. The mixture was concentrated, and the residue was purified by silica gel chromatography using 20-40% EtOAc/hexane as the eluent to give 5-((tetrahydro-2H-pyran-4-yl)oxy)-1H-indole (1.18 g, 5.43 mmol, 91% yield).

Step 2: Synthesis of 2-(3-(4-sulfamoylbenzyl)-5-((tetrahydro-2H-pyran-4-yl)oxy)-1H-indol-1-yl)thiazole-4-carboxylic acid, NH$_3$ (36)

According to similar procedures described above for 31, the title compound was prepared starting from 5-((tetrahydro-2H-pyran-4-yl)oxy)-1H-indole and the final product was purified by reverse phase HPLC chromatography under basic condition to give 2-(3-(4-sulfamoylbenzyl)-1H-pyrrolo[3,2-c]pyridin-1-yl)thiazole-4-carboxylic acid, NH$_3$ 36 (NH$_3$ salt). MS (M+H)$^+$=514.

Example 46

This example describes the synthesis of 2-(6-(morpholine-4-carbonyl)-3-(4-sulfamoylbenzyl)-1H-indol-1-yl)thiazole-4-carboxylic acid, NH$_3$ 37 in an embodiment of the invention.

SCHEME 22

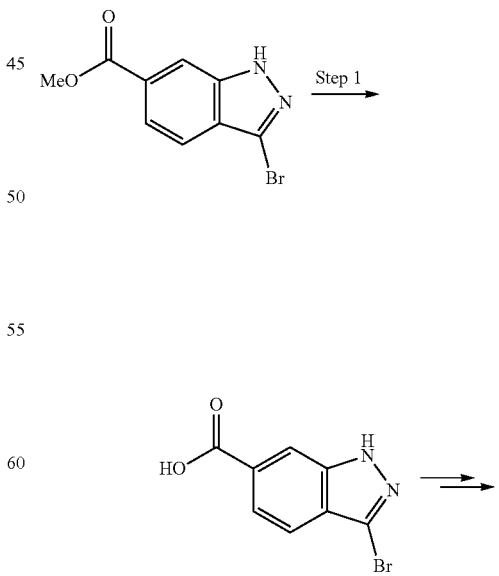

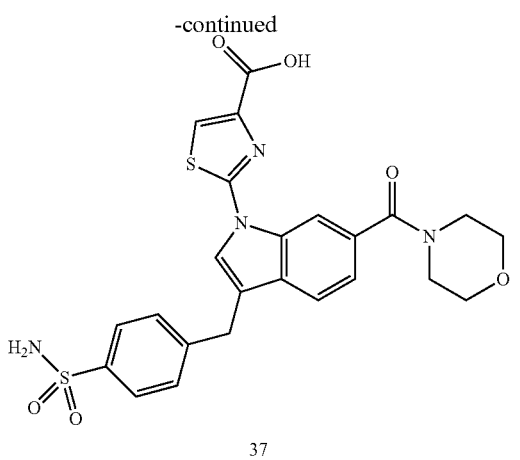

37

Step 1: Synthesis of 3-bromo-1H-indole-6-carboxylic acid

To a solution of methyl 3-bromo-1H-indole-6-carboxylate (1.270 g, 5 mmol) in THF (10 ml, ratio: 10.00) was added LiOH(aq) (1.5 N in H$_2$O, 12 mL, 18 mmol). The mixture was stirred at room temperature for 2 h. Then, 1N HCl(aq) was added and the pH of aqueous layer was around 4. Then, hexane (30 mL) was added and the resulting solid was filtered, triturated with H$_2$O (3 ml×2) and then hexane (5 mL×2), and dried to give 3-bromo-1H-indole-6-carboxylic acid (1.136 g, 4.73 mmol, 95% yield).

Step 2: Synthesis of 2-(6-(morpholine-4-carbonyl)-3-(4-sulfamoylbenzyl)-1H-indol-1-yl)thiazole-4-carboxylic acid, NH$_3$ 37

According to similar procedures described above for 30, the title compound was prepared starting from 3-bromo-1H-indole-6-carboxylic acid and the final product was purified by reverse phase HPLC chromatography under basic condition to give 2-(6-(morpholine-4-carbonyl)-3-(4-sulfamoylbenzyl)-1H-indol-1-yl)thiazole-4-carboxylic acid, NH$_3$ 37 (NH$_3$ salt). MS (M+H)$^+$=527.

Example 47

This example describes the synthesis of 1-(1H-benzo[d][1,2,3]triazol-1-yl)-ketones in an embodiment of the invention.

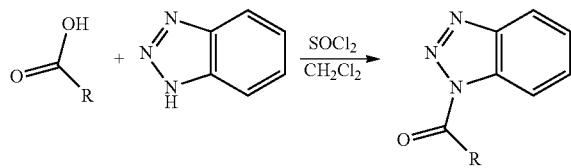

To a solution of 1H-benzo[d][1,2,3]triazole (4000 mmol) in CH$_2$Cl$_2$ was added thionyl chloride (SOCl$_2$, 1000 mmol) and stirred at rt for 0.5 h. Alkyl carboxylic acid (1000 mmol) was then added and the reaction mixture was stirred for 2 h. Upon completion as detected by LCMS, the reaction mixture was filtered and the filter cake was washed with CH$_2$Cl$_2$. The filtrate was neutralized with bicarbonate solution slowly and stirred for 30 minutes then transferred to a separatory funnel. The organic layer washed with bicarbonate solution then with brine, dried over Na$_2$SO$_4$, filtered, and concentrated. The residue was purified directly on silica using organic gradient (0-20% ethyl acetate in hexanes over 10 CV). The first peak was collected and dried to get an oil or solid.

Example 48

This example describes the synthesis of 4-(bromomethyl)benzenesulfonamides in an embodiment of the invention.

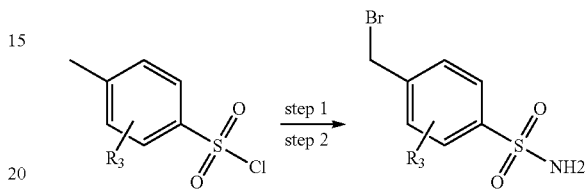

Step 1: Synthesis of 4-methylbenzenesulfonamide derivatives

A stirring solution of 4-methylbenzene-1-sulfonyl chloride (95 g, 455 mmol) in CH$_2$Cl$_2$ was bubbled with ammonia for 45 minutes. The reaction mixture was then filtered. The filtrate was concentrated and dried under reduced pressure. The resulting off-white powder was taken to the next step without further purification or characterization; (M+H)$^+$=190

Step 2: Synthesis of 4-(bromomethyl)benzenesulfonamide derivatives

A stirring solution of 4-methyl-2 or 3-fluorobenzenesulfonamide (7.3 mmol), N-bromosuccinimide (NBS 9.5 mmol) and AIBN (0.73 mmol) in CCl$_4$ (Volume: 20 mL) was refluxed for 24 h. The solvent was evaporated and the residue was suspended in ethyl acetate and filtered. The filtrate was washed with Na$_2$S$_2$O$_3$, NaHCO$_3$ and brine solutions, dried over Na$_2$SO$_4$, and filtered. Silica gel was added and the solvent was removed under reduced pressure. The dry loaded product was purified on silica using gradient elution (5-100% ethyl acetate in hexanes over 16 CV in a 120 g silica column). The pale colorless produced was used in the next step without further purification or characterization;

Example 49

This example describes the synthesis of 2-(5-(alkyl)-3-phenyl-4-(4-sulfamoylbenzyl)-1H-pyrazol-1-yl)thiazole-4-carboxylic acids and 2-(3-(alkyl)-5-phenyl-4-(4-sulfamoylbenzyl)-1H-pyrazol-1-yl)thiazole-4-carboxylic acids in an embodiment of the invention.

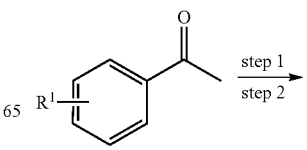

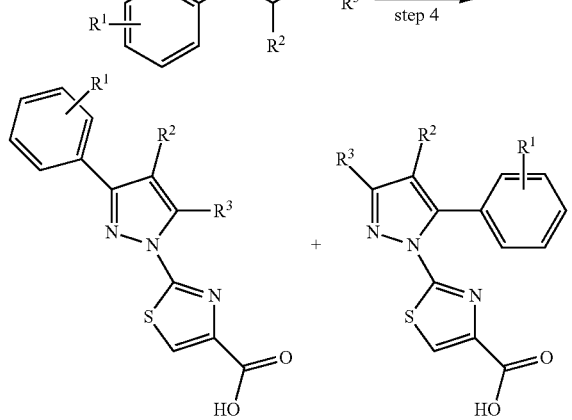

Step 1: Synthesis of 1-phenyl-3-alkyl-1,3-diones

To a stirring solution of 1-(1H-benzo[d][1,2,3]triazol-1-yl)-2-alkyl ketone (200 mmol) and magnesium bromide diethyl etherate (413 mmol) in $CH_2Cl_2$ was added 1-phenylethanone derivatives (165 mmol). Diisopropyl ethyl amine (500 mmol) was added dropwise over several minutes and the reaction mixture was stirred at rt for 2 h. Upon completion as detected by LCMS, the reaction was slowly quenched with 1.0 M HCl and washed with 1.0 M HCl and brine. The residue was dried over $Na_2SO_4$, filtered, and concentrated under reduced pressure. The residue was purified directly on silica using gradient elution (0-30% ethyl acetate in hexanes over 20 CV). The resulting oils were used in the next step without further purification or characterization.

Step 2: Synthesis of 4-(2-benzoyl-3-oxo)-3-alkyl-benzenesulfonamides 1-phenyl-3-alkyl-1,3-diones (150 mmol) and cesium carbonate ($Cs_2CO_3$, 226 mmol) were dissolved in DMSO (50 ml). The reaction mixture was stirred at rt for 10 minutes at which time potassium iodide were added (KI, 150 mmol) and 4-(bromomethyl)-benzenesulfonamides (165 mmol). The resulting mixture was stirred at rt for 1 h. Upon completion as detected by LCMS, the reaction mixture was diluted with a large excess of ethyl acetate and filtered through celite. The filtrate was washed with 1 M HCl, sat aq $NH_4Cl$ and brine, dried over $Na_2SO_4$, filtered, and concentrated under reduced pressure. The residue was purified directly on silica using gradient elution (20-40% ethyl acetate in hexanes over 16 CV).

Step 3: ethyl 2-(5-(alkyl)-3-phenyl)-4-(4-sulfamoylbenzyl)-1H-pyrazol-1-yl)thiazole-4-carboxylates Method A—A solution of 4-(2-benzoyl-3-oxo)-3-alkyl-benzenesulfonamide (6.7 mmol), ethyl 2-hydrazinylthiazole-4-carboxylate, 2 HBr (7.3 mmol) and p-toluene sulfonic acid (pTsOH, 20 mmol) in dioxane was heated in a sealed vessel in the microwave for 15 min at 160° C. Upon completion as detected by LCMS, the reaction mixture was diluted with ethyl acetate and filtered through celite. The solvent was removed under reduced pressure and the crude product was purified directly on silica using gradient elution (0-100% ethyl acetate in hexanes over 15 CV).

Method B—A solution of 4-(2-(benzoyl)-3-oxo-3-alkyl-benzenesulfonamide (113 mmol), p-toluene sulfonic acid (pTsOH, 57 mmol) and pyrrolidine (57 mmol) in ethanol was stirred at 100° C. for 1 h, after which time ethyl 2-hydrazinylthiazole-4-carboxylate, 2 HBr (136 mmol) was added. The resulting reaction mixture was refluxed overnight. Upon completion as detected by LCMS, the solvent was removed under reduced pressure and the residue was purified without work-up directly on silica using gradient elution (20-40% ethyl acetate in hexanes over 20 CV). A mixture of regioisomers were collected as a single peak. After removing the solvent, the regioisomers were separated via reverse phase preparative column using gradient elution (50-100% acetonitrile modified with 0.1% TFA in water modified with 0.1% TFA over 25 CV). The second elution peak was pooled and concentrated, and the resulting solid was stirred with a clear solution of $NaHCO_3$. The precipitate was collected by filtration, washed with water and sequentially dried, first under air overnight then by high vacuum under $P_2O_5$, resulting in a colorless powder.

Step 4: Synthesis of 2-(5-(alkyl)-3-phenyl)-4-(4-sulfamoylbenzyl)-1H-pyrazol-1-yl)thiazole-4-carboxylic acids To a solution of ethyl 2-(5-(alkyl)-3-phenyl)-4-(4-sulfamoylbenzyl)-1H-pyrazol-1-yl)thiazole-4-carboxylate (0.07 mmol) in THF/MeOH was added 1.5 M LiOH (0.27 mmol). The reaction mixture was stirred at rt for 1 h. Upon completion as detected by LCMS, the solvent was removed by forced air. The residue was taken into DMSO and purified directly via preparative reverse phase using gradient elution (4-100% acetonitrile modified with 0.1% TFA in water modified with 0.1% TFA). The product fractions were directly frozen and lyophilized overnight, yielding an off-white powder.

Example 50

This example describes the synthesis of 2-(5-(cyclopropylmethyl)-4-(4-sulfamoylbenzyl)-3-(meta substituted-phenyl)-1H-pyrazol-1-yl)thiazole-4-carboxylic acids in an embodiment of the invention.

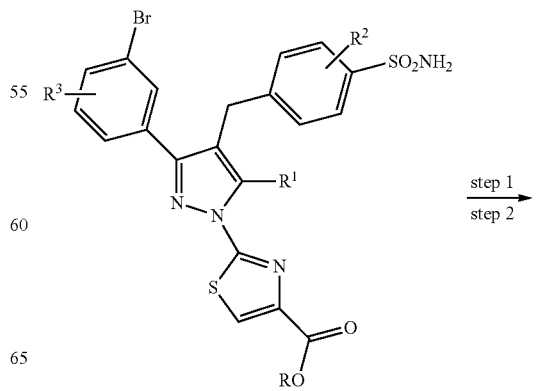

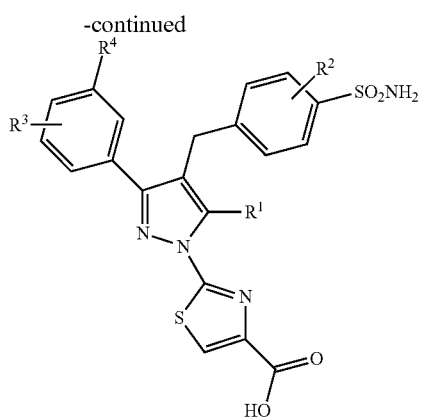

Step 1: Synthesis of ethyl 2-(5-(alkyl)-3-(3-(alk-1-yn-1-yl)phenyl)-4-(4-sulfamoylbenzyl)-1H-pyrazol-1-yl)thiazole-4-carboxylates A solution of ethyl 2-(3-(3-bromophenyl)-5-(alkyl)-4-(4-sulfamoylbenzyl)-1H-pyrazol-1-yl)thiazole-4-carboxylate (0.161 mmol, prepared according to the procedure outlined in Example 49, Steps 1-3, using method B in Step 3), tri(tert-butylphosphonium)tetrafluoroborate (0.016 mmol), allylpalladium chloride dimer (0.008 mmol) and DABCO (0.323 mmol) in dioxane was bubbled with argon for 5 minutes. Alkylethyne was then added and the reaction mixture was stirred at rt overnight. Upon completion as detected by LCMS, the reaction mixture was diluted with ethyl acetate and palladium scavenging silica (DMT) was added. After stirring for 2 h at rt the slurry was filtered through a plug of silica. The filtrate was concentrated and the residue was purified directly on silica using gradient elution (20-40% ethyl acetate in hexanes over 20 CV).

Step 2: Synthesis of 2-(5-(alkyl)-3-(3-(alk-1-yn-1-yl)phenyl)-4-(4-sulfamoylbenzyl)-1H-pyrazol-1-yl)thiazole-4-carboxylic acids The desired compounds were synthesized according to the procedure outlined in Step 4 of Example 49 providing 2-(5-(alkyl)-3-(3-(alk-1-yn-1-yl)phenyl)-4-(4-sulfamoylbenzyl)-1H-pyrazol-1-yl)thiazole-4-carboxylic acids as off-white solids.

Example 51

This example describes the synthesis of 4-((1-(4-oxo-3,4-dihydrothieno[3,2-d]pyrimidin-7-yl)-3-phenyl-1H-pyrazol-4-yl)methyl)benzenesulfonamide 210 in an embodiment of the invention.

SCHEME 23

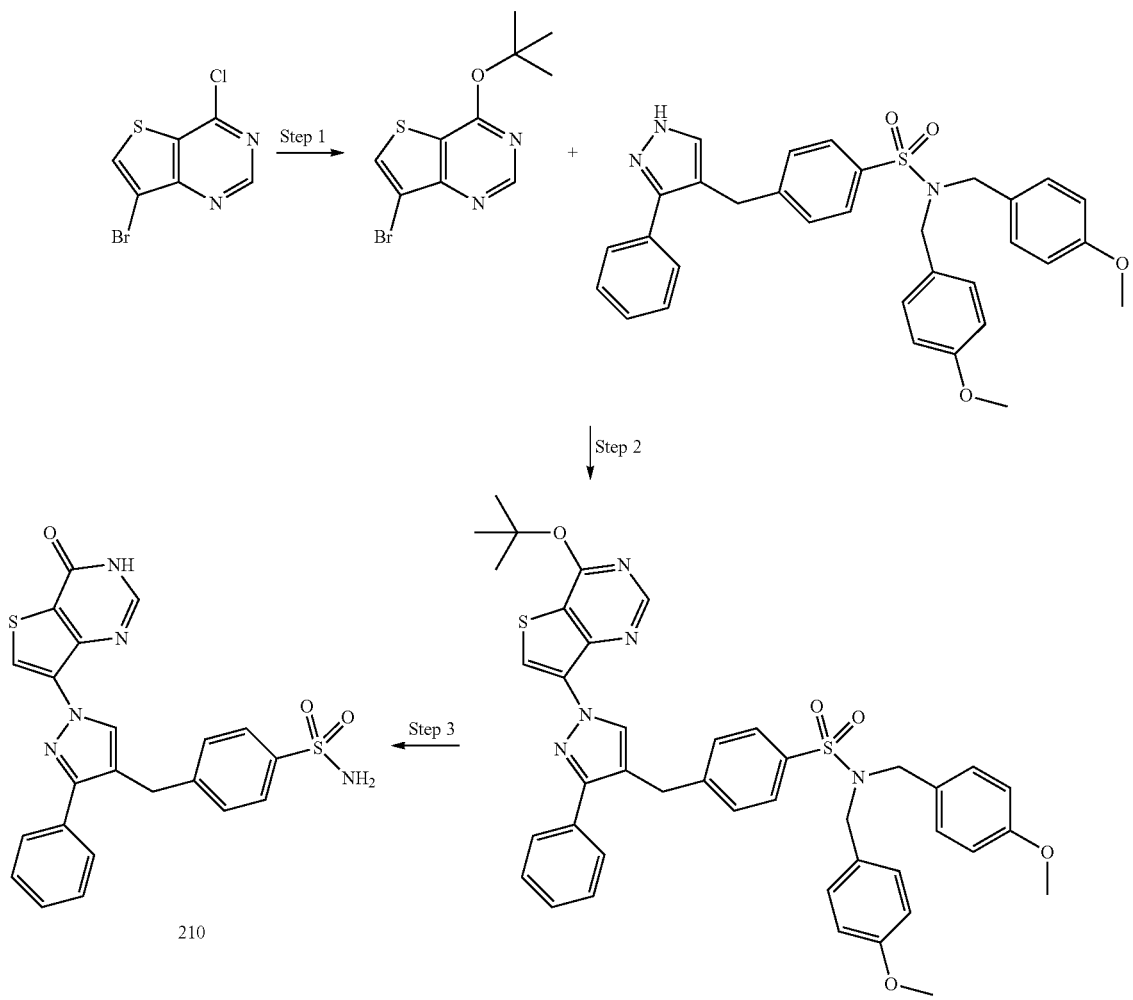

Step 1: Synthesis of 7-bromo-4-(tert-butoxy)thieno [3,2-d]pyrimidine

To a partial suspension of 7-bromo-4-chlorothieno[3,2-d] pyrimidine (998 mg, 4 mmol) in THF (12 ml) at 0° C. was added KOtBu (4.40 ml, 4.40 mmol) (1M solution in THF). The mixture was stirred at 0° C. for 1.5 h. The mixture was poured into $H_2O/NH_4Cl_{(aq)}$ (25 mL/25 mL) and extracted with EtOAc (50 mL×2). The combined organic layer was dried ($Na_2SO_4$) and filtered. After removal of solvent, the product was purified by silica gel chromatography using 5-10% EtOAc/hexane as the eluent to give 7-bromo-4-(tert-butoxy)thieno[3,2-d]pyrimidine (350 mg, 1.219 mmol, 30.5% yield).

Step 2: Synthesis of 4-((1-(4-(tert-butoxy)thieno[3, 2-d]pyrimidin-7-yl)-3-phenyl-1H-pyrazol-4-yl) methyl)-N,N-bis(4-methoxybenzyl)benzenesulfonamide In a microwave tube was placed N,N-bis(4-methoxybenzyl)-4-((3-phenyl-1H-pyrazol-4-yl)methyl)benzenesulfonamide (138 mg, 0.25 mmol), 7-bromo-4-(tert-butoxy)thieno [3,2-d]pyrimidine (71.8 mg, 0.250 mmol), (1S,2S)—N1,N2-dimethylcyclohexane-1,2-diamine (7.11 mg, 0.050 mmol), CuI (4.76 mg, 0.025 mmol), and Phosphoric acid, potassium salt (159 mg, 0.750 mmol). The air was removed and re-filled with $N_2$ (3 times). Then Toluene (Volume: 2 ml) was added and the mixture was stirred at 110° C. for overnight. After cooling to rt, the mixture was dilute with EtOAc (3 mL) and filtered through celite and eluted with EtOAc. The filtrate was concentrated and the mixture was purified by silica gel chromatography using 10-25% EtOAc/hexane as the eluent to give 4-((1-(4-(tert-butoxy)thieno[3,2-d]pyrimidin-7-yl)-3-phenyl-1H-pyrazol-4-yl)methyl)-N,N-bis(4-methoxybenzyl)benzenesulfonamide (64 mg, 0.084 mmol, 33.7% yield). MS (M+H)$^+$=760.

Step 3: Synthesis of 4-((1-(4-oxo-3,4-dihydrothieno [3,2-d]pyrimidin-7-yl)-3-phenyl-1H-pyrazol-4-yl) methyl)benzenesulfonamide (210)

To a solution of 4-((1-(4-(tert-butoxy)thieno[3,2-d]pyrimidin-7-yl)-3-phenyl-1H-pyrazol-4-yl)methyl)-N,N-bis (4-methoxybenzyl)benzenesulfonamide (64 mg, 0.084 mmol) in 1,2-Dichloroethane (1 ml) was add TFA (1 ml, 12.98 mmol). The tube was sealed and heated at 100° C. for 30 min under microwave irradiation. The mixture was poured into EtOAc/$H_2O$ (30 mL/30 mL) and $Na_2CO_{3(aq)}$ was added until the pH of aqueous layer is ca. 7.5-8. The organic layer with some suspension was washed with $H_2O$ (20 mL×3) and then concentrated to remove all the solvent and trace of $H_2O$. The product was dried in vacuo for 10 min. Then, to the product was added EtOAc (5 mL) and then hexane (50 mL). The solid was filtered and washed with 5% EtOAc/hexane (3 mL×3) and then dried to give 4-((1-(4-oxo-3,4-dihydrothieno[3,2-d]pyrimidin-7-yl)-3-phenyl-1H-pyrazol-4-yl)methyl)benzenesulfonamide 210 (36.5 mg, 0.079 mmol, 93% yield) as an off white solid. $^1$H NMR (400 MHz, DMSO-d$_6$) δ 12.79 (s, 1H), 8.71 (s, 1H), 8.35 (s, 1H), 8.27 (s, 1H), 7.74-7.68 (m, 2H), 7.68-7.62 (m, 2H), 7.45-7.39 (m, 2H), 7.39-7.34 (m, 3H), 7.25 (s, 2H), 4.16 (s, 2H); MS (M+H)$^+$=464.

Example 52

This example describes the synthesis of 4-((1-(4-aminothieno[3,2-d]pyrimidin-7-yl)-3-phenyl-1H-pyrazol-4-yl) methyl)benzenesulfonamide, TFA 211 in an embodiment of the invention.

SCHEME 24

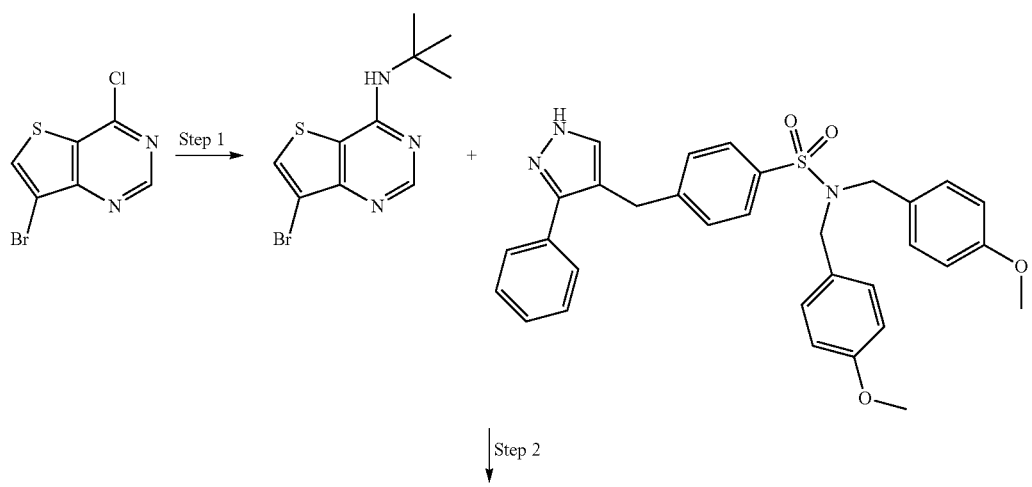

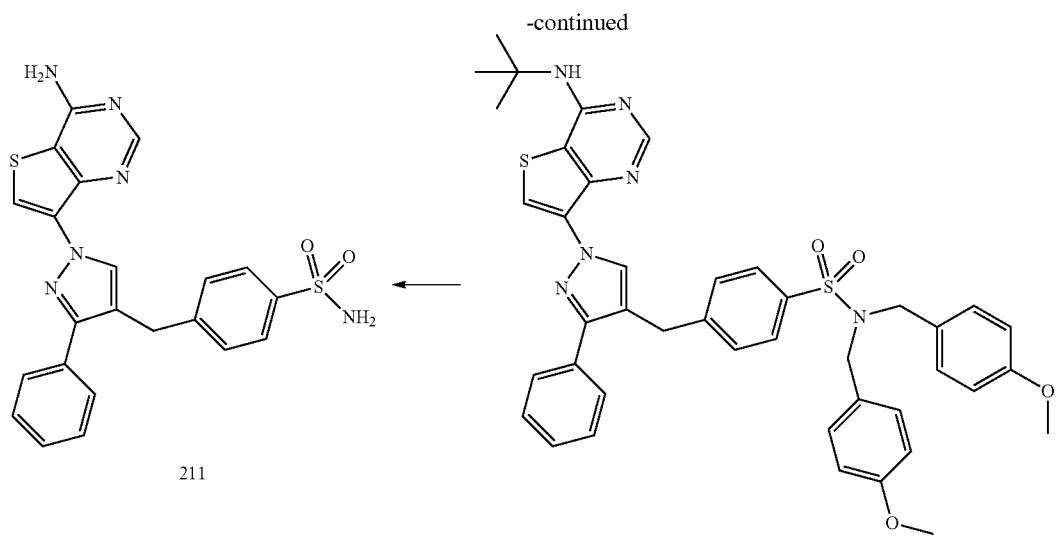

Step 1: Synthesis of 7-bromo-N-(tert-butyl)thieno[3,2-d]pyrimidin-4-amine

To a partial suspension of 7-bromo-4-chlorothieno[3,2-d]pyrimidine (0.998 g, 4 mmol) in EtOH (6 ml) at 80° C. was added 2-methylpropan-2-amine (0.585 g, 8.0 mmol) and then Hunig's Base (0.699 ml, 4.0 mmol). The mixture was seared and stirred at 80° C. for overnight. The mixture was diluted with $CH_2Cl_2$ and concentrated to remove all the solvent. The product was dissolved in EtOAc (50 mL) and washed with $H_2O$ (50 mL). The organic layer was dried ($Na_2SO_4$) and filtered. After removal of solvent, the product was purified by silica gel chromatography using 2-5-10% EtOAc/$CH_2Cl_2$ as the eluent to give 7-bromo-N-(tert-butyl)thieno[3,2-d]pyrimidin-4-amine (1.09 g, 3.81 mmol, 95% yield).

Step 2: Synthesis of 4-((1-(4-aminothieno[3,2-d]pyrimidin-7-yl)-3-phenyl-1H-pyrazol-4-yl)methyl)benzenesulfonamide, TFA (211)

In a microwave tube was placed N,N-bis(4-methoxybenzyl)-4-((3-phenyl-1H-pyrazol-4-yl)methyl)benzenesulfonamide (138 mg, 0.25 mmol), 7-bromo-N-(tert-butyl)thieno[3,2-d]pyrimidin-4-amine (71.5 mg, 0.250 mmol), (1S,2S)—N1,N2-dimethylcyclohexane-1,2-diamine (7.11 mg, 0.050 mmol), CuI (4.76 mg, 0.025 mmol), and Phosphoric acid, potassium salt (159 mg, 0.750 mmol). The air was removed and re-filled with $N_2$ (3 times). Then Toluene (2 ml) was added and the mixture was stirred at 110° C. for overnight. After cooling to rt, the mixture was dilute with EtOAc (3 mL) and filtered through celite and eluted with EtOAc. The filtrate was concentrated and the mixture was purified by silica gel chromatography using 10-25% EtOAc/hexane as the eluent to give 4-((1-(4-(tert-butylamino)thieno[3,2-d]pyrimidin-7-yl)-3-phenyl-1H-pyrazol-4-yl)methyl)-N,N-bis(4-methoxybenzyl)benzenesulfonamide. The product was contained some impurity and was subjected for removing the protection groups directly. The product was dissolved in TFA/dichloroethane (2 mL/1 mL) and was heated at 100° C. for 1 h under microwave irradiation. Then, the mixture heated at 120° C. for another 1.5 h under microwave irradiation. The mixture was concentrated and submit for purification to give 4-((1-(4-aminothieno[3,2-d]pyrimidin-7-yl)-3-phenyl-1H-pyrazol-4-yl)methyl)benzenesulfonamide, TFA 211 (5.7 mg, 9.89 μmol, 3.95% yield). $^1$H NMR (400 MHz, DMSO-$d_6$) δ 8.92 (d, J=4.9 Hz, 1H), 8.47 (d, J=1.6 Hz, 1H), 8.32 (d, J=2.2 Hz, 1H), 7.87 (s, 2H), 7.69 (m, 4H), 7.49-7.30 (m, 5H), 7.26 (s, 2H), 4.17 (s, 2H); MS (M+H)$^+$=463.

Example 53

This example describes the synthesis of 1-methyl-2-(3-phenyl-4-(4-sulfamoylbenzyl)-1H-pyrazol-1-yl)-1H-imidazole-5-carboxylic acid, TFA 212 in an embodiment of the invention.

SCHEME 25

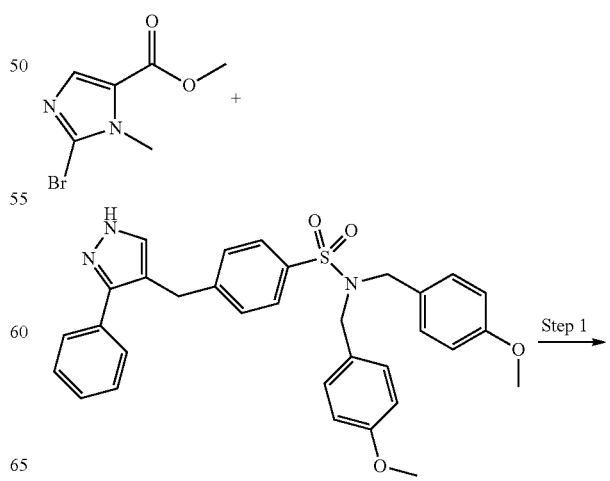

-continued

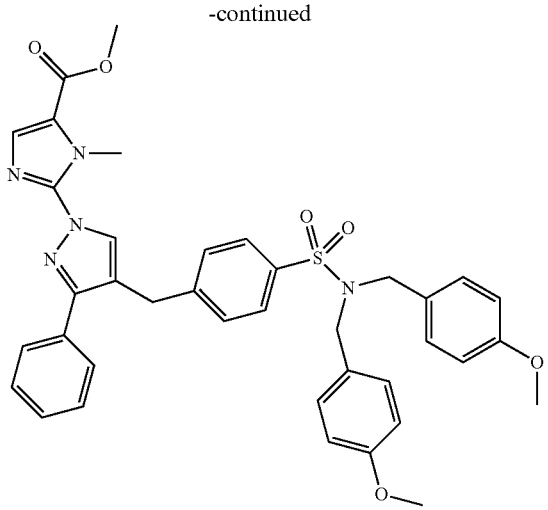

↓ Step 2

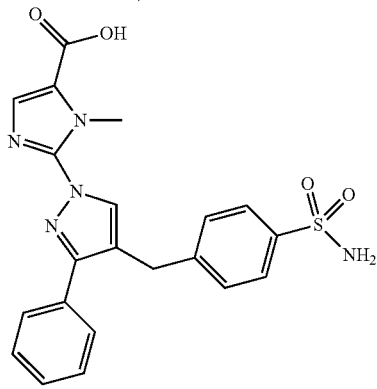

212

Step 1: Synthesis of methyl 2-(4-(4-(N,N-bis(4-methoxybenzyl)sulfamoyl)benzyl)-3-phenyl-1H-pyrazol-1-yl)-1-methyl-1H-imidazole-5-carboxylate In a microwave tube was placed N,N-bis(4-methoxybenzyl)-4-((3-phenyl-1H-pyrazol-4-yl)methyl)benzenesulfonamide (138 mg, 0.25 mmol), methyl 2-bromo-1-methyl-1H-imidazole-5-carboxylate (54.8 mg, 0.25 mmol), (1S,2S)—N1,N2-dimethylcyclohexane-1,2-diamine (14.22 mg, 0.100 mmol), CuI (9.52 mg, 0.050 mmol), and Phosphoric acid, potassium salt (159 mg, 0.750 mmol). The air was removed and re-filled with $N_2$ (3 times). Then Toluene (2 ml) was added and the mixture was stirred at 110° C. for overnight. After cooling to rt, the mixture was dilute with EtOAc (3 mL) and filtered through celite and eluted with EtOAc. The filtrate was concentrated and the mixture was purified by silica gel chromatography using 10-25% EtOAc/hexane as the eluent to give methyl 2-(4-(4-(N,N-bis(4-methoxybenzyl)sulfamoyl)benzyl)-3-phenyl-1H-pyrazol-1-yl)-1-methyl-1H-imidazole-5-carboxylate (57 mg, 0.082 mmol, 33.0% yield). MS $(M+H)^+$=692.

Step 2: Synthesis of 1-methyl-2-(3-phenyl-4-(4-sulfamoylbenzyl)-1H-pyrazol-1-yl)-1H-imidazole-5-carboxylic acid, TFA (212)

To a solution of methyl 2-(4-(4-(N,N-bis(4-methoxybenzyl)sulfamoyl)benzyl)-3-phenyl-1H-pyrazol-1-yl)-1-methyl-1H-imidazole-5-carboxylate (57 mg, 0.082 mmol) in THF (1 mL) was added LiOH(aq) (1.5 N, 0.4 mL, 0.6 mmol). The mixture was stirred at rt for 2 h. Then, 1 N HCl(aq) was added slowly until the pH of aqueous layer was about 4-5. The mixture was extracted with EtOAc (2 mL×10) until no product was detected by UV from organic layer. The combined organic layer was dried ($Na_2SO_4$) and filtered. After removal of solvent, the product was dried in vacuo to give crude acid intermediate. The intermediate was then dissolved in 1,2-dichloroethane/TFA (0.6 mL/0.6 mL) in a microwave tube. The tube was sealed and heat at 100° C. under microwave irradiation for 20 min. The mixture was concentrated and the residue was dissolved in DMF, filter, and submitted for purification to give 1-methyl-2-(3-phenyl-4-(4-sulfamoylbenzyl)-1H-pyrazol-1-yl)-1H-imidazole-5-carboxylic acid, TFA 212 (2 mg, 3.63 µmol, 4.40% yield). MS $(M+H)^+$=438.

Example 54

This example describes the synthesis of 5-(3-phenyl-4-(4-sulfamoylbenzyl)-1H-pyrazol-1-yl)thiophene-3-carboxylic acid, TFA 213 in an embodiment of the invention.

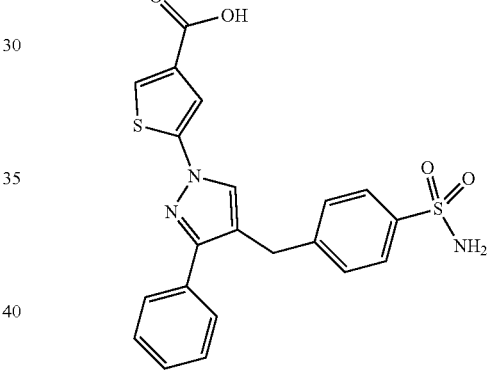

213

According to similar procedures described above for 212, the title compound was prepared starting from N,N-bis(4-methoxybenzyl)-4-((3-phenyl-1H-pyrazol-4-yl)methyl)benzenesulfonamide and ethyl 5-bromothiophene-3-carboxylate and then hydrolyzed. The final product was purified by reverse phase HPLC chromatography to give 5-(3-phenyl-4-(4-sulfamoylbenzyl)-1H-pyrazol-1-yl)thiophene-3-carboxylic acid, TFA 213. $^1$H NMR (400 MHz, DMSO-$d_6$) δ 12.88 (s, 1H), 8.45 (s, 1H), 7.96 (d, J=1.6 Hz, 1H), 7.73-7.66 (m, 2H), 7.63-7.55 (m, 3H), 7.44-7.32 (m, 5H), 7.26 (s, 2H), 4.08 (s, 2H); MS $(M+H)^+$=440.

Example 55

This example describes the synthesis of 2-(5-(cyclopropylmethyl)-3-(4-fluoro-3-(1-methyl-1H-pyrazol-4-yl)phenyl)-4-(2-fluoro-4-sulfamoylbenzyl)-1H-pyrazol-1-yl)thiazole-4-carboxylic acid, TFA 214 in an embodiment of the invention.

SCHEME 26
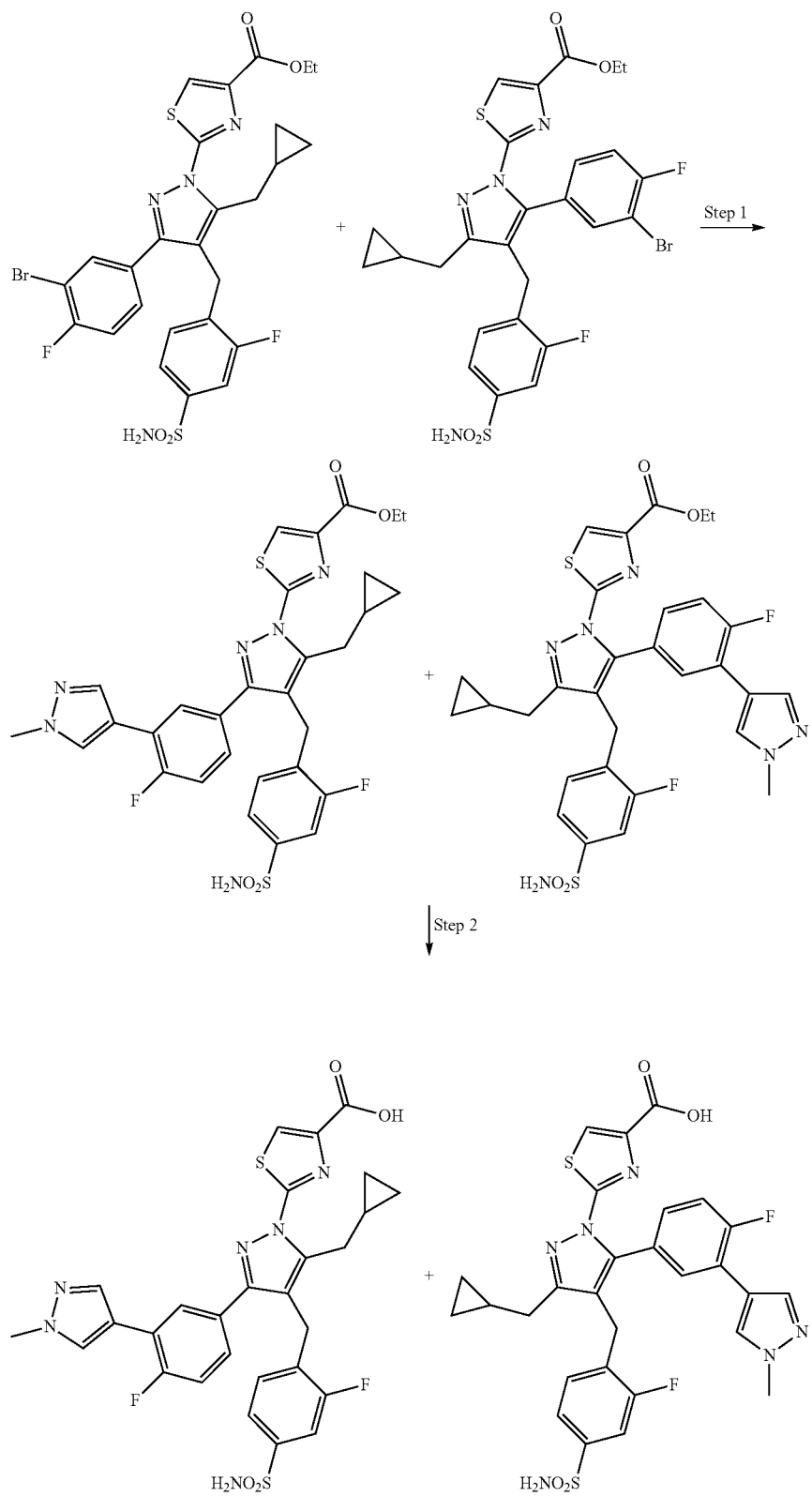

Step 1: Synthesis of ethyl 2-(5-(cyclopropylmethyl)-3-(4-fluoro-3-(1-methyl-1H-pyrazol-4-yl)phenyl)-4-(2-fluoro-4-sulfamoylbenzyl)-1H-pyrazol-1-yl)thiazole-4-carboxylate and ethyl 2-(3-(cyclopropylmethyl)-5-(4-fluoro-3-(1-methyl-1H-pyrazol-4-yl)phenyl)-4-(2-fluoro-4-sulfamoylbenzyl)-1H-pyrazol-1-yl)thiazole-4-carboxylate In a microwave tube was placed ethyl 2-(3-(3-bromo-4-fluorophenyl)-5-(cyclopropylmethyl)-4-(2-fluoro-4-sulfamoylbenzyl)-1H-pyrazol-1-yl)thiazole-4-carboxylate (63.8 mg, 0.1 mmol) (2 regio-isomers), 1-methyl-4-(4,4,5,5-tetramethyl-1,3,2-dioxaborolan-2-yl)-1H-pyrazole (41.6 mg, 0.20 mmol), PdCl$_2$(dppf)-CH$_2$Cl$_2$ adduct (8.17 mg, 10.0 μmol), and K$_2$CO$_3$ (69.1 mg, 0.50 mmol). The air was removed and re-filled with N$_2$ (repeat for 3 times). Then, a mixture of 1,4-Dioxane (1.5 ml)/Water (0.5 ml) was added. The mixture was stirred at 95° C. (pre-heated) for 1.5 h. After cooling to rt, the mixture was extracted with EtOAc (2 mL×3). The combined organic layer was dried (Na$_2$SO$_4$) and filtered. After removal of solvent, the product was purified by silica gel chromatography using 40-70% EtOAc/hexane as the eluent to give ethyl 2-(5-(cyclopropylmethyl)-3-(4-fluoro-3-(1-methyl-1H-pyrazol-4-yl)phenyl)-4-(2-fluoro-4-sulfamoylbenzyl)-1H-pyrazol-1-yl)thiazole-4-carboxylate (27 mg, 0.042 mmol, 42.3% yield) and ethyl 2-(3-(cyclopropylmethyl)-5-(4-fluoro-3-(1-methyl-1H-pyrazol-4-yl)phenyl)-4-(2-fluoro-4-sulfamoylbenzyl)-1H-pyrazol-1-yl)thiazole-4-carboxylate (27 mg, 0.042 mmol, 42.3% yield), total 54 mg.

Step 2: Synthesis of 2-(5-(cyclopropylmethyl)-3-(4-fluoro-3-(1-methyl-1H-pyrazol-4-yl)phenyl)-4-(2-fluoro-4-sulfamoylbenzyl)-1H-pyrazol-1-yl)thiazole-4-carboxylic acid, TFA (214)

To a solution of ethyl 2-(5-(cyclopropylmethyl)-3-(4-fluoro-3-(1-methyl-1H-pyrazol-4-yl)phenyl)-4-(2-fluoro-4-sulfamoylbenzyl)-1H-pyrazol-1-yl)thiazole-4-carboxylate (27 mg, 0.042 mmol) and ethyl 2-(3-(cyclopropylmethyl)-5-(4-fluoro-3-(1-methyl-1H-pyrazol-4-yl)phenyl)-4-(2-fluoro-4-sulfamoylbenzyl)-1H-pyrazol-1-yl)thiazole-4-carboxylate (27 mg, 0.042 mmol) in THF (1 ml)/MeOH (0.3 ml) was added LiOH(aq) (1.5 N, 0.4 mL, 0.6 mmol). The mixture was stirred at 50° C. for 2 h. After cooling to rt, 1N HCl$_{(aq)}$ was added until the pH of aqueous layer is ca. 4. The mixture was concentrated and the residue was dissolved in DMF, filtered through a filter, and submitted for purification to give 2-(5-(cyclopropylmethyl)-3-(4-fluoro-3-(1-methyl-1H-pyrazol-4-yl)phenyl)-4-(2-fluoro-4-sulfamoylbenzyl)-1H-pyrazol-1-yl)thiazole-4-carboxylic acid, TFA (0.9 mg, 1.242 μmol, 2.94% yield) 214 (powder weight: 0.9 mg, tR=5.30 min, final QC) and 2-(3-(cyclopropylmethyl)-5-(4-fluoro-3-(1-methyl-1H-pyrazol-4-yl)phenyl)-4-(2-fluoro-4-sulfamoylbenzyl)-1H-pyrazol-1-yl)thiazole-4-carboxylic acid, TFA (not collected) (for 214) $^1$H NMR (400 MHz, DMSO-d$_6$) δ 13.15 (s, 1H), 8.29 (s, 1H), 8.01 (d, J=2.1 Hz, 1H), 7.78-7.72 (m, 2H), 7.52 (dd, J=9.6, 1.8 Hz, 1H), 7.46 (dd, J=8.0, 1.8 Hz, 1H), 7.40 (s, 2H), 7.34 (ddd, J=8.5, 5.0, 2.2 Hz, 1H), 7.26 (dd, J=11.0, 8.5 Hz, 1H), 7.12 (t, J=7.8 Hz, 1H), 4.10 (s, 2H), 3.85 (s, 3H), 3.15 (d, J=7.0 Hz, 2H), 1.14-1.01 (m, 1H), 0.37-0.14 (m, 4H); MS (M+H)$^+$=611.

Example 56

This example describes the synthesis of 2-(5-(cyclopropylmethyl)-3-(3-(3,5-dimethylisoxazol-4-yl)-4-fluorophenyl)-4-(2-fluoro-4-sulfamoylbenzyl)-1H-pyrazol-1-yl)thiazole-4-carboxylic acid, TFA 215 and 2-(3-(cyclopropylmethyl)-5-(3-(3,5-dimethylisoxazol-4-yl)-4-fluorophenyl)-4-(2-fluoro-4-sulfamoylbenzyl)-1H-pyrazol-1-yl)thiazole-4-carboxylic acid, TFA 216 in an embodiment of the invention.

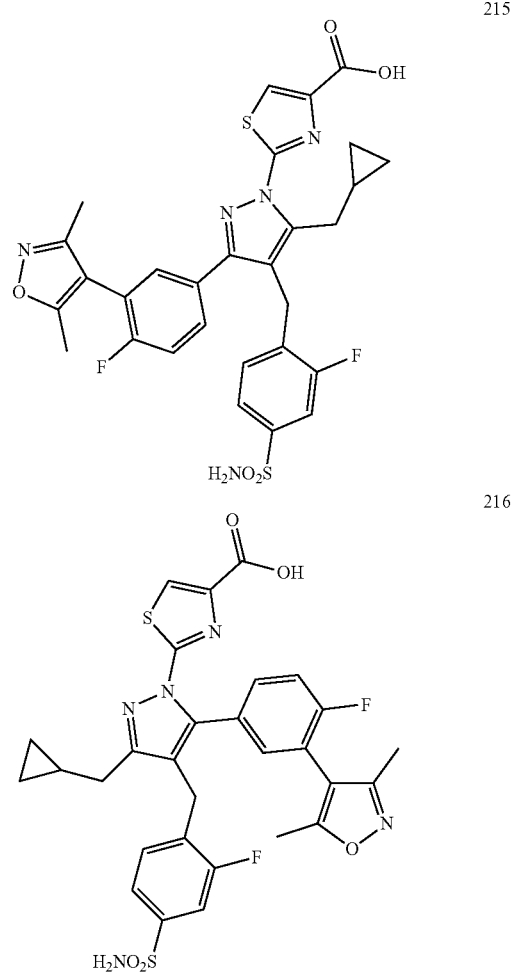

According to similar procedures described above for 212, the title compounds were prepared and the final product was purified by reverse phase HPLC chromatography to give 2-(5-(cyclopropylmethyl)-3-(3-(3,5-dimethylisoxazol-4-yl)-4-fluorophenyl)-4-(2-fluoro-4-sulfamoylbenzyl)-1H-pyrazol-1-yl)thiazole-4-carboxylic acid, TFA 215 and 2-(3-(cyclopropylmethyl)-5-(3-(3,5-dimethylisoxazol-4-yl)-4-fluorophenyl)-4-(2-fluoro-4-sulfamoylbenzyl)-1H-pyrazol-1-yl)thiazole-4-carboxylic acid, TFA 216. MS (M+H)$^+$=626.

Example 57

This example describes the synthesis of 2-(5-(cyclopropylmethyl)-3-(4-fluoro-3-(1-methyl-1H-pyrazol-4-yl)phenyl)-4-(3-fluoro-4-sulfamoylbenzyl)-1H-pyrazol-1-yl)thiazole-4-carboxylic acid, TFA 217 and 2-(3-(cyclopropylmethyl)-5-(4-fluoro-3-(1-methyl-1H-pyrazol-4-yl)phenyl)-4-(3-fluoro-4-sulfamoylbenzyl)-1H-pyrazol-1-yl)thiazole-4-carboxylic acid, TFA 218 in an embodiment of the invention.

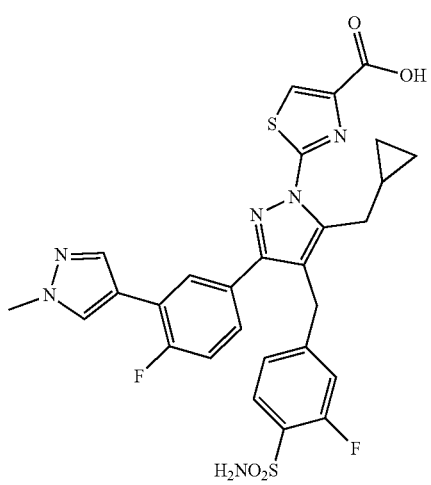

217

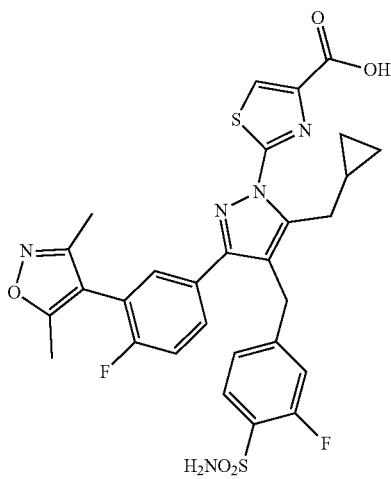

219

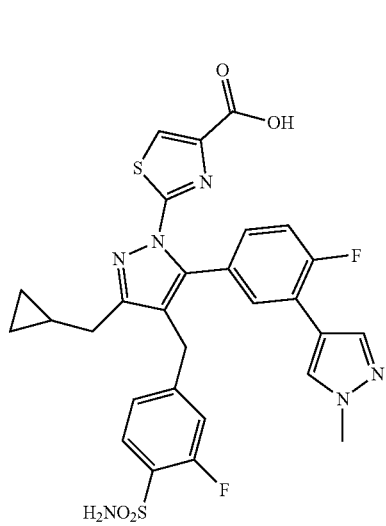

218

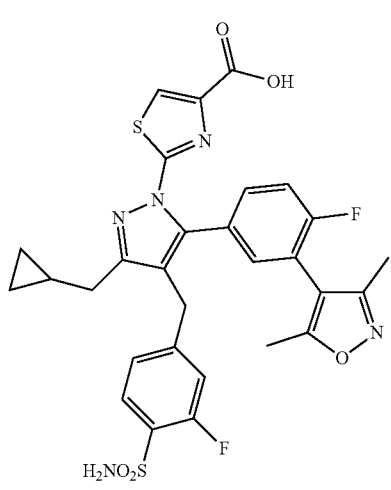

220

According to similar procedures described above for 212, the title compounds were prepared and the final product was purified by reverse phase HPLC chromatography to give 2-(5-(cyclopropylmethyl)-3-(4-fluoro-3-(1-methyl-1H-pyrazol-4-yl)phenyl)-4-(3-fluoro-4-sulfamoylbenzyl)-1H-pyrazol-1-yl)thiazole-4-carboxylic acid, TFA 217 and 2-(3-(cyclopropylmethyl)-5-(4-fluoro-3-(1-methyl-1H-pyrazol-4-yl)phenyl)-4-(3-fluoro-4-sulfamoylbenzyl)-1H-pyrazol-1-yl)thiazole-4-carboxylic acid, TFA 218. MS (M+H)$^+$=611.

Example 58

This example describes the synthesis of 2-(5-(cyclopropylmethyl)-3-(3-(3,5-dimethylisoxazol-4-yl)-4-fluorophenyl)-4-(3-fluoro-4-sulfamoylbenzyl)-1H-pyrazol-1-yl)thiazole-4-carboxylic acid, TFA 219 and 2-(3-(cyclopropylmethyl)-5-(3-(3,5-dimethylisoxazol-4-yl)-4-fluorophenyl)-4-(3-fluoro-4-sulfamoylbenzyl)-1H-pyrazol-1-yl)thiazole-4-carboxylic acid, TFA 220 in an embodiment of the invention.

According to similar procedures described above for 212, the title compounds were prepared and the final product was purified by reverse phase HPLC chromatography to give 2-(5-(cyclopropylmethyl)-3-(3-(3,5-dimethylisoxazol-4-yl)-4-fluorophenyl)-4-(3-fluoro-4-sulfamoylbenzyl)-1H-pyrazol-1-yl)thiazole-4-carboxylic acid, TFA 219 and 2-(3-(cyclopropylmethyl)-5-(3-(3,5-dimethylisoxazol-4-yl)-4-fluorophenyl)-4-(3-fluoro-4-sulfamoylbenzyl)-1H-pyrazol-1-yl)thiazole-4-carboxylic acid, TFA 220. MS (M+H)$^+$=626.

Example 59

This example describes the synthesis of 2-(5-(cyclopropylmethyl)-3-(4-fluoro-3-(4-methylthiophen-2-yl)phenyl)-4-(2-fluoro-4-sulfamoylbenzyl)-1H-pyrazol-1-yl)thiazole-4-carboxylic acid, TFA 221 and 2-(3-(cyclopropylmethyl)-5-(4-fluoro-3-(4-methylthiophen-2-yl)phenyl)-4-(2-fluoro-4-sulfamoylbenzyl)-1H-pyrazol-1-yl)thiazole-4-carboxylic acid, TFA 222 in an embodiment of the invention.

221

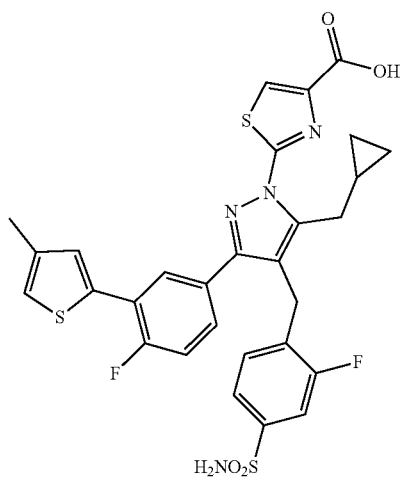

223

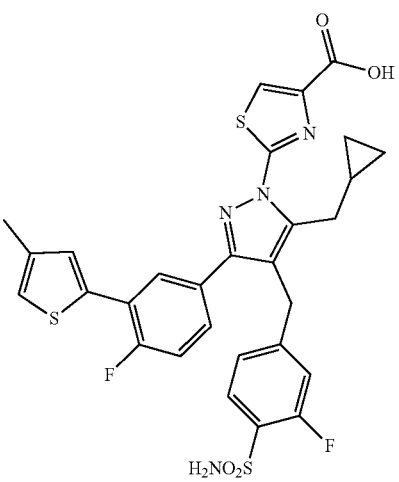

222

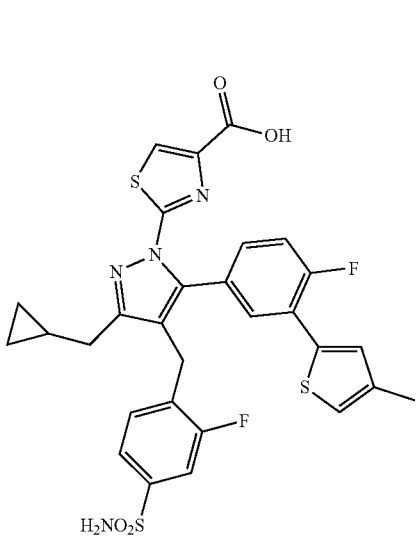

224

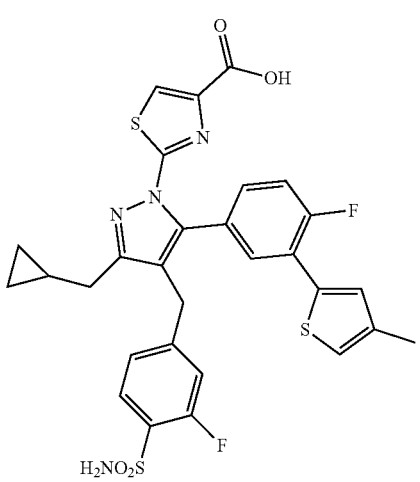

According to similar procedures described above for 212, the title compounds were prepared and the final product was purified by reverse phase HPLC chromatography to give 2-(5-(cyclopropylmethyl)-3-(4-fluoro-3-(4-methylthiophen-2-yl)phenyl)-4-(2-fluoro-4-sulfamoylbenzyl)-1H-pyrazol-1-yl)thiazole-4-carboxylic acid, TFA 221 and 2-(3-(cyclopropylmethyl)-5-(4-fluoro-3-(4-methylthiophen-2-yl)phenyl)-4-(2-fluoro-4-sulfamoylbenzyl)-1H-pyrazol-1-yl)thiazole-4-carboxylic acid, TFA 222. MS (M+H)$^+$=627.

Example 60

This example describes the synthesis of 2-(5-(cyclopropylmethyl)-3-(4-fluoro-3-(4-methylthiophen-2-yl)phenyl)-4-(3-fluoro-4-sulfamoylbenzyl)-1H-pyrazol-1-yl)thiazole-4-carboxylic acid, TFA 223 and 2-(3-(cyclopropylmethyl)-5-(4-fluoro-3-(4-methylthiophen-2-yl)phenyl)-4-(3-fluoro-4-sulfamoylbenzyl)-1H-pyrazol-1-yl)thiazole-4-carboxylic acid, TFA 224 in an embodiment of the invention.

According to similar procedures described above for 212, the title compounds were prepared and the final product was purified by reverse phase HPLC chromatography to give 2-(5-(cyclopropylmethyl)-3-(4-fluoro-3-(4-methylthiophen-2-yl)phenyl)-4-(3-fluoro-4-sulfamoylbenzyl)-1H-pyrazol-1-yl)thiazole-4-carboxylic acid, TFA 223 and 2-(3-(cyclopropylmethyl)-5-(4-fluoro-3-(4-methylthiophen-2-yl)phenyl)-4-(3-fluoro-4-sulfamoylbenzyl)-1H-pyrazol-1-yl)thiazole-4-carboxylic acid, TFA 224. MS (M+H)$^+$=627.

Example 61

This example describes the synthesis of 2-(5-(cyclopropylmethyl)-3-(4-fluoro-3-(5-methylthiophen-2-yl)phenyl)-4-(2-fluoro-4-sulfamoylbenzyl)-1H-pyrazol-1-yl)thiazole-4-carboxylic acid, TFA 225 and 2-(3-(cyclopropylmethyl)-5-(4-fluoro-3-(5-methylthiophen-2-yl)phenyl)-4-(2-fluoro-4-sulfamoylbenzyl)-1H-pyrazol-1-yl)thiazole-4-carboxylic acid, TFA 226 in an embodiment of the invention.

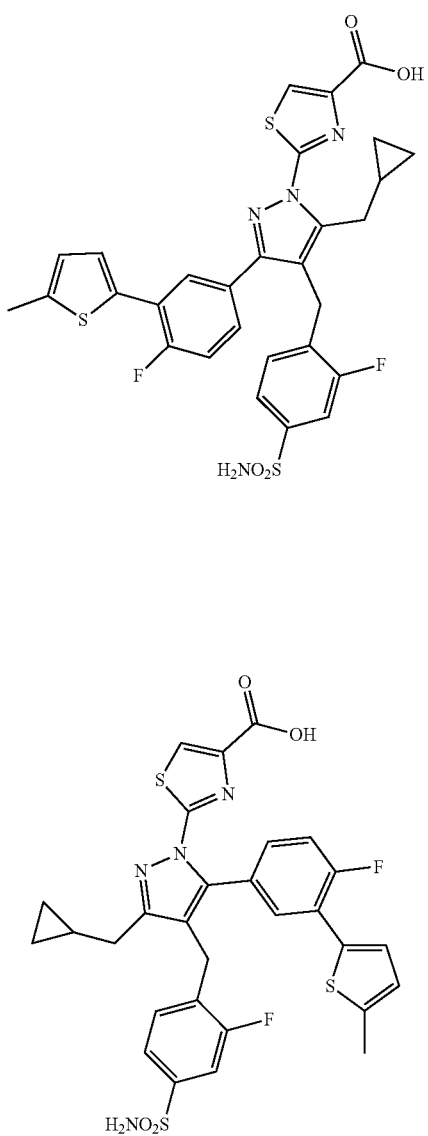

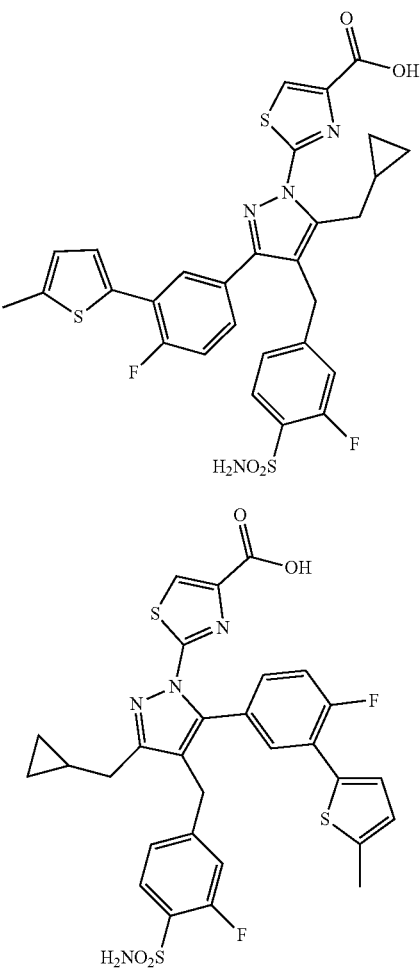

According to similar procedures described above for 212, the title compounds were prepared and the final product was purified by reverse phase HPLC chromatography to give 2-(5-(cyclopropylmethyl)-3-(4-fluoro-3-(5-methylthiophen-2-yl)phenyl)-4-(2-fluoro-4-sulfamoylbenzyl)-1H-pyrazol-1-yl)thiazole-4-carboxylic acid, TFA 225 and 2-(3-(cyclopropylmethyl)-5-(4-fluoro-3-(5-methylthiophen-2-yl)phenyl)-4-(2-fluoro-4-sulfamoylbenzyl)-1H-pyrazol-1-yl)thiazole-4-carboxylic acid, TFA 226. MS (M+H)$^+$=627.

Example 62

This example describes the synthesis of 2-(5-(cyclopropylmethyl)-3-(4-fluoro-3-(5-methylthiophen-2-yl)phenyl)-4-(3-fluoro-4-sulfamoylbenzyl)-1H-pyrazol-1-yl)thiazole-4-carboxylic acid, TFA 227 and 2-(3-(cyclopropylmethyl)-5-(4-fluoro-3-(5-methylthiophen-2-yl)phenyl)-4-(3-fluoro-4-sulfamoylbenzyl)-1H-pyrazol-1-yl)thiazole-4-carboxylic acid, TFA 228 in an embodiment of the invention.

According to similar procedures described above for 212, the title compounds were prepared and the final product was purified by reverse phase HPLC chromatography to give 2-(5-(cyclopropylmethyl)-3-(4-fluoro-3-(5-methylthiophen-2-yl)phenyl)-4-(3-fluoro-4-sulfamoylbenzyl)-1H-pyrazol-1-yl)thiazole-4-carboxylic acid, TFA 227 and 2-(3-(cyclopropylmethyl)-5-(4-fluoro-3-(5-methylthiophen-2-yl)phenyl)-4-(3-fluoro-4-sulfamoylbenzyl)-1H-pyrazol-1-yl)thiazole-4-carboxylic acid, TFA 228. MS (M+H)$^+$=627; (for 227, HCl salt). $^1$H NMR (400 MHz, DMSO-d$_6$) δ 13.13 (s, 1H), 8.29 (s, 1H), 7.67 (t, J=7.9 Hz, 1H), 7.62 (dd, J=7.6, 2.2 Hz, 1H), 7.58 (s, 2H), 7.50 (ddd, J=8.5, 4.8, 2.2 Hz, 1H), 7.34 (dd, J=11.3, 8.6 Hz, 1H), 7.19 (dd, J=11.3, 1.6 Hz, 1H), 7.13 (dd, J=3.6, 0.9 Hz, 1H), 7.06 (dd, J=8.1, 1.6 Hz, 1H), 6.81 (dt, J=3.6, 1.1 Hz, 1H), 4.14 (s, 2H), 3.15 (d, J=6.9 Hz, 2H), 2.44 (d, J=1.1 Hz, 3H), 1.19-1.03 (m, 1H), 0.39-0.28 (m, 2H), 0.24-0.14 (m, 2H).

Example 63

This example describes the synthesis of ethyl 2-(5-(cyclopropylmethyl)-3-(4-fluoro-3-(5-methylthiophen-2-yl)phenyl)-4-(3-fluoro-4-sulfamoylbenzyl)-1H-pyrazol-1-yl)thiazole-4-carboxylate 229 in an embodiment of the invention.

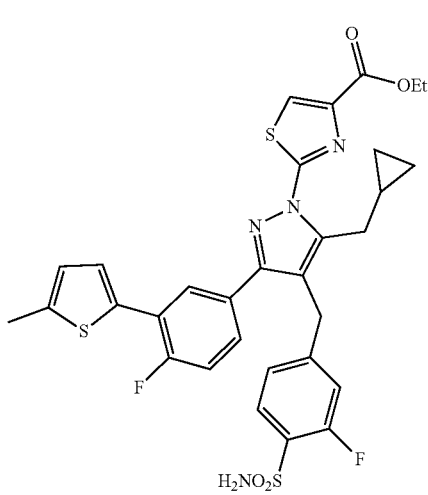

229

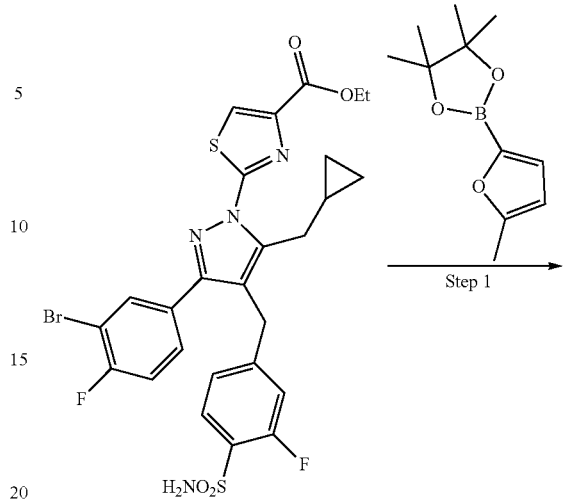

In a microwave tube was placed ethyl 2-(3-(3-bromo-4-fluorophenyl)-5-(cyclopropylmethyl)-4-(3-fluoro-4-sulfamoylbenzyl)-1H-pyrazol-1-yl)thiazole-4-carboxylate (287 mg, 0.45 mmol) (2 regio-isomers), PdCl₂(dppf)-CH₂Cl₂ adduct (55.1 mg, 0.068 mmol), and K₂CO₃ (466 mg, 3.38 mmol). The air was removed and re-filled with N₂ (repeat for 3 times). Then, a solution of 4,4,5,5-tetramethyl-2-(5-methylthiophen-2-yl)-1,3,2-dioxaborolane (252 mg, 1.125 mmol) in 1,4-Dioxane (4.5 ml) and Water (1.5 ml) was added. The mixture was stirred at 90° C. (pre-heated) for 1.5 h. After cooling to rt, the mixture was extracted with EtOAc (5 mL×3). The combined organic layer was dried (Na₂SO₄) and filtered. After removal of solvent, the product was purified by silica gel chromatography using 25-35% EtOAc/hexane as the eluent to give desired product. The product has light brown color and can be re-crystallized from CH₂Cl₂/hexane system. Dissolved the product in CH₂Cl₂ (5 mL) and then added hexane (ca. 10 mL). Then slowly removed solvent by air blow to ca. ¼ amount of solvent and then added hexane (15 mL). The solid was filtered and triturated with hexane (3 mL×3) and then dried to give ethyl 2-(5-(cyclopropylmethyl)-3-(4-fluoro-3-(5-methylthiophen-2-yl)phenyl)-4-(3-fluoro-4-sulfamoylbenzyl)-1H-pyrazol-1-yl)thiazole-4-carboxylate 229 (276 mg, 0.422 mmol, 94% yield) as a off-white solid. 241 mg+35 mg, total 276 mg (2 crops). ¹H NMR (400 MHz, Chloroform-d) δ 7.96 (s, 1H), 7.81 (t, J=7.8 Hz, 1H), 7.55 (dd, J=7.4, 2.2 Hz, 1H), 7.37 (ddd, J=8.5, 4.7, 2.2 Hz, 1H), 7.15-7.04 (m, 3H), 7.00 (dd, J=11.1, 1.6 Hz, 1H), 6.73 (dt, J=3.7, 1.0 Hz, 1H), 4.93 (s, 2H), 4.40 (q, J=7.1 Hz, 2H), 4.07 (s, 2H), 3.21 (d, J=6.8 Hz, 2H), 2.49 (d, J=1.1 Hz, 3H), 1.41 (t, J=7.1 Hz, 3H), 1.19-1.06 (m, 1H), 0.49-0.38 (m, 2H), 0.28 (dt, J=6.1, 4.7 Hz, 2H); MS (M+H)⁺=655.

Example 64

This example describes the synthesis of 2-(5-(cyclopropylmethyl)-3-(4-fluoro-3-(5-methylfuran-2-yl)phenyl)-4-(3-fluoro-4-sulfamoylbenzyl)-1H-pyrazol-1-yl)thiazole-4-carboxylic acid 230 in an embodiment of the invention.

Step 1: Synthesis of ethyl 2-(5-(cyclopropylmethyl)-3-(4-fluoro-3-(5-methylfuran-2-yl)phenyl)-4-(3-fluoro-4-sulfamoylbenzyl)-1H-pyrazol-1-yl)thiazole-4-carboxylate In a microwave tube was placed ethyl 2-(3-(3-bromo-4-fluorophenyl)-5-(cyclopropylmethyl)-4-(3-fluoro-4-sulfamoylbenzyl)-1H-pyrazol-1-yl)thiazole-4-carboxylate (31.9 mg, 0.05 mmol) (2 regio-isomers), PdCl$_2$(dppf)-CH$_2$Cl$_2$ adduct (8.17 mg, 10.0 μmol), and K$_2$CO$_3$ (51.8 mg, 0.375 mmol). The air was removed and re-filled with N$_2$ (repeat for 3 times). Then, a solution of 4,4,5,5-tetramethyl-2-(5-methylfuran-2-yl)-1,3,2-dioxaborolane (26.0 mg, 0.125 mmol) in 1,4-Dioxane (1 ml) and Water (0.5 ml) was added. The mixture was stirred at 90° C. (pre-heated) for 1.5 h. After cooling to rt, the mixture was extracted with EtOAc (3 mL×3). The combined organic layer was dried (Na$_2$SO$_4$) and filtered. After removal of solvent, the product was purified by silica gel chromatography using 20-40% EtOAc/hexane as the eluent to give ethyl 2-(5-(cyclopropylmethyl)-3-(4-fluoro-3-(5-methylfuran-2-yl)phenyl)-4-(3-fluoro-4-sulfamoylbenzyl)-1H-pyrazol-1-yl)thiazole-4-carboxylate (30 mg, 0.047 mmol, 94% yield). MS (M+H)$^+$=639.

Step 2: Synthesis of 2-(5-(cyclopropylmethyl)-3-(4-fluoro-3-(5-methylfuran-2-yl)phenyl)-4-(3-fluoro-4-sulfamoylbenzyl)-1H-pyrazol-1-yl)thiazole-4-carboxylic acid (230)

To a solution of ethyl 2-(5-(cyclopropylmethyl)-3-(4-fluoro-3-(5-methylfuran-2-yl)phenyl)-4-(3-fluoro-4-sulfamoylbenzyl)-1H-pyrazol-1-yl)thiazole-4-carboxylate (30 mg, 0.047 mmol) in THF (1 ml)/MeOH (0.3 ml) was added LiOH(aq) (1.5 N, 0.4 mL, 0.6 mmol). The mixture was stirred at 50° C. for 1 h. After cooling to rt, 1N HCl$_{(aq)}$ was added until the pH of aqueous layer is ca. 3-4. The mixture was poured into EtOAc/H$_2$O (5 mL/5 mL). The aqueous layer was extracted with EtOAc (5 mL×3). The combined organic layer was dried (Na$_2$SO$_4$) and filtered. After removal of solvent, the product was dissolved in CH$_2$Cl$_2$ (2 mL) and then added hexane (40 mL). The resulted solid was filtered and triturated with hexane (3 mL×3) and then dried under house vacuum at 50° C. for overnight to give 2-(5-(cyclopropylmethyl)-3-(4-fluoro-3-(5-methylfuran-2-yl)phenyl)-4-(3-fluoro-4-sulfamoylbenzyl)-1H-pyrazol-1-yl)thiazole-4-carboxylic acid 230 (22 mg, 0.036 mmol, 77% yield). $^1$H NMR (400 MHz, DMSO-d$_6$) δ 13.10 (s, 1H), 8.29 (s, 1H), 7.76 (dd, J=7.4, 2.3 Hz, 1H), 7.67 (t, J=7.9 Hz, 1H), 7.57 (s, 2H), 7.54 (ddd, J=8.6, 4.8, 2.3 Hz, 1H), 7.33 (dd, J=11.2, 8.6 Hz, 1H), 7.20 (dd, J=11.3, 1.6 Hz, 1H), 7.07 (dd, J=8.1, 1.6 Hz, 1H), 6.70 (t, J=3.5 Hz, 1H), 6.22 (dt, J=3.1, 1.0 Hz, 1H), 4.15 (s, 2H), 3.15 (d, J=6.9 Hz, 2H), 2.27 (s, 3H), 1.17-1.06 (m, 1H), 0.38-0.28 (m, 2H), 0.24-0.14 (m, 2H); MS (M+H)$^+$=611.

Example 65

This example describes the synthesis of 2-(5-(cyclopropylmethyl)-3-(4-fluoro-3-(5-methylthiazol-2-yl)phenyl)-4-(3-fluoro-4-sulfamoylbenzyl)-1H-pyrazol-1-yl)thiazole-4-carboxylic acid, TFA 231 in an embodiment of the invention.

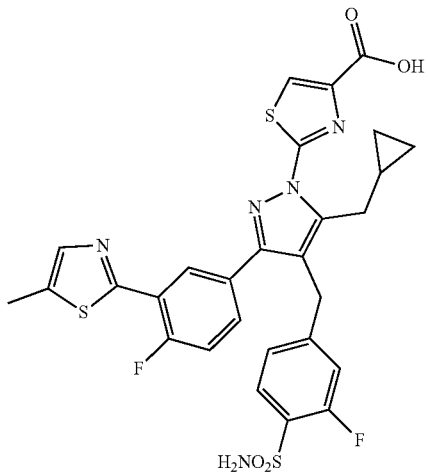

231

According to similar procedures described above for 230, the title compounds were prepared and the final product was purified by reverse phase HPLC chromatography to give 2-(5-(cyclopropylmethyl)-3-(4-fluoro-3-(5-methylthiazol-2-yl)phenyl)-4-(3-fluoro-4-sulfamoylbenzyl)-1H-pyrazol-1-yl)thiazole-4-carboxylic acid, TFA 231. $^1$H NMR (400 MHz, DMSO-d$_6$) δ 13.13 (s, 1H), 8.30 (dd, J=7.2, 2.3 Hz, 1H), 8.28 (s, 1H), 7.70-7.59 (m, 3H), 7.54 (s, 2H), 7.43 (dd, J=11.1, 8.7 Hz, 1H), 7.16 (dd, J=11.4, 1.6 Hz, 1H), 7.05 (dd, J=8.1, 1.6 Hz, 1H), 4.14 (s, 2H), 3.19-3.14 (m, 2H), 2.49 (d, J=1.2 Hz, 3H), 1.18-1.05 (m, 1H), 0.39-0.29 (m, 2H), 0.24-0.15 (m, 2H); MS (M+H)$^+$=628.

Example 66

This example describes the synthesis of 2-(5-(cyclopropylmethyl)-3-(4-fluoro-3-(2-methylthiazol-5-yl)phenyl)-4-(3-fluoro-4-sulfamoylbenzyl)-1H-pyrazol-1-yl)thiazole-4-carboxylic acid 232 in an embodiment of the invention.

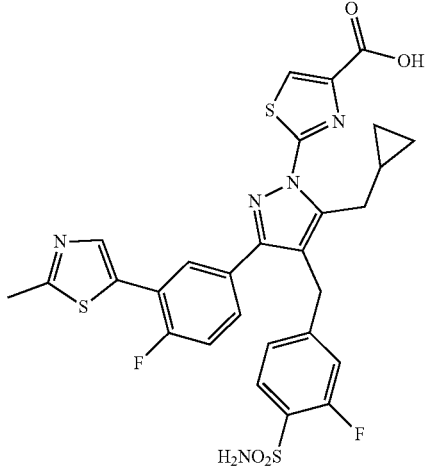

232

According to similar procedures described above for 230, the title compounds were prepared to give 2-(5-(cyclopropylmethyl)-3-(4-fluoro-3-(2-methylthiazol-5-yl)phenyl)-4-(3-fluoro-4-sulfamoylbenzyl)-1H-pyrazol-1-yl)thiazole-4-carboxylic acid 232. $^1$H NMR (400 MHz, DMSO-d$_6$) δ

13.13 (s, 1H), 8.27 (s, 1H), 7.97 (s, 1H), 7.68 (dd, J=7.4, 2.0 Hz, 1H), 7.64 (d, J=7.9 Hz, 1H), 7.57 (m, 3H), 7.39 (dd, J=10.8, 8.7 Hz, 1H), 7.17 (d, J=11.3 Hz, 1H), 7.05 (d, J=8.3 Hz, 1H), 4.15 (s, 2H), 3.16 (d, J=6.9 Hz, 2H), 2.66 (s, 3H), 1.18-1.01 (m, 1H), 0.37-0.27 (m, 2H), 0.21 (d, J=4.9 Hz, 2H); MS (M+H)⁺=628.

Example 67

This example describes the synthesis of 2-(5-(cyclopropylmethyl)-3-(4-fluoro-3-(5-methylthiophen-2-yl)phenyl)-4-(2-fluoro-4-sulfamoylbenzyl)-1H-pyrazol-1-yl)thiazole-4-carboxylic acid 233 in an embodiment of the invention.

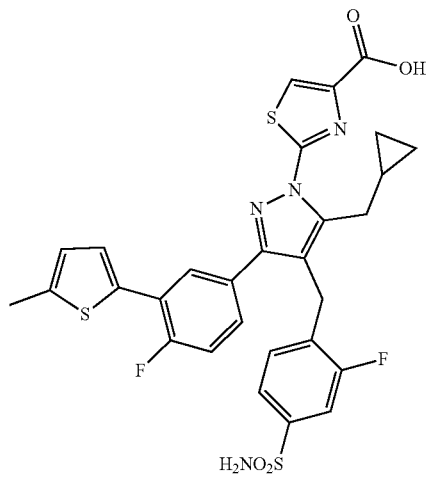

233

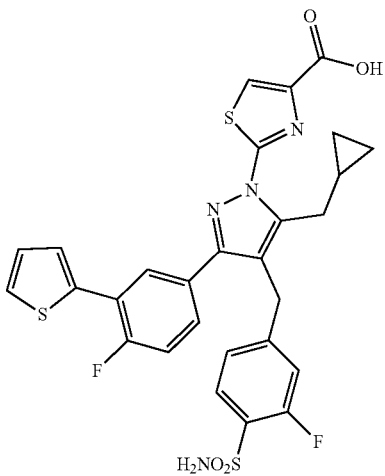 [SMILES: NS(=O)(=O)c1ccc(Cc2c(-c3ccc(F)c(-c4cccs4)c3)nn(-c3nc(C(=O)O)cs3)c2CC2CC2)cc1F]

According to similar procedures described above for 230, the title compounds were prepared and the final product was purified by reverse phase HPLC chromatography to give 2-(5-(cyclopropylmethyl)-3-(4-fluoro-3-(thiophen-2-yl)phenyl)-4-(3-fluoro-4-sulfamoylbenzyl)-1H-pyrazol-1-yl)thiazole-4-carboxylic acid, TFA 234. MS (M+H)⁺=613.

Example 69

2-(5-hydroxy-3-(naphthalen-2-yl)-4-(4-sulfamoylbenzyl)-1H-pyrazol-1-yl)thiazole-4-carboxylic acid 451

According to similar procedures described above for 230, the title compounds were prepared to give 2-(5-(cyclopropylmethyl)-3-(4-fluoro-3-(5-methylthiophen-2-yl)phenyl)-4-(2-fluoro-4-sulfamoylbenzyl)-1H-pyrazol-1-yl)thiazole-4-carboxylic acid 233. ¹H NMR (400 MHz, DMSO-d₆) δ 13.09 (s, 1H), 8.29 (s, 1H), 7.63 (dd, J=7.5, 2.2 Hz, 1H), 7.56 (dd, J=9.6, 1.8 Hz, 1H), 7.53-7.49 (m, 1H), 7.49-7.44 (m, 1H), 7.42 (s, 2H), 7.34 (dd, J=11.3, 8.6 Hz, 1H), 7.19-7.11 (m, 2H), 6.81 (dt, J=3.6, 1.1 Hz, 1H), 4.08 (s, 2H), 3.16 (d, J=6.9 Hz, 2H), 2.44 (d, J=1.1 Hz, 3H), 1.17-1.02 (m, 1H), 0.35-0.27 (m, 2H), 0.22-0.14 (m, 2H); MS (M+H)⁺=627.

Example 68

This example describes the synthesis of 2-(5-(cyclopropylmethyl)-3-(4-fluoro-3-(thiophen-2-yl)phenyl)-4-(3-fluoro-4-sulfamoylbenzyl)-1H-pyrazol-1-yl)thiazole-4-carboxylic acid, TFA 234 in an embodiment of the invention.

Route A

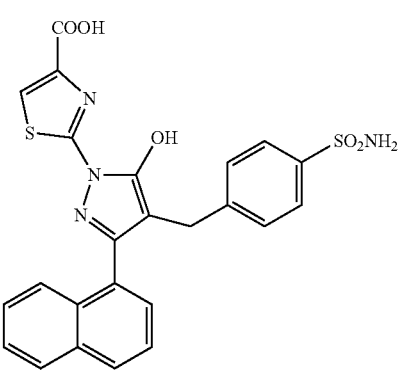

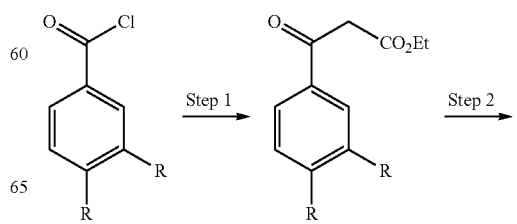

-continued

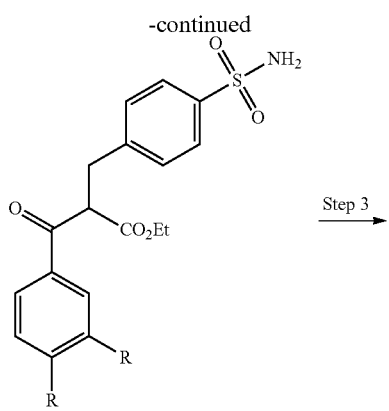

Step 3

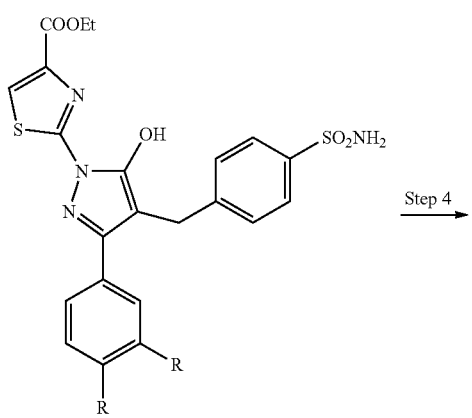

Step 4

COOH
<br>
(final pyrazole-thiazole structure with SO₂NH₂ and naphthyl-R,R substituents)

Step 1. Synthesis of ethyl 3-(naphthalen-1-yl)-3-oxopropanoate

Lithium hexamethyldisiloxane (LHMDS) (1 M in hexane, 7.8 mL, 7.8 mmol) was dissolved in dry THF (5 mL) and cooled down at −78° C. Ethyl acetate (760 μL, 7.8 mmol) was added dropwise and the reaction mixture was stirred for 30 min at −78° C. 1-Napthoyl chloride (1 mL, 5.2 mmol) was dissolved in dry THF (5 mL) and was cooled down at −78° C. To this solution, the ethyl acetate/LHMDS solution was added dropwise and the reaction mixture was warmed to ambient temperature over 2 h. Reaction was quenched with ammonium chloride, diluted with ethyl acetate (50 mL). The organic layer was separated and washed with water (50 mL), brine (50 mL) and dried with anhydrous magnesium sulfate. The residue was purified by flash chromatography (Combi-flash Rf, hexane ethyl/acetate=5% isocratic) to give ethyl 3-(naphthalen-1-yl)-3-oxopropanoate (300 mg, 24%).

Step 2. Synthesis of ethyl 3-(naphthalen-1-yl)-3-oxo-2-(4-sulfamoylbenzyl)propanoate Ethyl 3-(naphthalen-1-yl)-3-oxopropanoate (300 mg, 1.24 mmol) was dissolve in dry 1,4-dioxane (2 mL) and sodium hydride (70 mg, 1.74 mmol) was added. The reaction mixture was stirred at room temperature for 30 min and 4-(bromomethyl)benzenesulfonamide (372 mg, 1.48 mmol) was added. The reaction mixture was stirred overnight at room temperature. The residue was purified by flash chromatography (Combi-flash Rf, hexane/methanol, 0-60% gradient) to give ethyl 3-(naphthalen-1-yl)-3-oxo-2-(4-sulfamoylbenzyl)propanoate (380 mg, 75%).

Step 3. Synthesis of ethyl 2-(5-hydroxy-3-(naphthalen-2-yl)-4-(4-sulfamoylbenzyl)-1H-pyrazol-1-yl)thiazole-4-carboxylate Ethyl 3-(naphthalen-1-yl)-3-oxo-2-(4-sulfamoylbenzyl)propanoate (260 mg, 0.63 mmol), tert-butyl 2-hydrazinylthiazole-4-carboxylate (137 mg, 0.63 mmol), p-toluene sulfonic acid (120 mg, 0.63 mmol) and ethanol (6 mL) were placed in microwave vial and irradiated at 110° C. for 3 h. The reaction mixture was diluted with ethyl acetate (50 mL) and washed with saturated sodium bicarbonate (20 mL), brine (50 mL) and cried with anhydrous magnesium sulfate. The residue was purified by flash chromatography (Combi-flash Rf, DCM/methanol, 0-10% gradient) to give ethyl 2-(5-hydroxy-3-(naphthalen-2-yl)-4-(4-sulfamoylbenzyl)-1H-pyrazol-1-yl)thiazole-4-carboxylate (210 mg, 60%).

Step 4. 2-(5-hydroxy-3-(naphthalen-2-yl)-4-(4-sulfamoylbenzyl)-1H-pyrazol-1-yl)thiazole-4-carboxylic acid 451

Ethyl 2-(5-hydroxy-3-(naphthalen-2-yl)-4-(4-sulfamoylbenzyl)-1H-pyrazol-1-yl)thiazole-4-carboxylate (50 mg, 0.096 mmol) was dissolved in THF/MeOH (1 mL:1 mL) and LiOH (5 M, 500 μL) was added. The reaction mixture was stirred at room temperature overnight. The reaction mixture was neutralized by addition of hydrochloric acid (1.2 M), diluted with ethyl acetate (15 mL), washed with water (10 mL) and dried with anhydrous magnesium sulfate. The organic layer was concentrated down using rotary evaporator and dissolved in a mixture of DMSO and MEOH and purified by HPLC (Phenomenex Gemini C18, $H_2O/CH_3CN$ gradient from 20% to 85% $CH_3CN$ for 4 min, 0.1% TFA) to give the title compound 451 (76%). $^1$H-NMR ($d^6$-DMSO) δ 8.19 (s, 1H), 8.09 (d, 2H, J=1.6 Hz), 8.00 (d, 1H, J=8 Hz), 7.86 (d, 1H, J=8 Hz) 7.63-7.51 (m, 6H), 7.12 (d, 1H, J=8 Hz), 3.69 (s, 2H); MS (ES) 506.9 (M+H)$^+$ LCMS RT=0.88 min.

Example 70

2-(3-(3,4-difluorophenyl)-5-hydroxy-4-(4-sulfamoylbenzyl)-1H-pyrazol-1-yl)thiazole-4-carboxylic acid 452

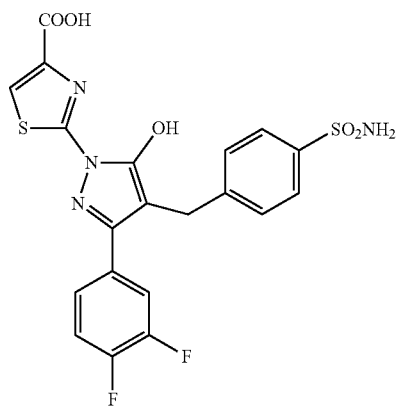 [SMILES: NS(=O)(=O)c1ccc(Cc2c(-c3ccc(F)c(F)c3)nn(-c3nc(C(=O)O)cs3)c2O)cc1]

Using procedures analogous to that described for the preparation of 451, the title compounds were prepared and purified by HPLC: 2-(3-(3,4-difluorophenyl)-5-hydroxy-4-(4-sulfamoylbenzyl)-1H-pyrazol-1-yl)thiazole-4-carboxylic acid 452 $^1$H-NMR (d$^6$-DMSO) δ 8.18 (s, 1H), 7.85 (d, 2H, J=8.4 Hz), 7.56 (m, 1H), 7.45-7.41 (m, 4H), 3.99 (s, 2H); MS (ES) 492.9 (M+H)$^+$ LCMS RT=0.88 min.

Example 71

2-(5-hydroxy-3-(pyridin-3-yl)-4-(4-sulfamoylbenzyl)-1H-pyrazol-1-yl)thiazole-4-carboxylic acid 453

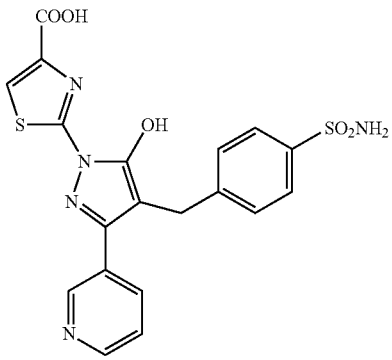 [SMILES: NS(=O)(=O)c1ccc(Cc2c(-c3cccnc3)nn(-c3nc(C(=O)O)cs3)c2O)cc1]

Using procedures analogous to that described for the preparation of 451, the title compounds were prepared and purified by HPLC: 2-(5-hydroxy-3-(pyridin-3-yl)-4-(4-sulfamoylbenzyl)-1H-pyrazol-1-yl)thiazole-4-carboxylic acid 453. MS (ES) 457.9 (M+H)+ LCMS RT=0.30 min.

Example 72

2-(3-(6-fluoronaphthalen-1-yl)-5-hydroxy-4-(4-sulfamoylbenzyl)-1H-pyrazol-1-yl)thiazole-4-carboxylic acid 454

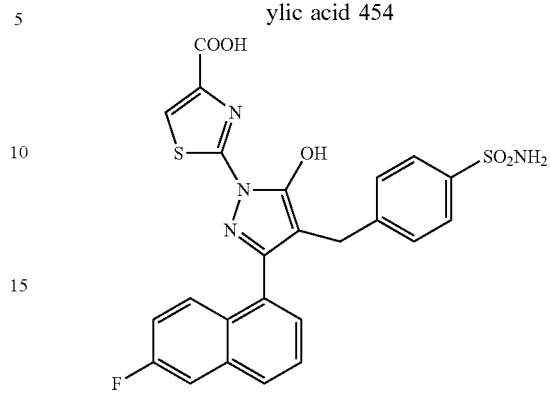

Using procedures analogous to that described for the preparation of 451, the title compounds were prepared and purified by HPLC: 2-(3-(6-fluoronaphthalen-1-yl)-5-hydroxy-4-(4-sulfamoylbenzyl)-1H-pyrazol-1-yl)thiazole-4-carboxylic acid 454. $^1$H-NMR (d$^6$-DMSO) δ 8.20 (m, 2H), 7.88 (d, 2H, J=8 Hz), 7.70-7.55 (m, 5H), 7.32 (m, 1H), 7.12 (d, 1H, J=8 Hz), 3.69 (s, 2H); MS (ES) 524.9 (M+H)$^+$ LCMS RT=0.94 min.

Example 73

2-(3-(3,4-difluorophenyl)-5-methoxy-4-(4-sulfamoylbenzyl)-1H-pyrazol-1-yl)thiazole-4-carboxylic acid 455

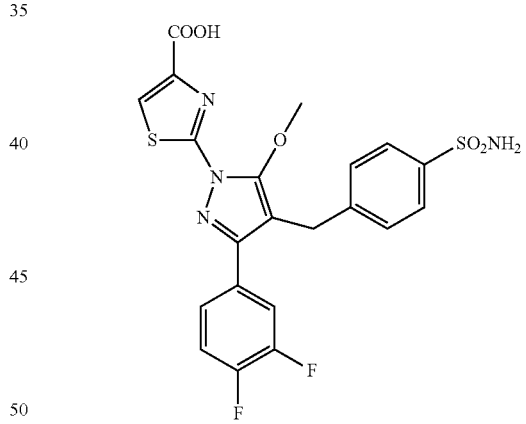

2-(3-(3,4-Difluorophenyl)-5-hydroxy-4-(4-sulfamoylbenzyl)-1H-pyrazol-1-yl)thiazole-4-carboxylic acid 452 (20 mg, 0.038 mmol) was dissolved in anhydrous DMF (300 µL). Anhydrous potassium carbonate (16 mg, 0.114 mmol) and methyl iodide (3 µL, 0.05 mmol) were added. The reaction mixture was stirred at room temperature overnight. The reaction mixture was diluted with ethyl acetate (5 mL) and washed with water (3×1 mL). The organic layers were concentrated by rotary evaporator and THF (500 µL) and sodium hydroxide (5 N, 200 µL) were added. After 1 h, the reaction mixture was neutralized with hydrochloric acid (0.1 M) and the residue was purified by HPLC (Phenomenex Gemini C18, H$_2$O/CH$_3$CN gradient from 20% to 95% CH$_3$CN for 4 min, 0.1% TFA) to give the title compound 455 (85%). $^1$H-NMR (d$^6$-DMSO) δ 8.20 (s, 1H), 7.81 (d, 2H, J=8 Hz), 7.54-7.50 (m, 2H), 7.39-7.36 (m, 3H), 3.69 (s, 2H), 3.49 (s, 3H); MS (ES) 506.9 (M+H)$^+$ LCMS RT=0.89 min.

Example 74
2-(3-(3-isopropoxyphenyl)-4-(4-sulfamoylbenzyl)-1H-pyrazol-1-yl)thiazole-4-carboxylic acid 459
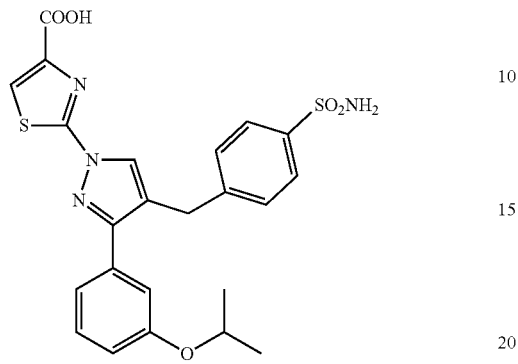
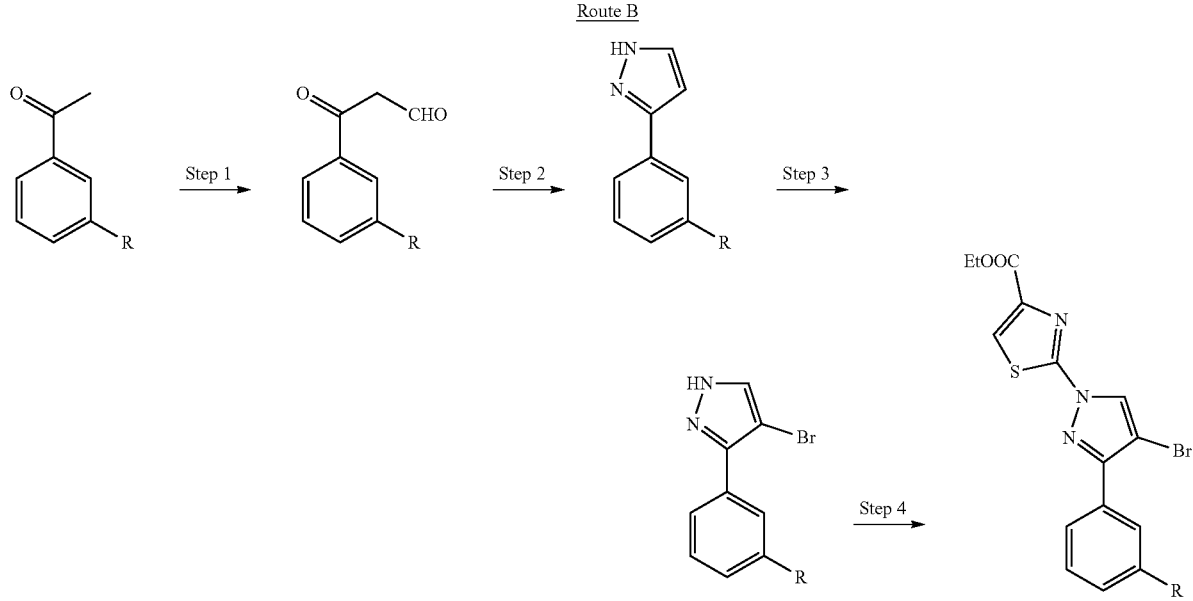
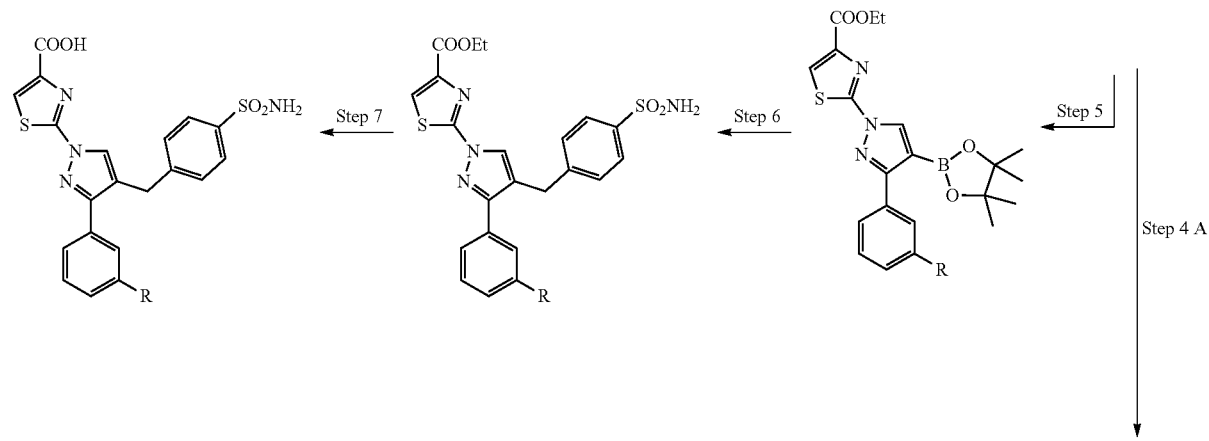

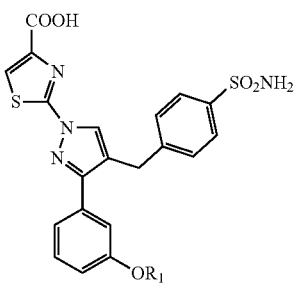
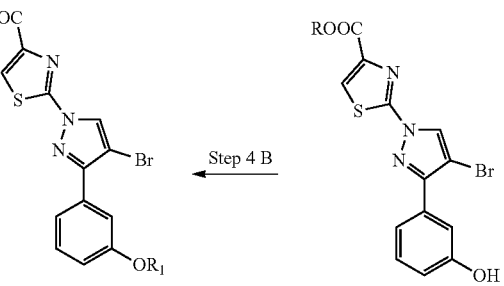

Step 1. Synthesis of 3-(3-methoxyphenyl)-3-oxopropanal

3-Methoxyphenyl acetophenone (3 g, 0.17 mol) was dissolved in anhydrous THF (25 mL) and cooled to 0° C. Sodium hydride (930 mg, 0.23 mol) and ethyl formate (4.3 mL, 0.53 mol) were added. The reaction mixture was stirred overnight at room temperature, quenched with sodium hydroxide (2 N), and washed with diethyl ether. The water layers were acidified with hydrochloric acid (2 N) and extracted with diethyl ether (3×50 mL). The organic layers were dried with anhydrous magnesium sulfate and concentrated down with rotary evaporator to give 3-(3-methoxyphenyl)-3-oxopropanal (quantitative yield) which was sufficiently pure to be used in subsequent reaction.

Step 2. Synthesis of 3-(3-methoxyphenyl)-1H-pyrazole

To a stirred solution of 3-(3-methoxyphenyl)-3-oxopropanal in ethanol, hydrazine (1 mL, 0.3 mmol) was added and the reaction mixture was refluxed for 3 h. The reaction mixture was concentrated to half of its original volume, water (50 mL) and sodium hydroxide (1 M, 100 mL) were added. The mixture was extracted with ethyl acetate (3×50 mL) and dried with anhydrous magnesium sulfate. The organic layers were filtered off and concentrated by rotary evaporator to give a yellow liquid (3 g, 92%). The product was sufficiently pure for the subsequent reaction.

Step 3. Synthesis of 4-bromo-3-(3-methoxyphenyl)-1H-pyrazole 3-(3-Methoxyphenyl)-1H-pyrazole (3 g, 0.017 mol) was dissolved in anhydrous DMF (30 mL) and cooled to 0° C. NBS (3.20 g, 0.018 mol) was added in three portions and the reaction mixture was stirred at room temperature for overnight. The reaction mixture was poured into a mixture of ethyl acetate and saturated sodium bicarbonate (1:1, 300 mL) and organic layer was separated, washed with brine (2×100 mL) and dried with anhydrous magnesium sulfate. The solvents were removed by rotary evaporator and purified by flash chromatography (Combi-flash Rf, hexane/ethyl acetate, 0-50% gradient) to give 4-bromo-3-(3-methoxyphenyl)-1H-pyrazole (3 g, 70%).

Step 4. Synthesis of ethyl 2-(4-bromo-3-(3-methoxyphenyl)-1H-pyrazol-1-yl)thiazole-4-carboxylate 4-Bromo-3-(3-methoxyphenyl)-1H-pyrazole (3 g, 0.012 mol) was dissolved in anhydrous DMSO (15 mL) and anhydrous potassium carbonate (2.46 g, 0.018 mol) and ethyl 2-bromothiazole-4-carboxylate (2.8 g, 0.012) were added. The reaction mixture was heated at 120° C. for 6 h. After cooling down, the reaction mixture was poured into water and the precipitate was filtered off to give ethyl 2-(4-bromo-3-(3-methoxyphenyl)-1H-pyrazol-1-yl)thiazole-4-carboxylate (3.54 g, 73%).

Step 4A. Synthesis of ethyl 2-(4-bromo-3-(3-hydroxyphenyl)-1H-pyrazol-1-yl)thiazole-4-carboxylic acid Ethyl 2-(4-bromo-3-(3-methoxyphenyl)-1H-pyrazol-1-yl)thiazole-4-carboxylate (3 g, 0.008 mol) was dissolved in anhydrous DCM (20 mL). Boron tribromide (1 M in DCM, 9.5 mL, 0.0096 mol) was added dropwise. The reaction mixture was stirred at room temperature for 30 min. The precipitate was filtered off and washed with DCM to give ethyl 2-(4-bromo-3-(3-hydroxyphenyl)-1H-pyrazol-1-yl)thiazole-4-carboxylic acid (2 g, 60%).

Step 4B. Synthesis of isopropyl 2-(4-bromo-3-(3-isopropoxyphenyl)-1H-pyrazol-1-yl)thiazole-4-carboxylate Ethyl 2-(4-bromo-3-(3-hydroxyphenyl)-1H-pyrazol-1-yl)thiazole-4-carboxylic acid (500 mg, 0.1 mmol) was dissolved in anhydrous DMF. Potassium carbonate (2.1 g, 15 mmol) and isopropyl bromide (1.4 mL, 10 mmol) were added and the reaction was irradiated at 130° C. for 40 min in a microwave reactor. The reaction mixture was poured into water and extracted with ethyl acetate (3×40 mL). The organic layers were washed with brine (2×50 mL) and dried with anhydrous magnesium sulfate. The solvents were removed by rotary evaporator and purified by purified by flash chromatography (Combi-flash Rf, hexane/ethyl acetate, 0-20% gradient) to give isopropyl 2-(4-bromo-3-(3-isopropoxyphenyl)-1H-pyrazol-1-yl)thiazole-4-carboxylate (520 mg, 84%).

Step 5. Synthesis of isopropyl 2-(3-(3-isopropoxyphenyl)-4-(4,4,5,5-tetramethyl-1,3,2-dioxaborolan-2-yl)-1H-pyrazol-1-yl)thiazole-4-carboxylate Isopropyl 2-(4-bromo-3-(3-isopropoxyphenyl)-1H-pyrazol-1-yl)thiazole-4-carboxylate (520 mg, 1.15 mmol) was dissolved in anhydrous THF (5 mL) and potassium acetate (340 mg, 3.46 mmol), PdCl$_2$(dppf) (0.9 mg, 0.0011 mmol) and bis(pinacolato)diborane (408 mg, 1.61 mmol) were added. The vial was purged with argon for 5 min. The reaction was heated at 100° C. for 2 h. The reaction mixture was diluted with ethyl acetate and filtered through a plug of celite. The solvent was removed by rotary evaporator and purified by flash chromatography (Combi-flash Rf, hexane/ethyl acetate, 0-40% gradient) to give a mixture of isopropyl 2-(3-(3-isopropoxyphenyl)-4-(4,4,5,5-tetramethyl-1,3,2-dioxaborolan-2-yl)-1H-pyrazol-1-yl)thiazole-4-carboxylate and isopropyl 2-(3-(3-isopropoxyphenyl)-1H-pyrazol-1-yl)thiazole-4-carboxylate.

Step 6. Synthesis of isopropyl 2-(3-(3-isopropoxyphenyl)-4-(4-sulfamoylbenzyl)-1H-pyrazol-1-yl)thiazole-4-carboxylate A mixture of isopropyl 2-(3-(3-isopropoxyphenyl)-4-(4,4,5,5-tetramethyl-1,3,2-dioxaborolan-2-yl)-1H-pyrazol-1-yl)thiazole-4-carboxylate and 2-(3-(3-isopropoxyphenyl)-1H-pyrazol-1-yl)thiazole-4-carboxylate (500 mg, 1 mmol), potassium carbonate (414 mg, 3 mmol), Pd(PPh$_3$)$_4$(1.2 mg, 0.001 mmol), and 4-(bromomethyl)benzenesulfonamide (275 mg, 1.1 mmol) were added to a microwave vial, followed by THF (8 mL) and water (3 mL). The vial was sealed and heated at 100° C. for 1 h. The reaction mixture was cooled, poured into water, and extracted with ethyl acetate (3×20 mL). The organic layers were washed with brine (2×20 mL) and dried with anhydrous magnesium sulfate. The solvents were removed by rotary evaporator and purified by purified by flash chromatography (Combi-flash Rf, hexane/ethyl acetate, 0-70% gradient) to give the title compound (150 mg, 27%).

Step 7. Synthesis of 2-(3-(3-isopropoxyphenyl)-4-(4-sulfamoylbenzyl)-1H-pyrazol-1-yl)thiazole-4-carboxylic acid 459

Isopropyl 2-(3-(3-isopropoxyphenyl)-4-(4-sulfamoylbenzyl)-1H-pyrazol-1-yl)thiazole-4-carboxylate (50 mg, 0.09 mmol) was dissolved in THF/MeOH (1 mL:1 mL) and LiOH (5 M, 500 μL) was added. The reaction mixture was stirred at room temperature overnight. The reaction mixture was neutralized by addition of hydrochloric acid (1.2 M), diluted with ethyl acetate (15 mL), washed with water (10 mL), and dried with anhydrous magnesium sulfate. The organic layer was concentrated using a rotary evaporator, dissolved in a mixture of DMSO and MEOH, and purified by HPLC (Phenomenex Gemini C18, H$_2$O/CH$_3$CN gradient from 45% to 85% CH$_3$CN for 7 min, 0.1% TFA) to give the title compound 459 (34 mg, 76%). $^1$H-NMR (d$^6$-DMSO) δ 8.24 (m, 2H), 7.78 (d, 2H, J=8 Hz), 7.44 (d, 2H, J=8 Hz), 7.39-7.30 (m, 3H), 7.22 (d, 1H, J=8 Hz), 7.09 (d, 1H, J=4 Hz), 6.99-6.96 (m, 1H), 4.51 (m, 1H), 4.15 (s, 2H), 1.27 (d, 6H, J=8 Hz); MS (ES) 499.0 (M+H)$^+$ LCMS RT=1.07 min.

Example 75

2-(3-(3-(cyclopentyloxy)phenyl)-4-(4-sulfamoylbenzyl)-1H-pyrazol-1-yl)thiazole-4-carboxylic acid 460

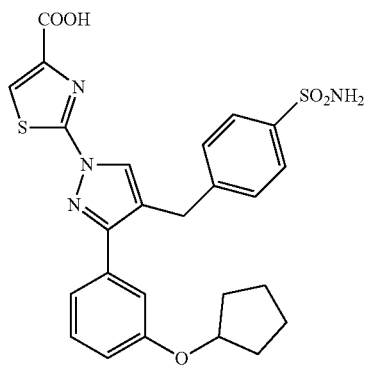 [SMILES: NS(=O)(=O)c1ccc(Cc2cn(-c3nc(C(=O)O)cs3)nc2-c2cccc(OC3CCCC3)c2)cc1]

Using procedures analogous to that described for the preparation of 459, the title compound was prepared and purified by HPLC: 2-(3-(3-(cyclopentyloxy)phenyl)-4-(4-sulfamoylbenzyl)-1H-pyrazol-1-yl)thiazole-4-carboxylic acid 460 $^1$H-NMR (d$^6$-DMSO) δ 8.55 (m, 2H), 8.25 (d, 2H, J=4 Hz), 7.77 (d, 2H, J=4 Hz), 7.55-7.26 (m, 3H), 7.22 (d, 1H, J=8 Hz), 7.09 (d, 1H, J=8 Hz), 6.99-6.96 (m, 1H), 4.74 (m, 1H), 4.15 (s, 2H), 1.91-1.82 (m, 2H), 1.69-1.58 (m, 4H), 1.23 (m, 2H); MS (ES) 525.0 (M+H)$^+$ LCMS RT=1.15 min.

Example 76

2-(4-(4-sulfamoylbenzyl)-3-(3-((tetrahydrofuran-3-yl)methoxy)phenyl)-1H-pyrazol-1-yl)thiazole-4-carboxylic acid 461

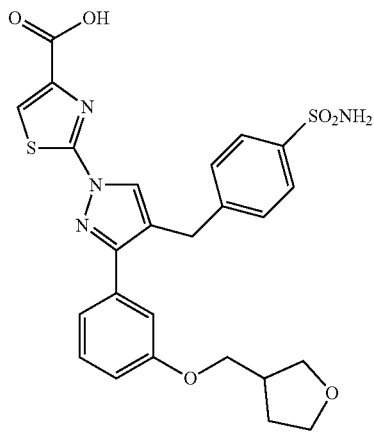 [SMILES: NS(=O)(=O)c1ccc(Cc2cn(-c3nc(C(=O)O)cs3)nc2-c2cccc(OCC3CCOC3)c2)cc1]

Using procedures analogous to that described for the preparation of 459, the title compound was prepared and purified by HPLC: 2-(4-(4-sulfamoylbenzyl)-3-(3-((tetrahydrofuran-3-yl)methoxy)phenyl)-1H-pyrazol-1-yl)thiazole-4-carboxylic acid 461 MS (ES) 540.7 (M+H)$^+$ LCMS RT=1.13 min.

Example 77

2-(3-(3-((3-methoxybenzyl)oxy)phenyl)-4-(4-sulfamoylbenzyl)-1H-pyrazol-1-yl)thiazole-4-carboxylic acid 462

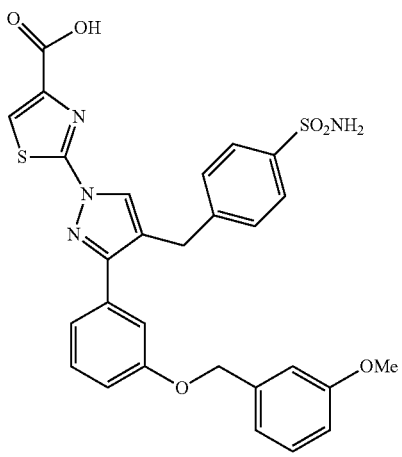 [SMILES: COc1cccc(COc2cccc(-c3nn(-c4nc(C(=O)O)cs4)cc3Cc3ccc(S(N)(=O)=O)cc3)c2)c1]

Using procedures analogous to that described for the preparation of 459, the title compound was prepared and purified by HPLC: 2-(3-(3-((3-methoxybenzyl)oxy)phenyl)-4-(4-sulfamoylbenzyl)-1H-pyrazol-1-yl)thiazole-4-carboxylic acid 462 MS (ES) 576.9 (M+H)+ LCMS RT=1.02 min.

Example 78

2-(4-(4-sulfamoylbenzyl)-3-(3-((tetrahydrofuran-2-yl)methoxy)phenyl)-1H-pyrazol-1-yl)thiazole-4-carboxylic acid 463

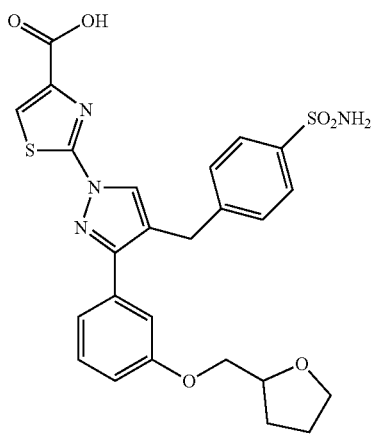 [SMILES: NS(=O)(=O)c1ccc(Cc2cn(-c3nc(C(=O)O)cs3)nc2-c2cccc(OCC3CCCO3)c2)cc1]

Using procedures analogous to that described for the preparation of 459, the title compound was prepared and purified by HPLC: 2-(4-(4-sulfamoylbenzyl)-3-(3-((tetrahydrofuran-2-yl)methoxy)phenyl)-1H-pyrazol-1-yl)thiazole-4-carboxylic acid 463. MS (ES) 540.9 (M+H)+ LCMS RT=0.76 min.

Example 79

2-(3-(3-phenoxyphenyl)-4-(4-sulfamoylbenzyl)-1H-pyrazol-1-yl)thiazole-4-carboxylic acid 464

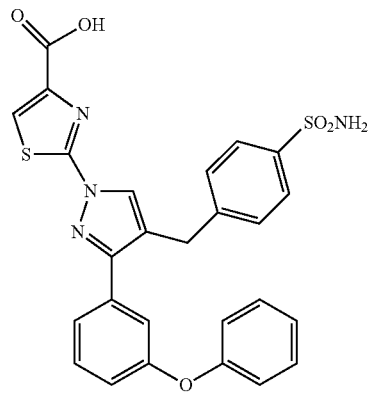 [SMILES: NS(=O)(=O)c1ccc(Cc2cn(-c3nc(C(=O)O)cs3)nc2-c2cccc(Oc3ccccc3)c2)cc1]

Using procedures analogous to that described for the preparation of 459, the title compound was prepared and purified by HPLC: 2-(3-(3-phenoxyphenyl)-4-(4-sulfamoylbenzyl)-1H-pyrazol-1-yl)thiazole-4-carboxylic acid 464 MS (ES) 532.9 (M+H)+ LCMS RT=0.98 min.

Example 80

2-(3-(3-(pyridin-3-ylmethoxy)phenyl)-4-(4-sulfamoylbenzyl)-1H-pyrazol-1-yl)thiazole-4-carboxylic acid, TFA 465

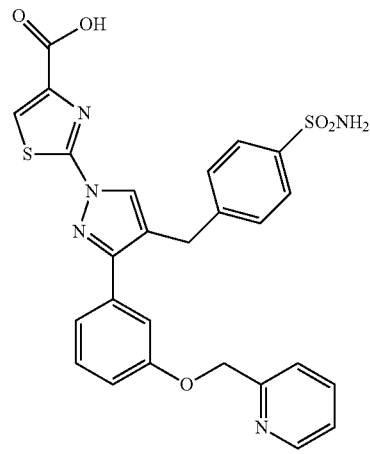 [SMILES: NS(=O)(=O)c1ccc(Cc2cn(-c3nc(C(=O)O)cs3)nc2-c2cccc(OCc3ccccn3)c2)cc1]

Using procedures analogous to that described for the preparation of 459, the title compound was prepared and purified by HPLC: 2-(3-(3-(pyridin-3-ylmethoxy)phenyl)-4-(4-sulfamoylbenzyl)-1H-pyrazol-1-yl)thiazole-4-carboxylic acid, TFA 465 MS (ES) 548.0 (M+H)+ LCMS RT=0.68 min.

Example 81

2-(3-(3-(pyridin-2-ylmethoxy)phenyl)-4-(4-sulfamoylbenzyl)-1H-pyrazol-1-yl)thiazole-4-carboxylic acid, TFA 466

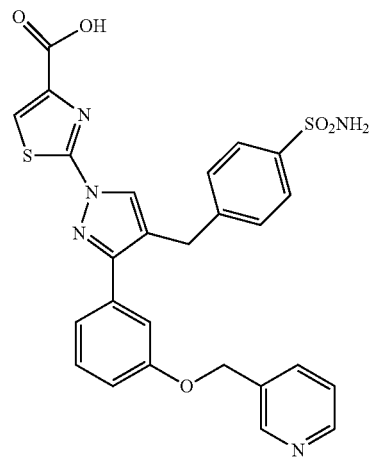 [SMILES: NS(=O)(=O)c1ccc(Cc2cn(-c3nc(C(=O)O)cs3)nc2-c2cccc(OCc3cccnc3)c2)cc1]

Using procedures analogous to that described for the preparation of 459, the title compound was prepared and purified by HPLC: 2-(3-(3-(pyridin-2-ylmethoxy)phenyl)-4-(4-sulfamoylbenzyl)-1H-pyrazol-1-yl)thiazole-4-carboxylic acid, TFA 466 MS (ES) 547.9 (M+H)+ LCMS RT=0.68 min.

Example 82

2-(5-(naphthalen-2-yl)-4-(4-sulfamoylbenzyl)-1H-pyrazol-1-yl)thiazole-4-carboxylic acid 474

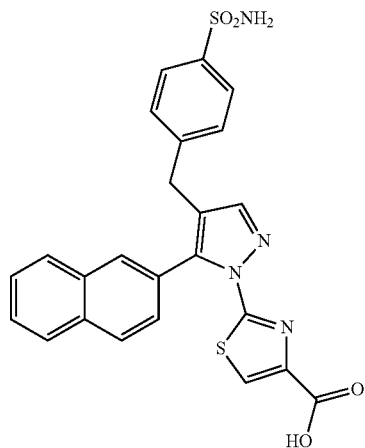 [SMILES: NS(=O)(=O)c1ccc(Cc2cnn(-c3nc(C(=O)O)cs3)c2-c2ccc3ccccc3c2)cc1]

Using procedures analogous to that described for the preparation of 459, the title compound was prepared and purified by HPLC: 2-(5-(naphthalen-2-yl)-4-(4-sulfamoylbenzyl)-1H-pyrazol-1-yl)thiazole-4-carboxylic acid 474 $^1$H-NMR (d$^6$-DMSO) δ 8.24 (s, 1H), 8.13 (s, 1H), 7.91-8.03 (m, 4H), 7.80 (d, J=8.2 Hz, 2H), 7.52-7.58 (m, 3H), 7.32 (s, 2H), 4.25 (s, 2H); MS (ES) 491 (M+H)$^+$ LCMS RT 1.04 min.

Example 83

2-(5-(pyridin-3-yl)-4-(4-sulfamoylbenzyl)-1H-pyrazol-1-yl)thiazole-4-carboxylic acid 475

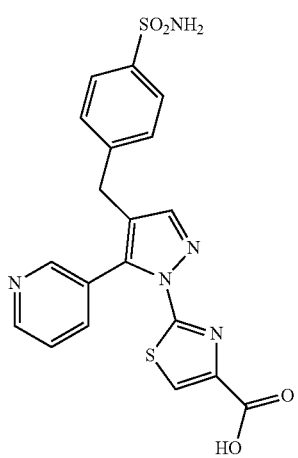 [SMILES: NS(=O)(=O)c1ccc(Cc2cnn(-c3nc(C(=O)O)cs3)c2-c2cccnc2)cc1]

Using procedures analogous to that described for the preparation of 459, the title compound was prepared and purified by HPLC: 2-(5-(pyridin-3-yl)-4-(4-sulfamoylbenzyl)-1H-pyrazol-1-yl)thiazole-4-carboxylic acid 475 MS (ES) 442 (M+H)$^+$ LCMS RT 0.64 min.

Example 84

2-(3-(6-fluoro-4'-methyl-[1,1'-biphenyl]-3-yl)-4-(4-sulfamoylbenzyl)-1H-pyrazol-1-yl)thiazole-4-carboxylic acid 476

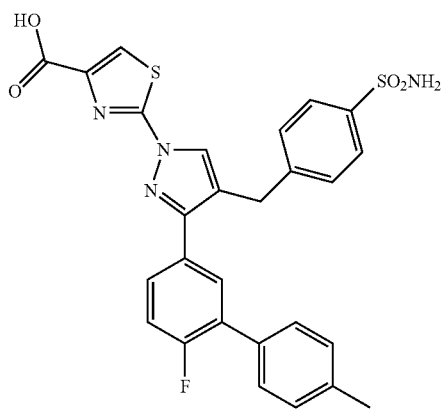 [SMILES: Cc1ccc(-c2cc(-c3nn(-c4nc(C(=O)O)cs4)cc3Cc3ccc(S(N)(=O)=O)cc3)ccc2F)cc1]

Using procedures analogous to that described for the preparation of 459, the title compound was prepared and purified by HPLC: 2-(3-(6-fluoro-4'-methyl-[1,1'-biphenyl]-3-yl)-4-(4-sulfamoylbenzyl)-1H-pyrazol-1-yl)thiazole-4-carboxylic acid 476. $^1$H-NMR (d$^6$-DMSO) δ 8.27 (d, J=9.24 Hz, 2H), 7.76-7.78 (m, 4H), 7.29-7.46 (m, 8H), 4.2 (s, 2H), 2.35 (s, 3H); MS (ES) 549 (M+H)$^+$ LCMS RT 1.27 min.

Example 85

2-(3-(6-fluoro-3'-methoxy-[1,1'-biphenyl]-3-yl)-4-(4-sulfamoylbenzyl)-1H-pyrazol-1-yl)thiazole-4-carboxylic acid 456

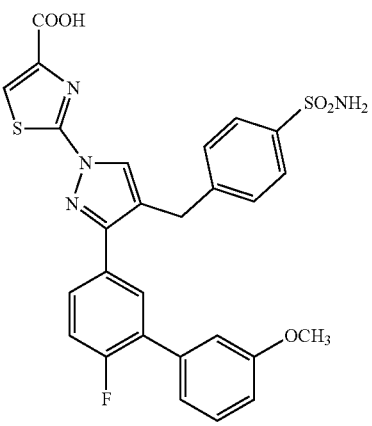 [SMILES: COc1cccc(-c2cc(-c3nn(-c4nc(C(=O)O)cs4)cc3Cc3ccc(S(N)(=O)=O)cc3)ccc2F)c1]

Route B-A
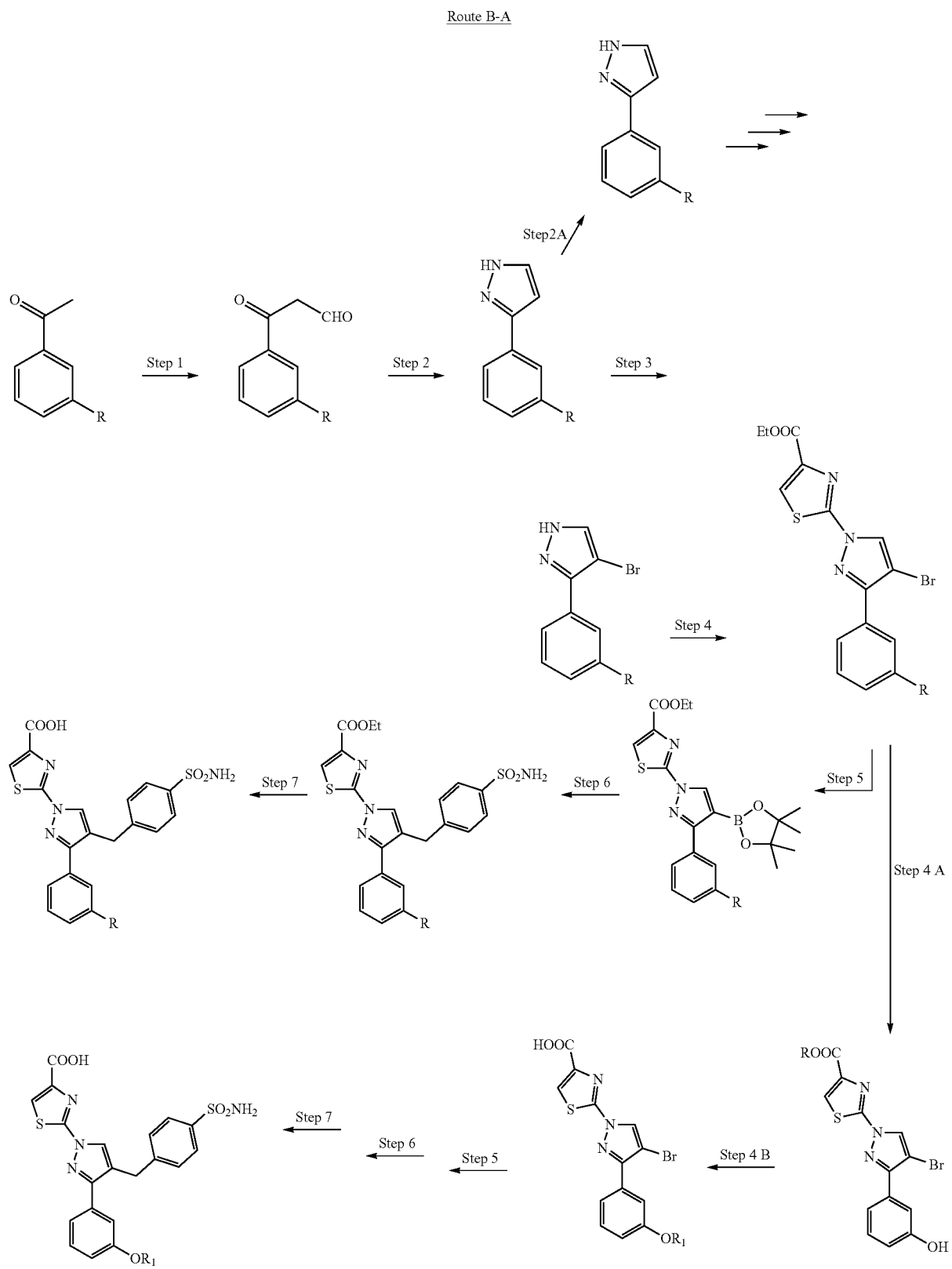
Using procedures analogous to those described in the preparation of 459, Step 1-2, 3-(3-bromo-4-fluorophenyl)-1H-pyrazole was prepared.
Step 2A: 3-(3-bromo-4-fluorophenyl)-1H-pyrazole (100 mg, 0.415 mmol), 3-methoxyphenyl boronic acid (95 mg, 0.622 mmol), K$_2$CO$_3$ (678 mg, 4.977 mmol), and a 2:1 mixture of dioxane/H$_2$O (8.0 mL) were combined in a microwave vial and then degassed and purged with argon (3×). Pd(dppf)Cl$_2$ was added and the reaction mixture was heated to 120° C. for 1 h. The reaction mixture was cooled to room temperature, NaOH (8 mL, 1M) was added and the mixture was extracted with EtOAc (3×50 mL). The combined organic layers were then washed with brine, dried over MgSO$_4$, filtered, and concentrated by rotary evaporator. The crude product was purified by flash chromatography (Combi-flash Rf, dichloromethane/methanol, 0-10% gradient) to give 3-[4-fluoro-3-(3-methoxyphenyl)phenyl]-1H-pyrazole (419 mg, 94%). $^1$H-NMR (CDCl$_3$) δ 7.69 (1H, d, J=2.2 Hz), 7.71 (1H, m), 7.63 (1H, d, J=2.2 Hz), 7.37 (1H, t, J=8.0 Hz), 7.21-7.09 (3H, m), 6.78 (1H, dd, J=8.2, 2.3 Hz), 6.61 (1H, d, J=2.3 Hz), 3.84 (3H, s). MS (M+H)$^+$=270.1.

Using procedures analogous to those described in the preparation of 459, Steps 3-7, the title compound was prepared was prepared and purified by HPLC: 2-(3-(6-fluoro-3'-methoxy-[1,1'-biphenyl]-3-yl)-4-(4-sulfamoylbenzyl)-1H-pyrazol-1-yl)thiazole-4-carboxylic acid 456 MS (ES) 565.0 (M+H)$^+$ LCMS RT=1.08 min.

Example 86

2-(3-(3'-chloro-6-fluoro-[1,1'-biphenyl]-3-yl)-4-(4-sulfamoylbenzyl)-1H-pyrazol-1-yl)thiazole-4-carboxylic acid 457

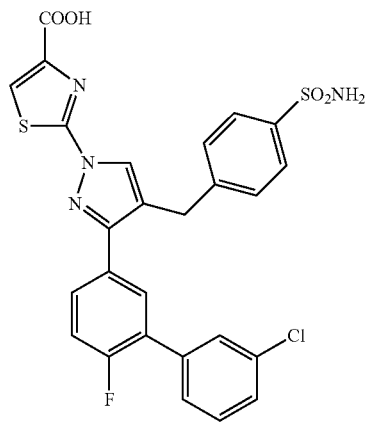 [SMILES: NS(=O)(=O)c1ccc(Cc2cn(-c3nc(C(=O)O)cs3)nc2-c2ccc(F)c(-c3cccc(Cl)c3)c2)cc1]

Using procedures analogous to those described in the preparation of 456, the title compound was prepared was prepared and purified by HPLC: 2-(3-(3'-chloro-6-fluoro-[1,1'-biphenyl]-3-yl)-4-(4-sulfamoylbenzyl)-1H-pyrazol-1-yl)thiazole-4-carboxylic acid 457 MS (ES) 568.9 (M+H)$^+$ LCMS RT=1.16 min.

Example 87

2-(3-(3',6-difluoro-[1,1'-biphenyl]-3-yl)-4-(4-sulfamoylbenzyl)-1H-pyrazol-1-yl)thiazole-4-carboxylic acid 458

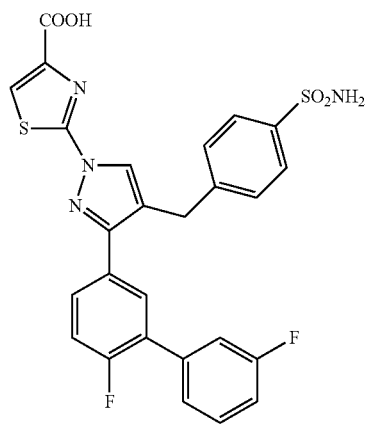 [SMILES: NS(=O)(=O)c1ccc(Cc2cn(-c3nc(C(=O)O)cs3)nc2-c2ccc(F)c(-c3cccc(F)c3)c2)cc1]

Using procedures analogous to those described in the preparation of 456, the title compound was prepared was prepared and purified by HPLC: 2-(3-(3',6-difluoro-[1,1'-biphenyl]-3-yl)-4-(4-sulfamoylbenzyl)-1H-pyrazol-1-yl)thiazole-4-carboxylic acid 458 MS (ES) 552.9 (M+H)$^+$ LCMS RT=1.12 min.

Example 88

2-(3-(4-methyl-3-(pyridin-3-yl)phenyl)-4-(4-sulfamoylbenzyl)-1H-pyrazol-1-yl)thiazole-4-carboxylic acid 486

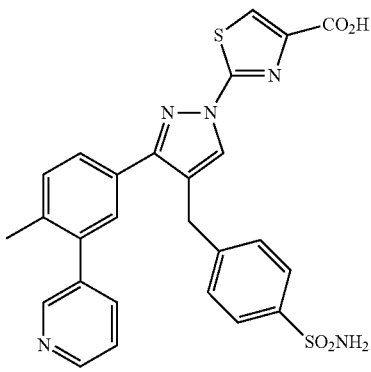 [SMILES: Cc1ccc(-c2nn(-c3nc(C(=O)O)cs3)cc2Cc2ccc(S(N)(=O)=O)cc2)cc1-c1cccnc1]

Using procedures analogous to those described in the preparation of 459, Steps 1-6, 2-(3-(3-chloro-4-methylphenyl)-4-(4-sulfamoylbenzyl)-1H-pyrazol-1-yl)thiazole-4-carboxylic acid was prepared.

Modified Step 7: A flame dried flask was charged with bis(tri-tert-butylphosphine)palladium (5.1 mg, 10 mol %), cesium carbonate (1 mL, 1 M solution), pyridin-3-ylboronic acid (25 mg, 0.2 mmol), 2-(3-(3-chloro-4-methylphenyl)-4-(4-sulfamoylbenzyl)-1H-pyrazol-1-yl)thiazole-4-carboxylic acid (51 mg, 0.1 mmol), and THF (2 mL). The reaction mixture was microwave irradiated at 120° C. for 20 min and the solvent was removed by rotary evaporator. The residue was filtered through celite pad with MeOH, then solvent was removed by rotary evaporator. The residue was purified by HPLC (Phenomenex Gemini C18, H₂O/CH₃CN gradient from 25% to 85% CH₃CN for 4 min, 0.1% TFA) to give the title compound 486 (32 mg, 60%). ¹H-NMR (MeOD) δ 8.77 (s, 1H), 8.72 (s, 1H), 8.40 (s, 1H), 8.25 (d, J=8.0 Hz, 1H), 8.16 (s, 1H), 7.92 (dd, J=7.6, 5.6 Hz, 1H), 7.81 (d, J=8.4 Hz, 2H), 7.74 (dd, J=7.6, 1.6 Hz, 1H), 7.47 (d, J=8.0 Hz, 2H), 7.39 (d, J=8.0 Hz, 2H), 4.21 (s, 2H), 2.34 (s, 3H); MS (ES) 532.7 (M+H)⁺, LCMS RT=0.82 min.

Example 89

2-(3-(3'-amino-6-methyl-[1,1'-biphenyl]-3-yl)-4-(4-sulfamoylbenzyl)-1H-pyrazol-1-yl)thiazole-4-carboxylic acid 487

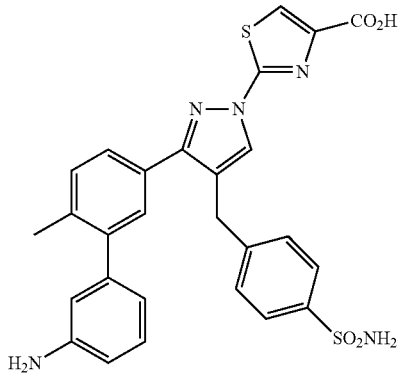 [SMILES: Cc1ccc(-c2nn(-c3nc(C(=O)O)cs3)cc2Cc2ccc(S(N)(=O)=O)cc2)cc1-c1cccc(N)c1]

Using procedures analogous to those described in the preparation of 486, the title compound was prepared and purified by HPLC: 2-(3-(3'-amino-6-methyl-[1,1'-biphenyl]-3-yl)-4-(4-sulfamoylbenzyl)-1H-pyrazol-1-yl)thiazole-4-carboxylic acid 487 ¹H-NMR (MeOD) δ 8.37 (s, 1H), 8.16 (s, 1H), 7.81 (d, J=8.4 Hz, 2H), 7.63 (dd, J=7.6, 6.6 Hz, 1H), 7.54 (t, J=8.0 Hz, 1H), 7.42 (d, J=1.6 Hz, 1H), 7.40 (s, 2H), 7.38 (s, 1H), 7.27-7.20 (m, 2H), 7.15 (s, 1H), 4.19 (s, 2H), 2.30 (s, 3H); MS (ES) 546.7 (M+H)⁺; LCMS RT=0.87 min.

Example 90

2-(3-(3'-ethyl-6-methyl-[1,1'-biphenyl]-3-yl)-4-(4-sulfamoylbenzyl)-1H-pyrazol-1-yl)thiazole-4-carboxylic acid 488

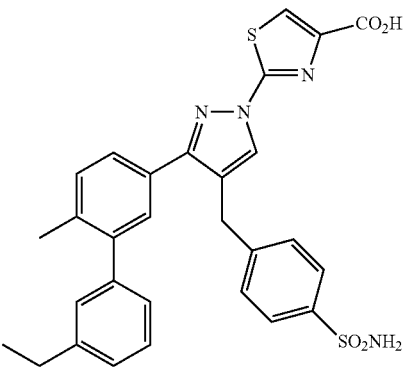 [SMILES: CCc1cccc(-c2cc(-c3nn(-c4nc(C(=O)O)cs4)cc3Cc3ccc(S(N)(=O)=O)cc3)ccc2C)c1]

Using procedures analogous to those described in the preparation of 486, the title compound was prepared and purified by HPLC: 2-(3-(3'-ethyl-6-methyl-[1,1'-biphenyl]-3-yl)-4-(4-sulfamoylbenzyl)-1H-pyrazol-1-yl)thiazole-4-carboxylic acid 488 ¹H-NMR (MeOD) δ 8.34 (s, 1H), 8.13 (s, 1H), 7.83 (d, J=8.4 Hz, 2H), 7.59 (dd, J=8.0, 2.0 Hz, 1H), 7.48 (d, J=2.0 Hz, 1H), 7.41 (d, J=8.0 Hz, 2H), 7.35 (d, J=8.0 Hz, 2H), 7.23 (d, J=8.0 Hz, 1H), 7.15 (s, 1H), 7.10 (d, J=8.0 Hz, 1H), 4.20 (s, 2H), 2.73 (q, J=8.0 Hz, 2H), 2.29 (s, 3H), 1.30 (t, J=8.0 Hz, 3H); MS (ES) 559.4 (M+H)⁺; LCMS RT=1.28 min.

Example 91

2-(3-(3',5'-difluoro-6-methyl-[1,1'-biphenyl]-3-yl)-4-(4-sulfamoylbenzyl)-1H-pyrazol-1-yl)thiazole-4-carboxylic acid 489

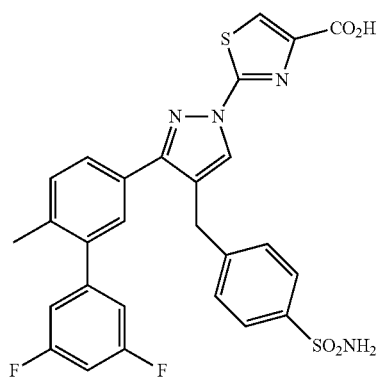 [SMILES: Cc1ccc(-c2nn(-c3nc(C(=O)O)cs3)cc2Cc2ccc(S(N)(=O)=O)cc2)cc1-c1cc(F)cc(F)c1]

Using procedures analogous to those described in the preparation of 486, the title compound was prepared and purified by HPLC: 2-(3-(3',5'-difluoro-6-methyl-[1,1'-biphenyl]-3-yl)-4-(4-sulfamoylbenzyl)-1H-pyrazol-1-yl)thiazole-4-carboxylic acid 489; MS (ES) 569.6 (M+H)⁺; LCMS RT=1.24 min.

Example 92

2-(3-(4-methyl-3-(pyridin-4-yl)phenyl)-4-(4-sulfamoylbenzyl)-1H-pyrazol-1-yl)thiazole-4-carboxylic acid 490

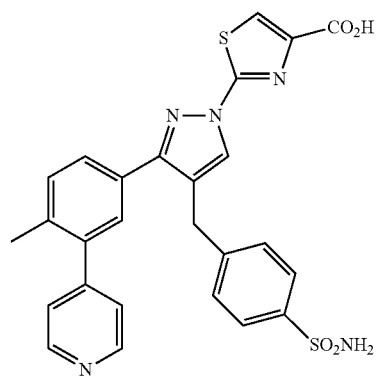 [SMILES: Cc1ccc(-c2nn(-c3nc(C(=O)O)cs3)cc2Cc2ccc(S(N)(=O)=O)cc2)cc1-c1ccncc1]

Using procedures analogous to those described in the preparation of 486, the title compound was prepared and purified by HPLC: 2-(3-(4-methyl-3-(pyridin-4-yl)phenyl)-4-(4-sulfamoylbenzyl)-1H-pyrazol-1-yl)thiazole-4-carboxylic acid 490; $^1$H-NMR (MeOD) δ 8.80 (br s, 2H), 8.44 (s, 1H), 8.17 (s, 1H), 7.85-7.76 (m, 5H), 7.49 (d, J=6.0 Hz, 1H), 7.41 (d, J=2.0 Hz, 1H), 7.40 (s, 1H), 7.38 (s, 1H), 4.21 (s, 2H), 2.39 (s, 3H); MS (ES) 533.6 (M+H)$^+$; LCMS RT=0.83 min.

Example 93

2-(3-(6-methyl-[1,1'-biphenyl]-3-yl)-4-(4-sulfamoylbenzyl)-1H-pyrazol-1-yl)thiazole-4-carboxylic acid 491

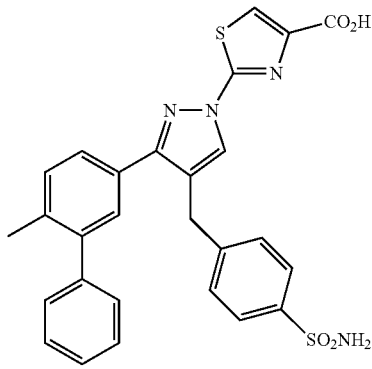 [SMILES: Cc1ccc(-c2nn(-c3nc(C(=O)O)cs3)cc2Cc2ccc(S(N)(=O)=O)cc2)cc1-c1ccccc1]

Using procedures analogous to those described in the preparation of 486, the title compound was prepared and purified by HPLC: 2-(3-(6-methyl-[1,1'-biphenyl]-3-yl)-4-(4-sulfamoylbenzyl)-1H-pyrazol-1-yl)thiazole-4-carboxylic acid 491 $^1$H-NMR (MeOD) δ 8.34 (s, 1H), 8.14 (s, 1H), 7.89-7.82 (m, 2H), 7.83 (d, J=8.4 Hz, 2H), 7.60 (dd, J=8.0, 2.0 Hz, 1H), 7.54 (d, J=8.0 Hz, 2H), 7.49-7.35 (m, 4H), 7.29 (d, J=8.0 Hz, 2H), 4.20 (s, 2H), 2.30 (s, H); MS (ES) 531.6 (M+H)$^+$; LCMS RT=1.18 min.

Example 94

2-(3-(3',4'-difluoro-6-methyl-[1,1'-biphenyl]-3-yl)-4-(4-sulfamoylbenzyl)-1H-pyrazol-1-yl)thiazole-4-carboxylic acid 492

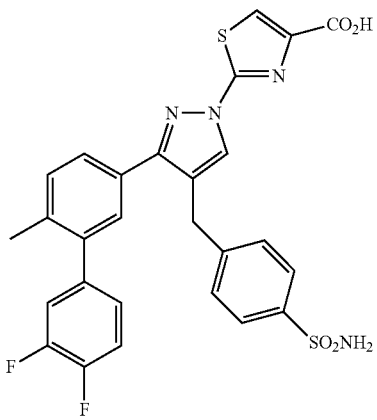 [SMILES: Cc1ccc(-c2nn(-c3nc(C(=O)O)cs3)cc2Cc2ccc(S(N)(=O)=O)cc2)cc1-c1ccc(F)c(F)c1]

Using procedures analogous to those described in the preparation of 486, the title compound was prepared and purified by HPLC: 2-(3-(3',4'-difluoro-6-methyl-[1,1'-biphenyl]-3-yl)-4-(4-sulfamoylbenzyl)-1H-pyrazol-1-yl)thiazole-4-carboxylic acid 492 MS (ES) 567.9 (M+H)$^+$; LCMS RT=1.20 min.

Example 95

2-(3-(4'-fluoro-3',6-dimethyl-[1,1'-biphenyl]-3-yl)-4-(4-sulfamoylbenzyl)-1H-pyrazol-1-yl)thiazole-4-carboxylic acid 493

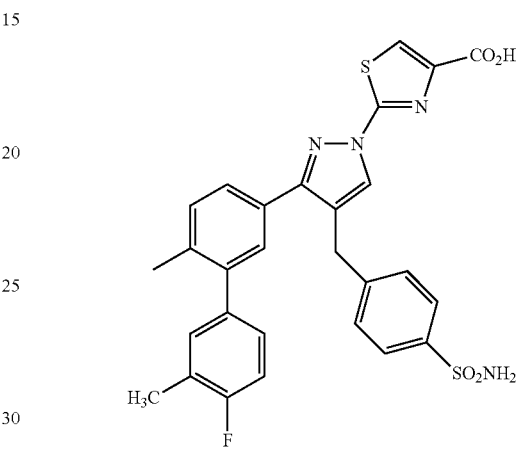

Using procedures analogous to those described in the preparation of 486, the title compound was prepared and purified by HPLC: 2-(3-(4'-fluoro-3',6-dimethyl-[1,1'-biphenyl]-3-yl)-4-(4-sulfamoylbenzyl)-1H-pyrazol-1-yl)thiazole-4-carboxylic acid 493 MS (ES) 563.9 (M+H)$^+$; LCMS RT=1.25 min.

Example 96

2-(3-(3'-fluoro-4'-methoxy-6-methyl-[1,1'-biphenyl]-3-yl)-4-(4-sulfamoylbenzyl)-1H-pyrazol-1-yl)thiazole-4-carboxylic acid 494

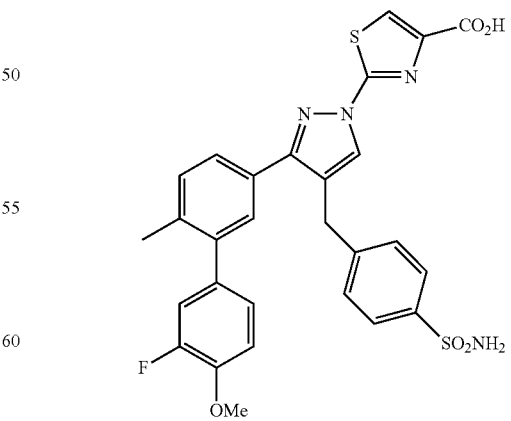

Using procedures analogous to those described in the preparation of 486, the title compound was prepared and purified by HPLC: 2-(3-(3'-fluoro-4'-methoxy-6-methyl-[1, 1'-biphenyl]-3-yl)-4-(4-sulfamoylbenzyl)-1H-pyrazol-1-yl)thiazole-4-carboxylic acid 494 MS (ES) 579.6 (M+H)+; LCMS RT=1.18 min.

Example 97

2-(4-(4-sulfamoylbenzyl)-3-(3',5',6-trimethyl-[1,1'-biphenyl]-3-yl)-1H-pyrazol-1-yl)thiazole-4-carboxylic acid 495

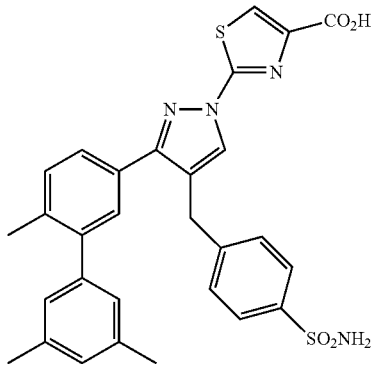 [SMILES: Cc1cc(C)cc(-c2cc(-c3nn(-c4nc(C(=O)O)cs4)cc3Cc3ccc(S(N)(=O)=O)cc3)ccc2C)c1]

Using procedures analogous to those described in the preparation of 486, the title compound was prepared and purified by HPLC: 2-(4-(4-sulfamoylbenzyl)-3-(3',5',6-trimethyl-[1,1'-biphenyl]-3-yl)-1H-pyrazol-1-yl)thiazole-4-carboxylic acid 495 MS (ES) 559.9 (M+H)+; LCMS RT=1.29 min.

Example 98

2-(3-(3'-cyano-4',6-dimethyl-[1,1'-biphenyl]-3-yl)-4-(4-sulfamoylbenzyl)-1H-pyrazol-1-yl)thiazole-4-carboxylic acid 496

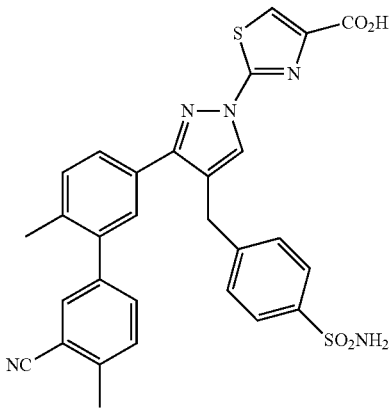 [SMILES: Cc1ccc(-c2cc(-c3nn(-c4nc(C(=O)O)cs4)cc3Cc3ccc(S(N)(=O)=O)cc3)ccc2C)cc1C#N]

Using procedures analogous to those described in the preparation of 486, the title compound was prepared and purified by HPLC: 2-(3-(3'-fluoro-6-methyl-[1,1'-biphenyl]-3-yl)-4-(4-sulfamoylbenzyl)-1H-pyrazol-1-yl)thiazole-4-carboxylic acid 496 MS (ES) 549.6 (M+H)+; LCMS RT=1.18 min.

Example 99

2-(3-(3'-fluoro-6-methyl-[1,1'-biphenyl]-3-yl)-4-(4-sulfamoylbenzyl)-1H-pyrazol-1-yl)thiazole-4-carboxylic acid 497

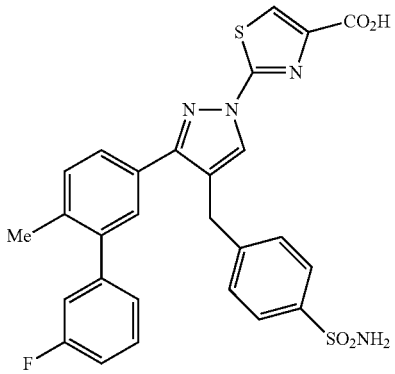 [SMILES: Cc1ccc(-c2nn(-c3nc(C(=O)O)cs3)cc2Cc2ccc(S(N)(=O)=O)cc2)cc1-c1cccc(F)c1]

Using procedures analogous to those described in the preparation of 486, the title compound was prepared and purified by HPLC: 2-(3-(3'-fluoro-6-methyl-[1,1'-biphenyl]-3-yl)-4-(4-sulfamoylbenzyl)-1H-pyrazol-1-yl)thiazole-4-carboxylic acid 497 MS (ES) 549.6 (M+H)+; LCMS RT=1.18 min.

Example 100

2-(3-(4'-fluoro-6-methyl-[1,1'-biphenyl]-3-yl)-4-(4-sulfamoylbenzyl)-1H-pyrazol-1-yl)thiazole-4-carboxylic acid 498(Compound VV)

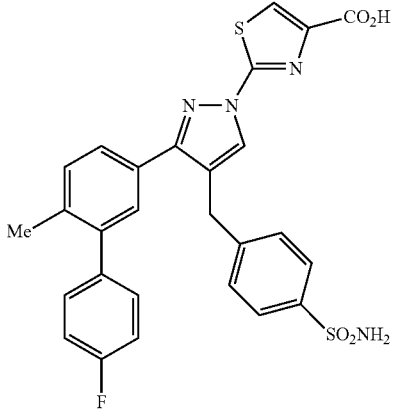 [SMILES: Cc1ccc(-c2nn(-c3nc(C(=O)O)cs3)cc2Cc2ccc(S(N)(=O)=O)cc2)cc1-c1ccc(F)cc1]

Using procedures analogous to those described in the preparation of 486, the title compound was prepared and purified by HPLC: 2-(3-(4'-fluoro-6-methyl-[1,1'-biphenyl]-3-yl)-4-(4-sulfamoylbenzyl)-1H-pyrazol-1-yl)thiazole-4-carboxylic acid 498 MS (ES) 549.6 (M+H)+; LCMS RT=1.16 min.

Example 101

2-(3-(3'-ethyl-6-fluoro-[1,1'-biphenyl]-3-yl)-4-(4-sulfamoylbenzyl)-1H-pyrazol-1-yl)thiazole-4-carboxylic acid 513

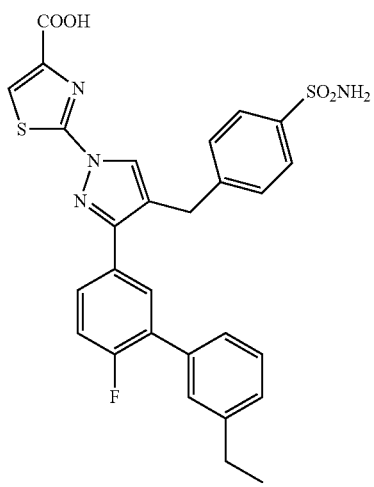 [SMILES: CCc1cccc(-c2cc(-c3nn(-c4nc(C(=O)O)cs4)cc3Cc3ccc(S(N)(=O)=O)cc3)ccc2F)c1]

Using procedures analogous to those described in the preparation of 459, Steps 1-6, 2-(3-(3-chloro-4-fluorophenyl)-4-(4-sulfamoylbenzyl)-1H-pyrazol-1-yl)thiazole-4-carboxylic acid was prepared.

Modified Step 7: To 2-(3-(3-chloro-4-fluorophenyl)-4-(4-sulfamoylbenzyl)-1H-pyrazol-1-yl)thiazole-4-carboxylic acid (50 mg, 0.10 mmol) in dioxane/water (2.5 mL, 4:1) was added 3-ethylphenyl)boronic acid (23 mg, 0.15 mmol), followed by $Cs_2CO_3$ (68 mg, 0.20 mmol), $Pd_2(dba)_3$ (10.0 mg, 0.01 mmol), and t-$Bu_3P$ (5 µL, 0.03 mmol). This solution was capped and purged with argon. The reaction mixture was heated at 95° C. for 24 h. The reaction mixture was cooled down and diluted with HCl (10 mL, 1M) and extracted with ethyl acetate (3×15 mL). The combined organic layers were then dried with MgSO4 and concentrated by rotary evaporator. The crude product was then purified by HPLC (Phenomenex Gemini C18, $H_2O/CH_3CN$ gradient from 25% to 85% $CH_3CN$ for 4 min, 0.1% TFA) to give 2-(3-(3'-ethyl-6-fluoro-[1,1'-biphenyl]-3-yl)-4-(4-sulfamoylbenzyl)-1H-pyrazol-1-yl)thiazole-4-carboxylic acid 513 (12 mg, 21%). $^1$H-NMR (MeOD) δ 8.37 (s, 1H), 8.17 (s, 1H), 7.86 (d, J=8.24 Hz, 2H), 7.77 (d, J=6.4 Hz, 2H), 7.44 (d, J=8.2 Hz, 2H), 7.33 (t, J=9.62 Hz, 1H), 7.16 (d, J=7.79 Hz, 2H), 7.03 (m, 1H), 4.23 (s, 2H), 3.63 (q, J=7.1, 14.2 Hz, 2H), 1.20 (t, J=7.1 Hz, 3H); MS (ES) 562.9 (M+H)$^+$; LCMS RT=1.24 min.

Example 102

2-(3-(3'-ethyl-6-fluoro-[1,1'-biphenyl]-3-yl)-4-(4-sulfamoylbenzyl)-1H-pyrazol-1-yl)thiazole-4-carboxylic acid 514

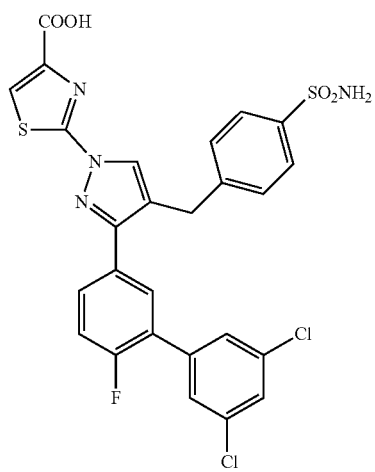 [SMILES: NS(=O)(=O)c1ccc(Cc2cn(-c3nc(C(=O)O)cs3)nc2-c2ccc(F)c(-c3cc(Cl)cc(Cl)c3)c2)cc1]

Using procedures analogous to those described in the preparation of 513, the title compound was prepared and purified by HPLC: 2-(3-(3'-ethyl-6-fluoro-[1,1'-biphenyl]-3-yl)-4-(4-sulfamoylbenzyl)-1H-pyrazol-1-yl)thiazole-4-carboxylic acid 514 $^1$H-NMR (MeOD) δ 8.36 (s, 1H), 8.16 (s, 1H), 7.87 (d, J=6.4 Hz, 2H), 7.81 (m, 2H), 7.75 (d, J=8.1 Hz, 2H), 7.46 (M, 2H), 7.34 (m, 2H), 4.24 (s, 2H); MS (ES) 602.9 (M+H)$^+$; LCMS RT=1.30 min.

Example 103

2-(3-(6-fluoro-[1,1'-biphenyl]-3-yl)-4-(4-sulfamoylbenzyl)-1H-pyrazol-1-yl)thiazole-4-carboxylic acid 515

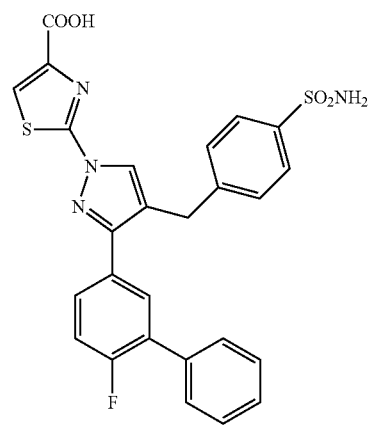 [SMILES: NS(=O)(=O)c1ccc(Cc2cn(-c3nc(C(=O)O)cs3)nc2-c2ccc(F)c(-c3ccccc3)c2)cc1]

Using procedures analogous to those described in the preparation of 513, the title compound was prepared and purified by HPLC: 2-(3-(6-fluoro-[1,1'-biphenyl]-3-yl)-4-(4-sulfamoylbenzyl)-1H-pyrazol-1-yl)thiazole-4-carboxylic acid 515 MS (ES) 544.0 (M+H)$^+$; LCMS RT=1.18 min.

Example 104

2-(3-(6-fluoro-3',4'-dimethyl-[1,1'-biphenyl]-3-yl)-4-(4-sulfamoylbenzyl)-1H-pyrazol-1-yl)thiazole-4-carboxylic acid 516

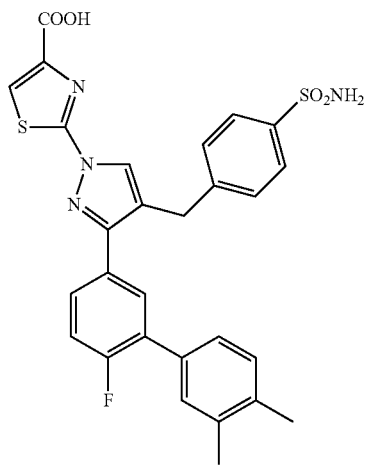 [SMILES: Cc1ccc(-c2cc(-c3nn(-c4nc(C(=O)O)cs4)cc3Cc3ccc(S(N)(=O)=O)cc3)ccc2F)cc1C]

Using procedures analogous to those described in the preparation of 513, the title compound was prepared and purified by HPLC: 2-(3-(6-fluoro-3',4'-dimethyl-[1,1'-biphenyl]-3-yl)-4-(4-sulfamoylbenzyl)-1H-pyrazol-1-yl)thiazole-4-carboxylic acid 516 MS (ES) 562.9 (M+H)$^+$; LCMS RT=1.23 min.

Example 105

2-(4-(4-sulfamoylbenzyl)-3-(3',4',6-trifluoro-[1,1'-biphenyl]-3-yl)-1H-pyrazol-1-yl)thiazole-4-carboxylic acid 517

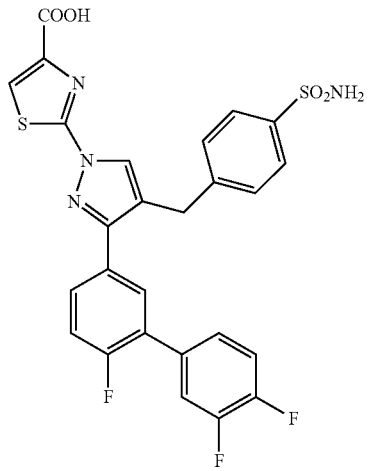

Using procedures analogous to those described in the preparation of 513, the title compound was prepared and purified by HPLC: 2-(4-(4-sulfamoylbenzyl)-3-(3',4',6-trifluoro-[1,1'-biphenyl]-3-yl)-1H-pyrazol-1-yl)thiazole-4-carboxylic acid 517 MS (ES) 571.0 (M+H)$^+$; LCMS RT=1.18 min.

Example 106

2-(3-(4',6-difluoro-3'-methoxy-[1,1'-biphenyl]-3-yl)-4-(4-sulfamoylbenzyl)-1H-pyrazol-1-yl)thiazole-4-carboxylic acid 518

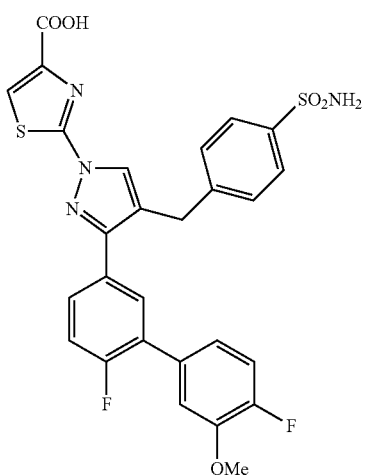 [SMILES: COc1cc(-c2cc(-c3nn(-c4nc(C(=O)O)cs4)cc3Cc3ccc(S(N)(=O)=O)cc3)ccc2F)ccc1F]

Using procedures analogous to those described in the preparation of 513, the title compound was prepared and purified by HPLC: 2-(3-(4',6-difluoro-3'-methoxy-[1,1'-biphenyl]-3-yl)-4-(4-sulfamoylbenzyl)-1H-pyrazol-1-yl)thiazole-4-carboxylic acid 518 MS (ES) 582.9 (M+H)$^+$; LCMS RT=1.14 min.

Example 107

2-(3-(3'-methyl-[1,1'-biphenyl]-3-yl)-4-(4-sulfamoylbenzyl)-1H-pyrazol-1-yl)thiazole-4-carboxylic acid 519

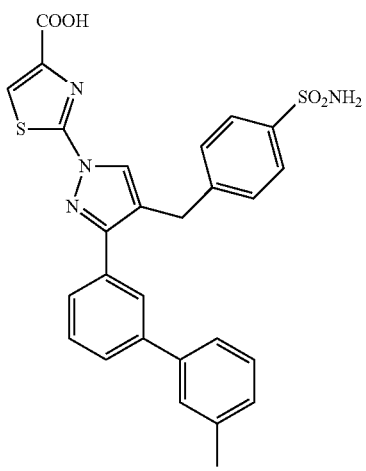 [SMILES: Cc1cccc(-c2cccc(-c3nn(-c4nc(C(=O)O)cs4)cc3Cc3ccc(S(N)(=O)=O)cc3)c2)c1]

Using procedures analogous to those described in the preparation of 513, the title compound was prepared and purified by HPLC: 2-(3-(3'-methyl-[1,1'-biphenyl]-3-yl)-4-(4-sulfamoylbenzyl)-1H-pyrazol-1-yl)thiazole-4-carboxylic acid 519 MS (ES) 530.9 (M+H)$^+$; LCMS RT=1.00 min.

Example 108

2-(3-(3',6-difluoro-4'-methyl-[1,1'-biphenyl]-3-yl)-4-(4-sulfamoylbenzyl)-1H-pyrazol-1-yl)thiazole-4-carboxylic acid 520

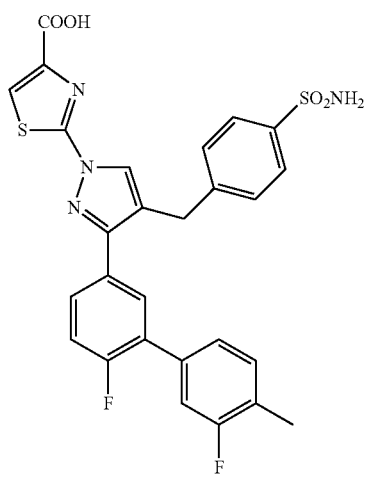 [SMILES: Cc1ccc(-c2cc(-c3nn(-c4nc(C(=O)O)cs4)cc3Cc3ccc(S(N)(=O)=O)cc3)ccc2F)cc1F]

Using procedures analogous to those described in the preparation of 513, the title compound was prepared and purified by HPLC: 2-(3-(3',6-difluoro-4'-methyl-[1,1'-biphenyl]-3-yl)-4-(4-sulfamoylbenzyl)-1H-pyrazol-1-yl)thiazole-4-carboxylic acid 520 MS (ES) 566.9 (M+H)⁺; LCMS RT=1.22 min.

Example 109

2-(3-(3'-methoxy-[1,1'-biphenyl]-3-yl)-4-(4-sulfamoylbenzyl)-1H-pyrazol-1-yl)thiazole-4-carboxylic acid 521

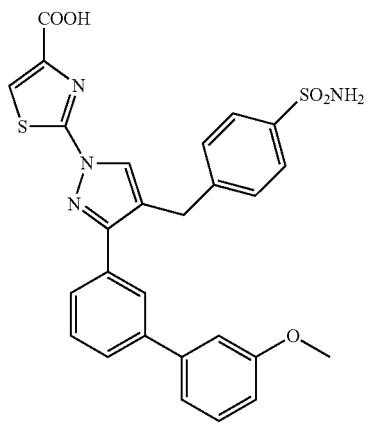 [SMILES: COc1cccc(-c2cccc(-c3nn(-c4nc(C(=O)O)cs4)cc3Cc3ccc(S(N)(=O)=O)cc3)c2)c1]

Using procedures analogous to those described in the preparation of 513, the title compound was prepared and purified by HPLC: 2-(3-(3'-methoxy-[1,1'-biphenyl]-3-yl)-4-(4-sulfamoylbenzyl)-1H-pyrazol-1-yl)thiazole-4-carboxylic acid 521 MS (ES) 546.9 (M+H)⁺; LCMS RT=0.89 min.

Example 110

2-(3-(3-(pyridin-3-yl)phenyl)-4-(4-sulfamoylbenzyl)-1H-pyrazol-1-yl)thiazole-4-carboxylic acid 522

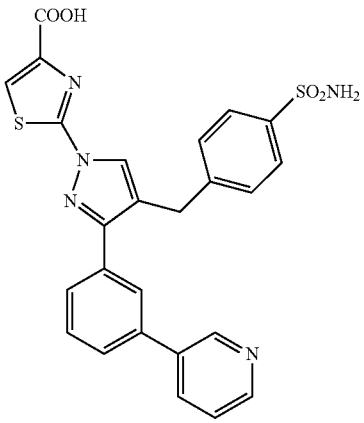 [SMILES: NS(=O)(=O)c1ccc(Cc2cn(-c3nc(C(=O)O)cs3)nc2-c2cccc(-c3cccnc3)c2)cc1]

Using procedures analogous to those described in the preparation of 513, the title compound was prepared and purified by HPLC: 2-(3-(3-(pyridin-3-yl)phenyl)-4-(4-sulfamoylbenzyl)-1H-pyrazol-1-yl)thiazole-4-carboxylic acid 522 MS (ES) 517.9 (M+H)⁺; LCMS RT=0.82 min.

Example 111

2-(3-(3'-amino-[1,1'-biphenyl]-3-yl)-4-(4-sulfamoylbenzyl)-1H-pyrazol-1-yl)thiazole-4-carboxylic acid 523

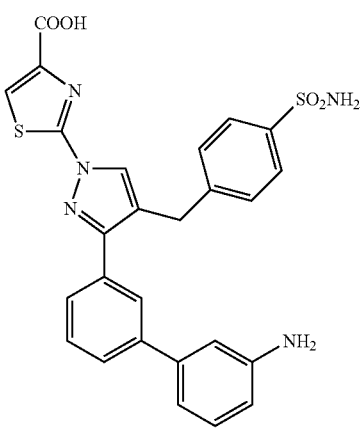 [SMILES: Nc1cccc(-c2cccc(-c3nn(-c4nc(C(=O)O)cs4)cc3Cc3ccc(S(N)(=O)=O)cc3)c2)c1]

Using procedures analogous to those described in the preparation of 513, the title compound was prepared and purified by HPLC: 2-(3-(3'-amino-[1,1'-biphenyl]-3-yl)-4-(4-sulfamoylbenzyl)-1H-pyrazol-1-yl)thiazole-4-carboxylic acid 524 MS (ES) 532.0 (M+H)⁺; LCMS RT=0.70 min.

Example 112

2-(5-cyclopropyl-3-(4',6-difluoro-[1,1'-biphenyl]-3-yl)-4-(4-sulfamoylbenzyl)-1H-pyrazol-1-yl)thiazole-4-carboxylic acid 482

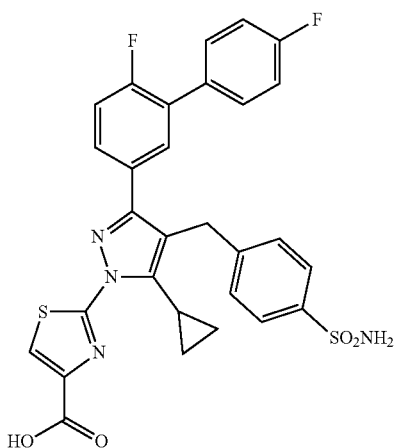

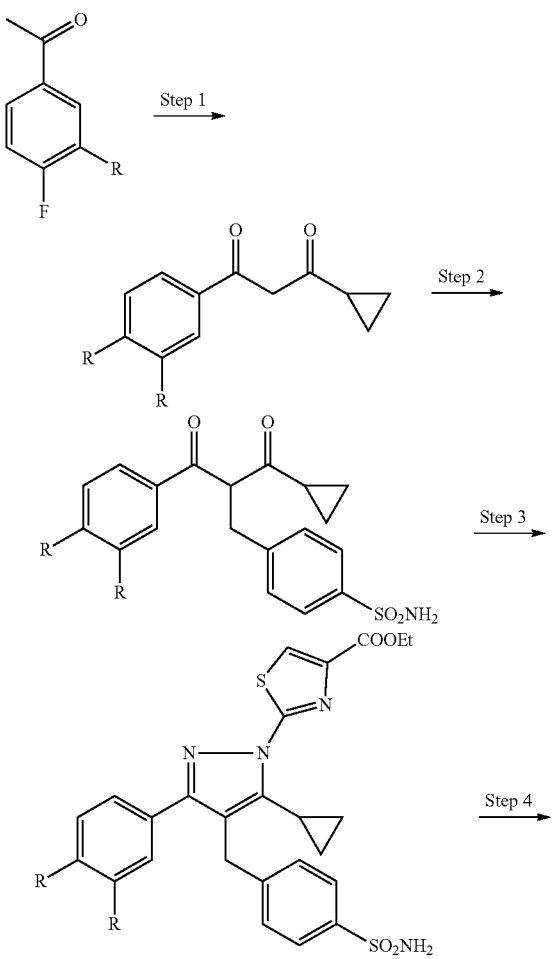

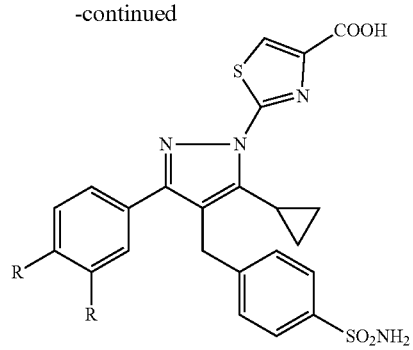

Step 1. Synthesis of 1-(3-chloro-4-fluorophenyl)-3-cyclopropylpropane-1,3-dione 1-(3-Chloro-4-fluorophenyl)ethan-1-one (1.5 g, 8.72 mmol, 1 eq) was dissolved in THF and cooled to −78° C. After 10 minutes of stirring, LHMDS (1 M in hexanes, 12.2 mL, 1.4 eq) was added dropwise over 20 minutes. This was allowed to stir for an additional 20 minutes then cyclopropanecarbonyl chloride (1.1 mL, 12.2 mmol, 1.4 eq) was added dropwise. The reaction was allowed to stir for 3 h at which time it was brought to room temperature. Reaction was quenched with 1 M HCl and extracted with ethyl acetate. The aqueous layer was back extracted three times with ethyl acetate. The organic layer was washed with brine and dried over MgSO$_4$. The reaction mixture was purified by flash chromatography (Combi-flash Rf, hexane/ethyl acetate, 0-20% gradient) to give 1-(3-chloro-4-fluorophenyl)-3-cyclopropylpropane-1,3-dione (1 g, 50%). MS (ES) 241 (M+H)$^+$; LCMS RT 1.357 min.

Step 2. Synthesis of 4-(2-(3-chloro-4-fluorobenzoyl)-3-cyclopropyl-3-oxopropyl)benzenesulfonamide 1-(3-Chloro-4-fluorophenyl)-3-cyclopropylpropane-1,3-dione (1 g, 4.16 mmol, 1 eq) was dissolved in DMSO (10 mL) and stirred. 4-(bromomethyl)benzenesulfonamide (1.34 g, 5.4 mmol, 1.3 eq), Cs$_2$CO$_3$ (1.75 g, 5.4 mmol, 1.3 eq), and sodium iodide (624 mg, 4.16 mmol, 1 eq) were added. The reaction was stirred at 50° C. for 1 hour. After this time, the reaction was poured into 1 M HCl and extracted with ethyl acetate. The aqueous layer was back extracted three times with ethyl acetate. The combined organics were washed with brine and dried over MgSO$_4$. The reaction was purified by flash chromatography (Combi-flash Rf, hexane/ethyl acetate, 0-80% gradient) to give 4-(2-(3-chloro-4-fluorobenzoyl)-3-cyclopropyl-3-oxopropyl)benzenesulfonamide (750 mg, 45%). MS: (ES) 410 (M+H)$^+$; LCMS RT 1.14 min.

Step 3. Synthesis of ethyl 2-(3-(3-chloro-4-fluorophenyl)-5-cyclopropyl-4-(4-sulfamoylbenzyl)-1H-pyrazol-1-yl)thiazole-4-carboxylate 4-(2-(3-Chloro-4-fluorobenzoyl)-3-cyclopropyl-3-oxopropyl)benzenesulfonamide (700 mg, 1.7 mmol, 1 eq) was added to a microwave vial with ethyl 2-hydrazinylthiazole-4-carboxylate (300 mg, 1.7 mmol, 1 eq) and p-toluenesulfonic acid (650 mg, 3.4 mmol, 2 eq). The reactants were purged with argon gas then dissolved with ethanol (4 mL). The reaction was run in the microwave reactor for 15 minutes at 100° C. The reaction was purified by flash chromatography (Combi-flash Rf, hexane/ethyl acetate=0-80% gradient) to give ethyl 2-(3-(3-chloro-4-fluorophenyl)-5-cyclopropyl-4-(4-sulfamoylbenzyl)-1H-pyrazol-1-yl)thiazole-4-carboxylate (300 mg).

Step 4. 2-(5-cyclopropyl-3-(4',6-difluoro-[1,1'-biphenyl]-3-yl)-4-(4-sulfamoylbenzyl)-1H-pyrazol-1-yl)thiazole-4-carboxylic acid 482

Ethyl 2-(3-(3-chloro-4-fluorophenyl)-5-cyclopropyl-4-(4-sulfamoylbenzyl)-1H-pyrazol-1-yl)thiazole-4-carboxylate (15 mg, 0.03 mmol,) was placed into a microwave vial along with (4-fluorophenyl)boronic acid (8 mg, 0.06 mmol, 2 eq) and the Pd(P(t-Bu)$_3$)$_2$(5 mg). The reaction mixture was purged with vacuum and argon gas. Following this, Cs$_2$CO$_3$ (1 M, 1 mL) and THF (2 mL) were added. The reaction was heated in the microwave for 15 minutes at 100° C. After LC/MS showed complete conversion to product along with hydrolysis of the ester, solvent was removed by rotary evaporation and the reaction was purified by HPLC (Phenomenex Gemini C18, H$_2$O/CH$_3$CN gradient from 45% to 85% CH$_3$CN for 7 min, 0.1% TFA) to give the title compound 482 (5 mg). $^1$H-NMR (MeOD): δ 8.27 (s, 1H) 7.85 (d, J=12 Hz, 2H); 7.57-7.63 (m, 1H), 7.5 (d, J=16 Hz, 1H), 7.29-7.42 (m, 4H), 7.12-7.25 (m, 4H), 4.25 (s, 2H), 2.32-2.41 (m, 1H), 1.15 (d, J=12 Hz, 2H), 0.7 (d, J=9 Hz, 2H); (ES) 593 (M+H)$^+$ LCMS RT=1.28 min.

Example 113

2-(5-cyclopropyl-3-(6-fluoro-3'-methoxy-[1,1'-biphenyl]-3-yl)-4-(4-sulfamoylbenzyl)-1H-pyrazol-1-yl)thiazole-4-carboxylic acid 483

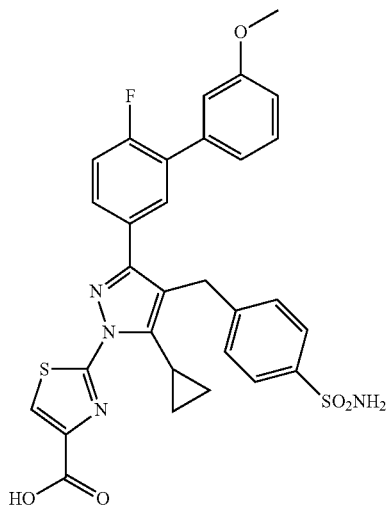 [SMILES: COc1cccc(-c2cc(-c3nn(-c4nc(C(=O)O)cs4)c(C4CC4)c3Cc3ccc(S(N)(=O)=O)cc3)ccc2F)c1]

Using procedures analogous to those described in the preparation of 482, the title compound was prepared and purified by HPLC: 2-(5-cyclopropyl-3-(6-fluoro-3'-methoxy-[1,1'-biphenyl]-3-yl)-4-(4-sulfamoylbenzyl)-1H-pyrazol-1-yl)thiazole-4-carboxylic acid 483 $^1$H-NMR (CDCl$_3$) δ 8.13 (s, 1H), 7.85 (d, J=8 Hz, 2H), 7.55-7.59 (m, 1H), 7.35-7.39 (m, 2H), 7.25-7.31 (m, 4H), 7.17 (t, J=18.84 Hz, 1H), 7.04 (d, J=7.56 Hz, 1H), 6.91-6.94 (dd, J=2, 2 Hz, 1H), 6.73 (s, 1H), 5.04 (s, Broad, 2H), 4.17 (s, 2H), 3.87 (s, 3H), 2.23-2.27 (m, 1H), 1.12 (d, J=7 Hz, 2H), 0.73 (d, J=5 Hz, 2H), MS (ES) 605 (M+H)$^+$ LCMS RT=1.25 min.

Example 114

2-(5-cyclopropyl-3-(6-fluoro-4'-methyl-[1,1'-biphenyl]-3-yl)-4-(4-sulfamoylbenzyl)-1H-pyrazol-1-yl)thiazole-4-carboxylic acid 484

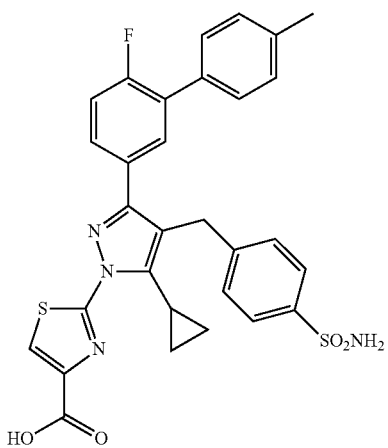 [SMILES: Cc1ccc(-c2cc(-c3nn(-c4nc(C(=O)O)cs4)c(C4CC4)c3Cc3ccc(S(N)(=O)=O)cc3)ccc2F)cc1]

Using procedures analogous to those described in the preparation of 482, the title compound was prepared and purified by HPLC: 2-(5-cyclopropyl-3-(6-fluoro-4'-methyl-[1,1'-biphenyl]-3-yl)-4-(4-sulfamoylbenzyl)-1H-pyrazol-1-yl)thiazole-4-carboxylic acid 484 $^1$H-NMR (CDCl$_3$) δ 8.10 (s, 1H), 7.82 (d, J=8 Hz, 2H), 7.5 (dd, J$_1$=2; J$_2$=2 Hz, 1H), 7.41-7.45 (m, 1H), 7.22-7.32 (m, 7H), 7.13 (t, J=19 Hz, 1H), 5.06 (s, 2H), 4.14 (s, 2H), 2.40 (s, 3H), 2.17-2.23 (m, 1H), 1.07 (d, J=8 Hz, 2H), 0.68 (d, J=5. Hz, 2H), MS (ES) 589 (M+H)$^+$ LCMS RT=1.31 min.

Example 115

2-(5-(cyclopropylmethyl)-3-(3-(phenylamino)phenyl)-4-(4-sulfamoylbenzyl)-1H-pyrazol-1-yl)thiazole-4-carboxylic acid 485

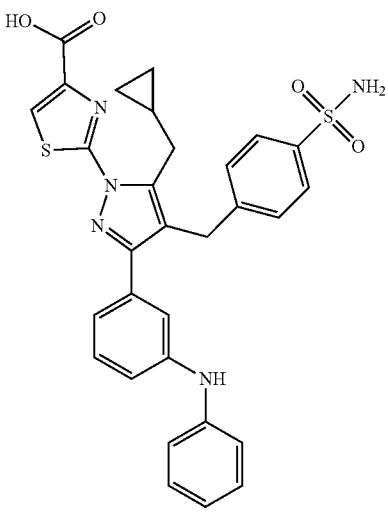 [SMILES: NS(=O)(=O)c1ccc(Cc2c(-c3cccc(Nc4ccccc4)c3)nn(-c3nc(C(=O)O)cs3)c2CC2CC2)cc1]

Using procedures analogous to those described in the preparation of 482, steps 1-3, ethyl-2-[3-(3-bromophenyl)-

5-(cyclopropylmethyl)-4-[(4-sulfamoylphenyl)methyl]-1H-pyrazol-1-yl]-1,3-thiazole-4-carboxylate was prepared.

Modified Step 4: Ethyl-2-[3-(3-bromophenyl)-5-(cyclopropylmethyl)-4-[(4-sulfamoylphenyl)methyl]-1H-pyrazol-1-yl]-1,3-thiazole-4-carboxylate (80 mg, 0.139 mmol), powdered $K_3PO_4$ (56.6 mg, 0.267 mmol), aniline (18 μL, 0.199 mmol), and dimethylacetamide (1.3 mL) were combined in a vial. The mixture was then degassed and purged with argon (×3) after which $Pd(P(tBu)_3)_2$ was added. The vial was then sealed, and the mixture was stirred at 100° C. for 16 hours. After completion, the reaction mixture was cooled to room temperature, diluted with EtOAc (40 mL), washed with $H_2O$ (2×10 mL), followed by brine (2×10 mL). The organic layer was then dried over $MgSO_4$, filtered, and concentrated by rotary evaporator. The reaction was purified by flash chromatography (Combi-flash Rf, hexane/ethyl acetate, 0-80% gradient) to give the title compound 485 (43 mg, 53%). $^1$H-NMR (CDCl$_3$) δ 7.96 (1H, s), 7.72 (2H, d, J=8.3 Hz), 7.23-7.18 (6H, m), 7.02-6.99 (4H, m), 6.88 (1H, t, J=7.4 Hz), 4.02 (2H, s), 3.10 (2H, d, J=6.8 Hz), 1.01 (1H, m), 0.33 (2H, dd, J=13.8, 5.8 Hz), 0.14 (2H, dd, J=10.2, 5.0 Hz); MS(ES) 585.7 (M+H)$^+$.

Example 116

2-(5-cyclopropyl-3-(4-methyl-3-(pyridin-3-yl)phenyl)-4-(4-sulfamoyl-benzyl)-1H-pyrazol-1-yl)thiazole-4-carboxylic acid 499

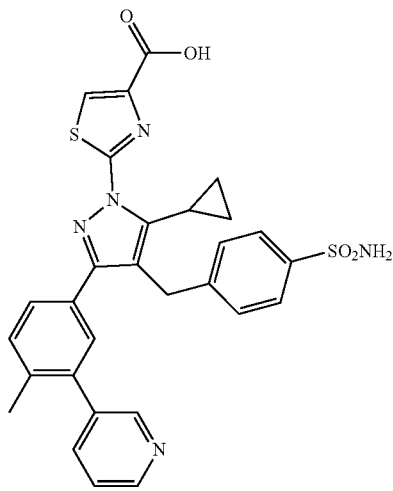 [SMILES: Cc1ccc(-c2nn(-c3nc(C(=O)O)cs3)c(C3CC3)c2Cc2ccc(S(N)(=O)=O)cc2)cc1-c1cccnc1]

Using procedures analogous to those described in the preparation of 482, Steps 1-3, 2-(3-(3-chloro-4-methylphenyl)-5-cyclopropyl-4-(4-sulfamoylbenzyl)-1H-pyrazol-1-yl)thiazole-4-carboxylate was prepared.

Modified Step 4: A flame dried flask was charged with Bis(tri-tert-butylphosphine)palladium (5.1 mg, 10 mol %), cesium carbonate (1 mL, 1 M solution), pyridin-3-ylboronic acid (22 mg, 0.2 mmol), ethyl 2-(3-(3-chloro-4-methylphenyl)-5-cyclopropyl-4-(4-sulfamoylbenzyl)-1H-pyrazol-1-yl)thiazole-4-carboxylate (50 mg, 0.1 mmol), and THF (2 mL). The reaction mixture was microwave irradiated at 120° C. for 20 min and the solvent was removed by rotary evaporator. The residue was filtered through a celite pad with MeOH then solvent was removed by rotary evaporator. The residue was purified by HPLC (Phenomenex Gemini C18, $H_2O$/CH$_3$CN gradient from 35% to 85% CH$_3$CN for 4 min, 0.1% TFA) to give the title compound 499 (15 mg, 30%). $^1$H-NMR (MeOD) δ 8.86 (d, J=5.2 Hz, 1H), 8.83 (s, 1H), 8.45 (d, J=8.4 Hz, 1H), 8.27 (s, 1H), 8.13 (dd, J=8.0, 1.6 Hz, 1H), 7.76 (d, J=8.4 Hz, 2H), 7.64 (dd, J=8.0, 1.6 Hz, 1H), 7.43 (d, J=8.0 Hz, 1H), 7.29 (s, 2H), 7.27 (s, 1H), 4.25 (s, 2H), 2.42-2.34 (m, 1H), 2.33 (s, 3H), 1.10 (dt, J=8.4, 4.6 Hz, 2H), 0.69 (dt, J=5.6, 4.6 Hz, 2H); MS (ES) 572.9 (M+H)$^+$; LCMS RT=0.87 min.

Example 117

2-(3-(3'-amino-6-methyl-[1,1'-biphenyl]-3-yl)-5-cyclopropyl-4-(4-sulfamoylbenzyl)-1H-pyrazol-1-yl)thiazole-4-carboxylic acid 500

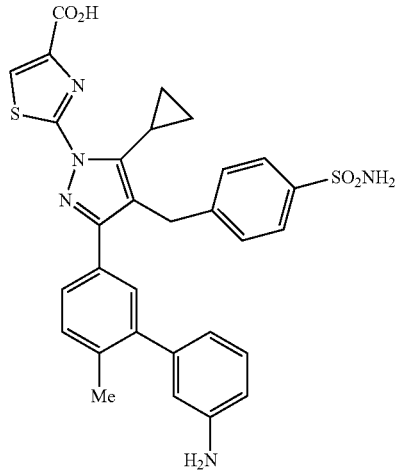 [SMILES: Cc1ccc(-c2nn(-c3nc(C(=O)O)cs3)c(C3CC3)c2Cc2ccc(S(N)(=O)=O)cc2)cc1-c1cccc(N)c1]

Using procedures analogous to those described in the preparation of 499, the title compound was prepared and purified by HPLC: 2-(3-(3'-amino-6-methyl-[1,1'-biphenyl]-3-yl)-5-cyclopropyl-4-(4-sulfamoylbenzyl)-1H-pyrazol-1-yl)thiazole-4-carboxylic acid 500: $^1$H-NMR (MeOD) δ 8.26 (s, 1H), 7.78 (d, J=8.4 Hz, 2H), 7.53 (t, J=8.0 Hz, 1H), 7.49 (dd, J=8.0, 1.6 Hz, 1H), 7.32 (d, J=8.0 Hz, 1H), 7.29 (s, 1H), 7.27 (s, 3H), 7.18 (d, J=8.0 Hz, 1H), 7.13 (s, 1H), 4.23 (s, 2H), 2.41-2.33 (m, 1H), 2.27 (s, 3H), 1.08 (dt, J=8.4, 6.4 Hz, 2H), 0.67 (dt, J=5.6, 4.6 Hz, 2H); MS (ES) 586.9 (M+H)$^+$; LCMS RT=0.92 min.

Example 118

2-(3-(3-(benzyloxy)phenyl)-5-cyclopropyl-4-(4-sulfamoylbenzyl)-1H-pyrazol-1-yl)thiazole-4-carboxylic acid 501

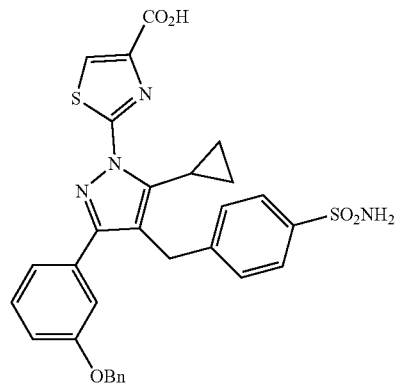 [SMILES: NS(=O)(=O)c1ccc(Cc2c(-c3cccc(OCc4ccccc4)c3)nn(-c3nc(C(=O)O)cs3)c2C2CC2)cc1]

Using procedures analogous to those described in the preparation of 482, the title compound was prepared and purified by HPLC: 2-(3-(3-(benzyloxy)phenyl)-5-cyclopropyl-4-(4-sulfamoylbenzyl)-1H-pyrazol-1-yl)thiazole-4-carboxylic acid 501: MS (ES) 549.6 (M+H)+; LCMS RT=1.16 min.

Example 119

2-(5-cyclopropyl-3-(3-phenoxyphenyl)-4-(4-sulfamoylbenzyl)-1H-pyrazol-1-yl)thiazole-4-carboxylic acid 502

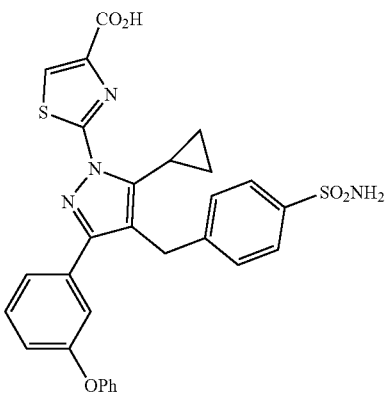 [SMILES: NS(=O)(=O)c1ccc(Cc2c(-c3cccc(Oc4ccccc4)c3)nn(-c3nc(C(=O)O)cs3)c2C2CC2)cc1]

Using procedures analogous to those described in the preparation of 482, the title compound was prepared and purified by HPLC: 2-(5-cyclopropyl-3-(3-phenoxyphenyl)-4-(4-sulfamoylbenzyl)-1H-pyrazol-1-yl)thiazole-4-carboxylic acid 502: $^1$H-NMR (MeOD) δ 8.24 (s, 1H), 7.76 (d, J=8.4 Hz, 2H), 7.40-7.31 (m, 4H), 7.19 (d, J=8.4 Hz, 2H), 7.13 (t, J=8.4 Hz, 1H), 7.07 (s, 1H), 7.00 (dd, J=8.0, 1.6 Hz, 1H), 6.93 (d, J=8.0 Hz, 2H), 4.15 (s, 2H), 2.37-2.29 (m, 1H), 1.03 (dt, J=8.4, 6.4 Hz, 2H), 0.62 (dt, J=5.6, 4.8 Hz, 2H); MS (ES) 573.6 (M+H)+; LCMS RT=0.94 min.

Example 120

2-(3-(3-(cyclopentyloxy)-4-methylphenyl)-5-(cyclopropylmethyl)-4-(4-sulfamoylbenzyl)-1H-pyrazol-1-yl)thiazole-4-carboxylic acid 467

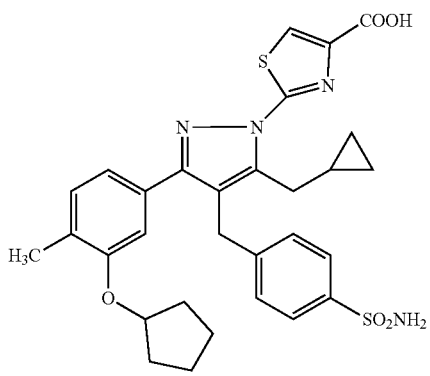 [SMILES: Cc1ccc(-c2nn(-c3nc(C(=O)O)cs3)c(CC3CC3)c2Cc2ccc(S(N)(=O)=O)cc2)cc1OC1CCCC1]

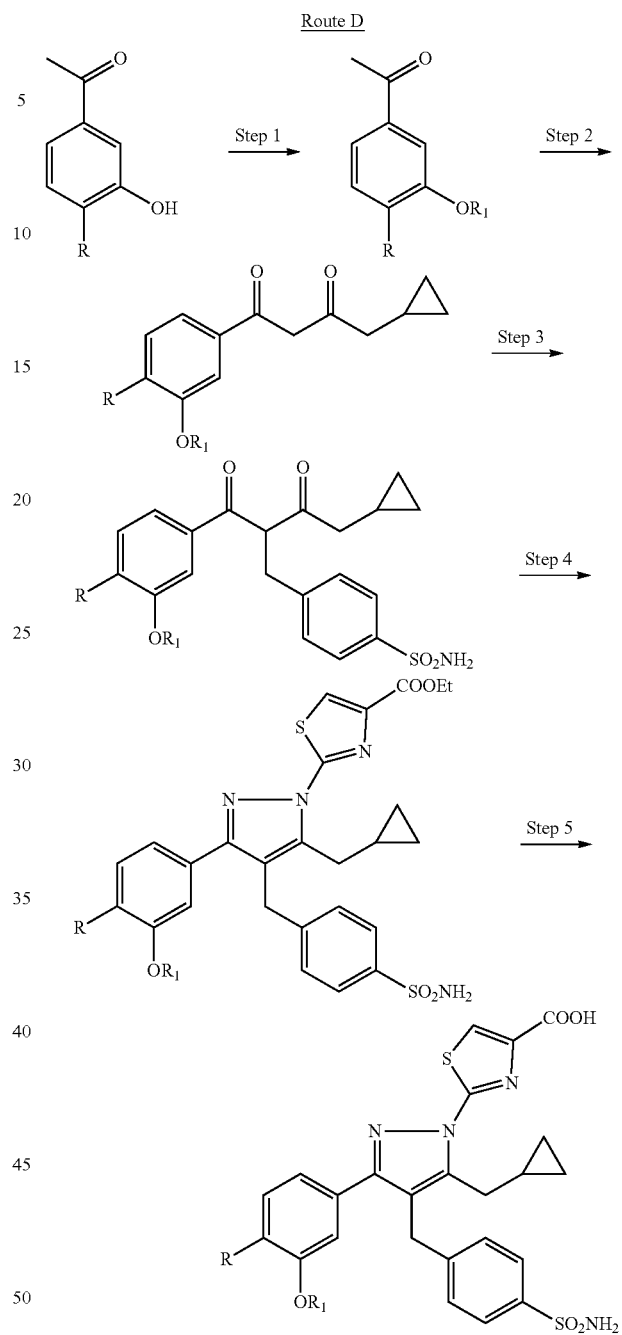

Route D

Step 1. Synthesis of 1-(3-(cyclopentyloxy)-4-methylphenyl)ethan-1-one

3-Hydroxy-4-methyl acetophenone (1 g, 0.0066 mol) was dissolved in anhydrous DMF and potassium carbonate (7.35 g, 0.053 mol) and cyclopentyl bromide (2.8 mL, 0.026 mol) were added and the reaction was irradiated at 140° C. for 40 min. The reaction mixture was poured into water and extracted with ethyl acetate (3×40 mL). The organic layers were washed with brine (2×50 mL) and dried with anhydrous magnesium sulfate. The solvents were removed by rotary evaporator and purified by flash chromatography (Combi-flash Rf, hexane/ethyl acetate, 0-50% gradient) to give 1-(3-(cyclopentyloxy)-4-methylphenyl)ethan-1-one (1.20 g, 83%).

Step 2. Synthesis of 1-(3-(cyclopentyloxy)-4-methylphenyl)-4-cyclopropylbutane-1,3-dione To a solution of the (1H-benzo[d][1,2,3]triazol-1-yl) derivative (1.20 g, 0.0055 mol) in DCM (30 mL) was added magnesium bromide diethyletherate (3.55 g, 0.013 mol) followed by 1-(3-(cyclopentyloxy)-4-methylphenyl)ethan-1-one (1.44 g, 0.007 mol) and DIPEA (2.88 mL, 0.016 mol). The reaction mixture was stirred at rt for 2 h. The reaction mixture was cooled in an ice bath, quenched with HCl (1 M), and extracted with DCM. The DCM layer was washed with HCl (1 M), water, and brine. The crude product was purified by flash chromatography (Combi-flash Rf, hexane/ethyl acetate, 0-20% gradient) to give 1-(3-(cyclopentyloxy)-4-methylphenyl)-4-cyclopropylbutane-1,3-dione (0.7 g, 42%).

Step 3. Synthesis of 4-(2-(3-(cyclopentyloxy)-4-methylbenzoyl)-4-cyclopropyl-3-oxobutyl)-benzenesulfonamide 1-(3-(Cyclopentyloxy)-4-methylphenyl)-4-cyclopropylbutane-1,3-dione (0.7 g, 0.0023 mol) and cesium carbonate (0.9 g, 0.0028 mol) in DMSO (10 mL) was stirred at rt for 5 minutes then KI (0.42 g, 0.0025 mol) and 4-(bromomethyl)benzenesulfonamide (0.63 g, 0.0025 mol) were added. The reaction mixture was stirred at 50° C. for 5 min. After completion of the reaction, the mixture was poured into HCl (1 M) and extracted with ethyl acetate. The organic layer was washed with saturated ammonium chloride and brine. The crude product was purified by flash chromatography (Combi-flash Rf, hexane/ethyl acetate=0-50% gradient) to give 4-(2-(3-(cyclopentyloxy)-4-methylbenzoyl)-4-cyclopropyl-3-oxobutyl)-benzenesulfonamide (0.82 g, 76%).

Step 4. Ethyl 2-(3-(3-(cyclopentyloxy)-4-methylphenyl)-5-(cyclopropylmethyl)-4-(4-sulfamoylbenzyl)-1H-pyrazol-1-yl)thiazole-4-carboxylate A mixture containing 4-(2-(3-(cyclopentyloxy)-4-methylbenzoyl)-4-cyclopropyl-3-oxobutyl)benzene-sulfonamide (082 g, 0.0017 mol), p-toluene sulfonic acid (0.16 g, 0.0009 mol), pyrrolidine (71 µL, 0.0009 mol), and ethanol (7 mL) was heated at 90° C. for 1 h. Ethyl 2-hydrazinylthiazole-4-carboxylate (0.41 g, 0.0022 mol) was added and the reaction was heated until completion. The reaction mixture was diluted with ethyl acetate and washed with water and brine. The organic layers were dried with magnesium sulfate and concentrated. The crude product was purified by flash chromatography (Combi-flash Rf, hexane/ethyl acetate, 0-80% gradient) to give ethyl 2-(3-(3-(cyclopentyloxy)-4-methylphenyl)-5-(cyclopropylmethyl)-4-(4-sulfamoylbenzyl)-1H-pyrazol-1-yl)thiazole-4-carboxylate as a mixture of regioisomers (0.99 g, 93%).

Step 5. 2-(3-(3-(cyclopentyloxy)-4-methylphenyl)-5-(cyclopropylmethyl)-4-(4-sulfamoylbenzyl)-1H-pyrazol-1-yl)thiazole-4-carboxylic acid 467

Ethyl 2-(3-(3-(cyclopentyloxy)-4-methylphenyl)-5-(cyclopropylmethyl)-4-(4-sulfamoylbenzyl)-1H-pyrazol-1-yl)thiazole-4-carboxylate (110 mg, 0.18 mmol) was dissolved in THF/MeOH (2 mL:2 mL) and LiOH (5 M, 500 µL) was added. The reaction mixture was stirred at room temperature overnight. The reaction mixture was neutralized by addition of hydrochloric acid (1.2 M), diluted with ethyl acetate (15 mL), washed with water (10 mL), and dried with anhydrous magnesium sulfate. The organic layer was concentrated using a rotary evaporator, dissolved in a mixture of DMSO and MeOH, and purified by HPLC (Phenomenex Gemini C18, H$_2$O/CH$_3$CN gradient from 55% to 90% CH$_3$CN for 4 min, 0.1% TFA) to give the title compound 467 (35 mg, 33%). $^1$H-NMR (d$^6$-DMSO) δ 8.07 (s, 1H), 7.53 (d, 2H, J=8 Hz), 7.12-7.07 (m, 5H), 6.95 (d, 1H, J=8 Hz), 6.87 (d, 1H, J=8 Hz), 6.63 (s, 1H), 4.16 (m, 1H), 3.90 (s, 2H), 2.93 (m, 2H), 1.87 (s, 3H), 1.40-1.29 (m, 8H), 0.91 (m, 1H), 0.11 (m, 2H), 0.014 (m, 2H); MS (ES) 593.4 (M+H)$^+$ LCMS RT=0.81 min.

Example 121

2-(5-(cyclopropylmethyl)-3-(4-fluoro-3-((tetrahydrofuran-2-yl)methoxy)phenyl)-4-(3-fluoro-4-sulfamoylbenzyl)-1H-pyrazol-1-yl)thiazole-4-carboxylic acid 469

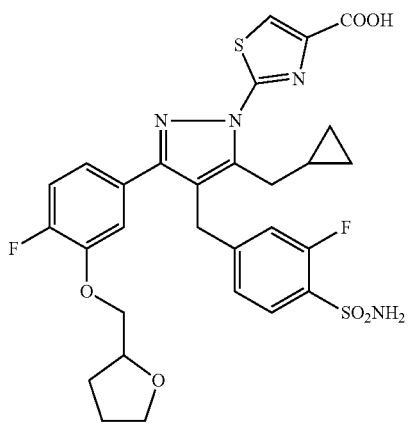 [SMILES: NS(=O)(=O)c1ccc(Cc2c(-c3ccc(F)c(OCC4CCCO4)c3)nn(-c3nc(C(=O)O)cs3)c2CC2CC2)cc1F]

Using procedures analogous to those described in the preparation of 467, the title compound was prepared and purified by HPLC: 2-(5-(cyclopropylmethyl)-3-(4-fluoro-3-((tetrahydrofuran-2-yl)methoxy)phenyl)-4-(3-fluoro-4-sulfamoylbenzyl)-1H-pyrazol-1-yl)thiazole-4-carboxylic acid 469; $^1$H-NMR (d$^6$-DMSO) δ 8.07 (s, 1H), 7.44 (m, 1H), 7.35 (s, 2H), 7.05-6.82 (m, 5H), 3.93 (s, 2H), 3.87-3.43 (m, 6H), 2.93 (m, 2H), 1.75-159 (m, 3H), 1.38 (m, 1H), 0.90 (m, 1H), 0.013 (m, 2H) 0.010 (m, 2H); MS (ES) 630.9 (M+H)$^+$ LCMS RT=1.10 min.

Example 122

2-(5-(cyclopropylmethyl)-3-(4-fluoro-3-((tetrahydrofuran-3-yl)methoxy)phenyl)-4-(3-fluoro-4-sulfamoylbenzyl)-1H-pyrazol-1-yl)thiazole-4-carboxylic acid 470

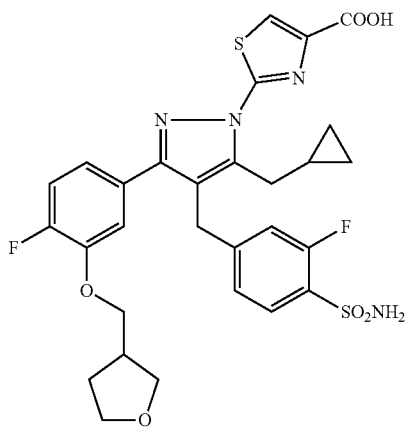 [SMILES: NS(=O)(=O)c1ccc(Cc2c(-c3ccc(F)c(OCC4CCOC4)c3)nn(-c3nc(C(=O)O)cs3)c2CC2CC2)cc1F]

Using procedures analogous to those described in the preparation of 467, the title compound was prepared and purified by HPLC: 2-(5-(cyclopropylmethyl)-3-(4-fluoro-3-((tetrahydrofuran-3-yl)methoxy)phenyl)-4-(3-fluoro-4-sulfamoylbenzyl)-1H-pyrazol-1-yl)thiazole-4-carboxylic acid 470 $^1$H-NMR (d$^6$-DMSO) δ 8.07 (s, 1H), 7.44 (m, 1H), 7.35 (s, 2H), 7.04-7.01 (m, 1H), 6.95-6.91 (m, 3H), 6.84-6.82 (m, 1H), 3.92 (s, 2H), 3.52-3.50 (m, 4H), 3.40-3.35 (m, 2H), 3.20 (m, 1H), 2.93 (m, 2H), 2.4 (m, 1H), 1.77 (m, 1H), 1.39 (m, 1H), 0.91 (m, 1H), 0.013 (m, 2H) 0.010 (m, 2H); MS (ES) 552.9 (M+H)$^+$ LCMS RT=1.12 min.

Example 123

2-(3-(3-cyclopropoxy-4-fluorophenyl)-5-(cyclopropylmethyl)-4-(3-fluoro-4-sulfamoylbenzyl)-1H-pyrazol-1-yl)thiazole-4-carboxylic acid 471

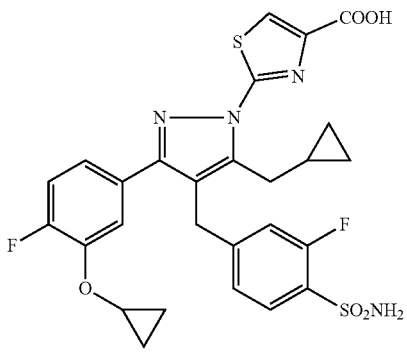 [SMILES: NS(=O)(=O)c1ccc(Cc2c(-c3ccc(F)c(OC4CC4)c3)nn(-c3nc(C(=O)O)cs3)c2CC2CC2)cc1F]

Using procedures analogous to those described in the preparation of 467, the title compound was prepared and purified by HPLC: 2-(3-(3-cyclopropoxy-4-fluorophenyl)-5-(cyclopropylmethyl)-4-(3-fluoro-4-sulfamoylbenzyl)-1H-pyrazol-1-yl)thiazole-4-carboxylic acid 471 $^1$H-NMR (d$^6$-DMSO) δ 8.07 (s, 1H), 7.46 (m, 1H), 7.37 (s, 2H), 7.19 (m, 1H), 7.05-6.85 (m, 5H), 3.92 (s, 2H), 3.50 (m, 1H), 2.93 (m, 2H), 0.91 (m, 1H), 0.013 (m, 2H) 0.010 (m, 2H); MS (ES) 586.9 (M+H)$^+$ LCMS RT=1.12 min.

Example 124

2-(5-(cyclopropylmethyl)-3-(6-fluoro-4'-methyl-[1,1'-biphenyl]-3-yl)-4-(2-fluoro-4-sulfamoylbenzyl)-1H-pyrazol-1-yl)thiazole-4-carboxylic acid 472

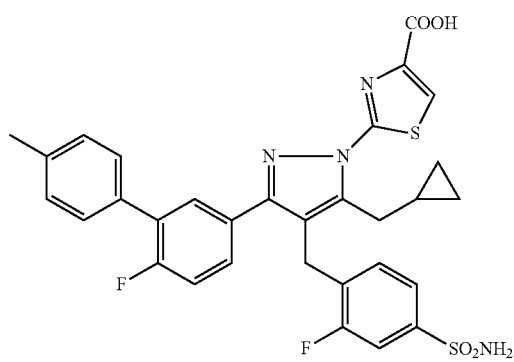 [SMILES: Cc1ccc(-c2cc(-c3nn(-c4nc(C(=O)O)cs4)c(CC4CC4)c3Cc3ccc(S(N)(=O)=O)cc3F)ccc2F)cc1]

Step 1: 1-(6-fluoro-4'-methyl-[1,1'-biphenyl]-3-yl)ethan-1-one

In a 20 mL microwave vial, 3-bromo-4-fluoro-acetophenone (1 g, 0.0046 mol), 4-methylphenyl boronic acid (0.75 g, 0.0055 mol), potassium carbonate (1.27 g, 0.009 mol), bis-(di-t-butylphosphinoferrocane)dichloropalladium(II) (150 mg, 5% mol), DMSO (12 mL), and water (4 mL) were added and the vial was purged with argon for 5 min. The vial was irradiated at 150° C. for 15 min. After completion of the reaction, the reaction mixture was poured into water and extracted with ethyl acetate. The organic layer was washed with brine and dried with magnesium sulfate. The crude product was purified by flash chromatography (Combi-flash Rf, hexane/ethyl acetate, 0-20% gradient) to give 1-(6-fluoro-4'-methyl-[1,1'-biphenyl]-3-yl)ethan-1-one (1 g, 90%).

Using procedures analogous to the procedures described to prepare 467, Steps 2-5, the title compound was prepared from 1-(6-fluoro-4'-methyl-[1,1'-biphenyl]-3-yl)ethan-1-one: 2-(5-(cyclopropylmethyl)-3-(6-fluoro-4'-methyl-[1,1'-biphenyl]-3-yl)-4-(2-fluoro-4-sulfamoylbenzyl)-1H-pyrazol-1-yl)thiazole-4-carboxylic acid 472; $^1$H-NMR (d$^6$-DMSO) δ 8.31 (s, 1H), 7.59-7.35 (m, 11H), 7.17 (m, 1H), 4.13 (s, 2H), 3.02 (m, 2H), 2.35 (s, 3H), 1.15 (m, 1H), 0.033 (m, 2H) 0.021 (m, 2H); MS (ES) 621.4 (M+H)$^+$ LCMS RT=0.79 min.

Example 125

2-(5-(cyclopropylmethyl)-3-(4-fluoro-3-((5-(trifluoromethyl)furan-2-yl)methoxy)phenyl)-4-(3-fluoro-4-sulfamoylbenzyl)-1H-pyrazol-1-yl)thiazole-4-carboxylic acid 473

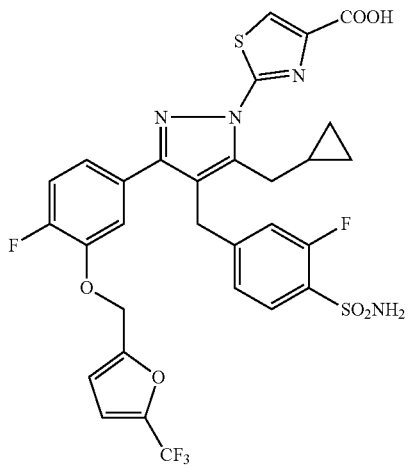 [SMILES: NS(=O)(=O)c1ccc(Cc2c(-c3ccc(F)c(OCc4ccc(C(F)(F)F)o4)c3)nn(-c3nc(C(=O)O)cs3)c2CC2CC2)cc1F]

Step 1: 1-(4-fluoro-3-((5-(trifluoromethyl)furan-2-yl)methoxy)phenyl)ethan-1-one A solution of di-t-butyl diazocarboxylate (480 mg, 2 mmol) in THF (11 mL) was cooled to 0° C. and triphenyl phosphine (553 mg, 2 mmol) was added. (5-(Trifluoromethyl)furan-2-yl)methanol (350 mg, 2 mmol) and 3-hydroxy-4-fluoroacetophenone (250 mg, 1.6 mmol) were sequentially added and the cooling was removed. The reaction mixture was stirred for 30 min, concentrated by rotary evaporator and purified by flash chromatography (Combiflash Rf, hexane/ethyl acetate, 0-30% gradient) to give 1-(4-fluoro-3-((5-(trifluoromethyl)furan-2-yl)methoxy)phenyl)ethan-1-one (0.66 g, 95%).

Using procedures analogous to the procedures described to prepare 467, Steps 2-5, the title compound 473 was prepared from 1-(4-fluoro-3-((5-(trifluoromethyl)furan-2-yl)methoxy)phenyl)ethan-1-one; MS (ES) 694.9 (M+H)$^+$ LCMS RT=1.20 min.

Example 126

2-(3-(3-(cyclopentyloxy)phenyl)-5-(cyclopropylmethyl)-4-(4-sulfamoylbenzyl)-1H-pyrazol-1-yl)thiazole-4-carboxylic acid 477

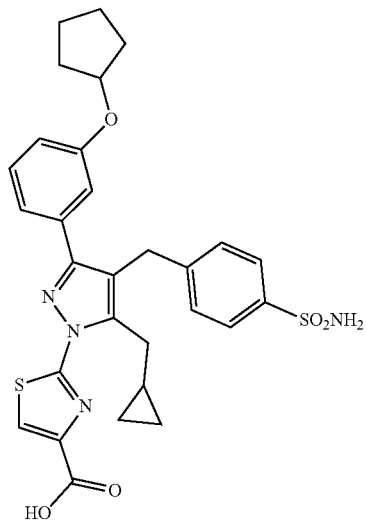 [SMILES: NS(=O)(=O)c1ccc(Cc2c(-c3cccc(OC4CCCC4)c3)nn(-c3nc(C(=O)O)cs3)c2CC2CC2)cc1]

Using procedures analogous to those described in the preparation of 467, the title compound was prepared and purified by HPLC: 2-(3-(3-(cyclopentyloxy)phenyl)-5-(cyclopropylmethyl)-4-(4-sulfamoylbenzyl)-1H-pyrazol-1-yl)thiazole-4-carboxylic acid 477 $^1$H-NMR (CDCl$_3$) δ 8.10 (s, 1H), 7.84 (d, J=8.4 Hz, 2H), 7.23-7.31 (m, 4H), 7.02-7.07 (m, 2H), 6.88 (dd, J=1.76, 1.8 Hz, 1H) 4.97 (s, 2H), 4.11 (s, 2H), 3.15 (d, J=6.64 Hz, 2H), 1.58-1.79 (m, 9H), 1.12-1.16 (m, 1H), 0.43 (d, J=8 Hz, 2H), 0.21 (d, J=5.4 Hz, 2H), MS (ES) 579 (M+H)$^+$ LCMS RT 1.15 min.

Example 127

2-(3-(3-(benzyloxy)-4-fluorophenyl)-5-(cyclopropylmethyl)-4-(4-sulfamoylbenzyl)-1H-pyrazol-1-yl)thiazole-4-carboxylic acid 480

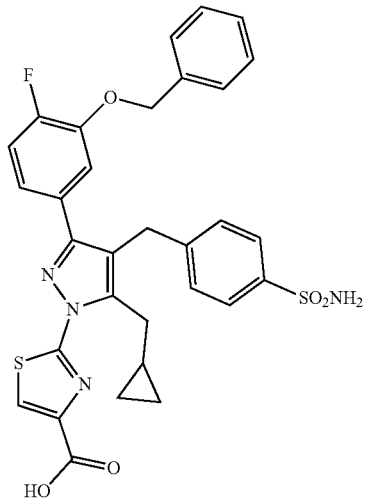 [SMILES: NS(=O)(=O)c1ccc(Cc2c(-c3ccc(F)c(OCc4ccccc4)c3)nn(-c3nc(C(=O)O)cs3)c2CC2CC2)cc1]

Using procedures analogous to those described in the preparation of 467, the title compound was prepared and purified by HPLC: 2-(3-(3-(benzyloxy)-4-fluorophenyl)-5-(cyclopropylmethyl)-4-(4-sulfamoylbenzyl)-1H-pyrazol-1-yl)thiazole-4-carboxylic acid 480 $^1$H-NMR (CDCl$_3$) δ 8.11 (s, 1H), 7.84 (d, J=8 Hz, 2H), 7.24-7.38 (m, 8H), 7.15 (d, J=7.4 Hz, 1H) 7.08 (d, J=8 Hz, 2H), 5.01 (s, 2H), 4.95 (s, 3H), 4.02 (s, 2H), 3.16 (d, J=6.7 Hz, 2H), 1.11-1.15 (m, 1H), 0.42 (d, J=7 Hz, 2H), 0.21 (d, J=5.24 Hz, 2H); MS (ES) 619 (M+H)$^+$ LCMS RT=1.28 min.

Example 128

2-(5-(cyclopropylmethyl)-4-(4-sulfamoylbenzyl)-3-(3-(4-(trifluoromethyl)phenoxy)-phenyl)-1H-pyrazol-1-yl)thiazole-4-carboxylic acid 481

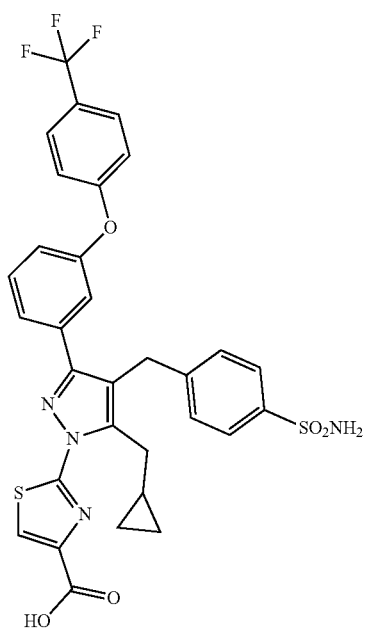 [SMILES: NS(=O)(=O)c1ccc(Cc2c(-c3cccc(Oc4ccc(C(F)(F)F)cc4)c3)nn(-c3nc(C(=O)O)cs3)c2CC2CC2)cc1]

Using procedures analogous to those described in the preparation of 467, the title compound was prepared and purified by HPLC: 2-(5-(cyclopropylmethyl)-4-(4-sulfamoylbenzyl)-3-(3-(4-(trifluoromethyl)phenoxy)-phenyl)-1H-pyrazol-1-yl)thiazole-4-carboxylic acid 481: ¹NMR (CDCl₃) δ 8.11 (s, 1H), 7.8 (d, J=8 Hz, 2H), 7.6 (d, J=8 Hz, 2H), 7.21-7.40 (m, 5H), 7.01-7.06 (m, 3H), 5.04 (s, 2H), 4.08 (s, 2H), 3.16 (d, J=6 Hz, 2H), 1.09-1.15 (m, 1H) 0.42 (d, J=8. Hz, 2H), 0.21 (d, J=5 Hz, 2H), MS (ES) 655 (M+H)⁺ LCMS RT=1.38 min.

Example 129

2-(5-(cyclopropylmethyl)-3-(3-phenoxyphenyl)-4-(4-sulfamoylbenzyl)-1H-pyrazol-1-yl)thiazole-4-carboxylic acid 503

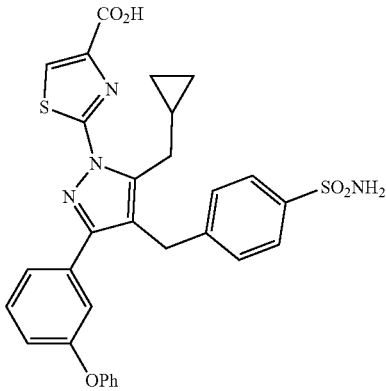 [SMILES: NS(=O)(=O)c1ccc(Cc2c(-c3cccc(Oc4ccccc4)c3)nn(-c3nc(C(=O)O)cs3)c2CC2CC2)cc1]

Using procedures analogous to those described in the preparation of 467, the title compound was prepared and purified by HPLC: 2-(5-(cyclopropylmethyl)-3-(3-phenoxyphenyl)-4-(4-sulfamoylbenzyl)-1H-pyrazol-1-yl)thiazole-4-carboxylic acid 503; ¹H-NMR (MeOD) δ 8.19 (s, 1H), 7.75 (d, J=8.4 Hz, 2H), 7.38-7.31 (m, 4H), 7.20 (d, J=8.4 Hz, 2H), 7.15-7.10 (m, 2H), 7.02-6.97 (m, 1H), 7.00 (dd, J=8.0, 1.2 Hz, 2H), 4.10 (s, 2H), 3.22 (d, J=6.8 Hz, 2H), 1.12-1.06 (m, 1H), 0.39-0.33 (m, 2H), 0.21 (dt, J=6.0, 5.2 Hz, 2H); MS (ES) 587.7 (M+H)⁺; LCMS RT=1.00 min.

Example 130

2-(5-(cyclopropylmethyl)-3-(3-isopropoxyphenyl)-4-(4-sulfamoylbenzyl)-1H-pyrazol-1-yl)thiazole-4-carboxylic acid 504

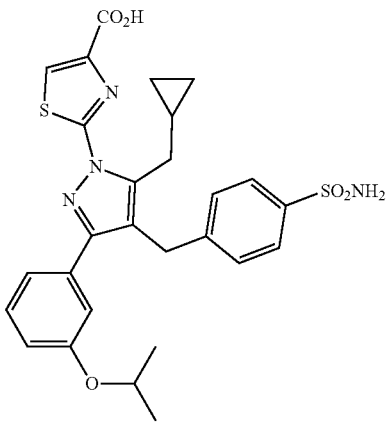 [SMILES: CC(C)Oc1cccc(-c2nn(-c3nc(C(=O)O)cs3)c(CC3CC3)c2Cc2ccc(S(N)(=O)=O)cc2)c1]

Using procedures analogous to those described in the preparation of 467, the title compound was prepared and purified by HPLC: 2-(5-(cyclopropylmethyl)-3-(3-isopropoxyphenyl)-4-(4-sulfamoylbenzyl)-1H-pyrazol-1-yl)thiazole-4-carboxylic acid 504; MS (ES) 552.6 (M+H)⁺; LCMS RT=0.98 min.

Example 131

2-(5-(cyclopropylmethyl)-3-(4-fluoro-3-((4-fluorobenzyl)oxy)phenyl)-4-(4-sulfamoylbenzyl)-1H-pyrazol-1-yl)thiazole-4-carboxylic acid 527

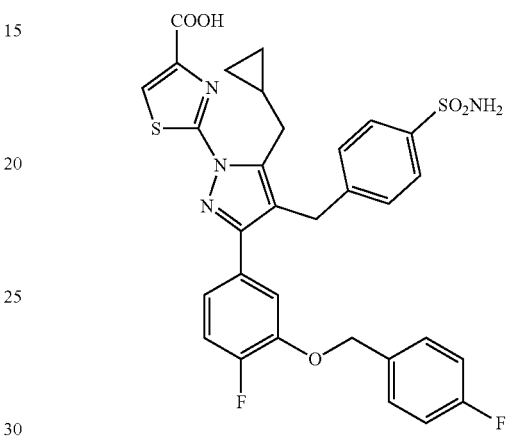

Using procedures analogous to those described in the preparation of 467, the title compound was prepared and purified by HPLC: 2-(5-(cyclopropylmethyl)-3-(4-fluoro-3-((4-fluorobenzyl)oxy)phenyl)-4-(4-sulfamoylbenzyl)-1H-pyrazol-1-yl)thiazole-4-carboxylic acid 527; ¹H-NMR (MeOD) δ 8.21 (s, 1H), 7.83 (d, J=8.4 Hz, 2H), 7.40 (m, 2H), 7.31 (d, J=8.3 Hz, 2H), 7.23 (m, 1H), 7.17 (m, 1H), 7.107 (m, 3H), 4.96 (s, 2H), 4.13 (s, 2H), 3.25 (d, J=6.83 Hz, 2H), 1.12 (m, 1H), 0.38 (d, J=8.1 Hz, 2H), 0.23 (d, J=5.1 Hz, 2H); MS (ES) 636.9 (M+H)⁺; LCMS RT=1.12 min.

Example 132

2-(5-(cyclopropylmethyl)-3-(4-fluoro-3-((3-fluorobenzyl)oxy)phenyl)-4-(3-fluoro-4-sulfamoylbenzyl)-1H-pyrazol-1-yl)thiazole-4-carboxylic acid 528

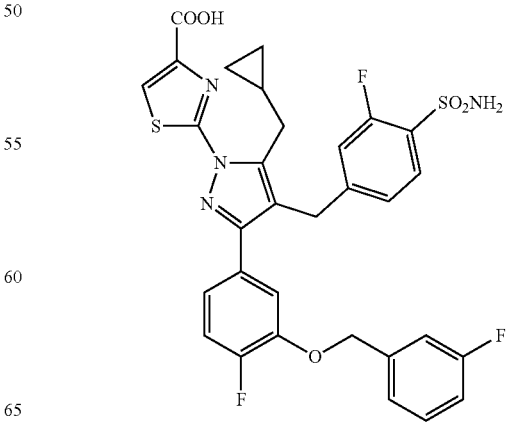

Using procedures analogous to those described in the preparation of 467, the title compound was prepared and purified by HPLC: 2-(5-(cyclopropylmethyl)-3-(4-fluoro-3-((3-fluorobenzyl)oxy)phenyl)-4-(3-fluoro-4-sulfamoylbenzyl)-1H-pyrazol-1-yl)thiazole-4-carboxylic acid 528; $^1$H-NMR (MeOD) δ 8.19 (s, 1H), 7.77 (t, J=7.7 Hz, 1H), 7.40 (m, 1H), 7.23 (m, 3H), 7.16 (m, 2H), 7.04 (m, 3H), 5.08 (s, 2H), 4.11 (s, 2H), 3.25 (d, J=6.5 Hz), 1.11 (m, 1H), 0.39 (d, J=7.8 Hz), 0.23 (d, J=4.6 Hz); MS (ES) 655.0 (M+H)$^+$; LCMS RT=1.19 min.

Example 133

4-((3-(cyclopropylmethyl)-5-(3',5-difluoro-[1,1'-biphenyl]-3-yl)-1-(4-((oxo-13-methyl)-13-oxidanyl)thiazol-2-yl)-1H-pyrazol-4-yl)methyl)benzenesulfonamide 525

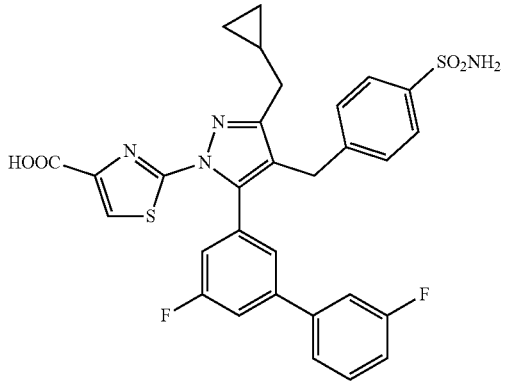 [SMILES: NS(=O)(=O)c1ccc(Cc2c(CC3CC3)nn(-c3nc(C(=O)O)cs3)c2-c2cc(F)cc(-c3cccc(F)c3)c2)cc1]

Using procedures analogous to those described in the preparation of 482, the title compound was prepared and purified by HPLC: 4-((3-(cyclopropylmethyl)-5-(3',5-difluoro-[1,1'-biphenyl]-3-yl)-1-(4-((oxo-13-methyl)-13-oxidanyl)thiazol-2-yl)-1H-pyrazol-4-yl)methyl)benzenesulfonamide 525: $^1$H-NMR (CDCl3) δ 7.96 (s, 1H), 7.84 (d, J=8.4 Hz, 2H), 7.39 (m, 2H), 7.24 (m, 4H) 7.06 (m, 4H), 3.93 (s, 2H) 2.53 (d, J=6.8 Hz, 2H), 1.05 (m, 1H), 0.55 (m, 2H), 0.22 (d, J=5.8 Hz, 2H); MS (ES) 607.0 (M+H)$^+$; LCMS RT=0.95 min.

Example 134

2-(5-(cyclopropylmethyl)-3-(3-(4-fluorophenoxy)phenyl)-4-(4-sulfamoylbenzyl)-1H-pyrazol-1-yl)thiazole-4-carboxylic acid 507

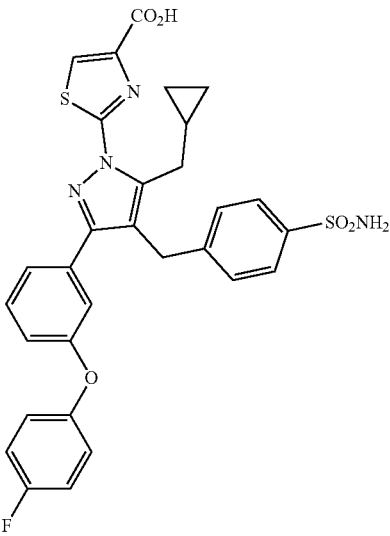 [SMILES: NS(=O)(=O)c1ccc(Cc2c(-c3cccc(Oc4ccc(F)cc4)c3)nn(-c3nc(C(=O)O)cs3)c2CC2CC2)cc1]

Step 1: 1-(3-(4-fluorophenoxy)phenyl)ethan-1-one

A mixture of 1-(3-hydroxyphenyl) ethan-1-one (1.0 g, 7.34 mmol), (4-fluorophenyl)boronic acid (2.06 g, 14.7 mmol), Cu(OAc)$_2$ (2.67 g, 14.7 mmol), and pyridine (1.18 mL, 14.7 mmol) in dichloromethane (20 mL) was stirred at room temperature for 48 h then quenched with water (25 mL), extracted with dichloromethane, and dried over MgSO$_4$. The residue was purified by flash chromatography (Combi-flash Rf, hexane/ethyl acetate, 0-40% gradient) to give the title compound (0.56 g, 30%). $^1$H-NMR (CDCl3) δ (ppm) 7.67 (dt, J=7.6, 1.2 Hz, 1H), 7.53 (t, J=2.0 Hz, 1H), 7.42 (t, J=8.0 Hz, 1H), 7.67 (dq, J=8.0, 0.8 Hz, 1H), 7.08-6.97 (m, 4H), 2.58 (s, 3H).

Step 2: Using procedures analogous to those described in the preparation of 467, Steps 2-5, the title compound was prepared from 1-(3-(4-fluorophenoxy)phenyl)ethan-1-one and purified by HPLC: 2-(5-(cyclopropylmethyl)-3-(3-(4-fluorophenoxy)phenyl)-4-(4-sulfamoylbenzyl)-1H-pyrazol-1-yl)thiazole-4-carboxylic acid 507 $^1$H-NMR (MeOD) δ (ppm) 8.14 (s, 1H), 7.78 (d, J=8.4 Hz, 2H), 7.40 (t, J=8.0 Hz, 1H), 7.23 (d, J=8.4 Hz, 2H), 7.10-7.04 (m, 2H), 7.01-6.96 (m, 4H), 6.84 (t, J=2.0 Hz, 1H), 3.92 (s, 2H), 2.46 (d, J=7.2 Hz, 2H), 1.00-0.90 (m, 1H), 0.44 (ddd, J=8.4, 6.0, 4.4 Hz, 2H), 0.13 (ddd, J=10.0, 4.4 Hz, 2H); MS (ES) 605.2 (M+H)$^+$; LCMS RT=1.20 min.

Example 135

2-(5-(cyclopropylmethyl)-3-(4-fluoro-3-phenoxyphenyl)-4-(4-sulfamoylbenzyl)-1H-pyrazol-1-yl)thiazole-4-carboxylic acid 508

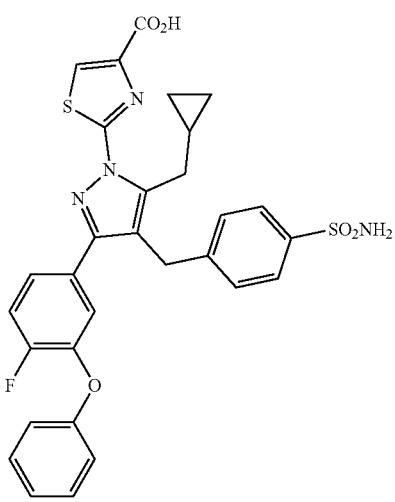 [SMILES: NS(=O)(=O)c1ccc(Cc2c(-c3ccc(F)c(Oc4ccccc4)c3)nn(-c3nc(C(=O)O)cs3)c2CC2CC2)cc1]

Using procedures analogous to those described in the preparation of 507, the title compound was prepared and purified by HPLC: 2-(5-(cyclopropylmethyl)-3-(4-fluoro-3-phenoxyphenyl)-4-(4-sulfamoylbenzyl)-1H-pyrazol-1-yl)thiazole-4-carboxylic acid 508; $^1$H-NMR (d$^6$-DMSO) δ 7.63 (d, J=8.4 Hz, 2H), 7.42-7.33 (m, 4H), 7.23 (s, 2H), 7.25 (d, J=8.8 Hz, 1H), 7.14 (d, J=8.4 Hz, 2H), 6.90 (d, J=7.6 Hz, 2H), 4.06 (s, 2H), 3.12 (d, J=6.8 Hz, 2H), 0.87-0.80 (m, 1H), 0.30 (ddd, J=10.0, 6.0, 4.4 Hz, 2H), 0.13 (ddd, J=10.0, 5.2 Hz, 2H); MS (ES) 605.2 (M+H)$^+$; LCMS RT=1.18 min.

Example 136

2-(5-(cyclopropylmethyl)-3-(4-fluoro-3-(3-fluoro-phenoxy)phenyl)-4-(3-fluoro-4-sulfamoylbenzyl)-1H-pyrazol-1-yl)thiazole-4-carboxylic acid 509

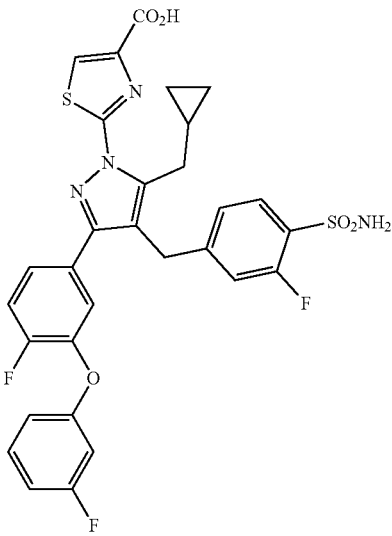 [SMILES: NS(=O)(=O)c1ccc(Cc2c(-c3ccc(F)c(Oc4cccc(F)c4)c3)nn(-c3nc(C(=O)O)cs3)c2CC2CC2)cc1F]

Using procedures analogous to those described in the preparation of 507, the title compound was prepared and purified by HPLC: 2-(5-(cyclopropylmethyl)-3-(4-fluoro-3-(3-fluorophenoxy)phenyl)-4-(3-fluoro-4-sulfamoylbenzyl)-1H-pyrazol-1-yl)thiazole-4-carboxylic acid 509; $^1$H-NMR (MeOD) δ 8.20 (s, 1H), 7.72 (t, J=8.0 Hz, 1H), 7.50-7.46 (m, 1H), 7.37-7.25 (m, 3H), 6.99 (s, 1H), 6.98 (d, J=16.8 Hz, 1H), 6.88 (dt, J=8.4, 2.0 Hz, 1H), 6.73 (dt, J=10.0, 2.0 Hz, 1H), 6.66 (dd, J=8.4, 2.4 Hz, 1H), 4.13 (s, 2H), 3.24 (d, J=6.8 Hz, 2H), 1.13-1.05 (m, 1H), 0.44 (ddd, J=8.0, 5.6, 4.0 Hz, 2H), 0.22 (dd, J=10.4, 5.2 Hz, 2H); MS (ES) 640.9 (M+H)$^+$; LCMS RT=1.19 min.

Example 137

2-(5-(cyclopropylmethyl)-3-(4-fluoro-3-(p-tolyloxy)phenyl)-4-(3-fluoro-4-sulfamoylbenzyl)-1H-pyrazol-1-yl)thiazole-4-carboxylic acid 510

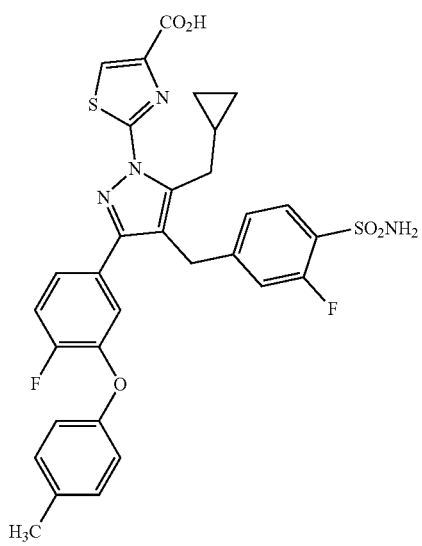 [SMILES: Cc1ccc(Oc2cc(-c3nn(-c4nc(C(=O)O)cs4)c(CC4CC4)c3Cc3ccc(S(N)(=O)=O)c(F)c3)ccc2F)cc1]

Using procedures analogous to those described in the preparation of 507, the title compound was prepared and purified by HPLC: 2-(5-(cyclopropylmethyl)-3-(4-fluoro-3-(p-tolyloxy)phenyl)-4-(3-fluoro-4-sulfamoylbenzyl)-1H-pyrazol-1-yl)thiazole-4-carboxylic acid 510; $^1$H-NMR (MeOD) δ 8.19 (s, 1H), 7.70 (t, J=8.4 Hz, 1H), 7.44-7.40 (m, 1H), 7.25 (dd, J=10.8, 8.8 Hz, 1H), 7.17-7.12 (m, 3H), 6.93 (s, 1H), 6.92 (d, J=17.6 Hz, 1H), 6.88 (d, J=8.4 Hz, 2H), 4.07 (s, 2H), 3.22 (d, J=6.8 Hz, 2H), 1.11-1.04 (m, 1H), 0.37 (ddd, J=8.0, 6.0, 4.8 Hz, 2H), 0.21 (dd, J=10.4, 5.2 Hz, 2H); MS (ES) 636.9 (M+H)$^+$; LCMS RT=1.12 min.

Example 138

2-(5-(cyclopropylmethyl)-3-(4-fluoro-3-(4-fluorophenoxy)phenyl)-4-(3-fluoro-4-sulfamoylbenzyl)-1H-pyrazol-1-yl)thiazole-4-carboxylic acid 511

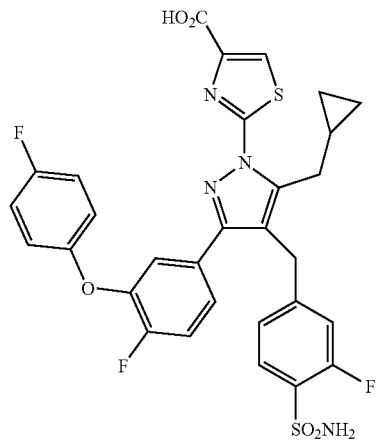 [SMILES: NS(=O)(=O)c1ccc(Cc2c(-c3ccc(F)c(Oc4ccc(F)cc4)c3)nn(-c3nc(C(=O)O)cs3)c2CC2CC2)cc1F]

Using procedures analogous to those described in the preparation of 507, the title compound was prepared and purified by HPLC: 2-(5-(cyclopropylmethyl)-3-(4-fluoro-3-(4-fluorophenoxy)phenyl)-4-(3-fluoro-4-sulfamoylbenzyl)-1H-pyrazol-1-yl)thiazole-4-carboxylic acid 511; $^1$H-NMR (MeOD): δ 8.19 (s, 1H), 7.71 (t, J=8.8 Hz, 1H), 7.45-7.41 (m, 1H), 7.26 (dd, J=8.8, 11.0 Hz, 1H), 7.15 (dd, J=2.2, 7.9 Hz, 1H), 7.09 (dd, J=8.5, 9.0 Hz, 2H), 6.98-6.89 (m, 4H), 4.09 (s, 2H), 3.23 (d, J=7.05 Hz, 2H), 1.13-1.04 (m, 1H), 0.40-0.35 (m, 2H), 0.23-0.19 (m, 2H); MS (ES) 641.0 (M+H)$^+$; LCMS RT=1.18 min.

Example 139

2-(5-(cyclopropylmethyl)-3-(4-fluoro-3-(4-(trifluoromethyl)phenoxy)phenyl)-4-(3-fluoro-4-sulfamoylbenzyl)-1H-pyrazol-1-yl)thiazole-4-carboxylic acid 512

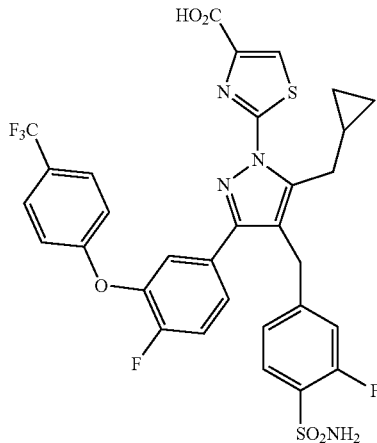 [SMILES: NS(=O)(=O)c1ccc(Cc2c(-c3ccc(F)c(Oc4ccc(C(F)(F)F)cc4)c3)nn(-c3nc(C(=O)O)cs3)c2CC2CC2)cc1F]

Using procedures analogous to those described in the preparation of 507, the title compound was prepared and purified by HPLC: 2-(5-(cyclopropylmethyl)-3-(4-fluoro-3-(4-(trifluoromethyl)phenoxy)phenyl)-4-(3-fluoro-4-sulfamoylbenzyl)-1H-pyrazol-1-yl)thiazole-4-carboxylic acid 512; $^1$H-NMR (MeOD) δ 8.28 (s, 1H), 7.73-7.67 (m, 3H), 7.52-7.48 (m, 1H), 7.38 (dd, J=2.1, 7.6 Hz, 1H), 7.30 (dd, J=8.5, 10.5 Hz, 1H), 7.03-6.96 (m, 4H), 4.16 (s, 2H), 3.27 (d, J=6.8 Hz, 2H), 1.18-1.08 (m, 1H), 0.42-0.38 (m, 2H), 0.26-0.23 (m, 2H); MS (ES) 691.0 (M+H)$^+$; LCMS RT=1.24 min.

Example 140

2-(5-(cyclopropylmethyl)-3-(3-(3-fluorophenoxy)phenyl)-4-(4-sulfamoylbenzyl)-1H-pyrazol-1-yl)thiazole-4-carboxylic acid 526

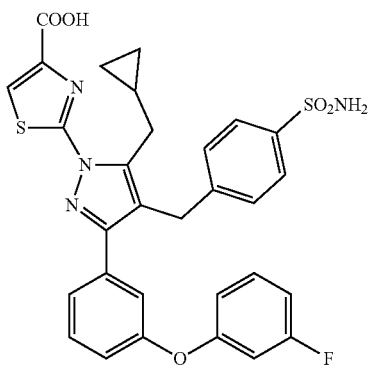 [SMILES: NS(=O)(=O)c1ccc(Cc2c(-c3cccc(Oc4cccc(F)c4)c3)nn(-c3nc(C(=O)O)cs3)c2CC2CC2)cc1]

Using procedures analogous to those described in the preparation of 507, the title compound was prepared and purified by HPLC: 2-(5-(cyclopropylmethyl)-3-(3-(3-fluorophenoxy)phenyl)-4-(4-sulfamoylbenzyl)-1H-pyrazol-1-yl)thiazole-4-carboxylic acid 526; $^1$H-NMR (MeOD) δ 7.89 (s, 1H), 7.75 (d, J=8.4 Hz, 2H), 7.42 (m, 2H), 7.34 (m, 2H), 7.23 (d, J=8.4 Hz, 2H), 7.12 (m, 1H) 8.87 (m, 2H), 6.70 (m, 2H), 4.13 (s, 2H), 3.25 (d, J=6.7 Hz, 2H), 0.32 (d, J=8.2 Hz, 2H), 0.12 (d, J=4.39 Hz, 2H); MS (ES) 605.2 (M+H)$^+$; LCMS RT=1.21 min.

Example 141

2-(5-(cyclopropylmethyl)-3-(3'-fluoro-5-methyl-[1,1'-biphenyl]-3-yl)-4-(4-sulfamoylbenzyl)-1H-pyrazol-1-yl)thiazole-4-carboxylic acid 505

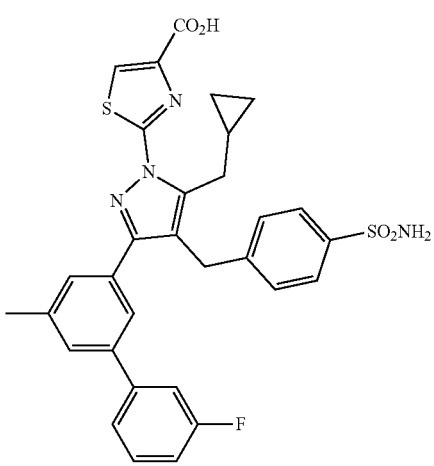 [SMILES: Cc1cc(-c2cccc(F)c2)cc(-c2nn(-c3nc(C(=O)O)cs3)c(CC3CC3)c2Cc2ccc(S(N)(=O)=O)cc2)c1]

Route E

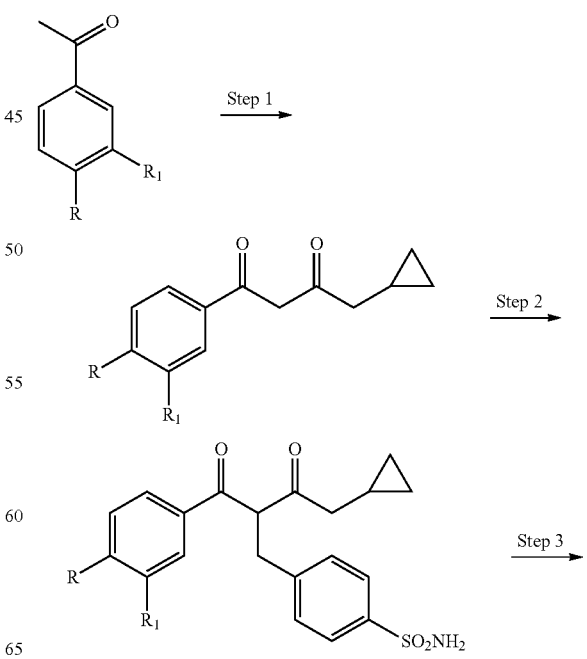

163

-continued

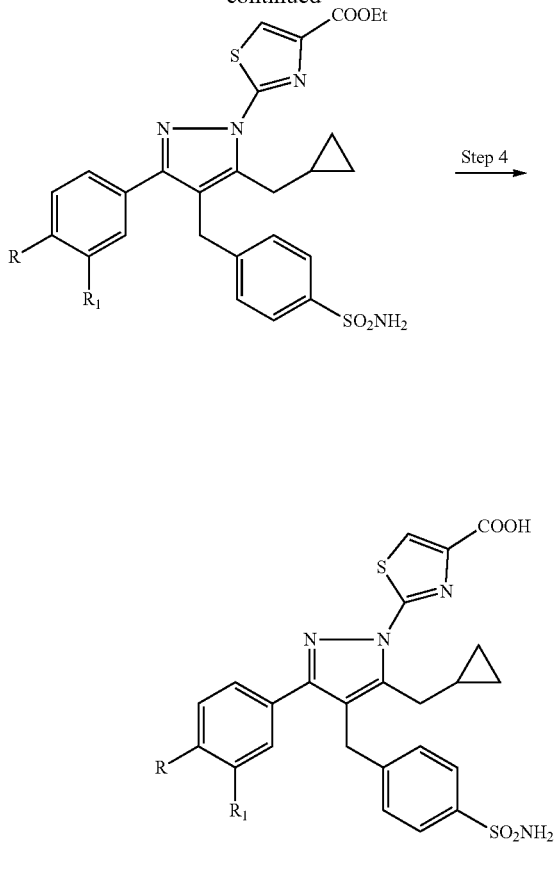

Using procedures similar to the procedures described to prepare 467, Steps 1-3, ethyl 2-(3-(3-bromo-5-methylphenyl)-5-(cyclopropylmethyl)-4-(4-sulfamoylbenzyl)-1H-pyrazol-1-yl)thiazole-4-carboxylate was prepared.

Step 4. 2-(5-(cyclopropylmethyl)-3-(3'-fluoro-5-methyl-[1,1'-biphenyl]-3-yl)-4-(4-sulfamoylbenzyl)-1H-pyrazol-1-yl)thiazole-4-carboxylic acid A flame dried flask was charged with bis(tri-tert-butylphosphine)palladium (4.0 mg, 10 mol %), cesium carbonate (0.5 mL, 1 M solution), (3-fluorophenyl)boronic acid (23 mg, 0.162 mmol), pyrazole regioisomer (50 mg, 0.081 mmol), and THF (2 mL). The reaction mixture was microwave irradiated at 120° C. for 20 min and the solvent was removed by rotary evaporator. After saponification and neutralization, the residue was purified by HPLC (Phenomenex Gemini C18, $H_2O/CH_3CN$ gradient from 40% to 90% $CH_3CN$ for 4 min, 0.1% TFA) to give the title compound 505 (10 mg, 21%). MS (ES) 603.7 $(M+H)^+$; LCMS RT=1.26 min.

164

Example 142

2-(5-(cyclopropylmethyl)-3-(4'-fluoro-5-methyl-[1,1'-biphenyl]-3-yl)-4-(4-sulfamoylbenzyl)-1H-pyrazol-1-yl)thiazole-4-carboxylic acid 506

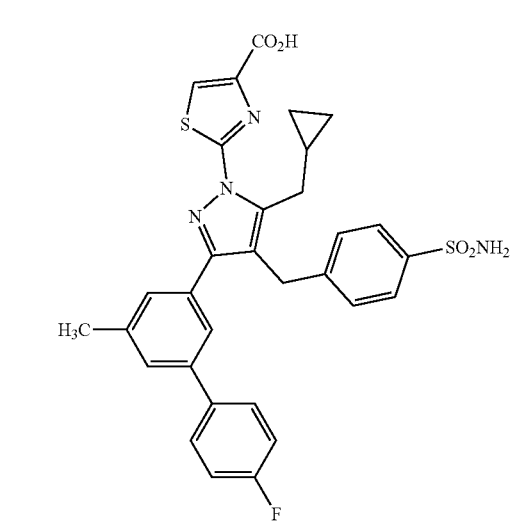 [SMILES: Cc1cc(-c2ccc(F)cc2)cc(-c2nn(-c3nc(C(=O)O)cs3)c(CC3CC3)c2Cc2ccc(S(N)(=O)=O)cc2)c1]

Using procedures similar to the procedures described to prepare 505, the title compound was prepared and purified by HPLC: 2-(5-(cyclopropylmethyl)-3-(4'-fluoro-5-methyl-[1,1'-biphenyl]-3-yl)-4-(4-sulfamoylbenzyl)-1H-pyrazol-1-yl)thiazole-4-carboxylic acid 506; MS (ES) 603.4 $(M+H)^+$; LCMS RT=1.26 min.

Example 143

2-(5-(cyclopropylmethyl)-3-(5-fluoro-3'-methoxy-[1,1'-biphenyl]-3-yl)-4-(4-sulfamoylbenzyl)-1H-pyrazol-1-yl)thiazole-4-carboxylic acid 478

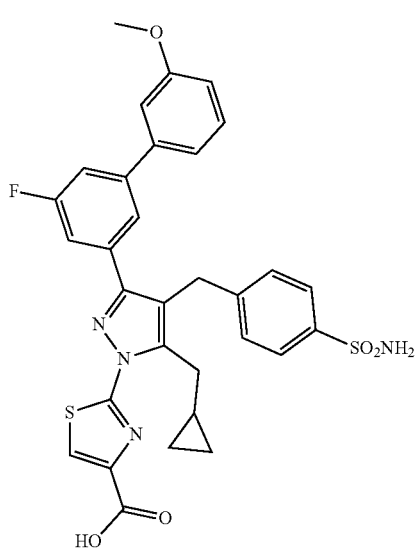 [SMILES: COc1cccc(-c2cc(F)cc(-c3nn(-c4nc(C(=O)O)cs4)c(CC4CC4)c3Cc3ccc(S(N)(=O)=O)cc3)c2)c1]

Using procedures similar to the procedures described to prepare 505, the title compound 478 was prepared and purified by HPLC; $^1$NMR (CDCl$_3$) δ 8.10 (s, 1H) 7.86 (d, J=8.32 Hz, 2H,) 7.23-7.29 (m, 7H), 7.00 (d, J=7.12 Hz, 1H), 6.91 (dd, J=1.88 1.88 Hz, 1H), 6.60 (t, J=3.92 Hz, 1H), 4.96 (s, 2H), 4.11 (s, 2H),), 3.87 (s, 3H), 3.21 (d, J=6.64 Hz, 2H) 1.17-1.25 (m, 1H) 0.47 (d, J=7.28 Hz, 2H), 0.24 (d, J=5.2 Hz, 2H), MS: (ES) 619 (M+H)$^+$ LCMS RT 1.32 min.

Example 144

2-(5-(cyclopropylmethyl)-3-(4',5-difluoro-[1,1'-biphenyl]-3-yl)-4-(4-sulfamoylbenzyl)-1H-pyrazol-1-yl)thiazole-4-carboxylic acid 479

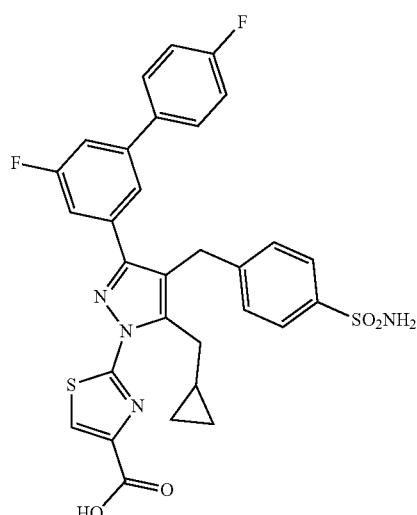

Using procedures similar to the procedures described to prepare 505, the title compound was prepared and purified by HPLC; 2-(5-(cyclopropylmethyl)-3-(5-fluoro-3'-methoxy-[1,1'-biphenyl]-3-yl)-4-(4-sulfamoylbenzyl)-1H-pyrazol-1-yl)thiazole-4-carboxylic acid 479; MS (ES) 607 (M+H)$^+$ LCMS RT 1.35 min.

Example 145

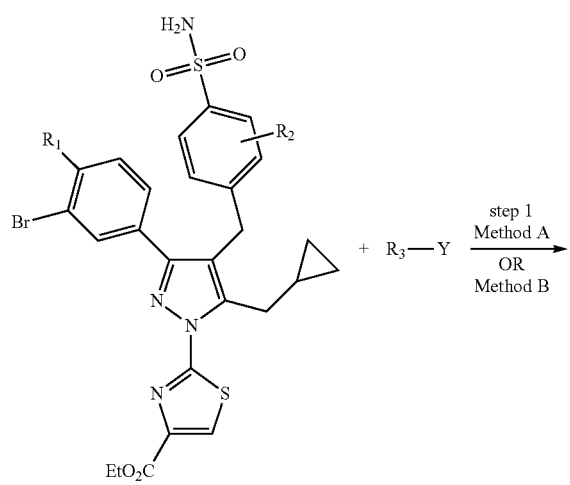

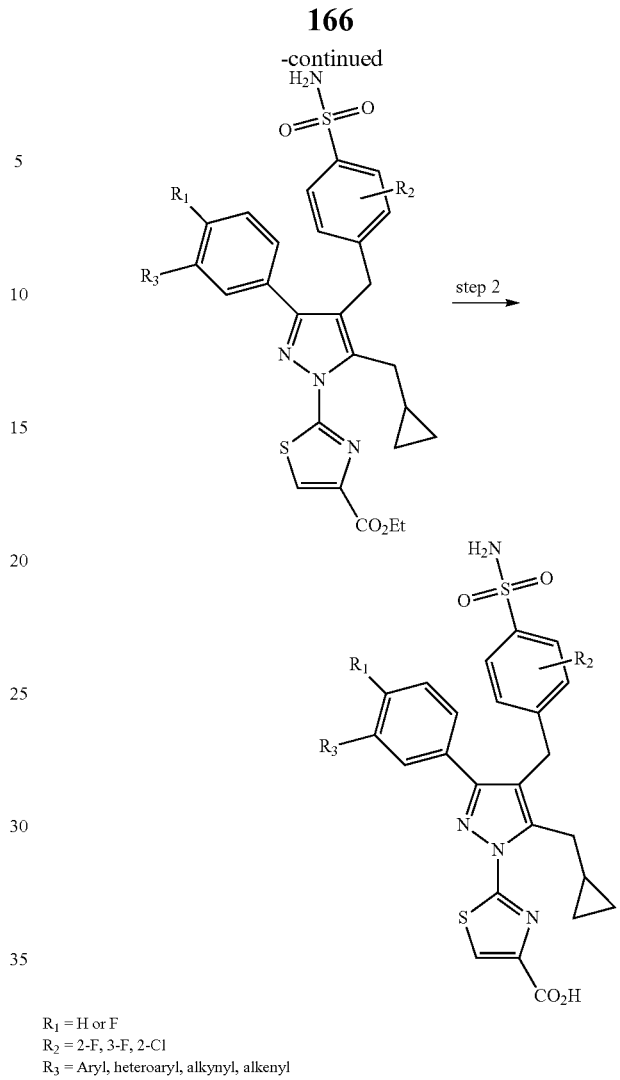

R$_1$ = H or F
R$_2$ = 2-F, 3-F, 2-Cl
R$_3$ = Aryl, heteroaryl, alkynyl, alkenyl Y = ——H, ——B(OH)$_2$, ——BF$_3$·K$^+$, ——B(pinacolato)

Step 1: General Synthesis of ethyl 2-(3-(3-substituted-4-substituted phenyl)-5-(cyclopropylmethyl)-4-(3-substituted-4-sulfamoylbenzyl)-1H-pyrazol-1-yl)thiazole-4-carboxylate Method A—Dioxane (2 mL) and water (0.5 mL) were added to a mixture of ethyl 2-(3-(3-bromo-4-substituted phenyl)-5-(cyclopropylmethyl)-4-(3-substituted-4-sulfamoylbenzyl)-1H-pyrazol-1-yl)thiazole-4-carboxylate (0.2 mmol, 1 eq), potassium phosphate (0.4 mmol, 2 eq), S-PHOS (5 mol %), SPhos Palladacycle G3 (2.5 mol %) and appropriate boronic acid/ester or potassium trifluoroborate in a sealed microwave vial. The reaction mixture was bubbled with argon for few minutes then stirred at 100° C. in a preheated heating block for 1-6 h. Upon completion of the reaction as detected by LCMS, the reaction mixture was cooled and stirred with a metal scavenger for 1 h. The reaction mixture was then diluted with ethyl acetate and filtered through a pad of celite. The filtrate was concentrated and purified directly on silica using gradient elution (20-40% ethyl acetate in hexanes).

Method B—A mixture of ethyl 2-(3-(3-bromo-4-substituted phenyl)-5-(substituted)-4-(3/4-fluoro-4-sulfamoylbenzyl)-1H-pyrazol-1-yl)thiazole-4-carboxylate (1 mmol), tri(tert-butylphosphonium)tetrafluoroborate (10 mol %), allylpalladium chloride dimer (5 mol %) and DABCO (2 mmol, 2 eq) in dioxane (0.5 molar concentration) was bubbled with argon for 5 minutes. The appropriate alkyne (1.5 mmol, 1.5 eq) was added and the reaction mixture was stirred at room temperature overnight. After completion of the reaction, silica bound palladium scavenger was added and the slurry was stirred at room temperature for 1 hr, subsequently diluted with ethyl acetate and filtered through a pad of celite. The filtrate was concentrated and the residue was purified directly on silica using gradient elution (20-40% ethyl acetate in hexanes) yielding the desired compound which was taken to the next step.

Step 2: 2-(3-(3-substituted-4-substituted phenyl)-5-(cyclopropylmethyl)-4-(3-substituted-4-sulfamoylbenzyl)-1H-pyrazol-1-yl)thiazole-4-carboxylic acid The titled compound was synthesized and purified in a similar manner as described in Example 18.

Example 146

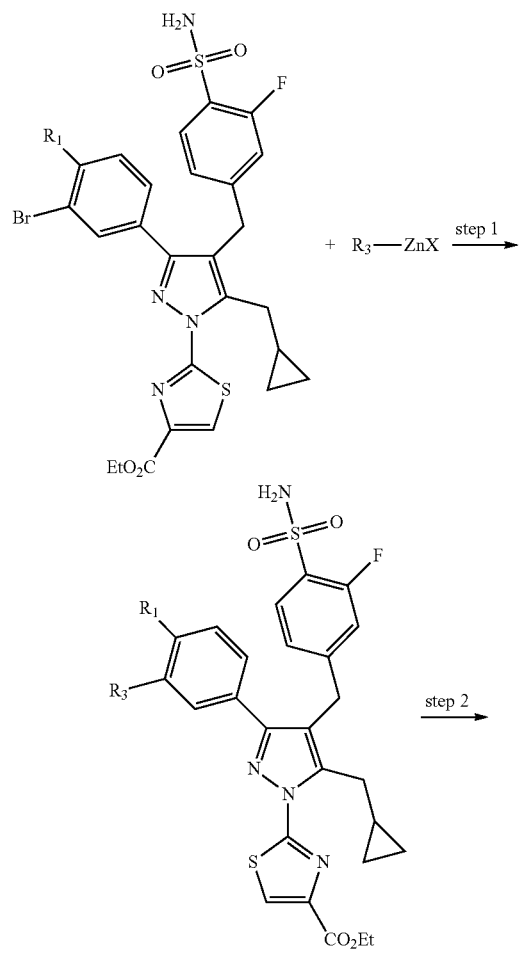

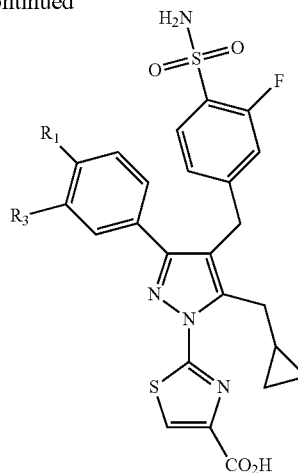

$R_3$ = alkyl and cycloalkyl

Step 1: General Synthesis of ethyl 2-(3-(3-substituted-4-substituted phenyl)-5-(cyclopropylmethyl)-4-(3-substituted-4-sulfamoylbenzyl)-1H-pyrazol-1-yl)thiazole-4-carboxylate using Negishi coupling A mixture of ethyl 2-(3-(3-bromo-4-substituted phenyl)-5-(cyclopropylmethyl)-4-(3-substituted-4-sulfamoylbenzyl)-1H-pyrazol-1-yl)thiazole-4-carboxylate (1 eq) (0.1 g, 0.157 mmol), CPhos (5 mol %), CPhos Pdcycle G3 (Sigma cat #763004, 2.5 mol %) in a Biotage microwave vial was backfilled with argon then added a THF solution of appropriate alkyl/cycloalkyl zinc halide (3-5 eq) under argon. The reaction mixture was stirred at room temperature or at 60° C. for 0.5-3 h. After completion, the reaction mixture was quenched with 1 molar HCl and extracted with ethyl acetate. The organic layer was washed with bicarbonate and brine subsequently dried under magnesium sulfate. The crude material was purified directly on silica using gradient elution (10-40% EA in hexanes over 20 column volumes).

Step 2: General Synthesis of ethyl 2-(3-(3-substituted-4-substituted phenyl)-5-(cyclopropylmethyl)-4-(3-substituted-4-sulfamoylbenzyl)-1H-pyrazol-1-yl)thiazole-4-carboxylic acids The titled compound was synthesized and purified in a similar manner as described in Example 18.

Example 147

This example describes the synthesis of 2-(5-(hydroxy)-3-phenyl-4-(4-sulfamoylbenzyl)-1H-pyrazol-1-yl)thiazole-4-carboxylic acids in an embodiment of the invention.

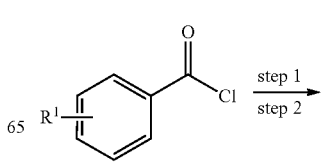

-continued

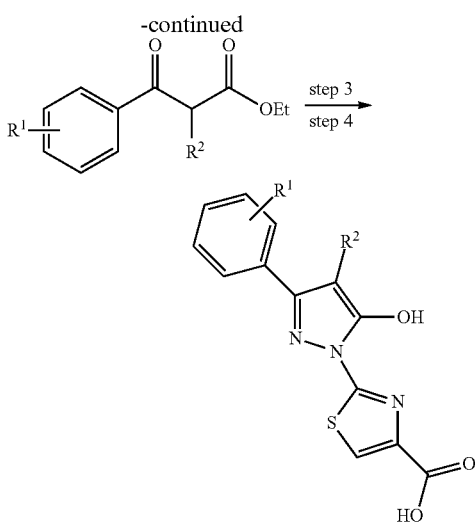

Step 1: Synthesis of ethyl 3-oxo-3-phenylpropanoates

Ethyl acetate (102 mmol) was added dropwise to a cooled solution of lithium stirred for 30 minutes at which time the appropriate benzoyl chloride (56.6 mmol) was added after which the reaction was allowed to attain rt. Upon completion as detected by LCMS, the reaction was quenched with sat. aq. $NH_4Cl$. The product was extracted with ethyl acetate and the organic layer washed with water and brine, dried over $Na_2SO_4$, filtered, and concentrated under reduced pressure. The residue was purified directly on silica using gradient elution (5-50% ethyl acetate in hexanes over 12 CV). The resulting yellow oils were used in the next step without further purification or characterization.

Step 2: Synthesis of ethyl 3-oxo-3-phenyl-2-(4-sulfamoylbenzyl)propanoates

Ethyl 3-oxo-3-phenylpropanoate (150 mmol) and cesium carbonate ($Cs_2CO_3$, 226 mmol) were dissolved in DMSO (50 ml). The reaction mixture was stirred at rt for 10 minutes at which time potassium iodide were added (KI, 150 mmol) and 4-(bromomethyl)-benzenesulfonamides (165 mmol). The resulting mixture was stirred at rt for 1 h. Upon completion as detected by LCMS, the reaction mixture was diluted with a large excess of ethyl acetate and filtered through celite. The filtrate was washed with 1 M HCl, sat aq $NH_4Cl$ and brine, dried over $Na_2SO_4$, filtered, and concentrated under reduced pressure. The residue was purified directly on silica using gradient elution (20-40% ethyl acetate in hexanes over 16 CV).

Step 3: ethyl 2-(5-hydroxy-3-phenyl)-4-(4-sulfamoylbenzyl)-1H-pyrazol-1-yl)thiazole-4-carboxylates A solution of ethyl 3-oxo-3-phenyl-2-(4-sulfamoylbenzyl)propanoate (6.7 mmol), ethyl 2-hydrazinylthiazole-4-carboxylate, 2 HBr (7.3 mmol) and p-toluene sulfonic acid (pTsOH, 20 mmol) in dioxane was heated in a sealed vessel in the microwave for 15 min at 160° C. Upon completion as detected by LCMS, the reaction mixture was diluted with ethyl acetate and filtered through celite. The solvent was removed under reduced pressure and the crude product was purified directly on silica using gradient elution (0-100% ethyl acetate in hexanes over 15 CV).

Step 4: Synthesis of 2-(5-hydroxy-3-phenyl)-4-(4-sulfamoylbenzyl)-1H-pyrazol-1-yl)thiazole-4-carboxylic acids To a solution of ethyl 2-(5-hydroxy-3-phenyl)-4-(4-sulfamoylbenzyl)-1H-pyrazol-1-yl)thiazole-4-carboxylate (0.07 mmol) in THF/MeOH was added 1.5 M LiOH (0.27 mmol). The reaction mixture was stirred at rt for 1 h. Upon completion as detected by LCMS, the solvent was removed by forced air. The residue was taken into DMSO and purified directly via preparative reverse phase using gradient elution (4-100% acetonitrile modified with 0.1% TFA in water modified with 0.1% TFA). The product fractions were directly frozen and lyophilized overnight, yielding an off-white powder.

Example 148

This example describes the synthesis of 2-(5-(hydroxy)-3-phenyl-4-(4-sulfamoylbenzyl)-1H-pyrazol-1-yl)thiazole-4-carboxylic acids in an embodiment of the invention.

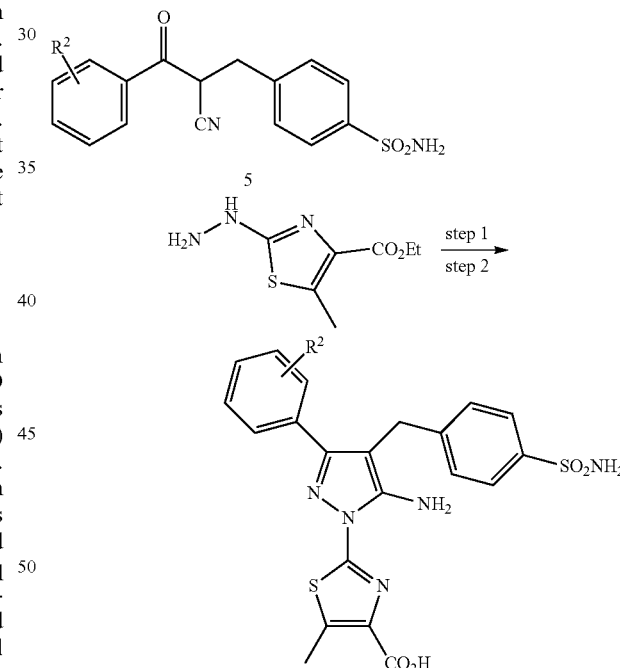

Step 1: Synthesis of 4-((5-amino-1-substituted-3-phenyl-1H-pyrazol-4-yl)methyl) benzenesulfonamide A solution of ethyl 2-hydrazinyl-5-methylthiazole-4-carboxylate (0.267 mmol), 4-(2-cyano-3-oxo-3-phenylpropyl) benzenesulfonamide (0.267 mmol) and tosic acid (0.534 mmol) in MeOH was heated in the microwave for 15 min. The crystals upon cooling was collected by filtration and washed with ethanol and dried used as such in the next step.

Step 2: 2-(5-amino-3-phenyl-4-(4-sulfamoylbenzyl)-1H-pyrazol-1-yl)-5-methylthiazole-4-carboxylic acid The titled compound was synthesized and purified in a similar manner as described in Example 18

Example 149

This example describes the synthesis of 4-(((5-hydroxy-3-phenyl-1H-pyrazol-4-yl)methyl)amino)benzenesulfonamide in an embodiment of the invention.

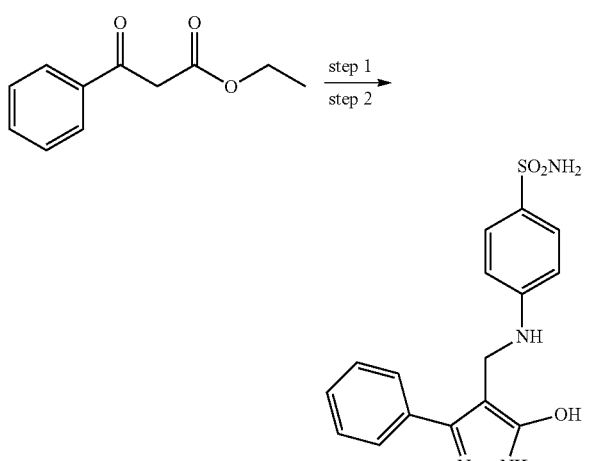

Step 1: Synthesis of 3-phenyl-1H-pyrazol-5-ol

To a solution of ethyl 3-oxo-3-phenylpropanoate (24.7 mmol) in ethanol (15 ml) was added hydrazine hydrate (49 mmol) at 0° C., then stirred at rt for 1 h. Upon completion, the product was extracted with ethyl acetate, washed with water, bicarbonate and brine, dried over Na₂SO₄, filtered, and concentrated under reduced pressure. The crude product obtained after evaporating the solvent was used as such in the next step.

Step 2: 4-(((5-hydroxy-3-phenyl-1H-pyrazol-4-yl)methyl)amino)-benzenesulfonamide 3-phenyl-1H-pyrazol-5-ol (0.5 g, 3.12 mmol and 4-aminobenzenesulfonamide (0.538 g, 3.12 mmol) in EtOH (Volume: 6.24 ml) was stirred in a sealed tube at 100° C. for 1 h. The product precipitated upon cooling, and the slurry was sonicated for 5 minutes and filtered. The precipitate was washed with ethanol, re-suspended in DMSO and purified directly on reverse phase using gradient elution (4-100% acetonitrile modified with 0.1% TFA in water modified with 0.1% TFA).

Example 150

This example describes the synthesis of 2-(3-(4-chlorophenyl)-5-(trifluoromethyl)-1H-pyrazol-1-yl)thiazole-4-carboxylic acid in an embodiment of the invention.

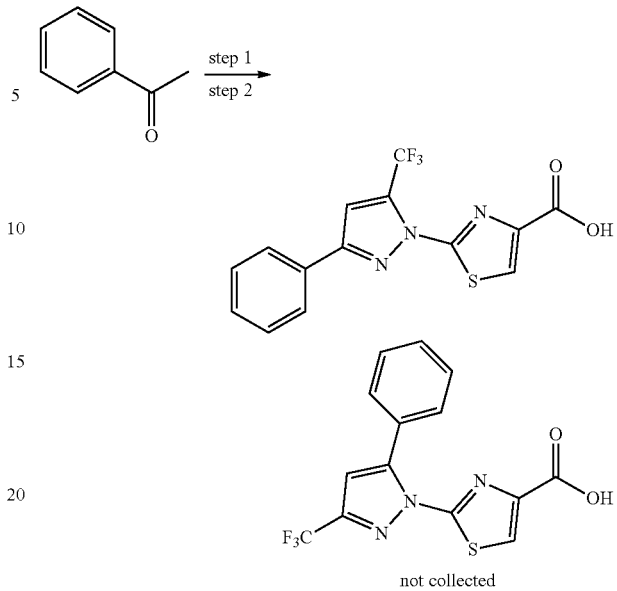

not collected

Step 1: Synthesis of 1-(3,4-difluorophenyl)-4,4,4-trifluorobutane-1,3-dione

A stirring solution of 1-(3,4-difluorophenyl)ethanone (3.20 mmol) in DMF (6 ml) was chilled to 0° C. before NaH (3.8 mmol) was added portionwise. The reaction mixture was stirred for 30 minutes at which time ethyl 2,2,2-trifluoroacetate (3.84 mmol) was added and the reaction mixture was allowed to attain rt. Upon completion the reaction was quenched with water the pH was adjusted with 1 N HCl and the product was extracted with ethyl acetate. The organic layer was washed with water and brine, dried over Na₂SO₄, filtered, and concentrated under reduced pressure. The residue was purified directly on silica using gradient elution (5-50% ethyl acetate in hexanes over 12 CV) to provide a yellow oil.

Step 2: Synthesis of 2-(3-(4-chlorophenyl)-5-(trifluoromethyl)-1H-pyrazol-1-yl)thiazole-4-carboxylic acid A solution of 1-(4-chlorophenyl)-4,4,4-trifluorobutane-1,3-dione (3.99 mmol) and hydrazinecarbothioamide (3.99 mmol) in EtOH was refluxed for 12 h. The solvent was removed under reduced pressure and the residue was boiled in chloroform and filtered. The filtrate was concentrated and taken up EtOH then added ethyl 3-bromo-2-oxopropanoate (3.99 mmol) and refluxed for 1 h. Added concentrated sulfuric acid and refluxed overnight. The solvent was concentrated and the product extracted with ethyl acetate. The organic layer was washed with bicarbonate and brine, dried over Na₂SO₄, filtered, and concentrated under reduced pressure. The crude product containing the mixture of products was purified on reverse phase preparative column. The second peak was collected and hydrolyzed with HCl/AcOH at 120° C. in a sealed tube for 1 h. After removing the solvent with forced air the crude product were purified directly on reverse phase preparative column (4-100% acetonitrile modified with 0.1% TFA in water modified with 0.1% TFA).

Example 151

This example describes the synthesis of 2-(3-(3,4-difluorophenyl)-5-(hydroxymethyl)-1H-pyrazol-1-yl)thiazole-4- carboxylic acid and 3-(3,4-difluorophenyl)-1-(4-(methoxycarbonyl)thiazol-2-yl)-1H-pyrazole-5-carboxylic acid in an embodiment of the invention

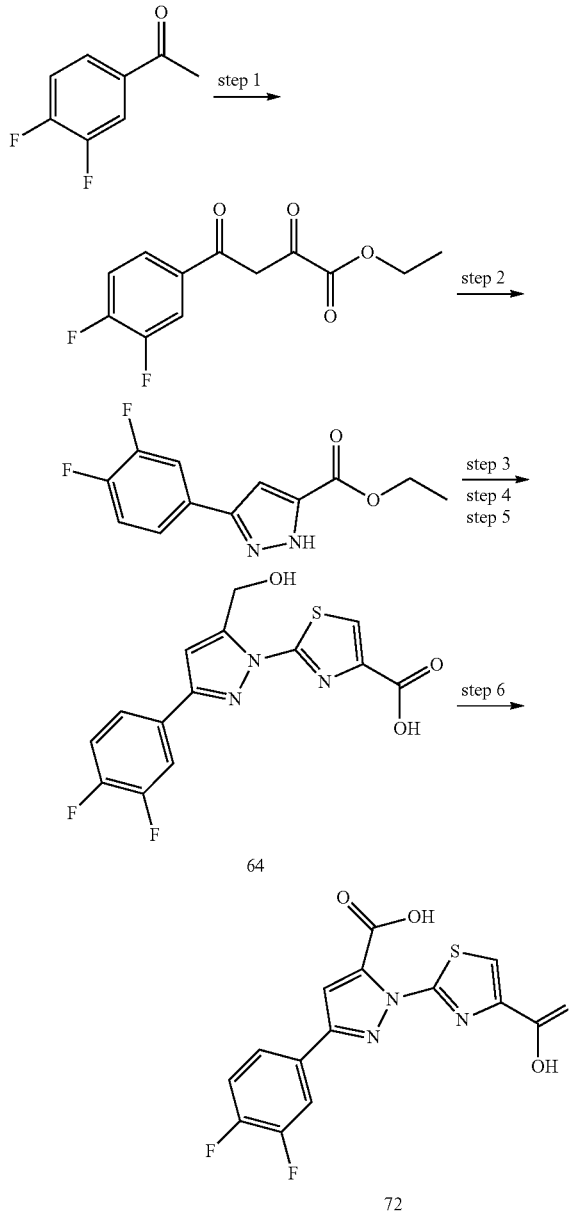

Step 1: Synthesis of ethyl 4-(3,4-difluorophenyl)-2,4-dioxobutanoate

A solution of NaOEt (144 mmol) in ethanol was added 1-(3,4-difluorophenyl)ethanone (96 mmol) was stirred for 5 minutes at which time diethyl oxalate (106 mmol) was added. The reaction mixture was stirred for 10 minutes and a thick ppt was formed. The reaction mixture was poured into ice water containing 7 mL of conc HCl. A precipitate formed and was collected by filtration and washed with water and dried under air. The crude product was used as such in the next step.

Step 2: Synthesis of ethyl 3-(3,4-difluorophenyl)-1H-pyrazole-5-carboxylate

To a solution of ethyl 4-(3,4-difluorophenyl)-2,4-dioxobutanoate (90 mmol) in ethanol was added hydrazine monohydrate (99 mmol) and the reaction mixture was stirred at rt for 12 h. The reaction becomes clear solution and eventually the product precipitates. The solvent was removed and the desired compound was purified by recrystallization in ethanol.

Step 3: Synthesis of (3-(3,4-difluorophenyl)-1H-pyrazol-5-yl)methanol

To a solution of ethyl 3-(3,4-difluorophenyl)-1H-pyrazole-5-carboxylate (5.67 mmol) in THF (20 ml) was added lithium aluminum hydride (11.34 mmol, 1.0 M in THF) slowly dropwise at 0° C. The reaction mixture was stirred for 1 h then quenched with sat. aq. $NH_4Cl$. The product was extracted with ethyl acetate and the organic layer washed with water and brine, dried over $Na_2SO_4$, filtered, and concentrated under reduced pressure. The residue was purified directly on silica using gradient elution (50-100% EA in hexanes).

Step 4: Synthesis of tert-butyl 2-(3-(3,4-difluorophenyl)-5-(hydroxymethyl)-1H-pyrazol-1-yl)thiazole-4-carboxylate A solution of (3-(3,4-difluorophenyl)-1H-pyrazol-5-yl)methanol (0.952 mmol), tert-butyl 2-bromothiazole-4-carboxylate (1.047 mmol), (1S,2S)—N1,N2-dimethylcyclohexane-1,2-diamine (0.190 mmol), CuI (0.095 mmol) and $K_3PO_4$ (2.093 mmol) in dioxane was stirred at 110° C. in a sealed tube for 12 h. Upon completion the reaction mixture was stirred with thiol resin and filtered through celite and the celite pad was washed with ethyl acetate. After concentration the crude product was purified directly on silica using gradient elution (10-50% ethyl acetate in hexanes) providing a white solid.

Step 5: Synthesis of 2-(3-(3,4-difluorophenyl)-5-(hydroxymethyl)-1H-pyrazol-1-yl)thiazole-4-carboxylic acid Tert-butyl 2-(3-(3,4-difluorophenyl)-5-(hydroxymethyl)-1H-pyrazol-1-yl)thiazole-4-carboxylate was deprotected with TFA/DCM. The product was purified directly on reverse phase preparative column (4-100% acetonitrile modified with 0.1% TFA in water modified with 0.1% TFA).

Step 6: Synthesis of 3-(3,4-difluorophenyl)-1-(4-(methoxycarbonyl)thiazol-2-yl)-1H-pyrazole-5-carboxylic acid To a 5 dram vial were added methyl 2-(3-(3,4-difluorophenyl)-5-formyl-1H-pyrazol-1-yl)thiazole-4-carboxylate (0.014 g, 0.04 mmol) and Oxone (0.025 g, 0.04 mmol). The reaction mixture was stirred at rt for 16 hr. The reaction was complete by LCMS. The reaction mixture was diluted with water and the product was extracted with EtOAc. The org layer was dried with brine and $Na_2SO_4$, filtered, and concentrated under reduced pressure. The residue was purified directly on reverse phase preparative column (4-100% acetonitrile modified with 0.1% TFA in water modified with 0.1% TFA).

Example 152

This example describes the synthesis of 2-(3-([1,1'-biphenyl]-3-yl)-5-hydroxy-4-(4-sulfamoylbenzyl)-1H-pyrazol-1-yl)thiazole-4-carboxamide 70 in an embodiment of the invention.

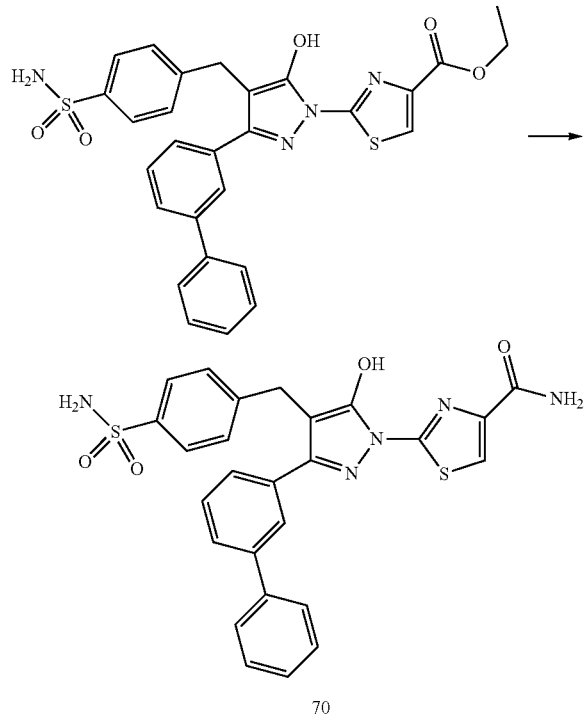

70

A stirring solution of ethyl 2-(3-([1,1'-biphenyl]-3-yl)-5-hydroxy-4-(4-sulfamoylbenzyl)-1H-pyrazol-1-yl)thiazole-4-carboxylate (0.019 mmol) and MeOH (0.5 ml) at 0° C. was bubbled with ammonia gas for 1 min. The reaction mixture was heated to 60° C. for 30 min. Upon completion, the reaction mixture was purified directly on reverse phase preparative column (4-100% acetonitrile modified with 0.1% TFA in water modified with 0.1% TFA).

Example 153

This example describes the synthesis of 4-((1-(4-(1H-tetrazol-5-yl)thiazol-2-yl)-3-([1,1'-biphenyl]-3-yl)-5-hydroxy-1H-pyrazol-4-yl)methyl)benzenesulfonamide 72 in an embodiment of the invention.

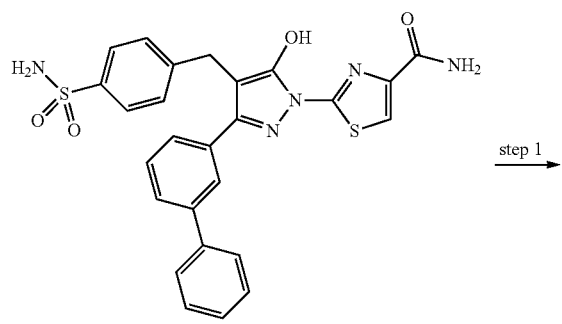

step 1

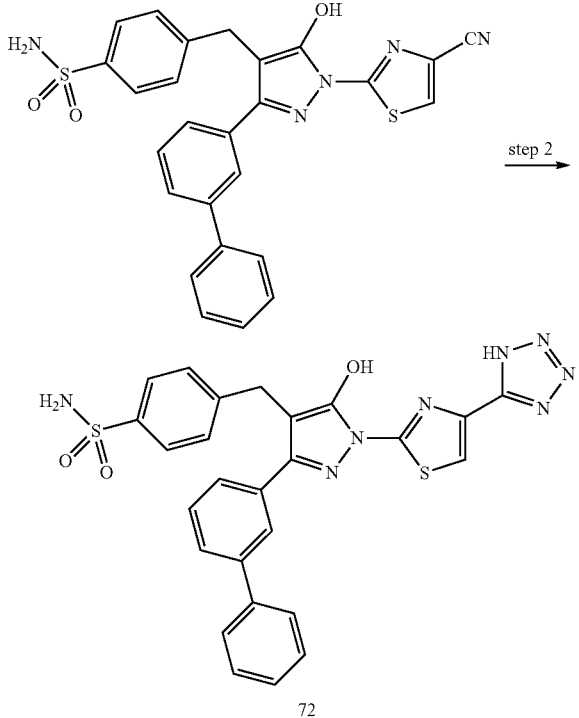

72

Step 1: Synthesis of 4-((3-([1,1'-biphenyl]-3-yl)-1-(4-cyanothiazol-2-yl)-5-hydroxy-1H-pyrazol-4-yl)methyl)benzenesulfonamide To a stirring solution of 2-(3-([1,1'-biphenyl]-3-yl)-5-hydroxy-4-(4-sulfamoylbenzyl)-1H-pyrazol-1-yl)thiazole-4-carboxamide (0.344 mmol) and diisopropylethylamine (1.030 mmol) in $CH_2Cl_2$ (3.4 mL) was added TFAA (0.687 mmol) dropwise at 0° C. The reaction mixture was stirred at rt for 5 hr. An additional 2 eq. of TFAA (0.687 mmol) and 3 eq of diisopropylethylamine (1.030 mmol) were added and the reaction mixture was stirred overnight. Upon completion, the reaction was diluted with $CH_2Cl_2$, washed with water, $NaHCO_2$, and brine. The organic layer was dried over $MgSO_4$ and concentrated under reduced pressure and the residue was purified directly on reverse phase preparative column (4-100% acetonitrile modified with 0.1% TFA in water modified with 0.1% TFA).

Step 2: Synthesis of 4-((1-(4-(1H-tetrazol-5-yl)thiazol-2-yl)-3-([1,1'-biphenyl]-3-yl)-5-hydroxy-1H-pyrazol-4-yl)methylbenzenesulfonamide A solution of N-((4-((3-([1,1'-biphenyl]-3-yl)-1-(4-cyanothiazol-2-yl)-5-hydroxy-1H-pyrazol-4-yl)methyl)phenyl)sulfonyl)-2,2,2-trifluoroacetamide (0.036 mmol), sodium azide (0.108 mmol) and $NH_4Cl$ (0.072 mmol) heated to 125° C. in DMF (0.4 ml) for 2 h. Upon completion, the reaction mixture was purified directly on reverse phase preparative column (4-100% acetonitrile modified with 0.1% TFA in water modified with 0.1% TFA).

Example 154

This example describes the synthesis of 2-(3-phenyl-5-(pyridin-3-ylamino)-4-(4-sulfamoylbenzyl)-1H-pyrazol-1-yl)thiazole-4-carboxylic acid 80 in an embodiment of the invention.

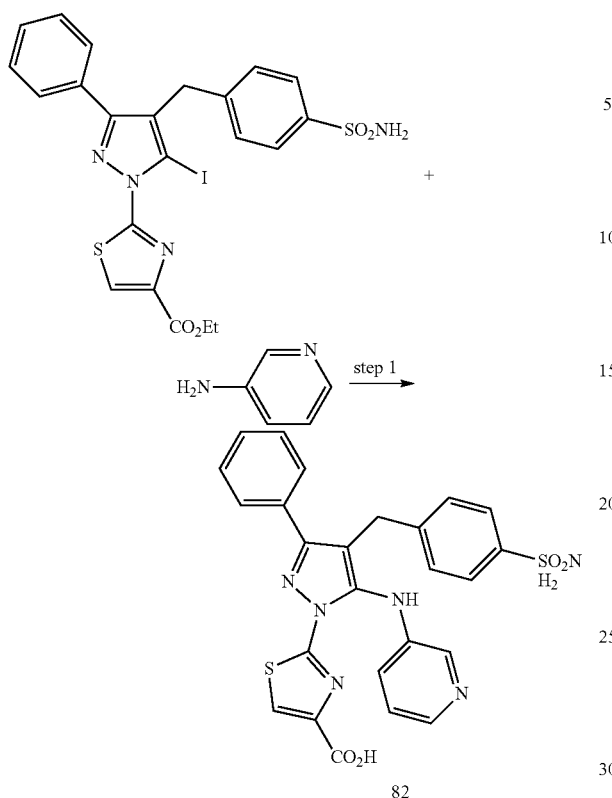

A mixture of ethyl 2-(5-iodo-3-phenyl-4-(4-sulfamoylbenzyl)-1H-pyrazol-1-yl)thiazole-4-carboxylate (0.168 mmol), pyridin-3-amine (0.252 mmol), XantPhos (0.168 mmol), $Pd_2(dba)_3$ (0.168 mmol) and sodium tert-butoxide (0.370 mmol) in a microwave vial was degassed with argon. 2 mL of dioxane was added and stirred at 100° C. overnight. The solvent was removed by forced air. The contents were suspended in DMSO and stirred with silica palladium scavenger at 70° C. for 1 h then filtered through a syringe filter. The crude product was hydrolyzed according to Example 18 and was purified directly on reverse phase preparative column (4-100% acetonitrile modified with 0.1% TFA in water modified with 0.1% TFA).

Example 155

This example describes the synthesis of 2-(3-phenyl-4-((4-sulfamoylpiperazin-1-yl)methyl)-1H-pyrazol-1-yl)thiazole-4-carboxylic acid 90 and 2-(3-phenyl-4-((piperazine-1-sulfonamido)methyl)-1H-pyrazol-1-yl)thiazole-4-carboxylic acid 138 in an embodiment of the invention.

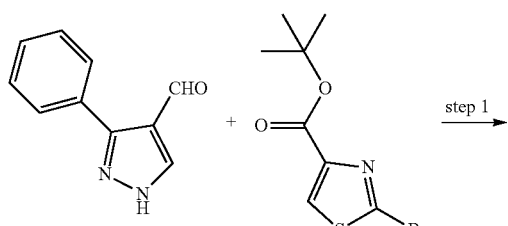

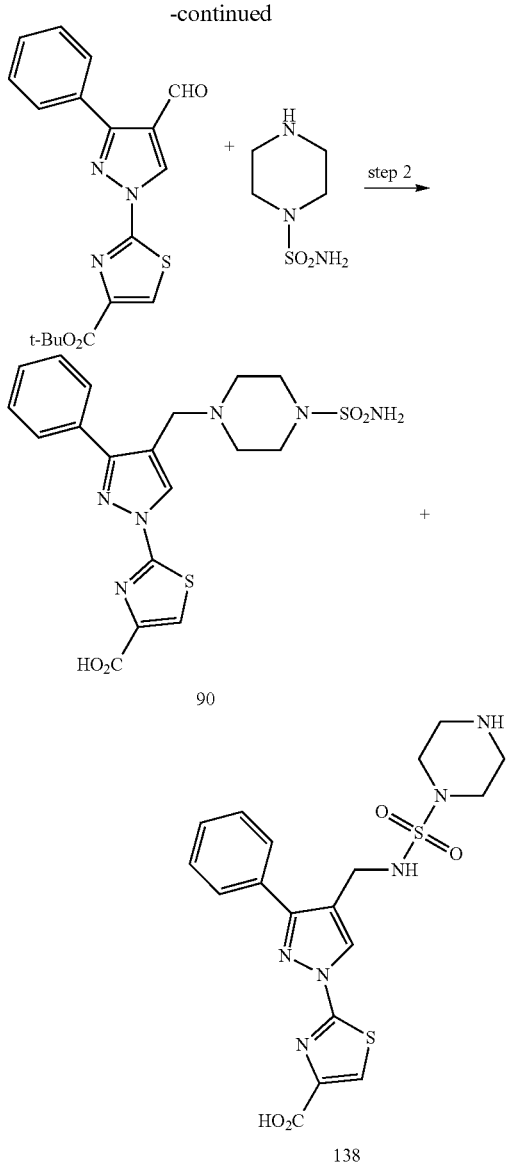

Step 1: Synthesis of tert-butyl 2-(4-formyl-3-phenyl-1H-pyrazol-1-yl)thiazole-4-carboxylate A solution of 3-phenyl-1H-pyrazole-4-carbaldehyde (2.323 mmol), $K_2CO_3$ (3.48 mmol), and tert-butyl 2-bromothiazole-4-carboxylate (2.439 mmol) in DMSO was stirred for 3 h. Upon completion the product was extracted with ethyl acetate, washed with sat. aq. $NH_4Cl$, water and brine, dried over $Na_2SO_4$, filtered, and concentrated under reduced pressure. The residue was purified directly on silica using gradient elution (50-100% EA in hexanes) providing a yellow solid.

Step 2: Synthesis of 2-(3-phenyl-4-((4-sulfamoylpiperazin-1-yl)methyl)-1H-pyrazol-1-yl)thiazole-4-carboxylic acid 90 and 2-(3-phenyl-4-((piperazine-1-sulfonamido)methyl)-1H-pyrazol-1-yl)thiazole-4-carboxylic acid 138

A mixture of tert-butyl 2-(4-formyl-3-phenyl-1H-pyrazol-1-yl)thiazole-4-carboxylate (0.422 mmol) and piperazine-1- sulfonamide (0.633 mmol) in methanol (2 mL) was stirred at 90° C. for 15 minutes in a sealed tube. The reaction mixture was cooled to room temperature then treated with sodium cyanoborohydride (0.844 mmol) and stirred at rt for another 1 h. The mixture of products was extracted with ethyl acetate. The organic layer was subsequently washed with water and brine. Upon removal of the solvent, the product was taken in dichloromethane (1 mL) and treated with TFA (0.5 mL) then stirred at rt for 1 h. The solvent was removed by forced air and the crude product was subsequently purified on a preparative HPLC.

Example 156

This example describes the synthesis of alkyl 2-(3-(3,4-difluorophenyl)-5-hydroxy-1H-pyrazol-1-yl)thiazole-4-carboxylate and alkyl 2-(3-(3,4-difluorophenyl)-5-alkyloxy-1H-pyrazol-1-yl)thiazole-4-carboxylate in an embodiment of the invention.

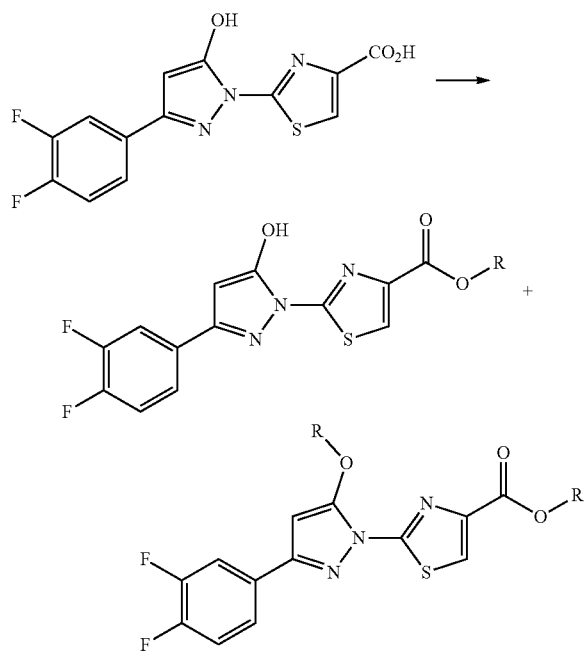

To a stirring solution of 2-(3-(3,4-difluorophenyl)-5-hydroxy-1H-pyrazol-1-yl)thiazole-4-carboxylic acid (0.155 mmol) in DMA (0.8 mL) were added 1-chloroethyl ethyl carbonate (0.155 mmol) and $K_2CO_3$ (0.309 mmol). The reaction mixture was stirred at rt for 2 h. Upon completion the reaction mixture was filtered and the filtrate was subsequently purified on a preparative HPLC.

Example 157

This example describes the synthesis of 2-(3,4-difluorophenyl)-5-oxo-4,5-dihydropyrazolo[1,5-a]thieno[3,2-e]pyrimidine-6-carboxylic acid 116 in an embodiment of the invention

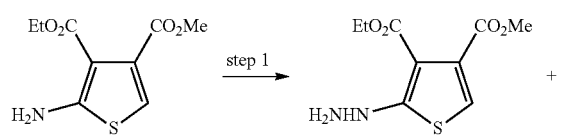

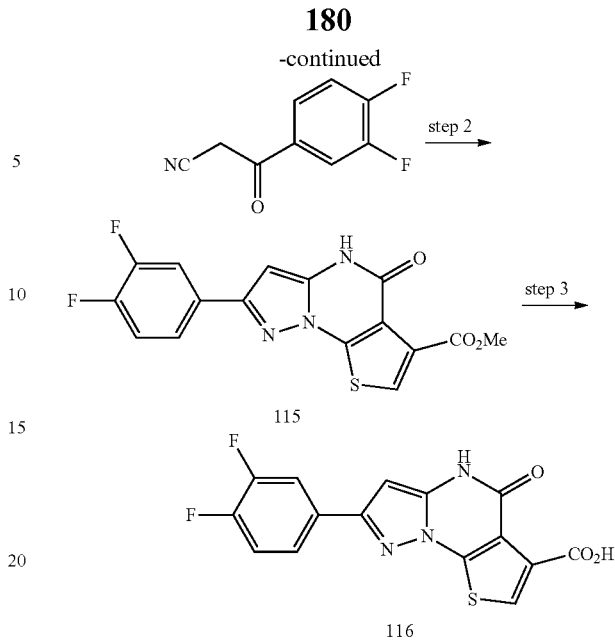

Step 1: Synthesis of 3-ethyl 4-methyl 2-hydrazinylthiophene-3,4-dicarboxylate

A solution of 3-ethyl 4-methyl 2-aminothiophene-3,4-dicarboxylate (4.86 g, 21.20 mmol, 1 eq) in conc. HCl (30 ml) was added sodium nitrite (1.609 g, 23.32 mmol, 1.1 eq) in 15 mL of water drop wise at 0° C. The reaction mixture was stirred for 30 min then added a solution of tin(II) chloride (16.08 g, 85 mmol, 4 eq) in 15 mL of conc. HCl and stirred for 15 minutes. The reaction mixture was carefully neutralized with 40% NaOH solution upon cooling in an ice bath. The solid tin salt was removed by filtration and the filtrate was extracted with ethyl acetate. The organic layer was washed with brine and dried over sodium sulfate. The crude product was purified on a flash system using a 220 G gold silica column eluting with 20-100% ethyl acetate in hexanes. The first peak with mass M+H=245 was pooled and concentrated to get a light yellow solid (1.36 g in 26% yield).

Step 2: Synthesis of methyl 2-(3,4-difluorophenyl)-5-oxo-4,5-dihydropyrazolo[1,5-a]thieno[3,2-e]pyrimidine-6-carboxylate 115

A thoroughly mixed mixture of 3-ethyl 4-methyl 2-hydrazinylthiophene-3,4-dicarboxylate (0.3 g, 1.228 mmol, 1 eq) and 3-(3,4-difluorophenyl)-3-oxopropanenitrile (0.222 g, 1.228 mmol, 1 eq) in an open vial was stirred neat at 130° C. for 1.5 h. The melted liquid becomes thick solid which is triturated in DCM/MeOH. The crude product was purified on flash system using a 24 g silica column eluting with 1-10% methanol in DCM over 12 column volumes. The pure fraction was pooled and concentrated to get 0.49 g (Yield=84%) of white solid.

Step 3: Synthesis of 2-(3,4-difluorophenyl)-5-oxo-4,5-dihydropyrazolo[1,5-a]thieno[3,2-e]pyrimidine-6-carboxylic acid 116

A solution methyl 2-(3,4-difluorophenyl)-5-oxo-4,5-dihydropyrazolo[1,5-a]thieno[3,2-e]pyrimidine-6-carboxylate (0.1 g, 0.277 mmol, 1 eq) in a mixture of THE/MeOH (3/1)

was treated with 1.5 molar solution of LiOH in water (4-5 eq) then stirred at room temperature for 1 h. The excess solvent was removed by forced air then the residue was acidified with 1 molar HCl. The crude product was taken in DMSO and purified on a preparative HPLC.

Example 158

This example describes the synthesis of 2-(3-phenyl-4-((4-sulfamoylbenzyl)amino)-1H-pyrazol-1-yl)thiazole-4-carboxylic acid and 2-(3-phenyl-4-(4-sulfamoylbenzamido)-1H-pyrazol-1-yl)thiazole-4-carboxylic acid in an embodiment of the invention

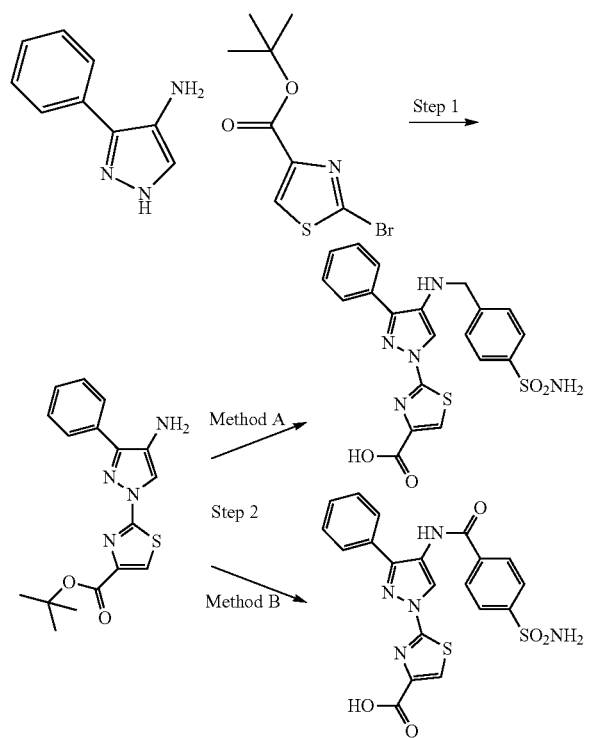

Step 1: Synthesis of tert-butyl 2-(4-amino-3-phenyl-1H-pyrazol-1-yl)thiazole-4-carboxylate A solution of 3-phenyl-1H-pyrazol-4-amine (0.25 g, 1.57 mmol), $K_2CO_3$ (0.33 g, 2.36 mmol), and tert-butyl 2-bromothiazole-4-carboxylate (0.47 g, 1.73 mmol) in DMSO was stirred for 24 h at 120° C. Upon completion the reaction mixture was cooled, diluted with ethyl acetate and filtered through celite. The organic layer was washed with ammonium chloride and brine, dried over $Na_2SO_4$, filtered, and concentrated under reduced pressure. The residue was purified directly on silica gel using gradient elution (5-80% ethyl acetate containing 1% TEA in hexanes over 15 CV) to afford the desired compound as a yellow solid.

Step 2—Method A—Synthesis of 2-(3-phenyl-4-((4-sulfamoylbenzyl)amino)-1H-pyrazol-1-yl)thiazole-4-carboxylic acid To a stirring solution of tert-butyl 2-(4-amino-3-phenyl-1H-pyrazol-1-yl)thiazole-4-carboxylate (0.13 g, 0.38 mmol) and 4-formylbenzenesulfonamide (0.09 g, 0.49 mmol) in MeOH (3 ml) was added few drops of acetic acid. The reaction mixture was stirred at 80° C. for 30 minutes in a sealed tube. The reaction mixture was cooled to rt then added sodium cyanoborohydride (0.048 g, 0.759 mmol) and stirred at rt for another 15 minutes. The crude reaction mixture was purified directly on reverse phase preparative chromatography without workup using gradient elution (4-100% acetonitrile modified with 0.1% TFA in water modified with 0.1% TFA). The pure product was deprotected with TFA/DCM finally purified on HPLC.

Step 2—Method B—Synthesis of 2-(3-phenyl-4-(4-sulfamoylbenzamido)-1H-pyrazol-1-yl)thiazole-4-carboxylic acid A solution of 4-sulfamoylbenzoic acid (0.09 g, 0.44 mmol) and HATU (0.22 g, 0.58 mmol) in DMF was stirred at rt for 15 minutes at which time tert-butyl 2-(4-amino-3-phenyl-1H-pyrazol-1-yl)thiazole-4-carboxylate (0.1 g, 0.29 mmol) and Hunig's Base (0.10 ml, 0.58 mmol) were added. The reaction mixture was stirred at 60° C. for 4 h. Upon completion the reaction mixture was cooled and extracted with ethyl acetate. The organic layer was washed with water, bicarbonate and brine, dried over $Na_2SO_4$, filtered, and concentrated under reduced pressure. The residue was purified directly on silica gel using gradient elution (20-100% ethyl acetate in hexanes over 15 CV). The first fraction was collected and dried. The pure product was deprotected with TFA/DCM, dried using forced air then taken up in DMSO and finally purified on HPLC.

Example 159

This example describes the synthesis of 4-((3-phenyl-1-(4-(2,2,2-trifluoro-1-hydroxyethyl)thiazol-2-yl)-1H-pyrazol-4-yl)methyl)benzenesulfonamide in an embodiment of the invention

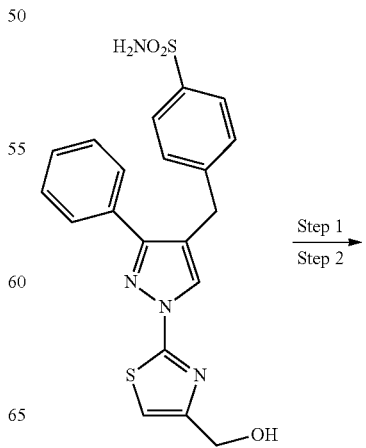

183

-continued

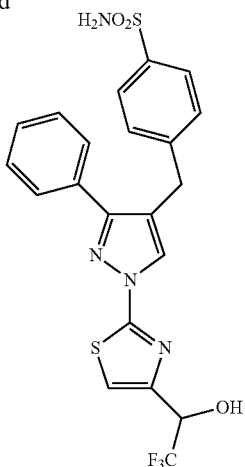

Step 1: Synthesis of 4-((1-(4-formylthiazol-2-yl)-3-phenyl-1H-pyrazol-4-yl)methyl)benzenesulfonamide To a stirring solution of 4-((1-(4-(hydroxymethyl)thiazol-2-yl)-3-phenyl-1H-pyrazol-4-yl)methyl)benzenesulfonamide (0.36 g, 0.84 mmol) in CHCl$_3$ (10 mL) was added manganese dioxide (0.37 g, 4.2 mmol). The reaction mixture was stirred at rt for 12 h. Upon completion the solution was filtered through celite and concentrated under reduced pressure to afford the title compound. The crude product was taken to the next step without purification.

Step 2: Synthesis of 4-((3-phenyl-1-(4-(2,2,2-trifluoro-1-hydroxyethyl)thiazol-2-yl)-1H-pyrazol-4-yl)methyl)benzenesulfonamide To a stirring solution of 4-((1-(4-formylthiazol-2-yl)-3-phenyl-1H-pyrazol-4-yl)methyl)benzenesulfonamide (0.15 g, 0.35 mmol) in THF (2 ml) was added (trifluoromethyl)trimethylsilane (0.16 ml, 1.060 mmol) followed by TBAF (0.18 ml, 0.18 mmol) at 0° C. The reaction mixture was stirred at rt for 4 h. Upon completion the product was extracted with ethyl acetate, washed with 1 molar HCl and brine, dried over Na$_2$SO$_4$, filtered, and concentrated under reduced pressure. The residue was purified directly was purified on reverse phase HPLC.

Example 160

This example describes the synthesis of 2-(5-(oxiran-2-yl)-3-phenyl-4-(4-sulfamoylbenzyl)-1H-pyrazol-1-yl)thiazole-4-carboxylic acid in an embodiment of the invention

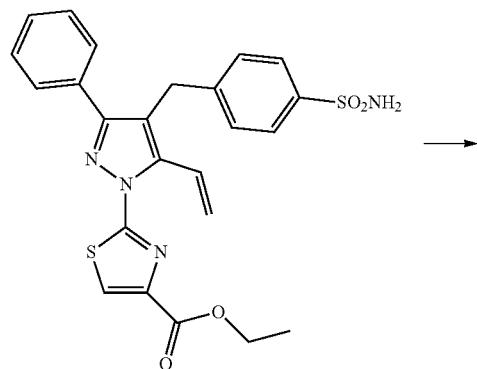

184

-continued

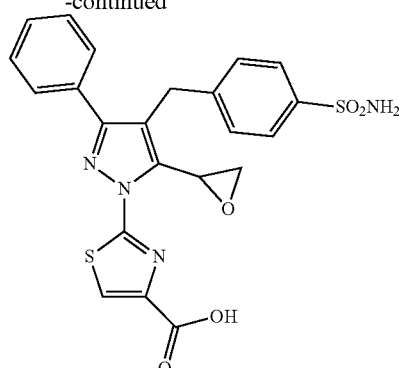

To a stirring solution of ethyl 2-(3-phenyl-4-(4-sulfamoylbenzyl)-5-vinyl-1H-pyrazol-1-yl)thiazole-4-carboxylate (0.1 g, 0.2 mmol) in ethyl acetate/acetone mixture was added a solution of sodium bicarbonate (0.09 g, 1.0 mmol) in 2 mL of water followed by addition of a solution of Oxone (0.373 g, 0.607 mmol) in 1 mL water. The reaction mixture was stirred vigorously at rt for 3 days. Upon completion the product was extracted with ethyl acetate, washed with water and brine, dried over Na$_2$SO$_4$, filtered, and concentrated under reduced pressure. The crude product was hydrolyzed with LiOH in THF/MeOH/water then purified in HPLC without using any acid modifiers.

Example 161

This example describes the synthesis of 2-(5-(oxiran-2-yl)-3-phenyl-4-(4-sulfamoylbenzyl)-1H-pyrazol-1-yl)thiazole-4-carboxylic acid in an embodiment of the invention

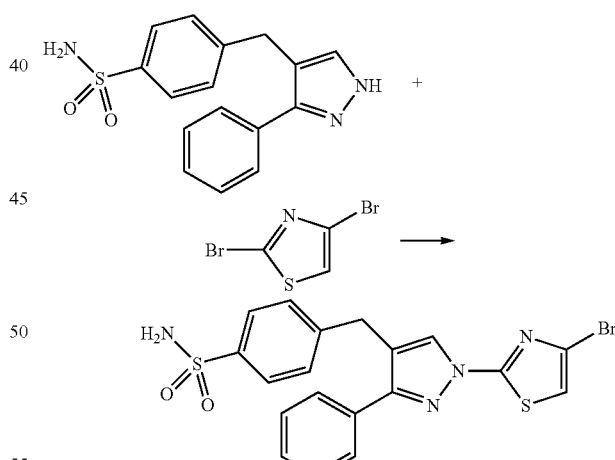

To a round bottom flask were added 4-((3-phenyl-1H-pyrazol-4-yl)methyl)benzenesulfonamide (0.03 g, 0.09 mmol) and DMF (0.5 ml), followed by NaH (3.6 mg, 0.09 mmol). The reaction mixture was stirred at rt for 20 mins, at which time 2,4-dibromothiazole (0.02 g, 0.09 mmol) was added. The reaction mixture was heated to 100° C. for 1 h. Reaction was predominantly finished with no visible starting material this time. The reaction was quenched with water and extracted with EtOAc and washed with water and brine, dried over Na$_2$SO$_4$, filtered, concentrated in vacuo. The residue was purified directly on silica using gradient elution (20-80% ethyl acetate in hexanes over 12 CV) to afford the title compound.

Example 162

This example describes the synthesis of 2-(3-(3-(tert-butylcarbamoyl)-4-fluorophenyl)-5-(cyclopropylmethyl)-4-(3-fluoro-4-sulfamoylbenzyl)-1H-pyrazol-1-yl) thiazole-4-carboxylic acid in an embodiment of the invention.

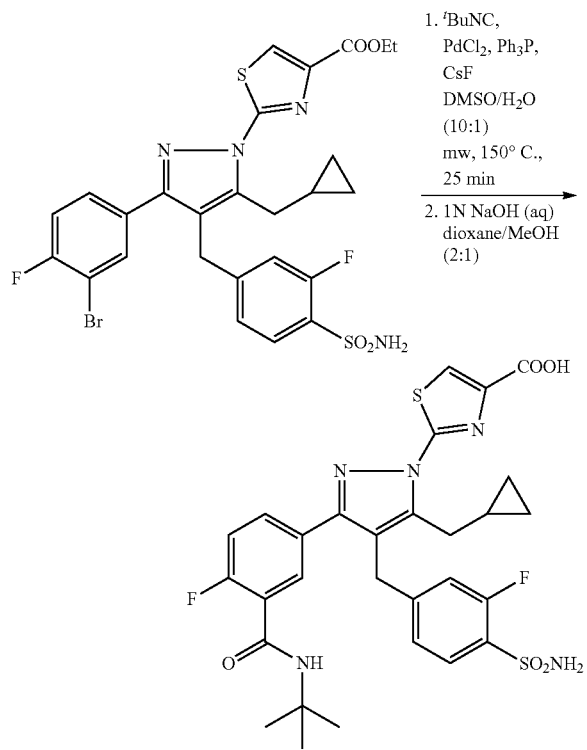

Step 1: Synthesis of ethyl 2-(3-(3-(tert-butylcarbamoyl)-4-fluorophenyl)-5-(cyclopropylmethyl)-4-(3-fluoro-4-sulfamoylbenzyl)-1H-pyrazol-1-yl)thiazole-4-carboxylate To a mixture of ethyl 2-(3-(3-bromo-4-fluorophenyl)-5-(cyclopropylmethyl)-4-(3-fluoro-4-sulfamoylbenzyl)-1H-pyrazol-1-yl)thiazole-4-carboxylate (100.0 mg, 0.156 mmol), PdCl$_2$ (1.38 mg, 0.0078 mmol) and PPh$_3$ (4.0 mg, 0.0156 mmol) in DMSO (1.8 mL) was added CsF (26.0 mg, 0.171 mmol) and water (0.2 mL) successively. The reaction mixture was allowed to stir for 5 min at rt, and tert-butyl isocyanide (26.4 µL, 0.234 mmol) was added. The reaction mixture was irradiated at 150° C. for 25 min in a microwave reactor. The reaction mixture was poured into water and extracted with ethyl acetate (3×15 mL). The organic layers were washed with brine (1×20 mL) and dried with anhydrous magnesium sulfate. The combined organic layer was concentrated in rotary evaporator and the crude (43.0 mg) was used in the next step.

Step 2. Synthesis of 2-(3-(3-(tert-butylcarbamoyl)-4-fluorophenyl)-5-(cyclopropylmethyl)-4-(3-fluoro-4-sulfamoylbenzyl)-1H-pyrazol-1-yl) thiazole-4-carboxylic acid Ethyl 2-(3-(3-(tert-butylcarbamoyl)-4-fluorophenyl)-5-(cyclopropylmethyl)-4-(3-fluoro-4-sulfamoylbenzyl)-1H-pyrazol-1-yl)thiazole-4-carboxylate from Step 1 (43.0 mg, 0.065 mmol) was dissolved in a mixture of dioxane and MeOH (1.0 mL/0.5 mL) and 1.0 mL of 1 N aqueous NaOH was added. The reaction mixture was stirred at room temperature for 2 h. The reaction mixture was neutralized by the addition of 1.0 M aqueous hydrochloric acid, diluted with ethyl acetate (15 mL), washed with water (10 mL), and dried with anhydrous magnesium sulfate. The organic layer was concentrated using a rotary evaporator and the residue was dissolved in DMSO and purified by HPLC (Phenomenex Gemini C18, H$_2$O/CH$_3$CN gradient from 40% to 100% CH$_3$CN for 4 min, 0.1% TFA) to give the title compound (11.0 mg, 26%). $^1$H-NMR (MeOD) δ: 8.21 (s, 1H), 7.79-7.69 (m, 3H), 7.19 (dd, J=8.6, 10.0 Hz, 1H), 7.11-7.05 (m, 2H), 4.21 (s, 2H), 3.28 (d, J=6.8 Hz, 2H), 1.44 (s, 9H), 1.18-1.10 (m, 1H), 0.43-0.39 (m, 2H), 0.28-0.24 (m, 2H); MS (ES) 630.1 [M+H]$^+$, LCMS RT=1.048 min.

Example 163

This example describes the synthesis of 2-(5-(cyclopropylmethyl)-3-(4-fluoro-3-(pyrrolidine-1-carbonyl)phenyl)-4-(3-fluoro-4-sulfamoylbenzyl)-1H-pyrazol-1-yl)thiazole-4-carboxylic acid (Cpd. C) in an embodiment of the invention.

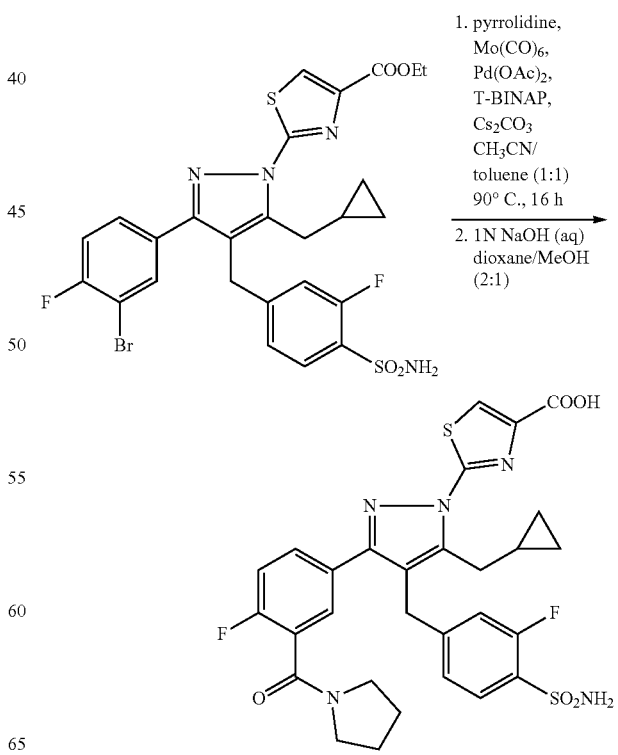

Step 1: Synthesis of ethyl 2-(5-(cyclopropylmethyl)-3-(4-fluoro-3-(pyrrolidine-1-carbonyl)phenyl)-4-(3-fluoro-4-sulfamoylbenzyl)-1H-pyrazol-1-yl)thiazole-4-carboxylate To a solution of ethyl 2-(3-(3-bromo-4-fluorophenyl)-5-(cyclopropylmethyl)-4-(3-fluoro-4-sulfamoylbenzyl)-1H-pyrazol-1-yl)thiazole-4-carboxylate (100.0 mg, 0.156 mmol) in $CH_3CN$ (1.0 mL) and toluene (1.0 mL) were added $Mo(CO)_6$ (61.7 mg, 0.234 mmol), $Pd(OAc)_2$ (3.5 mg, 0.0156 mmol), T-BINAP (10.5 mg, 0.0156 mmol), $Cs_2CO_3$ (76.2 mg, 0.234 mmol) and pyrrolidine (20.0 µL, 0.234 mmol). The reaction mixture was heated at 90° C. for 16 h. The reaction mixture was poured into water and extracted with ethyl acetate (3×15 mL). The organic layers were washed with brine (1×20 mL) and dried with anhydrous magnesium sulfate. The combined organic layer was concentrated in rotary evaporator and the crude (31.0 mg) was used for the next step.

Step 2: Synthesis of 2-(5-(cyclopropylmethyl)-3-(4-fluoro-3-(pyrrolidine-1-carbonyl)phenyl)-4-(3-fluoro-4-sulfamoylbenzyl)-1H-pyrazol-1-yl)thiazole-4-carboxylic acid Ethyl 2-(5-(cyclopropylmethyl)-3-(4-fluoro-3-(pyrrolidine-1-carbonyl)phenyl)-4-(3-fluoro-4-sulfamoylbenzyl)-1H-pyrazol-1-yl)thiazole-4-carboxylate from Step 1 (31.0 mg, 0.047 mmol) was dissolved in a mixture of dioxane and MeOH (1.0 mL/0.5 mL) and 1.0 mL of 1 N aqueous NaOH was added. The reaction mixture was stirred at room temperature 2 h. The reaction mixture was neutralized by addition of 1.0 M aqueous hydrochloric acid diluted with ethyl acetate (15 mL), washed with water (10 mL), and dried with anhydrous magnesium sulfate. The organic layer was concentrated using a rotary evaporator, and the residue was dissolved in DMSO and purified by HPLC (Phenomenex Gemini C18, $H_2O/CH_3CN$ gradient from 40% to 100% $CH_3CN$ for 4 min, 0.1% TFA) to give the title compound (10.0 mg, 24%). $^1$H-NMR (MeOD) δ: 8.22 (s, 1H), 7.75-7.71 (m, 2H), 7.54 (dd, J=2.2, 6.4 Hz, 1H), 7.24 (t, J=8.8 Hz, 1H), 7.07 (t, J=7.4 Hz, 2H), 4.20 (s, 2H), 3.59 (t, J=7.1 Hz, 2H), 3.30 (d, J=6.9 Hz, 2H), 3.19 (t, J=2H), 2.03-1.91 (m, 4H), 0.95-0.86 (m, 1H), 0.45-0.40 (m, 2H), 0.29-0.25 (in, 2H); MS (ES) 628.0 [M+H]$^+$, LCMS RT=0.968 min.

Example 164

This example describes the LDHA inhibitory activity, as measured by the assay set forth in Example 1, of exemplified compounds of formula (I) as embodiments. See Table 7. The compounds are assigned and activity level based on $IC_{50}$ as follows: +++<100 nM; ++100 nM-1000 nM; +>1000 nM-57000 nM; and −>57000 nM.

TABLE 7

| Cmpd ID | Structure | Compound name and physical data | Inhibitory activity $IC_{50}$ (µM) | Example Method |
| --- | --- | --- | --- | --- |
| 19 | 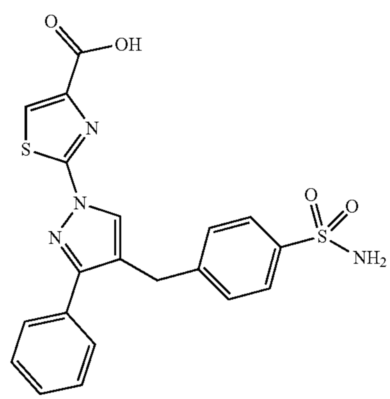 [SMILES: NS(=O)(=O)c1ccc(Cc2cn(-c3nc(C(=O)O)cs3)nc2-c2ccccc2)cc1] | 2-(3-phenyl-4-(4-sulfamoylbenzyl)-1H-pyrazol-1-yl)thiazole-4-carboxylic acid $^1$H NMR (400 MHz, DMSO-$d_6$) δ 13.18 (s, 1H), 8.21 (s, 2H), 7.80-7.71 (m, 2H), 7.72-7.63 (m, 2H), 7.52-7.37 (m, 5H), 7.28 (s, 2H), 4.15 (s, 2H); MS (M + H)$^+$ = 441 | +++ | 28 |
| 20 | 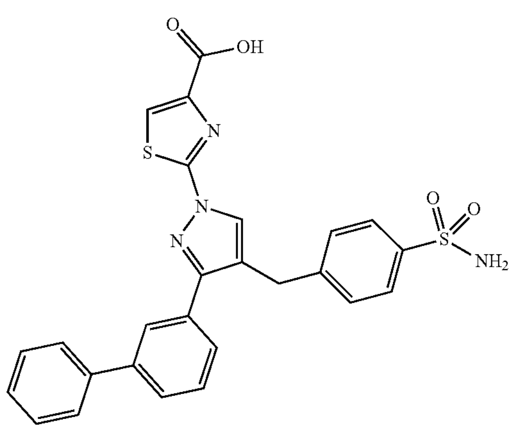 [SMILES: NS(=O)(=O)c1ccc(Cc2cn(-c3nc(C(=O)O)cs3)nc2-c2cccc(-c3ccccc3)c2)cc1] | 2-(3-([1,1'-biphenyl]-3-yl)-4-(4-sulfamoylbenzyl)-1H-pyrazol-1-yl)thiazole-4-carboxylic acid $^1$H NMR (400 MHz, DMSO-$d_6$) δ 13.20 (s, 1H), 8.29 (s, 1H), 8.24 (s, 1H), 7.81 (d, J = 1.8 Hz, 1H), 7.80-7.74 (m, 2H), 7.74-7.67 (m, 2H), 7.57 (d, J = 7.6 Hz, 3H), 7.50-7.42 (m, 4H), 7.37 (dd, J = 8.4, 6.3 Hz, 1H), 7.30 (s, 2H), 4.21 (s, 2H); MS (M + H)$^+$ = 517 | +++ | 29 |

TABLE 7-continued

| Cmpd ID | Structure | Compound name and physical data | Inhibitory activity IC$_{50}$ (μM) | Example Method |
|---|---|---|---|---|
| 21 | 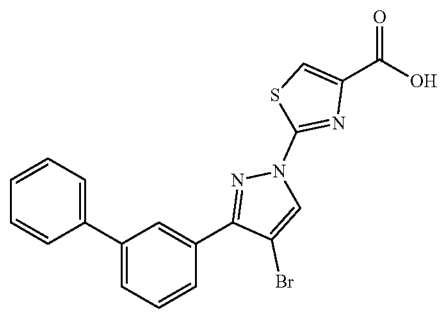 [SMILES: O=C(O)c1csc(-n2cc(Br)c(-c3cccc(-c4ccccc4)c3)n2)n1] | 2-(3-([1,1'-biphenyl]-3-yl)-4-bromo-1H-pyrazol-1-yl)thiazole-4-carboxylic acid, TFA<br>$^1$H NMR (400 MHz, DMSO-d$_6$) δ 13.25 (s, 1H), 8.93 (s, 1H), 8.28 (s, 1H), 8.12 (d, J = 1.8 Hz, 1H), 7.85 (dd, J = 7.7, 1.5 Hz, 1H), 7.79 (dd, J = 7.9, 1.5 Hz, 1H), 7.72 (dd, J = 7.5, 1.7 Hz, 2H), 7.63 (t, J = 7.8 Hz, 1H), 7.50 (t, J = 7.6 Hz, 2H), 7.40 (t, J = 7.4 Hz, 1H); MS (M + H)$^+$ = 427 | + | 30 |
| 22 | 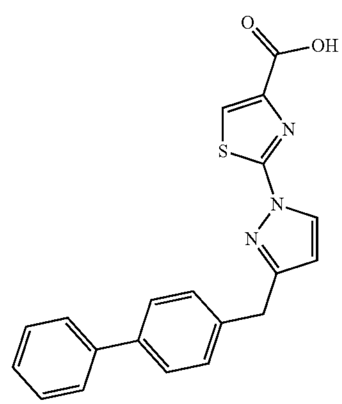 [SMILES: O=C(O)c1csc(-n2ccc(Cc3ccc(-c4ccccc4)cc3)n2)n1] | 2-(3-([1,1'-biphenyl]-3-yl)-1H-pyrazol-1-yl)thiazole-4-carboxylic acid, TFA<br>MS (M + H)$^+$ = 348 | + | 31 |
| 23 | 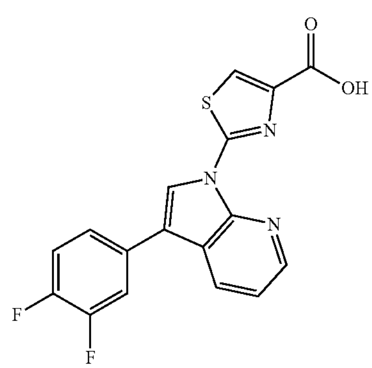 [SMILES: O=C(O)c1csc(-n2cc(-c3ccc(F)c(F)c3)c3cccnc32)n1] | 2-(3-(3,4-difluorophenyl)-1H-pyrrolo[2,3-b]pyridin-1-yl)thiazole-4-carboxylic acid, TFA<br>MS (M + H)$^+$ = 358 | − | 32 |
| 24 | 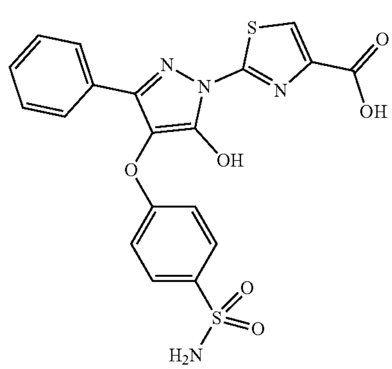 [SMILES: NS(=O)(=O)c1ccc(Oc2c(-c3ccccc3)nn(-c3nc(C(=O)O)cs3)c2O)cc1] | 2-(5-hydroxy-3-phenyl-4-(4-sulfamoylphenoxy)-1H-pyrazol-1-yl)thiazole-4-carboxylic acid, TFA<br>MS (M + H)$^+$ = 459 | ++ | 33 |

TABLE 7-continued

| Cmpd ID | Structure | Compound name and physical data | Inhibitory activity IC$_{50}$ (μM) | Example Method |
|---|---|---|---|---|
| 25 | 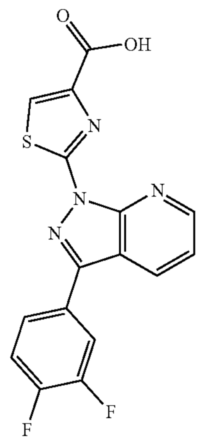 [SMILES: O=C(O)c1csc(-n2nc(-c3ccc(F)c(F)c3)c3cccnc32)n1] | 2-(3-(3,4-difluorophenyl)-1H-pyrazolo[3,4-b]pyridin-1-yl)thiazole-4-carboxylic acid<br>$^1$H NMR (400 MHz, DMSO-d$_6$) δ 13.16 (s, 1H), 8.88-8.78 (m, 2H), 8.33 (s, 1H), 8.15 (ddd, J = 11.7, 7.7, 2.2 Hz, 1H), 8.05-7.97 (m, 1H), 7.68 (dt, J = 10.8, 8.5 Hz, 1H), 7.60 (dd, J = 8.1, 4.6 Hz, 1H); MS (M + H)$^+$ = 359 | – | 34 |
| 26 | 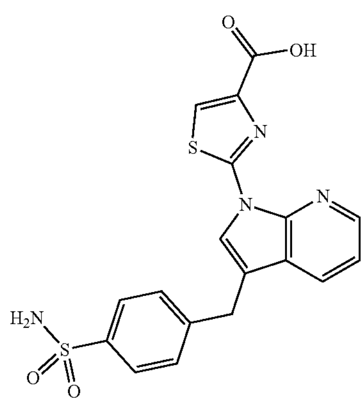 [SMILES: NS(=O)(=O)c1ccc(Cc2cn(-c3nc(C(=O)O)cs3)c3ncccc23)cc1] | 2-(3-(4-sulfamoylbenzyl)-1H-pyrrolo[2,3-b]pyridin-1-yl)thiazole-4-carboxylic acid<br>$^1$H NMR (400 MHz, DMSO-d$_6$) δ 13.04 (s, 1H), 8.46 (dd, J = 4.8, 1.5 Hz, 1H), 8.19 (s, 1H), 8.09 (dd, J = 7.8, 1.5 Hz, 1H), 8.07 (s, 1H), 7.80-7.72 (m, 2H), 7.58 (d, J = 8.2 Hz, 2H), 7.32 (dd, J = 7.9, 4.8 Hz, 1H), 7.27 (s, 2H), 4.23 (s, 2H); MS (M + H)$^+$ = 415 | ++ | 35 |
| 27 | 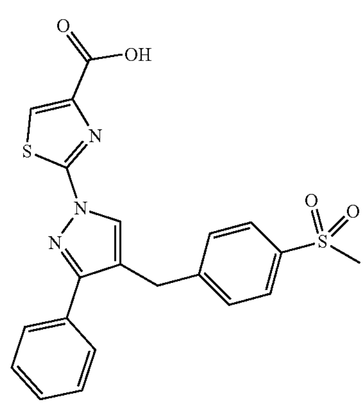 [SMILES: CS(=O)(=O)c1ccc(Cc2cn(-c3nc(C(=O)O)cs3)nc2-c2ccccc2)cc1] | 2-(4-(4-(methylsulfonyl)benzyl)-3-phenyl-1H-pyrazol-1-yl)thiazole-4-carboxylic acid<br>$^1$H NMR (400 MHz, DMSO-d$_6$) δ 13.17 (s, 1H), 8.34 (s, 1H), 8.23 (d, J = 1.7 Hz, 1H), 7.86-7.79 (m, 2H), 7.70-7.62 (m, 2H), 7.53-7.37 (m, 5H), 4.19 (s, 2H), 3.17 (s, 3H); MS (M + H)$^+$ = 440 | – | 36 |

TABLE 7-continued

| Cmpd ID | Structure | Compound name and physical data | Inhibitory activity IC$_{50}$ (μM) | Example Method |
|---|---|---|---|---|
| 28 | 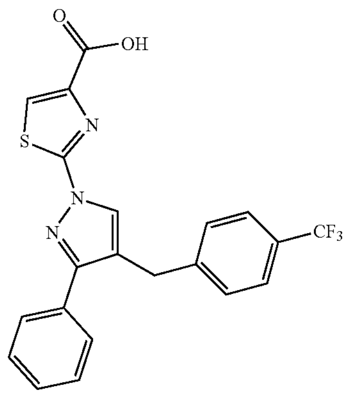 [SMILES: O=C(O)c1csc(-n2cc(Cc3ccc(C(F)(F)F)cc3)c(-c3ccccc3)n2)n1] | 2-(3-phenyl-4-(4-(trifluoromethyl)benzyl)-1H-pyrazol-1-yl)thiazole-4-carboxylic acid, TFA $^1$H NMR (400 MHz, DMSO-d$_6$) δ 13.17 (s, 1H), 8.33 (s, 1H), 8.23 (s, 1H), 7.69-7.59 (m, 4H), 7.50-7.36 (m, 5H), 4.18 (s, 2H); MS (M + H)$^+$ = 430 | − | 37 |
| 29 | 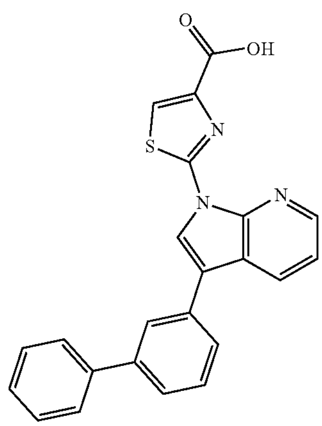 [SMILES: O=C(O)c1csc(-n2cc(-c3cccc(-c4ccccc4)c3)c3cccnc32)n1] | 2-(3-([1,1'-biphenyl]-3-yl)-1H-pyrrolo[2,3-b]pyridin-1-yl)thiazole-4-carboxylic acid, TFA $^1$H NMR (400 MHz, DMSO-d$_6$) δ 13.08 (s, 1H), 8.68 (s, 1H), 8.57 (d, J = 4.7 Hz, 1H), 8.55-8.50 (m, 1H), 8.28 (s, 1H), 8.07 (d, J = 2.0 Hz, 1H), 7.83 (m, 3H), 7.68 (d, J = 7.7 Hz, 1H), 7.61 (t, J = 7.6 Hz, 1H), 7.54-7.44 (m, 3H), 7.43-7.35 (m, 1H); MS (M + H)$^+$ = 398 | − | 38 |
| 30 | 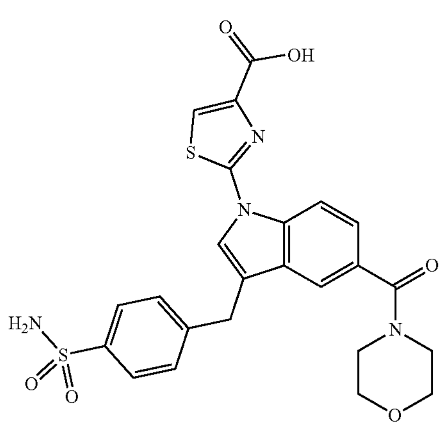 [SMILES: NS(=O)(=O)c1ccc(Cc2cn(-c3nc(C(=O)O)cs3)c3ccc(C(=O)N4CCOCC4)cc23)cc1] | 2-(5-(morpholine-4-carbonyl)-3-(4-sulfamoylbenzyl)-1H-indol-1-yl)thiazole-4-carboxylic acid $^1$H NMR (400 MHz, DMSO-d$_6$) δ 13.20 (s, 1H), 8.40 (d, J = 8.5 Hz, 1H), 8.20 (s, 1H), 7.95 (s, 1H), 7.73 (d, J = 8.0 Hz, 2H), 7.61 (s, 1H), 7.55 (d, J = 8.0 Hz, 2H), 7.43 (d, J = 8.6 Hz, 1H), 7.25 (s, 2H), 4.21 (s, 2H), 3.76-3.34 (m, 8H); MS (M + H)$^+$ = 527 | + | 39 |

TABLE 7-continued

| Cmpd ID | Structure | Compound name and physical data | Inhibitory activity IC$_{50}$ (μM) | Example Method |
|---|---|---|---|---|
| 31 | 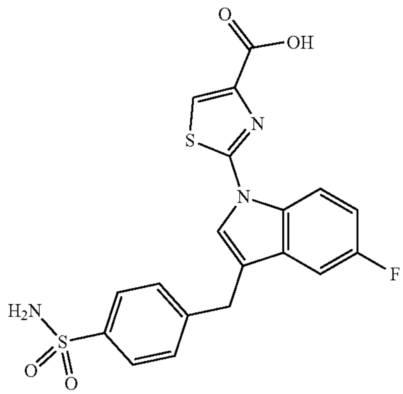 [SMILES: NS(=O)(=O)c1ccc(Cc2cn(-c3nc(C(=O)O)cs3)c3ccc(F)cc23)cc1] | 2-(5-fluoro-3-(4-sulfamoylbenzyl)-1H-indol-1-yl)thiazole-4-carboxylic acid <br> $^1$H NMR (400 MHz, DMSO-d$_6$) δ 13.17 (s, 1H), 8.40 (dd, J = 9.2, 4.5 Hz, 1H), 8.19 (d, J = 1.0 Hz, 1H), 7.93 (s, 1H), 7.73 (d, J = 8.0 Hz, 2H), 7.56 (d, J = 8.0 Hz, 2H), 7.37 (dd, J = 9.2, 2.6 Hz, 1H), 7.27-7.18 (m, 3H), 4.16 (s, 2H); MS (M + H)$^+$ = 432 | ++ | 40 |
| 32 | 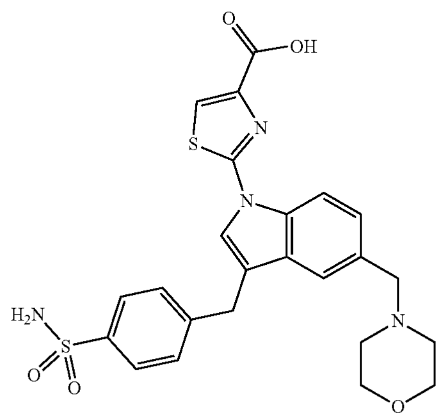 [SMILES: NS(=O)(=O)c1ccc(Cc2cn(-c3nc(C(=O)O)cs3)c3ccc(CN4CCOCC4)cc23)cc1] | 2-(5-(morpholinomethyl)-3-(4-sulfamoylbenzyl)-1H-indol-1-yl)thiazole-4-carboxylic acid <br> $^1$H NMR (400 MHz, DMSO-d$_6$) δ 13.11 (s, 1H), 8.25 (d, J = 8.5 Hz, 1H), 8.17 (s, 1H), 7.77 (s, 1H), 7.75-7.69 (m, 2H), 7.55-7.49 (m, 2H), 7.45 (d, J = 1.8 Hz, 1H), 7.32 (dd, J = 8.5, 1.6 Hz, 1H), 7.23 (s, 2H), 4.17 (s, 2H), 3.58-3.46 (m, 6H), 2.35-2.23 (m, 4H); MS (M + H)$^+$ = 513 | + | 41 |
| 33 | 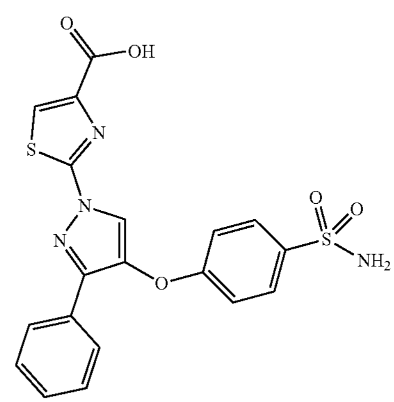 [SMILES: NS(=O)(=O)c1ccc(Oc2cn(-c3nc(C(=O)O)cs3)nc2-c2ccccc2)cc1] | 2-(3-phenyl-4-(4-sulfamoylphenoxy)-1H-pyrazol-1-yl)thiazole-4-carboxylic acid <br> $^1$H NMR (400 MHz, DMSO-d$_6$) δ 13.22 (s, 1H), 8.71 (s, 1H), 8.28 (s, 1H), 7.86-7.81 (m, 2H), 7.81-7.75 (m, 2H), 7.48-7.35 (m, 3H), 7.33-7.29 (m, 2H), 7.27 (s, 2H); MS (M + H)$^+$ = 443 | +++ | 42 |

TABLE 7-continued

| Cmpd ID | Structure | Compound name and physical data | Inhibitory activity IC$_{50}$ (μM) | Example Method |
|---|---|---|---|---|
| 34 | 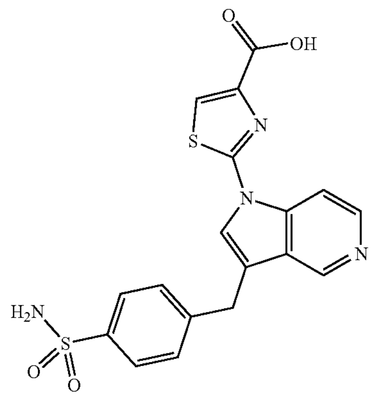 [SMILES: NS(=O)(=O)c1ccc(Cc2cn(-c3nc(C(=O)O)cs3)c3ccncc23)cc1] | 2-(3-(4-sulfamoylbenzyl)-1H-pyrrolo[3,2-c]pyridin-1-yl)thiazole-4-carboxylic acid, NH$_3$ $^1$H NMR (400 MHz, DMSO-d$_6$) δ 8.83 (d, J = 1.0 Hz, 1H), 8.46 (d, J = 5.8 Hz, 1H), 8.27 (s, 1H), 8.21 (dd, J = 5.8, 1.0 Hz, 1H), 7.95 (s, 1H), 7.74 (d, J = 8.3 Hz, 2H), 7.57 (d, J = 8.4 Hz, 2H), 7.23 (s, 2H), 4.25 (s, 2H) (acid OH not shown); MS (M + H)$^+$ = 415 | ++ | 43 |
| 35 | 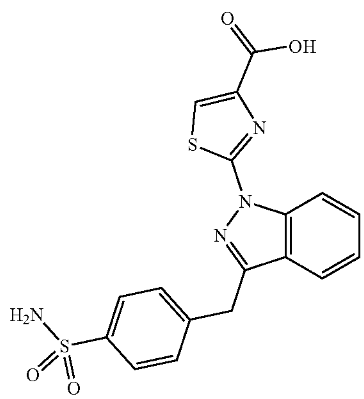 [SMILES: NS(=O)(=O)c1ccc(Cc2nn(-c3nc(C(=O)O)cs3)c3ccccc23)cc1] | 2-(3-(4-sulfamoylbenzyl)-1H-indazol-1-yl)thiazole-4-carboxylic acid $^1$H NMR (400 MHz, DMSO-d$_6$) δ 13.15 (s, 1H), 8.51 (d, J = 8.4 Hz, 1H), 8.18 (s, 1H), 7.80 (dd, J = 8.0, 1.0 Hz, 1H), 7.77-7.72 (m, 2H), 7.67 (ddd, J = 8.3, 7.0, 1.1 Hz, 1H), 7.59-7.51 (m, 2H), 7.35 (ddd, J = 8.1, 7.0, 0.9 Hz, 1H), 7.27 (s, 2H), 4.49 (s, 2H); MS (M + H)$^+$ = 415 | + | 44 |
| 36 | 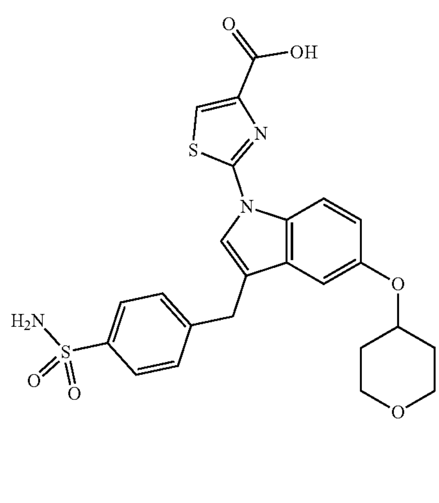 [SMILES: NS(=O)(=O)c1ccc(Cc2cn(-c3nc(C(=O)O)cs3)c3ccc(OC4CCOCC4)cc23)cc1] | 2-(3-(4-sulfamoylbenzyl)-5-((tetrahydro-2H-pyran-4-yl)oxy)-1H-indol-1-yl)thiazole-4-carboxylic acid, NH$_3$ $^1$H NMR (400 MHz, DMSO-d$_6$) δ 8.22 (d, J = 8.9 Hz, 1H), 8.04 (s, 1H), 7.74 (d, J = 3.6 Hz, 2H), 7.71 (d, J = 1.9 Hz, 1H), 7.58-7.50 (m, 2H), 7.23 (s, 2H), 7.06 (d, J = 2.4 Hz, 1H), 7.01 (dd, J = 9.0, 2.4 Hz, 1H), 4.57-4.41 (m, 1H), 4.14 (s, 2H), 3.83 (dt, J = 11.7, 4.4 Hz, 2H), 3.44 (ddd, J = 11.8, 9.5, 2.8 Hz, 2H), 1.90 (dd, J = 13.1, 3.5 Hz, 2H), 1.54 (ddd, J = 13.0, 8.8, 4.0 Hz, 2H) (acid OH not shown); MS (M + H)$^+$ = 514 | ++ | |

TABLE 7-continued

| Cmpd ID | Structure | Compound name and physical data | Inhibitory activity IC$_{50}$ (μM) | Example Method |
|---|---|---|---|---|
| 37 | 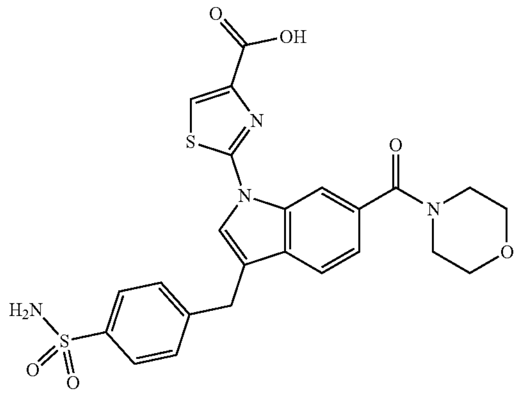 [SMILES: NS(=O)(=O)c1ccc(Cc2cn(-c3nc(C(=O)O)cs3)c3cc(C(=O)N4CCOCC4)ccc23)cc1] | 2-(6-(morpholine-4-carbonyl)-3-(4-sulfamoylbenzyl)-1H-indol-1-yl)thiazole-4-carboxylic acid, NH$_3$ $^1$H NMR (400 MHz, DMSO-d$_6$) δ 8.45 (dd, J = 1.4, 0.7 Hz, 1H), 7.98 (s, 1H), 7.93 (s, 1H), 7.75-7.67 (m, 2H), 7.58 (dd, J = 8.1, 0.7 Hz, 1H), 7.56-7.51 (m, 2H), 7.28-7.16 (m, 3H), 4.19 (s, 2H), 3.54 (d, J = 41.1 Hz, 8H) (acid OH not shown); MS (M + H)$^+$ = 527 | + | 46 |
| 38 | 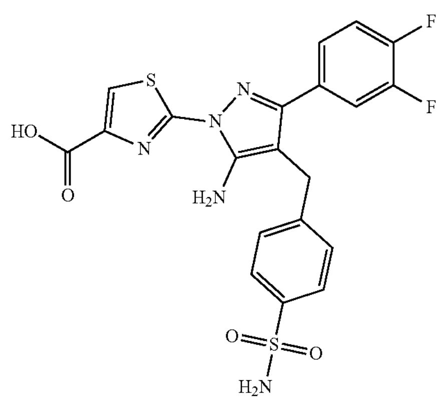 [SMILES: Nc1c(Cc2ccc(S(N)(=O)=O)cc2)c(-c2ccc(F)c(F)c2)nn1-c1nc(C(=O)O)cs1] | 2-(5-amino-3-(3,4-difluorophenyl)-4-(4-sulfamoylbenzyl)-1H-pyrazol-1-yl)thiazole-4-carboxylic acid MS (M + H)$^+$ = 492 | +++ | 12, 18 |
| 39 | 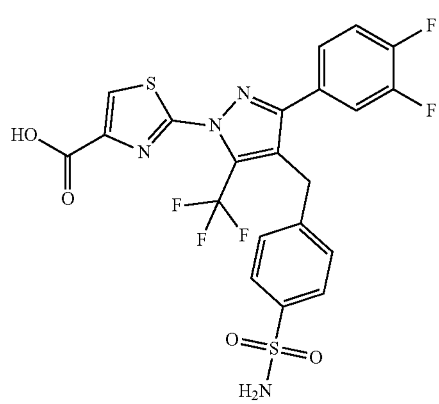 [SMILES: NS(=O)(=O)c1ccc(Cc2c(-c3ccc(F)c(F)c3)nn(-c3nc(C(=O)O)cs3)c2C(F)(F)F)cc1] | 2-(3-(3,4-difluorophenyl)-4-(4-sulfamoylbenzyl)-5-(trifluoromethyl)-1H-pyrazol-1-yl)thiazole-4-carboxylic acid 1H NMR (400 MHz, DMSO-d6) δ 13.29 (s, 1H), 8.47 (d, J = 1.2 Hz, 1H), 7.87-7.66 (m, 2H), 7.69-7.46 (m, 2H), 7.48-7.19 (m, 5H), 4.24 (s, 2H); MS (M + H)$^+$ = 545 | +++ | 14, 18 |

TABLE 7-continued

| Cmpd ID | Structure | Compound name and physical data | Inhibitory activity IC$_{50}$ (μM) | Example Method |
|---|---|---|---|---|
| 40 | 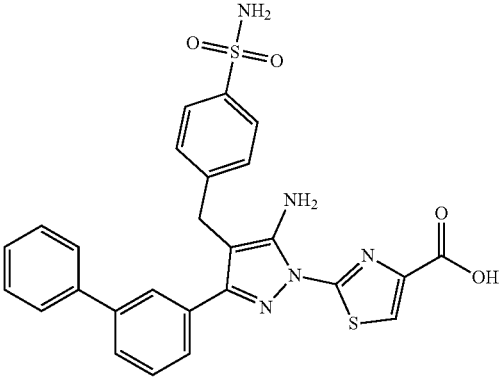 [SMILES: Nc1c(Cc2ccc(S(N)(=O)=O)cc2)c(-c2cccc(-c3ccccc3)c2)nn1-c1nc(C(=O)O)cs1] | 2-(3-([1,1'-biphenyl]-3-yl)-5-amino-4-(4-sulfamoylbenzyl)-1H-pyrazol-1-yl)thiazole-4-carboxylic acid<br>1H NMR (400 MHz, DMSO-d6) δ 13.06 (s, 1H), 8.21 (d, J = 1.1 Hz, 1H), 7.79-7.74 (m, 2H), 7.70-7.62 (m, 2H), 7.59-7.47 (m, 2H), 7.46-7.32 (m, 7H), 7.29 (s, 2H), 6.94 (s, 2H), 4.05 (s, 2H);<br>(M + H)$^+$ = 532 | +++ | 12, 18 |
| 41 | 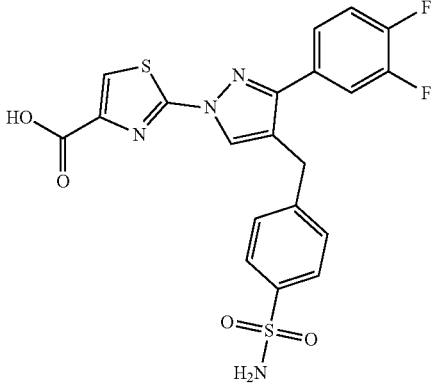 [SMILES: NS(=O)(=O)c1ccc(Cc2cn(-c3nc(C(=O)O)cs3)nc2-c2ccc(F)c(F)c2)cc1] | 2-(3-(3,4-difluorophenyl)-4-(4-sulfamoylbenzyl)-1H-pyrazol-1-yl)thiazole-4-carboxylic acid<br>1H NMR (400 MHz, DMSO-d6) δ 8.24 (s, 1H), 7.86-7.62 (m, 2H), 7.55 (q, J = 5.7, 4.9 Hz, 2H), 7.47-7.38 (m, 2H), 7.31 (s, 1H), 4.18 (s, 2H);<br>(M + H)$^+$ = 477 | +++ | 28 |
| 42 | 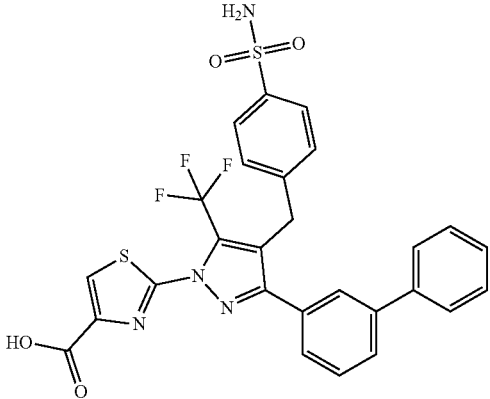 [SMILES: NS(=O)(=O)c1ccc(Cc2c(-c3cccc(-c4ccccc4)c3)nn(-c3nc(C(=O)O)cs3)c2C(F)(F)F)cc1] | 2-(3-([1,1'-biphenyl]-3-yl)-4-(4-sulfamoylbenzyl)-5-(trifluoromethyl)-1H-pyrazol-1-yl)thiazole-4-carboxylic acid<br>1H NMR (400 MHz, DMSO-d6) δ 13.27 (s, 1H), 8.45 (d, J = 1.2 Hz, 1H), 7.77 (tt, J = 6.6, 1.5 Hz, 3H), 7.67 (q, J = 1.6 Hz, 1H), 7.62-7.28 (m, 13H), 4.27 (s, 2H);<br>(M + H)$^+$ = 589 | +++ | 14, 18 |

TABLE 7-continued

| Cmpd ID | Structure | Compound name and physical data | Inhibitory activity IC$_{50}$ (μM) | Example Method |
|---|---|---|---|---|
| 43 | 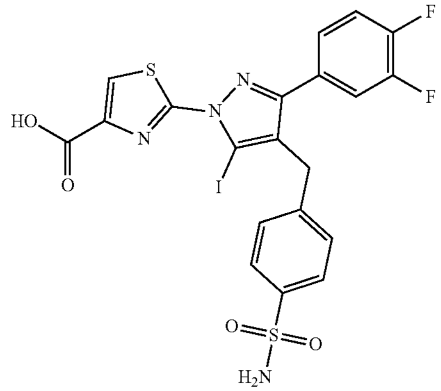 [SMILES: NS(=O)(=O)c1ccc(Cc2c(-c3ccc(F)c(F)c3)nn(-c3nc(C(=O)O)cs3)c2I)cc1] | 2-(3-(3,4-difluorophenyl)-5-iodo-4-(4-sulfamoylbenzyl)-1H-pyrazol-1-yl)thiazole-4-carboxylic acid<br>1H NMR (400 MHz, DMSO-d6) δ 13.23 (s, 1H), 8.41 (d, J = 1.1 Hz, 1H), 7.83-7.65 (m, 2H), 7.63-7.47 (m, 2H), 7.42-7.35 (m, 1H), 7.32-7.25 (m, 4H), 4.15 (s, 2H); (M + H)$^+$ = 603 | +++ | 13, 18 |
| 44 | 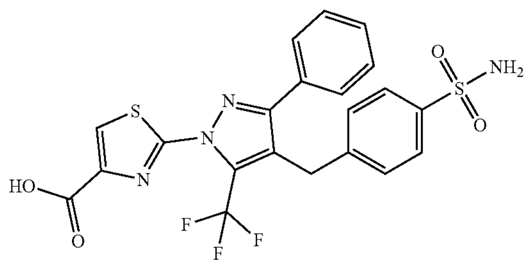 [SMILES: NS(=O)(=O)c1ccc(Cc2c(-c3ccccc3)nn(-c3nc(C(=O)O)cs3)c2C(F)(F)F)cc1] | 2-(3-phenyl-4-(4-sulfamoylbenzyl)-5-(trifluoromethyl)-1H-pyrazol-1-yl)thiazole-4-carboxylic acid<br>1H NMR (400 MHz, DMSO-d6) δ 13.27 (s, 1H), 8.46 (d, J = 0.9 Hz, 1H), 7.79-7.66 (m, 2H), 7.58-7.41 (m, 5H), 7.30 (s, 3H), 7.33-7.26 (m, 1H), 4.23 (s, 2H); (M + H)$^+$ = 509 | +++ | 14, 18 |
| 45 | 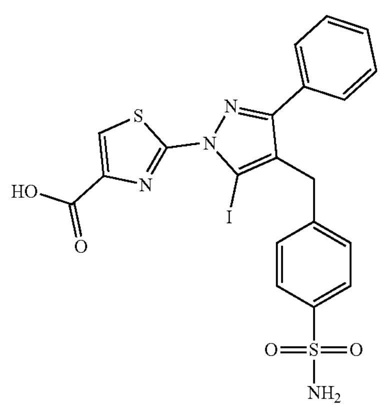 [SMILES: NS(=O)(=O)c1ccc(Cc2c(-c3ccccc3)nn(-c3nc(C(=O)O)cs3)c2I)cc1] | 2-(5-iodo-3-phenyl-4-(4-sulfamoylbenzyl)-1H-pyrazol-1-yl)thiazole-4-carboxylic acid<br>1H NMR (400 MHz, DMSO-d6) δ 13.19 (s, 1H), 8.37 (d, J = 1.2 Hz, 1H), 7.75-7.67 (m, 2H), 7.57-7.49 (m, 2H), 7.51-7.36 (m, 3H), 7.31-7.24 (m, 4H), 4.12 (s, 2H); (M + H)$^+$ = 567 | +++ | 13, 18 |
| 46 | 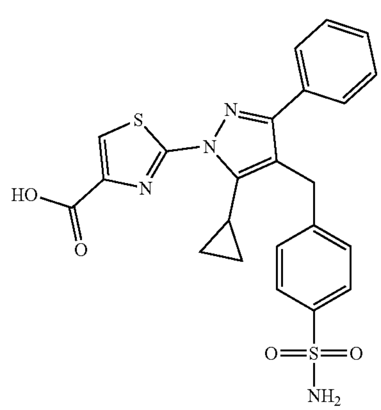 [SMILES: NS(=O)(=O)c1ccc(Cc2c(-c3ccccc3)nn(-c3nc(C(=O)O)cs3)c2C2CC2)cc1] | 2-(5-cyclopropyl-3-phenyl-4-(4-sulfamoylbenzyl)-1H-pyrazol-1-yl)thiazole-4-carboxylic acid<br>1H NMR (400 MHz, DMSO-d6) δ 13.11 (s, 1H), 8.32 (s, 1H), 7.74-7.70 (m, 2H), 7.53-7.49 (m, 2H), 7.43-7.37 (m, 3H), 7.31-7.26 (m, 4H), 4.14 (s, 2H), 2.25 (tt, J = 8.5, 5.6 Hz, 1H), 1.02-0.92 (m, 2H), 0.71-0.62 (m, 2H); (M + H)$^+$ = 481 | +++ | 112 |

TABLE 7-continued

| Cmpd ID | Structure | Compound name and physical data | Inhibitory activity IC$_{50}$ (μM) | Example Method |
|---|---|---|---|---|
| 47 | 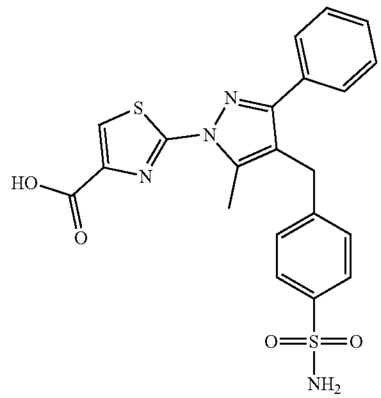 [SMILES: Cc1c(Cc2ccc(S(N)(=O)=O)cc2)c(-c2ccccc2)nn1-c1nc(C(=O)O)cs1] | 2-(5-methyl-3-phenyl-4-(4-sulfamoylbenzyl)-1H-pyrazol-1-yl)thiazole-4-carboxylic acid<br>1H NMR (400 MHz, DMSO-d6) δ 13.13 (s, 1H), 8.29-8.19 (m, 1H), 7.78-7.65 (m, 2H), 7.53 (dq, J = 6.8, 1.3 Hz, 2H), 7.49-7.33 (m, 3H), 7.32-7.23 (m, 4H), 4.08 (s, 2H), 2.67 (d, J = 1.1 Hz, 3H);<br>(M + H)$^+$ = 455 | +++ | 49 |
| 48 | 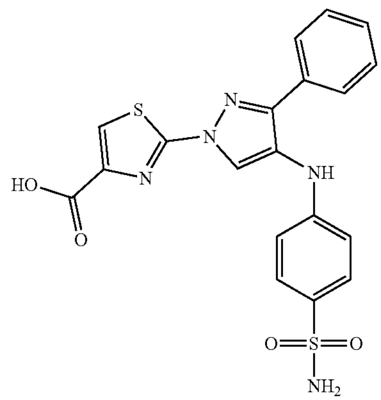 [SMILES: NS(=O)(=O)c1ccc(Nc2cn(-c3nc(C(=O)O)cs3)nc2-c2ccccc2)cc1] | 2-(3-phenyl-4-((4-sulfamoylphenyl)amino)-1H-pyrazol-1-yl)thiazole-4-carboxylic acid<br>1H NMR (400 MHz, DMSO-d6) δ 13.20 (s, 1H), 8.57 (s, 1H), 8.25 (d, J = 2.4 Hz, 2H), 7.82 (dt, J = 8.1, 1.3 Hz, 3H), 7.55 (dd, J = 8.7, 1.2 Hz, 3H), 7.48-7.33 (m, 4H), 6.98 (s, 2H), 6.85-6.76 (m, 2H);<br>(M + H)$^+$ = 442 | +++ | 27 |
| 49 | 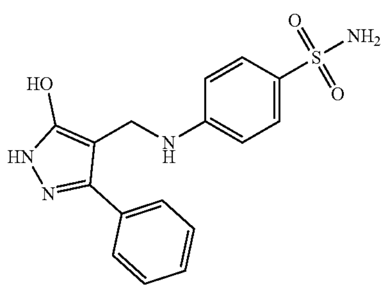 [SMILES: NS(=O)(=O)c1ccc(NCc2c(-c3ccccc3)n[nH]c2O)cc1] | 4-(((5-hydroxy-3-phenyl-1H-pyrazol-4-yl)methyl)amino)benzenesulfonamide<br>(M + H)$^+$ = 345 | – | 149 |
| 50 | 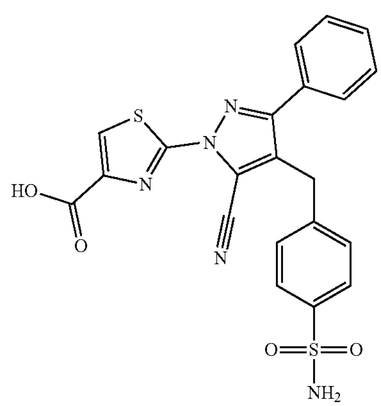 [SMILES: N#Cc1c(Cc2ccc(S(N)(=O)=O)cc2)c(-c2ccccc2)nn1-c1nc(C(=O)O)cs1] | 2-(5-carbamoyl-3-phenyl-4-(4-sulfamoylbenzyl)-1H-pyrazol-1-yl)thiazole-4-carboxylic acid<br>(M + H)$^+$ = 466 | +++ | 17, 18 |

TABLE 7-continued

| Cmpd ID | Structure | Compound name and physical data | Inhibitory activity IC$_{50}$ (μM) | Example Method |
|---|---|---|---|---|
| 51 | 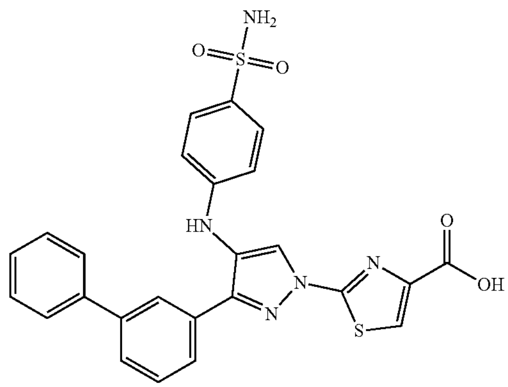 [SMILES: NS(=O)(=O)c1ccc(Nc2cn(-c3nc(C(=O)O)cs3)nc2-c2cccc(-c3ccccc3)c2)cc1] | 2-(3-([1,1'-biphenyl]-3-yl)-4-((4-sulfamoylphenyl)amino)-1H-pyrazol-1-yl)thiazole-4-carboxylic acid. (M + H)$^+$ = 518 | +++ | 27 |
| 52 | 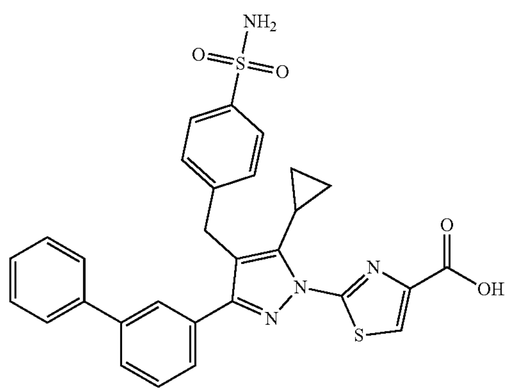 [SMILES: NS(=O)(=O)c1ccc(Cc2c(-c3cccc(-c4ccccc4)c3)nn(-c3nc(C(=O)O)cs3)c2C2CC2)cc1] | 2-(3-([1,1'-biphenyl]-3-yl)-5-cyclopropyl-4-(4-sulfamoylbenzyl)-1H-pyrazol-1-yl)thiazole-4-carboxylic acid<br>1H NMR (400 MHz, DMSO-d6) δ 13.12 (s, 1H), 7.80-7.73 (m, 2H), 7.73-7.59 (m, 2H), 7.60-7.47 (m, 2H), 7.42 (d, J = 4.3 Hz, 4H), 7.43-7.28 (m, 5H), 4.19 (s, 2H), 2.30 (tt, J = 8.6, 5.6 Hz, 1H), 1.04-0.95 (m, 2H), 0.73-0.64 (m, 2H); (M + H)$^+$ = 557 | +++ | 112 |
| 53 | 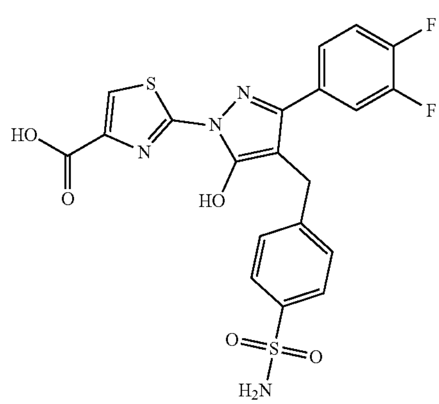 [SMILES: NS(=O)(=O)c1ccc(Cc2c(-c3ccc(F)c(F)c3)nn(-c3nc(C(=O)O)cs3)c2O)cc1] | 2-(3-(3,4-difluorophenyl)-5-hydroxy-4-(4-sulfamoylbenzyl)-1H-pyrazol-1-yl)thiazole-4-carboxylic acid (M + H)$^+$ = 493 | ++ | 147 |

TABLE 7-continued

| Cmpd ID | Structure | Compound name and physical data | Inhibitory activity IC$_{50}$ (µM) | Example Method |
|---|---|---|---|---|
| 54 | 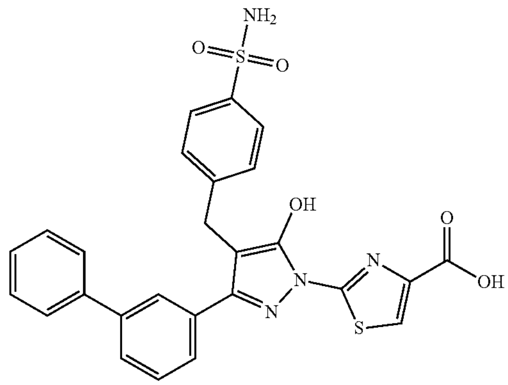 [SMILES: NS(=O)(=O)c1ccc(Cc2c(-c3cccc(-c4ccccc4)c3)nn(-c3nc(C(=O)O)cs3)c2O)cc1] | 2-(3-([1,1'-biphenyl]-3-yl)-5-hydroxy-4-(4-sulfamoylbenzyl)-1H-pyrazol-1-yl)thiazole-4-carboxylic acid (M + H)$^+$ = 533 | ++ | 147 |
| 55 | 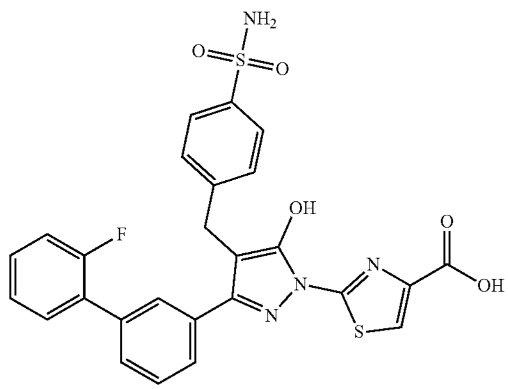 [SMILES: NS(=O)(=O)c1ccc(Cc2c(-c3cccc(-c4ccccc4F)c3)nn(-c3nc(C(=O)O)cs3)c2O)cc1] | 2-(3-(2'-fluoro-[1,1'-biphenyl]-3-yl)-5-hydroxy-4-(4-sulfamoylbenzyl)-1H-pyrazol-1-yl)thiazole-4-carboxylic acid (M + H)$^+$ = 551 | ++ | 147 |
| 56 | 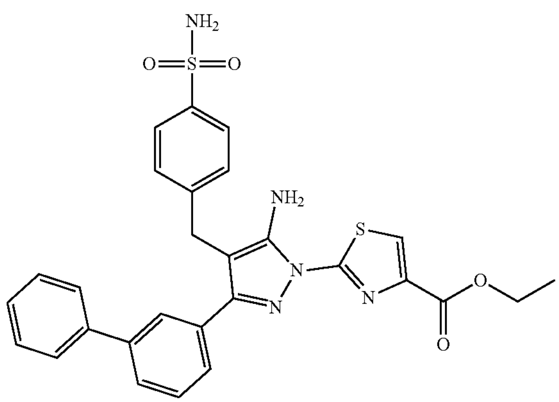 [SMILES: CCOC(=O)c1csc(-n2nc(-c3cccc(-c4ccccc4)c3)c(Cc3ccc(S(N)(=O)=O)cc3)c2N)n1] | ethyl 2-(3-([1,1'-biphenyl]-3-yl)-5-amino-4-(4-sulfamoylbenzyl)-1H-pyrazol-1-yl)thiazole-4-carboxylate (M + H)$^+$ = 560 | + | 12, 18 |
| 57 | 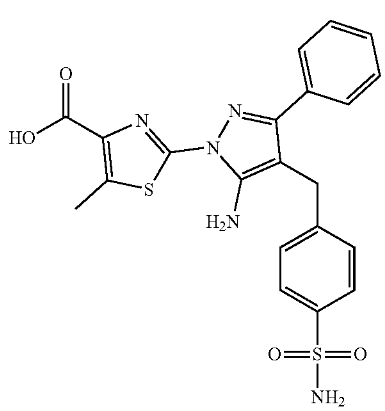 [SMILES: Cc1sc(-n2nc(-c3ccccc3)c(Cc3ccc(S(N)(=O)=O)cc3)c2N)nc1C(=O)O] | 2-(5-amino-3-phenyl-4-(4-sulfamoylbenzyl)-1H-pyrazol-1-yl)-5-methylthiazole-4-carboxylic acid. 1H NMR (400 MHz, DMSO-d6) δ 12.94 (s, 1H), 7.81-7.65 (m, 2H), 7.48 (dq, J = 6.8, 1.3 Hz, 2H), 7.49-7.26 (m, 5H), 7.24 (s, 2H), 6.82 (s, 2H), 3.97 (s, 2H), 2.68 (d, J = 1.2 Hz, 3H), 2.52 (d, J = 1.2 Hz, 1H); (M + H)$^+$ = 470 | ++ | 148 |

TABLE 7-continued

| Cmpd ID | Structure | Compound name and physical data | Inhibitory activity IC$_{50}$ (μM) | Example Method |
|---|---|---|---|---|
| 58 | 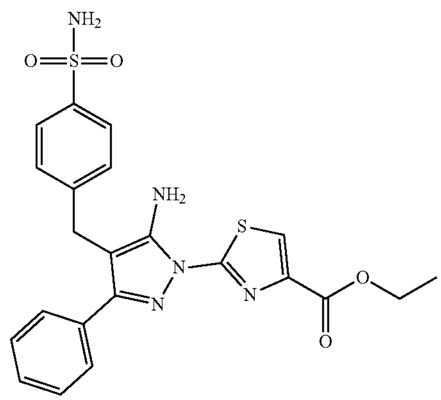 | ethyl 2-(5-amino-3-phenyl-4-(4-sulfamoylbenzyl)-1H-pyrazol-1-yl)thiazole-4-carboxylate (M + H)$^+$ = 484 | + | 12 |
| 59 | 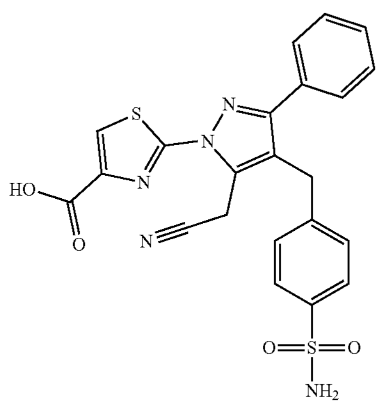 [SMILES: N#CCc1c(Cc2ccc(S(N)(=O)=O)cc2)c(-c2ccccc2)nn1-c1nc(C(=O)O)cs1] | 2-(5-(cyanomethyl)-3-phenyl-4-(4-sulfamoylbenzyl)-1H-pyrazol-1-yl)thiazole-4-carboxylic acid 1H NMR (400 MHz, DMSO-d6) δ 8.28 (s, 1H), 7.70-7.63 (m, 2H), 7.59-7.49 (m, 2H), 7.46-7.34 (m, 3H), 7.30-7.22 (m, 4H), 4.67 (s, 2H), 4.22 (s, 2H); (M + H)$^+$ = 480 | ++ | 19, 20 |
| 60 | 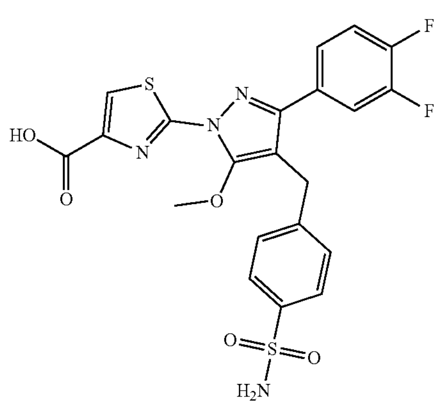 [SMILES: COc1c(Cc2ccc(S(N)(=O)=O)cc2)c(-c2ccc(F)c(F)c2)nn1-c1nc(C(=O)O)cs1] | 2-(3-(3,4-difluorophenyl)-5-methoxy-4-(4-sulfamoylbenzyl)-1H-pyrazol-1-yl)thiazole-4-carboxylic acid (M + H)$^+$ = 507 | ++ | 73 |

TABLE 7-continued

| Cmpd ID | Structure | Compound name and physical data | Inhibitory activity IC$_{50}$ (μM) | Example Method |
|---|---|---|---|---|
| 61 | 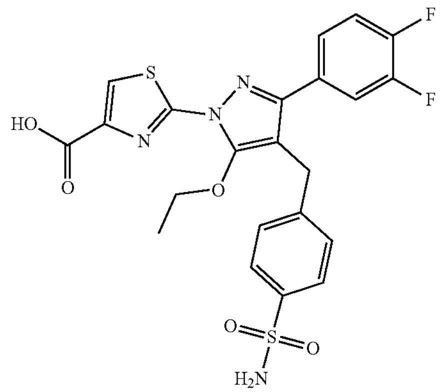 [SMILES: CCOc1c(Cc2ccc(S(N)(=O)=O)cc2)c(-c2ccc(F)c(F)c2)nn1-c1nc(C(=O)O)cs1] | 2-(3-(3,4-difluorophenyl)-5-ethoxy-4-(4-sulfamoylbenzyl)-1H-pyrazol-1-yl)thiazole-4-carboxylic acid | ++ | 73 |
| 62 | 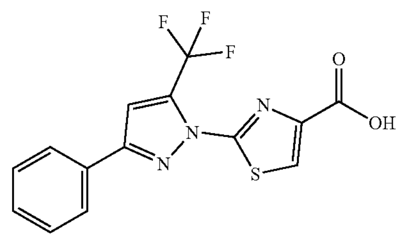 [SMILES: O=C(O)c1csc(-n2nc(-c3ccccc3)cc2C(F)(F)F)n1] | 2-(3-phenyl-5-(trifluoromethyl)-1H-pyrazol-1-yl)thiazole-4-carboxylic acid (M + H)$^+$ = 340 | + | 150 |
| 63 | 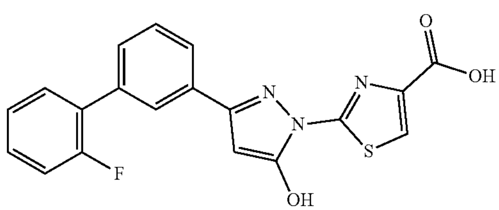 [SMILES: O=C(O)c1csc(-n2nc(-c3cccc(-c4ccccc4F)c3)cc2O)n1] | 2-(3-(2'-fluoro-[1,1'-biphenyl]-3-yl)-5-hydroxy-1H-pyrazol-1-yl)thiazole-4-carboxylic acid (M + H)$^+$ = 382 | − | 147 |
| 64 | 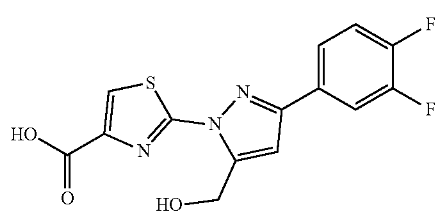 [SMILES: O=C(O)c1csc(-n2nc(-c3ccc(F)c(F)c3)cc2CO)n1] | 2-(3-(3,4-difluorophenyl)-5-(hydroxymethyl)-1H-pyrazol-1-yl)thiazole-4-carboxylic acid. (M + H)$^+$ = 338 | − | 151 |
| 65 | 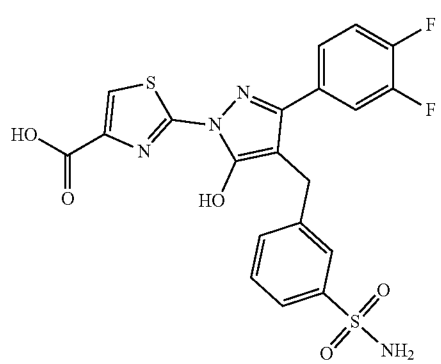 [SMILES: NS(=O)(=O)c1cccc(Cc2c(-c3ccc(F)c(F)c3)nn(-c3nc(C(=O)O)cs3)c2O)c1] | 2-(3-(3,4-difluorophenyl)-5-hydroxy-4-(4-sulfamoylbenzyl)-1H-pyrazol-1-yl)thiazole-4-carboxylic acid | − | 147 |

TABLE 7-continued

| Cmpd ID | Structure | Compound name and physical data | Inhibitory activity IC$_{50}$ (μM) | Example Method |
|---|---|---|---|---|
| 66 | 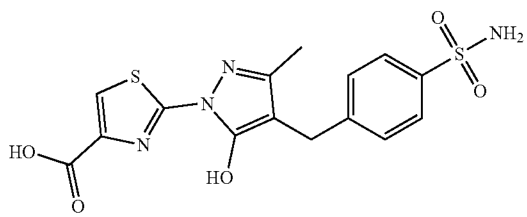 [SMILES: Cc1nn(-c2nc(C(=O)O)cs2)c(O)c1Cc1ccc(S(N)(=O)=O)cc1] | 2-(5-hydroxy-3-methyl-4-(4-sulfamoylbenzyl)-1H-pyrazol-1-yl)thiazole-4-carboxylic acid | − | 147 |
| 67 | 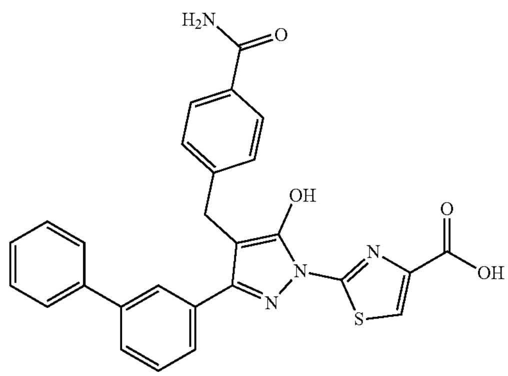 [SMILES: NC(=O)c1ccc(Cc2c(-c3cccc(-c4ccccc4)c3)nn(-c3nc(C(=O)O)cs3)c2O)cc1] | 2-(3-([1,1'-biphenyl]-3-yl)-4-(4-carbamoylbenzyl)-5-hydroxy-1H-pyrazol-1-yl)thiazole-4-carboxylic acid | − | 147 |
| 68 | 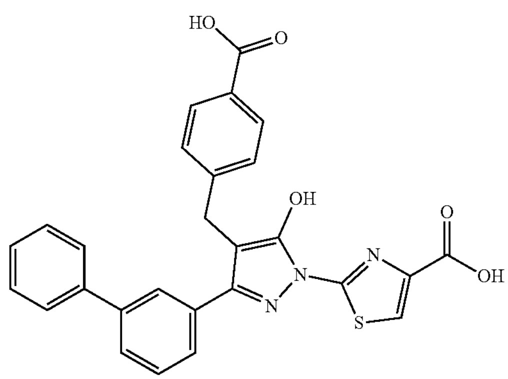 [SMILES: O=C(O)c1ccc(Cc2c(-c3cccc(-c4ccccc4)c3)nn(-c3nc(C(=O)O)cs3)c2O)cc1] | 2-(3-([1,1'-biphenyl]-3-yl)-4-(4-carboxybenzyl)-5-hydroxy-1H-pyrazol-1-yl)thiazole-4-carboxylic acid | − | 147 |
| 69 | 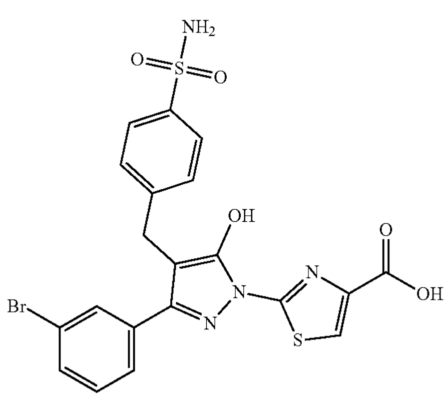 [SMILES: NS(=O)(=O)c1ccc(Cc2c(-c3cccc(Br)c3)nn(-c3nc(C(=O)O)cs3)c2O)cc1] | 2-(3-(3-bromophenyl)-5-hydroxy-4-(4-sulfamoylbenzyl)-1H-pyrazol-1-yl)thiazole-4-carboxylic acid | + | 147 |

TABLE 7-continued

| Cmpd ID | Structure | Compound name and physical data | Inhibitory activity IC$_{50}$ (μM) | Example Method |
|---|---|---|---|---|
| 70 | 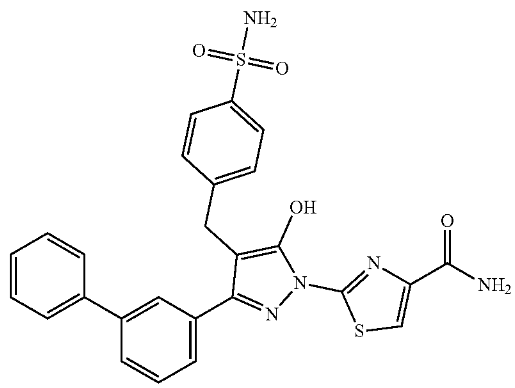 [SMILES: NC(=O)c1csc(-n2nc(-c3cccc(-c4ccccc4)c3)c(Cc3ccc(S(N)(=O)=O)cc3)c2O)n1] | 2-(3-([1,1'-biphenyl]-3-yl)-5-hydroxy-4-(4-sulfamoylbenzyl)-1H-pyrazol-1-yl)thiazole-4-carboxamide | − | 152 |
| 71 | 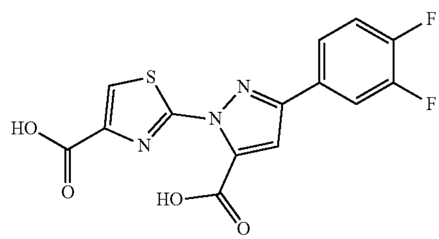 [SMILES: O=C(O)c1csc(-n2nc(-c3ccc(F)c(F)c3)cc2C(=O)O)n1] | 2-(5-carboxy-3-(3,4-difluorophenyl)-1H-pyrazol-1-yl)thiazole-4-carboxylic acid | − | 151 |
| 72 | 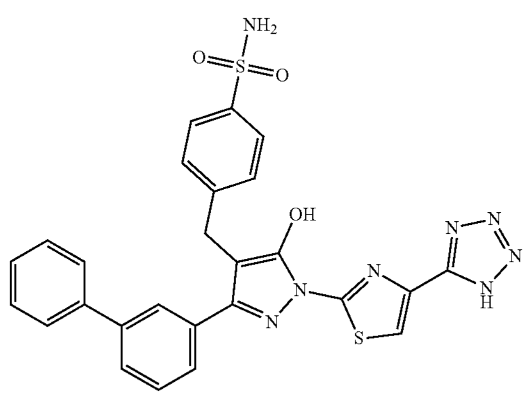 [SMILES: NS(=O)(=O)c1ccc(Cc2c(-c3cccc(-c4ccccc4)c3)nn(-c3nc(-c4nnn[nH]4)cs3)c2O)cc1] | 4-((1-(4-(1H-tetrazol-5-yl)thiazol-2-yl)-3-([1,1'-biphenyl]-3-yl)-5-hydroxy-1H-pyrazol-4-yl)methyl)benzenesulfonamide | + | 153 |
| 73 | 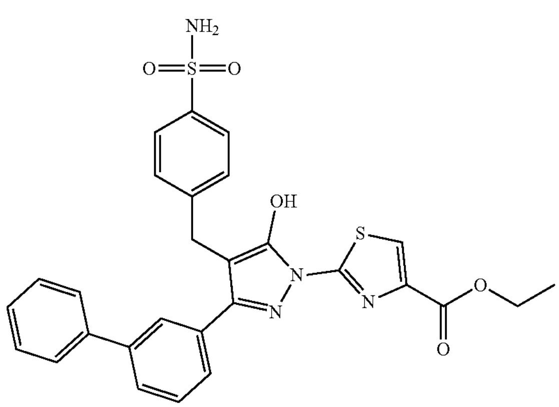 [SMILES: CCOC(=O)c1csc(-n2nc(-c3cccc(-c4ccccc4)c3)c(Cc3ccc(S(N)(=O)=O)cc3)c2O)n1] | ethyl 2-(3-([1,1'-biphenyl]-3-yl)-5-hydroxy-4-(4-sulfamoylbenzyl)-1H-pyrazol-1-yl)thiazole-4-carboxylate | + | 147 |

TABLE 7-continued

| Cmpd ID | Structure | Compound name and physical data | Inhibitory activity IC$_{50}$ (μM) | Example Method |
|---|---|---|---|---|
| 74 | 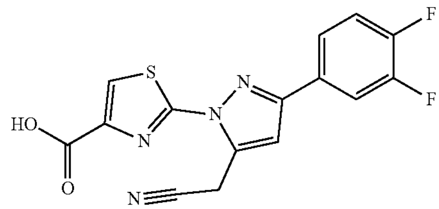 [SMILES: N#CCc1cc(-c2ccc(F)c(F)c2)nn1-c1nc(C(=O)O)cs1] | 2-(5-(cyanomethyl)-3-(3,4-difluorophenyl)-1H-pyrazol-1-yl)thiazole-4-carboxylic acid | + | 19, 20 |
| 75 | 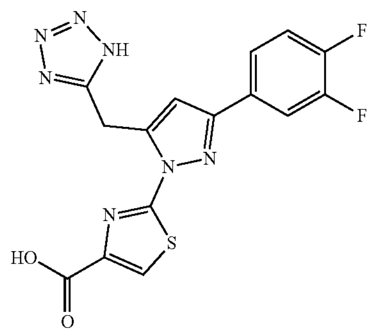 [SMILES: O=C(O)c1csc(-n2nc(-c3ccc(F)c(F)c3)cc2Cc2nnn[nH]2)n1] | 2-(5-((1H-tetrazol-5-yl)methyl)-3-(3,4-difluorophenyl)-1H-pyrazol-1-yl)thiazole-4-carboxylic acid | + | 21, 20 |
| 76 | 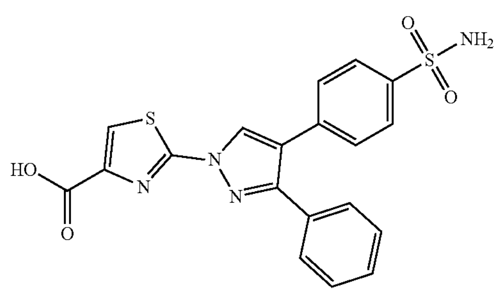 [SMILES: NS(=O)(=O)c1ccc(-c2cn(-c3nc(C(=O)O)cs3)nc2-c2ccccc2)cc1] | 2-(3-phenyl-4-(4-sulfamoylphenyl)-1H-pyrazol-1-yl)thiazole-4-carboxylic acid (M + H)$^+$ = 427 | + | 69 |
| 77 | 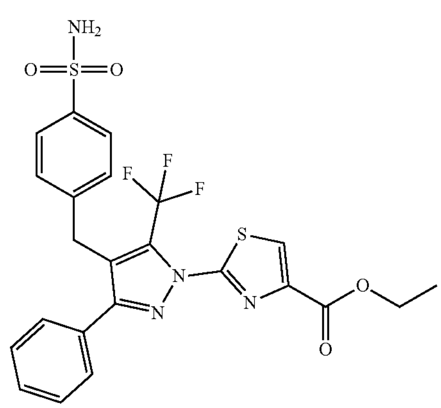 [SMILES: CCOC(=O)c1csc(-n2nc(-c3ccccc3)c(Cc3ccc(S(N)(=O)=O)cc3)c2C(F)(F)F)n1] | ethyl 2-(3-phenyl-4-(4-sulfamoylbenzyl)-5-(trifluoromethyl)-1H-pyrazol-1-yl)thiazole-4-carboxylate (M + H)$^+$ = 537 | + | 14 |

TABLE 7-continued

| Cmpd ID | Structure | Compound name and physical data | Inhibitory activity IC$_{50}$ (μM) | Example Method |
|---|---|---|---|---|
| 78 | 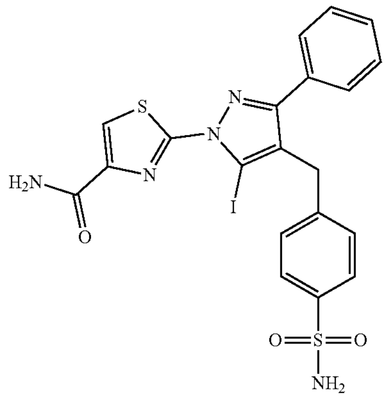 [SMILES: NC(=O)c1csc(-n2nc(-c3ccccc3)c(Cc3ccc(S(N)(=O)=O)cc3)c2I)n1] | 2-(5-iodo-3-phenyl-4-(4-sulfamoylbenzyl)-1H-pyrazol-1-yl)thiazole-4-carboxamide | + | 152 |
| 79 | 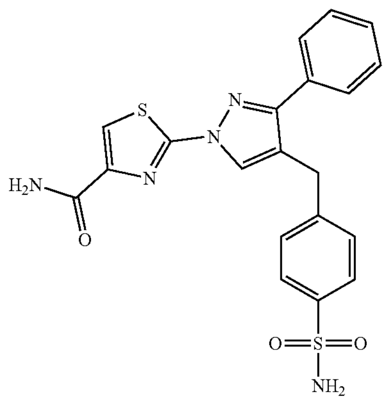 [SMILES: NC(=O)c1csc(-n2cc(Cc3ccc(S(N)(=O)=O)cc3)c(-c3ccccc3)n2)n1] | 2-(3-phenyl-4-(4-sulfamoylbenzyl)-1H-pyrazol-1-yl)thiazole-4-carboxamide | + | 152 |
| 80 | 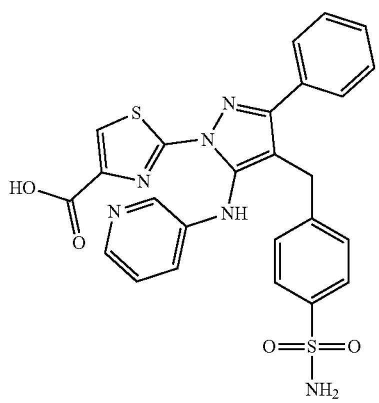 [SMILES: NS(=O)(=O)c1ccc(Cc2c(-c3ccccc3)nn(-c3nc(C(=O)O)cs3)c2Nc2cccnc2)cc1] | 2-(3-phenyl-5-(pyridin-3-ylamino)-4-(4-sulfamoylbenzyl)-1H-pyrazol-1-yl)thiazole-4-carboxylic acid (M + H)$^+$ = 533 | + | 154 |
| 81 | 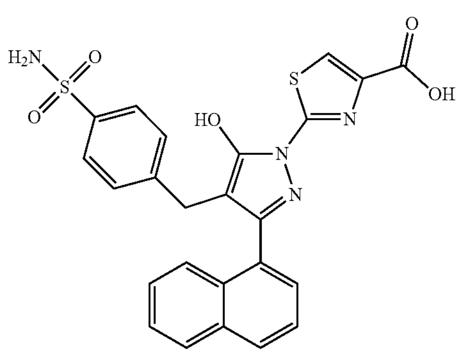 [SMILES: NS(=O)(=O)c1ccc(Cc2c(-c3cccc4ccccc34)nn(-c3nc(C(=O)O)cs3)c2O)cc1] | 2-(5-hydroxy-3-(naphthalen-1-yl)-4-(4-sulfamoylbenzyl)-1H-pyrazol-1-yl)thiazole-4-carboxylic acid | + | 69 |

TABLE 7-continued

| Cmpd ID | Structure | Compound name and physical data | Inhibitory activity IC$_{50}$ (μM) | Example Method |
|---|---|---|---|---|
| 82 | 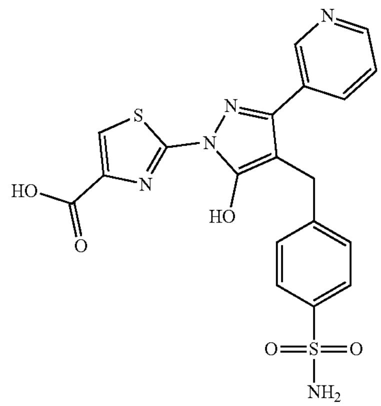 [SMILES: NS(=O)(=O)c1ccc(Cc2c(-c3cccnc3)nn(-c3nc(C(=O)O)cs3)c2O)cc1] | 2-(5-hydroxy-3-(pyridin-3-yl)-4-(4-sulfamoylbenzyl)-1H-pyrazol-1-yl)thiazole-4-carboxylic acid | + | 147 |
| 83 | 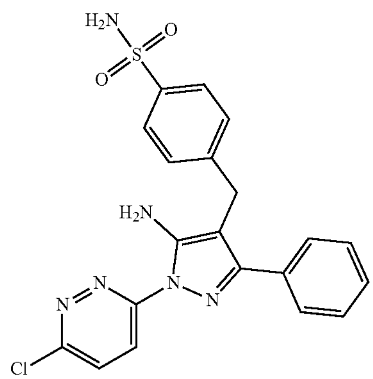 [SMILES: Nc1c(Cc2ccc(S(N)(=O)=O)cc2)c(-c2ccccc2)nn1-c1ccc(Cl)nn1] | 4-((5-amino-1-(6-chloropyridazin-3-yl)-3-phenyl-1H-pyrazol-4-yl)methyl)benzenesulfonamide | + | 148 |
| 84 | 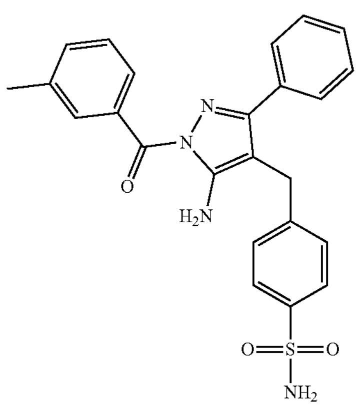 [SMILES: Cc1cccc(C(=O)n2nc(-c3ccccc3)c(Cc3ccc(S(N)(=O)=O)cc3)c2N)c1] | 4-((5-amino-1-(3-methylbenzoyl)-3-phenyl-1H-pyrazol-4-yl)methyl)benzenesulfonamide | + | 148 |
| 85 | 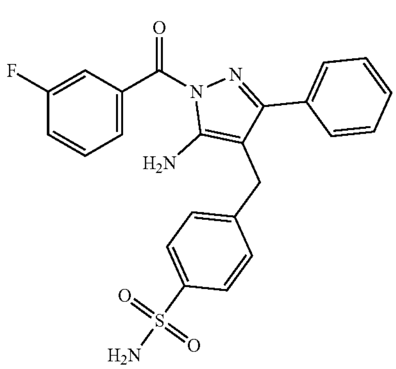 [SMILES: Nc1c(Cc2ccc(S(N)(=O)=O)cc2)c(-c2ccccc2)nn1C(=O)c1cccc(F)c1] | 4-((5-amino-1-(3-fluorobenzoyl)-3-phenyl-1H-pyrazol-4-yl)methyl)benzenesulfonamide | + | 148 |

TABLE 7-continued

| Cmpd ID | Structure | Compound name and physical data | Inhibitory activity IC$_{50}$ (μM) | Example Method |
|---|---|---|---|---|
| 86 | 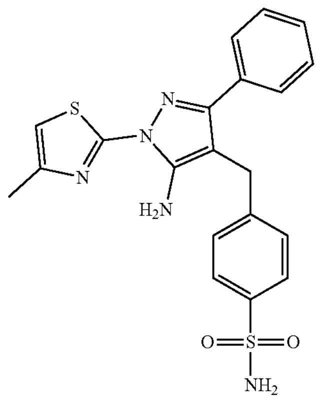 [SMILES: Cc1csc(-n2nc(-c3ccccc3)c(Cc3ccc(S(N)(=O)=O)cc3)c2N)n1] | 4-((5-amino-1-(4-methylthiazol-2-yl)-3-phenyl-1H-pyrazol-4-yl)methyl)benzenesulfonamide | + | 148 |
| 87 | 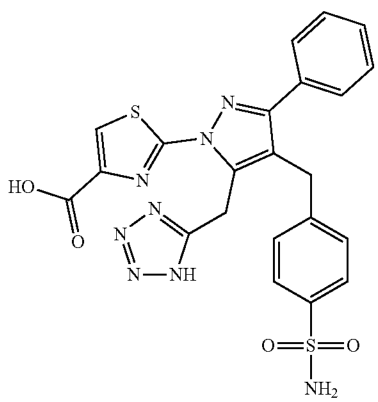 [SMILES: NS(=O)(=O)c1ccc(Cc2c(-c3ccccc3)nn(-c3nc(C(=O)O)cs3)c2Cc2nnn[nH]2)cc1] | 2-(5-((1H-tetrazol-5-yl)methyl)-3-phenyl-4-(4-sulfamoylbenzyl)-1H-pyrazol-1-yl)thiazole-4-carboxylic acid (M + H)$^+$ = 523 | + | 21, 18 |
| 88 | 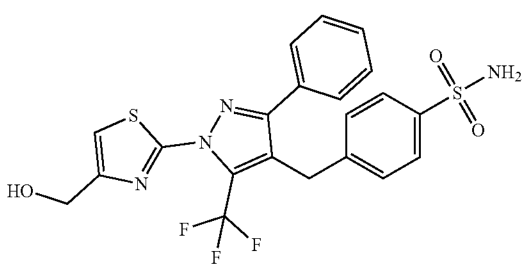 [SMILES: NS(=O)(=O)c1ccc(Cc2c(-c3ccccc3)nn(-c3nc(CO)cs3)c2C(F)(F)F)cc1] | 4-((1-(4-(hydroxymethyl)thiazol-2-yl)-3-phenyl-5-(trifluoromethyl)-1H-pyrazol-4-yl)methyl)benzenesulfonamide | + | 22 |
| 89 | 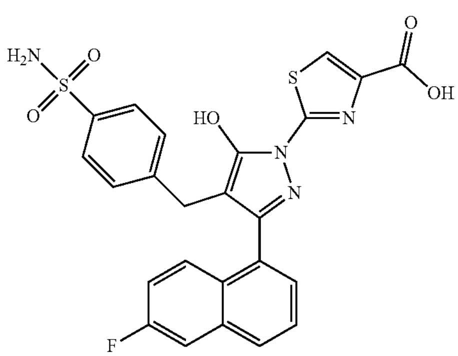 [SMILES: NS(=O)(=O)c1ccc(Cc2c(-c3cccc4cc(F)ccc34)nn(-c3nc(C(=O)O)cs3)c2O)cc1] | 2-(3-(6-fluoronaphthalen-1-yl)-5-hydroxy-4-(4-sulfamoylbenzyl)-1H-pyrazol-1-yl)thiazole-4-carboxylic acid | − | 69 |

TABLE 7-continued

| Cmpd ID | Structure | Compound name and physical data | Inhibitory activity IC$_{50}$ (μM) | Example Method |
|---|---|---|---|---|
| 90 | 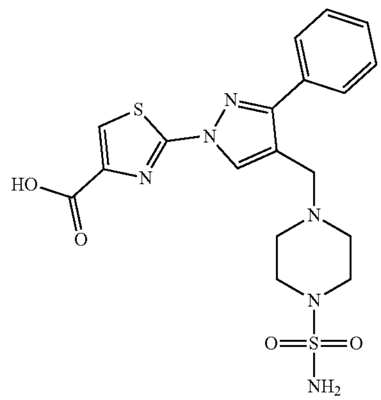 [SMILES: NS(=O)(=O)N1CCN(Cc2cn(-c3nc(C(=O)O)cs3)nc2-c2ccccc2)CC1] | 2-(3-phenyl-4-((4-sulfamoylpiperazin-1-yl)methyl)-1H-pyrazol-1-yl)thiazole-4-carboxylic acid (M + H)$^+$ = 449 | + | 155 |
| 91 | 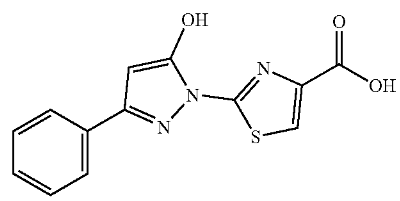 [SMILES: O=C(O)c1csc(-n2nc(-c3ccccc3)cc2O)n1] | 2-(5-hydroxy-3-phenyl-1H-pyrazol-1-yl)thiazole-4-carboxylic acid | − | 147 |
| 92 | 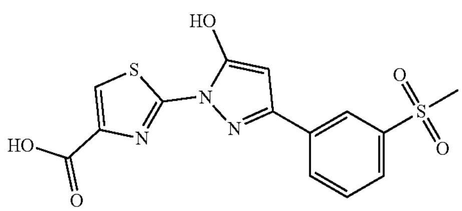 [SMILES: CS(=O)(=O)c1cccc(-c2cc(O)n(-c3nc(C(=O)O)cs3)n2)c1] | 2-(5-hydroxy-3-(3-(methylsulfonyl)phenyl)-1H-pyrazol-1-yl)thiazole-4-carboxylic acid | − | 147 |
| 93 | 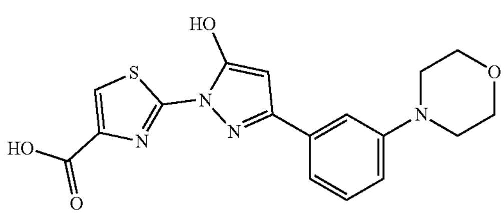 [SMILES: O=C(O)c1csc(-n2nc(-c3cccc(N4CCOCC4)c3)cc2O)n1] | 2-(5-hydroxy-3-(3-morpholinophenyl)-1H-pyrazol-1-yl)thiazole-4-carboxylic acid | − | 147 |
| 94 | 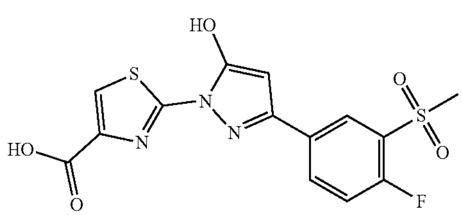 [SMILES: CS(=O)(=O)c1cc(-c2cc(O)n(-c3nc(C(=O)O)cs3)n2)ccc1F] | 2-(3-(4-fluoro-3-(methylsulfonyl)phenyl)-5-hydroxy-1H-pyrazol-1-yl)thiazole-4-carboxylic acid | − | 147 |
| 95 | 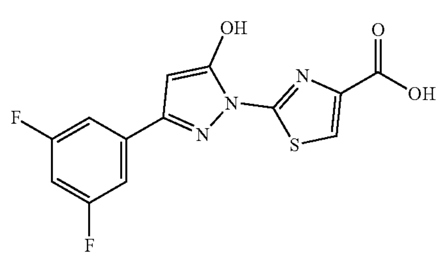 [SMILES: O=C(O)c1csc(-n2nc(-c3cc(F)cc(F)c3)cc2O)n1] | 2-(3-(3,5-difluorophenyl)-5-hydroxy-1H-pyrazol-1-yl)thiazole-4-carboxylic acid | − | 147 |

TABLE 7-continued

| Cmpd ID | Structure | Compound name and physical data | Inhibitory activity IC$_{50}$ (µM) | Example Method |
|---|---|---|---|---|
| 96 | 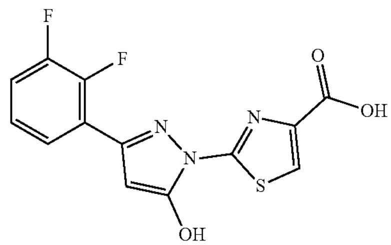 [SMILES: O=C(O)c1csc(-n2nc(-c3cccc(F)c3F)cc2O)n1] | 2-(3-(2,3-difluorophenyl)-5-hydroxy-1H-pyrazol-1-yl)thiazole-4-carboxylic acid | – | 147 |
| 97 | 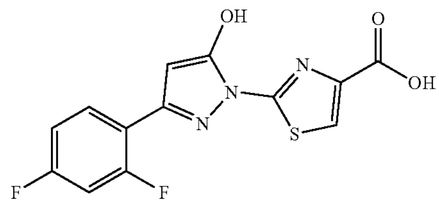 [SMILES: O=C(O)c1csc(-n2nc(-c3ccc(F)cc3F)cc2O)n1] | 2-(3-(2,4-difluorophenyl)-5-hydroxy-1H-pyrazol-1-yl)thiazole-4-carboxylic acid | – | 147 |
| 98 | 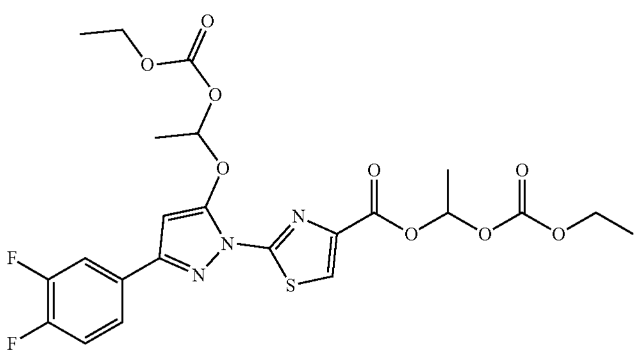 [SMILES: CCOC(=O)OC(C)OC(=O)c1csc(-n2nc(-c3ccc(F)c(F)c3)cc2OC(C)OC(=O)OCC)n1] | 1-((ethoxycarbonyl)oxy)ethyl 2-(3-(3,4-difluorophenyl)-5-(1-((ethoxycarbonyl)oxy)ethoxy)-1H-pyrazol-1-yl)thiazole-4-carboxylate | – | 156 |
| 99 | 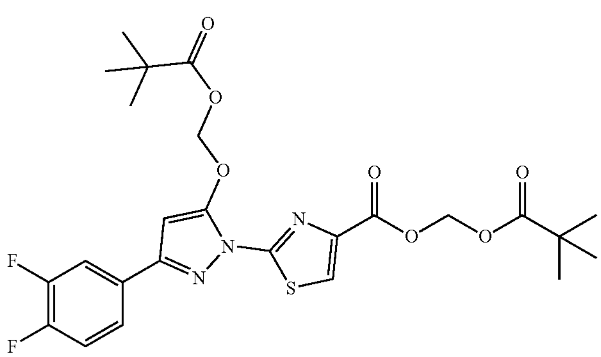 [SMILES: CC(C)(C)C(=O)OCOC(=O)c1csc(-n2nc(-c3ccc(F)c(F)c3)cc2OCOC(=O)C(C)(C)C)n1] | (pivaloyloxy)methyl 2-(3-(4-fluorophenyl)-5-((pivaloyloxy)methoxy)-1H-pyrazol-1-yl)thiazole-4-carboxylate | – | 156 |
| 100 | 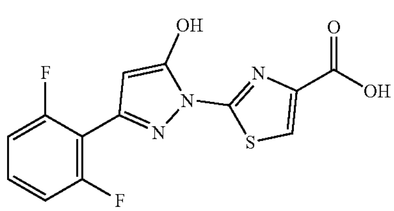 [SMILES: O=C(O)c1csc(-n2nc(-c3c(F)cccc3F)cc2O)n1] | 2-(3-(2,6-difluorophenyl)-5-hydroxy-1H-pyrazol-1-yl)thiazole-4-carboxylic acid | – | 147 |

TABLE 7-continued

| Cmpd ID | Structure | Compound name and physical data | Inhibitory activity IC$_{50}$ (μM) | Example Method |
|---|---|---|---|---|
| 101 | 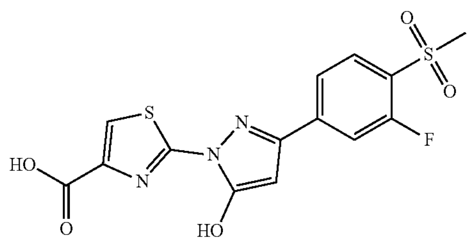 [SMILES: CS(=O)(=O)c1ccc(-c2cc(O)n(-c3nc(C(=O)O)cs3)n2)cc1F] | 3-(3-fluoro-4-(methylsulfonyl)phenyl)-1-(4-(hydroxymethyl)thiazol-2-yl)-1H-pyrazol-5-ol | – | 147 |
| 102 | 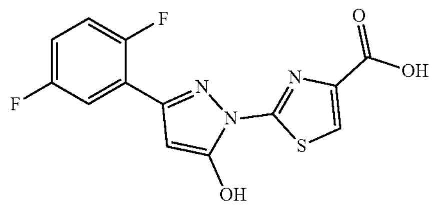 [SMILES: O=C(O)c1csc(-n2nc(-c3cc(F)ccc3F)cc2O)n1] | 2-(3-(2,5-difluorophenyl)-5-hydroxy-1H-pyrazol-1-yl)thiazole-4-carboxylic acid | – | 147 |
| 103 | 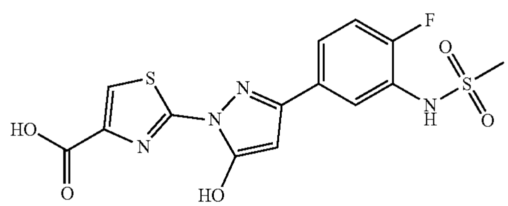 [SMILES: CS(=O)(=O)Nc1cc(-c2cc(O)n(-c3nc(C(=O)O)cs3)n2)ccc1F] | 2-(3-(4-fluoro-3-(methylsulfonamido)phenyl)-5-hydroxy-1H-pyrazol-1-yl)thiazole-4-carboxylic acid | – | 147 |
| 104 | 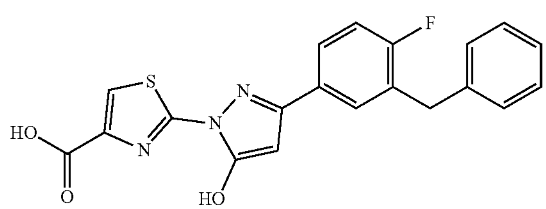 [SMILES: O=C(O)c1csc(-n2nc(-c3ccc(F)c(Cc4ccccc4)c3)cc2O)n1] | 2-(3-(3-benzyl-4-fluorophenyl)-5-hydroxy-1H-pyrazol-1-yl)thiazole-4-carboxylic acid | – | 147 |
| 105 | 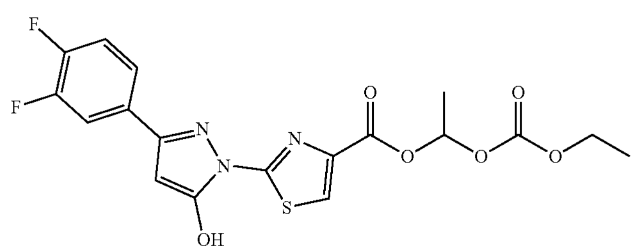 [SMILES: CCOC(=O)OC(C)OC(=O)c1csc(-n2nc(-c3ccc(F)c(F)c3)cc2O)n1] | 1-((ethoxycarbonyl)oxy)ethyl 2-(3-(3,4-difluorophenyl)-5-hydroxy-1H-pyrazol-1-yl)thiazole-4-carboxylate | – | 156 |
| 106 | 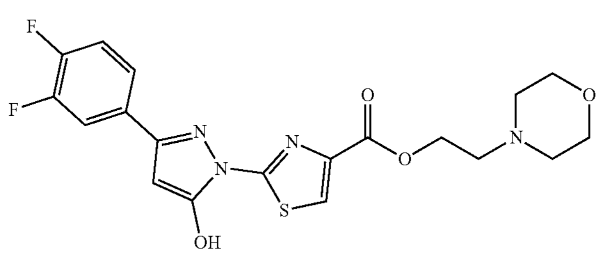 [SMILES: O=C(OCCN1CCOCC1)c1csc(-n2nc(-c3ccc(F)c(F)c3)cc2O)n1] | 2-morpholinoethyl 2-(3-(3,4-difluorophenyl)-5-hydroxy-1H-pyrazol-1-yl)thiazole-4-carboxylate | – | 156 |

TABLE 7-continued

| Cmpd ID | Structure | Compound name and physical data | Inhibitory activity IC₅₀ (μM) | Example Method |
|---|---|---|---|---|
| 107 | 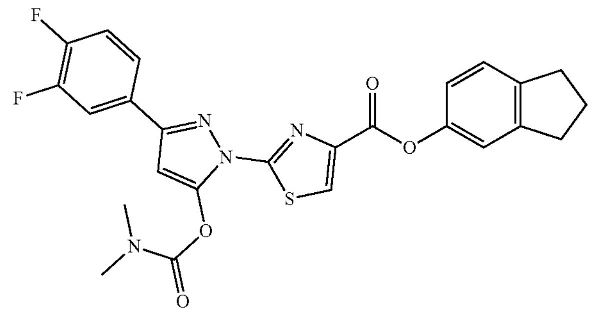 [SMILES: CN(C)C(=O)Oc1cc(-c2ccc(F)c(F)c2)nn1-c1nc(C(=O)Oc2ccc3c(c2)CCC3)cs1] | 2,3-dihydro-1H-inden-5-yl 2-(3-(3,4-difluorophenyl)-5-((dimethylcarbamoyl)oxy)-1H-pyrazol-1-yl)thiazole-4-carboxylate | – | 156 |
| 108 | 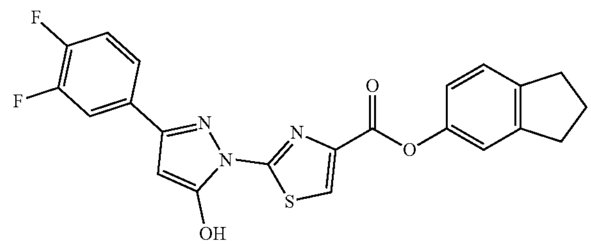 [SMILES: O=C(Oc1ccc2c(c1)CCC2)c1csc(-n2nc(-c3ccc(F)c(F)c3)cc2O)n1] | 2,3-dihydro-1H-inden-5-yl 2-(3-(3,4-difluorophenyl)-5-hydroxy-1H-pyrazol-1-yl)thiazole-4-carboxylate | – | 156 |
| 109 | 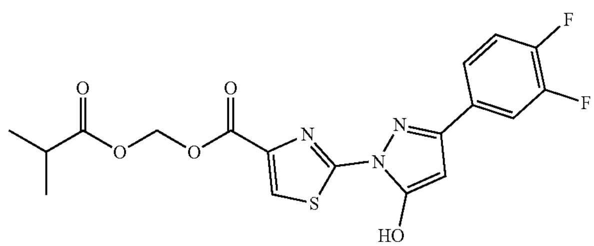 [SMILES: CC(C)C(=O)OCOC(=O)c1csc(-n2nc(-c3ccc(F)c(F)c3)cc2O)n1] | (isobutyryloxy)methyl 2-(3-(3,4-difluorophenyl)-5-hydroxy-1H-pyrazol-1-yl)thiazole-4-carboxylate | – | 156 |
| 110 | 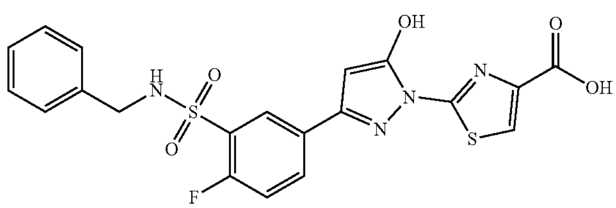 [SMILES: O=C(O)c1csc(-n2nc(-c3ccc(F)c(S(=O)(=O)NCc4ccccc4)c3)cc2O)n1] | 2-(3-(3-(N-benzylsulfamoyl)-4-fluorophenyl)-5-hydroxy-1H-pyrazol-1-yl)thiazole-4-carboxylic acid | – | 147 |
| 111 | 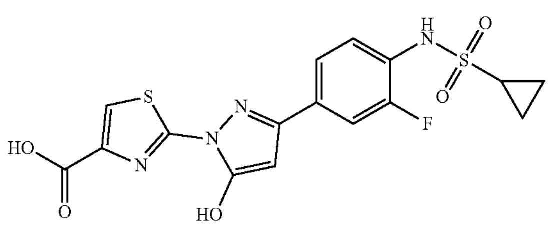 [SMILES: O=C(O)c1csc(-n2nc(-c3ccc(NS(=O)(=O)C4CC4)c(F)c3)cc2O)n1] | 2-(3-(4-(cyclopropanesulfonamido)-3-fluorophenyl)-5-hydroxy-1H-pyrazol-1-yl)thiazole-4-carboxylic acid | – | 147 |
| 112 | 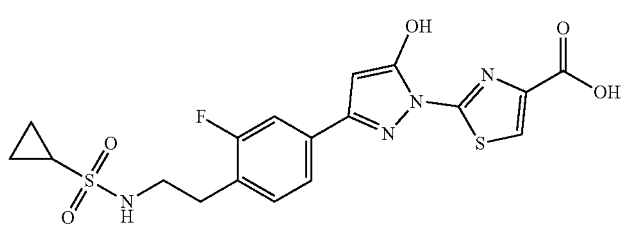 [SMILES: O=C(O)c1csc(-n2nc(-c3ccc(CCNS(=O)(=O)C4CC4)c(F)c3)cc2O)n1] | 2-(3-(4-(2-(cyclopropanesulfonamido)ethyl)-3-fluorophenyl)-5-hydroxy-1H-pyrazol-1-yl)thiazole-4-carboxylic acid | – | 147 |

TABLE 7-continued

| Cmpd ID | Structure | Compound name and physical data | Inhibitory activity IC$_{50}$ (μM) | Example Method |
|---|---|---|---|---|
| 113 | 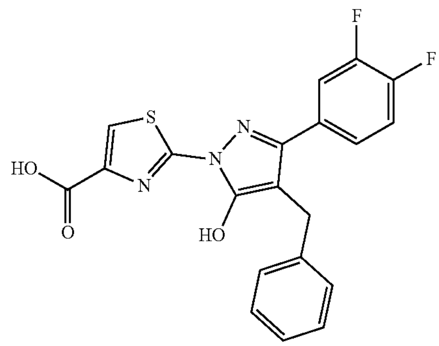 [SMILES: O=C(O)c1csc(-n2nc(-c3ccc(F)c(F)c3)c(Cc3ccccc3)c2O)n1] | 2-(4-benzyl-3-(3,4-difluorophenyl)-5-hydroxy-1H-pyrazol-1-yl)thiazole-4-carboxylic acid | – | 147 |
| 114 | 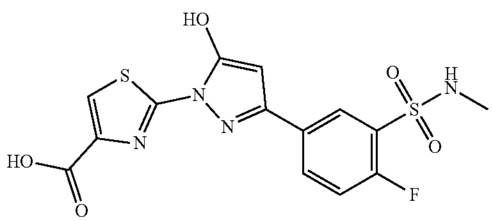 [SMILES: CNS(=O)(=O)c1cc(-c2cc(O)n(-c3nc(C(=O)O)cs3)n2)ccc1F] | 2-(3-(4-fluoro-3-(N-methylsulfamoyl)phenyl)-5-hydroxy-1H-pyrazol-1-yl)thiazole-4-carboxylic acid | – | 147 |
| 115 | 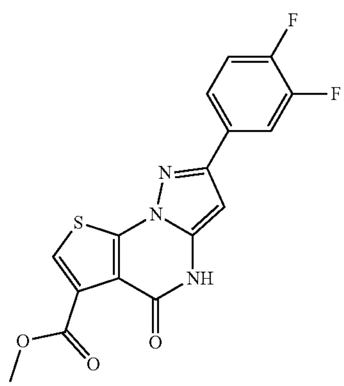 [SMILES: COC(=O)c1csc2c1c(=O)[nH]c1cc(-c3ccc(F)c(F)c3)nn12] | methyl 2-(3,4-difluorophenyl)-5-oxo-4,5-dihydropyrazolo[1,5-a]thieno[3,2-e]pyrimidine-6-carboxylate (M + H)$^+$ = 362 | – | 157 |
| 116 | 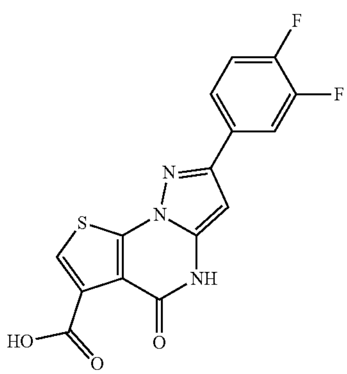 [SMILES: O=C(O)c1csc2c1c(=O)[nH]c1cc(-c3ccc(F)c(F)c3)nn12] | 2-(3,4-difluorophenyl)-5-oxo-4,5-dihydropyrazolo[1,5-a]thieno[3,2-e]pyrimidine-6-carboxylic acid (M + H)$^+$ = 348 | – | 157 |

TABLE 7-continued

| Cmpd ID | Structure | Compound name and physical data | Inhibitory activity IC$_{50}$ (μM) | Example Method |
|---|---|---|---|---|
| 117 | 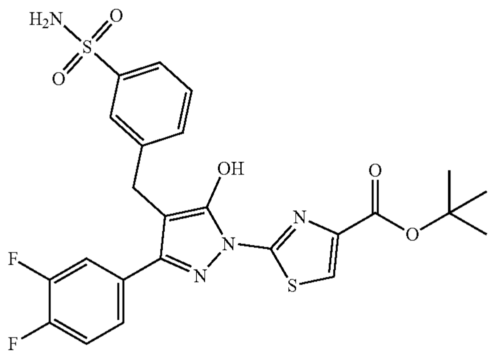 [SMILES: CC(C)(C)OC(=O)c1csc(-n2nc(-c3ccc(F)c(F)c3)c(Cc3cccc(S(N)(=O)=O)c3)c2O)n1] | tert-butyl 2-(3-(3,4-difluorophenyl)-5-hydroxy-4-(3-sulfamoylbenzyl)-1H-pyrazol-1-yl)thiazole-4-carboxylate | – | 69 |
| 118 | 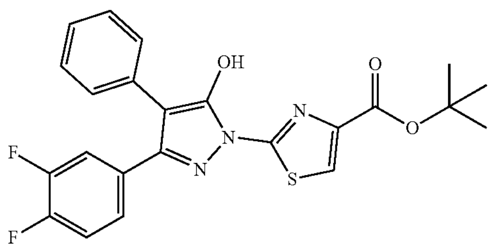 [SMILES: CC(C)(C)OC(=O)c1csc(-n2nc(-c3ccc(F)c(F)c3)c(-c3ccccc3)c2O)n1] | tert-butyl 2-(3-(3,4-difluorophenyl)-5-hydroxy-4-phenyl-1H-pyrazol-1-yl)thiazole-4-carboxylate | – | 69 |
| 119 | 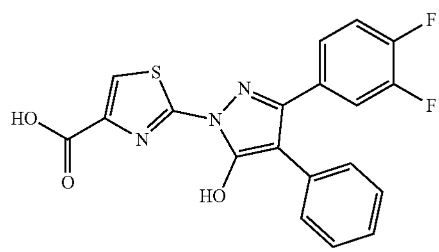 [SMILES: O=C(O)c1csc(-n2nc(-c3ccc(F)c(F)c3)c(-c3ccccc3)c2O)n1] | 2-(3-(3,4-difluorophenyl)-7-hydroxy-1H-indazol-1-yl)thiazole-4-carboxylic acid (M + H)$^+$ = 374 | – | 69 |
| 120 | 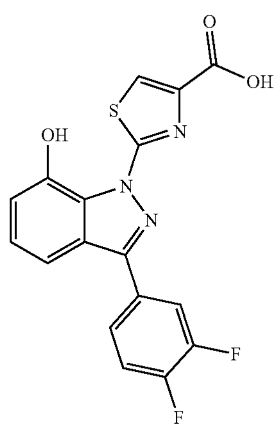 [SMILES: O=C(O)c1csc(-n2nc(-c3ccc(F)c(F)c3)c3cccc(O)c32)n1] | 2-(3-(3,4-difluorophenyl)-7-hydroxy-1H-indazol-1-yl)thiazole-4-carboxylic acid (M + H)$^+$ = 352 | – | 34 |
| 121 | 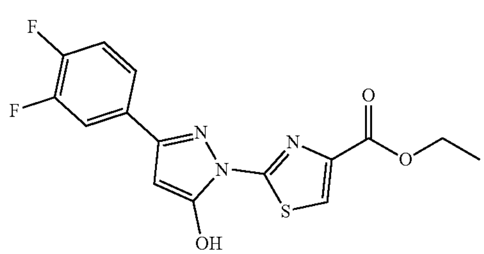 [SMILES: CCOC(=O)c1csc(-n2nc(-c3ccc(F)c(F)c3)cc2O)n1] | ethyl 2-(3-(3,4-difluorophenyl)-5-hydroxy-1H-pyrazol-1-yl)thiazole-4-carboxylate (M + H)$^+$ = 352 | – | 147 |

TABLE 7-continued

| Cmpd ID | Structure | Compound name and physical data | Inhibitory activity IC$_{50}$ (μM) | Example Method |
|---|---|---|---|---|
| 122 | 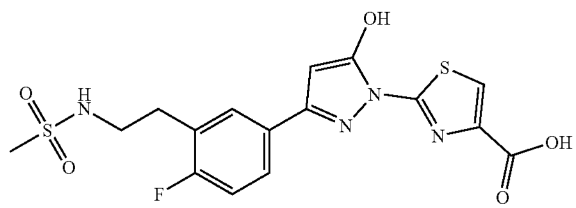 [SMILES: CS(=O)(=O)NCCc1cc(-c2cc(O)n(-c3nc(C(=O)O)cs3)n2)ccc1F] | 2-(3-(4-fluoro-3-(2-(methylsulfonamido)ethyl)phenyl)-5-hydroxy-1H-pyrazol-1-yl)thiazole-4-carboxylic acid (M + H)$^+$ = 427 | − | 147 |
| 123 | 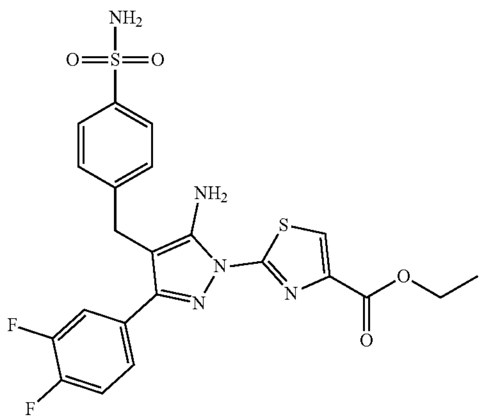 [SMILES: CCOC(=O)c1csc(-n2nc(-c3ccc(F)c(F)c3)c(Cc3ccc(S(N)(=O)=O)cc3)c2N)n1] | ethyl 2-(5-amino-3-(3,4-difluorophenyl)-4-(4-sulfamoylbenzyl)-1H-pyrazol-1-yl)thiazole-4-carboxylate (M + H)$^+$ = 520 | + | 12 |
| 124 | 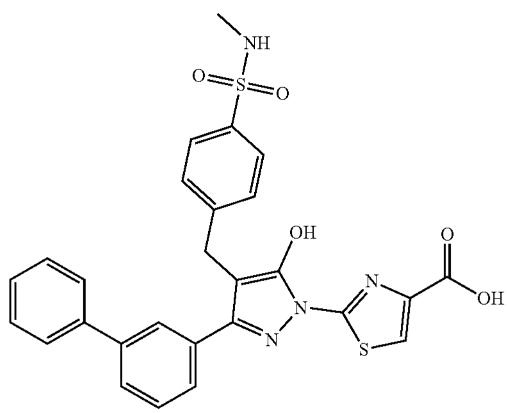 [SMILES: CNS(=O)(=O)c1ccc(Cc2c(-c3cccc(-c4ccccc4)c3)nn(-c3nc(C(=O)O)cs3)c2O)cc1] | 2-(3-([1,1'-biphenyl]-3-yl)-5-hydroxy-4-(4-(N-methylsulfamoyl)benzyl)-1H-pyrazol-1-yl)thiazole-4-carboxylic acid (M + H)$^+$ = 547 | − | 69 |
| 125 | 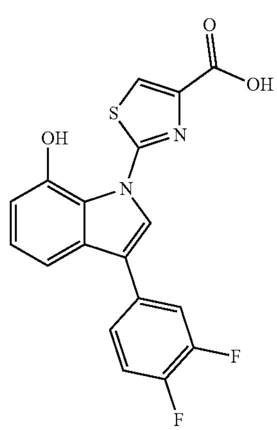 [SMILES: O=C(O)c1csc(-n2cc(-c3ccc(F)c(F)c3)c3cccc(O)c32)n1] | 2-(3-(3,4-difluorophenyl)-7-hydroxy-1H-indol-1-yl)thiazole-4-carboxylic acid (M + H)$^+$ = 373 | − | 32 |

TABLE 7-continued

| Cmpd ID | Structure | Compound name and physical data | Inhibitory activity IC$_{50}$ (μM) | Example Method |
|---|---|---|---|---|
| 126 | 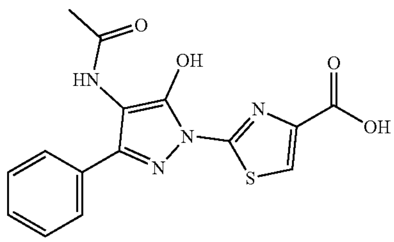 [SMILES: CC(=O)Nc1c(-c2ccccc2)nn(-c2nc(C(=O)O)cs2)c1O] | 2-(4-acetamido-5-hydroxy-3-phenyl-1H-pyrazol-1-yl)thiazole-4-carboxylic acid (M + H)$^+$ = 345 | – | 33 |
| 127 | 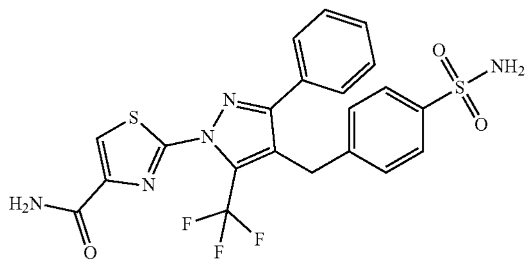 [SMILES: NC(=O)c1csc(-n2nc(-c3ccccc3)c(Cc3ccc(S(N)(=O)=O)cc3)c2C(F)(F)F)n1] | 2-(3-phenyl-4-(4-sulfamoylbenzyl)-5-(trifluoromethyl)-1H-pyrazol-1-yl)thiazole-4-carboxamide | – | 152 |
| 128 | 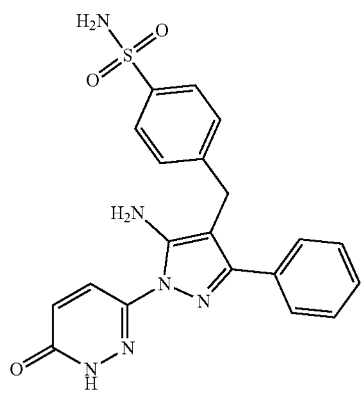 [SMILES: Nc1c(Cc2ccc(S(N)(=O)=O)cc2)c(-c2ccccc2)nn1-c1ccc(=O)[nH]n1] | 4-((5-amino-1-(6-oxo-1,6-dihydropyridazin-3-yl)-3-phenyl-1H-pyrazol-4-yl)methyl)benzenesulfonamide | – | 148 |
| 129 | 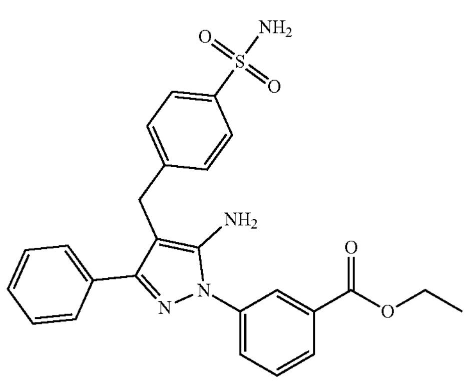 [SMILES: CCOC(=O)c1cccc(-n2nc(-c3ccccc3)c(Cc3ccc(S(N)(=O)=O)cc3)c2N)c1] | ethyl 3-(5-amino-3-phenyl-4-(4-sulfamoylbenzyl)-1H-pyrazol-1-yl)benzoate | – | 148 |

TABLE 7-continued

| Cmpd ID | Structure | Compound name and physical data | Inhibitory activity IC$_{50}$ (µM) | Example Method |
|---|---|---|---|---|
| 130 | 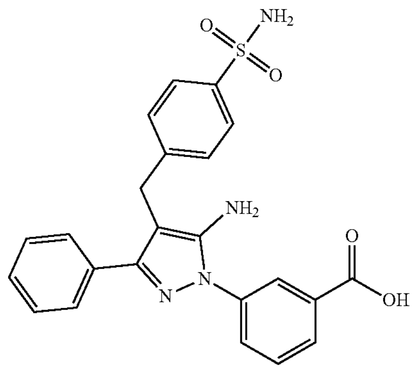 [SMILES: Nc1c(Cc2ccc(S(N)(=O)=O)cc2)c(-c2ccccc2)nn1-c1cccc(C(=O)O)c1] | 3-(5-amino-3-phenyl-4-(4-sulfamoylbenzyl)-1H-pyrazol-1-yl)benzoic acid | – | 148 |
| 131 | 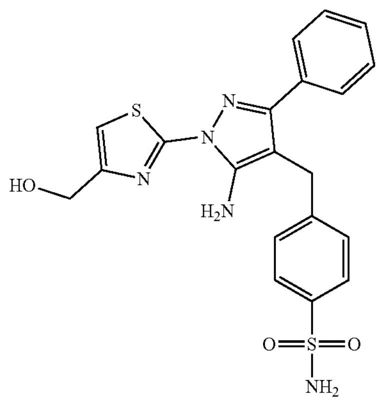 [SMILES: Nc1c(Cc2ccc(S(N)(=O)=O)cc2)c(-c2ccccc2)nn1-c1nc(CO)cs1] | 4-((5-amino-1-(4-(hydroxymethyl)thiazol-2-yl)-3-phenyl-1H-pyrazol-4-yl)methyl)benzenesulfonamide | – | 148 |
| 132 | 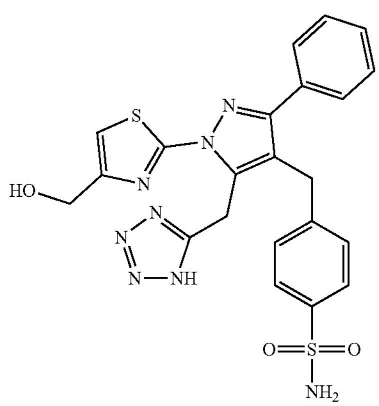 [SMILES: NS(=O)(=O)c1ccc(Cc2c(-c3ccccc3)nn(-c3nc(CO)cs3)c2Cc2nnn[nH]2)cc1] | 4-((5-((1H-tetrazol-5-yl)methyl)-1-(4-(hydroxymethyl)thiazol-2-yl)-3-phenyl-1H-pyrazol-4-yl)methyl)benzenesulfonamide (M + H)$^+$ = 509 | – | 22 |
| 133 | 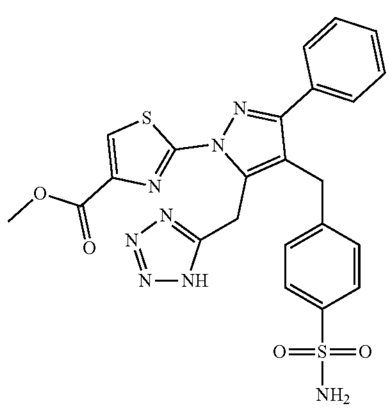 [SMILES: COC(=O)c1csc(-n2nc(-c3ccccc3)c(Cc3ccc(S(N)(=O)=O)cc3)c2Cc2nnn[nH]2)n1] | methyl)-3-phenyl-4-(4-sulfamoylbenzyl)-1H-pyrazol-1-yl)thiazole-4-carboxylate (M + H)$^+$ = 537 | – | 21 |

TABLE 7-continued

| Cmpd ID | Structure | Compound name and physical data | Inhibitory activity IC$_{50}$ (μM) | Example Method |
|---|---|---|---|---|
| 134 | 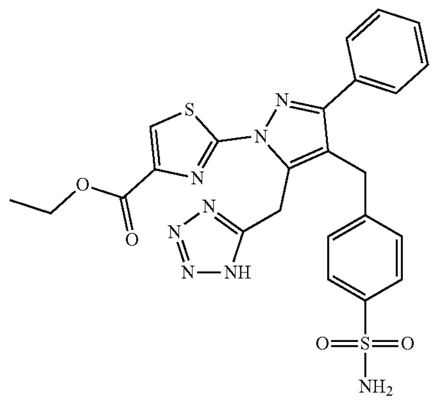 [SMILES: CCOC(=O)c1csc(-n2nc(-c3ccccc3)c(Cc3ccc(S(N)(=O)=O)cc3)c2Cc2nnn[nH]2)n1] | ethyl 2-(5-((1H-tetrazol-5-yl)methyl)-3-phenyl-4-(4-sulfamoylbenzyl)-1H-pyrazol-1-yl)thiazole-4-carboxylate (M + H)$^+$ = 551 | – | 21 |
| 135 | 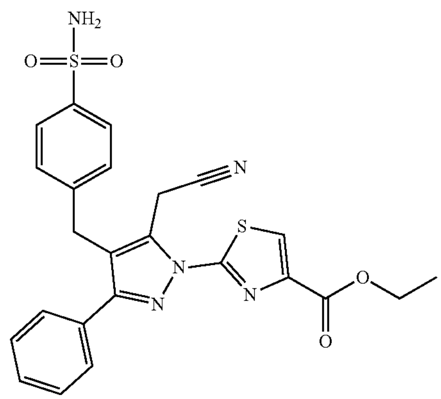 [SMILES: CCOC(=O)c1csc(-n2nc(-c3ccccc3)c(Cc3ccc(S(N)(=O)=O)cc3)c2CC#N)n1] | ethyl 2-(5-(cyanomethyl)-3-phenyl-4-(4-sulfamoylbenzyl)-1H-pyrazol-1-yl)thiazole-4-carboxylate (M + H)$^+$ = 508 | – | 19 |
| 136 | 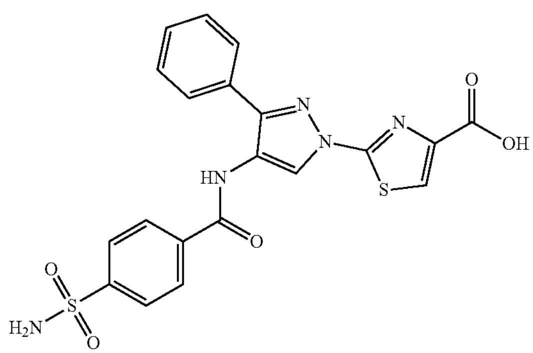 [SMILES: NS(=O)(=O)c1ccc(C(=O)Nc2cn(-c3nc(C(=O)O)cs3)nc2-c2ccccc2)cc1] | 2-(3-phenyl-4-(4-sulfamoylbenzamido)-1H-pyrazol-1-yl)thiazole-4-carboxylic acid (M + H)$^+$ = 449 | – | 158 |
| 137 | 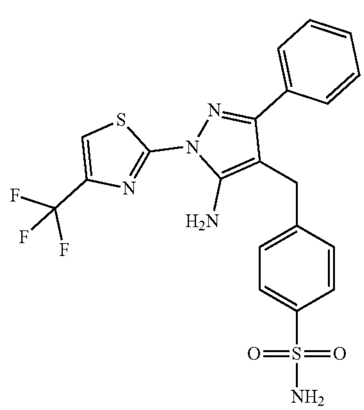 [SMILES: Nc1c(Cc2ccc(S(N)(=O)=O)cc2)c(-c2ccccc2)nn1-c1nc(C(F)(F)F)cs1] | 4-((5-amino-3-phenyl-1-(4-(trifluoromethyl)thiazol-2-yl)-1H-pyrazol-4-yl)methyl)benzenesulfonamide | – | 148 |

TABLE 7-continued

| Cmpd ID | Structure | Compound name and physical data | Inhibitory activity IC$_{50}$ (μM) | Example Method |
|---|---|---|---|---|
| 138 | 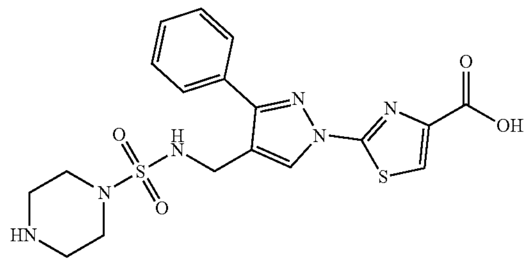 [SMILES: O=C(O)c1csc(-n2cc(CNS(=O)(=O)N3CCNCC3)c(-c3ccccc3)n2)n1] | 2-(3-phenyl-4-((piperazine-1-sulfonamido)methyl)-1H-pyrazol-1-yl)thiazole-4-carboxylic acid (M + H)$^+$ = 449 | — | 155 |
| 139 | 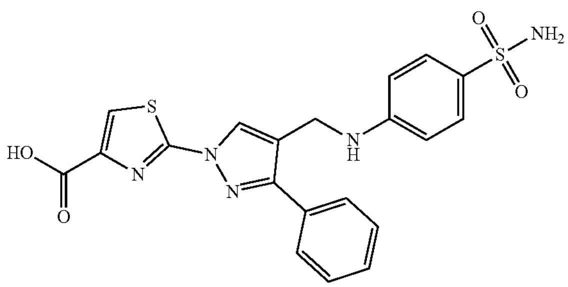 [SMILES: NS(=O)(=O)c1ccc(NCc2cn(-c3nc(C(=O)O)cs3)nc2-c2ccccc2)cc1] | 2-(3-phenyl-4-(((4-sulfamoylphenyl)amino)methyl)-1H-pyrazol-1-yl)thiazole-4-carboxylic acid (M + H)$^+$ = 456 | — | 155 |
| 140 | 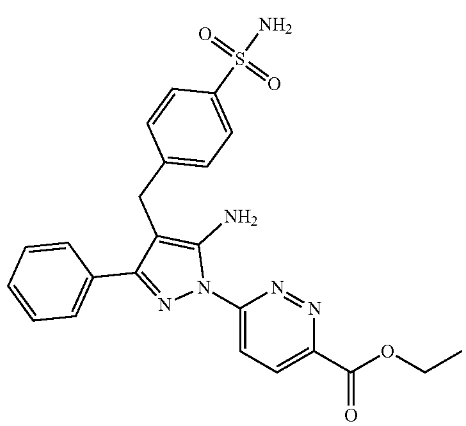 [SMILES: CCOC(=O)c1ccc(-n2nc(-c3ccccc3)c(Cc3ccc(S(N)(=O)=O)cc3)c2N)nn1] | ethyl 6-(5-amino-3-phenyl-4-(4-sulfamoylbenzyl)-1H-pyrazol-1-yl)pyridazine-3-carboxylate | — | 148 |
| 141 | 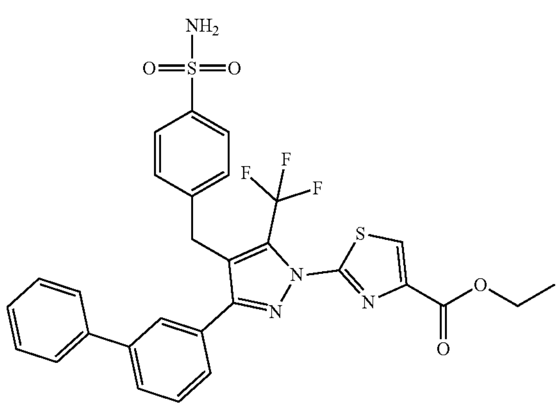 | ethyl 2-(3-([1,1'-bipheny]-3-yl)-4-(4-sulfamoylbenzyl)-5-(trifluoromethyl)-1H-pyrazol-1-yl)thiazole-4-carboxylate (M + H)$^+$ = 585 | — | 14 |

TABLE 7-continued

| Cmpd ID | Structure | Compound name and physical data | Inhibitory activity IC$_{50}$ (μM) | Example Method |
|---|---|---|---|---|
| 142 | 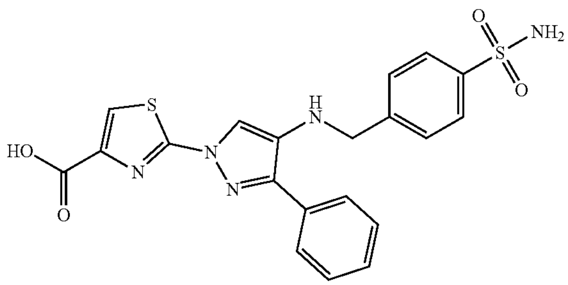 [SMILES: NS(=O)(=O)c1ccc(CNc2cn(-c3nc(C(=O)O)cs3)nc2-c2ccccc2)cc1] | 2-(3-phenyl-4-((4-sulfamoylbenzyl)amino)-1H-pyrazol-1-yl)thiazole-4-carboxylic acid (M + H)$^+$ = 456 | − | 158 |
| 143 | 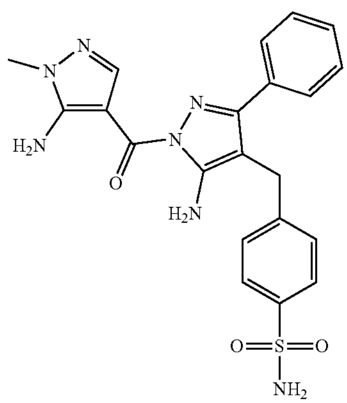 [SMILES: Cn1ncc(C(=O)n2nc(-c3ccccc3)c(Cc3ccc(S(N)(=O)=O)cc3)c2N)c1N] | 4-((5-amino-1-(5-amino-1-methyl-1H-pyrazole-4-carbonyl)-3-phenyl-1H-pyrazol-4-yl)methyl)benzenesulfonamide | − | 148 |
| 144 | 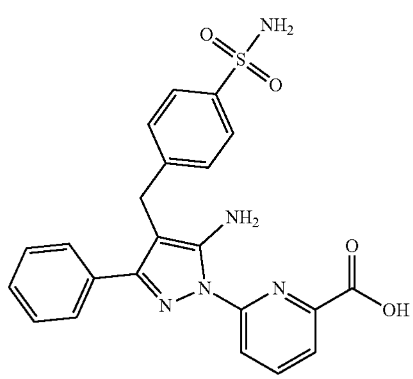 [SMILES: Nc1c(Cc2ccc(S(N)(=O)=O)cc2)c(-c2ccccc2)nn1-c1cccc(C(=O)O)n1] | 6-(5-amino-3-phenyl-4-(4-sulfamoylbenzyl)-1H-pyrazol-1-yl)picolinic acid | + | 148 |
| 145 | 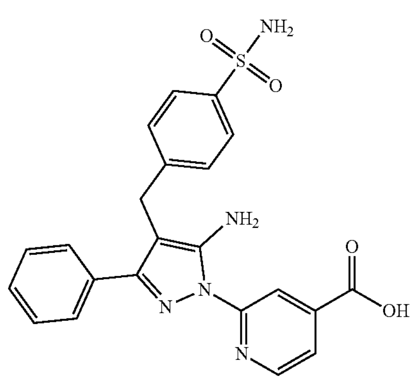 | 2-(5-amino-3-phenyl-4-(4-sulfamoylbenzyl)-1H-pyrazol-1-yl)isonicotinic acid | − | 148 |

TABLE 7-continued

| Cmpd ID | Structure | Compound name and physical data | Inhibitory activity IC$_{50}$ (μM) | Example Method |
|---|---|---|---|---|
| 146 | 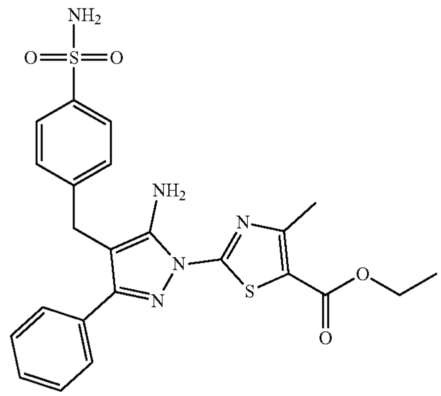 [SMILES: CCOC(=O)c1sc(-n2nc(-c3ccccc3)c(Cc3ccc(S(N)(=O)=O)cc3)c2N)nc1C] | ethyl 2-(5-amino-3-phenyl-4-(4-sulfamoylbenzyl)-1H-pyrazol-1-yl)-5-methylthiazole-4-carboxylate (M + H)$^+$ = 498 | − | 148 |
| 147 | 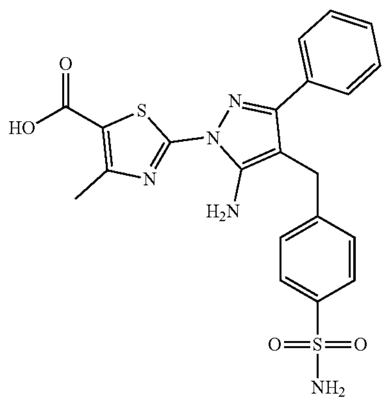 [SMILES: Cc1nc(-n2nc(-c3ccccc3)c(Cc3ccc(S(N)(=O)=O)cc3)c2N)sc1C(=O)O] | 2-(5-amino-3-phenyl-4-(4-sulfamoylbenzyl)-1H-pyrazol-1-yl)-5-methylthiazole-4-carboxylic acid (M + H)$^+$ = 470 | + | 148 |
| 148 | 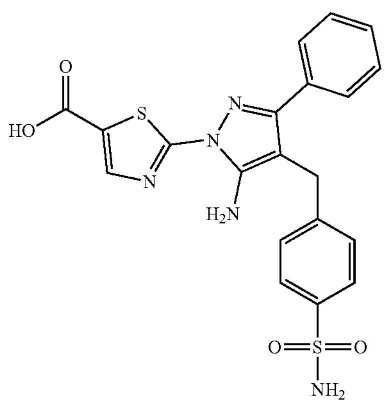 [SMILES: Nc1c(Cc2ccc(S(N)(=O)=O)cc2)c(-c2ccccc2)nn1-c1ncc(C(=O)O)s1] | 2-(5-amino-3-phenyl-4-(4-sulfamoylbenzyl)-1H-pyrazol-1-yl)thiazole-4-carboxylic acid (M + H)$^+$ = 456 | + | 148 |
| 149 | 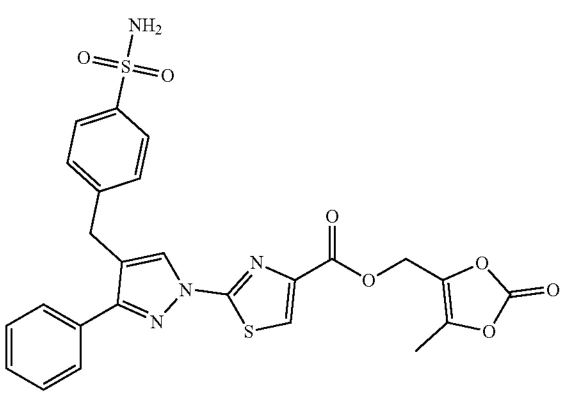 [SMILES: Cc1oc(=O)oc1COC(=O)c1csc(-n2cc(Cc3ccc(S(N)(=O)=O)cc3)c(-c3ccccc3)n2)n1] | (5-methyl-2-oxo-1,3-dioxol-4-yl)methyl 2-(3-phenyl-4-(4-sulfamoylbenzyl)-1H-pyrazol-1-yl)thiazole-4-carboxylate | ++ | 156 |

TABLE 7-continued

| Cmpd ID | Structure | Compound name and physical data | Inhibitory activity IC$_{50}$ (μM) | Example Method |
|---|---|---|---|---|
| 150 | 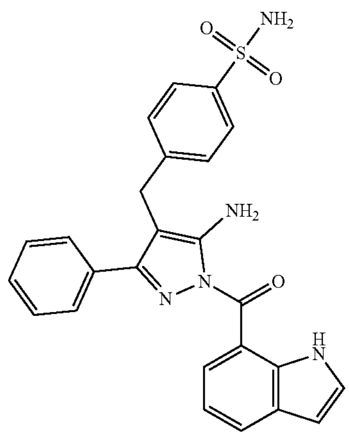 [SMILES: Nc1c(Cc2ccc(S(N)(=O)=O)cc2)c(-c2ccccc2)nn1C(=O)c1cccc2cc[nH]c12] | 4-((5-amino-1-(1H-indole-7-carbonyl)-3-phenyl-1H-pyrazol-4-yl)methyl)benzenesulfonamide | − | 148 |
| 151 | 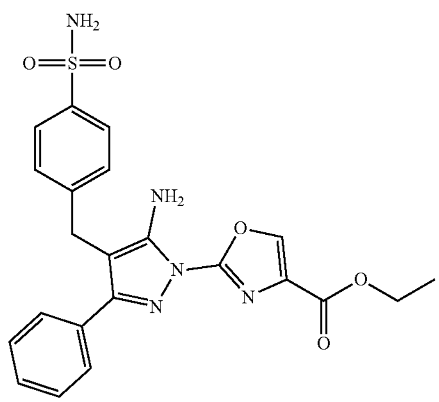 [SMILES: CCOC(=O)c1coc(-n2nc(-c3ccccc3)c(Cc3ccc(S(N)(=O)=O)cc3)c2N)n1] | ethyl 2-(5-amino-3-phenyl-4-(4-sulfamoylbenzyl)-1H-pyrazol-1-yl)oxazole-4-carboxylate (M + H)$^+$ = 468 | + | 148 |
| 152 | 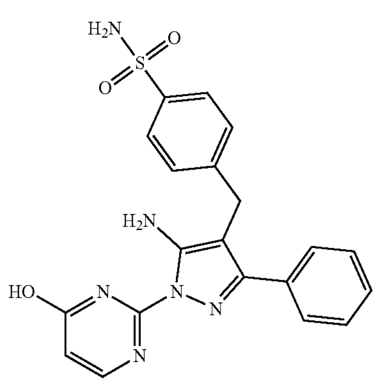 [SMILES: Nc1c(Cc2ccc(S(N)(=O)=O)cc2)c(-c2ccccc2)nn1-c1nccc(O)n1] | 4-((5-amino-1-(4-hydroxypyrimidin-2-yl)-3-phenyl-1H-pyrazol-4-yl)methyl)benzenesulfonamide | − | 148 |

TABLE 7-continued

| Cmpd ID | Structure | Compound name and physical data | Inhibitory activity IC$_{50}$ (μM) | Example Method |
|---|---|---|---|---|
| 153 | 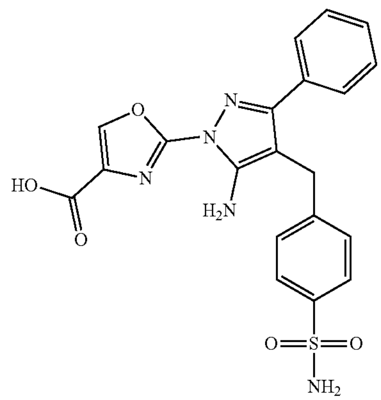 [SMILES: Nc1c(Cc2ccc(S(N)(=O)=O)cc2)c(-c2ccccc2)nn1-c1nc(C(=O)O)co1] | 2-(5-amino-3-phenyl-4-(4-sulfamoylbenzyl)-1H-pyrazol-1-yl)oxazole-4-carboxylic acid (M + H)$^+$ = 440 | ++ | 148 |
| 154 | 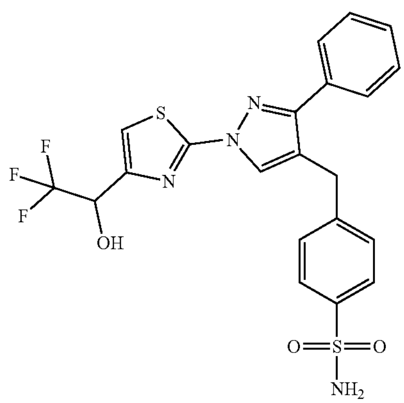 [SMILES: NS(=O)(=O)c1ccc(Cc2cn(-c3nc(C(O)C(F)(F)F)cs3)nc2-c2ccccc2)cc1] | 4-((3-phenyl-1-(4-(2,2,2-trifluoro-1-hydroxyethyl)thiazol-2-yl)-1H-pyrazol-4-yl)methyl)benzenesulfonamide 1H NMR (400 MHz, DMSO-d6) δ 8.21 (d, J = 0.8 Hz, 1H), 7.76-7.61 (m, 4H), 7.57 (d, J = 0.7 Hz, 1H), 7.49-7.35 (m, 5H), 7.26 (s, 2H), 6.99 (d, J = 6.3 Hz, 1H), 5.27-5.15 (m, 1H), 4.14 (s, 2H); (M + H)$^+$ = 495 | ++ | 159 |
| 155 | 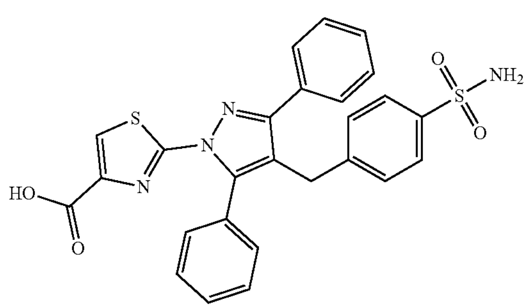 [SMILES: NS(=O)(=O)c1ccc(Cc2c(-c3ccccc3)nn(-c3nc(C(=O)O)cs3)c2-c2ccccc2)cc1] | 2-(3,5-diphenyl-4-(4-sulfamoylbenzyl)-1H-pyrazol-1-yl)thiazole-4-carboxylic acid 1H NMR (400 MHz, DMSO-d6) δ 12.86 (s, 1H), 8.23 (s, 1H), 7.75-7.67 (m, 0H), 7.66-7.55 (m, 4H), 7.40 (s, 4H), 7.47-7.30 (m, 4H), 7.30-7.15 (m, 5H), 3.98 (s, 2H); (M + H)$^+$ = 517 | +++ | 15 |
| 156 | 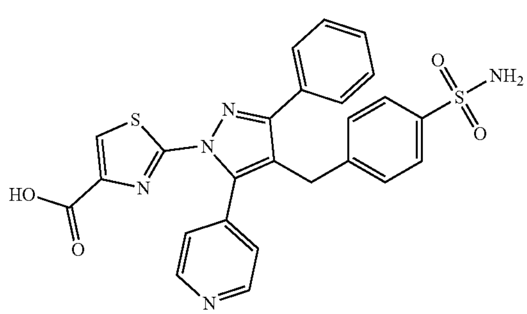 [SMILES: NS(=O)(=O)c1ccc(Cc2c(-c3ccccc3)nn(-c3nc(C(=O)O)cs3)c2-c2ccncc2)cc1] | 2-(3-phenyl-5-(pyridin-4-yl)-4-(4-sulfamoylbenzyl)-1H-pyrazol-1-yl)thiazole-4-carboxylic acid 1H NMR (400 MHz, DMSO-d6) δ 12.87 (s, 1H), 8.64-8.57 (m, 2H), 8.23 (s, 1H), 7.66-7.54 (m, 4H), 7.47-7.34 (m, 5H), 7.25-7.16 (m, 4H), 4.05 (q, J = 5.2 Hz, 1H), 4.01 (s, 2H), 3.14 (d, J = 5.2 Hz, 2H); (M + H)$^+$ = 518 | + | 15 |

TABLE 7-continued

| Cmpd ID | Structure | Compound name and physical data | Inhibitory activity IC$_{50}$ (μM) | Example Method |
|---|---|---|---|---|
| 157 | 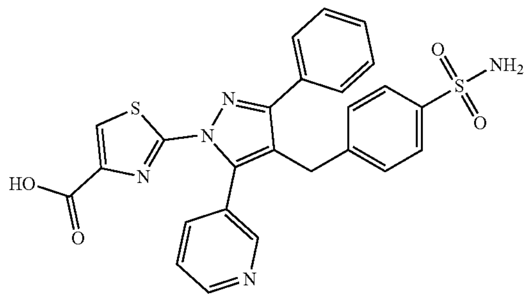 [SMILES: NS(=O)(=O)c1ccc(Cc2c(-c3ccccc3)nn(-c3nc(C(=O)O)cs3)c2-c2cccnc2)cc1] | 2-(3-phenyl-5-(pyridin-3-yl)-4-(4-sulfamoylbenzyl)-1H-pyrazol-1-yl)thiazole-4-carboxylic acid<br>1H NMR (400 MHz, DMSO-d6) δ 8.71-8.61 (m, 2H), 8.22 (s, 1H), 8.00 (ddd, J = 7.9, 2.2, 1.7 Hz, 1H), 7.66-7.57 (m, 4H), 7.52 (ddd, J = 7.9, 5.0, 0.9 Hz, 1H), 7.47-7.34 (m, 3H), 7.25-7.17 (m, 4H), 4.01 (s, 2H); (M + H)$^+$ = 518 | ++ | 15 |
| 158 | 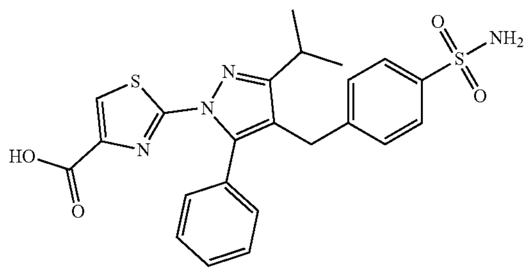 [SMILES: CC(C)c1nn(-c2nc(C(=O)O)cs2)c(-c2ccccc2)c1Cc1ccc(S(N)(=O)=O)cc1] | 2-(3-isopropyl-5-phenyl-4-(4-sulfamoylbenzyl)-1H-pyrazol-1-yl)thiazole-4-carboxylic acid<br>(M + H)$^+$ = 483 | + | 49 |
| 159 | 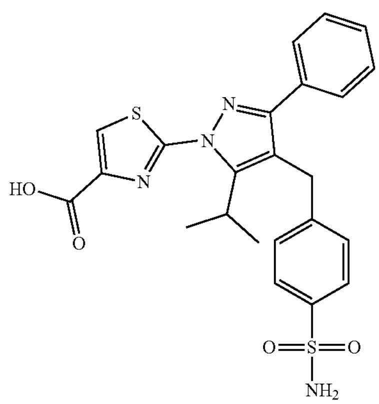 [SMILES: CC(C)c1c(Cc2ccc(S(N)(=O)=O)cc2)c(-c2ccccc2)nn1-c1nc(C(=O)O)cs1] | 2-(5-isopropyl-3-phenyl-4-(4-sulfamoylbenzyl)-1H-pyrazol-1-yl)thiazole-4-carboxylic acid<br>1H NMR (600 MHz, DMSO-d6) δ 13.14 (s, 1H), 8.28 (s, 1H), 7.74-7.68 (m, 2H), 7.51-7.45 (m, 2H), 7.42-7.34 (m, 3H), 7.31-7.25 (m, 4H), 4.21-4.12 (m, 1H), 4.15 (s, 2H), 1.28-1.24 (m, 6H); (M + H)$^+$ = 483 | ++ | 49 |
| 160 | 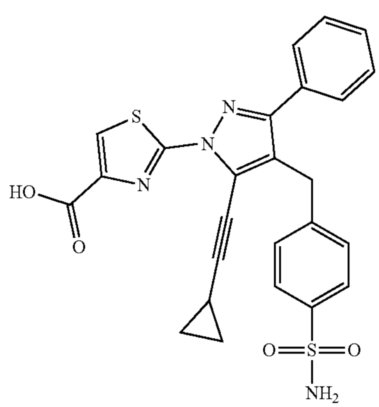 [SMILES: NS(=O)(=O)c1ccc(Cc2c(-c3ccccc3)nn(-c3nc(C(=O)O)cs3)c2C#CC2CC2)cc1] | 2-(5-(cyclopropylethynyl)-3-phenyl-4-(4-sulfamoylbenzyl)-1H-pyrazol-1-yl)thiazole-4-carboxylic acid<br>1H NMR (400 MHz, DMSO-d6) δ 13.13 (s, 1H), 8.31 (s, 1H), 7.76-7.68 (m, 2H), 7.65-7.55 (m, 2H), 7.50-7.37 (m, 3H), 7.36-7.21 (m, 4H), 4.17 (s, 2H), 1.60 (tt, J = 7.7, 5.3 Hz, 1H), 1.00-0.86 (m, 4H); (M + H)$^+$ = 505 | +++ | 16 |

TABLE 7-continued

| Cmpd ID | Structure | Compound name and physical data | Inhibitory activity IC$_{50}$ (μM) | Example Method |
|---|---|---|---|---|
| 161 | 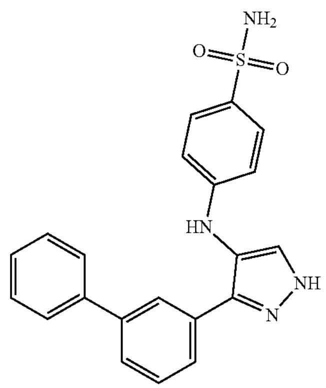 [SMILES: NS(=O)(=O)c1ccc(Nc2c[nH]nc2-c2cccc(-c3ccccc3)c2)cc1] | 4-((3-([1,1'-biphenyl-3-yl)-1H-pyrazol-4-yl)amino)benzenesulfonamide (M + H)$^+$ = 391 | − | 25 |
| 162 | 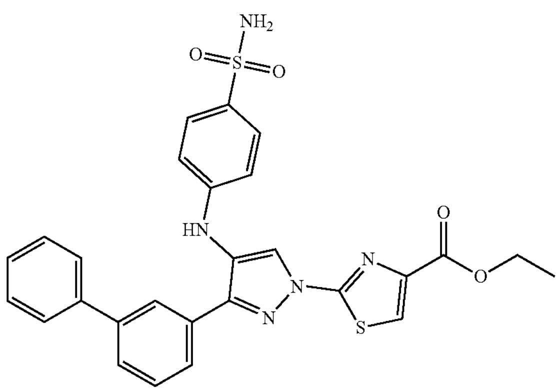 [SMILES: CCOC(=O)c1csc(-n2cc(Nc3ccc(S(N)(=O)=O)cc3)c(-c3cccc(-c4ccccc4)c3)n2)n1] | ethyl 2-(3-([1,1'-biphenyl]-3-yl)-4-((4-sulfamoylphenyl)amino)-1H-pyrazol-1-yl)thiazole-4-carboxylate (M + H)$^+$ = 546 | + | 26 |
| 163 | 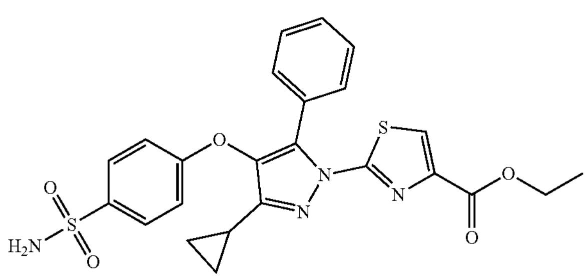 [SMILES: CCOC(=O)c1csc(-n2nc(C3CC3)c(Oc3ccc(S(N)(=O)=O)cc3)c2-c2ccccc2)n1] | ethyl 2-(3-cyclopropyl-5-phenyl-4-(4-sulfamoylphenoxy)-1H-pyrazol-1-yl)thiazole-4-carboxylate (M + H)$^+$ = 511 | − | 33 |
| 164 | 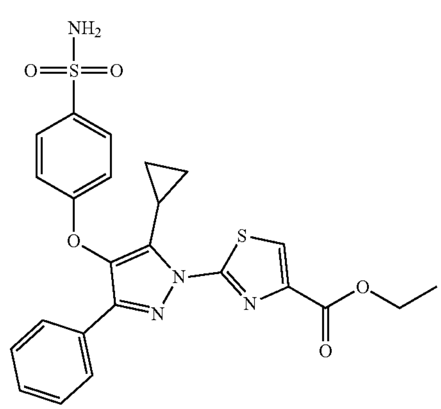 [SMILES: CCOC(=O)c1csc(-n2nc(-c3ccccc3)c(Oc3ccc(S(N)(=O)=O)cc3)c2C2CC2)n1] | ethyl 2-(5-cyclopropyl-3-phenyl-4-(4-sulfamoylphenoxy)-1H-pyrazol-1-yl)thiazole-4-carboxylate (M + H)$^+$ = 511 | + | 33 |

TABLE 7-continued

| Cmpd ID | Structure | Compound name and physical data | Inhibitory activity IC$_{50}$ (μM) | Example Method |
|---|---|---|---|---|
| 165 | 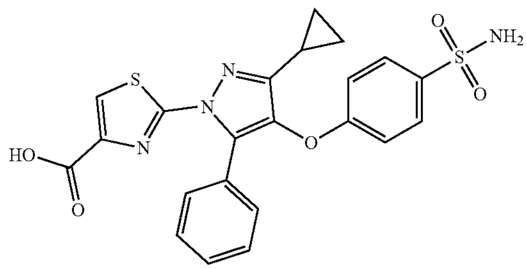 [SMILES: NS(=O)(=O)c1ccc(Oc2c(C3CC3)nn(-c3nc(C(=O)O)cs3)c2-c2ccccc2)cc1] | cyclopropyl-5-phenyl-4-(4-sulfamoylphenoxy)-1H-pyrazol-1-yl)thiazole-4-carboxylic acid (M + H)$^+$ = 483 | + | 33 |
| 166 | 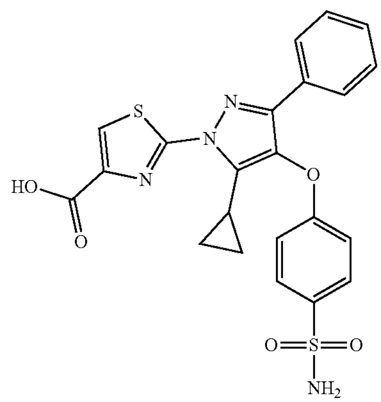 [SMILES: NS(=O)(=O)c1ccc(Oc2c(-c3ccccc3)nn(-c3nc(C(=O)O)cs3)c2C2CC2)cc1] | 2-(5-cyclopropyl-3-phenyl-4-(4-sulfamoylphenoxy)-1H-pyrazol-1-yl)thiazole-4-carboxylic acid 1H NMR (400 MHz, DMSO-d6) δ 13.16 (s, 1H), 8.35 (s, 1H), 7.83-7.71 (m, 4H), 7.45-7.31 (m, 3H), 7.29-7.15 (m, 4H), 3.31 (s, 2H), 2.63 (tt, J = 8.5, 5.5 Hz, 1H), 0.99-0.80 (m, 4H); (M + H)$^+$ = 483 | +++ | 33 |
| 167 | 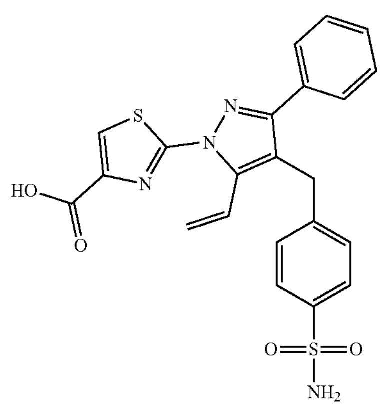 [SMILES: C=Cc1c(Cc2ccc(S(N)(=O)=O)cc2)c(-c2ccccc2)nn1-c1nc(C(=O)O)cs1] | 2-(3-phenyl-4-(4-sulfamoylbenzyl)-5-vinyl-1H-pyrazol-1-yl)thiazole-4-carboxylic acid 1H NMR (400 MHz, DMSO-d6) δ 13.18 (s, 1H), 8.32 (s, 1H), 7.80-7.72 (m, 2H), 7.65 (dd, J = 18.1, 11.9 Hz, 1H), 7.59-7.50 (m, 2H), 7.55-7.26 (m, 8H), 5.63-5.54 (m, 1H), 5.45 (dd, J = 18.1, 1.1 Hz, 1H), 4.21 (s, 2H); (M + H)$^+$ = 467 | +++ | 15 |
| 168 | 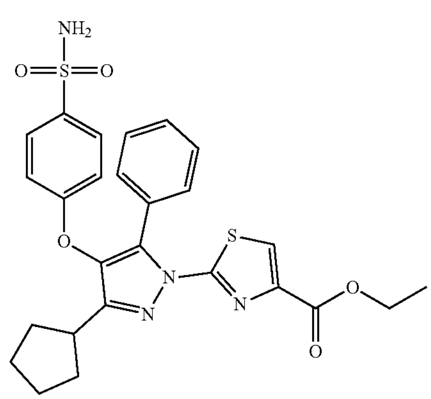 [SMILES: CCOC(=O)c1csc(-n2nc(C3CCCC3)c(Oc3ccc(S(N)(=O)=O)cc3)c2-c2ccccc2)n1] | ethyl 2-(3-cyclopentyl-5-phenyl-4-(4-sulfamoylphenoxy)-1H-pyrazol-1-yl)thiazole-4-carboxylate (M + H)$^+$ = 539 | − | 33 |

TABLE 7-continued

| Cmpd ID | Structure | Compound name and physical data | Inhibitory activity IC$_{50}$ (μM) | Example Method |
|---|---|---|---|---|
| 169 | 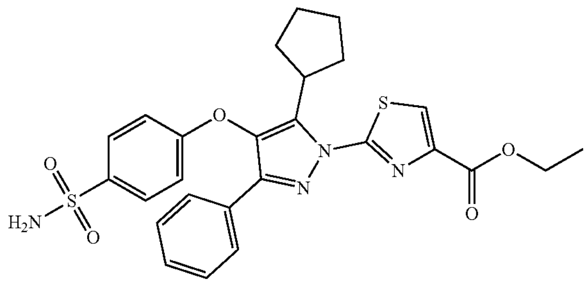 [SMILES: CCOC(=O)c1csc(-n2nc(-c3ccccc3)c(Oc3ccc(S(N)(=O)=O)cc3)c2C2CCCC2)n1] | ethyl 2-(5-cyclopentyl-3-phenyl-4-(4-sulfamoylphenoxy)-1H-pyrazol-1-yl)thiazole-4-carboxylate (M + H)$^+$ = 539 | – | 33 |
| 170 | 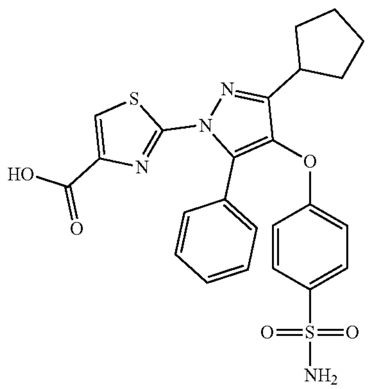 [SMILES: NS(=O)(=O)c1ccc(Oc2c(C3CCCC3)nn(-c3nc(C(=O)O)cs3)c2-c2ccccc2)cc1] | 2-(3-cyclopentyl-5-phenyl-4-(4-sulfamoylphenoxy)-1H-pyrazol-1-yl)thiazole-4-carboxylic acid (M + H)$^+$ = 511 | + | 33 |
| 171 | 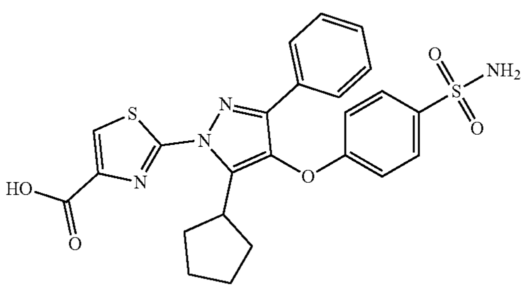 [SMILES: NS(=O)(=O)c1ccc(Oc2c(-c3ccccc3)nn(-c3nc(C(=O)O)cs3)c2C2CCCC2)cc1] | 2-(5-cyclopentyl-3-phenyl-4-(4-sulfamoylphenoxy)-1H-pyrazol-1-yl)thiazole-4-carboxylic acid (M + H)$^+$ = 511 | ++ | 33 |
| 172 | 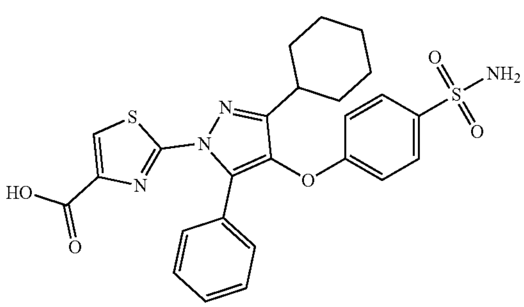 [SMILES: NS(=O)(=O)c1ccc(Oc2c(C3CCCCC3)nn(-c3nc(C(=O)O)cs3)c2-c2ccccc2)cc1] | 2-(3-cyclohexyl-5-phenyl-4-(4-sulfamoylphenoxy)-1H-pyrazol-1-yl)thiazole-4-carboxylic acid (M + H)$^+$ = 525 | + | 33 |
| 173 | 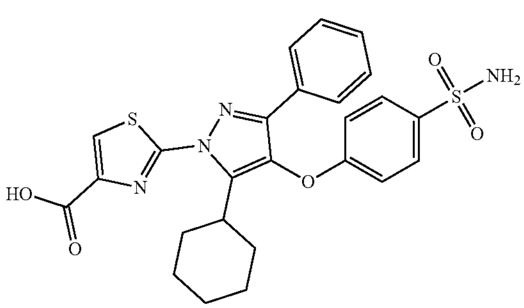 [SMILES: NS(=O)(=O)c1ccc(Oc2c(-c3ccccc3)nn(-c3nc(C(=O)O)cs3)c2C2CCCCC2)cc1] | 2-(5-cyclohexyl-3-phenyl-4-(4-sulfamoylphenoxy)-1H-pyrazol-1-yl)thiazole-4-carboxylic acid (M + H)$^+$ = 525 | + | 33 |

TABLE 7-continued

| Cmpd ID | Structure | Compound name and physical data | Inhibitory activity IC$_{50}$ (μM) | Example Method |
|---|---|---|---|---|
| 174 | 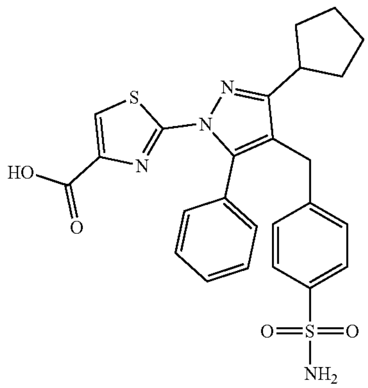 | 2-(3-cyclopentyl-5-phenyl-4-(4-sulfamoylphenoxy)-1H-pyrazol-1-yl)thiazole-4-carboxylic acid (M + H)$^+$ = 508 | + | 49 |
| 175 | 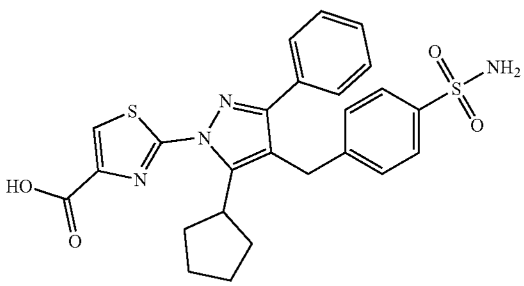 [SMILES: NS(=O)(=O)c1ccc(Cc2c(-c3ccccc3)nn(-c3nc(C(=O)O)cs3)c2C2CCCC2)cc1] | 2-(5-cyclopentyl-3-phenyl-4-(4-sulfamoylbenzyl)-1H-pyrazol-1-yl)thiazole-4-carboxylic acid (M + H)$^+$ = 508 | ++ | 49 |
| 176 | 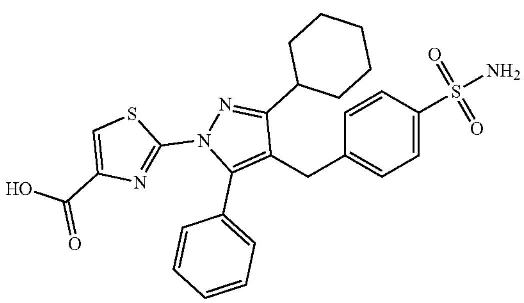 [SMILES: NS(=O)(=O)c1ccc(Cc2c(C3CCCCC3)nn(-c3nc(C(=O)O)cs3)c2-c2ccccc2)cc1] | 2-(3-cyclohexyl-5-phenyl-4-(4-sulfamoylbenzyl)-1H-pyrazol-1-yl)thiazole-4-carboxylic acid (M + H)$^+$ = 523 | + | 49 |
| 177 | 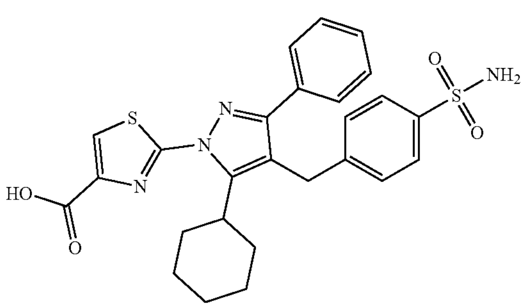 [SMILES: NS(=O)(=O)c1ccc(Cc2c(-c3ccccc3)nn(-c3nc(C(=O)O)cs3)c2C2CCCCC2)cc1] | 2-(5-cyclohexyl-3-phenyl-4-(4-sulfamoylbenzyl)-1H-pyrazol-1-yl)thiazole-4-carboxylic acid (M + H)$^+$ = 523 | + | 49 |

TABLE 7-continued

| Cmpd ID | Structure | Compound name and physical data | Inhibitory activity IC$_{50}$ (μM) | Example Method |
|---|---|---|---|---|
| 178 | 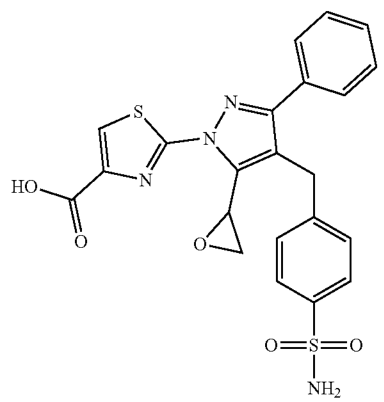 [SMILES: NS(=O)(=O)c1ccc(Cc2c(-c3ccccc3)nn(-c3nc(C(=O)O)cs3)c2C2CO2)cc1] | 2-(5-(oxiran-2-yl)-3-phenyl-4-(4-sulfamoylbenzyl)-1H-pyrazol-1-yl)thiazole-4-carboxylic acid (M + H)$^+$ = 483 | + | 160 |
| 179 | 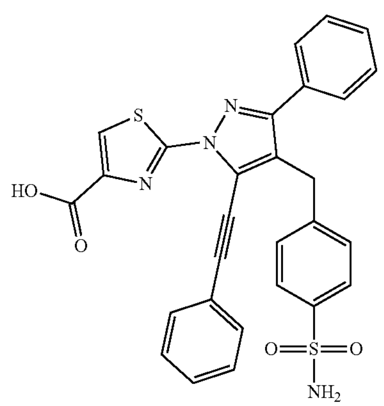 [SMILES: NS(=O)(=O)c1ccc(Cc2c(-c3ccccc3)nn(-c3nc(C(=O)O)cs3)c2C#Cc2ccccc2)cc1] | 2-(3-phenyl-5-(phenylethynyl)-4-(4-sulfamoylbenzyl)-1H-pyrazol-1-yl)thiazole-4-carboxylic acid (M + H)$^+$ = 541 | + | 16 |
| 180 | 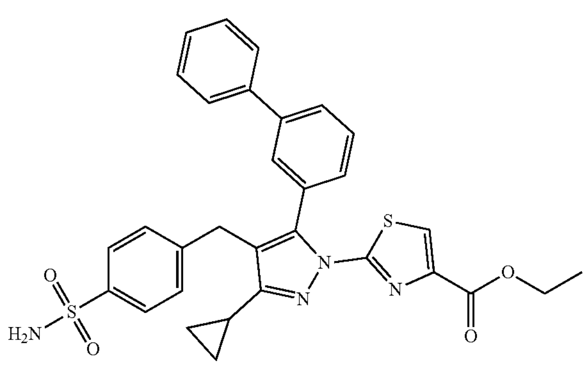 [SMILES: CCOC(=O)c1csc(-n2nc(C3CC3)c(Cc3ccc(S(N)(=O)=O)cc3)c2-c2cccc(-c3ccccc3)c2)n1] | ethyl 2-(5-([1,1'-biphenyl]-3-yl)-3-cyclopropyl-4-(4-sulfamoylbenzyl)-1H-pyrazol-1-yl)thiazole-4-carboxylate (M + H)$^+$ = 585 | − | 49 |

TABLE 7-continued

| Cmpd ID | Structure | Compound name and physical data | Inhibitory activity IC$_{50}$ (μM) | Example Method |
|---|---|---|---|---|
| 181 | 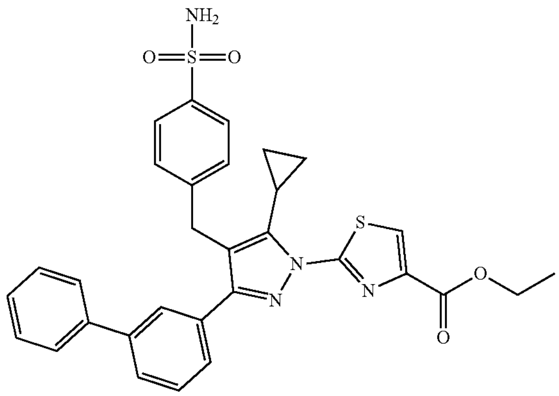 [SMILES: CCOC(=O)c1csc(-n2nc(-c3cccc(-c4ccccc4)c3)c(Cc3ccc(S(N)(=O)=O)cc3)c2C2CC2)n1] | ethyl 2-(3-([1,1'-biphenyl]-3-yl)-5-cyclopropyl-4-(4-sulfamoylbenzyl)-1H-pyrazol-1-yl)thiazole-4-carboxylate<br>1H NMR (400 MHz, DMSO-d6) δ 8.40 (s, 1H), 7.80-7.73 (m, 2H), 7.73-7.47 (m, 4H), 7.47-7.28 (m, 9H), 4.33 (q, J = 7.1 Hz, 2H), 4.20 (s, 2H), 3.35-3.25 (m, 1H), 2.25 (tt, J = 8.5, 5.6 Hz, 1H), 1.33 (t, J = 7.1 Hz, 3H), 1.06-0.96 (m, 2H), 0.75-0.65 (m, 2H);<br>(M + H)$^+$ = 585 | – | 49 |
| 182 | 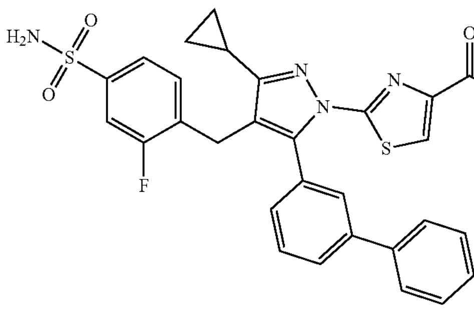 | cyclopropyl-4-(2-fluoro-4-sulfamoylbenzyl)-1H-pyrazol-1-yl)thiazole-4-carboxylic acid<br>(M + H)$^+$ = 575 | + | 49 |
| 183 | 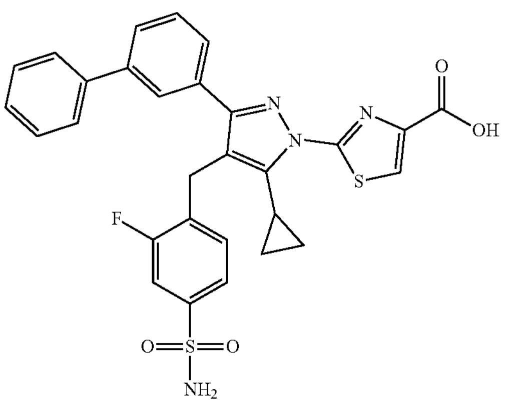 [SMILES: NS(=O)(=O)c1ccc(Cc2c(-c3cccc(-c4ccccc4)c3)nn(-c3nc(C(=O)O)cs3)c2C2CC2)c(F)c1] | 2-(3-([1,1'-biphenyl]-3-yl)-5-cyclopropyl-4-(2-fluoro-4-sulfamoylbenzyl)-1H-pyrazol-1-yl)thiazole-4-carboxylic acid<br>1H NMR (400 MHz, DMSO-d6) δ 13.11 (s, 1H), 8.34 (s, 1H), 7.70 (dt, J = 6.6, 2.1 Hz, 1H), 7.62 (dt, J = 2.7, 1.4 Hz, 2H), 7.61-7.49 (m, 4H), 7.49-7.40 (m, 6H), 7.39-7.33 (m, 1H), 7.28-7.19 (m, 1H), 4.14 (s, 2H), 2.24 (tt, J = 8.5, 5.6 Hz, 1H), 1.13-0.90 (m, 2H), 0.78-0.60 (m, 2H);<br>(M + H)$^+$ = 575 | +++ | 49 |
| 184 | 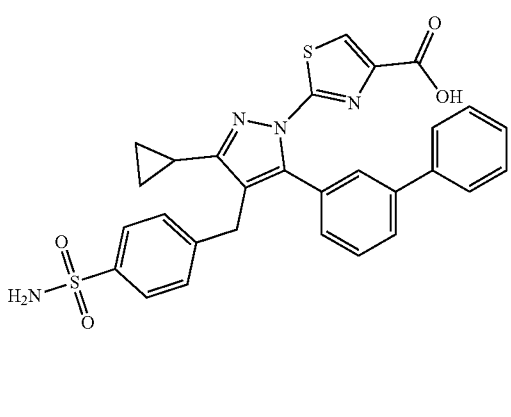 [SMILES: NS(=O)(=O)c1ccc(Cc2c(C3CC3)nn(-c3nc(C(=O)O)cs3)c2-c2cccc(-c3ccccc3)c2)cc1] | 2-(5-([1,1'-biphenyl]-3-yl)-3-cyclopropyl-4-(4-sulfamoylbenzyl)-1H-pyrazol-1-yl)thiazole-4-carboxylic acid<br>(M + H)$^+$ = 557 | + | 49 |

TABLE 7-continued

| Cmpd ID | Structure | Compound name and physical data | Inhibitory activity IC$_{50}$ (μM) | Example Method |
|---|---|---|---|---|
| 185 | 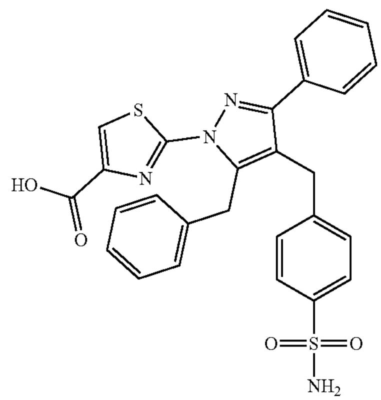 [SMILES: NS(=O)(=O)c1ccc(Cc2c(-c3ccccc3)nn(-c3nc(C(=O)O)cs3)c2Cc2ccccc2)cc1] | 2-(5-benzyl-3-phenyl-4-(4-sulfamoylbenzyl)-1H-pyrazol-1-yl)thiazole-4-carboxylic acid<br>1H NMR (400 MHz, DMSO-d6) δ 13.14 (s, 1H), 7.66-7.53 (m, 4H), 7.45-7.33 (m, 3H), 7.28-7.06 (m, 10H), 4.69 (s, 2H), 4.18 (s, 2H), 4.11-4.03 (m, 1H), 3.17 (d, J = 4.6 Hz, 2H); (M + H)$^+$ = 531 | ++ | 49 |
| 186 | 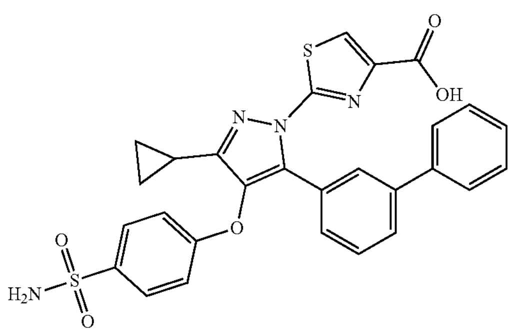 [SMILES: NS(=O)(=O)c1ccc(Oc2c(C3CC3)nn(-c3nc(C(=O)O)cs3)c2-c2cccc(-c3ccccc3)c2)cc1] | 2-(5-([1,1'-biphenyl]-3-yl)-3-cyclopropyl-4-(4-sulfamoylphenoxy)-1H-pyrazol-1-yl)thiazole-4-carboxylic acid<br>(M + H)$^+$ = 559 | + | 33 |
| 187 | 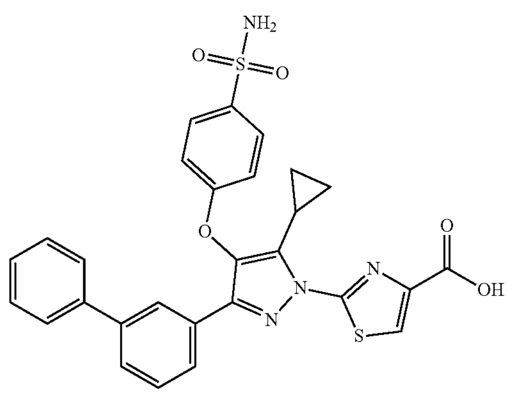 | 2-(3-([1,1'-biphenyl]-3-yl)-5-cyclopropyl-4-(4-sulfamoylphenoxy)-1H-pyrazol-1-yl)thiazole-4-carboxylic acid<br>1H NMR (400 MHz, DMSO-d6) δ 13.17 (s, 1H), 8.36 (s, 1H), 7.93 (td, J = 1.8, 0.5 Hz, 1H), 7.85-7.71 (m, 3H), 7.66 (ddd, J = 7.8, 1.9, 1.1 Hz, 1H), 7.56-7.32 (m, 6H), 7.30-7.21 (m, 4H), 2.73-2.61 (m, 1H), 1.02-0.90 (m, 2H), 0.93-0.83 (m, 2H); (M + H)$^+$ = 559 | +++ | 33 |
| 188 | 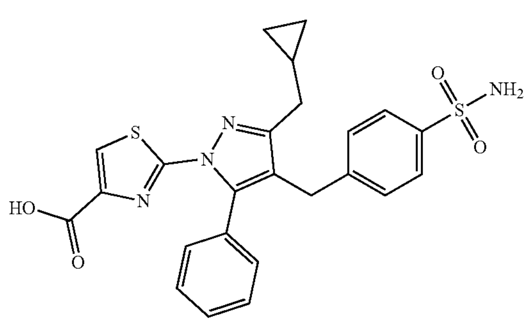 [SMILES: NS(=O)(=O)c1ccc(Cc2c(CC3CC3)nn(-c3nc(C(=O)O)cs3)c2-c2ccccc2)cc1] | 2-(3-(cyclopropylmethyl)-5-phenyl-4-(4-sulfamoylbenzyl)-1H-pyrazol-1-yl)thiazole-4-carboxylic acid<br>(M + H)$^+$ = 495 | ++ | 141 |

TABLE 7-continued

| Cmpd ID | Structure | Compound name and physical data | Inhibitory activity IC$_{50}$ (μM) | Example Method |
|---|---|---|---|---|
| 189 | 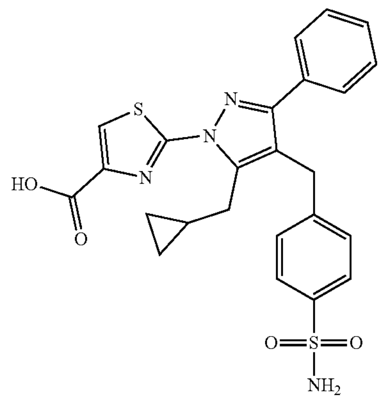 [SMILES: NS(=O)(=O)c1ccc(Cc2c(-c3ccccc3)nn(-c3nc(C(=O)O)cs3)c2CC2CC2)cc1] | 2-(5-(cyclopropylmethyl)-3-phenyl-4-(4-sulfamoylbenzyl)-1H-pyrazol-1-yl)thiazole-4-carboxylic acid (M + H)$^+$ = 495 | +++ | 141 |
| 190 | 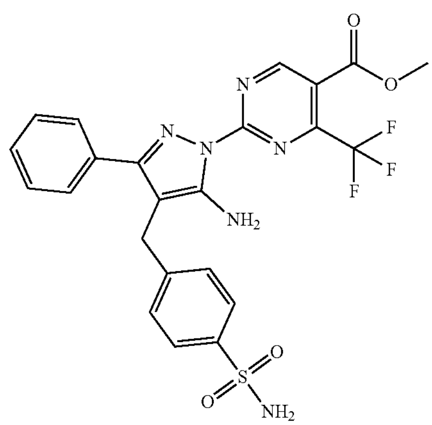 [SMILES: COC(=O)c1cnc(-n2nc(-c3ccccc3)c(Cc3ccc(S(N)(=O)=O)cc3)c2N)nc1C(F)(F)F] | methyl 2-(5-amino-3-phenyl-4-(4-sulfamoylbenzyl)-1H-pyrazol-1-yl)-4-(trifluoromethyl)pyrimidine-5-carboxylate | − | 148 |
| 191 | 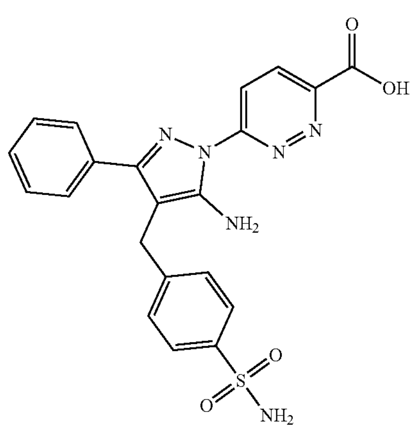 [SMILES: Nc1c(Cc2ccc(S(N)(=O)=O)cc2)c(-c2ccccc2)nn1-c1ccc(C(=O)O)nn1] | 6-(5-amino-3-phenyl-4-(4-sulfamoylbenzyl)-1H-pyrazol-1-yl)pyridazine-3-carboxylic acid | − | 148 |

TABLE 7-continued

| Cmpd ID | Structure | Compound name and physical data | Inhibitory activity IC$_{50}$ (μM) | Example Method |
|---|---|---|---|---|
| 192 | 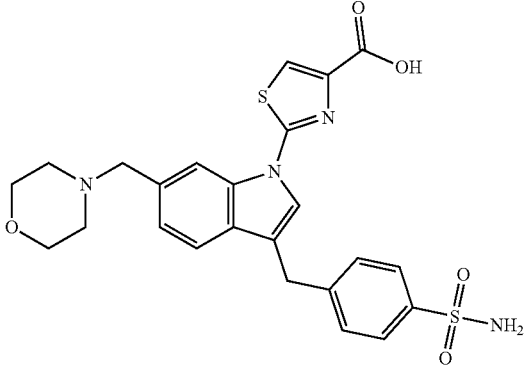 [SMILES: NS(=O)(=O)c1ccc(Cc2cn(-c3nc(C(=O)O)cs3)c3cc(CN4CCOCC4)ccc23)cc1] | 2-(6-(morpholinomethyl)-3-(4-sulfamoylbenzyl)-1H-indol-1-yl)thiazole-4-carboxylic acid, NH3 $^1$H NMR (400 MHz, DMSO-d$_6$) δ 8.13 (s, 1H), 7.76-7.71 (m, 2H), 7.69 (s, 1H), 7.56-7.50 (m, 2H), 7.50-7.46 (m, 1H), 7.45 (s, 1H), 7.23 (s, 2H), 7.14 (dd, J = 8.1, 1.4 Hz, 1H), 4.15 (s, 2H), 3.55 (dd, J = 8.9, 4.4 Hz, 6H), 2.34 (t, J = 4.6 Hz, 4H) (acid OH not shown); MS (M + H)$^+$ = 513 | ++ | 41 |
| 193 | 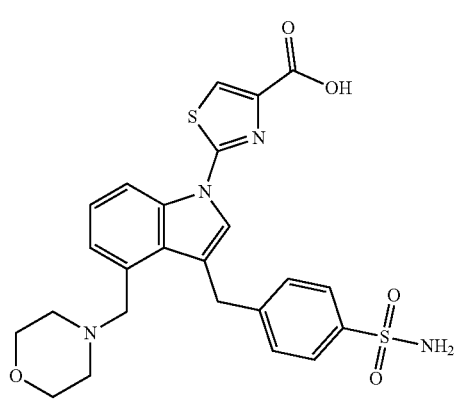 [SMILES: NS(=O)(=O)c1ccc(Cc2cn(-c3nc(C(=O)O)cs3)c3cccc(CN4CCOCC4)c23)cc1] | 2-(4-(morpholinomethyl)-3-(4-sulfamoylbenzyl)-1H-indol-1-yl)thiazole-4-carboxylic acid, NH3 $^1$H NMR (400 MHz, DMSO-d$_6$) δ 8.27 (d, J = 8.4 Hz, 1H), 7.79-7.70 (m, 2H), 7.48 (s, 1H), 7.46 (s, 1H), 7.41-7.34 (m, 2H), 7.31-7.23 (m, 3H), 7.06 (dd, J = 7.3, 1.0 Hz, 1H), 4.51 (s, 2H), 3.51 (dd, J = 9.5, 4.9 Hz, 6H), 2.35-2.21 (m, 4H) (acid OH not shown); MS (M + H)$^+$ = 513 | ++ | 41 |
| 194 | 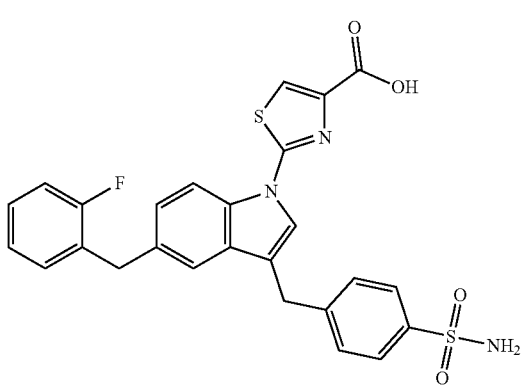 [SMILES: NS(=O)(=O)c1ccc(Cc2cn(-c3nc(C(=O)O)cs3)c3ccc(Cc4ccccc4F)cc23)cc1] | 2-(5-(2-fluorobenzyl)-3-(4-sulfamoylbenzyl)-1H-indol-1-yl)thiazole-4-carboxylic acid, NH3 $^1$H NMR (400 MHz, DMSO-d$_6$) δ 8.23-8.17 (m, 1H), 8.03 (s, 1H), 7.74 (s, 1H), 7.73-7.67 (m, 2H), 7.52-7.45 (m, 2H), 7.42 (d, J = 1.6 Hz, 1H), 7.23 (m, 5H), 7.17-7.05 (m, 2H), 4.12 (s, 2H), 4.02 (s, 2H) (acid OH not shown); MS (M + H)$^+$ = 522 | ++ | 40 |

TABLE 7-continued

| Cmpd ID | Structure | Compound name and physical data | Inhibitory activity IC$_{50}$ (μM) | Example Method |
|---|---|---|---|---|
| 195 | 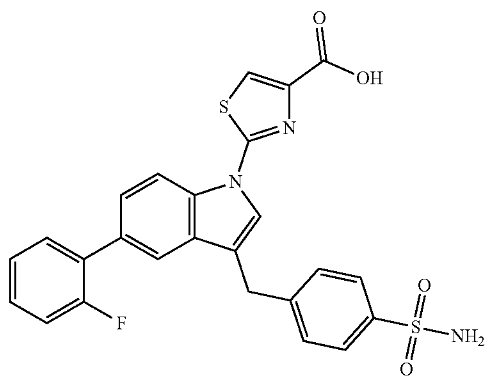 [SMILES: NS(=O)(=O)c1ccc(Cc2cn(-c3nc(C(=O)O)cs3)c3ccc(-c4ccccc4F)cc23)cc1] | 2-(5-(2-fluorophenyl)-3-(4-sulfamoylbenzyl)-1H-indol-1-yl)thiazole-4-carboxylic acid $^1$H NMR (400 MHz, DMSO-d$_6$) δ 13.14 (s, 1H), 8.42 (dd, J = 8.6, 0.6 Hz, 1H), 8.22 (s, 1H), 7.89 (s, 1H), 7.77-7.68 (m, 3H), 7.59-7.54 (m, 3H), 7.52 (td, J = 7.8, 1.7 Hz, 1H), 7.39 (tdd, J = 7.8, 5.1, 1.8 Hz, 1H), 7.33-7.24 (m, 2H), 7.21 (s, 2H), 4.22 (s, 2H); MS (M + H)$^+$ = 508 | +++ | 40 |
| 196 | 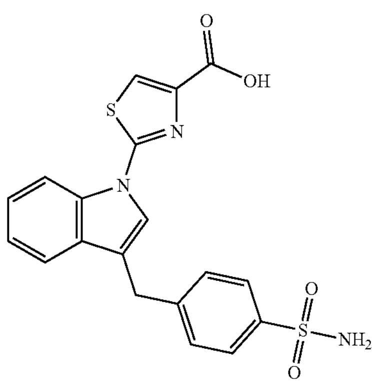 [SMILES: NS(=O)(=O)c1ccc(Cc2cn(-c3nc(C(=O)O)cs3)c3ccccc23)cc1] | 2-(3-(4-sulfamoylbenzyl)-1H-indol-1-yl)thiazole-4-carboxylic acid $^1$H NMR (400 MHz, DMSO-d$_6$) δ 13.13 (s, 1H), 8.34 (dt, J = 8.4, 0.9 Hz, 1H), 8.18 (s, 1H), 7.83 (s, 1H), 7.75-7.67 (m, 2H), 7.57-7.48 (m, 3H), 7.37 (ddd, J = 8.4, 7.1, 1.2 Hz, 1H), 7.22 (s, 2H), 7.21-7.16 (m, 1H), 4.18 (s, 2H); MS (M + H)$^+$ = 414 | ++ | 40 |
| 197 | 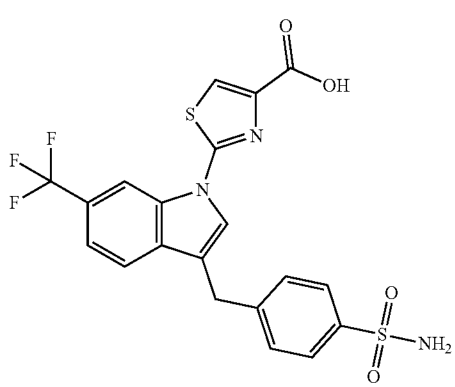 [SMILES: NS(=O)(=O)c1ccc(Cc2cn(-c3nc(C(=O)O)cs3)c3cc(C(F)(F)F)ccc23)cc1] | 2-(3-(4-sulfamoylbenzyl)-6-(trifluoromethyl)-1H-indol-1-yl)thiazole-4-carboxylic acid $^1$H NMR (400 MHz, DMSO-d$_6$) δ 13.20 (s, 1H), 8.79 (dd, J = 1.7, 0.9 Hz, 1H), 8.20 (s, 1H), 8.11 (s, 1H), 7.78-7.68 (m, 3H), 7.59-7.49 (m, 3H), 7.23 (s, 2H), 4.23 (s, 2H); MS (M + H)$^+$ = 482 | ++ | 40 |

TABLE 7-continued

| Cmpd ID | Structure | Compound name and physical data | Inhibitory activity IC$_{50}$ (μM) | Example Method |
|---|---|---|---|---|
| 198 | 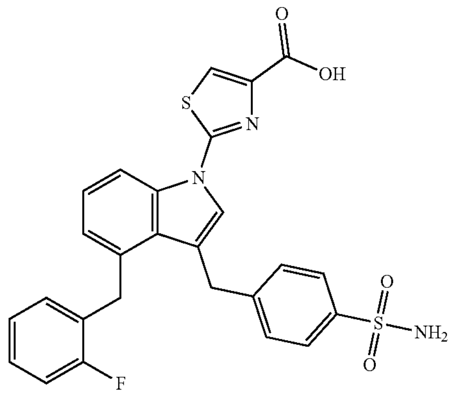 [SMILES: NS(=O)(=O)c1ccc(Cc2cn(-c3nc(C(=O)O)cs3)c3cccc(Cc4ccccc4F)c23)cc1] | 2-(4-(2-fluorobenzyl)-3-(4-sulfamoylbenzyl)-1H-indol-1-yl)thiazole-4-carboxylic acid<br>$^1$H NMR (400 MHz, DMSO-d$_6$) δ 13.15 (s, 1H), 8.34 (dd, J = 8.4, 0.9 Hz, 1H), 8.18 (s, 1H), 7.75-7.70 (m, 2H), 7.69 (s, 1H), 7.35-7.21 (m, 6H), 7.17 (ddd, J = 9.6, 8.2, 1.3 Hz, 1H), 7.04 (td, J = 7.4, 1.3 Hz, 1H), 6.81 (d, J = 7.4 Hz, 1H), 6.78-6.71 (m, 1H), 4.17 (s, 2H), 4.14 (s, 2H); MS (M + H)$^+$ = 522 | ++ | 40 |
| 199 | 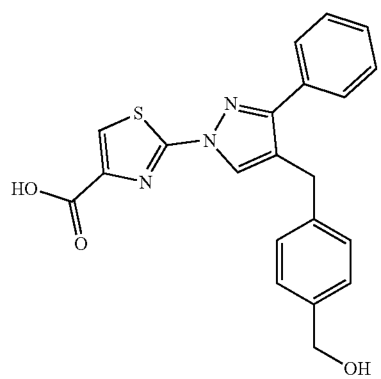 [SMILES: O=C(O)c1csc(-n2cc(Cc3ccc(CO)cc3)c(-c3ccccc3)n2)n1] | 2-(4-(4-(hydroxymethyl)benzyl)-3-phenyl-1H-pyrazol-1-yl)thiazole-4-carboxylic acid<br>$^1$H NMR (400 MHz, DMSO-d$_6$) δ 13.15 (s, 1H), 8.20 (s, 1H), 8.11 (s, 1H), 7.73-7.65 (m, 2H), 7.50-7.36 (m, 3H), 7.27-7.15 (m, 4H), 5.07 (t, J = 5.8 Hz, 1H), 4.44 (d, J = 5.5 Hz, 2H), 4.02 (s, 2H); MS (M + H)$^+$ = 392 | – | 28 |
| 200 | 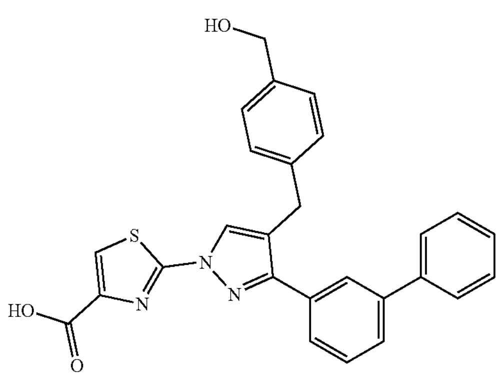 [SMILES: O=C(O)c1csc(-n2cc(Cc3ccc(CO)cc3)c(-c3cccc(-c4ccccc4)c3)n2)n1] | 2-(3-([1,1'-biphenyl]-3-yl)-4-(4-(hydroxymethyl)benzyl)-1H-pyrazol-1-yl)thiazole-4-carboxylic acid<br>$^1$H NMR (400 MHz, DMSO-d$_6$) δ 13.16 (s, 1H), 8.21 (d, J = 2.9 Hz, 2H), 7.83 (t, J = 1.8 Hz, 1H), 7.70 (ddt, J = 7.7, 6.0, 1.4 Hz, 2H), 7.61-7.49 (m, 3H), 7.44 (s, 1H), 7.45-7.31 (m, 2H), 7.29-7.17 (m, 4H), 5.09 (t, J = 5.8 Hz, 1H), 4.45 (d, J = 5.3 Hz, 2H), 4.09 (s, 2H); MS (M + H)$^+$ = 468 | + | 29 |

TABLE 7-continued

| Cmpd ID | Structure | Compound name and physical data | Inhibitory activity IC$_{50}$ (μM) | Example Method |
|---|---|---|---|---|
| 201 | 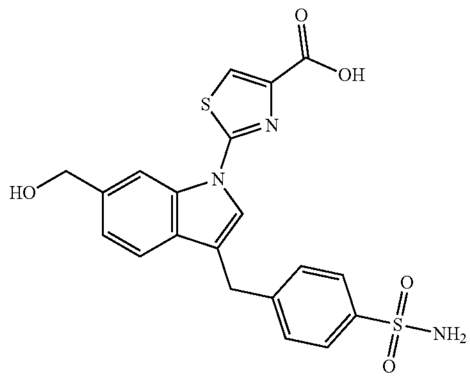 [SMILES: NS(=O)(=O)c1ccc(Cc2cn(-c3nc(C(=O)O)cs3)c3cc(CO)ccc23)cc1] | 2-(6-(hydroxymethyl)-3-(4-sulfamoylbenzyl)-1H-indol-1-yl)thiazole-4-carboxylic acid <br> $^1$H NMR (400 MHz, DMSO-d$_6$) δ 13.11 (s, 1H), 8.27-8.23 (m, 1H), 8.19 (s, 1H), 7.79 (d, J = 0.9 Hz, 1H), 7.74-7.69 (m, 2H), 7.55-7.49 (m, 2H), 7.49-7.43 (m, 1H), 7.22 (s, 2H), 7.15 (dd, J = 8.1, 1.4 Hz, 1H), 5.22 (t, J = 5.7 Hz, 1H), 4.59 (d, J = 4.6 Hz, 2H), 4.16 (s, 2H); MS (M + H)$^+$ = 444 | ++ | 40 |
| 202 | 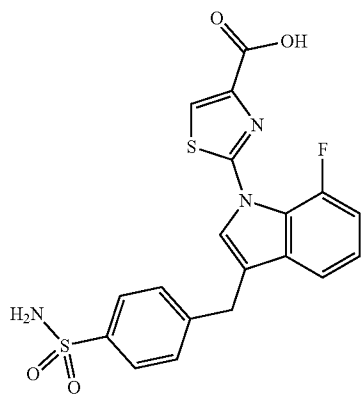 [SMILES: NS(=O)(=O)c1ccc(Cc2cn(-c3nc(C(=O)O)cs3)c3c(F)cccc23)cc1] | 2-(7-fluoro-3-(4-sulfamoylbenzyl)-1H-indol-1-yl)thiazole-4-carboxylic acid <br> $^1$H NMR (400 MHz, DMSO-d$_6$) δ 13.16 (s, 1H), 8.37 (s, 1H), 7.72 (m, 3H), 7.52 (d, J = 7.5 Hz, 2H), 7.39 (d, J = 7.5 Hz, 1H), 7.24 (s, 2H), 7.21-7.07 (m, 2H), 4.17 (s, 2H); MS (M + H)$^+$ = 432 | ++ | 40 |
| 203 | 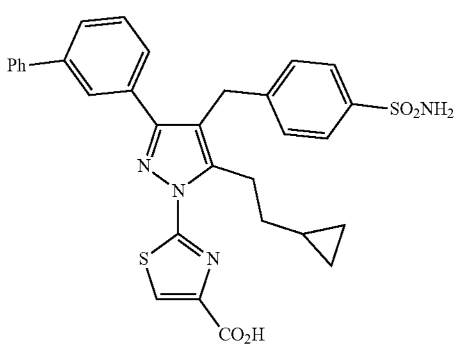 [SMILES: NS(=O)(=O)c1ccc(Cc2c(-c3cccc(-c4ccccc4)c3)nn(-c3nc(C(=O)O)cs3)c2CCC2CC2)cc1] | 2-(3-([1,1'-biphenyl]-3-yl)-5-(2-cyclopropylethyl)-4-(4-sulfamoylbenzyl)-1H-pyrazol-1-yl)thiazole-4-carboxylic acid (M + H)$^+$ = 585 | +++ | 49 |
| 204 | 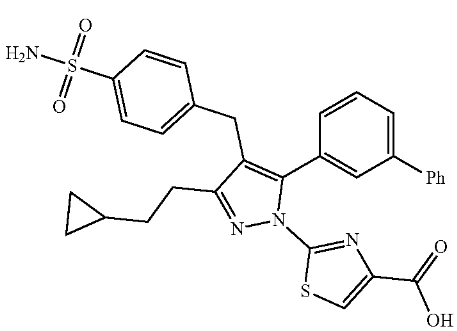 [SMILES: NS(=O)(=O)c1ccc(Cc2c(CCC3CC3)nn(-c3nc(C(=O)O)cs3)c2-c2cccc(-c3ccccc3)c2)cc1] | 2-(5-([1,1'-biphenyl]-3-yl)-3-(2-cyclopropylethyl)-4-(4-sulfamoylbenzyl)-1H-pyrazol-1-yl)thiazole-4-carboxylic acid (M + H)$^+$ = 585 | + | 49 |

TABLE 7-continued

| Cmpd ID | Structure | Compound name and physical data | Inhibitory activity IC$_{50}$ (μM) | Example Method |
|---|---|---|---|---|
| 205 | 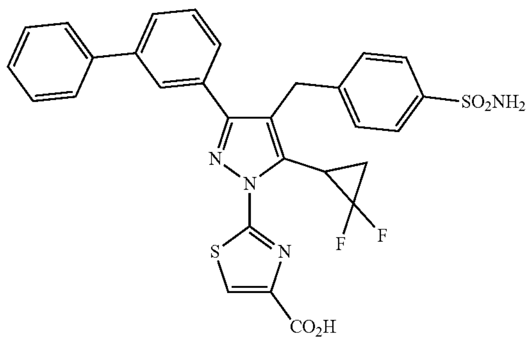 [SMILES: NS(=O)(=O)c1ccc(Cc2c(-c3cccc(-c4ccccc4)c3)nn(-c3nc(C(=O)O)cs3)c2C2CC2(F)F)cc1] | 2-(3-([1,1'-biphenyl]-difluorocyclopropyl)-4-(4-sulfamoylbenzyl)-1H-pyrazol-1-yl)thiazole-4-carboxylic acid<br>$^1$H NMR (400 MHz, DMSO-d6) δ 13.29-12.98 (m, 1H), 8.34 (s, 1H), 7.78-7.73 (m, 2H), 7.73-7.66 (m, 2H), 7.63-7.49 (m, 2H), 7.49-7.40 (m, 4H), 7.39-7.32 (m, 3H), 7.30 (s, 2H), 4.22 (s, 2H), 3.30-3.24 (m, 1H), 2.24-1.98 (m, 1H), 1.81-1.60 (m, 1H); (M + H)$^+$ = 593 | +++ | 49 |
| 206 | 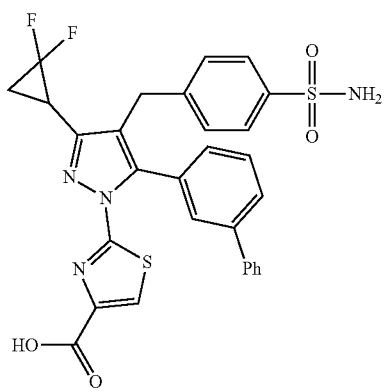 [SMILES: NS(=O)(=O)c1ccc(Cc2c(C3CC3(F)F)nn(-c3nc(C(=O)O)cs3)c2-c2cccc(-c3ccccc3)c2)cc1] | 2-(5-([1,1'-biphenyl]-3-yl)-3-(2,2-difluorocyclopropyl)-4-(4-sulfamoylbenzyl)-1H-pyrazol-1-yl)thiazole-4-carboxylic acid<br>(M + H)$^+$ = 593 | + | 49 |
| 207 | 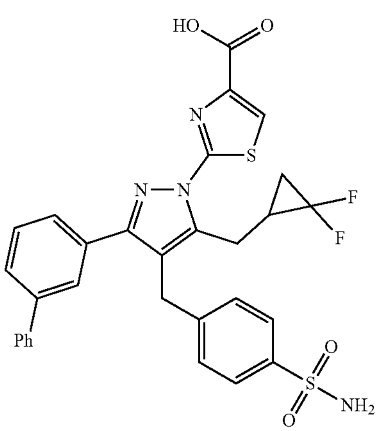 [SMILES: NS(=O)(=O)c1ccc(Cc2c(-c3cccc(-c4ccccc4)c3)nn(-c3nc(C(=O)O)cs3)c2CC2CC2(F)F)cc1] | 2-(3-([1,1'-biphenyl]-3-yl)-5-((2,2-difluorocyclopropyl)methyl)-4-(4-sulfamoylbenzyl)-1H-pyrazol-1-yl)thiazole-4-carboxylic acid<br>$^1$H NMR (400 MHz, DMSO-d6) δ 13.17 (s, 1H), 8.30 (s, 1H), 7.77-7.67 (m, 4H), 7.61 (dt, J = 7.8, 1.4 Hz, 1H), 7.52 (td, J = 7.6, 0.8 Hz, 1H), 7.48-7.40 (m, 4H), 7.38-7.33 (m, 3H), 7.30 (s, 2H), 4.19 (s, 2H), 3.40 (td, J = 19.2, 17.2, 7.3 Hz, 2H), 2.28-2.11 (m, 1H), 1.55-1.32 (m, 1H); (M + H)$^+$ = 607 | +++ | 49 |

TABLE 7-continued

| Cmpd ID | Structure | Compound name and physical data | Inhibitory activity IC$_{50}$ (μM) | Example Method |
|---|---|---|---|---|
| 208 | 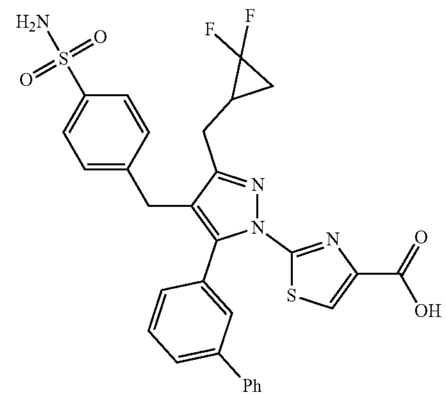 [SMILES: NS(=O)(=O)c1ccc(Cc2c(CC3CC3(F)F)nn(-c3nc(C(=O)O)cs3)c2-c2cccc(-c3ccccc3)c2)cc1] | 2-(5-([1,1'-biphenyl]-3-yl)-5-((2,2-difluorocyclopropyl)methyl)-4-(4-sulfamoylbenzyl)-1H-pyrazol-1-yl)thiazole-4-carboxylic acid (M + H)⁺ = 607 | + | 49 |
| 209 | 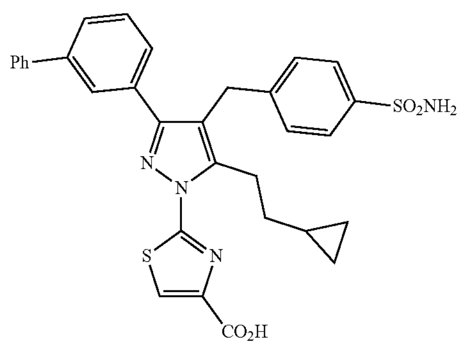 [SMILES: NS(=O)(=O)c1ccc(Cc2c(-c3cccc(-c4ccccc4)c3)nn(-c3nc(C(=O)O)cs3)c2CCC2CC2)cc1] | 2-(3-([1,1'-biphenyl]-3-yl)-5-(2-cyclopropylethyl)-4-(4-sulfamoylbenzyl)-1H-pyrazol-1-yl)thiazole-4-carboxylic acid (M + H)⁺ = 585 | +++ | 49 |
| 210 | 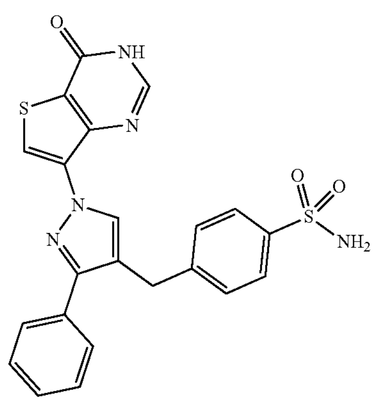 [SMILES: NS(=O)(=O)c1ccc(Cc2cn(-c3csc4c(=O)[nH]cnc34)nc2-c2ccccc2)cc1] | 4-((1-(4-oxo-3,4-dihydrothieno[3,2-d]pyrimidin-7-yl)-3-phenyl-1H-pyrazol-4-yl)methyl)benzenesulfonamide ¹H NMR (400 MHz, DMSO-d6) δ 12.79 (s, 1H), 8.71 (s, 1H), 8.35 (s, 1H), 8.27 (s, 1H), 7.74-7.68 (m, 2H), 7.68-7.62 (m, 2H), 7.45-7.39 (m, 2H), 7.39-7.34 (m, 3H), 7.25 (s, 2H), 4.16 (s, 2H); MS (M + H)⁺ = 464 | − | 51 |
| 211 | 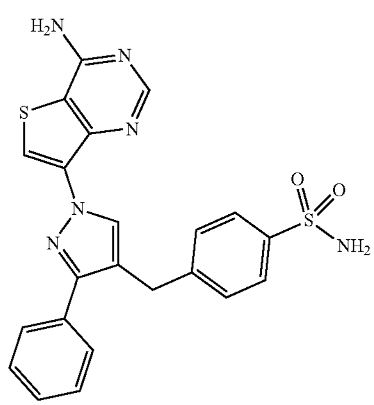 [SMILES: Nc1ncnc2c(-n3cc(Cc4ccc(S(N)(=O)=O)cc4)c(-c4ccccc4)n3)csc12] | 4-((1-(4-aminothieno[3,2-d]pyrimidin-7-yl)-3-phenyl-1H-pyrazol-4-yl)methyl)benzenesulfonamide, TFA ¹H NMR (400 MHz, DMSO-d6) δ 8.92 (d, J = 4.9 Hz, 1H), 8.47 (d, J = 1.6 Hz, 1H), 8.32 (d, J = 2.2 Hz, 1H), 7.87 (s, 2H), 7.69 (m, 4H), 7.49-7.30 (m, 5H), 7.26 (s, 2H), 4.17 (s, 2H); MS (M + H)⁺ = 463 | + | 52 |

TABLE 7-continued

| Cmpd ID | Structure | Compound name and physical data | Inhibitory activity IC$_{50}$ (μM) | Example Method |
|---|---|---|---|---|
| 212 | 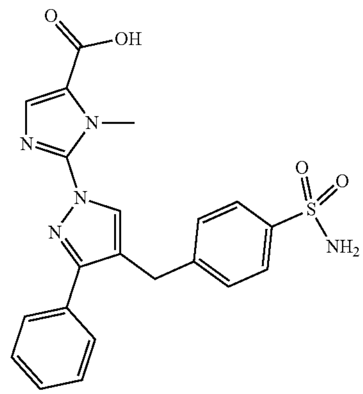 [SMILES: Cn1c(C(=O)O)cnc1-n1cc(Cc2ccc(S(N)(=O)=O)cc2)c(-c2ccccc2)n1] | 1-methyl-2-(3-phenyl-4-(4-sulfamoylbenzyl)-1H-pyrazol-1-yl)-1H-imidazole-5-carboxylic acid, TFA; MS (M + H)$^+$ = 438 | – | 53 |
| 213 | 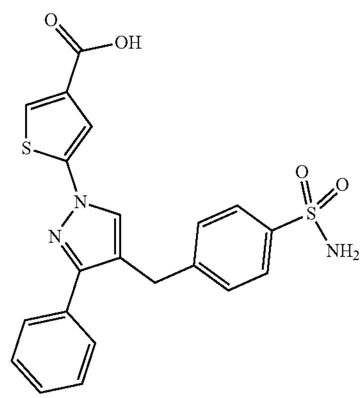 [SMILES: NS(=O)(=O)c1ccc(Cc2cn(-c3cc(C(=O)O)cs3)nc2-c2ccccc2)cc1] | 5-(3-phenyl-4-(4-sulfamoylbenzyl)-1H-pyrazol-1-yl)thiophene-3-carboxylic acid, TFA $^1$H NMR (400 MHz, DMSO-d6) δ 12.88 (s, 1H), 8.45 (s, 1H), 7.96 (d, J = 1.6 Hz, 1H), 7.73-7.66 (m, 2H), 7.63-7.55 (m, 3H), 7.44-7.32 (m, 5H), 7.26 (s, 2H), 4.08 (s, 2H); MS (M + H)$^+$ = 440 | + | 54 |
| 214 | 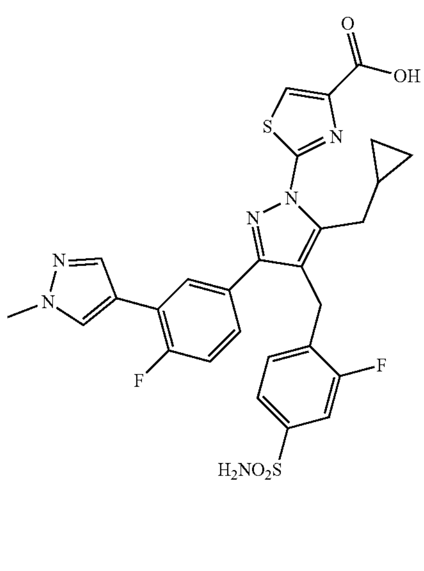 [SMILES: Cn1cc(-c2cc(-c3nn(-c4nc(C(=O)O)cs4)c(CC4CC4)c3Cc3ccc(S(N)(=O)=O)cc3F)ccc2F)cn1] | 2-(5-(cyclopropylmethyl)-3-(4-fluoro-3-(1-methyl-1H-pyrazol-4-yl)phenyl)-4-(2-fluoro-4-sulfamoylbenzyl)-1H-pyrazol-1-yl)thiazole-4-carboxylic acid, TFA $^1$H NMR (400 MHz, DMSO-d6) δ 13.15 (s, 1H), 8.29 (s, 1H), 8.01 (d, J = 2.1 Hz, 1H), 7.78-7.72 (m, 2H), 7.52 (dd, J = 9.6, 1.8 Hz, 1H), 7.46 (dd, J = 8.0, 1.8 Hz, 1H), 7.40 (s, 2H), 7.34 (ddd, J = 8.5, 5.0, 2.2 Hz, 1H), 7.26 (dd, J = 11.0, 8.5 Hz, 1H), 7.12 (t, J = 7.8 Hz, 1H), 4.10 (s, 2H), 3.85 (s, 3H), 3.15 (d, J = 7.0 Hz, 2H), 1.14-1.01 (m, 1H), 0.37-0.14 (m, 4H); MS (M + H)$^+$ = 611 | +++ | 55 |

TABLE 7-continued

| Cmpd ID | Structure | Compound name and physical data | Inhibitory activity IC$_{50}$ (μM) | Example Method |
|---|---|---|---|---|
| 215 | 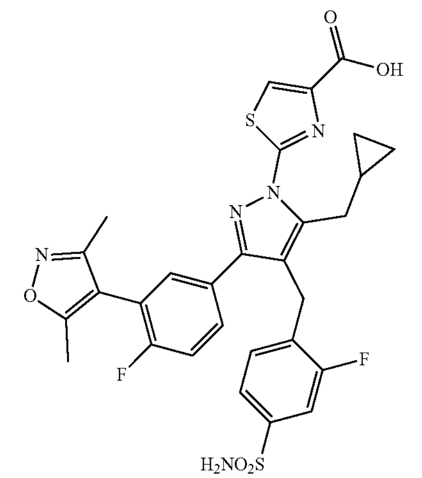 [SMILES: Cc1noc(C)c1-c1cc(-c2nn(-c3nc(C(=O)O)cs3)c(CC3CC3)c2Cc2ccc(S(N)(=O)=O)cc2F)ccc1F] | 2-(5-(cyclopropylmethyl)-3-(3-(3,5-dimethylisoxazol-4-yl)-4-fluorophenyl)-4-(2-fluoro-4-sulfamoylbenzyl)-1H-pyrazol-1-yl)thiazole-4-carboxylic acid, TFA MS (M + H)$^+$ = 626 | +++ | 56 |
| 216 | 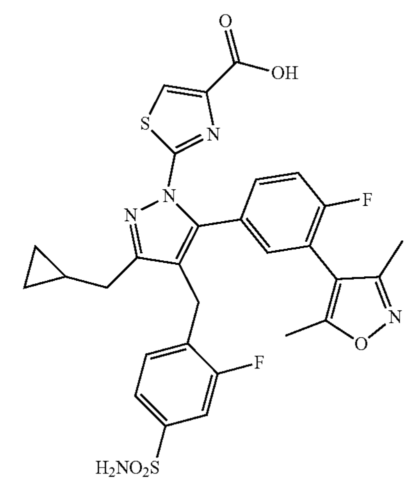 [SMILES: Cc1noc(C)c1-c1cc(-c2c(Cc3ccc(S(N)(=O)=O)cc3F)c(CC3CC3)nn2-c2nc(C(=O)O)cs2)ccc1F] | 2-(3-(cyclopropylmethyl)-5-(3-(3,5-dimethylisoxazol-4-yl)-4-fluorophenyl)-4-(2-fluoro-4-sulfamoylbenzyl)-1H-pyrazol-1-yl)thiazole-4-carboxylic acid, TFA MS (M + H)$^+$ = 626 | − | 56 |
| 217 | 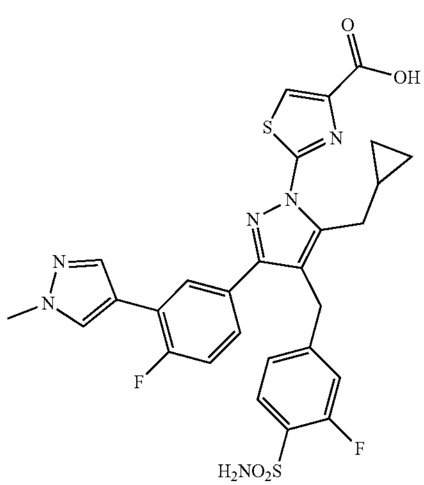 [SMILES: Cn1cc(-c2cc(-c3nn(-c4nc(C(=O)O)cs4)c(CC4CC4)c3Cc3ccc(S(N)(=O)=O)c(F)c3)ccc2F)cn1] | 2-(5-(cyclopropylmethyl)-3-(4-fluoro-3-(1-methyl-1H-pyrazol-4-yl)phenyl)-4-(3-fluoro-4-sulfamoylbenzyl)-1H-pyrazol-1-yl)thiazole-4-carboxylic acid, TFA MS (M + H)$^+$ = 611 | +++ | 57 |

TABLE 7-continued

| Cmpd ID | Structure | Compound name and physical data | Inhibitory activity IC$_{50}$ (μM) | Example Method |
|---|---|---|---|---|
| 218 | 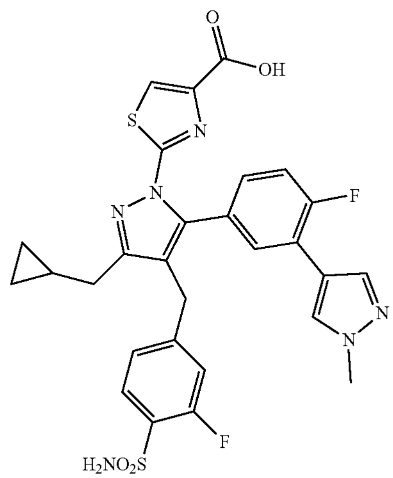 [SMILES: Cn1cc(-c2cc(-c3c(Cc4ccc(S(N)(=O)=O)c(F)c4)c(CC4CC4)nn3-c3nc(C(=O)O)cs3)ccc2F)cn1] | 2-(3-(cyclopropylmethyl)-5-(4-fluoro-3-(1-methyl-1H-pyrazol-4-yl)phenyl)-4-(3-fluoro-4-sulfamoylbenzyl)-1H-pyrazol-1-yl)thiazole-4-carboxylic acid, TFA MS (M + H)$^+$ = 611 | – | 57 |
| 219 | 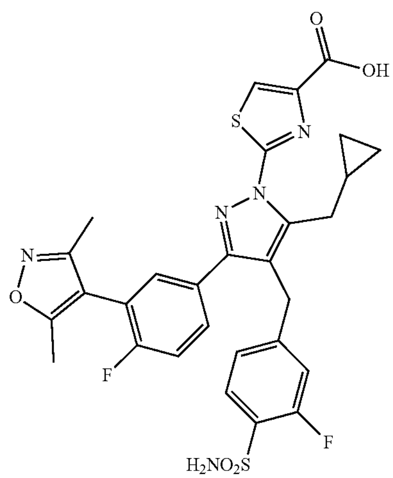 [SMILES: Cc1noc(C)c1-c1cc(-c2nn(-c3nc(C(=O)O)cs3)c(CC3CC3)c2Cc2ccc(S(N)(=O)=O)c(F)c2)ccc1F] | 2-(5-(cyclopropylmethyl)-3-(3-(3,5-dimethylisoxazol-4-yl)-4-fluorophenyl)-4-(3-fluoro-4-sulfamoylbenzyl)-1H-pyrazol-1-yl)thiazole-4-carboxylic acid, TFA MS (M + H)$^+$ = 626 | +++ | 58 |
| 220 | 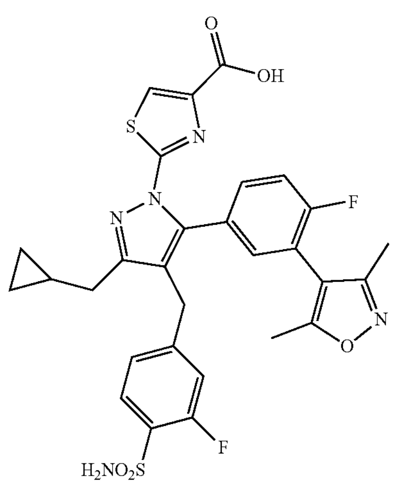 [SMILES: Cc1noc(C)c1-c1cc(-c2c(Cc3ccc(S(N)(=O)=O)c(F)c3)c(CC3CC3)nn2-c2nc(C(=O)O)cs2)ccc1F] | 2-(3-(cyclopropylmethyl)-5-(3-(3,5-dimethylisoxazol-4-yl)-4-fluorophenyl)-4-(3-fluoro-4-sulfamoylbenzyl)-1H-pyrazol-1-yl)thiazole-4-carboxylic acid, TFA MS (M + H)$^+$ = 626 | – | 58 |

TABLE 7-continued

| Cmpd ID | Structure | Compound name and physical data | Inhibitory activity IC$_{50}$ (μM) | Example Method |
|---|---|---|---|---|
| 221 | 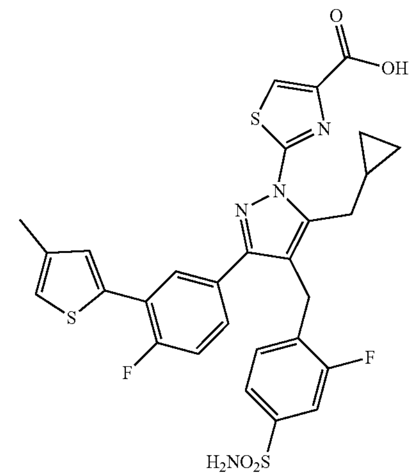 [SMILES: Cc1csc(-c2cc(-c3nn(-c4nc(C(=O)O)cs4)c(CC4CC4)c3Cc3ccc(S(N)(=O)=O)cc3F)ccc2F)c1] | 2-(5-(cyclopropylmethyl)-3-(4-fluoro-3-(4-methylthiophen-2-yl)phenyl)-4-(2-fluoro-4-sulfamoylbenzyl)-1H-pyrazol-1-yl)thiazole-4-carboxylic acid, TFA MS (M + H)$^+$ = 627 | +++ | 59 |
| 222 | 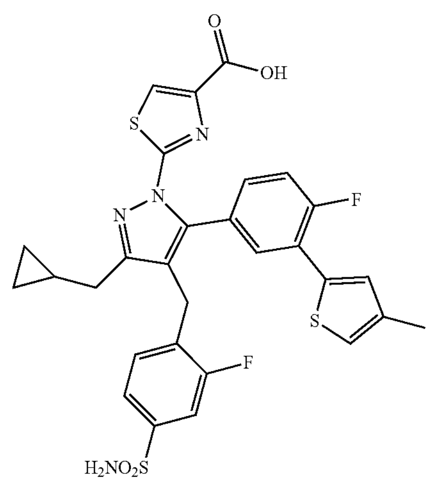 [SMILES: Cc1csc(-c2cc(-c3c(Cc4ccc(S(N)(=O)=O)cc4F)c(CC4CC4)nn3-c3nc(C(=O)O)cs3)ccc2F)c1] | 2-(3-(cyclopropylmethyl)-5-(4-fluoro-3-(4-methylthiophen-2-yl)phenyl)-4-(2-fluoro-4-sulfamoylbenzyl)-1H-pyrazol-1-yl)thiazole-4-carboxylic acid, TFA MS (M + H)$^+$ = 627 | − | 59 |
| 223 | 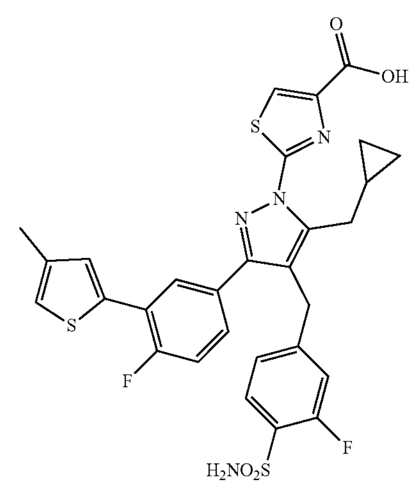 [SMILES: Cc1csc(-c2cc(-c3nn(-c4nc(C(=O)O)cs4)c(CC4CC4)c3Cc3ccc(S(N)(=O)=O)c(F)c3)ccc2F)c1] | 2-(5-(cyclopropylmethyl)-3-(4-fluoro-3-(4-methylthiophen-2-yl)phenyl)-4-(3-fluoro-4-sulfamoylbenzyl)-1H-pyrazol-1-yl)thiazole-4-carboxylic acid, TFA MS (M + H)$^+$ = 627 | +++ | 60 |

TABLE 7-continued

| Cmpd ID | Structure | Compound name and physical data | Inhibitory activity IC$_{50}$ (μM) | Example Method |
|---|---|---|---|---|
| 224 | 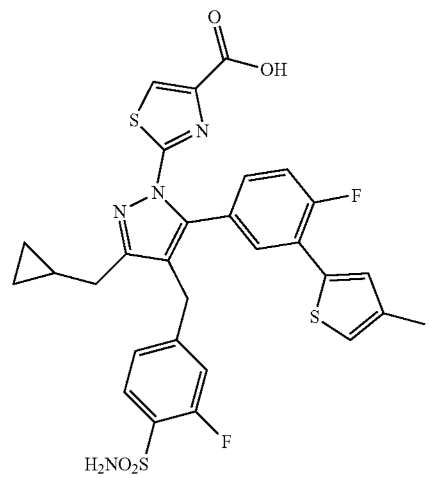 [SMILES: Cc1csc(-c2cc(-c3c(Cc4ccc(S(N)(=O)=O)c(F)c4)c(CC4CC4)nn3-c3nc(C(=O)O)cs3)ccc2F)c1] | 2-(3-(cyclopropylmethyl)-5-(4-fluoro-3-(4-methylthiophen-2-yl)phenyl)-4-(3-fluoro-4-sulfamoylbenzyl)-1H-pyrazol-1-yl)thiazole-4-carboxylic acid, TFA MS (M + H)$^+$ = 627 | — | 60 |
| 225 | 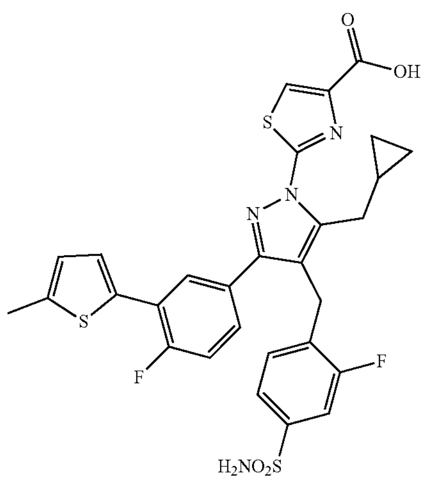 [SMILES: Cc1ccc(-c2cc(-c3nn(-c4nc(C(=O)O)cs4)c(CC4CC4)c3Cc3ccc(S(N)(=O)=O)cc3F)ccc2F)s1] | 2-(5-(cyclopropylmethyl)-3-(4-fluoro-3-(5-methylthiophen-2-yl)phenyl)-4-(2-fluoro-4-sulfamoylbenzyl)-1H-pyrazol-1-yl)thiazole-4-carboxylic acid, TFA MS (M + H)$^+$ = 627 | NA | 61 |
| 226 | 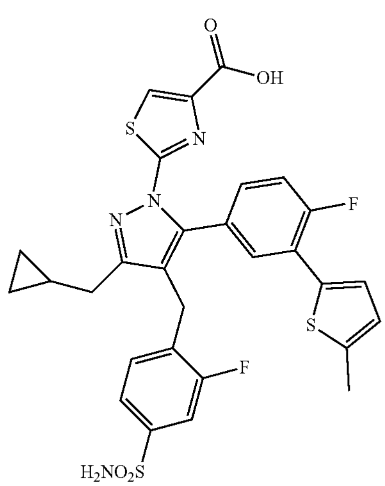 [SMILES: Cc1ccc(-c2cc(-c3c(Cc4ccc(S(N)(=O)=O)cc4F)c(CC4CC4)nn3-c3nc(C(=O)O)cs3)ccc2F)s1] | 2-(3-(cyclopropylmethyl)-5-(4-fluoro-3-(5-methylthiophen-2-yl)phenyl)-4-(2-fluoro-4-sulfamoylbenzyl)-1H-pyrazol-1-yl)thiazole-4-carboxylic acid, TFA MS (M + H)$^+$ = 627 | — | 61 |

TABLE 7-continued

| Cmpd ID | Structure | Compound name and physical data | Inhibitory activity IC$_{50}$ (μM) | Example Method |
|---|---|---|---|---|
| 227 | 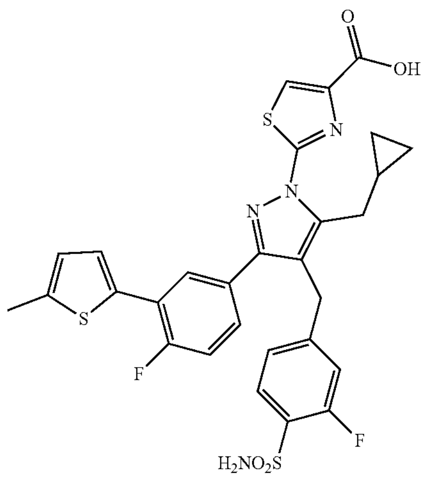 | 2-(5-(cyclopropylmethyl)-3-(4-fluoro-3-(5-methylthiophen-2-yl)phenyl)-4-(3-fluoro-4-sulfamoylbenzyl)-1H-pyrazol-1-yl)thiazole-4-carboxylic acid, TFA MS (M + H)$^+$ = 627 NMR (HCl salt) from YSM14-67 $^1$H NMR (400 MHz, DMSO-d6) δ 13.13 (s, 1H), 8.29 (s, 1H), 7.67 (t, J = 7.9 Hz, 1H), 7.62 (dd, J = 7.6, 2.2 Hz, 1H), 7.58 (s, 2H), 7.50 (ddd, J = 8.5, 4.8, 2.2 Hz, 1H), 7.34 (dd, J = 11.3, 8.6 Hz, 1H), 7.19 (dd, J = 11.3, 1.6 Hz, 1H), 7.13 (dd, J = 3.6, 0.9 Hz, 1H), 7.06 (dd, J = 8.1, 1.6 Hz, 1H), 6.81 (dt, J = 3.6, 1.1 Hz, 1H), 4.14 (s, 2H), 3.15 (d, J = 6.9 Hz, 2H), 2.44 (d, J = 1.1 Hz, 3H), 1.19-1.03 (m, 1H), 0.39-0.28 (m, 2H), 0.24-0.14 (m, 2H) | +++ | 62 |
| 228 | 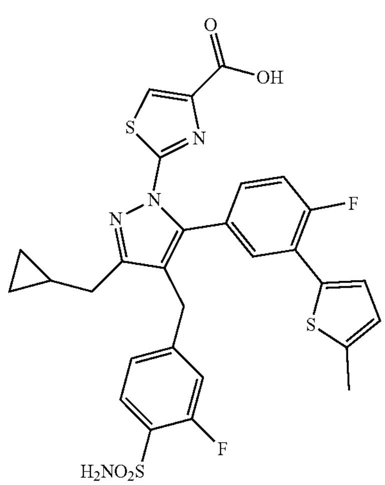 [SMILES: Cc1ccc(-c2cc(-c3c(Cc4ccc(S(N)(=O)=O)c(F)c4)c(CC4CC4)nn3-c3nc(C(=O)O)cs3)ccc2F)s1] | 2-(3-(cyclopropylmethyl)-5-(4-fluoro-3-(5-methylthiophen-2-yl)phenyl)-4-(3-fluoro-4-sulfamoylbenzyl)-1H-pyrazol-1-yl)thiazole-4-carboxylic acid, TFA MS (M + H)$^+$ = 627 | − | 62 |

TABLE 7-continued

| Cmpd ID | Structure | Compound name and physical data | Inhibitory activity IC$_{50}$ (μM) | Example Method |
|---|---|---|---|---|
| 229 | 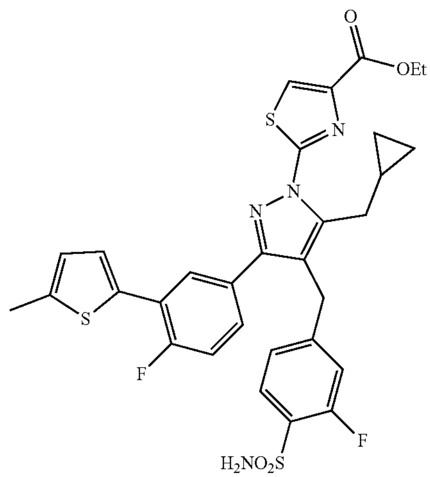 [SMILES: CCOC(=O)c1csc(-n2nc(-c3ccc(F)c(-c4ccc(C)s4)c3)c(Cc3ccc(S(N)(=O)=O)c(F)c3)c2CC2CC2)n1] | ethyl 2-(5-(cyclopropylmethyl)-3-(4-fluoro-3-(5-methylthiophen-2-yl)phenyl)-4-(3-fluoro-4-sulfamoylbenzyl)-1H-pyrazol-1-yl)thiazole-4-carboxylate <br> $^1$H NMR (400 MHz, Chloroform-d) δ 7.96 (s, 1H), 7.81 (t, J = 7.8 Hz, 1H), 7.55 (dd, J = 7.4, 2.2 Hz, 1H), 7.37 (ddd, J = 8.5, 4.7, 2.2 Hz, 1H), 7.15-7.04 (m, 3H), 7.00 (dd, J = 11.1, 1.6 Hz, 1H), 6.73 (dt, J = 3.7, 1.0 Hz, 1H), 4.93 (s, 2H), 4.40 (q, J = 7.1 Hz, 2H), 4.07 (s, 2H), 3.21 (d, J = 6.8 Hz, 2H), 2.49 (d, J = 1.1 Hz, 3H), 1.41 (t, J = 7.1 Hz, 3H), 1.19-1.06 (m, 1H), 0.49-0.38 (m, 2H), 0.28 (dt, J = 6.1, 4.7 Hz, 2H); MS (M + H)$^+$ = 655 | – | 63 |
| 230 | 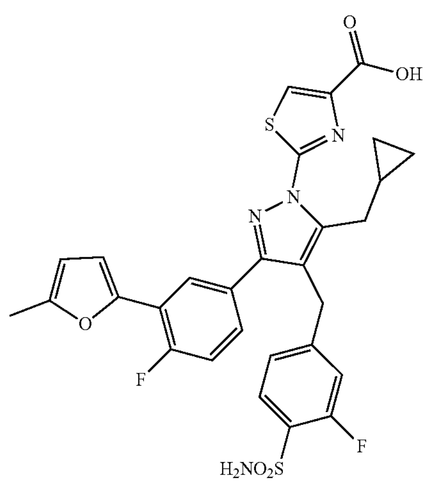 [SMILES: Cc1ccc(-c2cc(-c3nn(-c4nc(C(=O)O)cs4)c(CC4CC4)c3Cc3ccc(S(N)(=O)=O)c(F)c3)ccc2F)o1] | 2-(5-(cyclopropylmethyl)-3-(4-fluoro-3-(5-methylfuran-2-yl)phenyl)-4-(3-fluoro-4-sulfamoylbenzyl)-1H-pyrazol-1-yl)thiazole-4-carboxylic acid <br> $^1$H NMR (400 MHz, DMSO-d6) δ 13.10 (s, 1H), 8.29 (s, 1H), 7.76 (dd, J = 7.4, 2.3 Hz, 1H), 7.67 (t, J = 7.9 Hz, 1H), 7.57 (s, 2H), 7.54 (ddd, J = 8.6, 4.8, 2.3 Hz, 1H), 7.33 (dd, J = 11.2, 8.6 Hz, 1H), 7.20 (dd, J = 11.3, 1.6 Hz, 1H), 7.07 (dd, J = 8.1, 1.6 Hz, 1H), 6.70 (t, J = 3.5 Hz, 1H), 6.22 (dt, J = 3.1, 1.0 Hz, 1H), 4.15 (s, 2H), 3.15 (d, J = 6.9 Hz, 2H), 2.27 (s, 3H), 1.17-1.06 (m, 1H), 0.38-0.28 (m, 2H), 0.24-0.14 (m, 2H); MS (M + H)$^+$ = 611 | +++ | 64 |

TABLE 7-continued

| Cmpd ID | Structure | Compound name and physical data | Inhibitory activity IC$_{50}$ (μM) | Example Method |
|---|---|---|---|---|
| 231 | 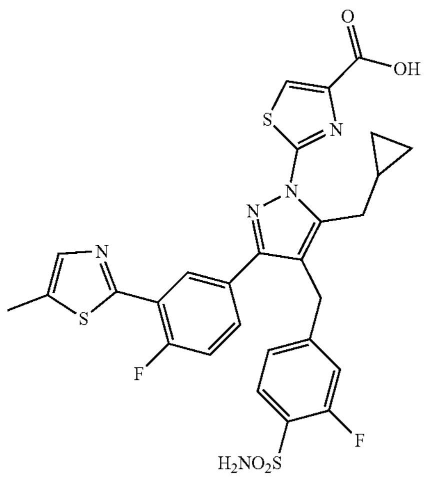 [SMILES: Cc1cnc(-c2cc(-c3nn(-c4nc(C(=O)O)cs4)c(CC4CC4)c3Cc3ccc(S(N)(=O)=O)c(F)c3)ccc2F)s1] | 2-(5-(cyclopropylmethyl)-3-(4-fluoro-3-(5-methylthiazol-2-yl)phenyl)-4-(3-fluoro-4-sulfamoylbenzyl)-1H-pyrazol-1-yl)thiazole-4-carboxylic acid, TFA $^1$H NMR (400 MHz, DMSO-d6) δ 13.13 (s, 1H), 8.30 (dd, J = 7.2, 2.3 Hz, 1H), 8.28 (s, 1H), 7.70-7.59 (m, 3H), 7.54 (s, 2H), 7.43 (dd, J = 11.1, 8.7 Hz, 1H), 7.16 (dd, J = 11.4, 1.6 Hz, 1H), 7.05 (dd, J = 8.1, 1.6 Hz, 1H), 4.14 (s, 2H), 3.19-3.14 (m, 2H), 2.49 (d, J = 1.2 Hz, 3H), 1.18-1.05 (m, 1H), 0.39-0.29 (m, 2H), 0.24-0.15 (m, 2H); MS (M + H)$^+$ = 628 | +++ | 65 |
| 232 | 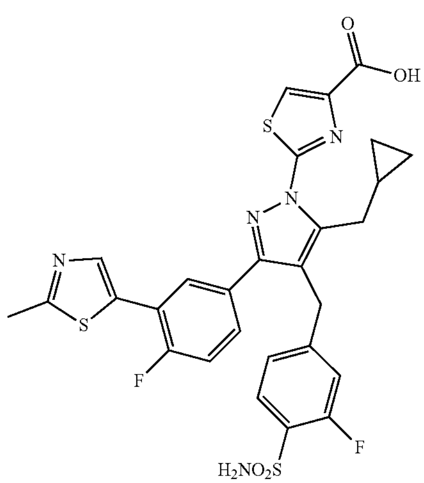 [SMILES: Cc1ncc(-c2cc(-c3nn(-c4nc(C(=O)O)cs4)c(CC4CC4)c3Cc3ccc(S(N)(=O)=O)c(F)c3)ccc2F)s1] | 2-(5-(cyclopropylmethyl)-3-(4-fluoro-3-(2-methylthiazol-5-yl)phenyl)-4-(3-fluoro-4-sulfamoylbenzyl)-1H-pyrazol-1-yl)thiazole-4-carboxylic acid $^1$H NMR (400 MHz, DMSO-d6) δ 13.13 (s, 1H), 8.27 (s, 1H), 7.97 (s, 1H), 7.68 (dd, J = 7.4, 2.0 Hz, 1H), 7.64 (d, J = 7.9 Hz, 1H), 7.57 (m, 3H), 7.39 (dd, J = 10.8, 8.7 Hz, 1H), 7.17 (d, J = 11.3 Hz, 1H), 7.05 (d, J = 8.3 Hz, 1H), 4.15 (s, 2H), 3.16 (d, J = 6.9 Hz, 2H), 2.66 (s, 3H), 1.18-1.01 (m, 1H), 0.37-0.27 (m, 2H), 0.21 (d, J = 4.9 Hz, 2H); MS (M + H)$^+$ = 628 | +++ | 66 |

TABLE 7-continued

| Cmpd ID | Structure | Compound name and physical data | Inhibitory activity IC$_{50}$ (μM) | Example Method |
|---|---|---|---|---|
| 233 | 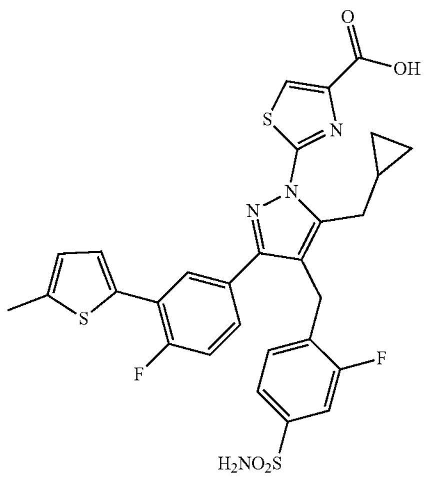 [SMILES: Cc1ccc(-c2cc(-c3nn(-c4nc(C(=O)O)cs4)c(CC4CC4)c3Cc3ccc(S(N)(=O)=O)cc3F)ccc2F)s1] | 2-(5-(cyclopropylmethyl)-3-(4-fluoro-3-(5-methylthiophen-2-yl)phenyl)-4-(2-fluoro-4-sulfamoylbenzyl)-1H-pyrazol-1-yl)thiazole-4-carboxylic acid $^1$H NMR (400 MHz, DMSO-d6) δ 13.09 (s, 1H), 8.29 (s, 1H), 7.63 (dd, J = 7.5, 2.2 Hz, 1H), 7.56 (dd, J = 9.6, 1.8 Hz, 1H), 7.53-7.49 (m, 1H), 7.49-7.44 (m, 1H), 7.42 (s, 2H), 7.34 (dd, J = 11.3, 8.6 Hz, 1H), 7.19-7.11 (m, 2H), 6.81 (dt, J = 3.6, 1.1 Hz, 1H), 4.08 (s, 2H), 3.16 (d, J = 6.9 Hz, 2H), 2.44 (d, J = 1.1 Hz, 3H), 1.17-1.02 (m, 1H), 0.35-0.27 (m, 2H), 0.22-0.14 (m, 2H); MS (M + H)$^+$ = 627 | +++ | 67 |
| 234 | 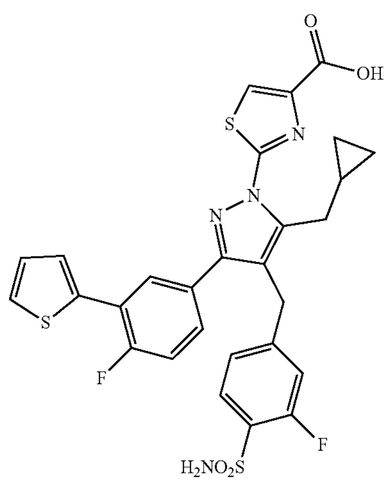 [SMILES: NS(=O)(=O)c1ccc(Cc2c(-c3ccc(F)c(-c4cccs4)c3)nn(-c3nc(C(=O)O)cs3)c2CC2CC2)cc1F] | 2-(5-(cyclopropylmethyl)-3-(4-fluoro-3-(thiophen-2-yl)phenyl)-4-(3-fluoro-4-sulfamoylbenzyl)-1H-pyrazol-1-yl)thiazole-4-carboxylic acid, TFA; MS (M + H)$^+$ = 613 | +++ | 68 |
| 235 | 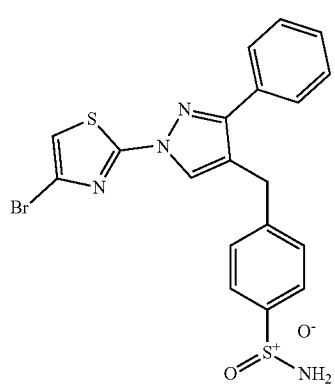 | $^1$H NMR (400 MHz, DMSO-d6) δ 8.30 (d, J = 0.8 Hz, 1H), 7.74-7.68 (m, 2H), 7.67-7.63 (m, 2H), 7.62 (s, 1H), 7.47-7.41 (m, 2H), 7.41-7.37 (m, 2H), 7.26 (s, 2H), 4.13 (s, 2H); (M + H)$^+$ = 476.4 | + | 161 |

TABLE 7-continued

| Cmpd ID | Structure | Compound name and physical data | Inhibitory activity IC$_{50}$ (μM) | Example Method |
|---|---|---|---|---|
| 236 | 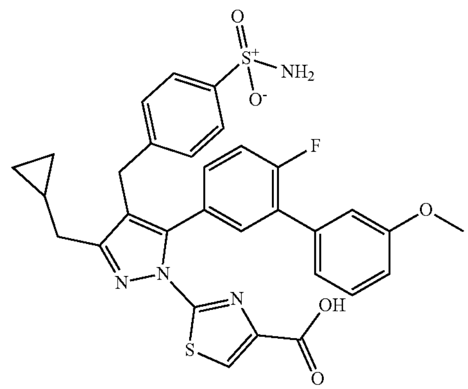 [SMILES: COc1cccc(-c2cc(-c3c(Cc4ccc([S+](N)(=O)[O-])cc4)c(CC4CC4)nn3-c3nc(C(=O)O)cs3)ccc2F)c1] | (M + H)$^+$ = 619.7 | − | 141 |
| 237 | 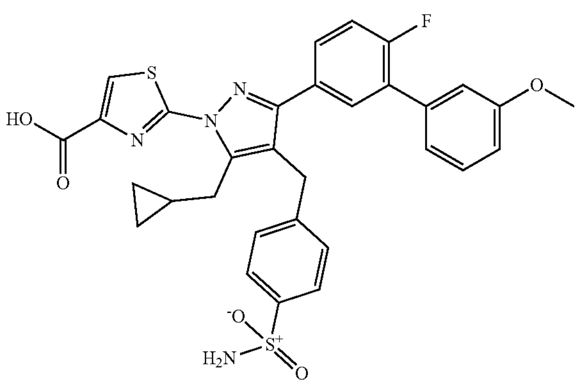 | $^1$H NMR (400 MHz, DMSO-d6) δ 13.12 (s, 1H), 8.27 (s, 1H), 7.71-7.64 (m, 2H), 7.63-7.55 (m, 2H), 7.37-7.23 (m, 6H), 6.99 (dt, J = 2.9, 1.6 Hz, 1H), 6.95 (ddd, J = 8.2, 2.6, 0.9 Hz, 1H), 6.89 (dtd, J = 7.6, 1.6, 0.9 Hz, 1H), 4.14 (s, 2H), 3.75 (s, 3H), 3.13 (d, J = 6.9 Hz, 2H), 1.17-1.04 (m, 1H), 0.36-0.27 (m, 2H), 0.22-0.15 (m, 2H); (M + H)$^+$ = 619.7 | +++ | 141 |
| 238 | 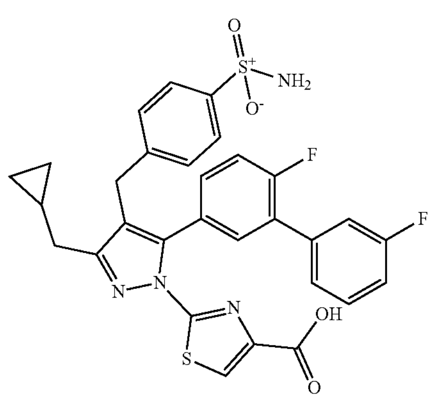 [SMILES: N[S+](=O)([O-])c1ccc(Cc2c(CC3CC3)nn(-c3nc(C(=O)O)cs3)c2-c2ccc(F)c(-c3cccc(F)c3)c2)cc1] | (M + H)$^+$ = 607.7 | + | 141 |

TABLE 7-continued

| Cmpd ID | Structure | Compound name and physical data | Inhibitory activity IC$_{50}$ (μM) | Example Method |
|---|---|---|---|---|
| 239 | 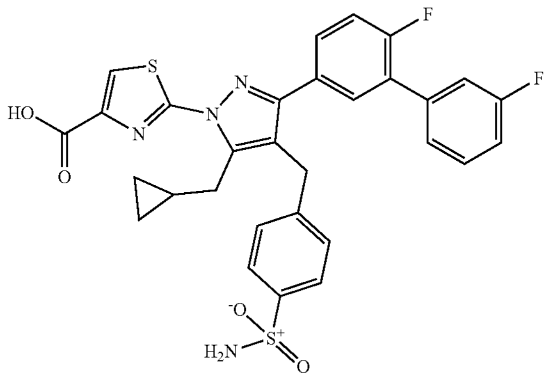 | $^1$H NMR (400 MHz, DMSO-d6) δ 13.15 (s, 1H), 8.30 (s, 1H), 7.73-7.68 (m, 2H), 7.68-7.64 (m, 1H), 7.62 (dd, J = 7.6, 2.3 Hz, 1H), 7.54-7.46 (m, 1H), 7.39 (dd, J = 10.8, 8.6 Hz, 1H), 7.35 (dd, J = 2.7, 1.4 Hz, 0H), 7.34-7.27 (m, 5H), 7.26-7.22 (m, 1H), 7.18 (dq, J = 7.8, 1.3 Hz, 1H), 4.18 (s, 2H), 3.17 (d, J = 6.9 Hz, 2H), 1.14 (ddd, J = 12.8, 7.7, 4.9 Hz, 0H), 0.45-0.27 (m, 2H), 0.28-0.14 (m, 2H); (M + H)$^+$ = 607.7 | +++ | 141 |
| 240 | 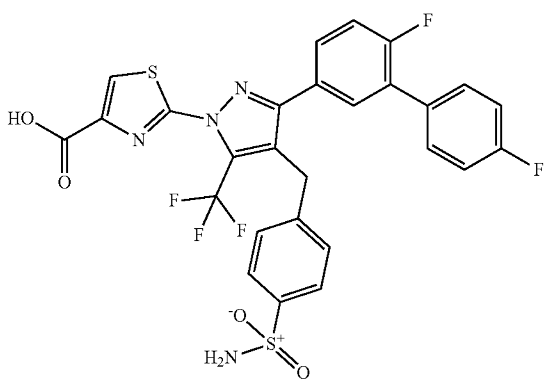 | $^1$H NMR (400 MHz, DMSO-d6) δ 13.29 (s, 1H), 8.46 (s, 1H), 7.80-7.72 (m, 2H), 7.59 (ddd, J = 8.5, 4.8, 2.3 Hz, 1H), 7.56 (dd, J = 7.5, 2.3 Hz, 1H), 7.50-7.43 (m, 3H), 7.36-7.25 (m, 6H), 4.27 (s, 2H); (M + H)$^+$ = 621.6 | +++ | 14 |
| 241 | 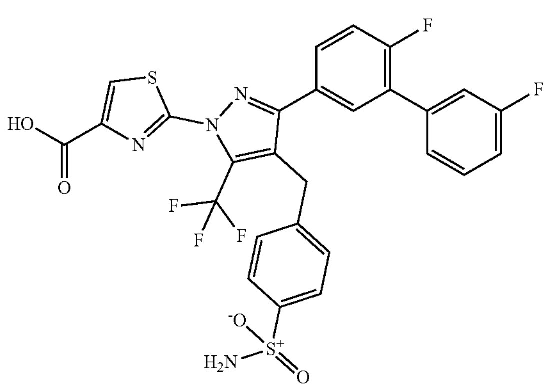 | $^1$H NMR (400 MHz, DMSO-d6) δ 13.27 (s, 1H), 8.44 (s, 1H), 7.75-7.69 (m, 2H), 7.62 (dd, J = 7.5, 2.3 Hz, 1H), 7.58 (ddd, J = 8.5, 4.8, 2.3 Hz, 1H), 7.51-7.42 (m, 2H), 7.39-7.33 (m, 1H), 7.32-7.26 (m, 4H), 7.27-7.20 (m, 2H), 4.25 (s, 2H); (M + H)$^+$ = 621.6 | +++ | 14 |

TABLE 7-continued

| Cmpd ID | Structure | Compound name and physical data | Inhibitory activity IC$_{50}$ (μM) | Example Method |
|---|---|---|---|---|
| 242 | 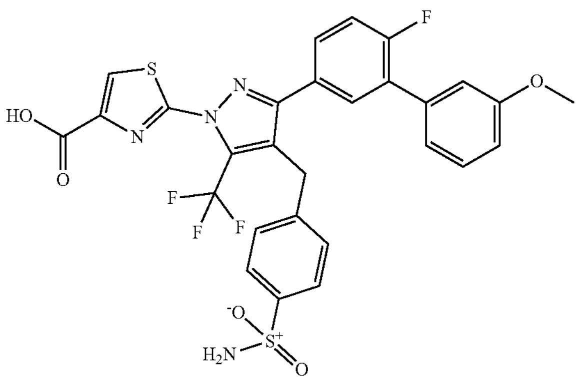 | $^1$H NMR (400 MHz, DMSO-d6) δ 13.30 (s, 1H), 8.45 (s, 1H), 7.78-7.72 (m, 2H), 7.63 (dd, J = 7.5, 2.3 Hz, 1H), 7.58 (ddd, J = 8.5, 4.7, 2.3 Hz, 1H), 7.46 (dd, J = 10.6, 8.5 Hz, 1H), 7.40-7.29 (m, 6H), 7.04 (q, J = 1.8 Hz, 1H), 7.01-6.95 (m, 2H), 4.27 (s, 2H), 3.76 (s, 3H); (M + H)$^+$ = 633.6 | +++ | 14 |
| 243 | 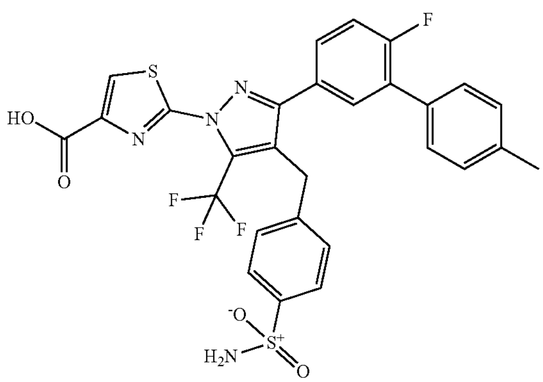 | $^1$H NMR (400 MHz, DMSO-d6) δ 13.27 (s, 1H), 8.42 (s, 1H), 7.77-7.70 (m, 2H), 7.56-7.50 (m, 2H), 7.41 (dd, J = 10.7, 9.1 Hz, 1H), 7.33-7.26 (m, 6H), 7.23 (dd, J = 8.4, 0.8 Hz, 2H), 4.23 (s, 2H), 2.31 (s, 3H); (M + H)$^+$ = 617.6 | +++ | 14 |
| 244 | 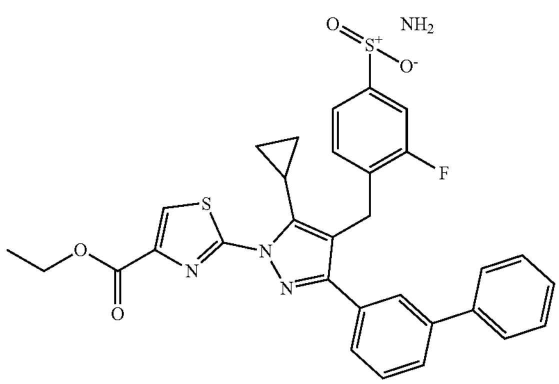 | $^1$H NMR (400 MHz, DMSO-d6) δ 8.37 (d, J = 0.8 Hz, 1H), 7.66 (dt, J = 6.7, 2.1 Hz, 1H), 7.59 (q, J = 1.6 Hz, 2H), 7.55 (dd, J = 10.9, 1.8 Hz, 1H), 7.53-7.46 (m, 2H), 7.45-7.36 (m, 6H), 7.33 (ddd, J = 6.7, 4.9, 2.8 Hz, 1H), 7.21 (t, J = 7.7 Hz, 1H), 4.29 (q, J = 7.1 Hz, 2H), 4.11 (s, 2H), 2.17 (tt, J = 8.6, 5.6 Hz, 1H), 1.29 (t, J = 7.1 Hz, 3H), 0.97 (dt, J = 11.2, 3.2 Hz, 2H), 0.73-0.58 (m, 2H); (M + H)$^+$ = 603.7 | − | 112 |

TABLE 7-continued

| Cmpd ID | Structure | Compound name and physical data | Inhibitory activity IC$_{50}$ (μM) | Example Method |
|---|---|---|---|---|
| 245 | 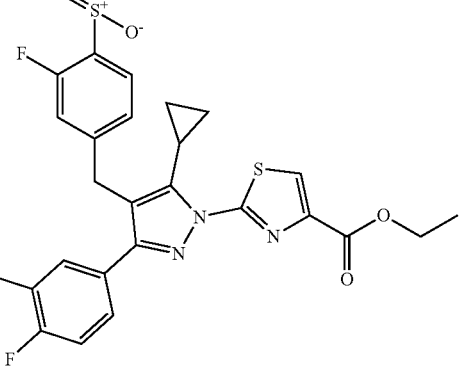 | $^1$H NMR (400 MHz, DMSO-d6) δ 8.37 (d, J = 0.3 Hz, 1H), 7.67 (t, J = 7.9 Hz, 1H), 7.58 (s, 2H), 7.54 (ddd, J = 8.5, 4.8, 2.3 Hz, 1H), 7.44 (dd, J = 7.6, 2.3 Hz, 1H), 7.33 (dd, J = 10.7, 8.5 Hz, 1H), 7.23 (d, J = 0.7 Hz, 4H), 7.23-7.17 (m, 1H), 7.05 (dd, J = 8.2, 1.6 Hz, 1H), 4.30 (q, J = 7.1 Hz, 2H), 4.16 (s, 2H), 2.31 (s, 3H), 2.19 (tt, J = 8.6, 5.6 Hz, 1H), 1.29 (t, J = 7.1 Hz, 3H), 1.03-0.91 (m, 2H), 0.70-0.60 (m, 2H); (M + H)$^+$ = 635.7 | + | 112 |
| 246 | 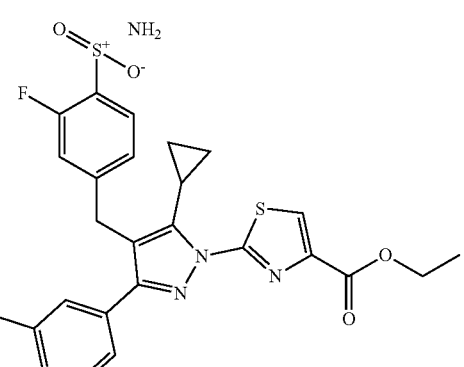 | $^1$H NMR (400 MHz, DMSO-d6) δ 8.37 (d, J = 0.4 Hz, 1H), 7.65 (t, J = 7.9 Hz, 1H), 7.60-7.43 (m, 5H), 7.38 (dd, J = 10.7, 8.5 Hz, 1H), 7.34-7.27 (m, 1H), 7.27-7.13 (m, 3H), 7.06 (dd, J = 8.2, 1.6 Hz, 1H), 4.30 (q, J = 7.1 Hz, 2H), 4.17 (s, 2H), 2.26-2.09 (m, 1H), 1.35-1.22 (m, 3H), 1.03-0.90 (m, 2H), 0.65 (td, J = 6.1, 4.4 Hz, 2H); (M + H)$^+$ = 639.7 | + | 112 |
| 247 | 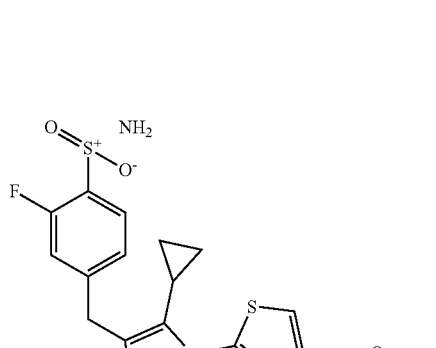 | $^1$H NMR (400 MHz, DMSO-d6) δ 8.40 (s, 1H), 7.70 (t, J = 7.9 Hz, 1H), 7.64-7.55 (m, 3H), 7.47 (dd, J = 7.6, 2.3 Hz, 1H), 7.44-7.35 (m, 3H), 7.28 (t, J = 8.9 Hz, 2H), 7.22 (d, J = 11.2 Hz, 1H), 7.08 (dd, J = 8.1, 1.6 Hz, 1H), 4.33 (q, J = 7.1 Hz, 2H), 4.19 (s, 2H), 2.22 (tt, J = 8.5, 5.7 Hz, 1H), 1.32 (t, J = 7.1 Hz, 3H), 1.08-0.92 (m, 2H), 0.73-0.64 (m, 2H); (M + H)$^+$ = 639.7 | + | 112 |

TABLE 7-continued

| Cmpd ID | Structure | Compound name and physical data | Inhibitory activity IC$_{50}$ (μM) | Example Method |
|---|---|---|---|---|
| 248 | 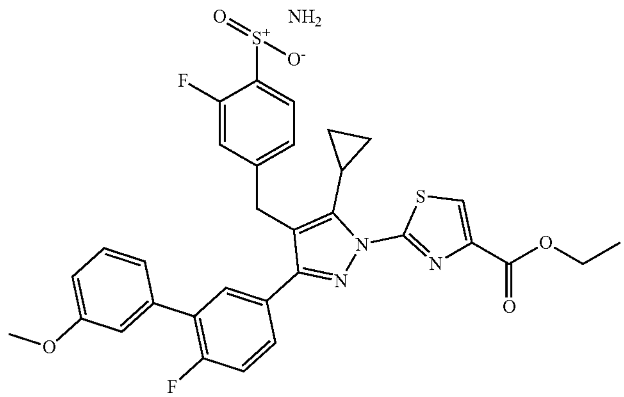 | $^1$H NMR (400 MHz, DMSO-d6) δ 8.39 (d, J = 0.5 Hz, 1H), 7.69 (t, J = 7.9 Hz, 1H), 7.62-7.50 (m, 4H), 7.42-7.33 (m, 2H), 7.24-7.16 (m, 1H), 7.09 (dd, J = 8.2, 1.6 Hz, 1H), 7.03-6.96 (m, 2H), 6.92 (dt, J = 7.7, 1.4 Hz, 1H), 4.32 (q, J = 7.1 Hz, 2H), 4.19 (s, 2H), 3.78 (s, 3H), 3.17 (dd, J = 5.2, 0.5 Hz, 1H), 2.21 (tt, J = 8.5, 5.6 Hz, 1H), 1.36-1.27 (m, 3H), 1.06-0.95 (m, 2H), 0.67 (td, J = 6.2, 4.4 Hz, 2H); (M + H)$^+$ = 651.7 | — | 112 |
| 249 | 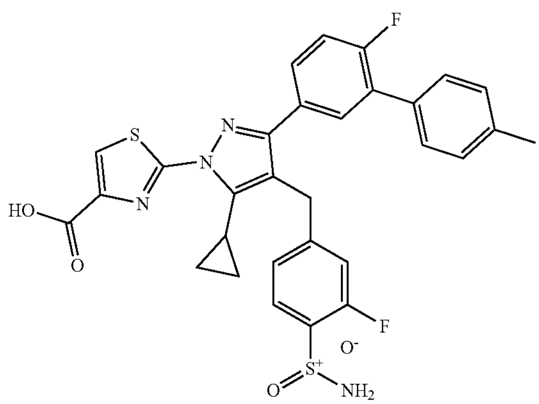 | $^1$H NMR (400 MHz, DMSO-d6) δ 13.10 (s, 1H), 8.28 (s, 1H), 7.67 (t, J = 7.9 Hz, 1H), 7.58 (s, 2H), 7.53 (ddd, J = 8.5, 4.8, 2.3 Hz, 1H), 7.44 (dd, J = 7.7, 2.3 Hz, 1H), 7.33 (dd, J = 10.7, 8.6 Hz, 1H), 7.23 (s, 4H), 7.20 (dd, J = 11.3, 1.6 Hz, 1H), 7.05 (dd, J = 8.1, 1.6 Hz, 1H), 4.15 (s, 2H), 3.14 (d, J = 3.9 Hz, 1H), 2.31 (s, 3H), 2.23 (tt, J = 8.6, 5.6 Hz, 1H), 1.01-0.89 (m, 2H), 0.68-0.59 (m, 2H); (M + H)$^+$ = 607.7 | +++ | 112 |
| 250 | 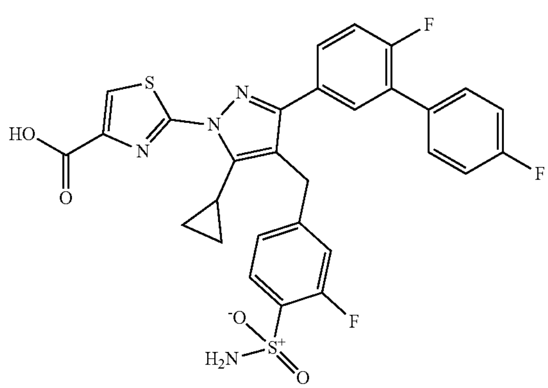 | $^1$H NMR (400 MHz, DMSO-d6) δ 13.10 (s, 1H), 8.29 (s, 1H), 7.65 (t, J = 7.9 Hz, 1H), 7.61-7.54 (m, 3H), 7.52 (dd, J = 7.5, 2.3 Hz, 1H), 7.47 (td, J = 8.0, 6.1 Hz, 1H), 7.37 (dd, J = 10.7, 8.5 Hz, 1H), 7.31 (dd, J = 10.2, 2.2 Hz, 1H), 7.26-7.20 (m, 1H), 7.20 (s, 0H), 7.05 (dd, J = 8.0, 1.5 Hz, 1H), 4.17 (s, 2H), 2.23 (tt, J = 8.5, 5.5 Hz, 1H), 1.03-0.90 (m, 2H), 0.68-0.52 (m, 2H); (M + H)$^+$ = 611.6 | +++ | 112 |

TABLE 7-continued

| Cmpd ID | Structure | Compound name and physical data | Inhibitory activity IC$_{50}$ (μM) | Example Method |
|---|---|---|---|---|
| 251 | 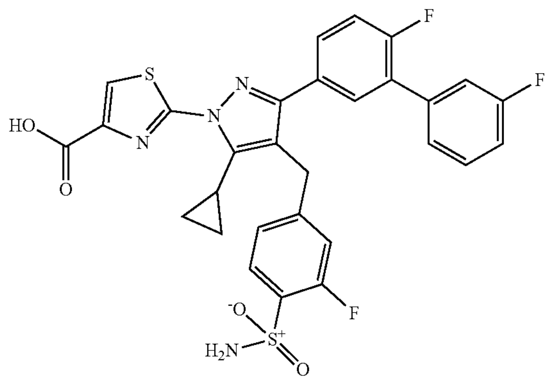 | $^1$H NMR (400 MHz, DMSO-d6) δ 13.13 (s, 1H), 8.31 (s, 1H), 7.68 (t, J = 7.9 Hz, 1H), 7.64-7.57 (m, 3H), 7.55 (dd, J = 7.6, 2.3 Hz, 1H), 7.50 (td, J = 8.1, 6.2 Hz, 1H), 7.40 (dd, J = 10.7, 8.5 Hz, 1H), 7.34 (d, J = 10.2 Hz, 1H), 7.29-7.23 (m, 1H), 7.23 (s, 0H), 7.08 (dd, J = 8.0, 1.6 Hz, 1H), 4.20 (s, 2H), 2.38-2.17 (m, 1H), 1.08-0.86 (m, 2H), 0.76-0.52 (m, 2H); (M + H)$^+$ = 611.6 | +++ | 112 |
| 252 | 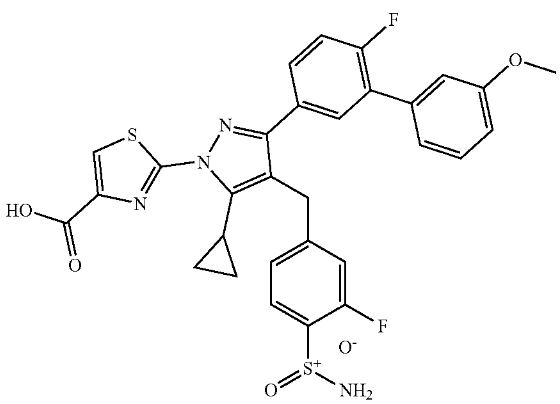 | $^1$H NMR (400 MHz, DMSO-d6) δ 13.13 (s, 1H), 8.30 (s, 1H), 7.69 (t, J = 7.9 Hz, 1H), 7.58 (d, J = 4.8 Hz, 2H), 7.56-7.52 (m, 1H), 7.41-7.34 (m, 2H), 7.24-7.17 (m, 1H), 7.08 (dd, J = 8.1, 1.6 Hz, 1H), 7.02-6.99 (m, 1H), 6.98 (ddd, J = 8.2, 2.6, 0.9 Hz, 1H), 6.92 (dd, J = 7.7, 1.3 Hz, 1H), 4.19 (s, 2H), 3.78 (s, 3H), 2.34-2.13 (m, 1H), 1.10-0.93 (m, 2H), 0.71-0.61 (m, 2H); (M + H)$^+$ = 623.7 | +++ | 112 |
| 253 | 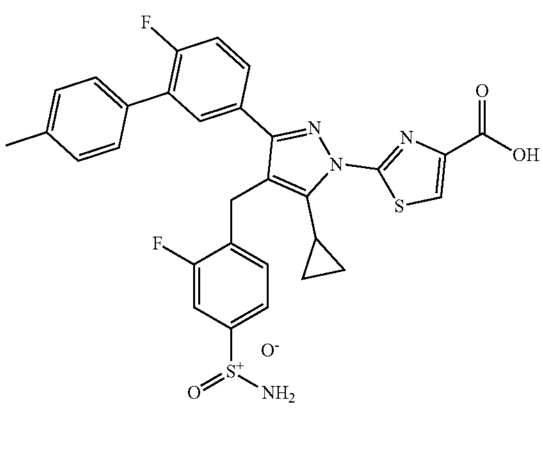 | $^1$H NMR (400 MHz, DMSO-d6) δ 7.59-7.44 (m, 3H), 7.42 (s, 2H), 7.33 (dd, J = 10.7, 8.5 Hz, 1H), 7.24 (d, J = 1.6 Hz, 3H), 7.17 (t, J = 7.8 Hz, 1H), 4.10 (s, 2H), 2.34-2.27 (m, 3H), 2.19 (s, 0H), 0.95 (d, J = 9.0 Hz, 2H), 0.62 (d, J = 5.6 Hz, 2H); (M + H)$^+$ = 607.7 | +++ | 112 |

TABLE 7-continued

| Cmpd ID | Structure | Compound name and physical data | Inhibitory activity IC$_{50}$ (μM) | Example Method |
|---|---|---|---|---|
| 254 | 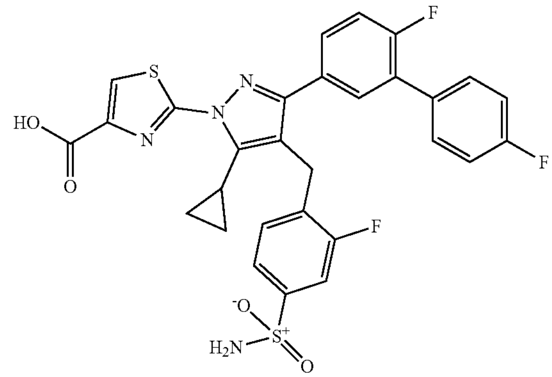 | (M + H)$^+$ = 611.6 | +++ | 112 |
| 255 | 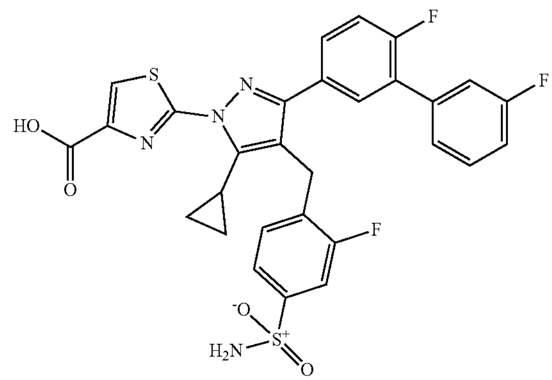 | $^1$H NMR (400 MHz, DMSO-d6) δ 7.62-7.44 (m, 4H), 7.44-7.27 (m, 3H), 7.28-7.11 (m, 3H), 4.11 (s, 2H), 2.18 (s, 0H), 0.96 (d, J = 8.1 Hz, 2H), 0.62 (d, J = 5.6 Hz, 2H); (M + H)$^+$ = 611.6 | +++ | 112 |
| 256 | 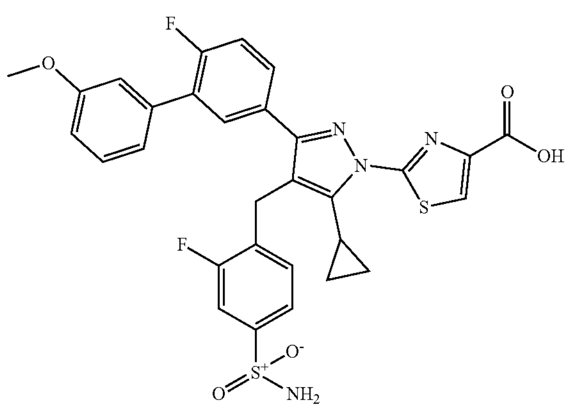 [SMILES: COc1cccc(-c2cc(-c3nn(-c4nc(C(=O)O)cs4)c(C4CC4)c3Cc3ccc([S+](N)(=O)[O-])cc3F)ccc2F)c1] | $^1$H NMR (400 MHz, DMSO-d6) δ 13.10 (s, 1H), 8.30 (s, 1H), 7.60-7.46 (m, 4H), 7.40 (s, 2H), 7.40-7.29 (m, 2H), 7.17 (t, J = 7.8 Hz, 1H), 7.05-6.83 (m, 3H), 4.11 (s, 2H), 3.75 (s, 3H), 2.18 (tt, J = 8.5, 5.6 Hz, 1H), 1.03-0.89 (m, 2H), 0.68-0.55 (m, 2H); (M + H)$^+$ = 623.7 | +++ | 112 |
| 257 | 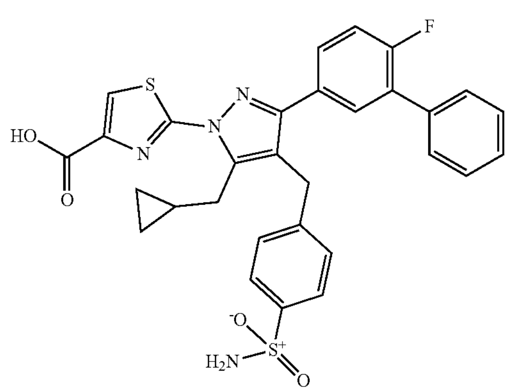 | $^1$H NMR (400 MHz, DMSO-d6) δ 13.17 (s, 1H), 8.29 (s, 1H), 7.72 (d, J = 8.2 Hz, 2H), 7.64 (ddd, J = 8.6, 4.7, 2.3 Hz, 1H), 7.57 (dd, J = 7.6, 2.3 Hz, 1H), 7.48-7.42 (m, 2H), 7.42-7.34 (m, 4H), 7.32 (d, J = 9.4 Hz, 4H), 4.17 (s, 2H), 3.17 (d, J = 6.9 Hz, 2H), 1.14 (h, J = 5.9, 5.3 Hz, 1H), 0.33 (dt, J = 8.3, 2.8 Hz, 2H), 0.28-0.15 (m, 2H); (M + H)$^+$ = 589.7 | +++ | 112 |

TABLE 7-continued

| Cmpd ID | Structure | Compound name and physical data | Inhibitory activity IC$_{50}$ (μM) | Example Method |
|---|---|---|---|---|
| 258 | 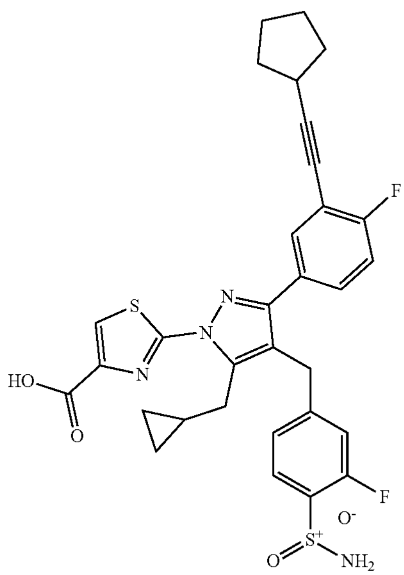 | $^1$H NMR (400 MHz, DMSO-d6) δ 13.16 (s, 1H), 8.29 (d, J = 2.7 Hz, 1H), 7.64 (t, J = 7.9 Hz, 1H), 7.60-7.49 (m, 4H), 7.35-7.23 (m, 1H), 7.14 (dd, J = 11.3, 1.6 Hz, 1H), 7.03 (dd, J = 8.2, 1.5 Hz, 1H), 4.13 (s, 2H), 3.15 (d, J = 6.8 Hz, 2H), 2.87 (p, J = 7.3 Hz, 1H), 2.05-1.86 (m, 2H), 1.69 (tdd, J = 9.3, 5.2, 2.7 Hz, 1H), 1.58 (dddd, J = 11.9, 10.4, 6.0, 2.9 Hz, 3H), 1.11 (pd, J = 7.7, 3.7 Hz, 1H), 0.39-0.29 (m, 2H), 0.21 (dd, J = 5.0, 1.6 Hz, 2H); (M + H)$^+$ = 623.7 | +++ | 145 |
| 259 | 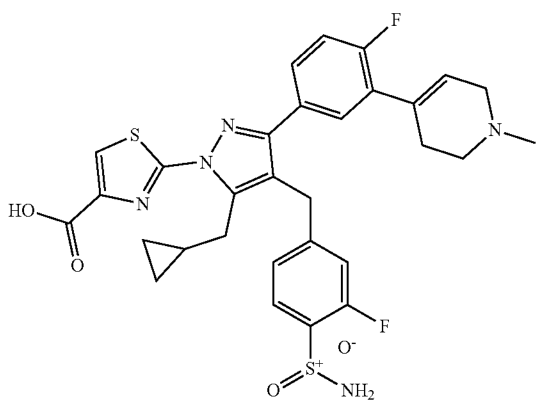 | $^1$H NMR (400 MHz, DMSO-d6) δ 8.23 (s, 1H), 7.73-7.53 (m, 3H), 7.49 (ddd, J = 8.5, 4.8, 2.3 Hz, 1H), 7.37-7.09 (m, 3H), 7.03 (dd, J = 8.1, 1.6 Hz, 1H), 5.93-5.74 (m, 1H), 4.11 (s, 2H), 3.21-3.05 (m, 4H), 2.62 (t, J = 5.7 Hz, 2H), 2.31 (d, J = 13.8 Hz, 5H), 1.11 (dd, J = 9.3, 3.9 Hz, 1H), 0.31 (dt, J = 8.2, 2.8 Hz, 2H), 0.27-0.12 (m, 2H); (M + H)$^+$ = 626.7 | +++ | 145 |
| 260 | 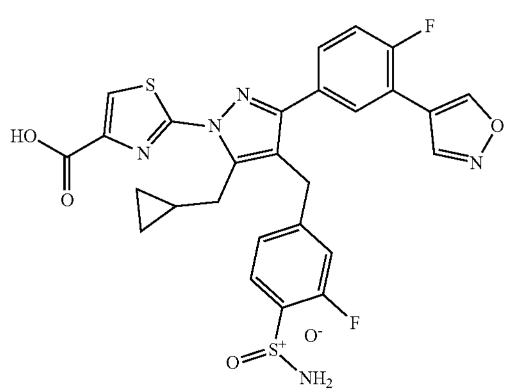 | $^1$H NMR (400 MHz, DMSO-d6) δ 8.36 (d, J = 0.7 Hz, 1H), 7.76 (dd, J = 7.3, 2.2 Hz, 1H), 7.62 (t, J = 7.9 Hz, 1H), 7.57-7.49 (m, 3H), 7.30 (dd, J = 9.8, 8.6 Hz, 1H), 7.14-7.07 (m, 1H), 7.06-6.99 (m, 1H), 4.37-4.24 (m, 2H), 4.16 (s, 2H), 4.08 (s, 2H), 3.15 (d, J = 6.9 Hz, 2H), 1.31 (td, J = 7.1, 0.8 Hz, 3H), 1.18-1.05 (m, 1H), 0.33 (dt, J = 8.2, 2.8 Hz, 2H), 0.27-0.19 (m, 2H); (M + H)$^+$ = 599 | + | 145 |

TABLE 7-continued

| Cmpd ID | Structure | Compound name and physical data | Inhibitory activity IC$_{50}$ (μM) | Example Method |
|---|---|---|---|---|
| 261 | 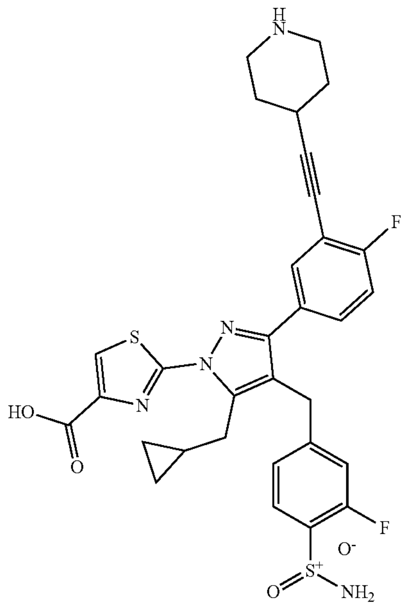 | $^1$H NMR (400 MHz, DMSO-d6) δ 8.29 (s, 1H), 8.15 (s, 1H), 7.64 (td, J = 7.9, 3.0 Hz, 2H), 7.61-7.53 (m, 5H), 7.50 (dd, J = 6.9, 2.2 Hz, 1H), 7.44 (ddd, J = 8.6, 5.1, 2.3 Hz, 1H), 7.31 (td, J = 9.0, 3.6 Hz, 2H), 7.16-6.98 (m, 4H), 4.13 (s, 2H), 3.80 (s, 2H), 3.25-3.12 (m, 6H), 3.02 (qd, J = 8.8, 3.4 Hz, 6H), 2.42 (d, J = 6.8 Hz, 2H), 2.11-1.93 (m, 4H), 1.75 (ddq, J = 13.6, 9.1, 4.3 Hz, 4H), 1.19-1.04 (m, 1H), 1.00-0.85 (m, 1H), 0.43-0.37 (m, 2H), 0.36-0.30 (m, 2H), 0.24-0.18 (m, 2H), 0.14-0.08 (m, 2H); (M + H)$^+$ = 639 | +++ | 145 |
| 262 | 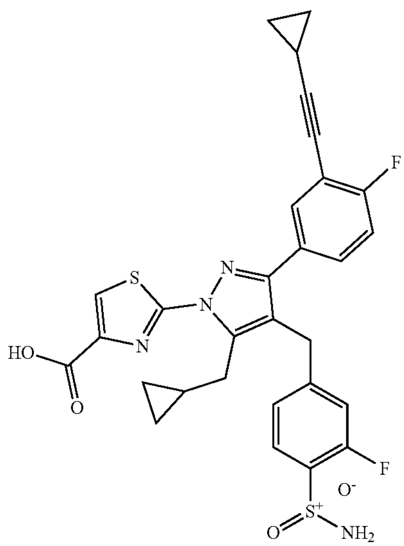 | $^1$H NMR (400 MHz, DMSO-d6) δ 13.15 (s, 1H), 8.29 (s, 1H), 7.63 (t, J = 7.9 Hz, 1H), 7.57 (s, 2H), 7.56-7.47 (m, 2H), 7.27 (t, J = 9.0 Hz, 1H), 7.13 (dd, J = 11.2, 1.5 Hz, 1H), 7.02 (dd, J = 8.2, 1.6 Hz, 1H), 4.12 (s, 2H), 3.15 (d, J = 6.9 Hz, 2H), 1.57 (tt, J = 8.3, 5.0 Hz, 1H), 1.11 (ddd, J = 13.1, 9.1, 5.9 Hz, 1H), 0.95-0.86 (m, 2H), 0.78-0.70 (m, 2H), 0.37-0.27 (m, 2H), 0.25-0.16 (m, 2H); (M + H)$^+$ = 597 | +++ | 145 |
| 263 | 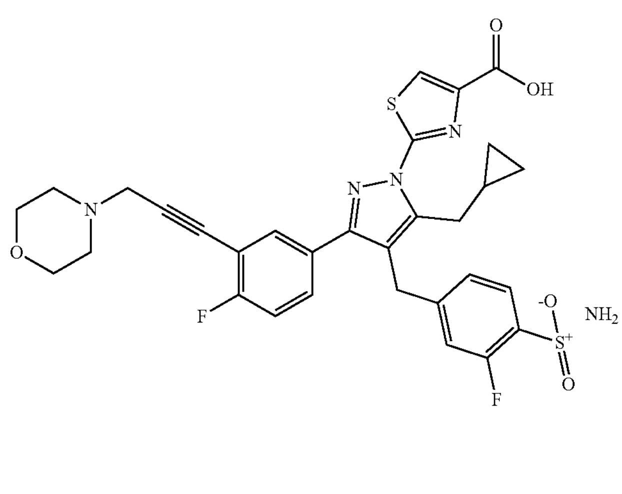 | $^1$H NMR (400 MHz, DMSO-d6) δ 12.82 (s, 1H), 8.16 (s, 1H), 7.63 (t, J = 7.9 Hz, 1H), 7.58 (s, 2H), 7.55-7.46 (m, 1H), 7.36 (t, J = 9.0 Hz, 1H), 7.12-6.99 (m, 2H), 3.81 (s, 2H), 3.63 (s, 8H), 2.41 (d, J = 6.8 Hz, 2H), 0.99-0.86 (m, 1H), 0.45-0.35 (m, 2H), 0.16-0.05 (m, 2H); (M + H)$^+$ = 654.7 | +++ | 145 |

TABLE 7-continued

| Cmpd ID | Structure | Compound name and physical data | Inhibitory activity IC$_{50}$ (μM) | Example Method |
|---|---|---|---|---|
| 264 | 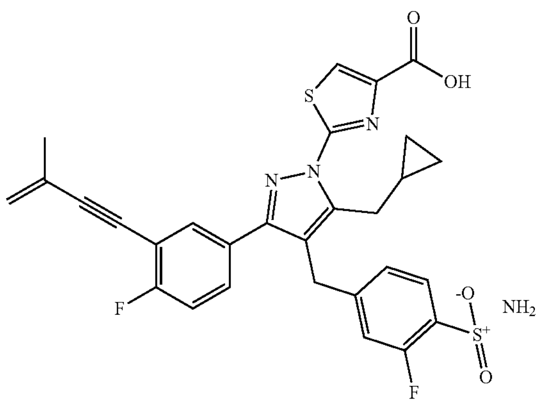 | $^1$H NMR (400 MHz, DMSO-d6) δ 13.17 (s, 1H), 8.28 (s, 1H), 7.63 (t, J = 7.9 Hz, 1H), 7.57 (s, 2H), 7.54 (dd, J = 7.3, 1.9 Hz, 1H), 7.52-7.48 (m, 1H), 7.27 (t, J = 9.0 Hz, 1H), 7.13 (dd, J = 11.3, 1.6 Hz, 1H), 7.02 (dd, J = 8.1, 1.6 Hz, 1H), 4.12 (s, 2H), 3.15 (d, J = 6.8 Hz, 2H), 1.57 (tt, J = 8.3, 5.0 Hz, 1H), 1.11 (ddd, J = 12.8, 7.9, 5.4 Hz, 1H), 0.98-0.84 (m, 2H), 0.79-0.67 (m, 2H), 0.32 (dt, J = 8.2, 2.8 Hz, 2H), 0.23-0.14 (m, 2H); (M + H)$^+$ = 595.6 | +++ | 145 |
| 265 | 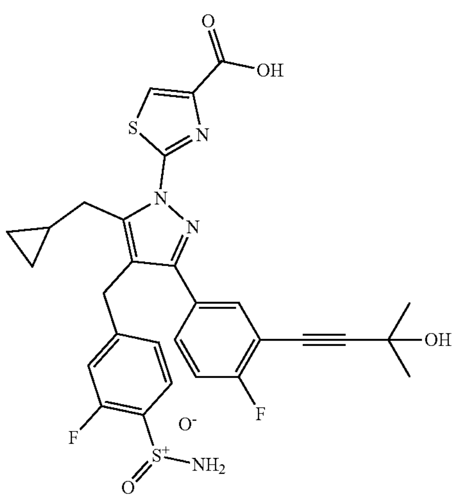 | $^1$H NMR (400 MHz, DMSO-d6) δ 13.16 (s, 1H), 8.28 (s, 1H), 7.64 (t, J = 7.9 Hz, 1H), 7.59-7.52 (m, 4H), 7.30 (t, J = 9.4 Hz, 1H), 7.14 (dd, J = 11.3, 1.6 Hz, 1H), 7.03 (dd, J = 8.2, 1.6 Hz, 1H), 5.53 (s, 1H), 4.14 (s, 2H), 3.15 (d, J = 6.9 Hz, 2H), 1.45 (s, 6H), 1.20-1.05 (m, 1H), 0.37-0.27 (m, 2H), 0.26-0.12 (m, 2H); (M + H)$^+$ = 613.7 | +++ | 145 |
| 266 | 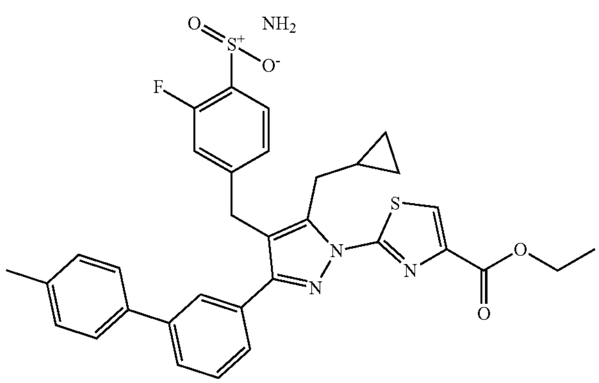 | $^1$H NMR (400 MHz, DMSO-d6) δ 8.35 (d, J = 2.5 Hz, 1H), 7.71-7.52 (m, 6H), 7.47 (td, J = 7.6, 2.2 Hz, 1H), 7.34 (dd, J = 8.2, 2.3 Hz, 2H), 7.27-7.16 (m, 3H), 7.08 (d, J = 8.0 Hz, 1H), 4.30 (qd, J = 7.1, 2.3 Hz, 2H), 4.17 (s, 2H), 3.21-3.08 (m, 2H), 2.30 (d, J = 2.1 Hz, 3H), 1.30 (td, J = 7.1, 2.3 Hz, 3H), 1.15 (ddd, J = 9.8, 5.2, 2.0 Hz, 1H), 0.32 (td, J = 5.8, 5.4, 2.7 Hz, 2H), 0.24 (d, J = 4.9 Hz, 2H); (M + H)$^+$ = 631.8 | + | 145 |

TABLE 7-continued

| Cmpd ID | Structure | Compound name and physical data | Inhibitory activity IC$_{50}$ (μM) | Example Method |
|---|---|---|---|---|
| 267 | 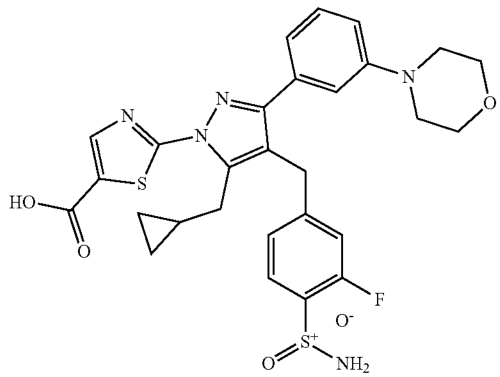 | $^1$H NMR (400 MHz, DMSO-d6) δ 8.27 (s, 1H), 7.67 (t, J = 7.9 Hz, 1H), 7.59 (s, 2H), 7.26 (t, J = 7.9 Hz, 1H), 7.17 (dd, J = 11.4, 1.6 Hz, 1H), 7.04 (ddd, J = 14.9, 7.5, 1.5 Hz, 2H), 6.95 (dd, J = 8.3, 2.5 Hz, 1H), 6.81 (t, J = 2.0 Hz, 1H), 4.10 (s, 2H), 3.72-3.60 (m, 4H), 3.15 (d, J = 6.9 Hz, 2H), 2.95-2.83 (m, 4H), 1.12 (dtt, J = 14.8, 7.2, 3.7 Hz, 1H), 0.37-0.27 (m, 2H), 0.24-0.17 (m, 2H); (M + H)$^+$ = 598.7 | +++ | 145 |
| 268 | 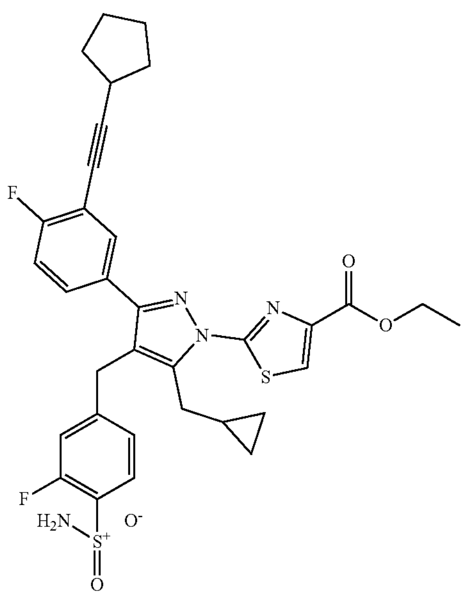 | $^1$H NMR (400 MHz, DMSO-d6) δ 8.36 (d, J = 0.7 Hz, 1H), 7.64 (t, J = 7.9 Hz, 1H), 7.59-7.49 (m, 4H), 7.31-7.23 (m, 1H), 7.14 (dd, J = 11.3, 1.6 Hz, 1H), 7.03 (dd, J = 8.1, 1.5 Hz, 1H), 4.30 (qd, J = 7.1, 0.8 Hz, 2H), 4.13 (s, 2H), 3.15 (d, J = 6.8 Hz, 2H), 2.87 (p, J = 7.2 Hz, 1H), 2.05-1.90 (m, 2H), 1.79-1.66 (m, 1H), 1.64-1.50 (m, 4H), 1.31 (td, J = 7.1, 0.7 Hz, 3H), 1.18-1.02 (m, 2H), 0.33 (dt, J = 8.1, 2.8 Hz, 2H), 0.28-0.17 (m, 2H); (M + H)$^+$ = 651.8 | – | 145 |
| 269 | 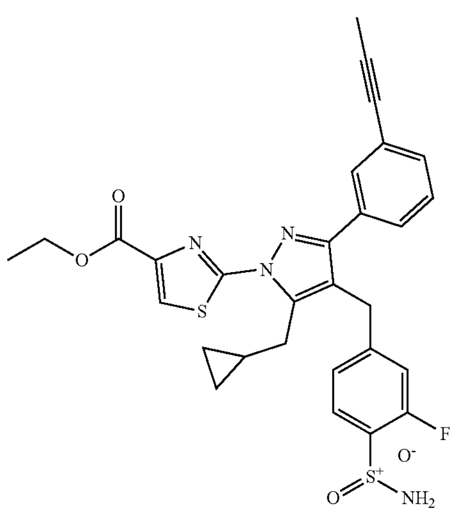 | $^1$H NMR (400 MHz, DMSO-d6) δ 8.36 (d, J = 0.7 Hz, 1H), 7.63 (t, J = 8.0 Hz, 1H), 7.53 (d, J = 6.7 Hz, 3H), 7.51-7.44 (m, 0H), 7.41-7.30 (m, 2H), 7.12 (d, J = 11.3 Hz, 1H), 7.03 (d, J = 8.1 Hz, 1H), 4.30 (q, J = 7.1 Hz, 2H), 4.13 (s, 2H), 3.14 (d, J = 6.9 Hz, 2H), 2.02 (s, 3H), 1.41-1.22 (m, 3H), 1.12 (s, 2H), 0.43-0.29 (m, 2H), 0.23 (q, J = 4.9 Hz, 2H); (M + H)$^+$ = 579.7 | + | 145 |

TABLE 7-continued

| Cmpd ID | Structure | Compound name and physical data | Inhibitory activity IC$_{50}$ (μM) | Example Method |
|---|---|---|---|---|
| 270 | 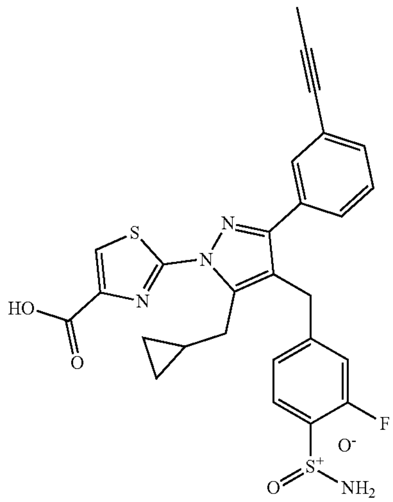 | $^1$H NMR (400 MHz, DMSO-d6) δ 13.14 (s, 1H), 8.25 (s, 1H), 7.63 (t, J = 7.9 Hz, 1H), 7.59-7.50 (m, 3H), 7.50-7.44 (m, 1H), 7.39-7.30 (m, 2H), 7.12 (dd, J = 11.5, 1.6 Hz, 1H), 7.03 (dd, J = 8.1, 1.6 Hz, 1H), 4.13 (s, 2H), 3.19-3.07 (m, 3H), 2.02 (s, 3H), 1.19-0.97 (m, 1H), 0.38-0.27 (m, 2H), 0.27-0.10 (m, 2H); (M + H)$^+$ = 551.6 | +++ | 145 |
| 271 | 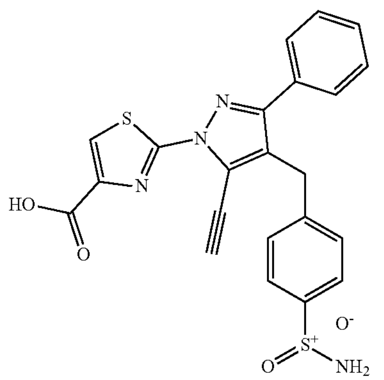 | (M + H)$^+$ = 465 | + | 16 |
| 272 | 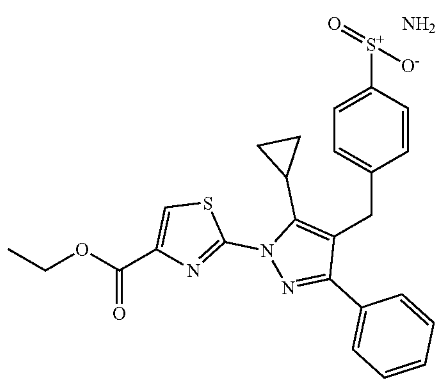 | (M + H)$^+$ = 509 | − | 112 |
| 273 | 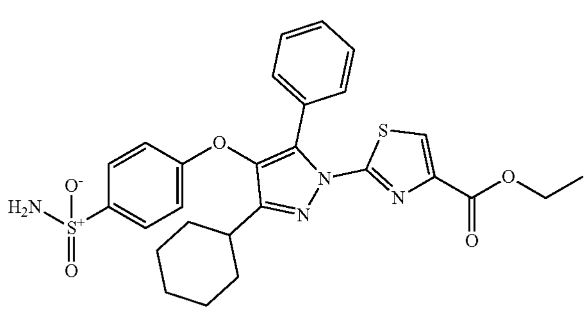 [SMILES: CCOC(=O)c1csc(-n2nc(C3CCCCC3)c(Oc3ccc([S+](N)(=O)[O-])cc3)c2-c2ccccc2)n1] | $^1$H NMR (400 MHz, DMSO-d6) δ 8.28 (s, 1H), 7.74-7.64 (m, 2H), 7.45-7.35 (m, 2H), 7.34-7.27 (m, 3H), 7.22 (s, 2H), 7.14-7.07 (m, 2H), 4.15 (q, J = 7.1 Hz, 2H), 2.55-2.49 (m, 1H), 1.94-1.39 (m, 7H), 1.26-1.11 (m, 6H); (M + H)$^+$ = 553 | − | 33 |

TABLE 7-continued

| Cmpd ID | Structure | Compound name and physical data | Inhibitory activity IC$_{50}$ (μM) | Example Method |
|---|---|---|---|---|
| 274 | 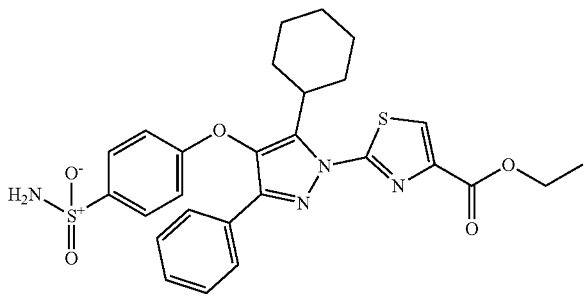 [SMILES: CCOC(=O)c1csc(-n2nc(-c3ccccc3)c(Oc3ccc([S+](N)(=O)[O-])cc3)c2C2CCCCC2)n1] | $^1$H NMR (400 MHz, DMSO-d6) δ 8.38 (s, 1H), 7.78-7.68 (m, 4H), 7.42-7.26 (m, 3H), 7.22 (s, 2H), 7.18-7.09 (m, 2H), 4.30 (q, J = 7.1 Hz, 2H), 3.88 (tt, J = 12.0, 3.1 Hz, 1H), 1.96-1.44 (m, 7H), 1.39-0.98 (m, 6H); (M + H)$^+$ = 553 | − | 33 |
| 275 | 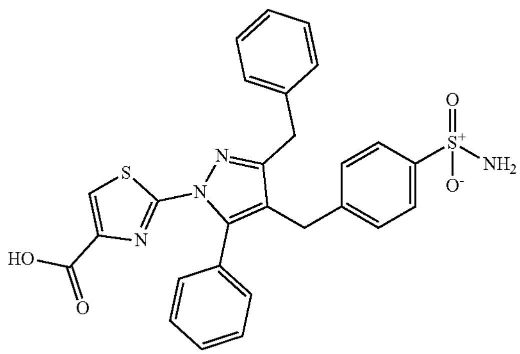 [SMILES: N[S+](=O)([O-])c1ccc(Cc2c(Cc3ccccc3)nn(-c3nc(C(=O)O)cs3)c2-c2ccccc2)cc1] | (M + H)$^+$ = 531 | + | 112 |
| 276 | 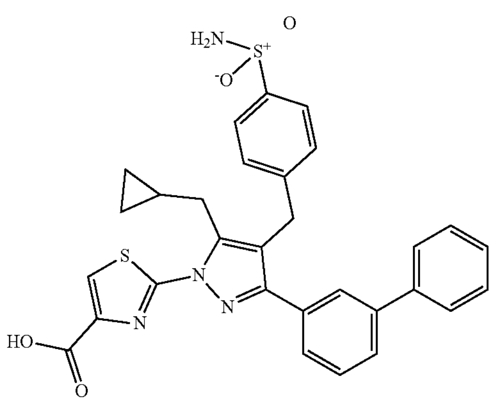 | $^1$H NMR (400 MHz, DMSO-d6) δ 13.12 (s, 1H), 8.28 (s, 1H), 7.75-7.64 (m, 4H), 7.59 (dt, J = 7.7, 1.3 Hz, 1H), 7.52-7.46 (m, 1H), 7.45-7.37 (m, 4H), 7.37-7.30 (m, 3H), 7.28 (s, 2H), 4.16 (s, 2H), 3.16 (m, 2H), 1.13 (ddtd, J = 13.0, 8.0, 6.9, 4.9 Hz, 1H), 0.37-0.27 (m, 2H), 0.25-0.16 (m, 2H); (M + H)$^+$ = 571 | +++ | 141 |
| 277 | 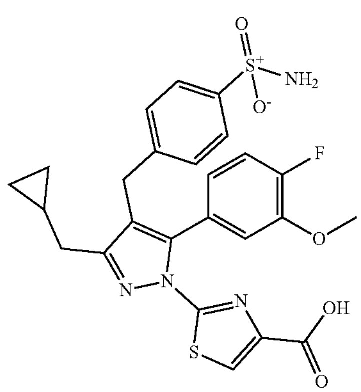 [SMILES: COc1cc(-c2c(Cc3ccc([S+](N)(=O)[O-])cc3)c(CC3CC3)nn2-c2nc(C(=O)O)cs2)ccc1F] | $^1$H NMR (400 MHz, DMSO-d6) δ 12.87 (s, 1H), 8.16 (s, 1H), 7.79-7.61 (m, 2H), 7.37-7.09 (m, 6H), 6.89 (ddd, J = 8.3, 4.3, 2.0 Hz, 1H), 3.84 (s, 2H), 3.71 (s, 3H), 2.40 (d, J = 6.8 Hz, 2H), 0.99-0.82 (m, 1H), 0.43-0.33 (m, 2H), 0.13-0.05 (m, 2H); (M + H)$^+$ = 543 | + | 141 |

TABLE 7-continued
| Cmpd ID | Structure | Compound name and physical data | Inhibitory activity IC$_{50}$ (μM) | Example Method |
|---|---|---|---|---|
| 278 | 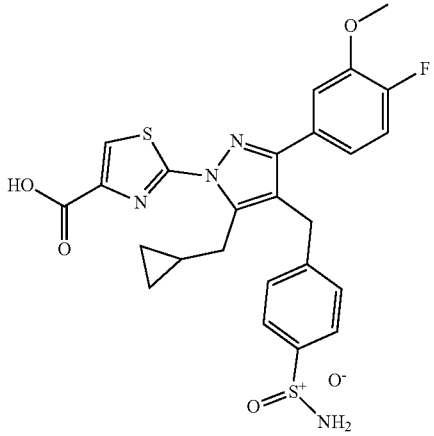 | $^1$H NMR (400 MHz, DMSO-d6) δ 12.87 (s, 1H), 8.16 (s, 1H), 7.79-7.61 (m, 2H), 7.37-7.09 (m, 6H), 6.89 (ddd, J = 8.3, 4.3, 2.0 Hz, 1H), 3.84 (s, 2H), 3.71 (s, 3H), 2.40 (d, J = 6.8 Hz, 2H), 0.99-0.82 (m, 1H), 0.43-0.33 (m, 2H), 0.13-0.05 (m, 2H); (M + H)$^+$ = 543 | +++ | 141 |
| 279 | 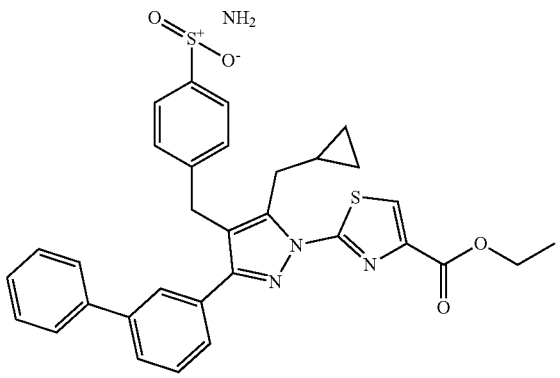 | (M + H)$^+$ = 599 | + | 141 |
| 280 | 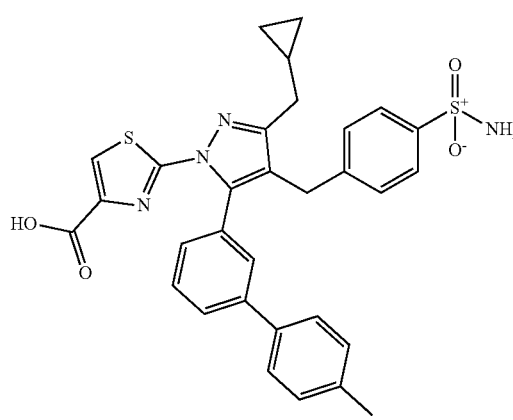 | (M + H)$^+$ = 585 | + | 141 |

TABLE 7-continued

| Cmpd ID | Structure | Compound name and physical data | Inhibitory activity IC$_{50}$ (μM) | Example Method |
|---|---|---|---|---|
| 281 | 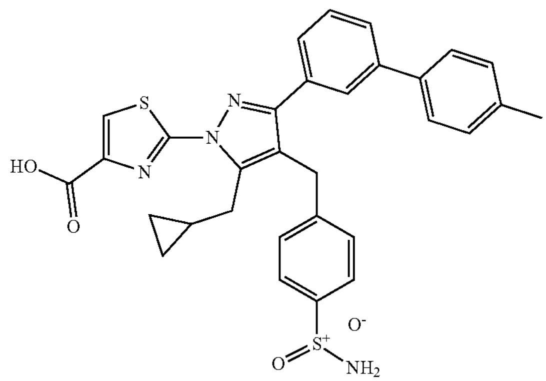 | (M + H)$^+$ = 585 | +++ | 141 |
| 282 | 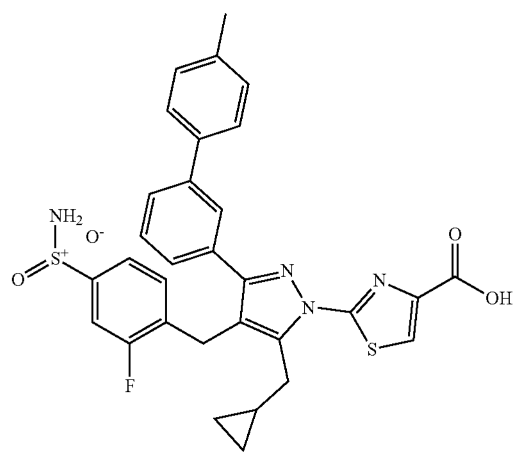 | (M + H)$^+$ = 603 | +++ | 141 |
| 283 | 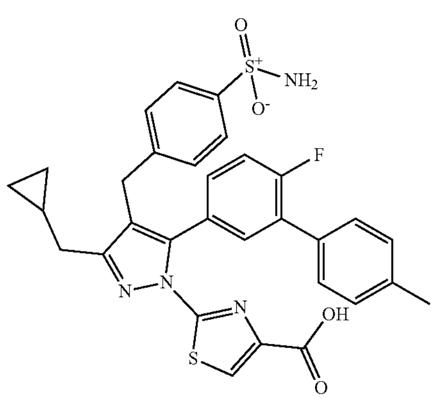 [SMILES: Cc1ccc(-c2cc(-c3c(Cc4ccc([S+](N)(=O)[O-])cc4)c(CC4CC4)nn3-c3nc(C(=O)O)cs3)ccc2F)cc1] | $^1$H NMR (400 MHz, DMSO-d6) δ 12.87 (s, 1H), 8.16 (s, 1H), 7.70-7.63 (m, 2H), 7.52 (dd, J = 7.6, 2.2 Hz, 1H), 7.40-7.15 (m, 11H), 3.85 (s, 2H), 2.39 (d, J = 6.8 Hz, 2H), 2.29 (s, 3H), 0.91 (dddd, J = 11.6, 8.1, 5.0, 2.0 Hz, 1H), 0.42-0.33 (m, 2H), 0.13-0.04 (m, 2H); (M + H)$^+$ = 603 | + | 141 |

TABLE 7-continued

| Cmpd ID | Structure | Compound name and physical data | Inhibitory activity IC$_{50}$ (μM) | Example Method |
|---|---|---|---|---|
| 284 | 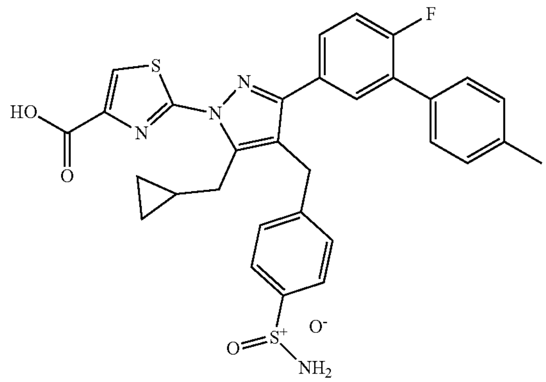 | $^1$H NMR (400 MHz, DMSO-d6) δ 13.11 (s, 1H), 8.26 (s, 1H), 7.72-7.66 (m, 2H), 7.61-7.48 (m, 2H), 7.35-7.19 (m, 10H), 4.13 (s, 2H), 3.14 (d, J = 6.9 Hz, 2H), 2.31 (s, 3H), 1.17-1.05 (m, 1H), 0.33-0.26 (m, 2H), 0.22-0.15 (m, 2H); (M + H)$^+$ = 603 | +++ | 141 |
| 285 | 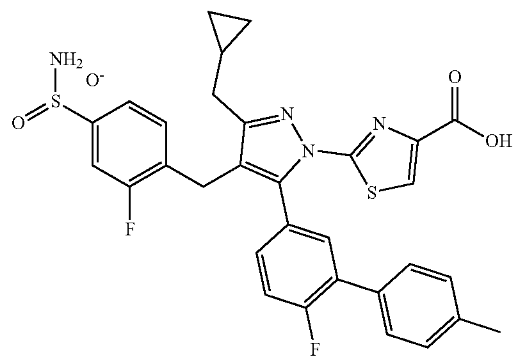 | $^1$H NMR (400 MHz, DMSO-d6) δ 12.87 (s, 1H), 8.16 (s, 1H), 7.55-7.44 (m, 3H), 7.39 (s, 2H), 7.39-7.13 (m, 8H), 3.83 (s, 2H), 2.43 (d, J = 6.8 Hz, 2H), 2.30 (s, 3H), 0.98-0.86 (m, 1H), 0.43-0.33 (m, 2H), 0.15-0.06 (m, 2H); (M + H)$^+$ = 621 | + | 145 |
| 286 | 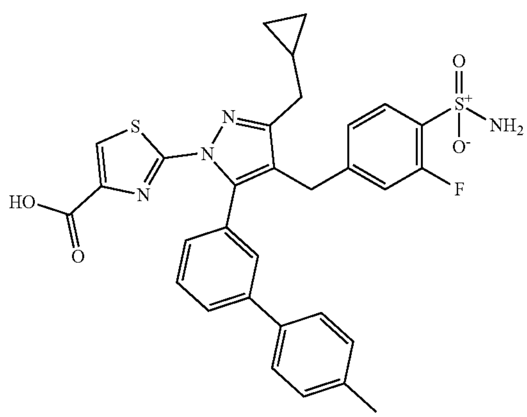 [SMILES: Cc1ccc(-c2cccc(-c3c(Cc4ccc([S+](N)(=O)[O-])c(F)c4)c(CC4CC4)nn3-c3nc(C(=O)O)cs3)c2)cc1] | $^1$H NMR (400 MHz, DMSO-d6) δ 12.84 (s, 1H), 8.18 (s, 1H), 7.68-7.57 (m, 3H), 7.55 (s, 2H), 7.48-7.38 (m, 3H), 7.30 (ddd, J = 7.6, 1.8, 1.1 Hz, 1H), 7.22-7.15 (m, 2H), 7.09 (dd, J = 11.3, 1.6 Hz, 1H), 7.02 (dd, J = 8.1, 1.6 Hz, 1H), 3.86 (s, 2H), 2.42 (d, J = 6.8 Hz, 2H), 2.28 (s, 3H), 1.00-0.87 (m, 1H), 0.44-0.34 (m, 2H), 0.15-0.06 (m, 2H); (M + H)$^+$ = 603 | + | 145 |
| 287 | 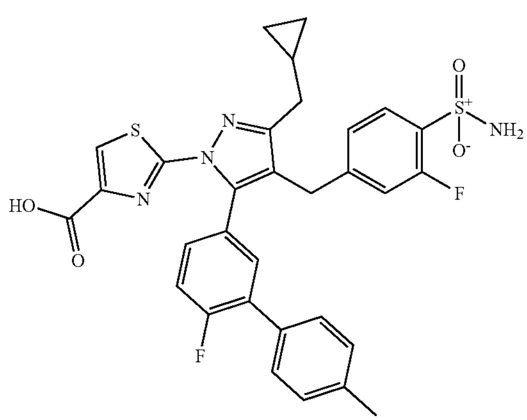 [SMILES: Cc1ccc(-c2cc(-c3c(Cc4ccc([S+](N)(=O)[O-])c(F)c4)c(CC4CC4)nn3-c3nc(C(=O)O)cs3)ccc2F)cc1] | $^1$H NMR (400 MHz, DMSO-d6) δ 12.86 (s, 1H), 8.17 (s, 1H), 7.62 (t, J = 7.9 Hz, 1H), 7.55 (s, 2H), 7.58-7.47 (m, 1H), 7.40-7.24 (m, 5H), 7.24-7.17 (m, 2H), 7.22-7.06 (m, 2H), 7.09-6.97 (m, 1H), 3.86 (s, 2H), 2.41 (d, J = 6.8 Hz, 2H), 2.30 (s, 3H), 0.92 (dddd, J = 11.6, 8.1, 5.0, 1.9 Hz, 1H), 0.43-0.34 (m, 2H), 0.14-0.06 (m, 2H); (M + H)$^+$ = 621 | + | 145 |

TABLE 7-continued

| Cmpd ID | Structure | Compound name and physical data | Inhibitory activity IC$_{50}$ (μM) | Example Method |
|---|---|---|---|---|
| 288 | 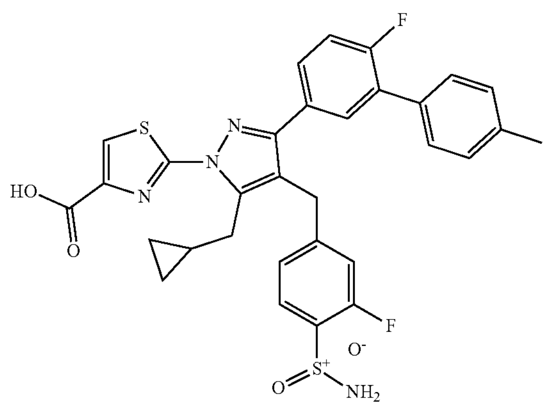 | $^1$H NMR (400 MHz, DMSO-d6) δ 13.12 (s, 1H), 8.24 (s, 1H), 7.69-7.53 (m, 2H), 7.57 (s, 2H), 7.49 (dd, J = 7.6, 2.3 Hz, 1H), 7.32 (dd, J = 10.7, 8.5 Hz, 1H), 7.24 (s, 3H), 7.26-7.12 (m, 2H), 7.04 (dd, J = 8.1, 1.6 Hz, 1H), 4.14 (s, 2H), 3.14 (d, J = 6.9 Hz, 2H), 2.31 (s, 3H), 1.18-1.00 (m, 1H), 0.36-0.25 (m, 2H), 0.23-0.15 (m, 2H); (M + H)$^+$ = 621 | +++ | 145 |
| 289 | 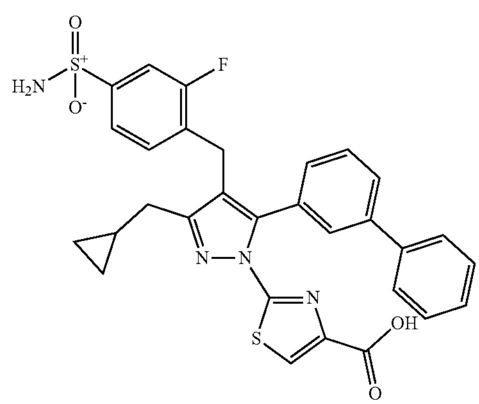 [SMILES: N[S+](=O)([O-])c1ccc(Cc2c(CC3CC3)nn(-c3nc(C(=O)O)cs3)c2-c2cccc(-c3ccccc3)c2)c(F)c1] | (M + H)$^+$ = 589 | + | 145 |
| 290 | 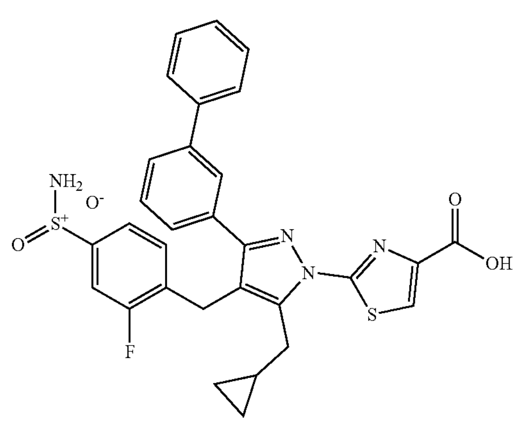 | (M + H)$^+$ = 589 | +++ | 145 |

TABLE 7-continued

| Cmpd ID | Structure | Compound name and physical data | Inhibitory activity IC$_{50}$ (μM) | Example Method |
|---|---|---|---|---|
| 291 | 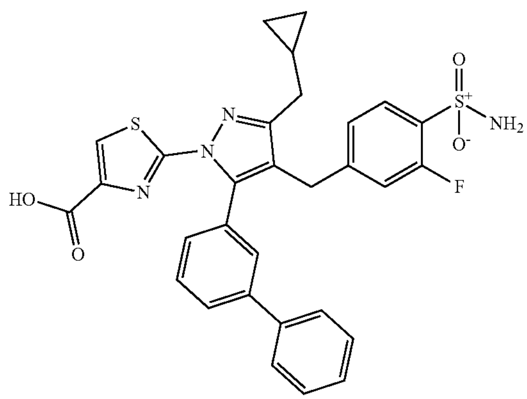 [SMILES: N[S+](=O)([O-])c1ccc(Cc2c(CC3CC3)nn(-c3nc(C(=O)O)cs3)c2-c2cccc(-c3ccccc3)c2)cc1F] | $^1$H NMR (400 MHz, DMSO-d6) δ 12.86 (s, 1H), 8.18 (s, 1H), 7.71-7.57 (m, 3H), 7.57-7.49 (m, 4H), 7.46 (td, J = 7.7, 0.6 Hz, 1H), 7.43-7.34 (m, 2H), 7.37-7.26 (m, 2H), 7.13-6.99 (m, 2H), 3.87 (s, 2H), 2.43 (d, J = 6.8 Hz, 2H), 1.02-0.86 (m, 1H), 0.44-0.34 (m, 2H), 0.15-0.07 (m, 2H); (M + H)+ = 589 | + | 145 |
| 292 | 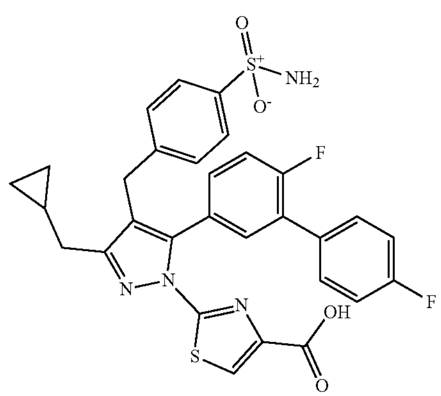 [SMILES: N[S+](=O)([O-])c1ccc(Cc2c(CC3CC3)nn(-c3nc(C(=O)O)cs3)c2-c2ccc(F)c(-c3ccc(F)cc3)c2)cc1] | $^1$H NMR (400 MHz, DMSO-d6) δ 12.89 (s, 1H), 8.16 (s, 1H), 7.77.63 (m, 2H), 7.68-7.43 (m, 3H), 7.42-7.27 (m, 2H), 7.28-7.17 (m, 6H), 3.85 (s, 2H), 2.39 (d, J = 6.8 Hz, 2H), 0.92 (dddd, J = 13.3, 8.1, 5.0, 2.0 Hz, 1H), 0.42-0.33 (m, 2H), 0.13-0.04 (m, 2H); (M + H)+ = 607 | + | 145 |
| 293 | 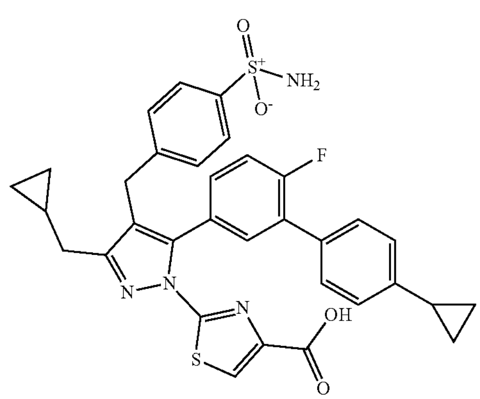 [SMILES: N[S+](=O)([O-])c1ccc(Cc2c(CC3CC3)nn(-c3nc(C(=O)O)cs3)c2-c2ccc(F)c(-c3ccc(C4CC4)cc3)c2)cc1] | $^1$H NMR (400 MHz, DMSO-d6) δ 12.89 (s, 1H), 8.16 (s, 1H), 7.72-7.63 (m, 2H), 7.50 (dd, J = 7.6, 2.2 Hz, 1H), 7.40-7.26 (m, 4H), 7.29-7.20 (m, 4H), 7.12-7.04 (m, 2H), 3.85 (s, 2H), 2.39 (d, J = 6.8 Hz, 2H), 1.90 (tt, J = 8.3, 5.1 Hz, 1H), 0.98-0.88 (m, 3H), 0.73-0.62 (m, 2H), 0.42-0.31 (m, 2H), 0.15-0.04 (m, 2H); (M + H)$^+$ = 629 | + | 145 |

TABLE 7-continued

| Cmpd ID | Structure | Compound name and physical data | Inhibitory activity IC$_{50}$ (μM) | Example Method |
|---|---|---|---|---|
| 294 | 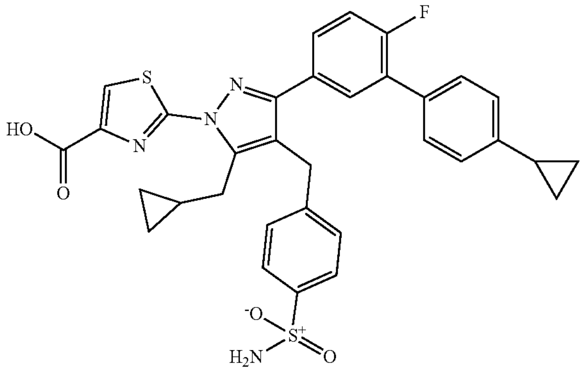 | $^1$H NMR (400 MHz, DMSO-d6) δ 13.15 (s, 1H), 8.30 (s, 1H), 7.77-7.64 (m, 2H), 7.60 (ddd, J = 8.5, 4.7, 2.3 Hz, 1H), 7.52 (dd, J = 7.7, 2.3 Hz, 1H), 7.41-7.28 (m, 4H), 7.31-7.18 (m, 2H), 7.18-7.08 (m, 2H), 4.16 (s, 2H), 3.21-3.14 (m, 2H), 1.94 (tt, J = 8.3, 5.0 Hz, 1H), 1.21-1.07 (m, 1H), 1.05-0.92 (m, 2H), 0.79-0.65 (m, 2H), 0.38-0.30 (m, 2H), 0.25-0.18 (m, 2H); (M + H)$^+$ = 629 | +++ | 145 |
| 295 | 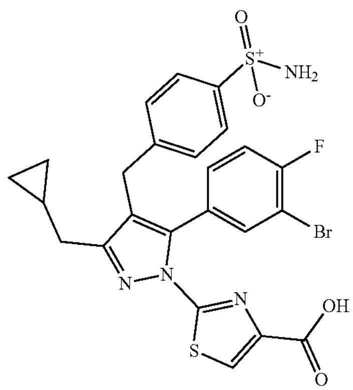 [SMILES: N[S+](=O)([O-])c1ccc(Cc2c(CC3CC3)nn(-c3nc(C(=O)O)cs3)c2-c2ccc(F)c(Br)c2)cc1] | (M + H)$^+$ = 592 | + | 141 |
| 296 | 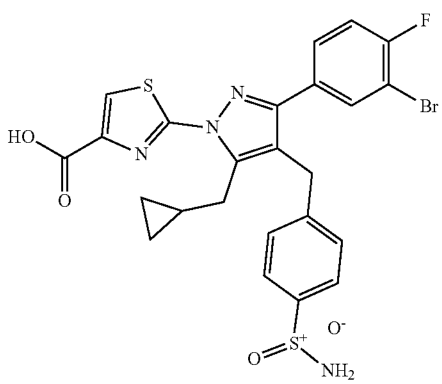 | (M + H)$^+$ = 592 | +++ | 141 |
| 297 | 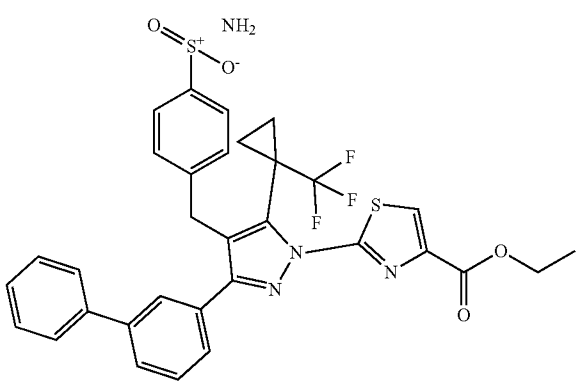 | $^1$H NMR (400 MHz, DMSO-d6) δ 8.41 (s, 1H), 7.76-7.70 (m, 2H), 7.69-7.62 (m, 3H), 7.48 (td, J = 7.6, 0.7 Hz, 1H), 7.45-7.31 (m, 8H), 7.30 (s, 2H), 4.40-4.35 (m, 2H), 4.33 (q, J = 7.1 Hz, 2H), 1.33 (t, J = 7.1 Hz, 7H); (M + H)$^+$ = 653 | − | 49 |

TABLE 7-continued

| Cmpd ID | Structure | Compound name and physical data | Inhibitory activity IC$_{50}$ (μM) | Example Method |
|---|---|---|---|---|
| 298 | 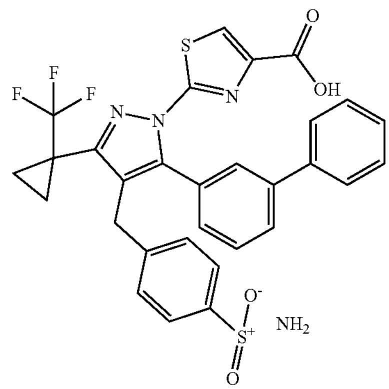 | $^1$H NMR (400 MHz, DMSO-d6) δ 12.95 (s, 1H), 7.68-7.58 (m, 4H), 7.49-7.43 (m, 2H), 7.44-7.33 (m, 3H), 7.34-7.27 (m, 2H), 7.25-7.18 (m, 4H), 3.99 (s, 2H), 1.37-1.24 (m, 2H), 1.04 (s, 2H); (M + H)$^+$ = 653 | + | 49 |
| 299 | 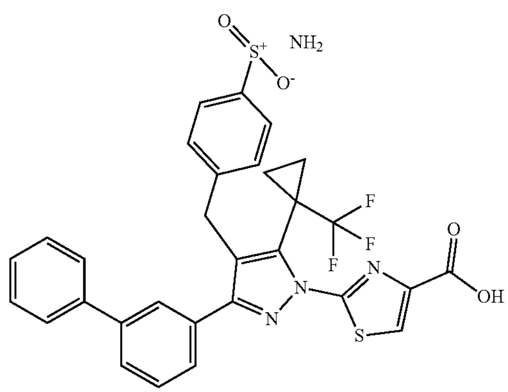 | $^1$H NMR (400 MHz, DMSO-d6) δ 13.07 (s, 1H), 8.31 (s, 1H), 7.73-7.65 (m, 2H), 7.70-7.57 (m, 3H), 7.49-7.40 (m, 1H), 7.43-7.24 (m, 10H), 4.33 (s, 2H), 1.81-0.93 (m, 4H); (M + H)$^+$ = 625 | + | 49 |
| 300 | 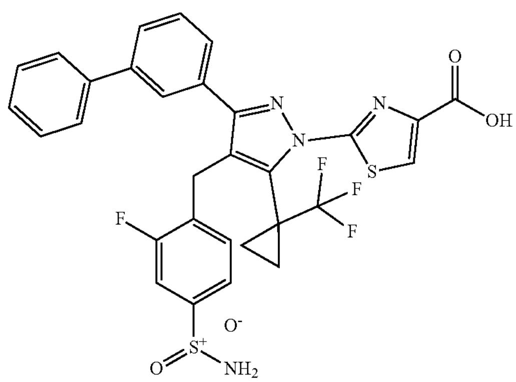 | $^1$H NMR (400 MHz, DMSO-d6) δ 13.07 (s, 1H), 8.31 (s, 1H), 7.68-7.48 (m, 4H), 7.50-7.36 (m, 8H), 7.39-7.28 (m, 1H), 7.09 (t, J = 7.8 Hz, 1H), 4.27 (s, 2H), 1.73-1.10 (m, 4H); (M + H)$^+$ = 643 | ++ | 49 |
| 301 | 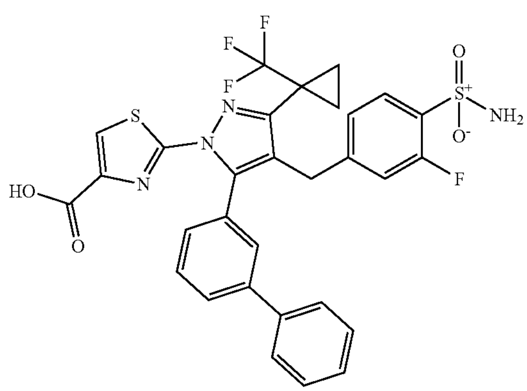 [SMILES: N[S+](=O)([O-])c1ccc(Cc2c(C3(C(F)(F)F)CC3)nn(-c3nc(C(=O)O)cs3)c2-c2cccc(-c3ccccc3)c2)cc1F] | (M + H)$^+$ = 643 | + | 49 |

TABLE 7-continued

| Cmpd ID | Structure | Compound name and physical data | Inhibitory activity IC$_{50}$ (μM) | Example Method |
|---|---|---|---|---|
| 302 | 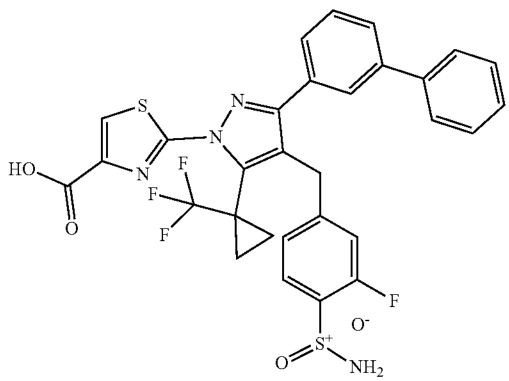 | $^1$H NMR (400 MHz, DMSO-d6) δ 13.09 (s, 1H), 8.30 (s, 1H), 7.67-7.54 (m, 6H), 7.50-7.40 (m, 1H), 7.44-7.34 (m, 4H), 7.39-7.27 (m, 1H), 7.19 (dd, J = 11.4, 1.6 Hz, 1H), 7.06 (dd, J = 8.1, 1.6 Hz, 1H), 4.34 (s, 2H), 1.81-0.93 (m, 4H); (M + H)$^+$ = 643 | + | 49 |
| 303 | 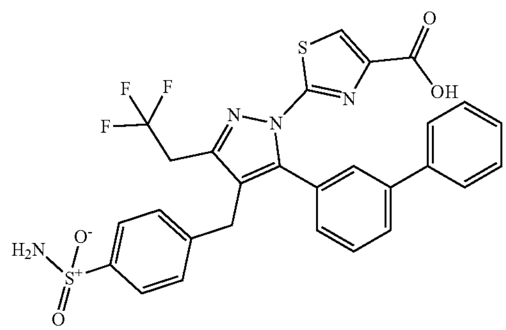 [SMILES: N[S+](=O)([O-])c1ccc(Cc2c(CC(F)(F)F)nn(-c3nc(C(=O)O)cs3)c2-c2cccc(-c3ccccc3)c2)cc1] | $^1$H NMR (400 MHz, DMSO-d6) δ 12.93 (s, 1H), 8.23 (s, 1H), 7.72-7.56 (m, 4H), 7.54-7.28 (m, 7H), 7.32-7.16 (m, 4H), 3.93 (s, 2H), 3.70 (q, J = 11.2 Hz, 2H); (M + H)$^+$ = 599 | + | 49 |
| 304 | 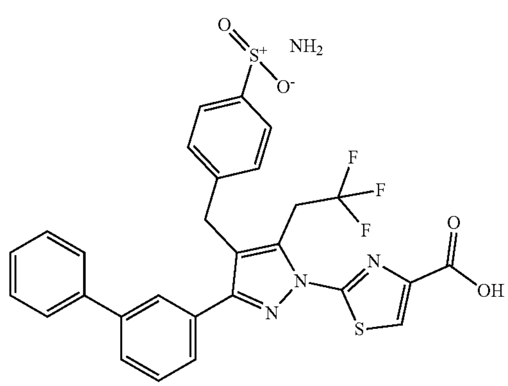 | $^1$H NMR (400 MHz, DMSO-d6) δ 13.20 (s, 1H), 8.30 (s, 1H), 7.72-7.57 (m, 5H), 7.47 (td, J = 7.7, 0.6 Hz, 1H), 7.45-7.23 (m, 9H), 4.66 (q, J = 10.5 Hz, 2H), 4.26 (s, 2H); (M + H)$^+$ = 599 | ++ | 49 |
| 305 | 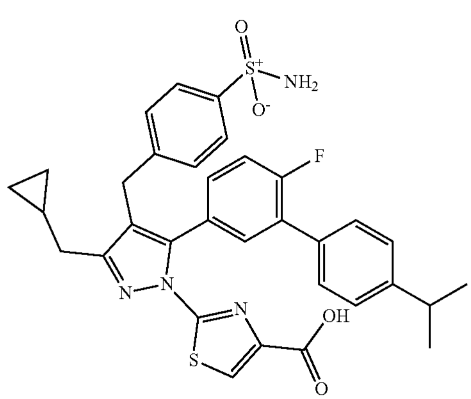 [SMILES: CC(C)c1ccc(-c2cc(-c3c(Cc4ccc([S+](N)(=O)[O-])cc4)c(CC4CC4)nn3-c3nc(C(=O)O)cs3)ccc2F)cc1] | $^1$H NMR (400 MHz, DMSO-d6) δ 12.88 (s, 1H), 7.71-7.63 (m, 2H), 7.53 (dd, J = 7.6, 2.2 Hz, 1H), 7.40-7.26 (m, 4H), 7.29-7.21 (m, 6H), 3.85 (s, 2H), 2.88 (hept, J = 6.9 Hz, 1H), 2.39 (d, J = 6.8 Hz, 2H), 1.19 (s, sH), 1.18 (s, 3H), 0.92 (dddd, J = 11.8, 6.8, 5.6, 2.9 Hz, 1H), 0.44-0.31 (m, 2H), 0.15-0.04 (m, 2H); (M + H)$^+$ = 631 | + | 145 |

TABLE 7-continued

| Cmpd ID | Structure | Compound name and physical data | Inhibitory activity IC$_{50}$ (μM) | Example Method |
|---|---|---|---|---|
| 306 | 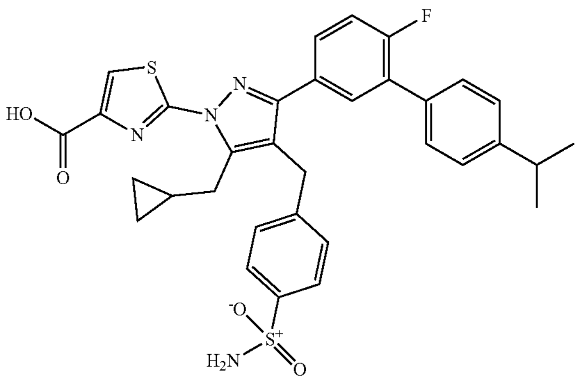 | $^1$H NMR (400 MHz, DMSO-d6) δ 13.13 (s, 1H), 8.26 (s, 1H), 7.73-7.66 (m, 2H), 7.61-7.46 (m, 2H), 7.38-7.20 (m, 10H), 4.13 (s, 2H), 3.14 (d, J = 6.9 Hz, 2H), 2.89 (hept, J = 6.9 Hz, 1H), 1.21 (s, 3H), 1.19 (s, 3H), 1.15-1.04 (m, 1H), 0.35-0.26 (m, 2H), 0.23-0.14 (m, 2H); (M + H)$^+$ = 631 | +++ | 145 |
| 307 | 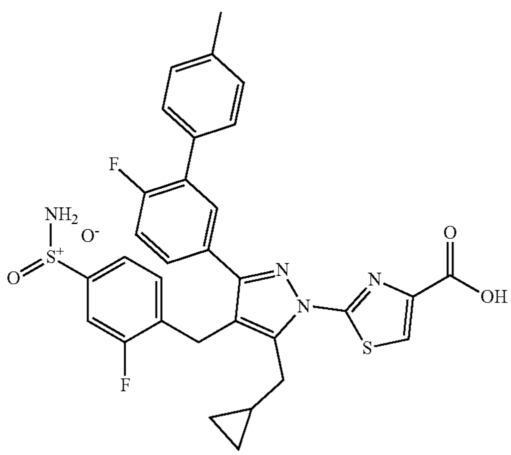 | $^1$H NMR (400 MHz, DMSO-d6) δ 13.12 (s, 1H), 8.27 (s, 1H), 7.59-7.44 (m, 4H), 7.42 (s, 2H), 7.32 (dd, J = 10.8, 8.5 Hz, 1H), 7.24 (s, 1H), 7.24 (s, 3H), 7.14 (t, J = 7.8 Hz, 1H), 4.09 (s, 2H), 3.15 (d, J = 6.9 Hz, 2H), 2.50 (s, 1H), 2.31 (s, 3H), 1.15-1.02 (m, 1H), 0.35-0.14 (m, 4H); (M + H)$^+$ = 621 | +++ | 145 |
| 308 | 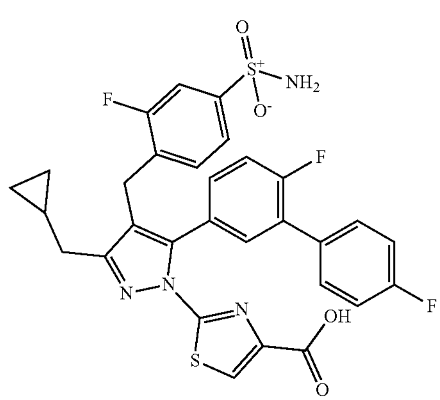 [SMILES: N[S+](=O)([O-])c1ccc(Cc2c(CC3CC3)nn(-c3nc(C(=O)O)cs3)c2-c2ccc(F)c(-c3ccc(F)cc3)c2)c(F)c1] | $^1$H NMR (400 MHz, DMSO-d6) δ 12.89 (s, 1H), 8.17 (s, 1H), 7.60-7.41 (m, 5H), 7.44-7.14 (m, 7H), 3.84 (s, 2H), 2.52-2.51 (m, 2H), 0.99-0.84 (m, 1H), 0.43-0.34 (m, 2H), 0.15-0.06 (m, 2H); (M + H)$^+$ = 625 | + | 145 |

TABLE 7-continued

| Cmpd ID | Structure | Compound name and physical data | Inhibitory activity IC$_{50}$ (μM) | Example Method |
|---|---|---|---|---|
| 309 | 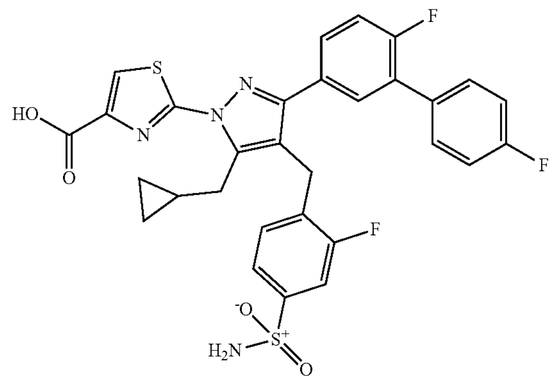 | ¹H NMR (400 MHz, DMSO-d6) δ 13.12 (s, 1H), 8.28 (s, 1H), 7.62-7.49 (m, 2H), 7.49 (ddd, J = 8.4, 6.3, 2.1 Hz, 2H), 7.42 (s, 2H), 7.39 (ddd, J = 8.9, 5.4, 1.4 Hz, 2H), 7.34 (dd, J = 10.7, 8.6 Hz, 1H), 7.31-7.21 (m, 2H), 7.14 (t, J = 7.8 Hz, 1H), 4.09 (s, 2H), 3.15 (d, J = 6.9 Hz, 2H), 1.15-1.02 (m, 1H), 0.35-0.26 (m, 2H), 0.29-0.15 (m, 2H); (M + H)⁺ = 625 | +++ | 145 |
| 310 | 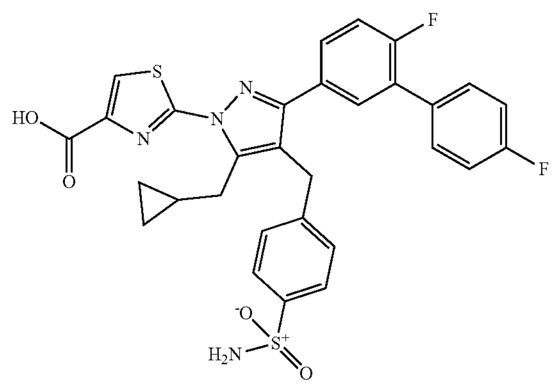 | ¹H NMR (400 MHz, DMSO-d6) δ 13.12 (s, 1H), 8.26 (s, 1H), 7.73-7.65 (m, 2H), 7.62 (ddd, J = 8.6, 4.7, 2.3 Hz, 1H), 7.49 (dd, J = 7.6, 2.3 Hz, 1H), 7.41-7.29 (m, 3H), 7.32-7.19 (m, 6H), 4.13 (s, 2H), 3.15 (d, J = 6.9 Hz, 2H), 2.50 (s, 1H), 1.19-1.02 (m, 1H), 0.35-0.24 (m, 2H), 0.27-0.15 (m, 2H); (M + H)⁺ = 607 | +++ | 145 |
| 311 | 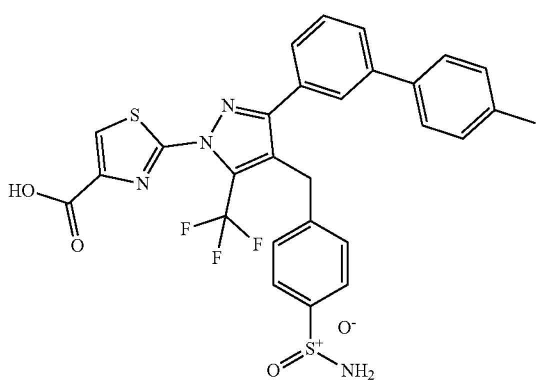 | (M + H)⁺ = 599 | +++ | 14, 18 |
| 312 | 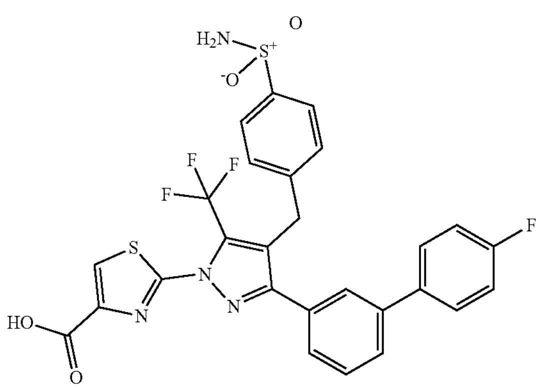 | (M + H)⁺ = 603 | +++ | 14, 18 |

TABLE 7-continued

| Cmpd ID | Structure | Compound name and physical data | Inhibitory activity IC$_{50}$ (μM) | Example Method |
|---|---|---|---|---|
| 313 | 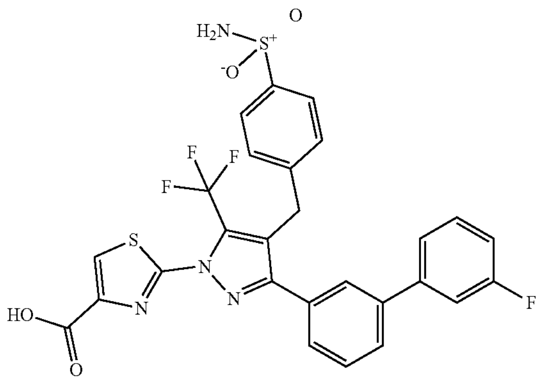 | (M + H)$^+$ = 603 | +++ | 14, 18 |
| 314 | 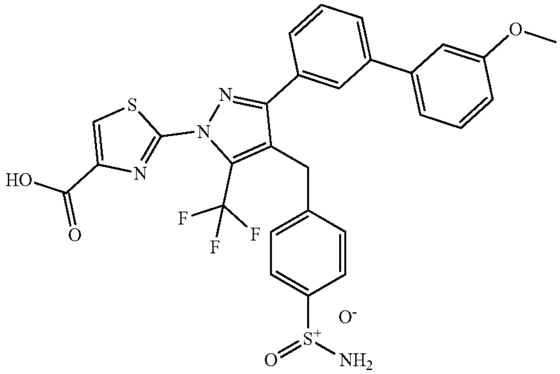 | (M + H)$^+$ = 615 | +++ | 14, 18 |
| 315 | 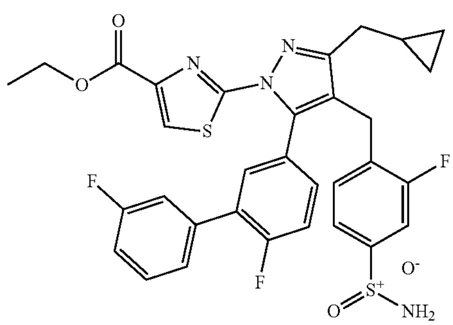 | $^1$H NMR (400 MHz, DMSO-d6) δ 8.22 (s, 1H), 7.66 (dd, J = 7.6, 2.2 Hz, 1H), 7.52-7.36 (m, 5H), 7.40-7.27 (m, 4H), 7.26-7.16 (m, 2H), 4.10 (q, J = 7.1 Hz, 2H), 3.85 (s, 2H), 2.44 (d, J = 6.8 Hz, 2H), 1.10 (t, J = 7.1 Hz, 3H), 0.99-0.86 (m, 1H), 0.44-0.34 (m, 2H), 0.16-0.07 (m, 2H); (M + H)$^+$ = 653 | – | 141 |
| 316 | 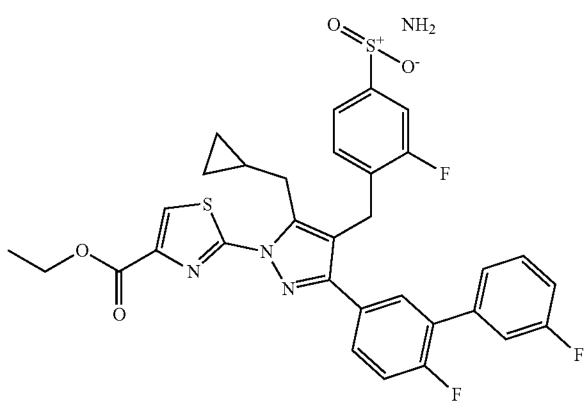 | (M + H)$^+$ = 653 | + | 141 |

TABLE 7-continued

| Cmpd ID | Structure | Compound name and physical data | Inhibitory activity IC$_{50}$ (μM) | Example Method |
|---|---|---|---|---|
| 317 | 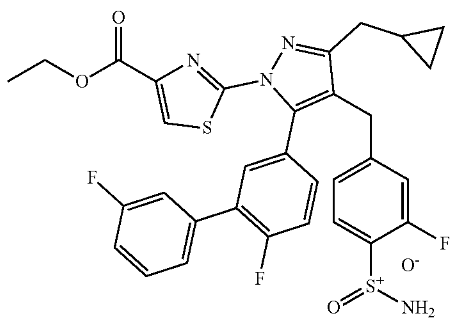 | $^1$H NMR (400 MHz, DMSO-d6) δ 8.22 (s, 1H), 7.69 (dd, J = 7.6, 2.2 Hz, 1H), 7.62 (t, J = 7.9 Hz, 1H), 7.55 (s, 2H), 7.52-7.34 (m, 2H), 7.38-7.31 (m, 1H), 7.35-7.27 (m, 2H), 7.21 (dddd, J = 9.0, 8.3, 2.6, 1.0 Hz, 1H), 7.11 (dd, J = 11.4, 1.5 Hz, 1H), 7.04 (dd, J = 8.1, 1.6 Hz, 1H), 4.10 (q, J = 7.1 Hz, 2H), 3.88 (s, 2H), 2.41 (d, J = 6.8 Hz, 2H), 1.10 (t, J = 7.1 Hz, 3H), 0.99-0.87 (m, 1H), 0.44-0.34 (m, 2H), 0.15-0.06 (m, 2H); (M + H)$^+$ = 653 | – | 141 |
| 318 | 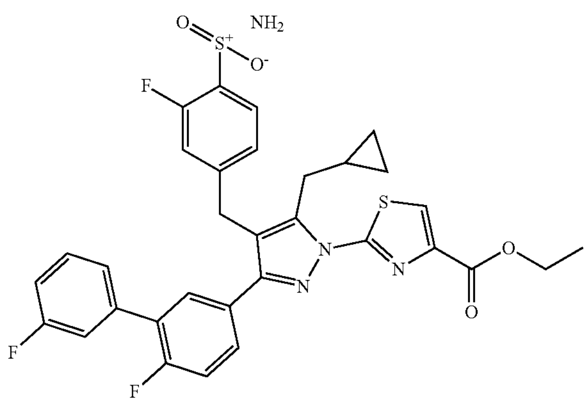 | $^1$H NMR (400 MHz, DMSO-d6) δ 8.35 (s, 1H), 7.68-7.55 (m, 3H), 7.56 (s, 2H), 7.48 (ddd, J = 8.4, 7.7, 6.2 Hz, 1H), 7.42-7.29 (m, 2H), 7.34-7.16 (m, 2H), 7.21-7.11 (m, 2H), 7.05 (dd, J = 8.1, 1.6 Hz, 1H), 4.29 (q, J = 7.1 Hz, 2H), 4.17 (s, 2H), 3.15 (d, J = 6.9 Hz, 2H), 1.30 (t, J = 7.1 Hz, 3H), 1.25-0.96 (m, 1H), 0.37-0.19 (m, 4H); (M + H)$^+$ = 653 | – | 141 |
| 319 | 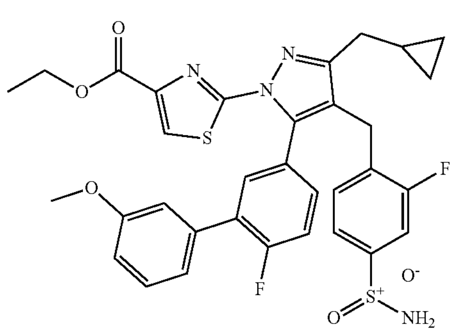 | (M + H)$^+$ = 665 | – | 141 |

TABLE 7-continued

| Cmpd ID | Structure | Compound name and physical data | Inhibitory activity IC$_{50}$ (μM) | Example Method |
|---|---|---|---|---|
| 320 | 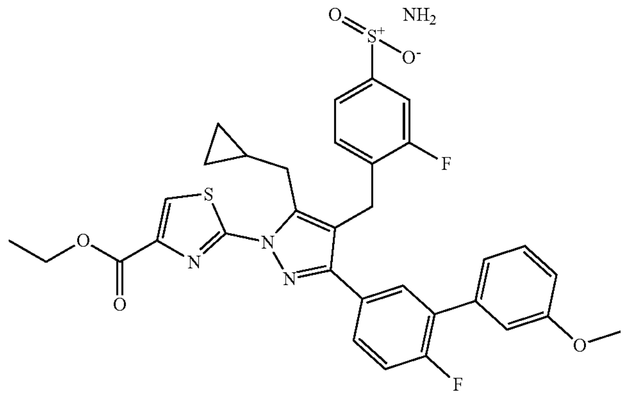 | $^1$H NMR (400 MHz, DMSO-d6) δ 8.35 (s, 1H), 7.61-7.44 (m, 4H), 7.43-7.29 (m, 4H), 7.14 (t, J = 7.8 Hz, 1H), 7.02-6.94 (m, 1H), 6.99-6.87 (m, 1H), 4.29 (q, J = 7.1 Hz, 2H), 4.11 (s, 2H), 3.76 (s, 3H), 3.15 (d, J = 6.9 Hz, 2H), 1.30 (t, J = 7.1 Hz, 3H), 1.20-0.95 (m, 0H), 0.36-0.17 (m, 4H); (M + H)$^+$ = 665 | − | 141 |
| 321 | 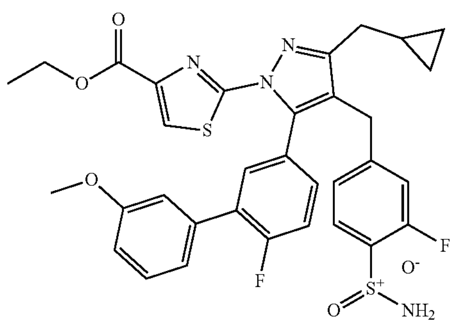 | $^1$H NMR (400 MHz, DMSO-d6) δ 8.22 (s, 1H), 7.67-7.58 (m, 2H), 7.55 (s, 2H), 7.44-7.27 (m, 3H), 7.15-6.89 (m, 6H), 4.10 (q, J = 7.1 Hz, 2H), 3.88 (s, 2H), 3.72 (s, 3H), 2.41 (d, J = 6.8 Hz, 2H), 1.11 (t, J = 7.1 Hz, 3H), 1.01-0.78 (m, 1H), 0.43-0.34 (m, 2H), 0.15-0.06 (m, 2H); (M + H)$^+$ = 665 | − | 141 |
| 322 | 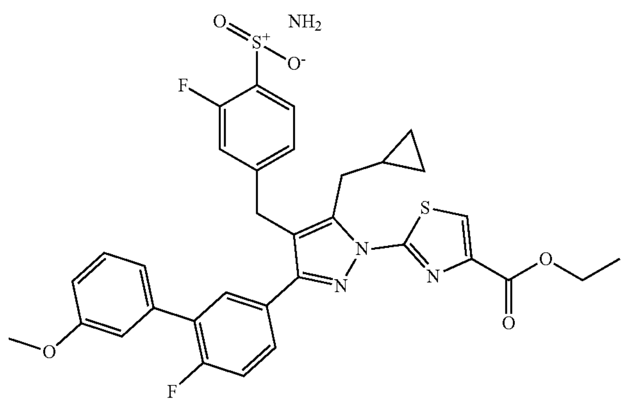 | (M + H)$^+$ = 665 | + | 141 |
| 323 | 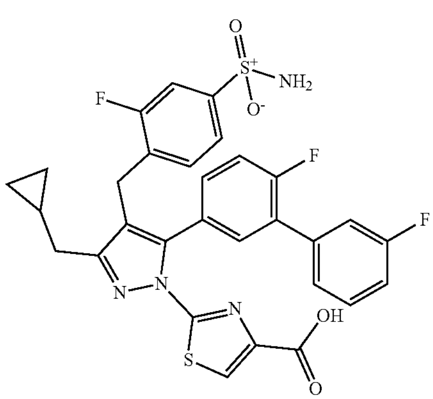 [SMILES: N[S+](=O)([O-])c1ccc(Cc2c(CC3CC3)nn(-c3nc(C(=O)O)cs3)c2-c2ccc(F)c(-c3cccc(F)c3)c2)c(F)c1] | $^1$H NMR (400 MHz, DMSO-d6) δ 12.91 (s, 1H), 8.18 (s, 1H), 7.66 (dd, J = 7.6, 2.2 Hz, 1H), 7.52-7.25 (m, 7H), 7.39 (s, 2H), 7.26-7.15 (m, 2H), 3.85 (s, 2H), 2.44 (d, J = 6.8 Hz, 2H), 1.00-0.85 (m, 1H), 0.44-0.34 (m, 2H), 0.15-0.07 (m, 2H); (M + H)$^+$ = 625 | + | 141 |

TABLE 7-continued

| Cmpd ID | Structure | Compound name and physical data | Inhibitory activity IC$_{50}$ (μM) | Example Method |
|---|---|---|---|---|
| 324 | 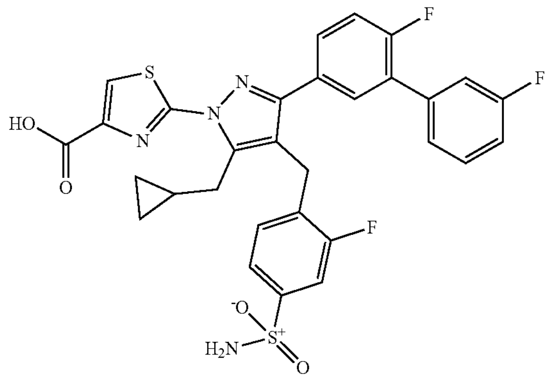 | $^1$H NMR (400 MHz, DMSO-d6) δ 13.14 (s, 1H), 8.27 (s, 1H), 7.64-7.55 (m, 2H), 7.55-7.43 (m, 3H), 7.43-7.09 (m, 7H), 4.11 (s, 2H), 3.16 (d, J = 6.9 Hz, 2H), 1.21-0.95 (m, 1H), 0.36-0.25 (m, 2H), 0.28-0.15 (m, 2H); (M + H)$^+$ = 625 | +++ | 141 |
| 325 | 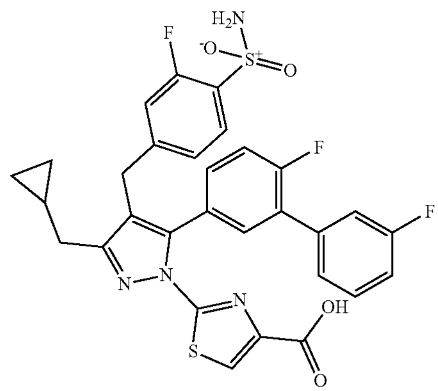 | $^1$H NMR (400 MHz, DMSO-d6) δ 12.91 (s, 1H), 8.17 (s, 1H), 7.73-7.58 (m, 2H), 7.55 (s, 2H), 7.50-7.40 (m, 1H), 7.44-7.33 (m, 2H), 7.37-7.29 (m, 2H), 7.21 (dddd, J = 9.1, 8.3, 2.6, 1.0 Hz, 1H), 7.14-6.99 (m, 2H), 3.88 (s, 2H), 2.41 (d, J = 6.8 Hz, 2H), 1.00-0.85 (m, 1H), 0.44-0.34 (m, 2H), 0.15-0.06 (m, 2H); (M + H)$^+$ = 625 | + | 141 |
| 326 | 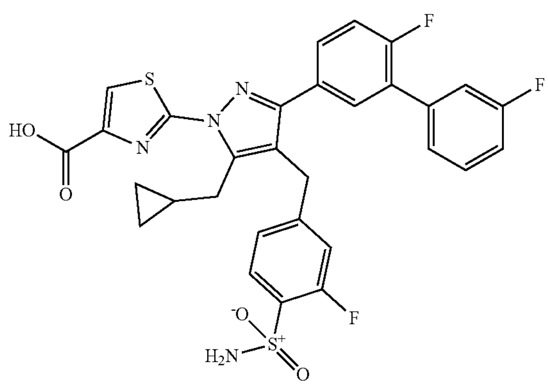 | (M + H)$^+$ = 625 | +++ | 141 |
| 327 | 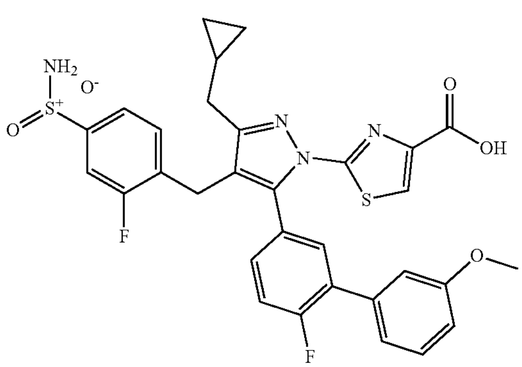 | $^1$H NMR (400 MHz, DMSO-d6) δ 12.89 (s, 1H), 8.18 (s, 1H), 7.57 (dd, J = 7.6, 2.2 Hz, 1H), 7.53-7.44 (m, 2H), 7.42-7.23 (m, 5H), 7.20 (t, J = 7.9 Hz, 1H), 7.06-6.97 (m, 2H), 6.92 (ddd, J = 8.3, 2.6, 1.0 Hz, 1H), 3.85 (s, 2H), 3.72 (s, 3H), 2.43 (d, J = 6.8 Hz, 2H), 1.06-0.78 (m, 1H), 0.43-0.32 (m, 2H), 0.17-0.04 (m, 2H); (M + H)$^+$ = 637 | + | 141 |

TABLE 7-continued

| Cmpd ID | Structure | Compound name and physical data | Inhibitory activity IC$_{50}$ (μM) | Example Method |
|---|---|---|---|---|
| 328 | 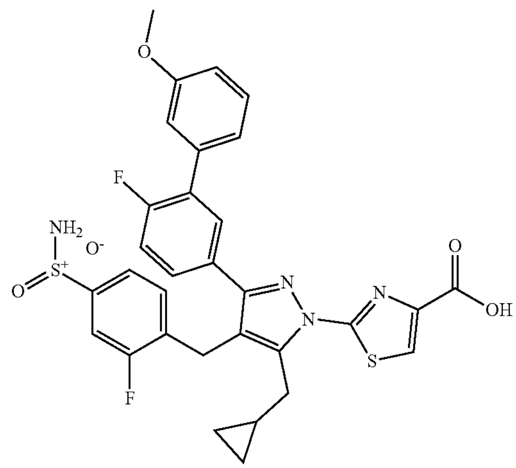 | $^1$H NMR (400 MHz, DMSO-d6) δ 13.14 (s, 1H), 8.27 (s, 1H), 7.61-7.44 (m, 4H), 7.41 (s, 2H), 7.39-7.29 (m, 2H), 7.14 (t, J = 7.8 Hz, 1H), 7.02-6.87 (m, 3H), 4.11 (s, 2H), 3.76 (s, 3H), 3.15 (d, J = 6.9 Hz, 2H), 1.20-0.98 (m, 1H), 0.35-0.26 (m, 2H), 0.29-0.15 (m, 2H); (M + H)$^+$ = 637 | +++ | 141 |
| 329 | 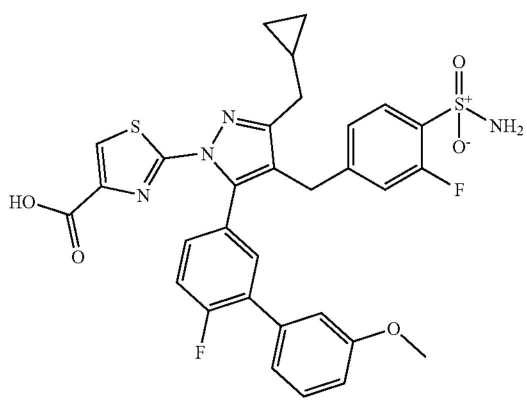 [SMILES: COc1cccc(-c2cc(-c3c(Cc4ccc([S+](N)(=O)[O-])c(F)c4)c(CC4CC4)nn3-c3nc(C(=O)O)cs3)ccc2F)c1] | $^1$H NMR (400 MHz, DMSO-d6) δ 12.88 (s, 1H), 8.17 (s, 1H), 7.67-7.57 (m, 2H), 7.55 (s, 2H), 7.43-7.26 (m, 3H), 7.15-6.97 (m, 4H), 6.92 (ddd, J = 8.3, 2.6, 0.9 Hz, 1H), 3.88 (s, 2H), 3.72 (s, 3H), 2.40 (d, J = 6.8 Hz, 2H), 0.92 (dddd, J = 14.8, 8.0, 5.0, 1.9 Hz, 1H), 0.43-0.34 (m, 2H), 0.14-0.06 (m, 2H); (M + H)$^+$ = 637 | + | 141 |
| 330 | 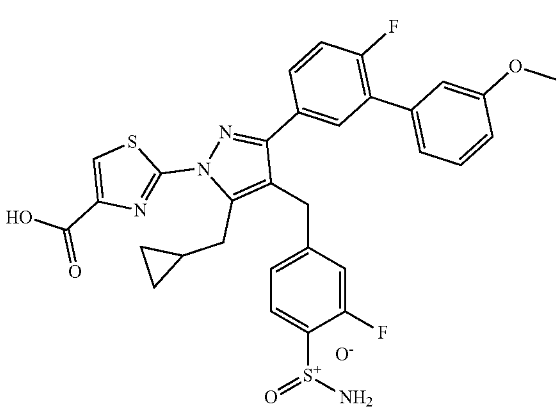 | $^1$H NMR (400 MHz, DMSO-d6) δ 13.13 (s, 1H), 8.27 (s, 1H), 7.68-7.54 (m, 3H), 7.56 (s, 2H), 7.39-7.29 (m, 2H), 7.15 (dd, J = 11.3, 1.6 Hz, 1H), 7.09-6.86 (m, 4H), 4.16 (s, 2H), 3.75 (s, 3H), 3.14 (d, J = 6.9 Hz, 2H), 1.11 (s, 1H), 0.36-0.27 (m, 2H), 0.24-0.15 (m, 2H); (M + H)$^+$ = 637 | +++ | 141 |

TABLE 7-continued

| Cmpd ID | Structure | Compound name and physical data | Inhibitory activity IC$_{50}$ (μM) | Example Method |
|---|---|---|---|---|
| 331 | 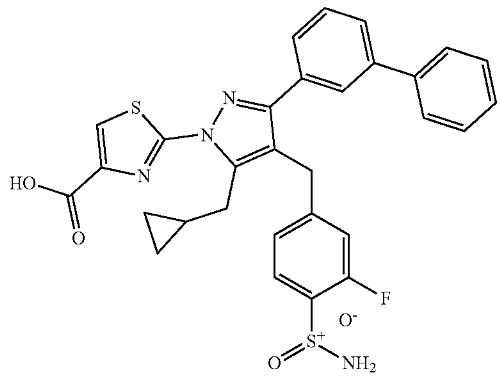 | $^1$H NMR (400 MHz, DMSO-d6) δ 13.13 (s, 1H), 8.27 (s, 1H), 7.71-7.62 (m, 2H), 7.66-7.53 (m, 2H), 7.58 (s, 2H), 7.56-7.29 (m, 6H), 7.19 (dd, J = 11.4, 1.6 Hz, 1H), 7.08 (dd, J = 8.1, 1.6 Hz, 1H), 4.17 (s, 2H), 3.16 (d, J = 6.9 Hz, 2H), 1.23-1.07 (m, 1H), 0.37-0.28 (m, 2H), 0.31-0.17 (m, 2H); (M + H)$^+$ = 589 | +++ | 141 |
| 332 | 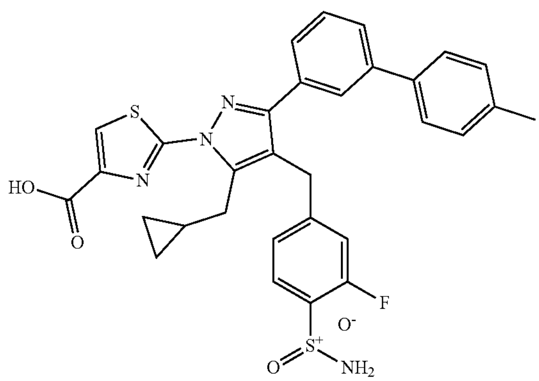 | $^1$H NMR (400 MHz, DMSO-d6) δ 13.13 (s, 1H), 8.27 (s, 1H), 7.71-7.53 (m, 4H), 7.58 (s, 2H), 7.57-7.40 (m, 2H), 7.34 (d, J = 8.2 Hz, 2H), 7.26-7.15 (m, 3H), 7.08 (dd, J = 8.1, 1.6 Hz, 1H), 4.16 (s, 2H), 3.16 (d, J = 6.9 Hz, 2H), 2.30 (s, 3H), 1.23-1.01 (m, 1H), 0.37-0.28 (m, 2H), 0.25-0.16 (m, 2H); (M + H)$^+$ = 603 | +++ | 141 |
| 333 | 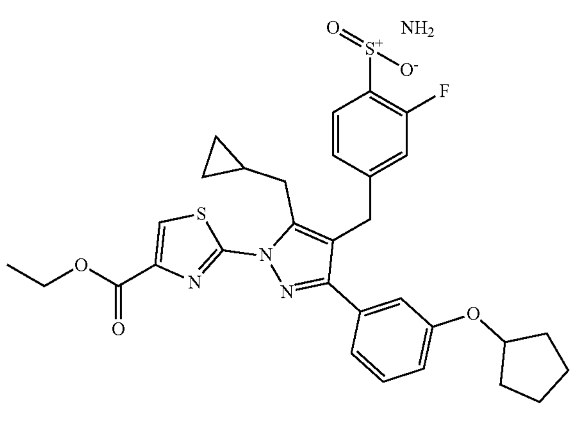 | $^1$H NMR (400 MHz, DMSO-d6) δ 8.33 (s, 1H), 7.65 (t, J = 8.0 Hz, 1H), 7.56 (s, 2H), 7.32-7.23 (m, 1H), 7.14 (dd, J = 11.3, 1.5 Hz, 1H), 7.12-7.01 (m, 2H), 6.94-6.83 (m, 2H), 4.58 (dq, J = 6.0, 3.0 Hz, 1H), 4.29 (q, J = 7.1 Hz, 2H), 4.11 (s, 2H), 3.12 (d, J = 6.9 Hz, 2H), 1.80-1.68 (m, 2H), 1.68-1.59 (m, 3H), 1.59-1.47 (m, 3H), 1.30 (t, J = 7.1 Hz, 3H), 1.16-1.04 (m, 1H), 0.36-0.27 (m, 2H), 0.27-0.17 (m, 2H); (M + H)$^+$ = 625 | + | 120 |

TABLE 7-continued

| Cmpd ID | Structure | Compound name and physical data | Inhibitory activity IC$_{50}$ (μM) | Example Method |
|---|---|---|---|---|
| 334 | 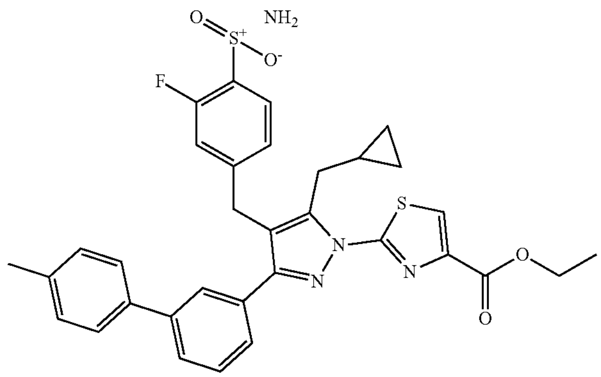 | $^1$H NMR (400 MHz, DMSO-d6) δ 8.33 (s, 1H), 7.73-7.65 (m, 2H), 7.32-7.22 (m, 5H), 7.09 (ddd, J = 7.6, 1.6, 1.0 Hz, 1H), 6.95-6.83 (m, 2H), 4.54 (dq, J = 6.1, 3.1 Hz, 1H), 4.29 (q, J = 7.1 Hz, 2H), 4.10 (s, 2H), 3.11 (d, J = 6.9 Hz, 2H), 1.78-1.41 (m, 8H), 1.30 (t, J = 7.1 Hz, 3H), 1.14-1.10 m, 1H), 0.35-0.25 (m, 2H), 0.25-0.16 (m, 2H); (M + H)$^+$ = 607 | – | 141 |
| 335 | 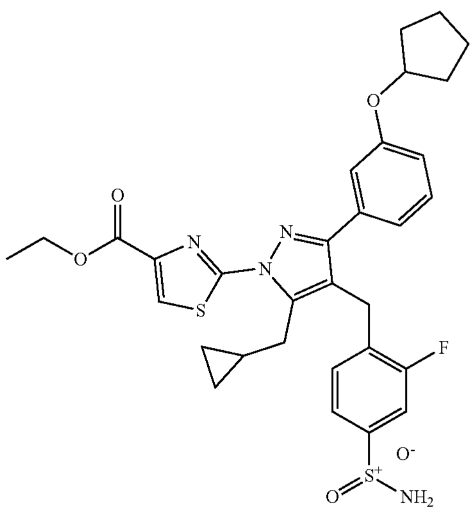 | $^1$H NMR (400 MHz, DMSO-d6) δ 8.49-8.24 (m, 1H), 7.60-7.45 (m, 2H), 7.41 (s, 2H), 7.27 (ddd, J = 8.2, 7.7, 0.5 Hz, 1H), 7.18-7.02 (m, 2H), 6.96-6.83 (m, 2H), 4.57 (dq, J = 5.9, 3.0 Hz, 1H), 4.29 (q, J = 7.1 Hz, 2H), 4.06 (s, 2H), 3.13 (d, J = 7.0 Hz, 2H), 1.92-1.40 (m, 8H), 1.30 (t, J = 7.1 Hz, 3H), 1.23-0.93 (m, 1H), 0.39-0.26 (m, 2H), 0.24-0.13 (m, 2H); (M + H)$^+$ = 625 | + | 120 |
| 336 | 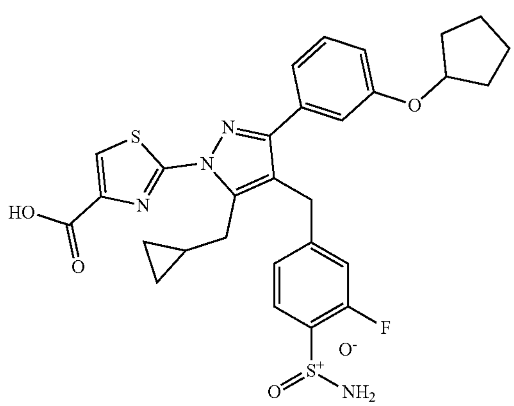 | $^1$H NMR (400 MHz, DMSO-d6) δ 13.11 (s, 0H), 8.27 (s, 1H), 7.65 (t, J = 7.9 Hz, 1H), 7.55 (s, 2H), 7.27 (t, J = 7.9 Hz, 1H), 7.18-7.07 (m, 2H), 7.04 (dd, J = 8.1, 1.6 Hz, 1H), 6.94-6.83 (m, 2H), 4.58 (tt, J = 5.7, 2.5 Hz, 1H), 4.11 (s, 2H), 3.12 (d, J = 6.9 Hz, 2H), 1.78-1.46 (m, 8H), 1.23-0.93 (m, 1H), 0.35-0.14 (m, 4H); (M + H)$^+$ = 597 | +++ | 120 |

TABLE 7-continued

| Cmpd ID | Structure | Compound name and physical data | Inhibitory activity IC$_{50}$ (μM) | Example Method |
|---|---|---|---|---|
| 337 | 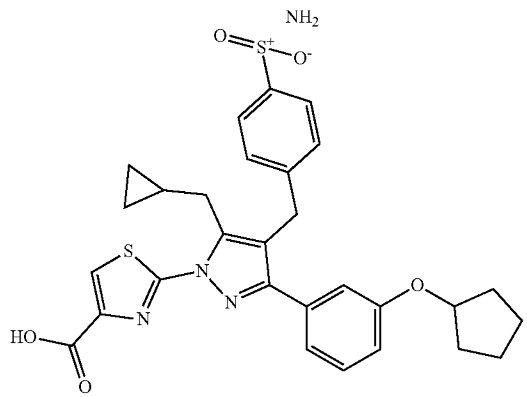 | $^1$H NMR (400 MHz, DMSO-d6) δ 13.11 (s, 1H), 8.27 (s, 1H), 7.72-7.65 (m, 2H), 7.32-7.19 (m, 6H), 7.09 (ddd, J = 7.6, 1.6, 1.0 Hz, 1H), 6.95-6.82 (m, 3H), 4.54 (dq, J = 6.1, 3.1 Hz, 1H), 4.09 (s, 2H), 3.11 (d, J = 6.9 Hz, 2H), 1.78-1.69 (m, 2H), 1.69-1.57 (m, 4H), 1.57-1.46 (m, 4H), 1.21-0.93 (m, 1H), 0.34-0.25 (m, 2H), 0.22-0.13 (m, 2H); (M + H)$^+$ = 579 | +++ | 120 |
| 338 | 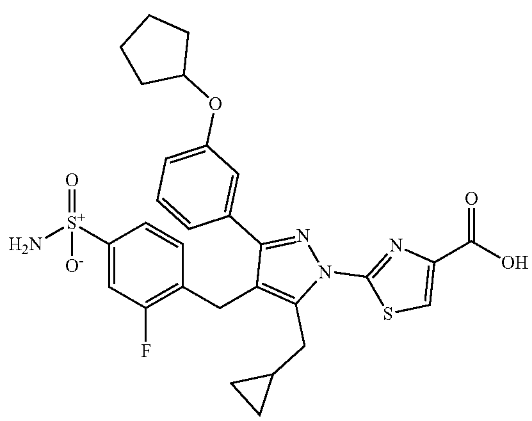 [SMILES: N[S+](=O)([O-])c1ccc(Cc2c(-c3cccc(OC4CCCC4)c3)nn(-c3nc(C(=O)O)cs3)c2CC2CC2)c(F)c1] | $^1$H NMR (400 MHz, DMSO-d6) δ 13.12 (s, 1H), 7.58-7.45 (m, 2H), 7.41 (s, 2H), 7.27 (t, J = 7.9 Hz, 1H), 7.16-7.02 (m, 2H), 6.93-6.83 (m, 2H), 4.56 (tt, J = 5.6, 2.5 Hz, 1H), 4.05 (s, 2H), 3.13 (d, J = 6.9 Hz, 2H), 1.80-1.46 (m, 8H), 1.20-0.82 (m, 1H), 0.34-0.26 (m, 2H), 0.26-0.14 (m, 2H); (M + H)$^+$ = 597 | +++ | 120 |
| 339 | 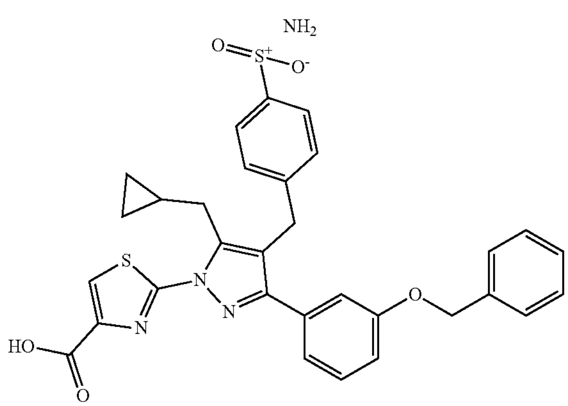 | $^1$H NMR (400 MHz, DMSO-d6) δ 13.12 (s, 1H), 8.27 (s, 1H), 7.72-7.64 (m, 2H), 7.42-7.20 (m, 10H), 7.16-7.07 (m, 2H), 7.00 (ddd, J = 8.3, 2.6, 1.0 Hz, 1H), 5.01 (s, 2H), 4.09 (s, 2H), 3.11 (d, J = 6.9 Hz, 2H), 1.09 (ddtd, J = 13.0, 7.9, 6.9, 5.0 Hz, 1H), 0.35-0.25 (m, 2H), 0.22-0.13 (m, 2H); (M + H)$^+$ = 601 | +++ | 120 |

TABLE 7-continued

| Cmpd ID | Structure | Compound name and physical data | Inhibitory activity IC$_{50}$ (μM) | Example Method |
|---|---|---|---|---|
| 340 | 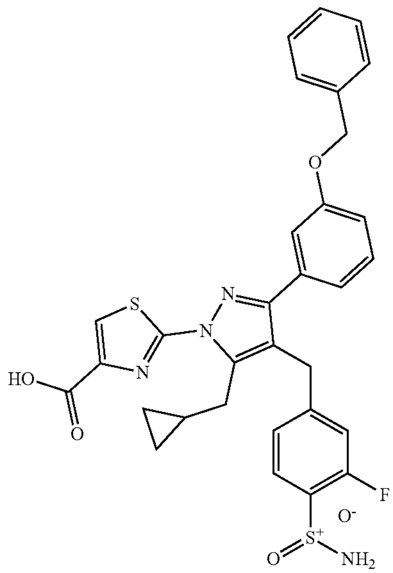 | $^1$H NMR (400 MHz, DMSO-d6) δ 13.13 (s, 1H), 8.27 (s, 1H), 7.63 (t, J = 7.9 Hz, 1H), 7.55 (s, 2H), 7.42-7.24 (m, 6H), 7.16-7.05 (m, 3H), 7.00 (ddt, J = 8.3, 2.6, 1.2 Hz, 2H), 5.03 (s, 2H), 4.10 (s, 2H), 3.12 (d, J = 6.9 Hz, 2H), 1.14-0.98 (m, 1H), 0.35-0.24 (m, 2H), 0.25-0.14 (m, 2H); (M + H)$^+$ = 619 | +++ | 120 |
| 341 | 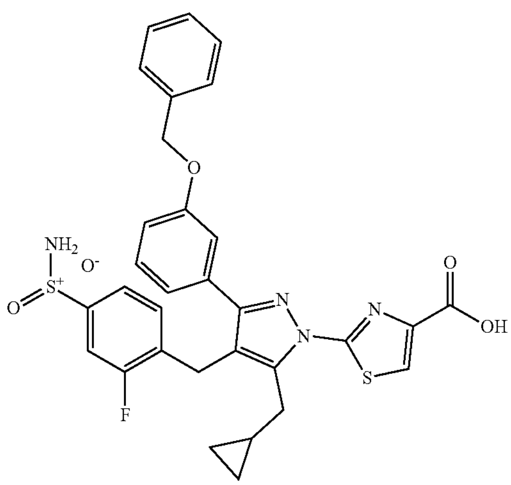 | $^1$H NMR (400 MHz, DMSO-d6) δ 13.13 (s, 1H), 8.27 (s, 1H), 7.58-7.43 (m, 2H), 7.43-7.24 (m, 8H), 7.16-6.96 (m, 4H), 5.04 (s, 2H), 4.05 (s, 2H), 3.12 (d, J = 6.9 Hz, 2H), 1.18-0.96 (m, 1H), 0.34-0.25 (m, 2H), 0.22-0.13 (m, 2H); (M + H)$^+$ = 619 | +++ | 120 |
| 342 | 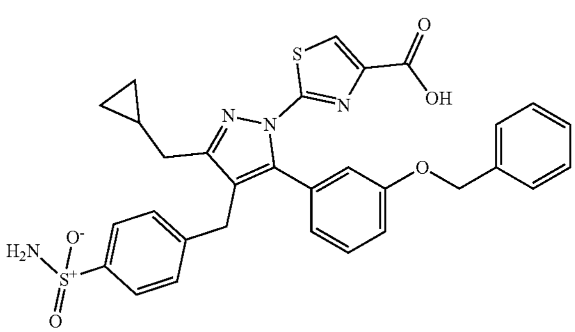 [SMILES: N[S+](=O)([O-])c1ccc(Cc2c(CC3CC3)nn(-c3nc(C(=O)O)cs3)c2-c2cccc(OCc3ccccc3)c2)cc1] | $^1$H NMR (400 MHz, DMSO-d6) δ 12.91 (s, 1H), 8.18 (s, 1H), 7.73-7.63 (m, 2H), 7.50-7.05 (m, 12H), 7.03 (ddd, J = 8.4, 2.6, 1.0 Hz, 1H), 6.90 (dt, J = 7.6, 1.1 Hz, 1H), 5.05 (s, 2H), 3.79 (s, 2H), 2.36 (d, J = 6.8 Hz, 2H), 0.98-0.83 (m, 1H), 0.43-0.31 (m, 2H), 0.12-0.03 (m, 2H); (M + H)$^+$ = 601 | + | 120 |

TABLE 7-continued

| Cmpd ID | Structure | Compound name and physical data | Inhibitory activity IC$_{50}$ (μM) | Example Method |
|---|---|---|---|---|
| 343 | 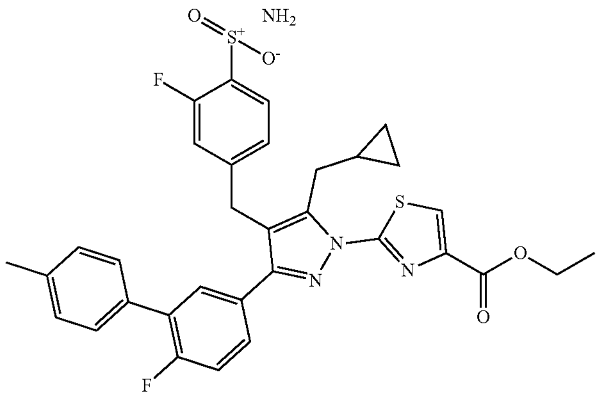 | $^1$H NMR (400 MHz, DMSO-d6) δ 8.34 (s, 1H), 7.69-7.54 (m, 2H), 7.58 (s, 2H), 7.50 (dd, J = 7.6, 2.3 Hz, 1H), 7.33 (dd, J = 10.7, 8.6 Hz, 1H), 7.24 (s, 3H), 7.29-7.13 (m, 2H), 7.05 (dd, J = 8.1, 1.6 Hz, 1H), 4.29 (q, J = 7.1 Hz, 2H), 4.15 (s, 2H), 3.15 (d, J = 6.9 Hz, 2H), 2.32 (s, 3H), 1.30 (t, J = 7.1 Hz, 3H), 1.21-1.00 (m, 1H), 0.37-0.26 (m, 2H), 0.23 (dt, J = 5.1, 2.6 Hz, 2H); (M + H)$^+$ = 649 | + | 141 |
| 344 | 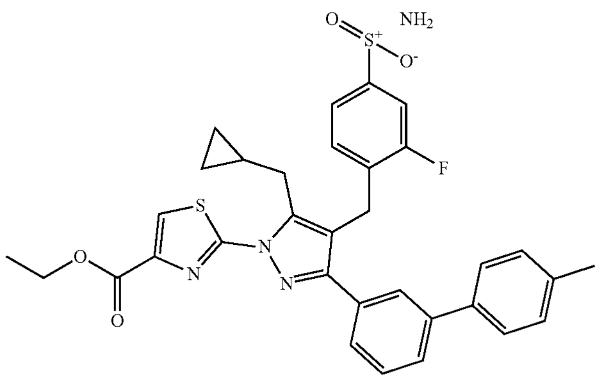 | $^1$H NMR (400 MHz, DMSO-d6) δ 8.35 (s, 1H), 7.67-7.41 (m, 9H), 7.38-7.29 (m, 2H), 7.26-7.13 (m, 3H), 4.30 (q, J = 7.1 Hz, 2H), 4.11 (s, 2H), 3.15 (dd, J = 9.8, 6.1 Hz, 3H), 2.30 (s, 3H), 1.30 (t, J = 7.1 Hz, 3H), 1.25-0.96 (m, 0H), 0.37-0.19 (m, 4H); (M + H)$^+$ = 631 | − | 145 |
| 345 | 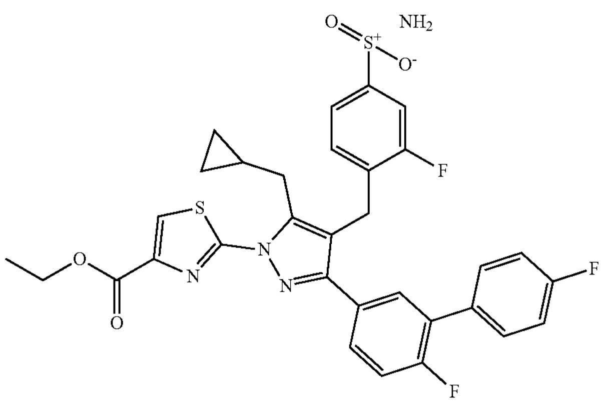 | $^1$H NMR (400 MHz, DMSO-d6) δ 8.35 (s, 1H), 7.63-7.45 (m, 4H), 7.43 (s, 2H), 7.45-7.30 (m, 3H), 7.32-7.21 (m, 2H), 7.15 (t, J = 7.8 Hz, 1H), 4.29 (q, J = 7.1 Hz, 2H), 4.10 (s, 2H), 3.16 (d, J = 6.9 Hz, 2H), 1.30 (t, J = 7.1 Hz, 3H), 1.20-0.91 (m, 0H), 0.37-0.18 (m, 4H); (M + H)$^+$ = 653 | + | 145 |
| 346 | 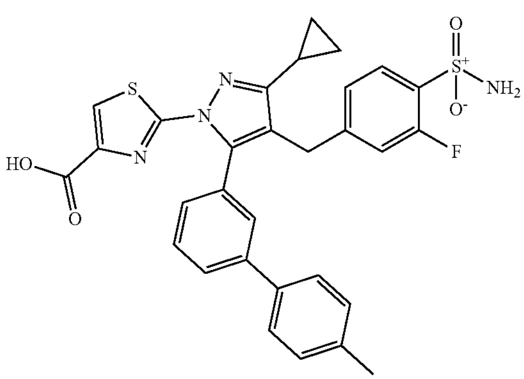 [SMILES: Cc1ccc(-c2cccc(-c3c(Cc4ccc([S+](N)(=O)[O-])c(F)c4)c(C4CC4)nn3-c3nc(C(=O)O)cs3)c2)cc1] | $^1$H NMR (400 MHz, DMSO-d6) δ 12.84 (s, 1H), 8.15 (s, 1H), 7.70-7.54 (m, 5H), 7.50-7.40 (m, 3H), 7.30 (dt, J = 7.7, 1.3 Hz, 1H), 7.24-7.08 (m, 3H), 7.13-7.02 (m, 1H), 3.92 (s, 2H), 2.29 (s, 3H), 1.77 (tt, J = 7.5, 5.6 Hz, 1H), 0.85 (ddd, J = 6.9, 3.5, 1.6 Hz, 4H); (M + H)$^+$ = 589 | + | 112 |

TABLE 7-continued

| Cmpd ID | Structure | Compound name and physical data | Inhibitory activity IC$_{50}$ (µM) | Example Method |
|---|---|---|---|---|
| 347 | 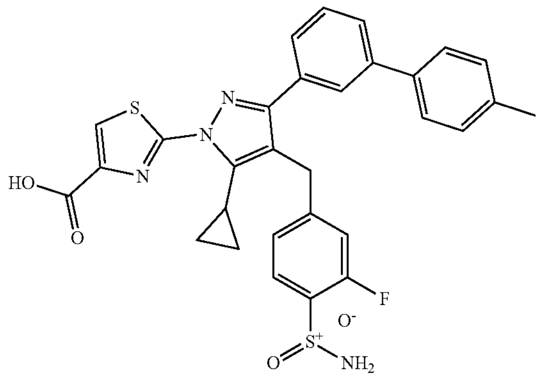 | $^1$H NMR (400 MHz, DMSO-d6) δ 13.09 (s, 1H), 8.31 (s, 1H), 7.73-7.41 (m, 7H), 7.31 (d, J = 8.2 Hz, 2H), 7.26-7.17 (m, 3H), 7.08 (dd, J = 8.2, 1.6 Hz, 1H), 4.16 (s, 2H), 2.30 (s, 3H), 2.30-2.19 (m, 1H), 1.02-0.92 (m, 2H), 0.70-0.61 (m, 2H); (M + H)$^+$ = 589 | +++ | 112 |
| 348 | 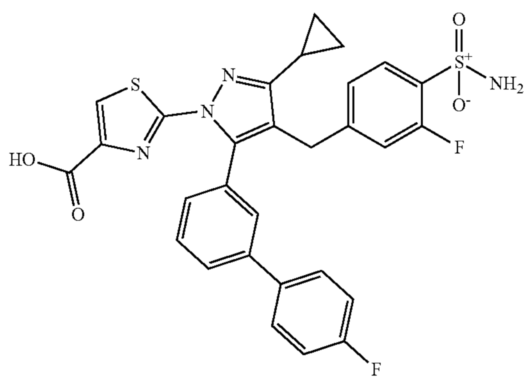 [SMILES: N[S+](=O)([O-])c1ccc(Cc2c(C3CC3)nn(-c3nc(C(=O)O)cs3)c2-c2cccc(-c3ccc(F)cc3)c2)cc1F] | (M + H)$^+$ = 593 | + | 112 |
| 349 | 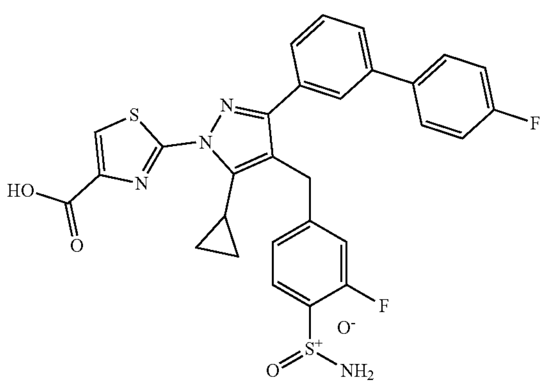 | $^1$H NMR (400 MHz, DMSO-d6) δ 13.10 (s, 1H), 8.31 (s, 1H), 7.74-7.60 (m, 2H), 7.60 (s, 2H), 7.59-7.39 (m, 5H), 7.27-7.18 (m, 3H), 7.08 (dd, J = 8.1, 1.6 Hz, 1H), 4.17 (s, 2H), 2.25 (tt, J = 8.5, 5.5 Hz, 1H), 1.04-0.93 (m, 2H), 0.73-0.62 (m, 2H); (M + H)$^+$ = 593 | +++ | 112 |
| 350 | 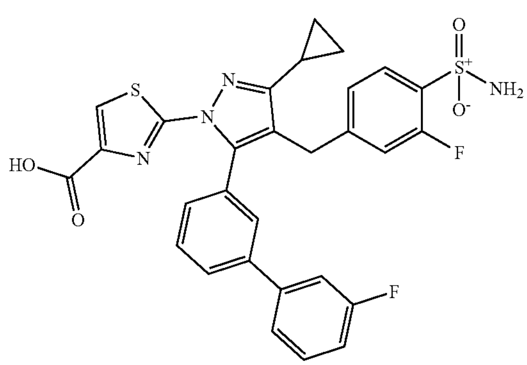 [SMILES: N[S+](=O)([O-])c1ccc(Cc2c(C3CC3)nn(-c3nc(C(=O)O)cs3)c2-c2cccc(-c3cccc(F)c3)c2)cc1F] | $^1$H NMR (400 MHz, DMSO-d6) δ 12.85 (s, 1H), 8.15 (s, 1H), 7.78-7.69 (m, 2H), 7.64 (t, J = 7.9 Hz, 1H), 7.55 (s, 2H), 7.52-7.39 (m, 4H), 7.43-7.32 (m, 1H), 7.20-7.02 (m, 3H), 3.93 (s, 2H), 1.76 (tt, J = 7.6, 5.5 Hz, 1H), 0.90-0.78 (m, 4H); (M + H)$^+$ = 593 | + | 112 |

TABLE 7-continued

| Cmpd ID | Structure | Compound name and physical data | Inhibitory activity IC$_{50}$ (µM) | Example Method |
|---|---|---|---|---|
| 351 | 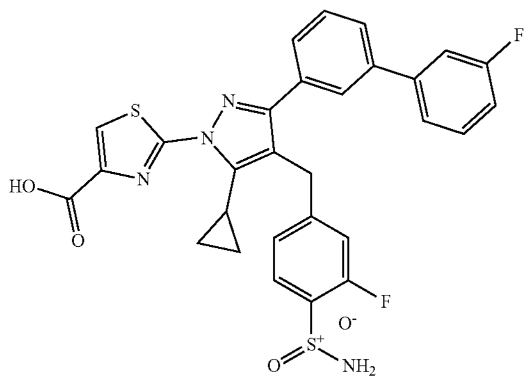 | $^1$H NMR (400 MHz, DMSO-d6) δ 13.10 (s, 1H), 8.31 (s, 1H), 7.74-7.61 (m, 3H), 7.59-7.44 (m, 4H), 7.49-7.35 (m, 2H), 7.26-7.04 (m, 4H), 4.18 (s, 2H), 2.24 (tt, J = 8.5, 5.6 Hz, 1H), 1.04-0.91 (m, 2H), 0.72-0.61 (m, 2H); (M + H)$^+$ = 593 | +++ | 112 |
| 352 | 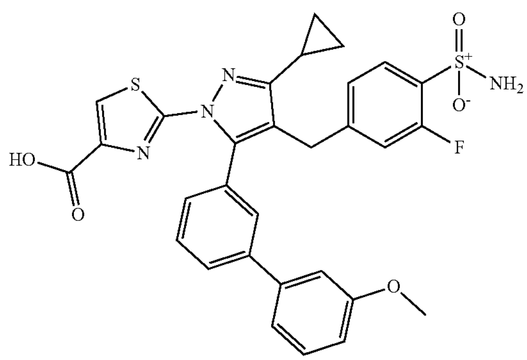 [SMILES: COc1cccc(-c2cccc(-c3c(Cc4ccc([S+](N)(=O)[O-])c(F)c4)c(C4CC4)nn3-c3nc(C(=O)O)cs3)c2)c1] | $^1$H NMR (400 MHz, DMSO-d6) δ 12.84 (s, 1H), 8.15 (s, 1H), 7.73-7.60 (m, 3H), 7.55 (s, 2H), 7.48 (td, J = 7.7, 0.5 Hz, 1H), 7.37-7.25 (m, 2H), 7.17-7.03 (m, 4H), 6.88 (ddd, J = 8.2, 2.5, 1.0 Hz, 1H), 3.93 (s, 2H), 3.29 (s, 9H), 1.75 (tt, J = 7.5, 5.6 Hz, 1H), 0.90-0.78 (m, 4H); (M + H)$^+$ = 605 | + | 112 |
| 353 | 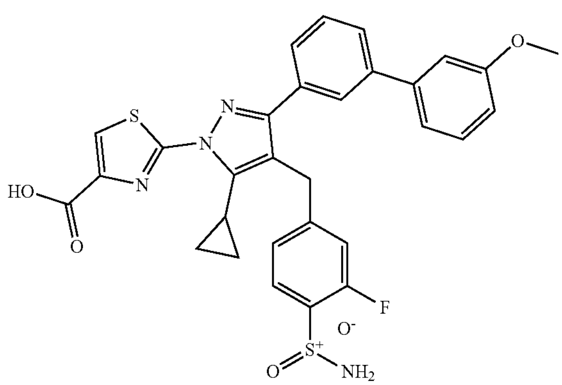 | $^1$H NMR (400 MHz, DMSO-d6) δ 13.10 (s, 1H), 8.30 (s, 1H), 7.72-7.59 (m, 3H), 7.59-7.40 (m, 4H), 7.36-7.25 (m, 1H), 7.20 (dd, J = 11.3, 1.6 Hz, 1H), 7.12-7.03 (m, 2H), 6.93 (dddd, J = 21.2, 8.3, 2.2, 0.9 Hz, 2H), 4.17 (s, 2H), 3.76 (s, 3H), 2.24 (tt, J = 8.5, 5.6 Hz, 1H), 1.01-0.90 (m, 2H), 0.71-0.58 (m, 2H); (M + H)$^+$ = 605 | +++ | 112 |
| 354 | 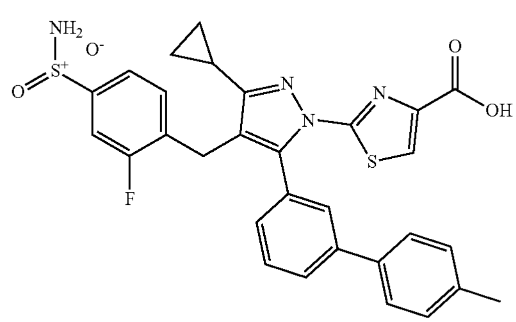 | $^1$H NMR (400 MHz, DMSO-d6) δ 12.85 (s, 1H), 8.16 (s, 1H), 7.69-7.49 (m, 3H), 7.54-7.46 (m, 1H), 7.50-7.39 (m, 5H), 7.33-7.15 (m, 4H), 3.90 (s, 2H), 2.29 (s, 3H), 1.76 (p, J = 6.8 Hz, 1H), 0.87-0.80 (m, 4H); (M + H)$^+$ = 589 | + | 112 |

TABLE 7-continued

| Cmpd ID | Structure | Compound name and physical data | Inhibitory activity IC$_{50}$ (μM) | Example Method |
|---|---|---|---|---|
| 355 | 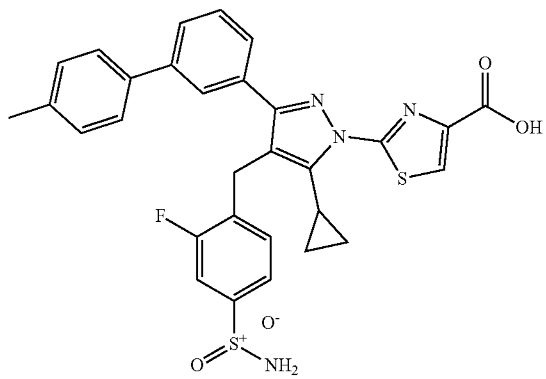 | 1H NMR (400 MHz, DMSO-d6) δ 13.11 (s, 1H), 8.31 (s, 1H), 7.69-7.49 (m, 4H), 7.52-7.42 (m, 2H), 7.43 (s, 2H), 7.37-7.28 (m, 2H), 7.25-7.16 (m, 3H), 4.11 (s, 2H), 2.30 (s, 3H), 2.21 (tt, J = 8.5, 5.6 Hz, 1H), 1.02-0.92 (m, 2H), 0.69-0.60 (m, 2H); (M + H)+ = 589 | +++ | 112 |
| 356 | 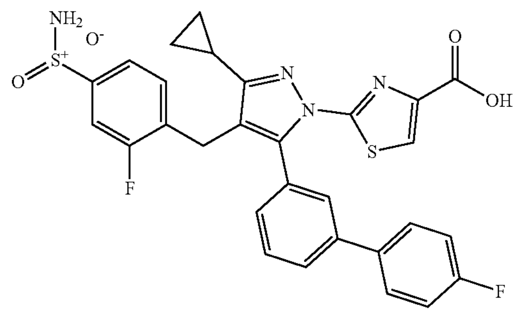 | (M + H)$^+$ = 593 | + | 112 |
| 357 | 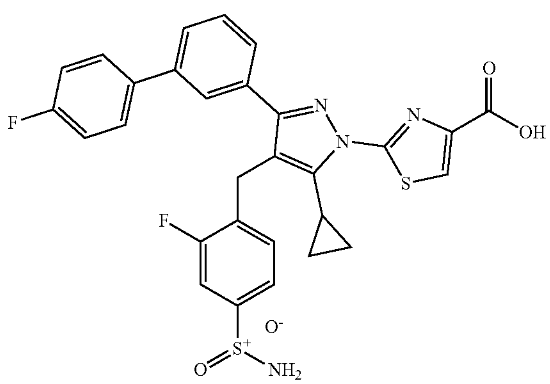 | $^1$H NMR (400 MHz, DMSO-d6) δ 13.11 (s, 1H), 8.30 (s, 1H), 7.65 (dt, J = 6.6, 2.1 Hz, 1H), 7.58-7.46 (m, 2H), 7.50-7.41 (m, 3H), 7.50-7.41 (m, 4H), 7.29-7.16 (m, 3H), 4.11 (s, 2H), 2.21 (tt, J = 8.6, 5.6 Hz, 1H), 1.02-0.91 (m, 2H), 0.71-0.60 (m, 2H); (M + H)$^+$ = 593 | +++ | 112 |
| 358 | 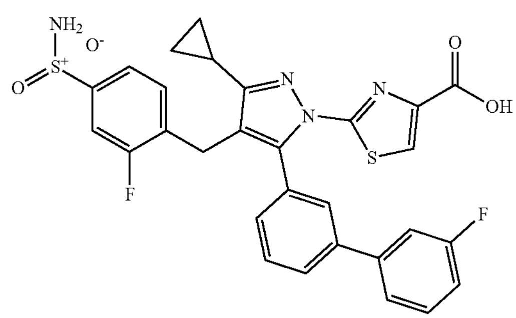 | $^1$H NMR (400 MHz, DMSO-d6) δ 12.85 (s, 1H), 8.15 (s, 1H), 7.72 (ddd, J = 9.7, 1.8, 0.9 Hz, 2H), 7.55-7.46 (m, 1H), 7.50 (s, 1H), 7.51-7.38 (m, 4H), 7.40 (s, 2H), 7.36-7.10 (m, 3H), 3.91 (s, 2H), 1.82-1.70 (m, 1H), 0.89-0.78 (m, 4H); (M + H)$^+$ = 593 | + | 112 |

TABLE 7-continued

| Cmpd ID | Structure | Compound name and physical data | Inhibitory activity IC$_{50}$ (μM) | Example Method |
|---|---|---|---|---|
| 359 | 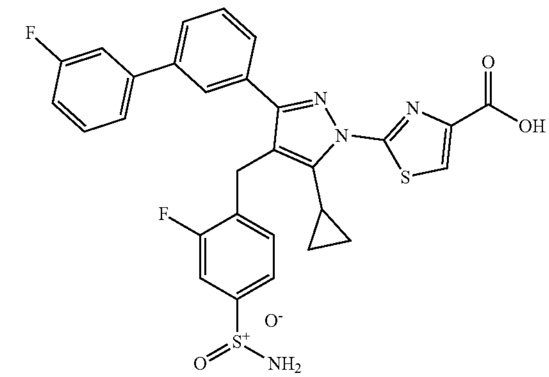 | $^1$H NMR (400 MHz, DMSO-d6) δ 13.11 (s, 1H), 8.30 (s, 1H), 7.65 (dt, J = 6.6, 2.1 Hz, 1H), 7.65-7.53 (m, 2H), 7.58-7.46 (m, 3H), 7.50-7.41 (m, 4H), 7.29-7.16 (m, 3H), 4.11 (s, 2H), 3.14 (d, J = 2.7 Hz, 1H), 2.21 (tt, J = 8.6, 5.6 Hz, 1H), 1.02-0.91 (m, 2H), 0.71-0.60 (m, 2H); (M + H)$^+$ = 593 | +++ | 112 |
| 360 | 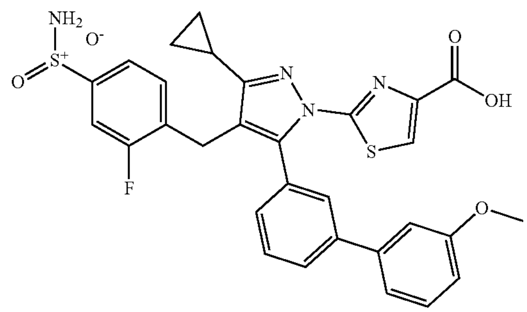 | $^1$H NMR (400 MHz, DMSO-d6) δ 12.84 (s, 1H), 8.16 (s, 1H), 7.72-7.61 (m, 2H), 7.55-7.43 (m, 3H), 7.39 (s, 2H), 7.34-7.21 (m, 3H), 7.10 (dd, J = 6.9, 1.3 Hz, 2H), 6.92-6.84 (m, 1H), 3.90 (s, 2H), 3.74 (s, 3H), 1.81-1.69 (m, 1H), 0.89-0.79 (m, 4H); (M + H)$^+$ = 605 | + | 112 |
| 361 | 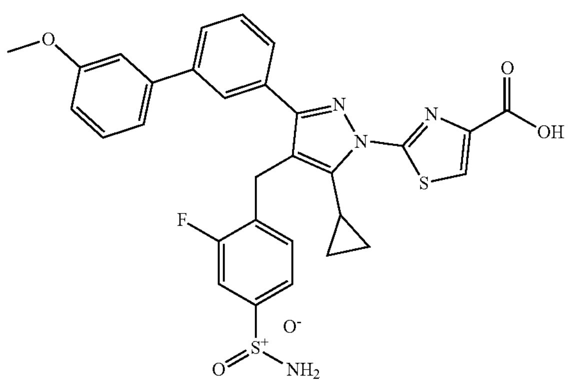 | $^1$H NMR (400 MHz, DMSO-d6) δ 13.10 (s, 1H), 8.31 (s, 1H), 7.72-7.60 (m, 2H), 7.64-7.48 (m, 2H), 7.53-7.43 (m, 2H), 7.41 (s, 2H), 7.36-7.27 (m, 1H), 7.20 (t, J = 7.8 Hz, 1H), 7.07 (dd, J = 2.5, 1.7 Hz, 1H), 6.93 (dddd, J = 24.5, 8.3, 2.1, 0.9 Hz, 2H), 4.12 (s, 2H), 3.76 (s, 3H), 2.20 (tt, J = 8.5, 5.6 Hz, 1H), 1.01-0.90 (m, 2H), 0.70-0.57 (m, 2H); (M + H)$^+$ = 605 | +++ | 112 |
| 362 | 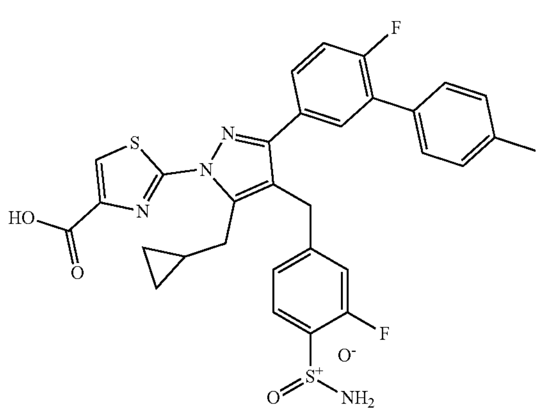 | $^1$H NMR (400 MHz, DMSO-d6) δ 13.13 (s, 1H), 8.26 (s, 1H), 7.69-7.54 (m, 2H), 7.58 (s, 2H), 7.50 (dd, J = 7.6, 2.3 Hz, 1H), 7.33 (dd, J = 10.7, 8.6 Hz, 1H), 7.24 (s, 3H), 7.29-7.13 (m, 2H), 7.04 (dd, J = 8.2, 1.6 Hz, 1H), 4.15 (s, 2H), 3.15 (d, J = 6.9 Hz, 2H), 2.32 (s, 3H), 1.20-0.96 (m, 1H), 0.37-0.27 (m, 2H), 0.28-0.16 (m, 2H); (M + H)$^+$ = 621 | +++ | 145 |

TABLE 7-continued

| Cmpd ID | Structure | Compound name and physical data | Inhibitory activity IC$_{50}$ (μM) | Example Method |
|---|---|---|---|---|
| 363 | 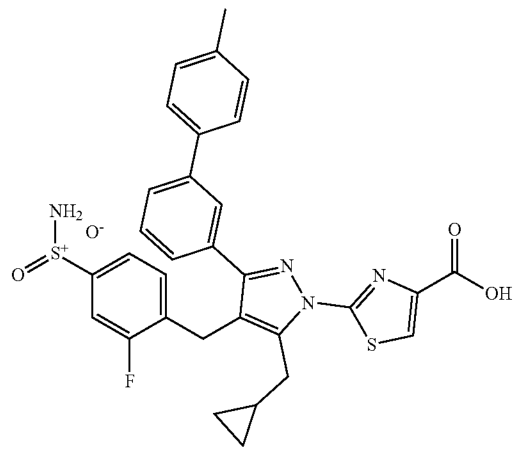 | $^1$H NMR (400 MHz, DMSO-d6) δ 13.14 (s, 1H), 8.25 (s, 1H), 7.67-7.59 (m, 2H), 7.61-7.42 (m, 4H), 7.43 (s, 2H), 7.33 (d, J = 8.2 Hz, 2H), 7.26-7.12 (m, 3H), 4.11 (s, 2H), 3.16 (d, J = 6.9 Hz, 2H), 2.30 (s, 3H), 1.18-1.01 (m, 1H), 0.36-0.27 (m, 2H), 0.24-0.17 (m, 2H); (M + H)$^+$ = 603 | +++ | 145 |
| 364 | 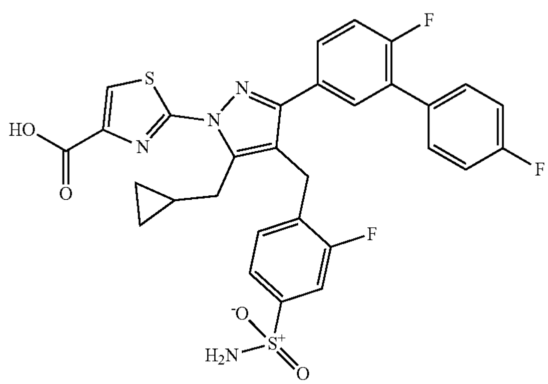 | $^1$H NMR (400 MHz, DMSO-d6) δ 13.13 (s, 1H), 8.28 (s, 1H), 7.63-7.45 (m, 4H), 7.43 (s, 2H), 7.44-7.21 (m, 5H), 7.14 (t, J = 7.8 Hz, 1H), 4.10 (s, 2H), 3.16 (d, J = 6.9 Hz, 2H), 1.15-1.02 (m, 0H), 0.36-0.15 (m, 4H); (M + H)$^+$ = 625 | +++ | 145 |
| 365 | 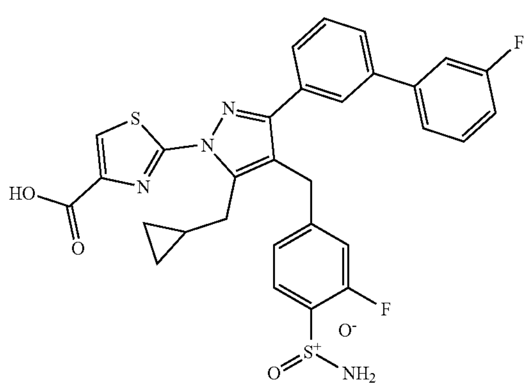 | $^1$H NMR (400 MHz, DMSO-d6) δ 13.12 (s, 1H), 8.27 (s, 1H), 7.74-7.62 (m, 3H), 7.66-7.56 (m, 1H), 7.55 (s, 2H), 7.54-7.43 (m, 1H), 7.47-7.38 (m, 2H), 7.29-7.16 (m, 2H), 7.21-7.12 (m, 1H), 7.07 (dd, J = 8.1, 1.6 Hz, 1H), 4.18 (s, 2H), 3.15 (dd, J = 9.4, 5.6 Hz, 2H), 1.23-1.06 (m, 1H), 0.37-0.17 (m, 4H); (M + H)$^+$ = 607 | +++ | 145 |

TABLE 7-continued

| Cmpd ID | Structure | Compound name and physical data | Inhibitory activity IC$_{50}$ (μM) | Example Method |
|---|---|---|---|---|
| 366 | 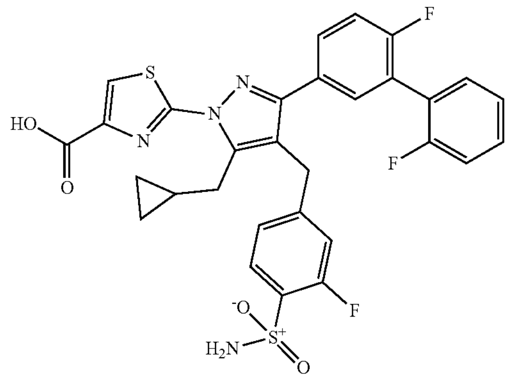 | $^1$H NMR (400 MHz, DMSO-d6) δ 13.12 (s, 1H), 8.27 (s, 1H), 7.70-7.58 (m, 2H), 7.55 (s, 2H), 7.56-7.41 (m, 2H), 7.41-7.23 (m, 4H), 7.17-6.99 (m, 2H), 4.15 (s, 2H), 3.15 (dd, J = 5.8, 4.1 Hz, 2H), 1.21-1.00 (m, 1H), 0.37-0.25 (m, 2H), 0.27-0.16 (m, 2H); (M + H)$^+$ = 625 | +++ | 145 |
| 367 | 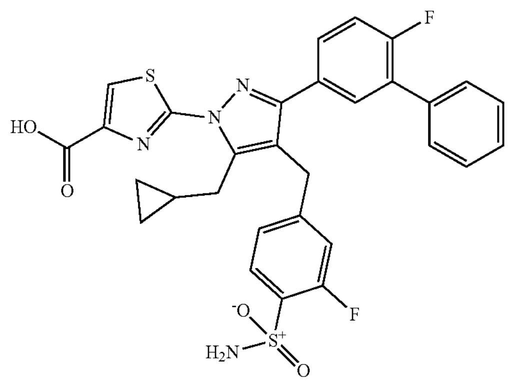 | $^1$H NMR (400 MHz, DMSO-d6) δ 13.13 (s, 1H), 8.27 (s, 1H), 7.69-7.30 (m, 11H), 7.17 (dd, J = 11.3, 1.6 Hz, 1H), 7.05 (dd, J = 8.1, 1.6 Hz, 1H), 4.16 (s, 2H), 3.19-3.11 (m, 2H), 1.19-1.05 (m, 1H), 0.37-0.26 (m, 2H), 0.26-0.16 (m, 2H); (M + H)$^+$ = 607 | +++ | 145 |
| 368 | 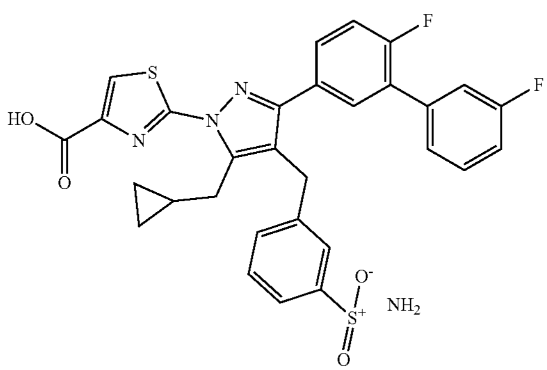 | $^1$H NMR (400 MHz, DMSO-d6) δ 13.14 (s, 1H), 8.26 (s, 1H), 7.65-7.17 (m, 11H), 7.27 (s, 2H), 4.14 (s, 2H), 3.19-3.11 (m, 3H), 1.18-0.96 (m, 1H), 0.37-0.27 (m, 2H), 0.23-0.14 (m, 2H); (M + H)$^+$ = 607 | + | 145 |
| 369 | 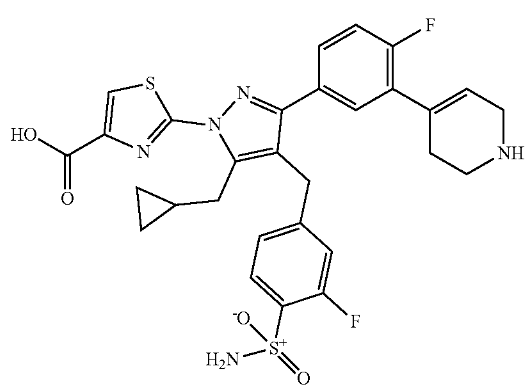 | $^1$H NMR (400 MHz, DMSO-d6) δ 13.10 (s, 1H), 8.80 (s, 2H), 8.27 (s, 1H), 7.64 (t, J = 7.9 Hz, 1H), 7.60-7.47 (m, 3H), 7.39-7.21 (m, 2H), 7.12 (dd, J = 11.3, 1.6 Hz, 1H), 7.03 (dd, J = 8.1, 1.6 Hz, 1H), 5.93-5.87 (m, 1H), 4.14-4.01 (m, 3H), 3.75-3.68 (m, 2H), 3.25 (t, J = 6.0 Hz, 2H), 3.15 (dd, J = 7.2, 5.8 Hz, 4H), 1.12 (dddd, J = 15.0, 10.0, 5.0, 2.1 Hz, 1H), 0.37-0.28 (m, 2H), 0.25-0.16 (m, 2H); (M + H)$^+$ = 612 | +++ | 145 |

TABLE 7-continued

| Cmpd ID | Structure | Compound name and physical data | Inhibitory activity IC$_{50}$ (μM) | Example Method |
|---|---|---|---|---|
| 370 | 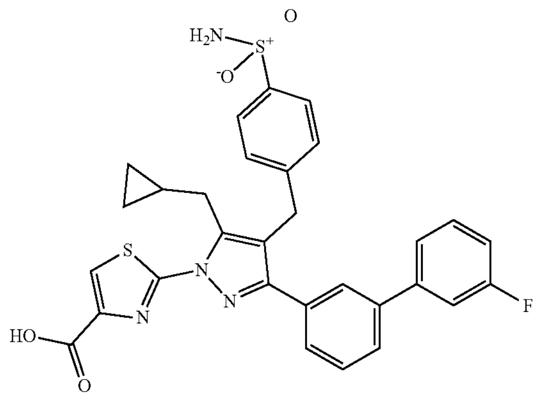 | $^1$H NMR (400 MHz, DMSO-d6) δ 13.13 (s, 1H), 8.29 (s, 1H), 7.76-7.66 (m, 4H), 7.65-7.57 (m, 1H), 7.55-7.38 (m, 3H), 7.36-7.13 (m, 6H), 4.18 (s, 2H), 3.17 (d, J = 6.9 Hz, 2H), 1.23-0.98 (m, 1H), 0.38-0.17 (m, 4H); (M + H)$^+$ = 589 | +++ | 141 |
| 371 | 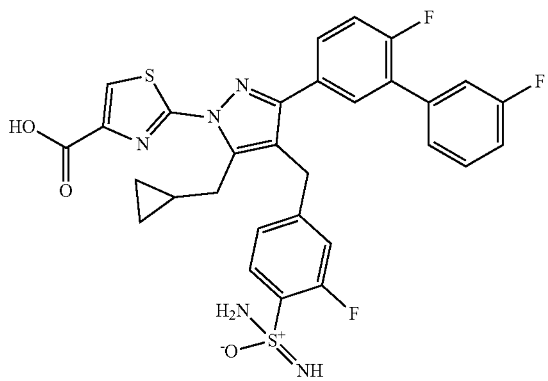 | $^1$H NMR (400 MHz, DMSO-d6) δ 8.29 (s, 1H), 7.75 (t, J = 8.0 Hz, 1H), 7.64 (ddq, J = 7.3, 3.5, 2.3, 1.8 Hz, 2H), 7.59-7.46 (m, 1H), 7.43-7.29 (m, 2H), 7.30-7.12 (m, 3H), 7.12-7.02 (m, 1H), 4.20 (s, 2H), 3.20-3.09 (m, 2H), 1.23-0.93 (m, 0H), 0.38-0.25 (m, 2H), 0.29-0.16 (m, 2H); (M + H)$^+$ = 624 | +++ | 141 |
| 372 | 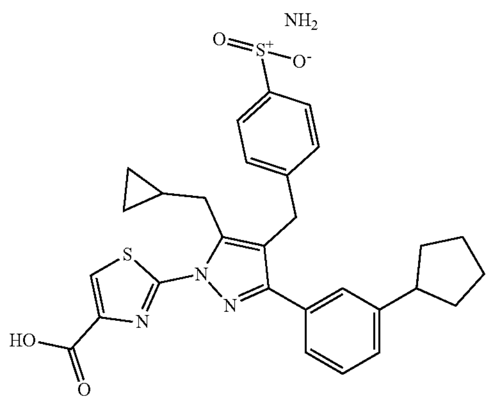 | $^1$H NMR (400 MHz, DMSO-d6) δ 8.10 (s, 1H), 7.74-7.65 (m, 2H), 7.36 (dt, J = 7.6, 1.5 Hz, 1H), 7.33-7.18 (m, 7H), 4.09 (s, 2H), 3.14 (d, J = 6.9 Hz, 2H), 2.89 (tt, J = 9.8, 7.5 Hz, 1H), 1.96-1.84 (m, 1H), 1.71-1.48 (m, 3H), 1.42-1.25 (m, 1H), 1.16-1.03 (m, 1H), 0.36-0.15 (m, 4H); (M + H)$^+$ = 563 | +++ | 146 |
| 373 | 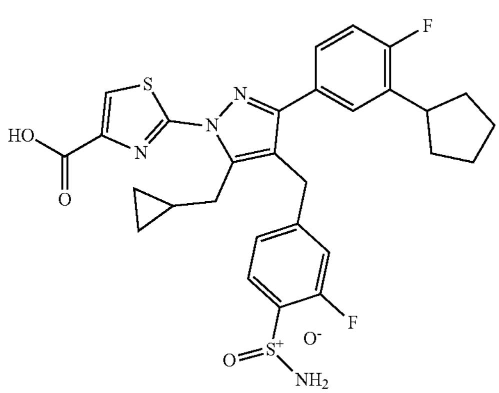 | (M + H)$^+$ = 599 | +++ | 146 |

TABLE 7-continued

| Cmpd ID | Structure | Compound name and physical data | Inhibitory activity IC$_{50}$ (μM) | Example Method |
|---|---|---|---|---|
| 374 | 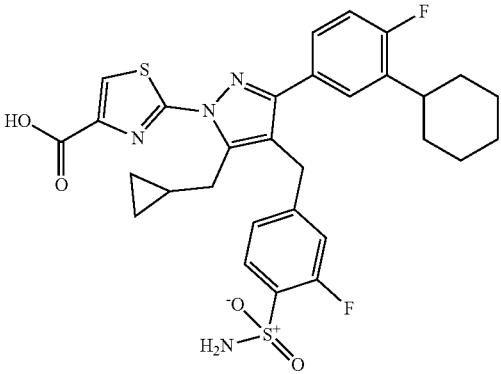 | $^1$H NMR (400 MHz, DMSO-d6) δ 13.13 (s, 1H), 8.26 (s, 1H), 7.66 (t, J = 7.9 Hz, 1H), 7.56 (s, 2H), 7.44 (ddd, J = 8.5, 5.0, 2.3 Hz, 1H), 7.27-7.16 (m, 2H), 7.20-7.11 (m, 2H), 7.04 (dd, J = 8.1, 1.6 Hz, 1H), 4.10 (s, 2H), 3.16 (d, J = 6.9 Hz, 2H), 2.78-2.66 (m, 1H), 1.72 (dd, J = 9.7, 6.4 Hz, 2H), 1.61 (d, J = 11.8 Hz, 3H), 1.37-1.23 (m, 2H), 1.15 (s, 2H), 1.20-1.03 (m, 2H), 0.38-0.29 (m, 2H), 0.26-0.17 (m, 2H); (M + H)$^+$ = 613 | +++ | 146 |
| 375 | 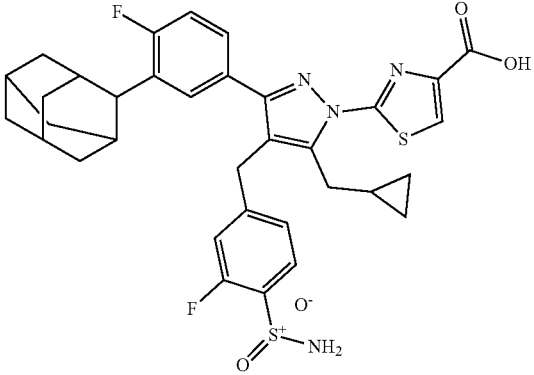 | $^1$H NMR (400 MHz, DMSO-d6) δ 8.12 (s, 1H), 7.65 (t, J = 7.9 Hz, 1H), 7.56 (s, 2H), 7.52-7.38 (m, 2H), 7.23-7.09 (m, 2H), 7.04 (dd, J = 8.1, 1.6 Hz, 1H), 4.09 (s, 2H), 3.16-3.09 (m, 3H), 2.07 (d, J = 3.8 Hz, 2H), 1.90-1.79 (m, 2H), 1.85 (s, 4H), 1.69-1.64 (m, 3H), 1.52 (d, J = 12.9 Hz, 3H), 1.42 (d, J = 12.6 Hz, 2H), 1.18-1.02 (m, 1H), 0.35-0.24 (m, 2H), 0.25-0.14 (m, 2H); (M + H)$^+$ = 665 | ++ | 146 |
| 376 | 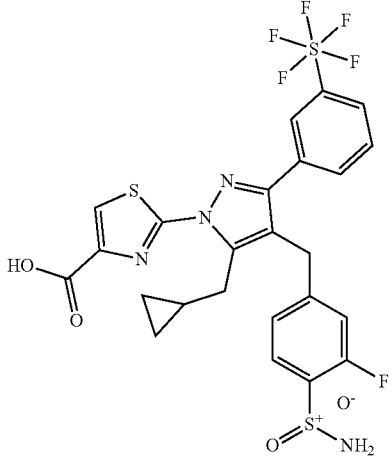 | $^1$H NMR (400 MHz, DMSO-d6) δ 13.17 (s, 1H), 8.31 (s, 1H), 7.96-7.81 (m, 3H), 7.64 (td, J = 7.9, 5.8 Hz, 2H), 7.56 (s, 2H), 7.13 (dd, J = 11.4, 1.6 Hz, 1H), 7.03 (dd, J = 8.2, 1.6 Hz, 1H), 4.17 (s, 2H), 3.18 (d, J = 6.9 Hz, 2H), 1.31-1.00 (m, 1H), 0.39-0.25 (m, 2H), 0.29-0.18 (m, 2H); (M + H)$^+$ = 639 | +++ | 141 |

TABLE 7-continued

| Cmpd ID | Structure | Compound name and physical data | Inhibitory activity IC$_{50}$ (μM) | Example Method |
|---|---|---|---|---|
| 377 | 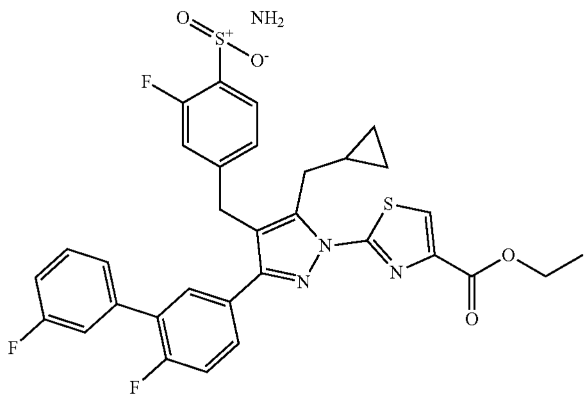 | $^1$H NMR (400 MHz, DMSO-d6) δ 8.36 (s, 1H), 7.69-7.56 (m, 3H), 7.58 (s, 2H), 7.49 (ddd, J = 8.4, 7.7, 6.2 Hz, 1H), 7.43-7.29 (m, 2H), 7.30-7.13 (m, 3H), 7.06 (dd, J = 8.1, 1.6 Hz, 1H), 4.30 (q, J = 7.1 Hz, 2H), 3.31 (s, 1H), 3.16 (d, J = 6.9 Hz, 2H), 1.31 (t, J = 7.1 Hz, 3H), 1.15 (td, J = 7.4, 5.6 Hz, 1H), 0.38-0.20 (m, 4H); (M + H)$^+$ = 653 | – | 141 |
| 378 | 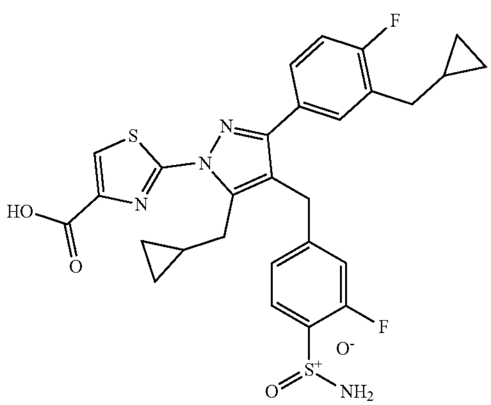 | $^1$H NMR (400 MHz, DMSO-d6) δ 13.12 (s, 1H), 8.27 (s, 1H), 7.67-7.54 (m, 1H), 7.55 (s, 2H), 7.46-7.36 (m, 2H), 7.22-7.06 (m, 2H), 7.02 (dd, J = 8.1, 1.6 Hz, 1H), 5.81-5.66 (m, 1H), 5.00-4.87 (m, 2H), 4.13 (s, 2H), 3.15 (d, J = 6.9 Hz, 2H), 2.66 (t, J = 7.5 Hz, 2H), 2.27-2.17 (m, 2H), 1.24-1.05 (m, 1H), 0.38-0.26 (m, 2H), 0.29-0.16 (m, 2H); (M + H)$^+$ = 585 | +++ | 146 |
| 379 | 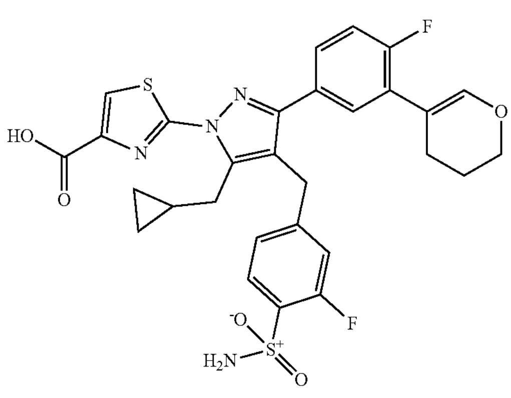 | (M + H)$^+$ = 613 | +++ | 145 |

TABLE 7-continued

| Cmpd ID | Structure | Compound name and physical data | Inhibitory activity IC$_{50}$ (μM) | Example Method |
|---|---|---|---|---|
| 380 | 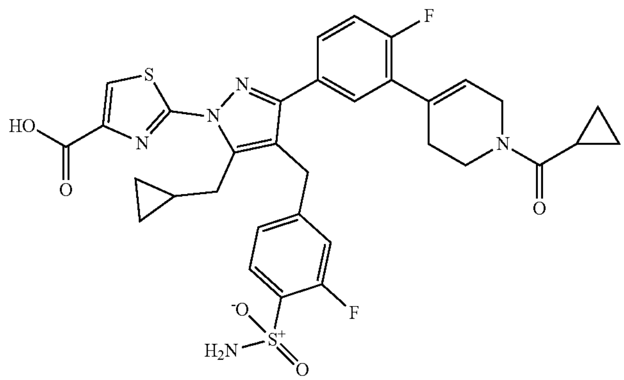 | $^1$H NMR (400 MHz, DMSO-d6) δ 13.14 (s, 1H), 8.27 (s, 1H), 7.66 (t, J = 7.9 Hz, 1H), 7.60-7.47 (m, 3H), 7.32 (s, 1H), 7.29-7.13 (m, 2H), 7.04 (dd, J = 8.1, 1.6 Hz, 1H), 5.91 (d, J = 16.9 Hz, 1H), 4.33 (s, 1H), 4.13 (s, 2H), 4.06 (s, 1H), 3.79 (s, 1H), 3.61 (s, 1H), 3.16 (d, J = 6.9 Hz, 2H), 2.25 (s, 1H), 2.02 (s, 1H), 2.11-1.75 (m, 1H), 1.22-1.05 (m, 1H), 0.74 (s, 3H), 0.72 (s, 1H), 0.38-0.28 (m, 2H), 0.26-0.17 (m, 2H); (M + H)$^+$ = 680 | +++ | 145 |
| 381 | 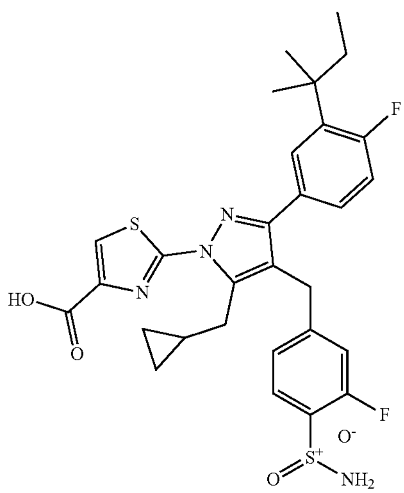 | $^1$H NMR (400 MHz, DMSO-d6) δ 13.13 (s, 1H), 8.26 (s, 1H), 7.62 (t, J = 7.9 Hz, 1H), 7.54 (s, 2H), 7.48-7.30 (m, 2H), 7.21-7.05 (m, 2H), 7.01 (dd, J = 8.2, 1.6 Hz, 1H), 4.13 (s, 2H), 3.15 (d, J = 6.9 Hz, 2H), 2.60-2.49 (m, 1H), 2.32 (dd, J = 13.2, 7.9 Hz, 1H), 1.48 (dp, J = 13.5, 6.9 Hz, 1H), 1.37-1.18 (m, 1H), 1.17-1.00 (m, 1H), 0.89-0.77 (m, 3H), 0.70 (d, J = 6.6 Hz, 3H), 0.37-0.28 (m, 2H), 0.25-0.16 (m, 2H); (M + H)$^+$ = 601 | +++ | 146 |
| 382 | 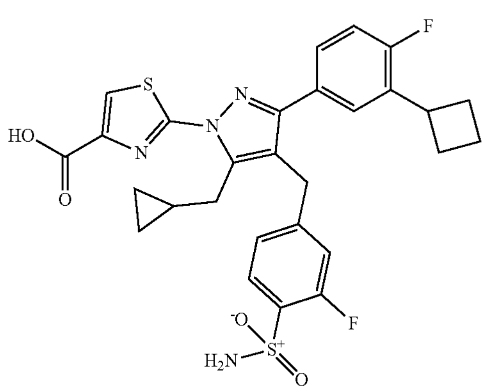 | $^1$H NMR (400 MHz, DMSO-d6) δ 13.13 (s, 1H), 8.26 (s, 1H), 7.62 (t, J = 7.9 Hz, 1H), 7.54 (s, 2H), 7.48-7.30 (m, 2H), 7.21-7.05 (m, 2H), 7.01 (dd, J = 8.2, 1.6 Hz, 1H), 4.13 (s, 2H), 3.15 (d, J = 6.9 Hz, 2H), 2.60-2.49 (m, 1H), 2.32 (dd, J = 13.2, 7.9 Hz, 1H), 1.48 (dp, J = 13.5, 6.9 Hz, 1H), 1.37-1.18 (m, 1H), 1.17-1.00 (m, 1H), 0.89-0.77 (m, 3H), 0.70 (d, J = 6.6 Hz, 3H), 0.37-0.28 (m, 2H), 0.25-0.16 (m, 2H); (M + H)$^+$ = 585 | +++ | 146 |

TABLE 7-continued

| Cmpd ID | Structure | Compound name and physical data | Inhibitory activity IC$_{50}$ (μM) | Example Method |
|---|---|---|---|---|
| 383 | 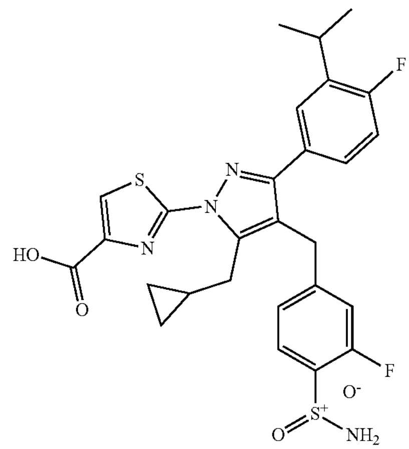 | $^1$H NMR (400 MHz, DMSO-d6) δ 13.13 (s, 1H), 8.26 (s, 1H), 7.68-7.58 (m, 1H), 7.56 (s, 2H), 7.46-7.30 (m, 2H), 7.20-7.06 (m, 2H), 7.03 (ddd, J = 8.4, 6.8, 1.6 Hz, 1H), 4.12 (d, J = 5.3 Hz, 2H), 3.19-3.02 (m, 3H), 1.09-1.02 (d, J = 6.9 Hz, 6H), 0.81 (t, J = 7.3 Hz, 1H), 0.38-0.28 (m, 2H), 0.25-0.17 (m, 2H); (M + H)$^+$ = 573 | +++ | 146 |
| 384 | 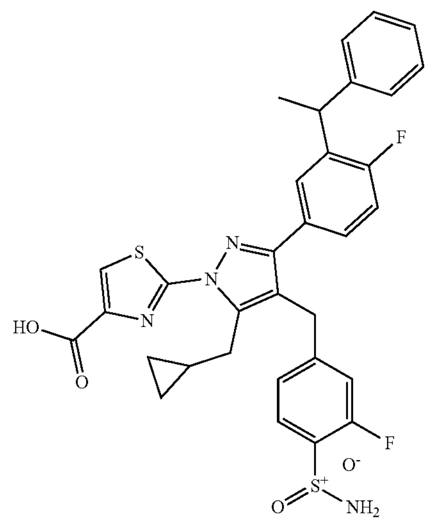 | $^1$H NMR (400 MHz, DMSO-d6) δ 13.14 (s, 1H), 8.25 (s, 1H), 7.63 (t, J = 7.9 Hz, 1H), 7.58 (s, 2H), 7.50-7.35 (m, 2H), 7.28-7.19 (m, 2H), 7.21-7.11 (m, 2H), 7.16-7.01 (m, 3H), 6.98 (dd, J = 8.1, 1.6 Hz, 1H), 4.35 (q, J = 7.2 Hz, 1H), 4.08 (s, 2H), 3.13 (dd, J = 7.0, 4.0 Hz, 2H), 1.41 (d, J = 7.2 Hz, 3H), 1.20-0.96 (m, 1H), 0.31 (dt, J = 9.1, 2.9 Hz, 2H), 0.24-0.15 (m, 2H); (M + H)$^+$ = 635 | +++ | 146 |
| 385 | 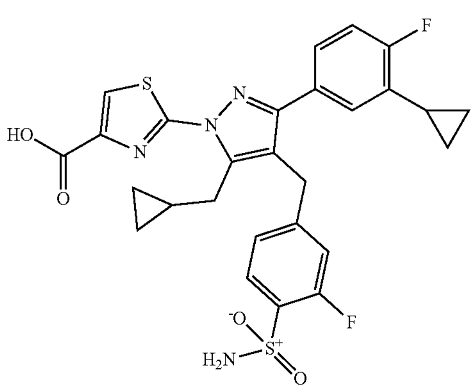 | $^1$H NMR (400 MHz, DMSO-d6) δ 13.13 (s, 1H), 8.26 (s, 1H), 7.65 (t, J = 7.9 Hz, 1H), 7.57 (s, 2H), 7.38 (ddd, J = 8.5, 5.0, 2.3 Hz, 1H), 7.21-7.08 (m, 2H), 7.02 (dd, J = 8.1, 1.6 Hz, 1H), 6.94 (dd, J = 7.4, 2.2 Hz, 1H), 4.09 (s, 2H), 3.13 (d, J = 6.9 Hz, 2H), 1.97 (tt, J = 8.5, 5.2 Hz, 1H), 1.18-1.04 (m, 1H), 0.94-0.83 (m, 2H), 0.54-0.40 (m, 2H), 0.36-0.25 (m, 2H), 0.26-0.15 (m, 2H); (M + H)$^+$ = 571 | +++ | 146 |

TABLE 7-continued

| Cmpd ID | Structure | Compound name and physical data | Inhibitory activity IC$_{50}$ (μM) | Example Method |
|---|---|---|---|---|
| 386 | 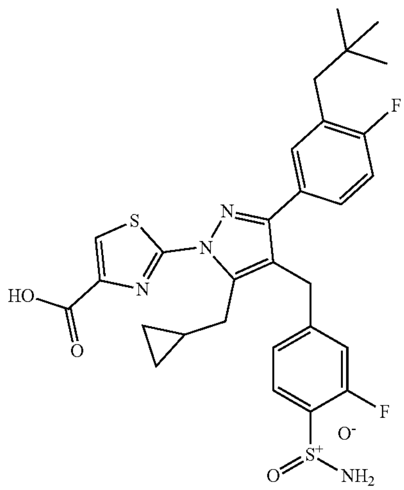 | $^1$H NMR (400 MHz, DMSO-d6) δ 13.13 (s, 1H), 8.26 (s, 1H), 7.63 (t, J = 7.9 Hz, 1H), 7.55 (s, 2H), 7.47 (ddd, J = 8.5, 5.0, 2.3 Hz, 1H), 7.30-7.14 (m, 2H), 7.12-6.98 (m, 2H), 4.11 (s, 2H), 3.14 (d, J = 6.9 Hz, 2H), 2.44 (d, J = 1.6 Hz, 2H), 1.11 (ddt, J = 10.3, 7.7, 2.9 Hz, 1H), 0.80-0.75 (m, 9H), 0.36-0.25 (m, 2H), 0.27-0.15 (m, 2H); (M + H)$^+$ = 601 | +++ | 146 |
| 387 | 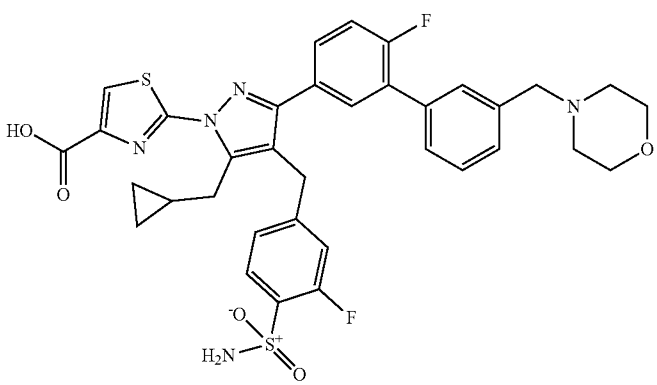 | $^1$H NMR (400 MHz, DMSO-d6) δ 13.16 (s, 1H), 9.84 (s, 1H), 8.30 (s, 1H), 7.69-7.56 (m, 3H), 7.58 (s, 2H), 7.56-7.49 (m, 4H), 7.39 (dd, J = 10.6, 8.5 Hz, 1H), 7.16 (dd, J = 11.4, 1.5 Hz, 1H), 7.06 (dd, J = 8.1, 1.6 Hz, 1H), 4.39 (s, 2H), 4.16 (s, 2H), 3.95 (d, J = 12.9 Hz, 2H), 3.60 (t, J = 11.9 Hz, 2H), 3.26 (s, 1H), 3.17 (d, J = 6.8 Hz, 2H), 3.07 (s, 1H), 1.22-1.04 (m, 1H), 0.38-0.29 (m, 2H), 0.26-0.17 (m, 2H); (M + H)$^+$ = 706 | +++ | 146 |
| 388 | 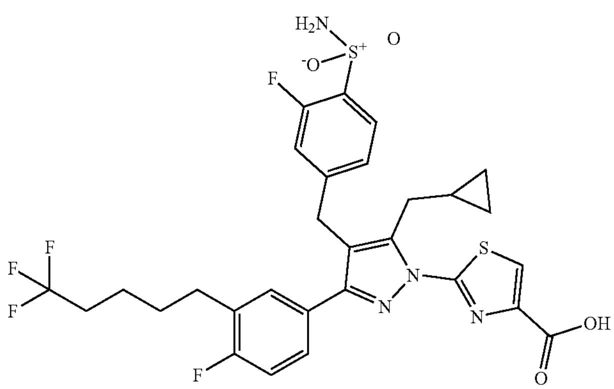 | $^1$H NMR (400 MHz, DMSO-d6) δ 13.15 (s, 1H), 8.28 (s, 1H), 7.64 (t, J = 7.9 Hz, 1H), 7.57 (s, 2H), 7.43 (ddd, J = 10.1, 5.8, 2.4 Hz, 2H), 7.24-7.09 (m, 2H), 7.03 (dd, J = 8.2, 1.5 Hz, 1H), 4.14 (s, 2H), 3.17 (d, J = 6.9 Hz, 2H), 2.72-2.56 (m, 3H), 2.36-2.17 (m, 2H), 1.65-1.39 (m, 5H), 1.25-1.05 (m, 1H), 0.40-0.30 (m, 2H), 0.26-0.18 (m, 2H); (M + H)$^+$ = 655 | +++ | 146 |

TABLE 7-continued

| Cmpd ID | Structure | Compound name and physical data | Inhibitory activity IC$_{50}$ (μM) | Example Method |
|---|---|---|---|---|
| 389 | 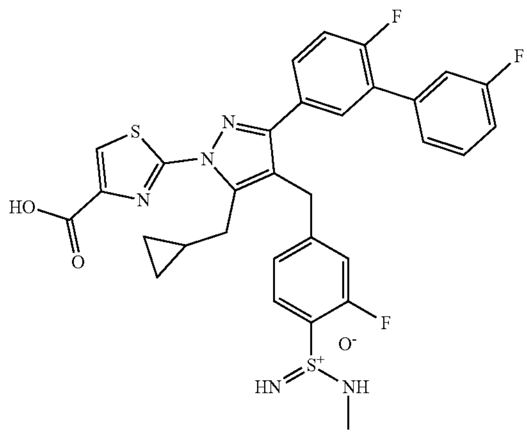 | $^1$H NMR (400 MHz, DMSO-d6) δ 8.29 (s, 1H), 7.74-7.61 (m, 2H), 7.58-7.44 (m, 2H), 7.37 (dd, J = 10.7, 8.6 Hz, 1H), 7.31 (ddt, J = 10.3, 2.9, 1.5 Hz, 1H), 7.29-7.17 (m, 2H), 7.17-7.04 (m, 2H), 4.18 (s, 2H), 3.17 (d, J = 6.9 Hz, 2H), 2.32 (s, 3H), 1.21-1.06 (m, 1H), 0.38-0.26 (m, 2H), 0.28-0.17 (m, 2H); (M + H)$^+$ = 638 | ++ | 141 |
| 390 | 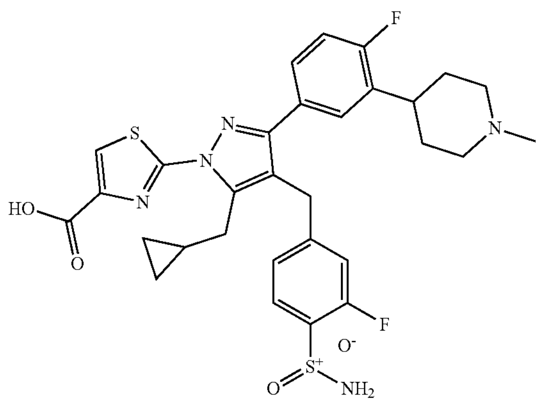 | (M + H)$^+$ = 628 | +++ | 146 |
| 391 | 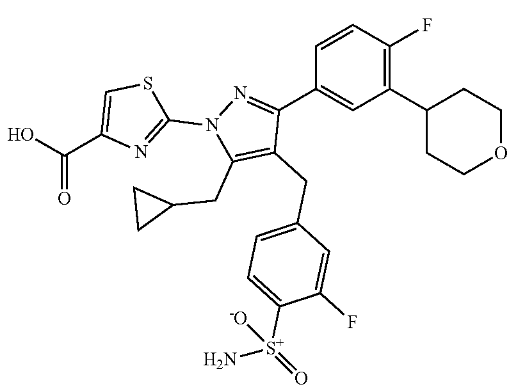 | $^1$H NMR (400 MHz, DMSO-d6) δ 13.13 (s, 1H), 8.26 (s, 1H), 7.64 (t, J = 7.9 Hz, 1H), 7.55 (s, 2H), 7.45 (ddd, J = 8.5, 5.0, 2.2 Hz, 1H), 7.31 (dd, J = 7.3, 2.3 Hz, 1H), 7.23-7.09 (m, 2H), 7.03 (dd, J = 8.1, 1.6 Hz, 1H), 4.12 (s, 2H), 3.89 (dt, J = 11.3, 2.9 Hz, 2H), 3.39 (td, J = 11.2, 3.5 Hz, 2H), 3.16 (d, J = 6.9 Hz, 2H), 2.98 (tt, J = 10.2, 5.0 Hz, 1H), 1.50 (td, J = 11.4, 10.3, 4.0 Hz, 4H), 1.25-1.00 (m, 1H), 0.38-0.29 (m, 2H), 0.30-0.17 (m, 2H); (M + H)$^+$ = 615 | +++ | 146 |

TABLE 7-continued

| Cmpd ID | Structure | Compound name and physical data | Inhibitory activity IC$_{50}$ (μM) | Example Method |
|---|---|---|---|---|
| 392 | 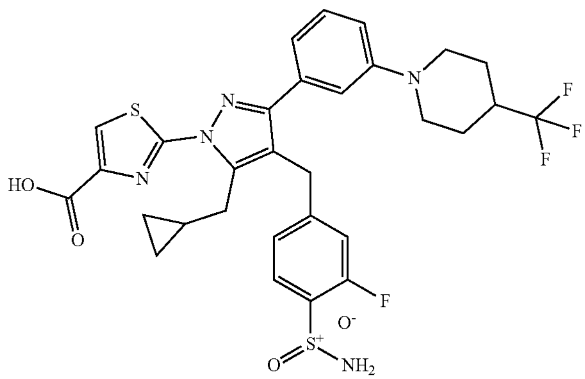 | $^1$H NMR (400 MHz, DMSO-d6) δ 8.27 (s, 1H), 7.66 (t, J = 7.9 Hz, 1H), 7.57 (s, 2H), 7.24 (dd, J = 8.3, 7.6 Hz, 1H), 7.15 (dd, J = 11.3, 1.6 Hz, 1H), 7.05 (dd, J = 8.2, 1.6 Hz, 1H), 7.03-6.92 (m, 2H), 6.85 (t, J = 1.9 Hz, 1H), 4.10 (s, 2H), 3.48-3.3 (m, 1H), 3.14 (d, J = 6.9 Hz, 2H), 2.68-2.53 (m, 2H), 2.47-2.27 (m, 2H), 1.80 (d, J = 12.4 Hz, 2H), 1.45 (qd, J = 12.4, 4.0 Hz, 2H), 1.19-1.04 (m, 1H), 0.36-0.28 (m, 2H), 0.23-0.16 (m, 2H); (M + H)$^+$ = 664 | +++ | 145 |
| 393 | 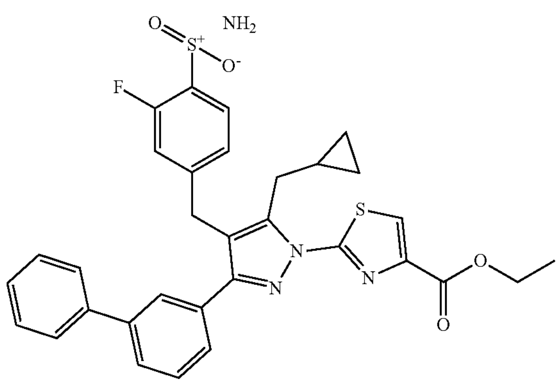 | $^1$H NMR (400 MHz, DMSO-d6) δ 8.35 (s, 1H), 7.72-7.64 (m, 2H), 7.68-7.54 (m, 2H), 7.59 (s, 2H), 7.55-7.30 (m, 6H), 7.21 (dd, J = 11.4, 1.6 Hz, 1H), 7.10 (dd, J = 8.1, 1.6 Hz, 1H), 4.31 (q, J = 7.1 Hz, 2H), 4.18 (s, 2H), 3.29 (s, 2H), 3.18 (d, J = 6.9 Hz, 2H), 1.32 (t, J = 7.1 Hz, 3H), 1.23-1.08 (m, 1H), 0.39-0.28 (m, 2H), 0.32-0.21 (m, 2H); (M + H)$^+$ = 617 | − | 141 |
| 394 | 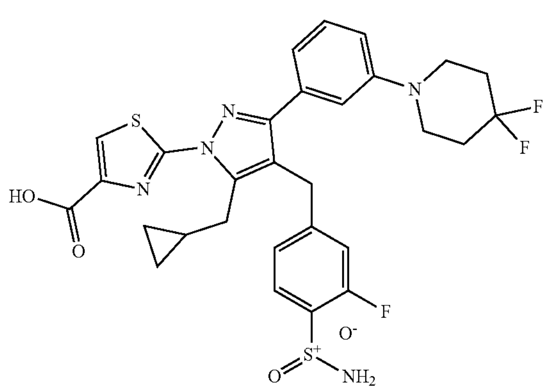 | $^1$H NMR (400 MHz, DMSO-d6) δ 13.10 (s, 1H), 8.27 (s, 1H), 7.67 (t, J = 7.9 Hz, 1H), 7.59 (s, 2H), 7.25 (dd, J = 8.3, 7.6 Hz, 1H), 7.16 (dd, J = 11.4, 1.6 Hz, 1H), 7.10-6.96 (m, 3H), 6.87 (dd, J = 2.6, 1.5 Hz, 1H), 4.10 (s, 2H), 3.18-3.09 (m, 6H), 1.95 (tt, J = 14.1, 5.7 Hz, 4H), 1.23-1.00 (m, 1H), 0.37-0.27 (m, 2H), 0.25-0.16 (m, 2H); (M + H)$^+$ = 632 | +++ | 141 |

TABLE 7-continued

| Cmpd ID | Structure | Compound name and physical data | Inhibitory activity IC$_{50}$ (μM) | Example Method |
|---|---|---|---|---|
| 395 | 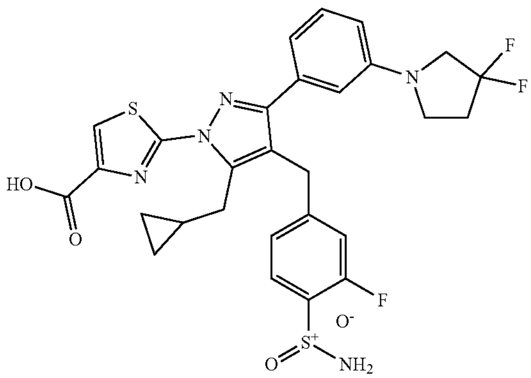 | $^1$H NMR (400 MHz, DMSO-d6) δ 13.12 (s, 1H), 8.26 (s, 1H), 7.65 (t, J = 7.9 Hz, 1H), 7.56 (s, 2H), 7.22 (t, J = 7.8 Hz, 1H), 7.14 (dd, J = 11.3, 1.6 Hz, 1H), 7.05 (dd, J = 8.1, 1.6 Hz, 1H), 6.90 (dt, J = 7.7, 1.1 Hz, 1H), 6.70-6.50 (m, 2H), 4.12 (s, 2H), 3.59 (t, J = 13.3 Hz, 2H), 3.4-3.29 (m, 2H), 2.31-2.29 (m, 2H), 3.14 (d, J = 6.9 Hz, 2H), 1.21-1.02 (m, 1H), 0.38-0.26 (m, 2H), 0.24-0.14 (m, 2H); (M + H)$^+$ = 618 | + | 141 |
| 396 | 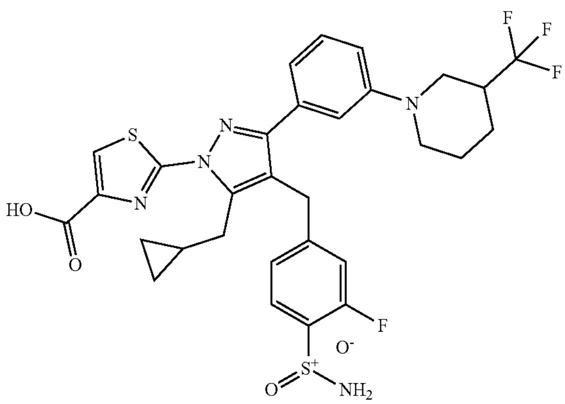 | $^1$H NMR (400 MHz, DMSO-d6) δ 8.27 (s, 1H), 7.65 (t, J = 7.9 Hz, 1H), 7.56 (s, 2H), 7.29-7.20 (m, 1H), 7.13 (dd, J = 11.4, 1.6 Hz, 1H), 7.08-6.90 (m, 4H), 4.11 (s, 2H), 3.36 (d, J = 12.8 Hz, 1H), 3.13 (d, J = 6.9 Hz, 2H), 2.68 (dd, J = 12.1, 11.0 Hz, 1H), 2.62-2.49 (m, 3H), 2.01-1.75 (m, 0H), 1.69 (d, J = 12.9 Hz, 1H), 1.57-1.32 (m, 3H), 1.19-1.04 (m, 1H), 0.36-0.27 (m, 2H), 0.24-0.15 (m, 2H); (M + H)$^+$ = 664 | +++ | 141 |
| 397 | 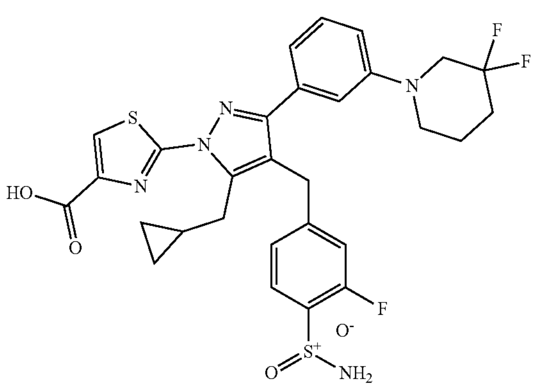 | $^1$H NMR (400 MHz, DMSO-d6) δ 13.11 (s, 1H), 8.27 (s, 1H), 7.66 (t, J = 7.9 Hz, 1H), 7.56 (s, 2H), 7.24 (dd, J = 8.2, 7.6 Hz, 1H), 7.18-6.94 (m, 4H), 6.89 (dd, J = 2.6, 1.5 Hz, 1H), 4.11 (s, 2H), 3.37 (t, J = 11.9 Hz, 2H), 3.19-3.08 (m, 2H), 3.00 (t, J = 5.5 Hz, 2H), 1.98 (tt, J = 13.8, 6.4 Hz, 2H), 1.72-1.52 (m, 2H), 1.18-1.04 (m, 1H), 0.37-0.25 (m, 2H), 0.25-0.16 (m, 2H); (M + H)$^+$ = 632 | +++ | 141 |

TABLE 7-continued

| Cmpd ID | Structure | Compound name and physical data | Inhibitory activity IC$_{50}$ (μM) | Example Method |
|---|---|---|---|---|
| 398 | 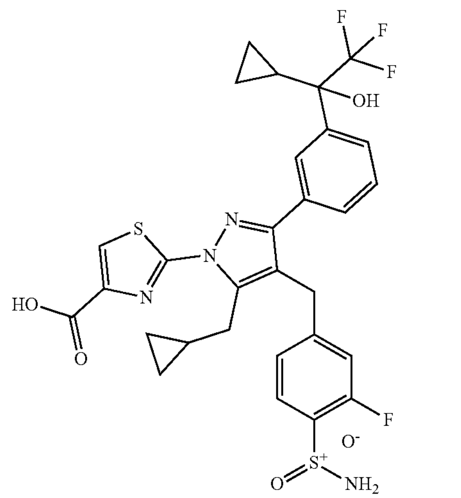 | $^1$H NMR (400 MHz, DMSO-d6) δ 13.14 (s, 1H), 8.27 (s, 1H), 7.77 (d, J = 1.8 Hz, 1H), 7.68-7.57 (m, 2H), 7.57-7.50 (m, 2H), 7.44 (t, J = 7.8 Hz, 1H), 7.12-6.99 (m, 2H), 6.11 (s, 1H), 4.12 (s, 1H), 3.14 (d, J = 6.8 Hz, 2H), 1.39 (tt, J = 8.4, 5.3 Hz, 1H), 1.18-1.04 (m, 1H), 0.70 (dq, J = 10.0, 5.1 Hz, 1H), 0.54-0.42 (m, 1H), 0.37-0.09 (m, 5H); (M + H)$^+$ = 651 | +++ | 141 |
| 399 | 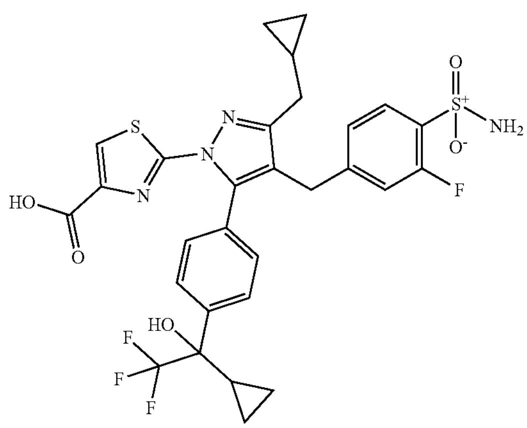 [SMILES: N[S+](=O)([O-])c1ccc(Cc2c(CC3CC3)nn(-c3nc(C(=O)O)cs3)c2-c2ccc(C(O)(C3CC3)C(F)(F)F)cc2)cc1F] | $^1$H NMR (400 MHz, DMSO-d6) δ 12.87 (s, 1H), 8.21 (s, 1H), 7.70-7.63 (m, 2H), 7.63-7.56 (m, 1H), 7.56 (s, 2H), 7.49-7.36 (m, 2H), 7.06-6.95 (m, 2H), 6.03 (s, 1H), 3.85 (s, 2H), 2.42 (d, J = 6.8 Hz, 2H), 1.48 (tt, J = 8.3, 5.3 Hz, 1H), 1.01-0.86 (m, 2H), 0.67 (dq, J = 10.0, 5.1 Hz, 1H), 0.49-0.33 (m, 4H), 0.27-0.04 (m, 5H); (M + H)$^+$ = 651 | + | 141 |
| 400 | 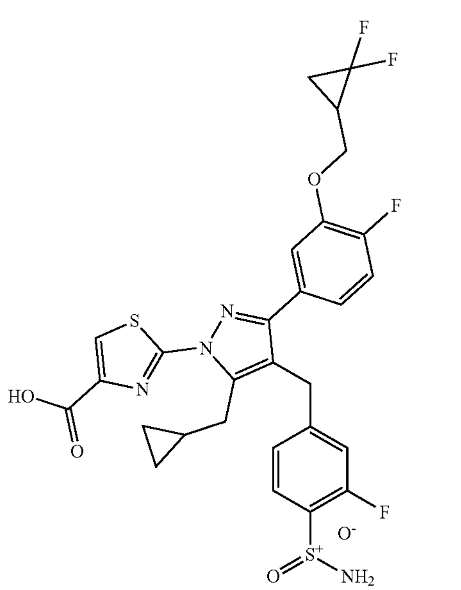 | $^1$H NMR (400 MHz, DMSO-d6) δ 13.14 (s, 1H), 8.27 (s, 1H), 7.63 (t, J = 7.9 Hz, 1H), 7.56 (s, 2H), 7.31-7.09 (m, 4H), 7.03 (dd, J = 8.1, 1.6 Hz, 1H), 4.16-4.05 (m, 3H), 3.85 (ddd, J = 10.6, 8.6, 1.6 Hz, 1H), 3.15 (d, J = 6.7 Hz, 2H), 2.29-1.99 (m, 0H), 1.70 (tdd, J = 12.0, 8.0, 4.9 Hz, 2H), 1.43 (dtd, J = 13.8, 7.8, 4.2 Hz, 1H), 1.26-0.93 (m, 1H), 0.37-0.16 (m, 4H); (M + H)$^+$ = 637 | +++ | 120 |

TABLE 7-continued

| Cmpd ID | Structure | Compound name and physical data | Inhibitory activity IC$_{50}$ (μM) | Example Method |
|---|---|---|---|---|
| 401 | 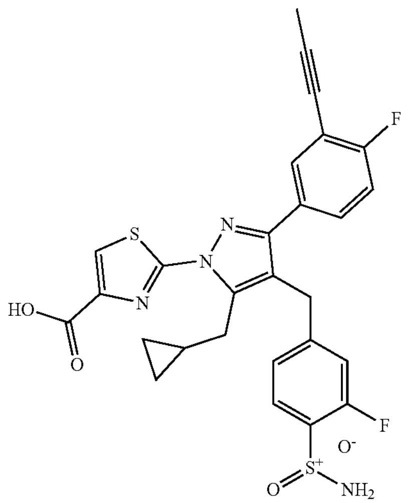 | $^1$H NMR (400 MHz, DMSO-d6) δ 13.15 (s, 1H), 8.28 (s, 1H), 7.68-7.46 (m, 5H), 7.28 (dd, J = 9.5, 8.7 Hz, 1H), 7.12 (dd, J = 11.3, 1.6 Hz, 1H), 7.02 (dd, J = 8.1, 1.6 Hz, 1H), 4.12 (s, 2H), 3.14 (d, J = 6.2 Hz, 3H), 2.07 (s, 3H), 1.11 (dddd, J = 12.5, 8.0, 4.9, 1.9 Hz, 1H), 0.37-0.27 (m, 2H), 0.27-0.16 (m, 2H); (M + H)$^+$ = 569 | +++ | 145 |
| 402 | 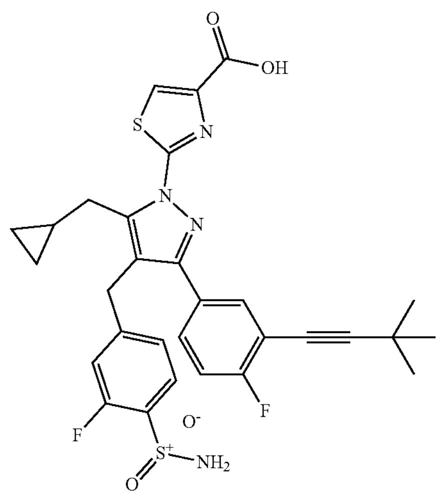 | $^1$H NMR (400 MHz, DMSO-d6) δ 13.15 (s, 1H), 8.28 (s, 1H), 7.69-7.44 (m, 6H), 7.27 (dd, J = 9.4, 8.7 Hz, 1H), 7.15 (dd, J = 11.4, 1.6 Hz, 1H), 7.03 (dd, J = 8.1, 1.6 Hz, 1H), 4.13 (s, 2H), 3.16 (d, J = 6.8 Hz, 2H), 1.27 (s, 9H), 1.18-0.96 (m, 1H), 0.37-0.27 (m, 2H), 0.27-0.16 (m, 2H); (M + H)$^+$ = 611 | +++ | 145 |
| 403 | 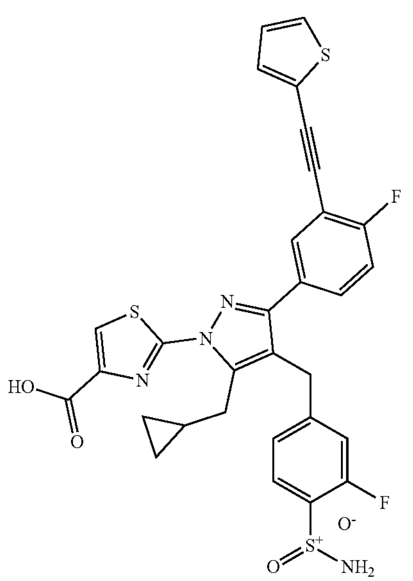 | $^1$H NMR (400 MHz, DMSO-d6) δ 13.16 (s, 1H), 8.29 (s, 1H), 7.78-7.68 (m, 2H), 7.68-7.58 (m, 2H), 7.56 (s, 2H), 7.47 (dd, J = 3.7, 1.2 Hz, 1H), 7.37 (dd, J = 9.4, 8.7 Hz, 1H), 7.19-7.11 (m, 2H), 7.04 (dd, J = 8.1, 1.6 Hz, 1H), 4.16 (s, 2H), 3.16 (d, J = 7.0 Hz, 2H), 1.20-1.05 (m, 1H), 0.38-0.27 (m, 2H), 0.27-0.17 (m, 2H); (M + H)$^+$ = 637 | +++ | 145 |

TABLE 7-continued

| Cmpd ID | Structure | Compound name and physical data | Inhibitory activity IC$_{50}$ (μM) | Example Method |
|---|---|---|---|---|
| 404 | 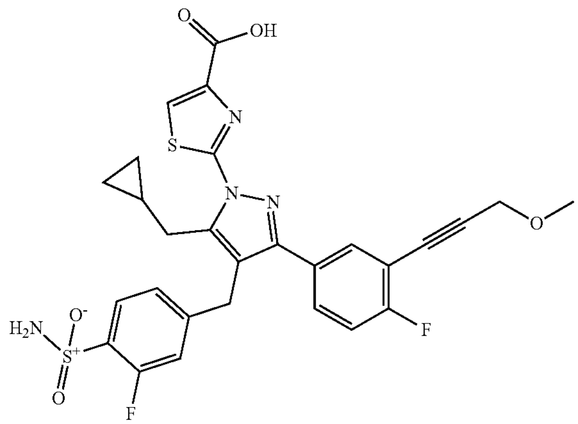 [SMILES: COCC#Cc1cc(-c2nn(-c3nc(C(=O)O)cs3)c(CC3CC3)c2Cc2ccc([S+](N)(=O)[O-])c(F)c2)ccc1F] | $^1$H NMR (400 MHz, DMSO-d6) δ 13.15 (s, 1H), 8.27 (s, 1H), 7.68-7.56 (m, 3H), 7.56 (s, 1H), 7.38-7.29 (m, 1H), 7.13 (dd, J = 11.3, 1.5 Hz, 1H), 7.03 (dd, J = 8.1, 1.6 Hz, 1H), 4.34 (s, 2H), 4.14 (s, 2H), 3.31 (s, 3H), 3.15 (d, J = 6.5 Hz, 2H), 1.33-0.83 (m, 0H), 0.37-0.27 (m, 2H), 0.24-0.16 (m, 2H); (M + H)$^+$ = 599 | +++ | 145 |
| 405 | 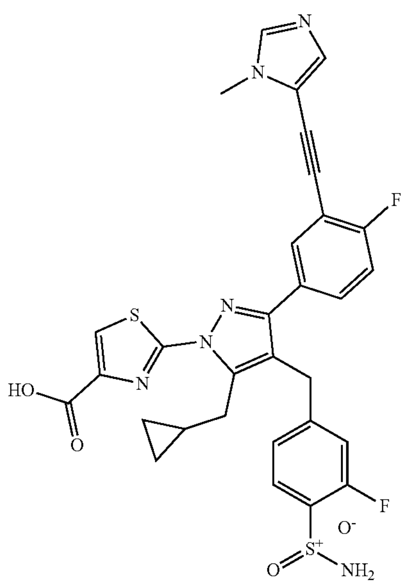 | $^1$H NMR (400 MHz, DMSO-d6) δ 13.15 (s, 1H), 8.30 (s, 1H), 7.86 (s, 1H), 7.74-7.60 (m, 3H), 7.57 (s, 2H), 7.43-7.34 (m, 2H), 7.16 (dd, J = 11.3, 1.6 Hz, 1H), 7.04 (dd, J = 8.2, 1.6 Hz, 1H), 4.16 (s, 2H), 3.67 (d, J = 0.5 Hz, 3H), 3.16 (d, J = 6.9 Hz, 2H), 1.26-0.96 (m, 1H), 0.38-0.28 (m, 2H), 0.25-0.17 (m, 2H); (M + H)$^+$ = 635 | +++ | 145 |
| 406 | 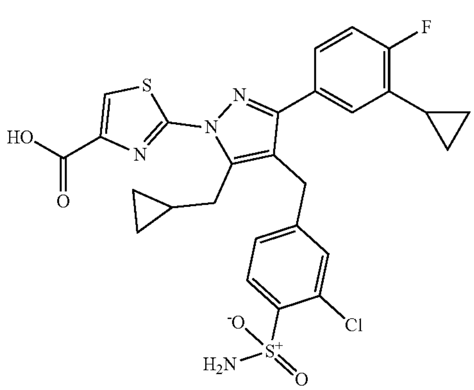 | $^1$H NMR (400 MHz, DMSO-d6) δ 13.14 (s, 1H), 8.26 (s, 1H), 7.82 (d, J = 8.1 Hz, 1H), 7.52 (s, 2H), 7.42-7.31 (m, 2H), 7.21-7.11 (m, 2H), 6.94 (dd, J = 7.4, 2.2 Hz, 1H), 4.08 (s, 2H), 3.14 (d, J = 6.9 Hz, 2H), 1.97 (tt, J = 8.4, 5.2 Hz, 1H), 1.19-1.04 (m, 2H), 0.96-0.83 (m, 2H), 0.54-0.40 (m, 2H), 0.37-0.26 (m, 2H), 0.26-0.15 (m, 2H); (M + H)$^+$ = 588 | +++ | 146 |

TABLE 7-continued

| Cmpd ID | Structure | Compound name and physical data | Inhibitory activity IC$_{50}$ (μM) | Example Method |
|---|---|---|---|---|
| 407 | 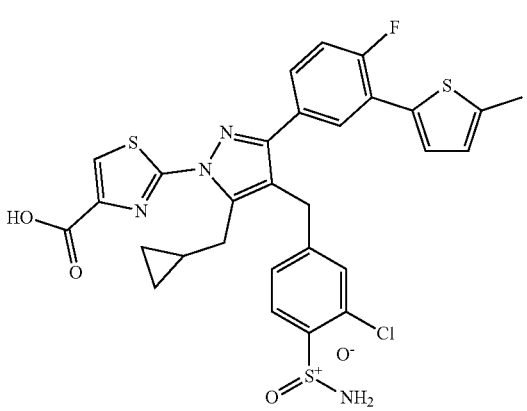 | $^1$H NMR (400 MHz, DMSO-d6) δ 13.17 (s, 1H), 8.28 (s, 1H), 7.85 (d, J = 8.2 Hz, 1H), 7.61-7.43 (m, 6H), 7.35 (dd, J = 11.3, 8.6 Hz, 1H), 7.22-7.10 (m, 2H), 6.82 (dt, J = 3.6, 1.1 Hz, 1H), 4.15 (s, 2H), 3.17 (d, J = 6.9 Hz, 2H), 1.20-0.98 (m, 1H), 0.38-0.29 (m, 2H), 0.28-0.17 (m, 2H); (M + H)$^+$ = 644 | +++ | 145 |
| 408 | 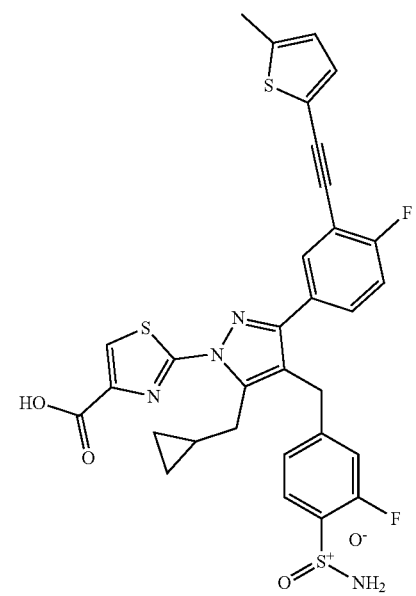 | $^1$H NMR (400 MHz, DMSO-d6) δ 13.15 (s, 1H), 8.29 (s, 1H), 7.72 (dd, J = 6.9, 2.3 Hz, 1H), 7.68-7.58 (m, 2H), 7.56 (s, 2H), 7.36 (dd, J = 9.4, 8.7 Hz, 1H), 7.27 (d, J = 3.4 Hz, 1H), 7.14 (dd, J = 11.3, 1.6 Hz, 1H), 7.04 (dd, J = 8.1, 1.6 Hz, 1H), 6.83 (dt, J = 3.4, 1.1 Hz, 1H), 4.16 (s, 2H), 3.16 (d, J = 6.9 Hz, 2H), 1.20-1.05 (m, 1H), 0.38-0.27 (m, 2H), 0.27-0.16 (m, 2H); (M + H)$^+$ = 651 | +++ | 145 |
| 409 | 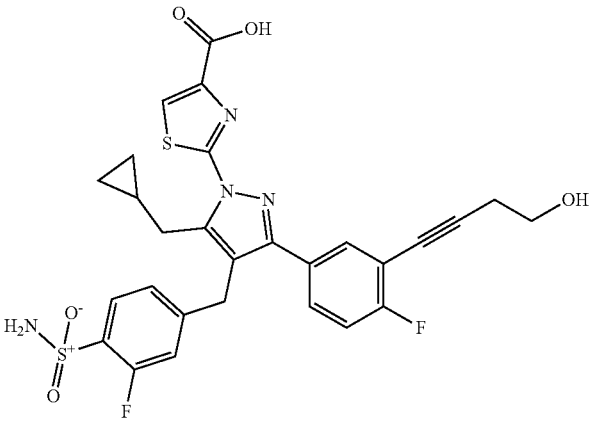 [SMILES: N[S+](=O)([O-])c1ccc(Cc2c(-c3ccc(F)c(C#CCCO)c3)nn(-c3nc(C(=O)O)cs3)c2CC2CC2)cc1F] | $^1$H NMR (400 MHz, DMSO-d6) δ 8.28 (s, 1H), 7.68-7.57 (m, 2H), 7.56 (s, 2H), 7.52 (ddd, J = 8.7, 5.0, 2.3 Hz, 1H), 7.28 (dd, J = 9.4, 8.7 Hz, 1H), 7.12 (dd, J = 11.3, 1.6 Hz, 1H), 7.02 (dd, J = 8.2, 1.6 Hz, 1H), 4.89 (d, J = 6.3 Hz, 1H), 4.13 (s, 2H), 3.57 (q, J = 6.6 Hz, 2H), 3.15 (d, J = 6.7 Hz, 2H), 2.58 (t, J = 6.8 Hz, 2H), 1.11 (dddd, J = 15.0, 10.0, 5.0, 2.2 Hz, 1H), 0.37-0.27 (m, 2H), 0.24-0.16 (m, 2H); (M + H)$^+$ = 599 | +++ | 145 |

TABLE 7-continued

| Cmpd ID | Structure | Compound name and physical data | Inhibitory activity IC$_{50}$ (μM) | Example Method |
|---|---|---|---|---|
| 410 | 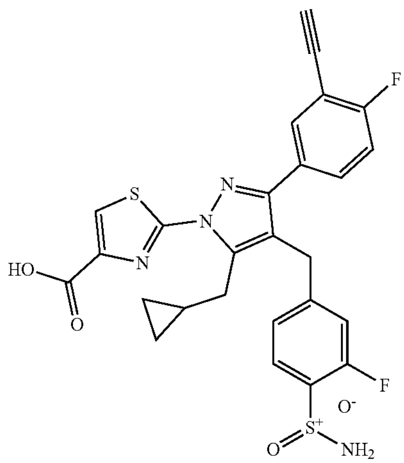 | $^1$H NMR (400 MHz, DMSO-d6) δ 13.14 (s, 1H), 8.29 (s, 1H), 7.72-7.57 (m, 3H), 7.55 (s, 2H), 7.33 (t, J = 9.0 Hz, 1H), 7.12 (dd, J = 11.4, 1.6 Hz, 1H), 7.03 (dd, J = 8.1, 1.6 Hz, 1H), 4.53 (s, 1H), 4.14 (s, 2H), 3.15 (d, J = 6.9 Hz, 2H), 1.18-1.04 (m, 1H), 0.37-0.27 (m, 2H), 0.24-0.16 (m, 2H); M + H)$^+$ = 556 | +++ | 145 |
| 411 | 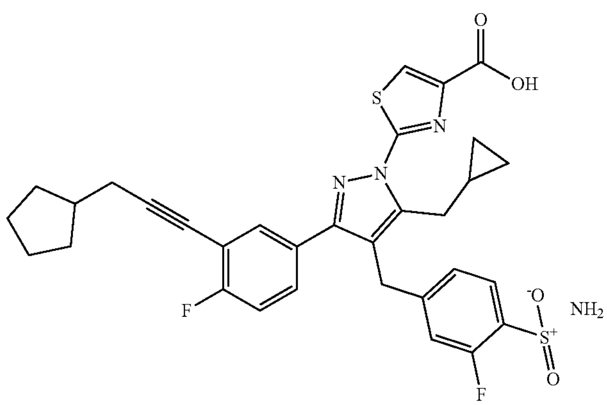 | (M + H)$^+$ = 637 | +++ | 145 |
| 412 | 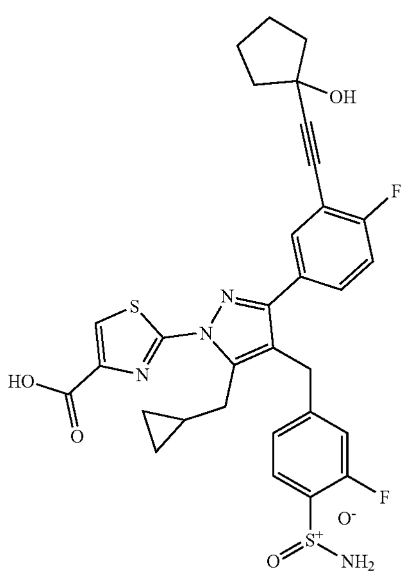 | $^1$H NMR (400 MHz, DMSO-d6) δ 8.09 (s, 1H), 7.68-7.51 (m, 4H), 7.30 (dd, J = 9.4, 8.6 Hz, 1H), 7.13 (dd, J = 11.3, 1.6 Hz, 1H), 7.02 (dd, J = 8.1, 1.6 Hz, 1H), 5.39 (s, 1H), 4.13 (s, 2H), 3.18-3.11 (m, 2H), 1.96-1.79 (m, 4H), 1.79-1.59 (m, 4H), 1.10 (s, 1H), 0.36-0.15 (m, 4H); (M + H)$^+$ = 639 | +++ | 145 |

TABLE 7-continued

| Cmpd ID | Structure | Compound name and physical data | Inhibitory activity IC$_{50}$ (μM) | Example Method |
|---|---|---|---|---|
| 413 | 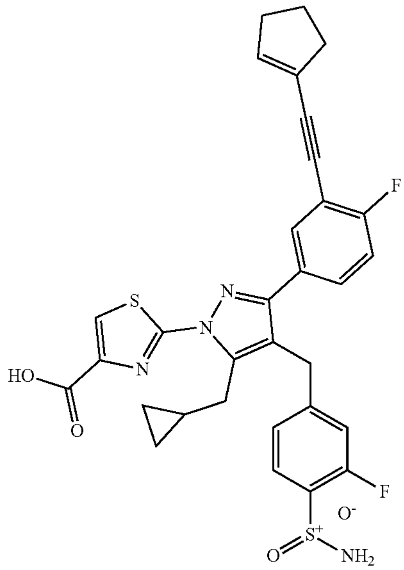 | (M + H)$^+$ = 641 | +++ | 145 |
| 414 | 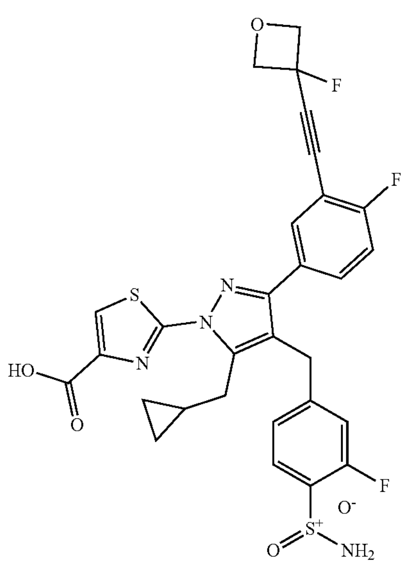 | $^1$H NMR (400 MHz, DMSO-d6) δ 13.17 (s, 1H), 8.30 (s, 1H), 7.76 (dd, J = 6.7, 2.3 Hz, 1H), 7.72-7.58 (m, 2H), 7.57 (s, 2H), 7.39 (t, J = 9.0 Hz, 1H), 7.14 (dd, J = 11.3, 1.6 Hz, 1H), 7.02 (dd, J = 8.2, 1.6 Hz, 1H), 4.99-4.81 (m, 4H), 4.15 (s, 2H), 3.16 (d, J = 7.2 Hz, 2H), 1.21-0.05 (m, 1H), 0.38-0.27 (m, 2H), 0.27-0.17 (m, 2H); (M + H)$^+$ = 629 | +++ | 145 |

TABLE 7-continued

| Cmpd ID | Structure | Compound name and physical data | Inhibitory activity IC$_{50}$ (μM) | Example Method |
|---|---|---|---|---|
| 415 | 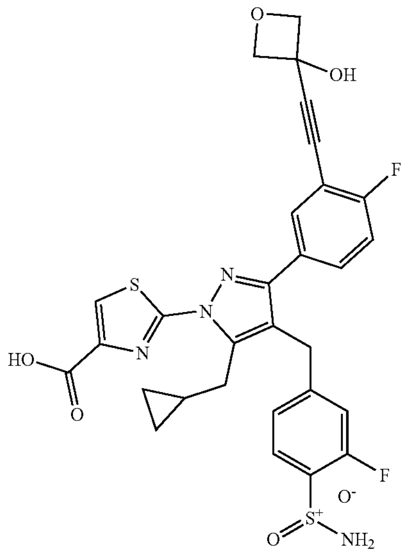 | $^1$H NMR (400 MHz, DMSO-d6) δ 8.18 (s, 1H), 7.74-7.53 (m, 4H), 7.39-7.26 (m, 1H), 7.13 (dd, J = 11.4, 1.6 Hz, 1H), 7.03 (dd, J = 8.1, 1.6 Hz, 1H), 6.69 (s, 1H), 4.78-4.71 (m, 2H), 4.62-4.55 (m, 2H), 4.15 (s, 2H), 3.15 (d, J = 6.5 Hz, 2H), 1.18-1.03 (m, 1H), 0.37-0.25 (m, 2H), 0.25-0.13 (m, 2H); (M + H)$^+$ = 627 | +++ | 145 |
| 416 | 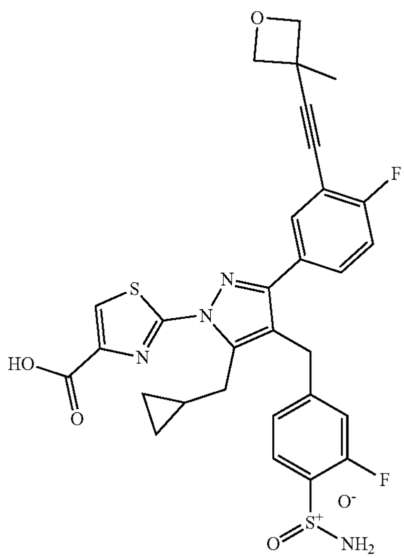 | $^1$H NMR (400 MHz, DMSO-d6) δ 13.17 (s, 1H), 8.29 (s, 1H), 7.68-7.58 (m, 2H), 7.58-7.54 (m, 3H), 7.36-7.26 (m, 1H), 7.15 (dd, J = 11.3, 1.6 Hz, 1H), 7.03 (dd, J = 8.1, 1.6 Hz, 1H), 4.72 (d, J = 5.5 Hz, 2H), 4.43 (d, J = 5.7 Hz, 2H), 4.14 (s, 2H), 3.16 (d, J = 6.9 Hz, 2H), 1.62 (s, 3H), 1.12 (s, 1H), 0.38-0.28 (m, 2H), 0.25-0.17 (m, 2H); (M + H)$^+$ = 625 | +++ | 145 |
| 417 | 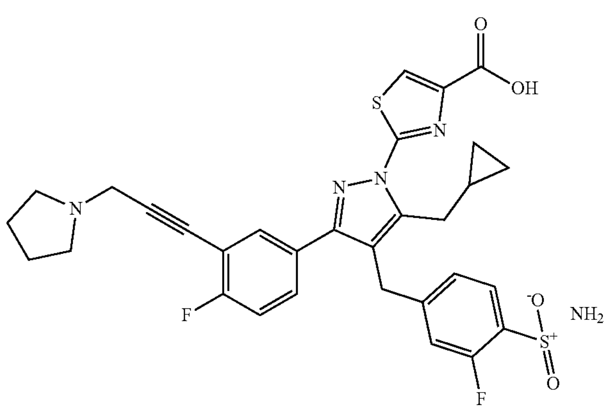 | $^1$H NMR (400 MHz, DMSO-d6) δ 13.20 (s, 1H), 10.36 (s, 1H), 8.32 (s, 1H), 7.79-7.55 (m, 5H), 7.40 (t, J = 9.0 Hz, 1H), 7.14 (dd, J = 11.3, 1.6 Hz, 1H), 7.04 (dd, J = 8.2, 1.6 Hz, 1H), 4.40 (s, 2H), 4.16 (s, 2H), 3.17 (d, J = 6.9 Hz, 2H), 1.96 (s, 4H), 1.23-1.00 (m, 0H), 0.39-0.29 (m, 2H), 0.26-0.18 (m, 2H); (M + H)$^+$ = 638 | +++ | 145 |

TABLE 7-continued

| Cmpd ID | Structure | Compound name and physical data | Inhibitory activity IC$_{50}$ (μM) | Example Method |
|---|---|---|---|---|
| 418 | 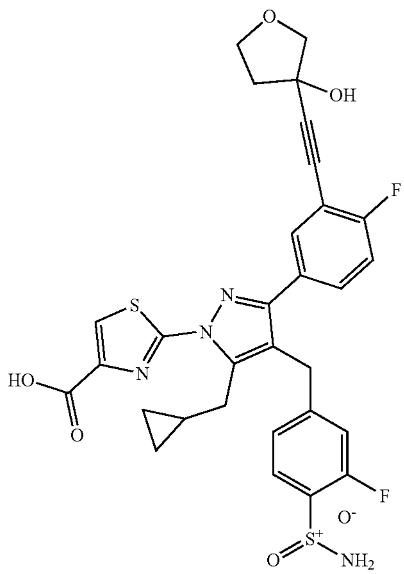 | $^1$H NMR (400 MHz, DMSO-d6) δ 13.15 (s, 1H), 8.27 (s, 1H), 7.68-7.58 (m, 3H), 7.57 (d, J = 4.7 Hz, 2H), 7.37-7.27 (m, 1H), 7.13 (dd, J = 11.5, 1.5 Hz, 1H), 7.03 (dd, J = 8.2, 1.6 Hz, 1H), 5.92 (s, 1H), 4.14 (s, 2H), 3.91-3.83 (m, 2H), 3.83-3.72 (m, 2H), 3.15 (d, J = 6.7 Hz, 2H), 2.24-2.13 (m, 2H), 0.98 (s, 1H), 0.57 (s, 1H), 0.37-0.28 (m, 2H), 0.25-0.16 (m, 2H); (M + H)$^+$ = 641 | +++ | 145 |
| 419 | 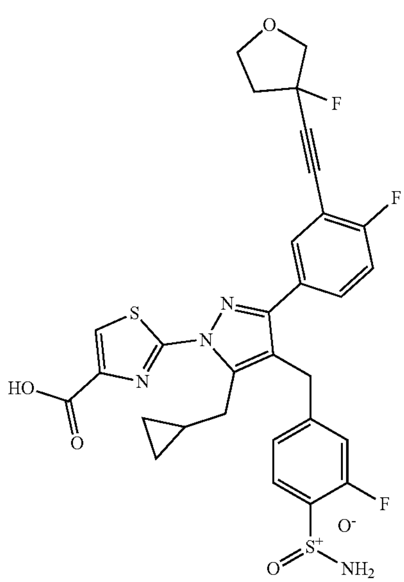 | $^1$H NMR (400 MHz, DMSO-d6) δ 13.17 (s, 1H), 8.29 (s, 1H), 7.72-7.59 (m, 3H), 7.57 (s, 2H), 7.37 (t, J = 9.3 Hz, 1H), 7.15 (dd, J = 11.4, 1.6 Hz, 1H), 7.02 (dd, J = 8.1, 1.6 Hz, 1H), 4.23-4.10 (m, 3H), 4.00-3.85 (m, 3H), 3.16 (d, J = 7.0 Hz, 2H), 2.61-2.33 (m, 13H), 1.12 (dddd, J = 13.0, 8.0, 4.9, 1.9 Hz, 1H), 0.38-0.17 (m, 4H); (M + H)$^+$ = 643 | +++ | 145 |

TABLE 7-continued

| Cmpd ID | Structure | Compound name and physical data | Inhibitory activity IC$_{50}$ (μM) | Example Method |
|---|---|---|---|---|
| 420 | 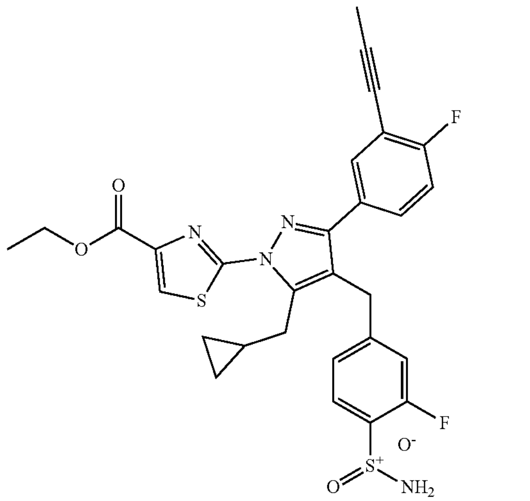 | $^1$H NMR (400 MHz, DMSO-d6) δ 8.36 (s, 1H), 7.64 (t, J = 7.9 Hz, 1H), 7.61-7.54 (m, 3H), 7.51 (ddd, J = 8.6, 5.0, 2.3 Hz, 1H), 7.28 (dd, J = 9.4, 8.7 Hz, 1H), 7.13 (dd, J = 11.3, 1.6 Hz, 1H), 7.02 (dd, J = 8.2, 1.6 Hz, 1H), 4.30 (q, J = 7.1 Hz, 2H), 3.14 (d, J = 6.9 Hz, 2H), 2.07 (s, 3H), 1.31 (t, J = 7.1 Hz, 3H), 1.18-1.07 (m, 1H), 0.38-0.29 (m, 2H), 0.25-0.17 (m, 2H); (M + H)$^+$ = 597 | + | 145 |
| 421 | 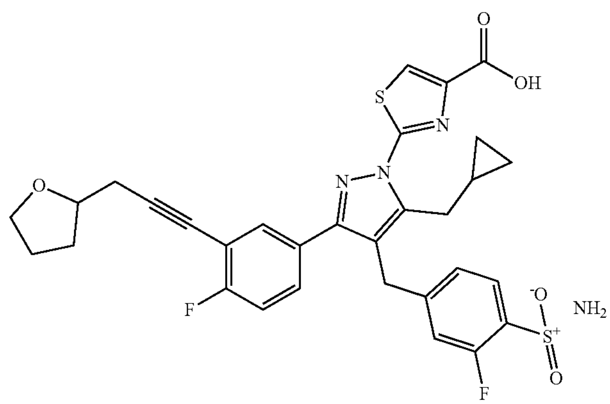 | (M + H)$^+$ = 639 | +++ | 145 |
| 422 | 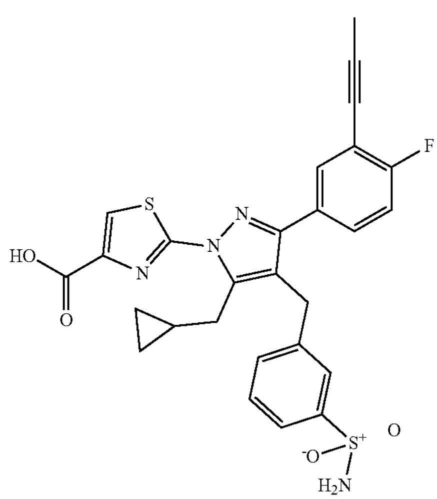 | $^1$H NMR (400 MHz, DMSO-d6) δ 13.13 (s, 1H), 8.27 (s, 1H), 7.65-7.38 (m, 5H), 7.34-7.21 (m, 4H), 4.11 (s, 2H), 3.14 (dd, J = 5.8, 3.3 Hz, 2H), 2.06 (s, 3H), 1.17-1.03 (m, 1H), 0.36-0.25 (m, 2H), 0.25-0.14 (m, 2H); (M + H)$^+$ = 551 | +++ | 145 |

TABLE 7-continued

| Cmpd ID | Structure | Compound name and physical data | Inhibitory activity IC$_{50}$ (μM) | Example Method |
|---|---|---|---|---|
| 423 | 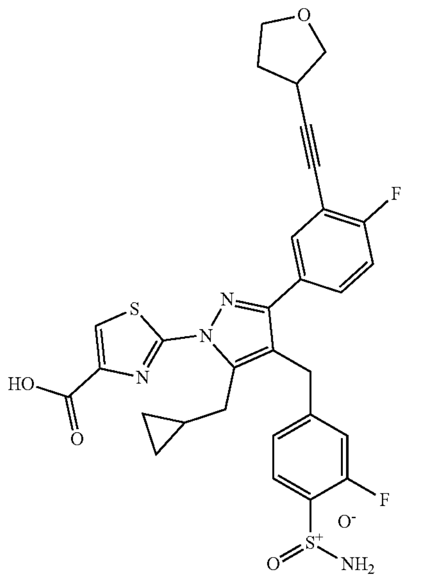 | $^1$H NMR (400 MHz, DMSO-d6) δ 13.14 (s, 1H), 8.29 (s, 1H), 7.64 (t, J = 7.9 Hz, 1H), 7.60-7.51 (m, 4H), 7.34-7.24 (m, 1H), 7.14 (dd, J = 11.4, 1.6 Hz, 1H), 7.03 (dd, J = 8.1, 1.6 Hz, 1H), 4.13 (s, 2H), 3.95 (dd, J = 8.1, 7.3 Hz, 1H), 3.87-3.68 (m, 2H), 3.58 (dd, J = 8.1, 6.5 Hz, 1H), 3.34-3.22 (m, 6H), 3.15 (d, J = 6.9 Hz, 2H), 2.25 (dddd, J = 12.1, 8.5, 7.4, 6.0 Hz, 1H), 1.92 (ddt, J = 12.1, 7.8, 6.6 Hz, 1H), 1.12 (s, 1H), 0.37-0.28 (m, 2H), 0.25-0.16 (m, 2H); M + H$^+$ = 625 | +++ | 145 |
| 424 | 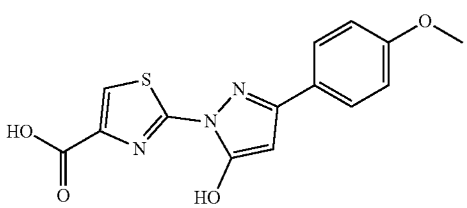 [SMILES: COc1ccc(-c2cc(O)n(-c3nc(C(=O)O)cs3)n2)cc1] | $^1$H NMR (400 MHz, DMSO-d6) δ 12.98 (s, 1H), 8.14 (s, 1H), 7.80 (d, J = 8.2 Hz, 2H), 7.05 (s, 2H), 5.96 (s, 1H), 3.81 (s, 3H); (M + H)$^+$ = 318 | – | 147 |
| 425 | 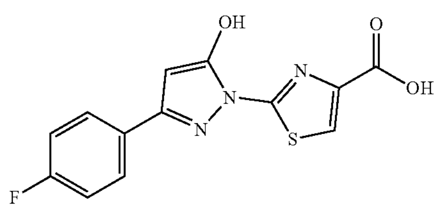 [SMILES: O=C(O)c1csc(-n2nc(-c3ccc(F)cc3)cc2O)n1] | (M + H)$^+$ = 306 | – | 147 |
| 426 | 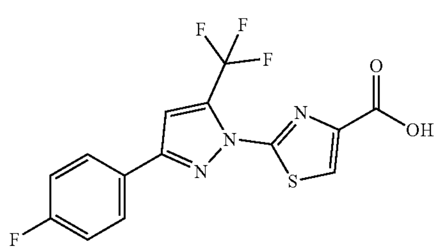 [SMILES: O=C(O)c1csc(-n2nc(-c3ccc(F)cc3)cc2C(F)(F)F)n1] | $^1$H NMR (400 MHz, DMSO-d 6.09-7.99 (m, 2H), 7.92 (s, 1H), 7.41-7.30 (m, 2H); (M + H)$^+$ = 358 | + | 150 |
| 427 | 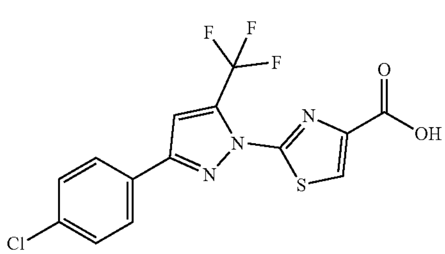 [SMILES: O=C(O)c1csc(-n2nc(-c3ccc(Cl)cc3)cc2C(F)(F)F)n1] | $^1$H NMR (400 MHz, DMSO-d6) δ 13.25 (s, 1H), 8.40 (s, 1H), 8.05-7.93 (m, 4H), 7.63-7.52 (m, 2H); (M + H)$^+$ = 374 | + | 150 |

TABLE 7-continued
| Cmpd ID | Structure | Compound name and physical data | Inhibitory activity IC$_{50}$ (μM) | Example Method |
|---|---|---|---|---|
| 428 | 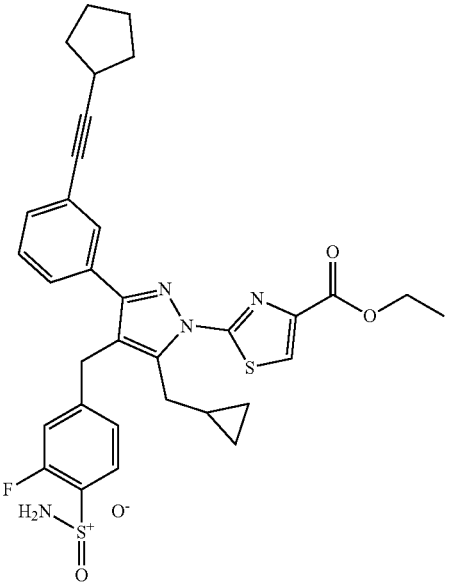 | $^1$H NMR (400 MHz, DMSO-d6) δ 8.34 (d, J = 0.5 Hz, 1H), 7.65 (t, J = 7.9 Hz, 1H), 7.57-7.44 (m, 4H), 7.37-7.31 (m, 2H), 7.13 (dd, J = 11.3, 1.5 Hz, 1H), 7.04 (dd, J = 8.2, 1.6 Hz, 1H), 4.30 (q, J = 7.1 Hz, 2H), 4.13 (s, 2H), 3.15 (d, J = 6.9 Hz, 2H), 2.82 (p, J = 7.3 Hz, 1H), 2.00-1.87 (m, 2H), 1.75-1.47 (m, 6H), 1.35-1.28 (m, 2H), 1.26 (d, J = 19.9 Hz, 1H), 1.18-1.07 (m, 1H), 0.38-0.28 (m, 2H), 0.28-0.19 (m, 2H); (M + H)$^+$ = 633 | – | 145 |
| 429 | 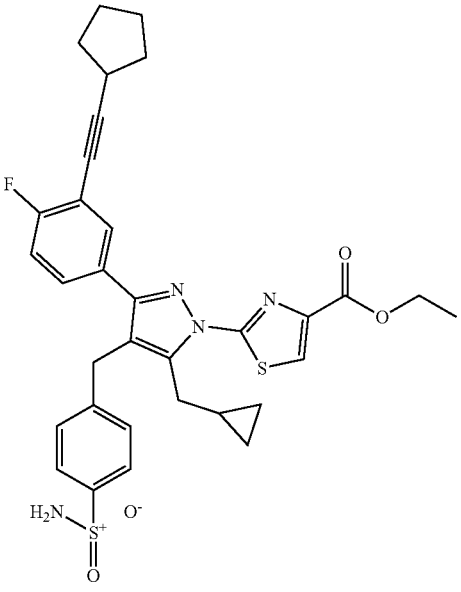 | (M + H)$^+$ = 633 | + | 145 |
| 430 | 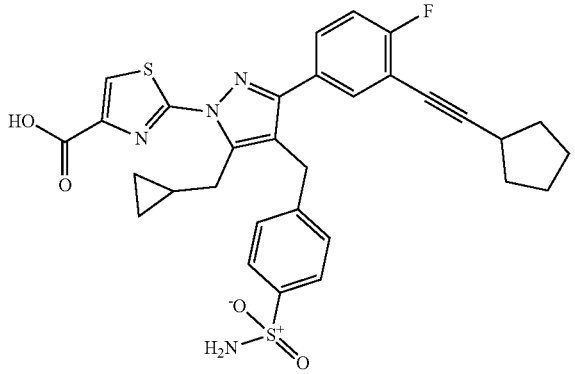 | (M + H)$^+$ = 605 | +++ | 145 |

TABLE 7-continued
| Cmpd ID | Structure | Compound name and physical data | Inhibitory activity IC$_{50}$ (μM) | Example Method |
|---|---|---|---|---|
| 431 | 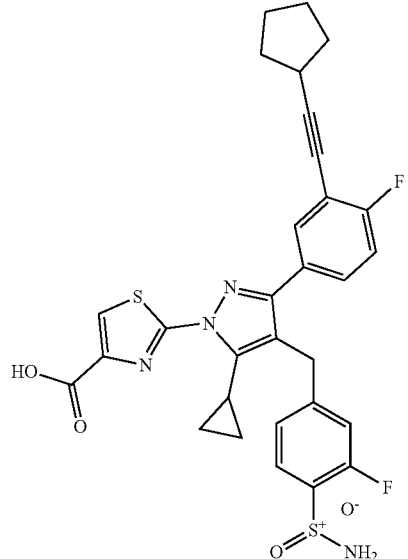 | (M + H)$^+$ = 609 | +++ | 145 |
| 432 | 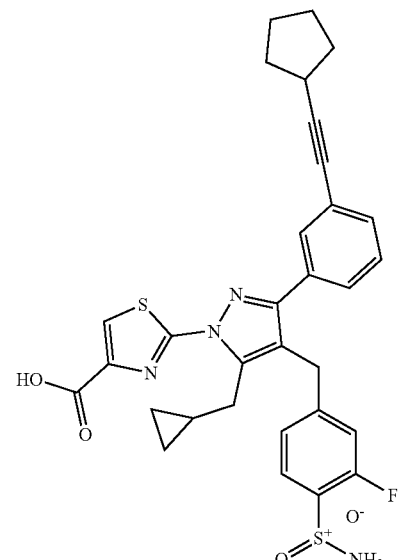 | (M + H)$^+$ = 605 | +++ | 145 |
| 433 | 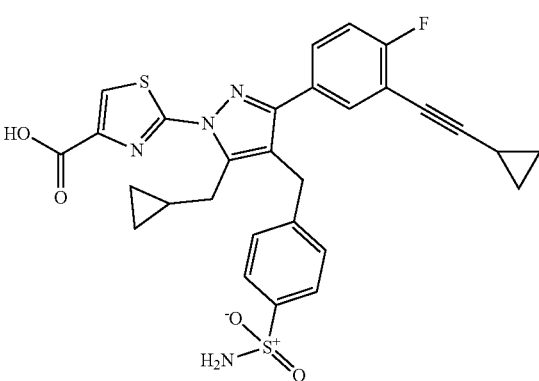 | (M + H)$^+$ = 577 | +++ | 145 |

TABLE 7-continued

| Cmpd ID | Structure | Compound name and physical data | Inhibitory activity IC$_{50}$ (μM) | Example Method |
|---|---|---|---|---|
| 434 | 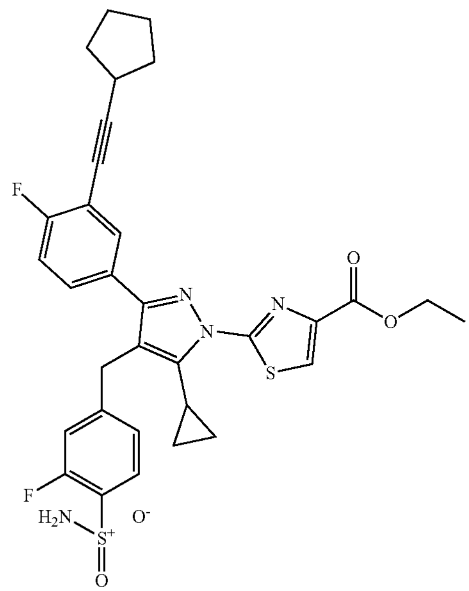 | (M + H)$^+$ = 637 | + | 145 |
| 435 | 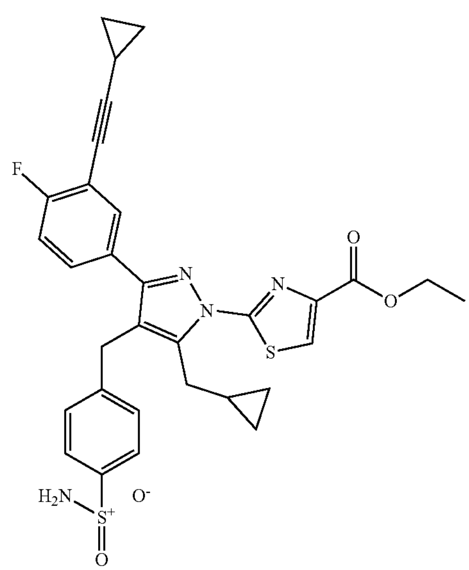 | (M + H)$^+$ = 605 | + | 145 |

TABLE 7-continued

| Cmpd ID | Structure | Compound name and physical data | Inhibitory activity IC$_{50}$ (µM) | Example Method |
|---|---|---|---|---|
| 436 | 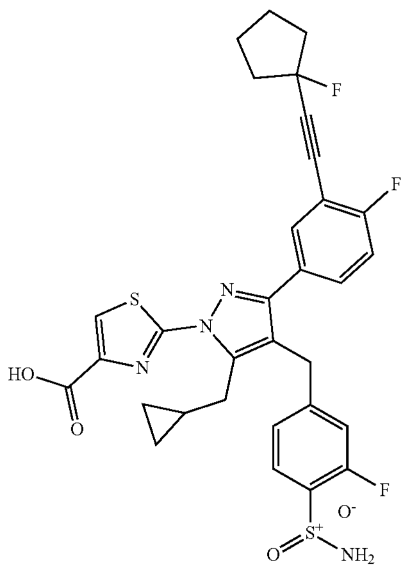 | (M + H)$^+$ = 641 | +++ | 145 |
| 437 | 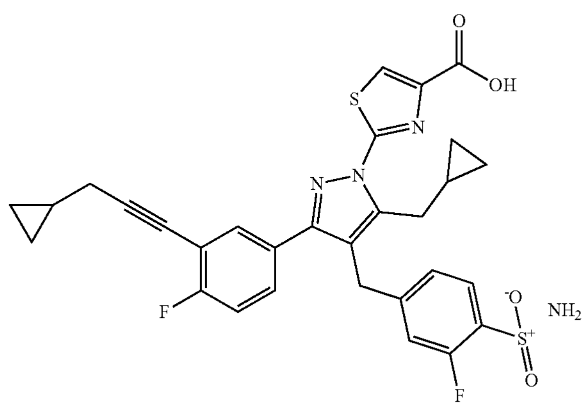 | $^1$H NMR (400 MHz, DMSO-d6) δ 13.13 (s, 1H), 8.29 (s, 1H), 7.64 (t, J = 7.9 Hz, 1H), 7.60-7.50 (m, 4H), 7.29 (dd, J = 9.4, 8.5 Hz, 1H), 7.13 (dd, J = 11.3, 1.6 Hz, 1H), 7.03 (dd, J = 8.2, 1.6 Hz, 1H), 4.13 (s, 2H), 3.14 (d, J = 6.9 Hz, 2H), 2.51 (d, J = 5.9 Hz, 2H), 1.11 (dddd, J = 15.0, 10.0, 5.1, 2.2 Hz, 1H), 1.05-0.92 (m, 1H), 0.51-0.41 (m, 2H), 0.37-0.28 (m, 2H), 0.27-0.16 (m, 4H); (M + H)$^+$ = 609 | +++ | 145 |
| 438 | 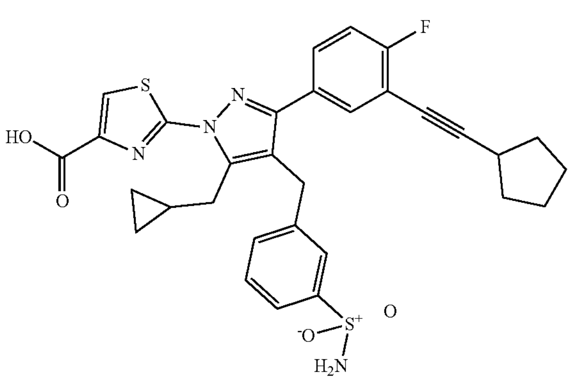 | $^1$H NMR (400 MHz, DMSO-d6) δ 13.14 (s, 1H), 8.28 (s, 1H), 7.61 (dt, J = 7.9, 1.4 Hz, 1H), 7.56-7.38 (m, 4H), 7.32 (dt, J = 7.7, 1.4 Hz, 1H), 7.27 (s, 2H), 7.24 (d, J = 8.9 Hz, 1H), 4.10 (s, 2H), 3.15 (d, J = 6.8 Hz, 2H), 2.87 (p, J = 7.2 Hz, 1H), 2.02-1.49 (m, 8H), 1.10 (tdd, J = 12.0, 7.1, 2.4 Hz, 1H), 0.37-0.27 (m, 2H), 0.23-0.14 (m, 2H); (M + H)$^+$ = 605 | ++ | 145 |

TABLE 7-continued

| Cmpd ID | Structure | Compound name and physical data | Inhibitory activity IC$_{50}$ (μM) | Example Method |
|---|---|---|---|---|
| 439 | 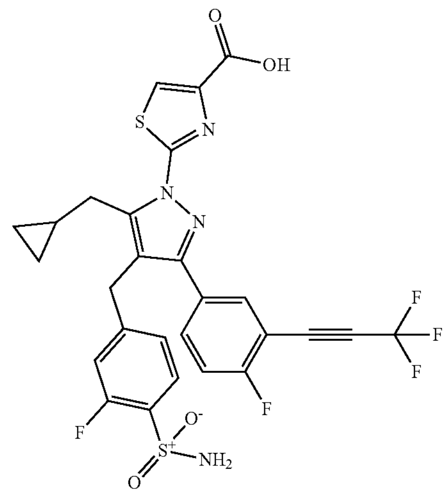 [SMILES: N[S+](=O)([O-])c1ccc(Cc2c(-c3ccc(F)c(C#CC(F)(F)F)c3)nn(-c3nc(C(=O)O)cs3)c2CC2CC2)cc1F] | (M + H)$^+$ = 641 | ++ | 145 |
| 440 | 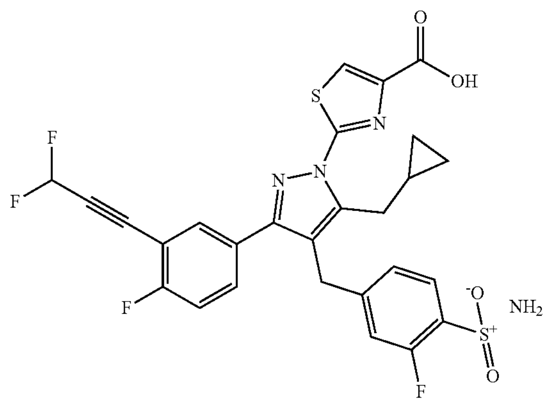 | $^1$H NMR (400 MHz, DMSO-d6) δ 13.15 (s, 1H), 8.28 (s, 1H), 7.83 (dd, J = 6.7, 2.3 Hz, 1H), 7.72 (ddd, J = 8.7, 5.1, 2.3 Hz, 1H), 7.62 (t, J = 7.9 Hz, 1H), 7.55 (s, 2H), 7.42 (t, J = 9.1 Hz, 1H), 7.15-7.07 (m, 1H), 7.06-6.97 (m, 1H), 4.16 (s, 2H), 3.16 (d, J = 7.0 Hz, 2H), 1.18-1.02 (m, 1H), 0.36-0.28 (m, 2H), 0.24-0.17 (m, 2H); (M + H)+ = 606 | +++ | 145 |
| 441 | 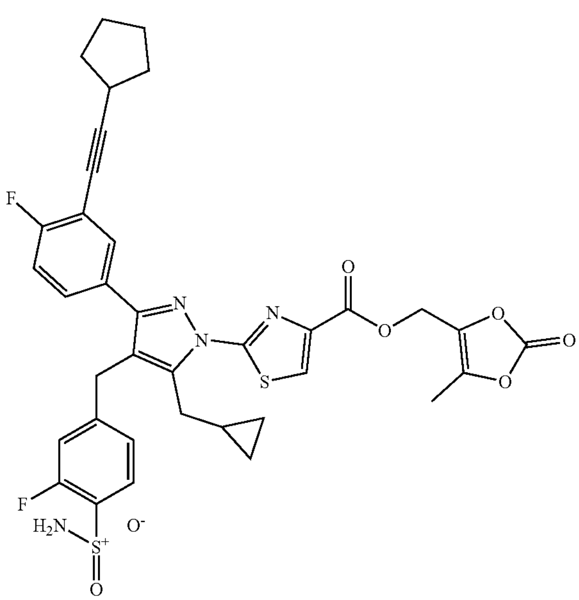 | $^1$H NMR (400 MHz, Chloroform-d) δ 8.03 (s, 1H), 7.79 (t, J = 7.8 Hz, 1H), 7.51 (dd, J = 6.8, 2.3 Hz, 1H), 7.33 (ddd, J = 8.6, 4.9, 2.3 Hz, 1H), 7.08-6.90 (m, 3H), 5.30 (s, 2H), 5.10 (s, 2H), 4.99 (s, 2H), 4.05 (s, 2H), 3.18 (d, J = 6.8 Hz, 2H), 2.85 (p, J = 7.4 Hz, 1H), 2.25 (s, 3H), 2.12-1.93 (m, 1H), 1.86-1.54 (m, 7H), 1.17-1.02 (m, 1H), 0.47-0.39 (m, 2H), 0.28-0.22 (m, 2H); (M + H)$^+$ = 735 | – | 145 |

TABLE 7-continued

| Cmpd ID | Structure | Compound name and physical data | Inhibitory activity IC$_{50}$ (μM) | Example Method |
|---|---|---|---|---|
| 442 | 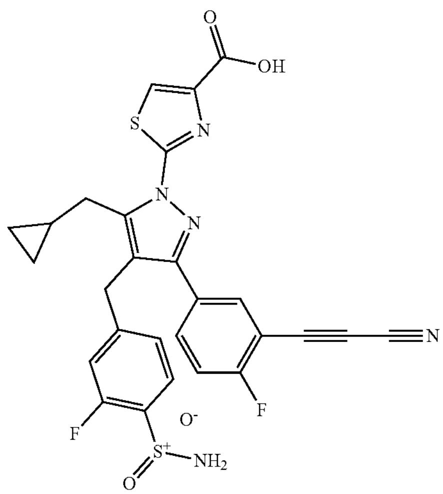 | (M + H)$^+$ = 580 | +++ | 145 |
| 443 | 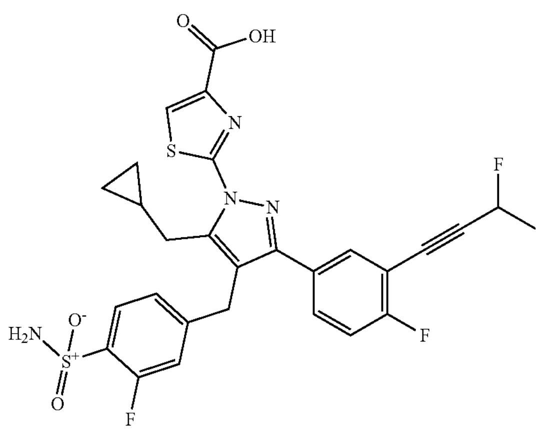 [SMILES: CC(F)C#Cc1cc(-c2nn(-c3nc(C(=O)O)cs3)c(CC3CC3)c2Cc2ccc([S+](N)(=O)[O-])c(F)c2)ccc1F] | $^1$H NMR (400 MHz, DMSO-d6) δ 13.34-12.89 (m, 1H), 8.29 (s, 1H), 7.71-7.58 (m, 3H), 7.56 (s, 2H), 7.36 (t, J = 8.9 Hz, 1H), 7.18-6.96 (m, 2H), 5.77-5.53 (m, 1H), 4.14 (s, 2H), 3.16 (d, J = 6.9 Hz, 2H), 1.60 (dd, J = 23.0, 6.5 Hz, 3H), 1.12 (tq, J = 9.8, 3.4, 2.4 Hz, 1H), 0.38-0.28 (m, 2H), 0.25-0.16 (m, 2H); (M + H)$^+$ = 601 | +++ | 145 |
| 444 | 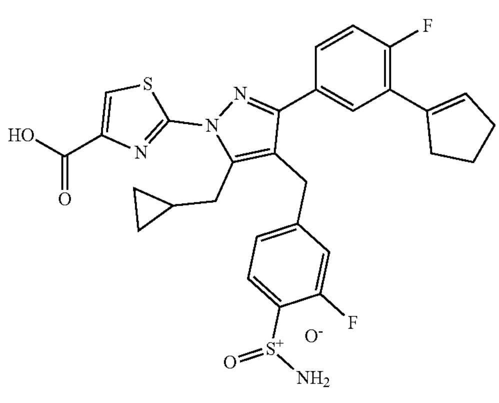 | $^1$H NMR (400 MHz, DMSO-d6) δ 13.12 (s, 1H), 8.28 (s, 1H), 7.66 (t, J = 7.9 Hz, 1H), 7.57 (s, 2H), 7.35 (dd, J = 7.6, 2.3 Hz, 1H), 7.29-7.01 (m, 3H), 6.25 (p, J = 2.1 Hz, 1H), 4.12 (s, 2H), 3.18-3.11 (m, 2H), 2.49-2.38 (m, 4H), 1.85 (p, J = 7.6 Hz, 2H), 1.12 (tdd, J = 11.3, 6.4, 2.0 Hz, 1H), 0.37-0.27 (m, 2H), 0.25-0.16 (m, 2H); (M + H)$^+$ = 597 | +++ | 145 |

TABLE 7-continued

| Cmpd ID | Structure | Compound name and physical data | Inhibitory activity IC$_{50}$ (μM) | Example Method |
|---|---|---|---|---|
| 445 | 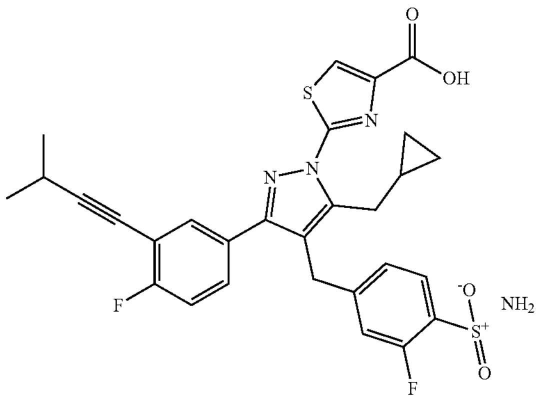 | $^1$H NMR (400 MHz, DMSO-d6) δ 13.15 (s, 1H), 8.28 (s, 1H), 7.64 (t, J = 7.9 Hz, 1H), 7.60-7.48 (m, 4H), 7.28 (t, J = 9.0 Hz, 1H), 7.14 (dd, J = 11.4, 1.6 Hz, 1H), 7.03 (dd, J = 8.2, 1.6 Hz, 1H), 4.12 (s, 2H), 3.15 (d, J = 6.9 Hz, 2H), 2.82 (hept, J = 6.8 Hz, 1H), 1.20 (d, J = 6.9 Hz, 6H), 1.12 (tq, J = 9.9, 3.5, 2.2 Hz, 1H), 0.38-0.28 (m, 2H), 0.25-0.17 (m, 2H); (M + H)$^+$ = 597 | +++ | 145 |
| 446 | 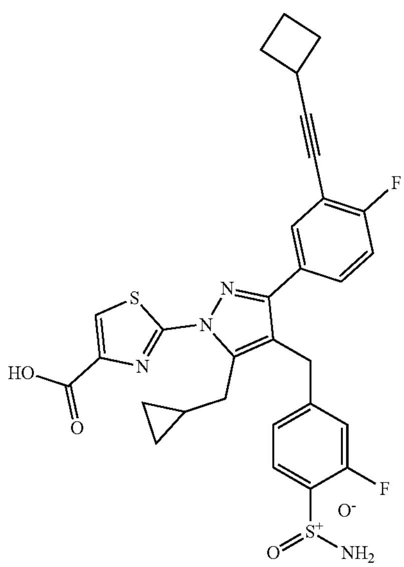 | $^1$H NMR (400 MHz, DMSO-d6) δ 13.14 (s, 1H), 8.29 (s, 1H), 7.64 (t, J = 7.9 Hz, 1H), 7.58-7.49 (m, 4H), 7.28 (dd, J = 9.5, 8.3 Hz, 1H), 7.14 (dd, J = 11.3, 1.6 Hz, 1H), 7.03 (dd, J = 8.2, 1.6 Hz, 1H), 4.13 (s, 2H), 3.36-3.23 (m, 1H), 3.15 (d, J = 6.6 Hz, 2H), 2.34-2.23 (m, 2H), 2.19-2.07 (m, 2H), 2.01-1.81 (m, 2H), 1.19-1.04 (m, 1H), 0.37-0.28 (m, 2H), 0.25-0.16 (m, 2H); (M + H)+ = 609 | +++ | 145 |
| 447 | 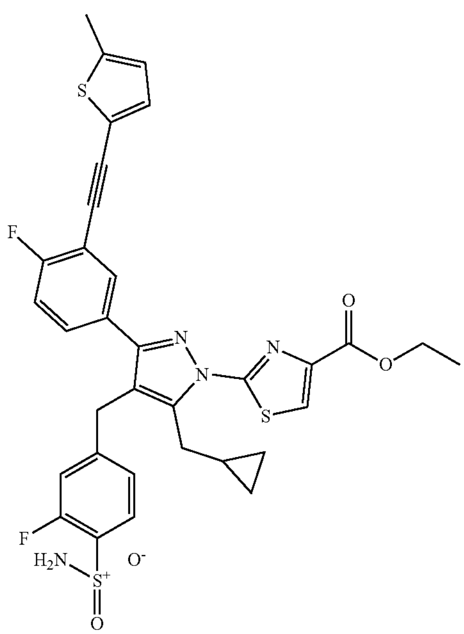 | $^1$H NMR (400 MHz, DMSO-d6) δ 8.37 (s, 1H), 7.72 (dd, J = 6.9, 2.3 Hz, 1H), 7.69-7.51 (m, 4H), 7.36 (t, J = 9.0 Hz, 1H), 7.27 (d, J = 3.6 Hz, 1H), 7.15 (dd, J = 11.3, 1.6 Hz, 1H), 7.04 (dd, J = 8.2, 1.6 Hz, 1H), 6.83 (dt, J = 3.6, 1.2 Hz, 1H), 4.30 (q, J = 7.1 Hz, 2H), 4.16 (s, 2H), 3.16 (d, J = 6.9 Hz, 2H), 1.31 (t, J = 7.1 Hz, 3H), 1.19-1.04 (m, 1H), 0.40-0.29 (m, 2H), 0.27-0.19 (m, 2H); (M + H)$^+$ = 679 | − | 145 |

TABLE 7-continued

| Cmpd ID | Structure | Compound name and physical data | Inhibitory activity IC$_{50}$ (μM) | Example Method |
|---|---|---|---|---|
| 448 | 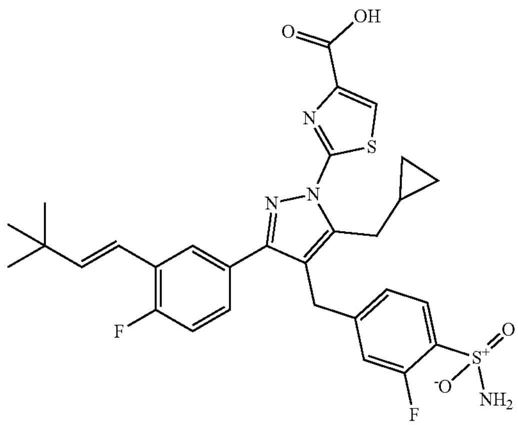 | (M + H)$^+$ = 613 | +++ | 145 |
| 449 | 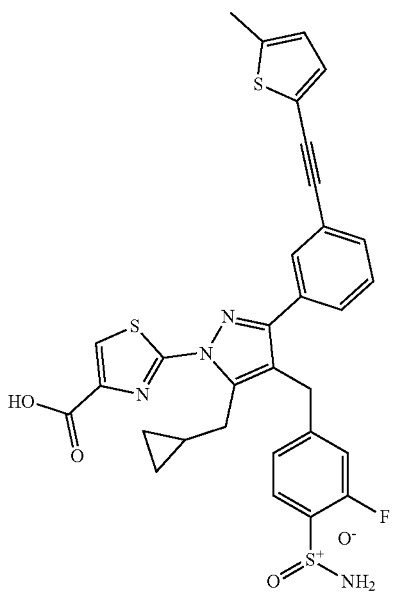 | $^1$H NMR (400 MHz, DMSO-d6) δ 13.15 (s, 1H), 8.29 (s, 1H), 7.69-7.60 (m, 2H), 7.59-7.47 (m, 4H), 7.42 (t, J = 7.7 Hz, 1H), 7.22 (d, J = 3.6 Hz, 1H), 7.14 (dd, J = 11.3, 1.5 Hz, 1H), 7.04 (dd, J = 8.1, 1.5 Hz, 1H), 6.81 (dd, J = 3.6, 1.3 Hz, 1H), 4.16 (s, 2H), 3.16 (d, J = 7.1 Hz, 2H), 2.47-2.44 (m, 3H), 1.13 (dqd, J = 14.8, 7.2, 5.0 Hz, 1H), 0.38-0.28 (m, 2H), 0.26-0.15 (m, 2H); (M + H)$^+$ = 633 | +++ | 145 |
| 450 | 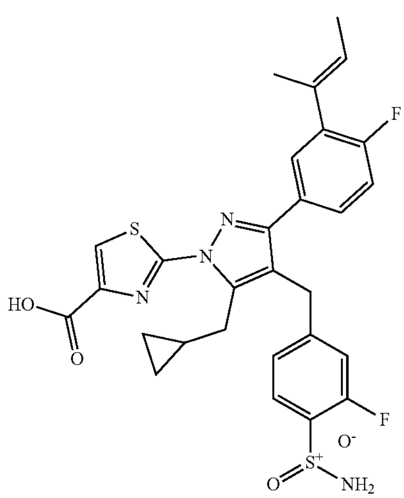 | (M + H)$^+$ = 585 | +++ | 145 |

TABLE 7-continued

| Cmpd ID | Structure | Compound name and physical data | Inhibitory activity IC$_{50}$ (μM) | Example Method |
|---|---|---|---|---|
| 451 | 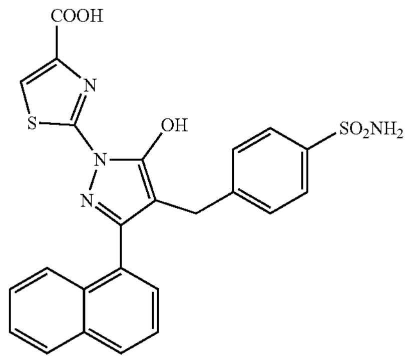 [SMILES: NS(=O)(=O)c1ccc(Cc2c(-c3cccc4ccccc34)nn(-c3nc(C(=O)O)cs3)c2O)cc1] | 2-(5-hydroxy-3-(naphthalen-2-yl)-4-(4-sulfamoylbenzyl)-1H-pyrazol-1-yl)thiazole-4-carboxylic acid; $^1$H-NMR (d6-DMSO) δ 8.19 (s, 1H), 8.09 (d, 2H, J = 1.6 Hz), 8.00 (d, 1H, J = 8Hz), 7.86 (d, 1H, J = 8Hz) 7.63-7.51 (m, 6H), 7.12 (d, 1H, J = 8Hz), 3.69 (s, 2H); MS (ES) 506.9 (M + H)$^+$ LCMS RT = 0.88 min. | + | Example 69 |
| 452 | 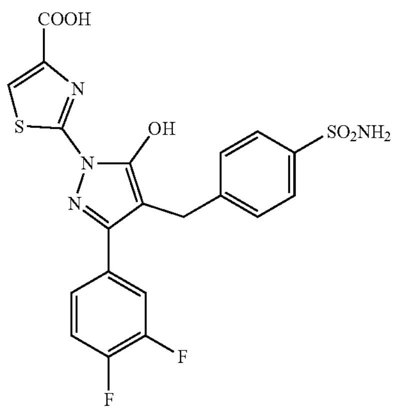 [SMILES: NS(=O)(=O)c1ccc(Cc2c(-c3ccc(F)c(F)c3)nn(-c3nc(C(=O)O)cs3)c2O)cc1] | 2-(3-(3,4-difluorophenyl)-5-hydroxy-4-(4-sulfamoylbenzyl)-1H-pyrazol-1-yl)thiazole-4-carboxylic acid; $^1$H-NMR (d6-DMSO) δ 8.18 (s, 1H), 7.85 (d, 2H, J = 8.4 Hz), 7.56 (m, 1H), 7.45-7.41 (m, 4H), 3.99 (s, 2H); MS (ES) 492.9 (M + H)$^+$ LCMS RT = 0.88 min. | ++ | Example 70 |
| 453 | 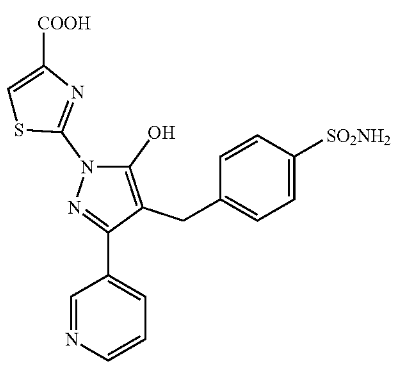 [SMILES: NS(=O)(=O)c1ccc(Cc2c(-c3cccnc3)nn(-c3nc(C(=O)O)cs3)c2O)cc1] | 2-(5-hydroxy-3-(pyridin-3-yl)-4-(4-sulfamoylbenzyl)-1H-pyrazol-1-yl)thiazole-4-carboxylic acid, TFA: VU0657478 (PC-6-098); MS (ES) 457.9 (M + H)$^+$ LCMS RT = 0.30 min. | + | Example 71 |
| 454 | 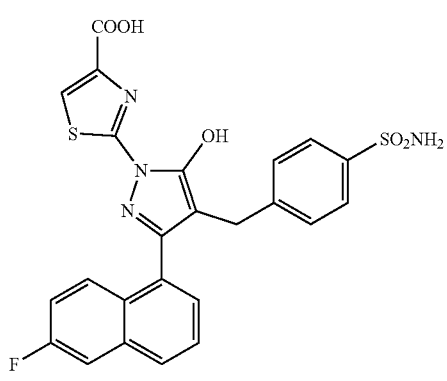 [SMILES: NS(=O)(=O)c1ccc(Cc2c(-c3cccc4cc(F)ccc34)nn(-c3nc(C(=O)O)cs3)c2O)cc1] | 2-(3-(6-fluoronaphthalen-1-(57%) yl)-5-hydroxy-4-(4-sulfamoylbenzyl)-1H-pyrazol-1-yl)thiazole-4-carboxylic acid; $^1$H-NMR (d6-DMSO) δ 8.20 (m, 2H), 7.88 (d, 2H, J = 8 Hz), 7.70-7.55 (m, 5H), 7.32 (m, 1H), 7.12 (d, 1H, J = 8Hz), 3.69 (s, 2H); MS (ES) 524.9 (M + H)$^+$ LCMS RT = 0.94 min. | + | Example 72 |

TABLE 7-continued

| Cmpd ID | Structure | Compound name and physical data | Inhibitory activity IC$_{50}$ (μM) | Example Method |
|---|---|---|---|---|
| 455 | 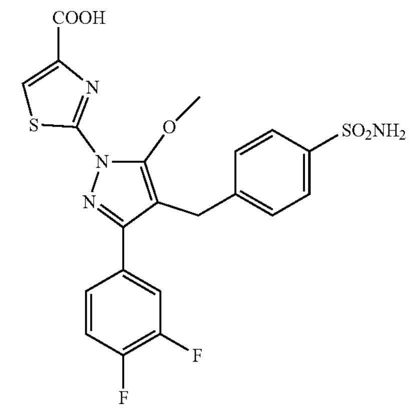 [SMILES: COc1c(Cc2ccc(S(N)(=O)=O)cc2)c(-c2ccc(F)c(F)c2)nn1-c1nc(C(=O)O)cs1] | 2-(3-(3,4-difluorophenyl)-5-methoxy-4-(4-sulfamoylbenzyl)-1H-pyrazol-1-yl)thiazole-4-carboxylic acid; $^1$H-NMR (d6-DMSO) δ 8.20 (s, 1H), 7.81 (d, 2H, J = 8 Hz), 7.54-7.50 (m, 2H), 7.39-7.36 (m, 3H), 3.69 (s, 2H), 3.49 (s, 3H); MS (ES) 506.9 (M + H)$^+$ LCMS RT = 0.89 min. | ++ | Example 73 |
| 456 | 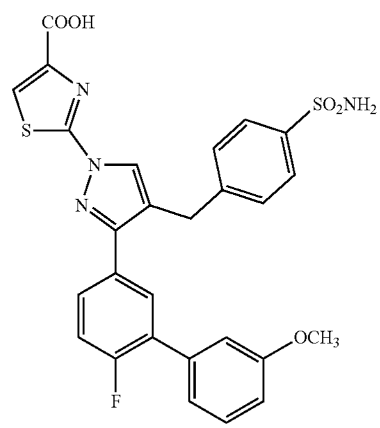 [SMILES: COc1cccc(-c2cc(-c3nn(-c4nc(C(=O)O)cs4)cc3Cc3ccc(S(N)(=O)=O)cc3)ccc2F)c1] | 2-(3-(6-fluoro-3'-methoxy-[1,1'-biphenyl]-3-yl)-4-(4-sulfamoylbenzyl)-1H-pyrazol-1-yl)thiazole-4-carboxylic acid; MS (ES) 565.0 (M + H)$^+$ LCMS RT = 1.08 min. | +++ | Example 85 |
| 457 | 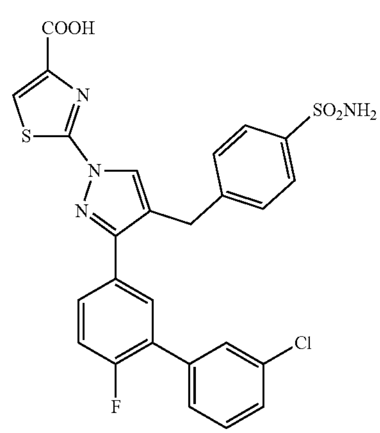 | 2-(3-(3'-chloro-6-fluoro-[1,1'-biphenyl]-3-yl)-4-(4-sulfamoylbenzyl)-1H-pyrazol-1-yl)thiazole-4-carboxylic acid; MS (ES) 568.9 (M + H)$^+$ LCMS RT = 1.16 min. | +++ | Example 86 |

TABLE 7-continued

| Cmpd ID | Structure | Compound name and physical data | Inhibitory activity IC$_{50}$ (μM) | Example Method |
|---|---|---|---|---|
| 458 | 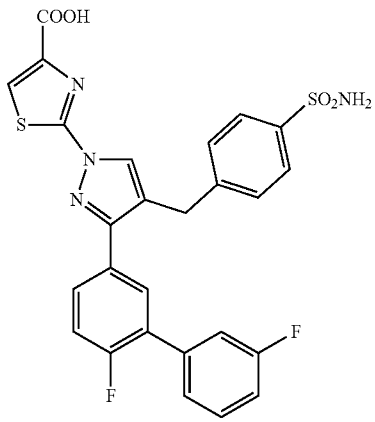 | 2-(3-(3',6-difluoro-[1,1'-biphenyl]-3-yl)-4-(4-sulfamoylbenzyl)-1H-pyrazol-1-yl)thiazole-4-carboxylic acid; MS (ES) 552.9 (M + H)$^+$ LCMS RT = 1.12 min. | +++ | Example 87 |
| 459 | 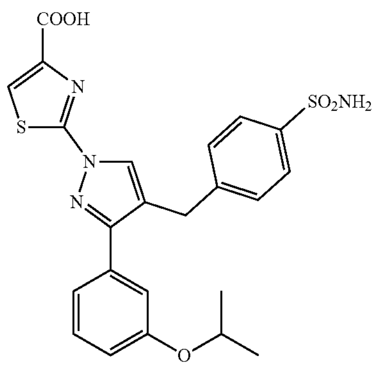 [SMILES: CC(C)Oc1cccc(-c2nn(-c3nc(C(=O)O)cs3)cc2Cc2ccc(S(N)(=O)=O)cc2)c1] | 2-(3-(3-isopropoxyphenyl)-4-(4-sulfamoylbenzyl)-1H-pyrazol-1-yl)thiazole-4-carboxylic acid; $^1$H-NMR (d6-DMSO) δ 8.24 (m, 2H), 7.78 (d, 2H, J = 8 Hz), 7.44 (d, 2H, J = 8Hz), 7.39-7.30 (m, 3H), 7.22 (d, 1H, J = 8Hz), 7.09 (d, 1H, J = 4 Hz), 6.99-6.96 (m, 1H), 4.51 (m, 1H), 4.15 (s, 2H), 1.27 (d, 6H, J = 8 Hz); MS (ES) 499.0 (M + H)$^+$ LCMS RT = 1.07 min. | +++ | Example 74 |
| 460 | 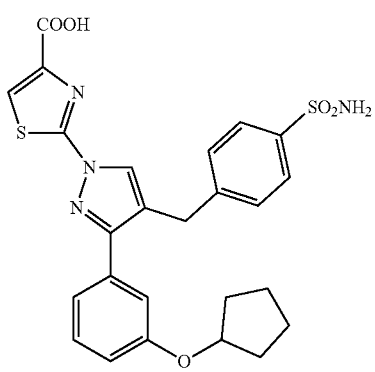 [SMILES: NS(=O)(=O)c1ccc(Cc2cn(-c3nc(C(=O)O)cs3)nc2-c2cccc(OC3CCCC3)c2)cc1] | 2-(3-(3-(cyclopentyloxy)phenyl)-4-(4-sulfamoylbenzyl)-1H-pyrazol-1-yl)thiazole-4-carboxylic acid; $^1$H-NMR (d6-DMSO) δ 8.55 (m, 2H), 8.25 (d, 2H, J = 4 Hz), 7.77 (d, 2H, J = 4 Hz), 7.55-7.26 (m, 3H), 7.22 (d, 1H, J = 8Hz), 7.09 (d, 1H, J = 8 Hz), 6.99-6.96 (m, 1H), 4.74 (m, 1H), 4.15 (s, 2H), 1.91-1.82 (m, 2H), 1.69-1.58 (m, 4H), 1.23 (m, 2H); MS (ES) 525.0 (M + H)$^+$ LCMS RT = 1.15 min. | +++ | Example 75 |

TABLE 7-continued

| Cmpd ID | Structure | Compound name and physical data | Inhibitory activity IC$_{50}$ (μM) | Example Method |
|---|---|---|---|---|
| 461 | 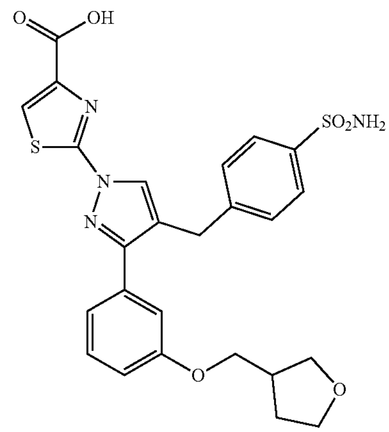 [SMILES: NS(=O)(=O)c1ccc(Cc2cn(-c3nc(C(=O)O)cs3)nc2-c2cccc(OCC3CCOC3)c2)cc1] | 2-(4-(4-sulfamoylbenzyl)-3-(3-((tetrahydrofuran-3-yl)methoxy)phenyl)-1H-pyrazol-1-yl)thiazole-4-carboxylic acid; MS (ES) 540.7 (M + H)$^+$ LCMS RT = 1.13 min. | +++ | Example 76 |
| 462 | 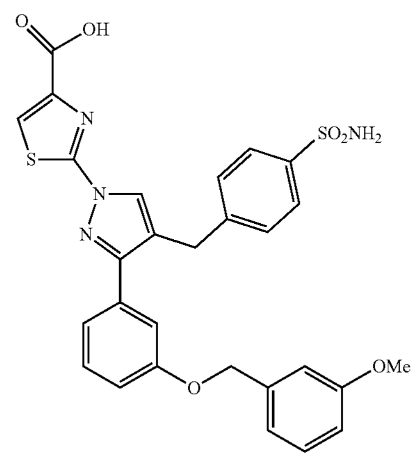 [SMILES: COc1cccc(COc2cccc(-c3nn(-c4nc(C(=O)O)cs4)cc3Cc3ccc(S(N)(=O)=O)cc3)c2)c1] | 2-(3-(3-((3-methoxybenzyl)oxy)phenyl)-4-(4-sulfamoylbenzyl)-1H-pyrazol-1-yl)thiazole-4-carboxylic acid; MS (ES) 576.9 (M + H)$^+$ LCMS RT = 1.02 min. | +++ | Example 77 |
| 463 | 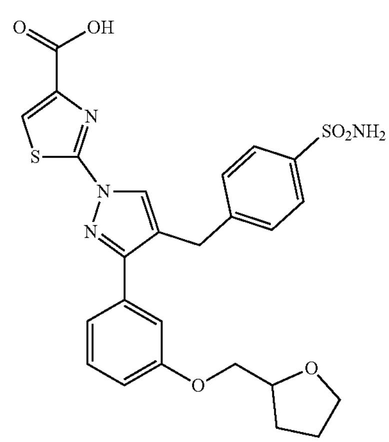 [SMILES: NS(=O)(=O)c1ccc(Cc2cn(-c3nc(C(=O)O)cs3)nc2-c2cccc(OCC3CCCO3)c2)cc1] | 2-(4-(4-sulfamoylbenzyl)-3-(3-((tetrahydrofuran-2-yl)methoxy)phenyl)-1H-pyrazol-1-yl)thiazole-4-carboxylic acid; MS (ES) 540.9 (M + H)$^+$ LCMS RT = 0.76 min. | +++ | Example 78 |

TABLE 7-continued

| Cmpd ID | Structure | Compound name and physical data | Inhibitory activity IC$_{50}$ (μM) | Example Method |
|---|---|---|---|---|
| 464 | 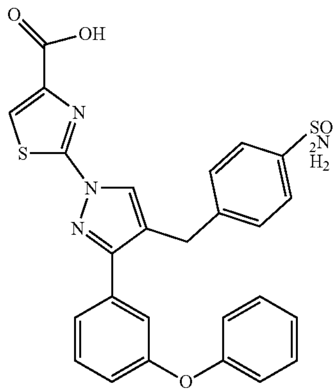 [SMILES: NS(=O)(=O)c1ccc(Cc2cn(-c3nc(C(=O)O)cs3)nc2-c2cccc(Oc3ccccc3)c2)cc1] | 2-(3-(3-phenoxyphenyl)-4-(4-sulfamoylbenzyl)-1H-pyrazol-1-yl)thiazole-4-carboxylic acid; MS (ES) 532.9(M + H)$^+$ LCMS RT = 0.98 min. | +++ | Example 79 |
| 465 | 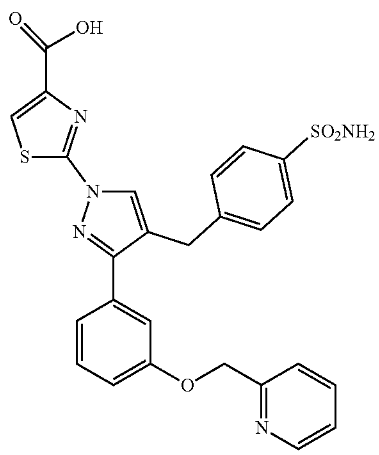 [SMILES: NS(=O)(=O)c1ccc(Cc2cn(-c3nc(C(=O)O)cs3)nc2-c2cccc(OCc3ccccn3)c2)cc1] | 2-(3-(3-(pyridin-3-ylmethoxy)phenyl)-4-(4-sulfamoylbenzyl)-1H-pyrazol-1-yl)thiazole-4-carboxylic acid, TFA MS (ES) 548.0 (M + H)$^+$ LCMS RT = 0.68 min. | +++ | Example 80 |
| 466 | 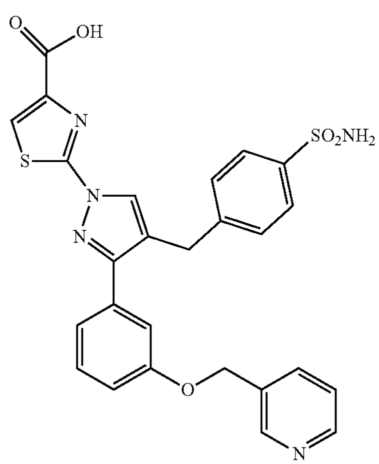 [SMILES: NS(=O)(=O)c1ccc(Cc2cn(-c3nc(C(=O)O)cs3)nc2-c2cccc(OCc3cccnc3)c2)cc1] | 2-(3-(3-(pyridin-2-ylmethoxy)phenyl)-4-(4-sulfamoylbenzyl)-1H-pyrazol-1-yl)thiazole-4-carboxylic acid TFA; MS (ES) 547.9 (M + H)$^+$, LCMS RT = 0.68 min. | +++ | Example 81 |

TABLE 7-continued

| Cmpd ID | Structure | Compound name and physical data | Inhibitory activity IC$_{50}$ (μM) | Example Method |
|---|---|---|---|---|
| 467 | 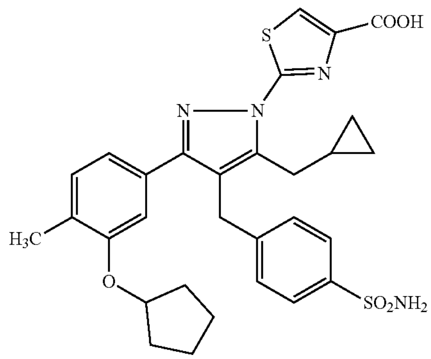 [SMILES: Cc1ccc(-c2nn(-c3nc(C(=O)O)cs3)c(CC3CC3)c2Cc2ccc(S(N)(=O)=O)cc2)cc1OC1CCCC1] | Synthesis of 2-(3-(3-(cyclopentyloxy)-4-methylphenyl)-5-(cyclopropylmethyl)-4-(4-sulfamoylbenzyl)-1H-pyrazol-1-yl)thiazole-4-carboxylic acid; $^1$H-NMR (d6-DMSO) δ 8.07 (s, 1H), 7.53 (d, 2H, J = 8 Hz), 7.12-7.07 (m, 5H), 6.95 (d, 1H, J = 8Hz), 6.87 (d, 1H, J = 8 Hz), 6.63 (s, 1H), 4.16 (m, 1H), 3.90 (s, 2H), 2.93 (m, 2H), 1.87 (s, 3H), 1.40-1.29 (m, 8H), 0.91 (m, 1H), 0.11 (m, 2H), 0.014 (m, 2H); MS (ES) 593.4 (M + H)$^+$, LCMS RT = 0.81 min. | +++ | Example 120 |
| 468 | 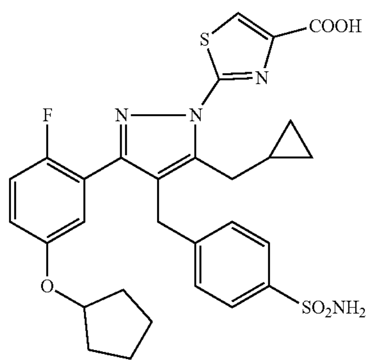 | 2-(3-(5-(cyclopentyloxy)-2-fluorophenyl)-5-(cyclopropylmethyl)-4-(4-sulfamoylbenzyl)-1H-pyrazol-1-yl)thiazole-4-carboxylic acid; $^1$H-NMR (d6-DMSO) δ 8.07 (s, 1H), 7.43 (d, 2H, J = 8 Hz), 7.02-6.93 (m, 5H), 6.73 (m, 1H), 6.60 (m, 1H), 4.40 (m, 1H), 2.93 (m, 2H), 1.59-1.54 (m, 2H), 1.52-1.32 (m, 6H), 0.91 (m, 1H), 0.013 (m, 2H), 0.010 (m, 2H); MS (ES) 597.4 (M + H)$^+$, LCMS RT = 067 min. | ++ | By analogy with Example 120 |
| 469 | 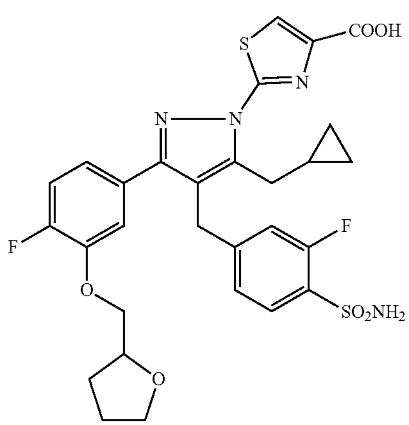 | 2-(5-(cyclopropylmethyl)-3-(4-fluoro-3-((tetrahydrofuran-2-yl)methoxy)phenyl)-4-(3-fluoro-4-sulfamoylbenzyl)-1H-pyrazol-1-yl)thiazole-4-carboxylic acid; $^1$H-NMR (d6-DMSO) δ 8.07 (s, 1H), 7.44 (m, 1H), 7.35 (s, 2H), 7.05-6.82 (m, 5H), 3.93 (s, 2H), 3.87-3.43 (m, 6H), 2.93 (m, 2H), 1.75-159 (m, 3H), 1.38 (m, 1H), 0.90 (m, 1H), 0.013 (m, 2H) 0.010 (m, 2H); MS (ES) 630.9 (M + H)$^+$, LCMS RT = 1.10 min. | +++ | Example 121 |

TABLE 7-continued

| Cmpd ID | Structure | Compound name and physical data | Inhibitory activity IC$_{50}$ (μM) | Example Method |
|---|---|---|---|---|
| 470 | 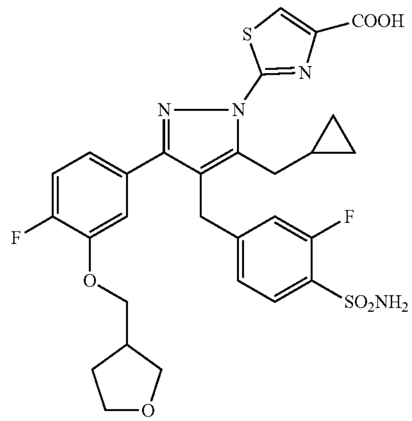 | 2-(5-(cyclopropylmethyl)-3-(4-fluoro-3-((tetrahydrofuran-3-yl)methoxy)phenyl)-4-(3-fluoro-4-sulfamoylbenzyl)-1H-pyrazol-1-yl)thiazole-4-carboxylic acid; $^1$H-NMR (d6-DMSO) δ 8.07 (s, 1H), 7.44 (m, 1H), 7.35 (s, 2H), 7.04-7.01 (m, 1H), 6.95-6.91 (m, 3H), 6.84-6.82 (m, 1H), 3.92 (s, 2H), 3.52-3.50 (m, 4H), 3.40-3.35 (m, 2H), 3.20 (m, 1H), 2.93 (m, 2H), 2.4 (m, 1H), 1.77 (m, 1H), 1.39 (m, 1H), 0.91 (m, 1H), 0.013 (m, 2H) 0.010 (m, 2H); MS (ES) 552.9 (M + H)$^+$, LCMS RT = 1.12 min. | +++ | Example 122 |
| 471 | 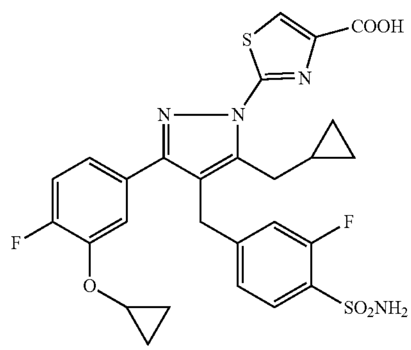 | 2-(3-(3-cyclopropoxy-4-fluorophenyl)-5-(cyclopropylmethyl)-4-(3-fluoro-4-sulfamoylbenzyl)-1H-pyrazol-1-yl)thiazole-4-carboxylic acid; $^1$H-NMR (d6-DMSO) δ 8.07 (s, 1H), 7.46 (m, 1H), 7.37 (s, 2H), 7.19 (m, 1H), 7.05-6.85 (m, 5H), 3.92 (s, 2H), 3.50 (m, 1H), 2.93 (m, 2H), 0.91 (m, 1H), 0.013 (m, 2H) 0.010 (m, 2H); MS (ES) 586.9 (M + H)$^+$, LCMS RT = 1.12 min. | +++ | Example 123 |
| 472 | 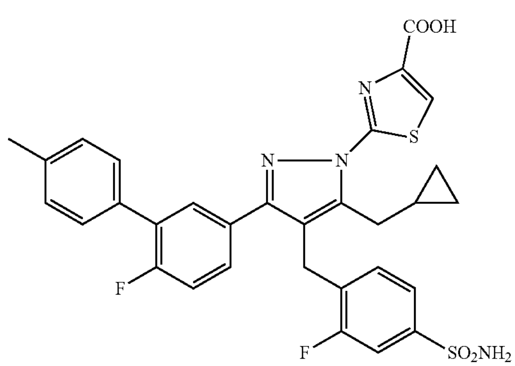 [SMILES: Cc1ccc(-c2cc(-c3nn(-c4nc(C(=O)O)cs4)c(CC4CC4)c3Cc3ccc(S(N)(=O)=O)cc3F)ccc2F)cc1] | 2-(5-(cyclopropylmethyl)-3-(6-fluoro-4'-methyl-[1,1'-biphenyl]-3-yl)-4-(2-fluoro-4-sulfamoylbenzyl)-1H-pyrazol-1-yl)thiazole-4-carboxylic acid; $^1$H-NMR (d6-DMSO) δ 8.31 (s, 1H), 7.59-7.35 (m, 11H), 7.17 (m, 1H), 4.13 (s, 2H), 3.02 (m, 2H), 2.35 (s, 3H), 1.15 (m, 1H), 0.033 (m, 2H) 0.021 (m, 2H); MS (ES) 621.4 (M + H)$^+$, LCMS RT = 0.79 min. | | Example 124 |

TABLE 7-continued

| Cmpd ID | Structure | Compound name and physical data | Inhibitory activity IC$_{50}$ (μM) | Example Method |
|---|---|---|---|---|
| 473 | 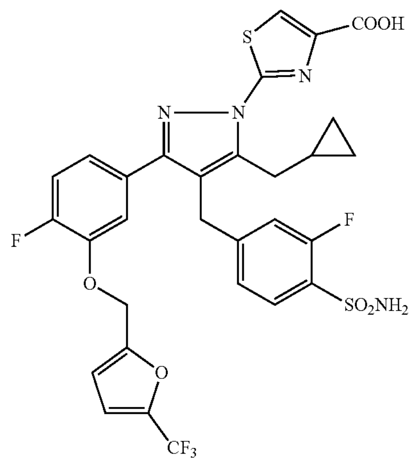 | 2-(5-(cyclopropylmethyl)-3-(4-fluoro-3-((5-(trifluoromethyl)furan-2-yl)methoxy)phenyl)-4-(3-fluoro-4-sulfamoylbenzyl)-1H-pyrazol-1-yl)thiazole-4-carboxylic acid; MS (ES) 694.9 (M + H)$^+$, LCMS RT = 1.20 min. | +++ | Example 125 |
| 474 | 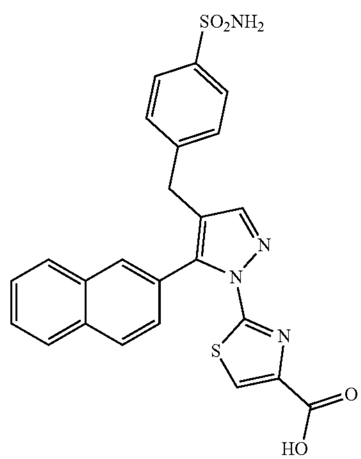 [SMILES: NS(=O)(=O)c1ccc(Cc2cnn(-c3nc(C(=O)O)cs3)c2-c2ccc3ccccc3c2)cc1] | 2-(5-(naphthalen-2-yl)-4-(4-sulfamoylbenzyl)-1H-pyrazol-1-yl)thiazole-4-carboxylic acid; $^1$H-NMR (d6-DMSO) δ 8.24 (s, 1H). 8.13(s, 1H), 7.91-8.03(m, 4H), 7.80(d, J = 8.2 Hz, 2H), 7.52-7.58(m, 3H), 7.32(s, 2H), 4.25(s, 2H); MS (ES) 491 (M + H)$^+$ LCMS RT 1.04 min. | +++ | Example 82 |
| 475 | 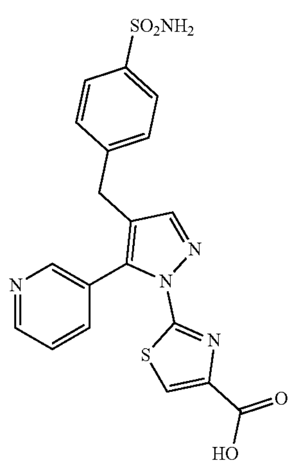 [SMILES: NS(=O)(=O)c1ccc(Cc2cnn(-c3nc(C(=O)O)cs3)c2-c2cccnc2)cc1] | 2-(5-(pyridin-3-yl)-4-(4-sulfamoylbenzyl)-1H-pyrazol-1-yl)thiazole-4-carboxylic acid; MS (ES) 442 (M + H)$^+$ LCMS RT 0.64 min. | ++ | Example 83 |

TABLE 7-continued

| Cmpd ID | Structure | Compound name and physical data | Inhibitory activity IC$_{50}$ (μM) | Example Method |
|---|---|---|---|---|
| 476 | 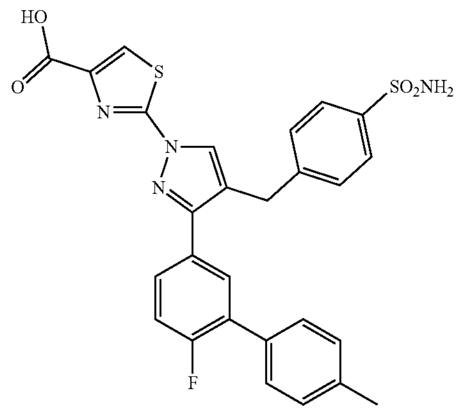 [SMILES: Cc1ccc(-c2cc(-c3nn(-c4nc(C(=O)O)cs4)cc3Cc3ccc(S(N)(=O)=O)cc3)ccc2F)cc1] | 2-(3-(6-fluoro-4'-methyl-[1,1'-biphenyl]-3-yl)-4-(4-sulfamoylbenzyl)-1H-pyrazol-1-yl)thiazole-4-carboxylic acid; $^1$H-NMR (d6-DMSO) δ 8.27 (d, J = 9.24 Hz, 2H), 7.76-7.78 (m, 4H), 7.29-7.46 (m, 8H), 4.2 (s, 2H), 2.35 (s, 3H); MS (ES) 549 (M + H)$^+$ LCMS RT 1.27 min. | +++ | Example 84 |
| 477 | 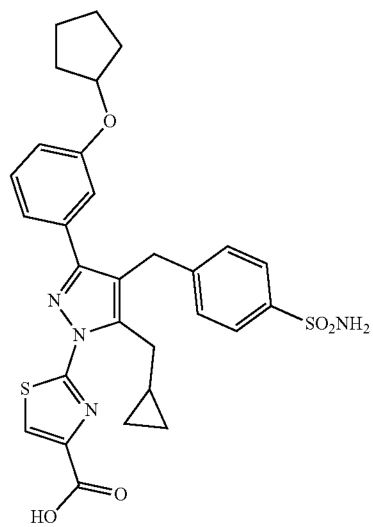 [SMILES: NS(=O)(=O)c1ccc(Cc2c(-c3cccc(OC4CCCC4)c3)nn(-c3nc(C(=O)O)cs3)c2CC2CC2)cc1] | 2-(3-(3-(cyclopentyloxy)phenyl)-5-(cyclopropylmethyl)-4-(4-sulfamoylbenzyl)-1H-pyrazol-1-yl)thiazole-4-carboxylic acid; $^1$H-NMR (CDCl$_3$) δ 8.10 (s, 1H), 7.84(d, J = 8.4 Hz, 2H), 7.23-7.31(m, 4H), 7.02-7.07(m, 2H), 6.88(dd, J = 1.76, 1.8 Hz, 1H) 4.97(s, 2H), 4.11(s, 2H), 3.15(d, J = 6.64 Hz, 2H), 1.58-1.79(m, 9H), 1.12-1.16(m, 1H), 0.43 (d, J = 8Hz, 2H), 0.21 (d, J = 5.4 Hz, 2H), MS (ES) 579 (M + H)$^+$ LCMS RT 1.15 min. | | Example 126 |
| 478 | 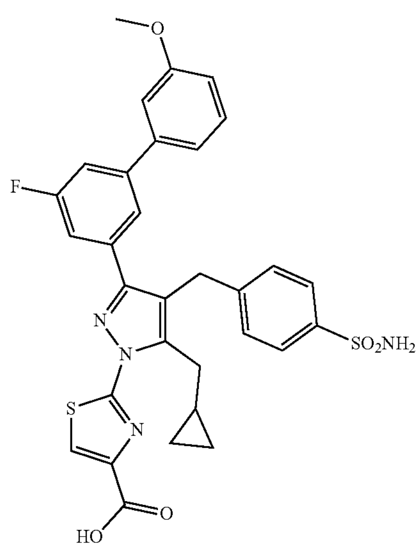 [SMILES: COc1cccc(-c2cc(F)cc(-c3nn(-c4nc(C(=O)O)cs4)c(CC4CC4)c3Cc3ccc(S(N)(=O)=O)cc3)c2)c1] | 2-(5-(cyclopropylmethyl)-3-(5-fluoro-3'-methoxy-[1,1'-biphenyl]-3-yl)-4-(4-sulfamoylbenzyl)-1H-pyrazol-1-yl)thiazole-4-carboxylic acid; $^1$H-NMR (CDCl$_3$) δ 8.10(s, 1H) 7.86(d, J = 8.32 Hz, 2H,) 7.23-7.29(m, 7H), 7.00 (d, J = 7.12 Hz, 1H), 6.91(dd, J = 1.88 1.88 Hz, 1H), 6.60(t, J = 3.92 Hz, 1H), 4.96(s, 2H), 4.11(s, 2H), ), 3.87(s, 3H), 3.21(d, J = 6.64 Hz, 2H) 1.17-1.25(m, 1H) 0.47(d, J = 7.28 Hz, 2H), 0.24 (d, J = 5.2 Hz, 2H), MS: (ES) 619 (M + H)$^+$ LCMS RT 1.32 min. | +++ | Example 143 |

TABLE 7-continued

| Cmpd ID | Structure | Compound name and physical data | Inhibitory activity IC$_{50}$ (μM) | Example Method |
|---|---|---|---|---|
| 479 | 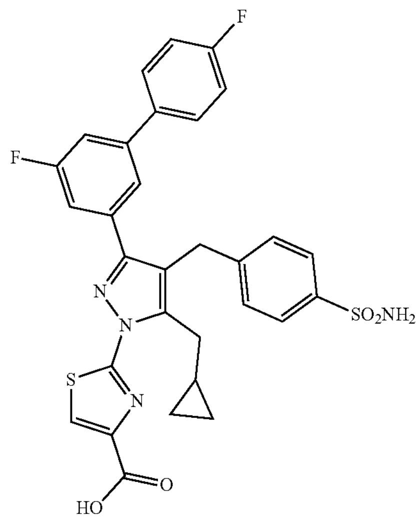 [SMILES: NS(=O)(=O)c1ccc(Cc2c(-c3cc(F)cc(-c4ccc(F)cc4)c3)nn(-c3nc(C(=O)O)cs3)c2CC2CC2)cc1] | 2-(5-(cyclopropylmethyl)-3-(4',5-difluoro-[1,1'-biphenyl]-3-yl)-4-(4-sulfamoylbenzyl)-1H-pyrazol-1-yl)thiazole-4-carboxylic acid; MS (ES) 607 (M + H)$^+$ LCMS RT 1.35 min. | +++ | Example 144 |
| 480 | 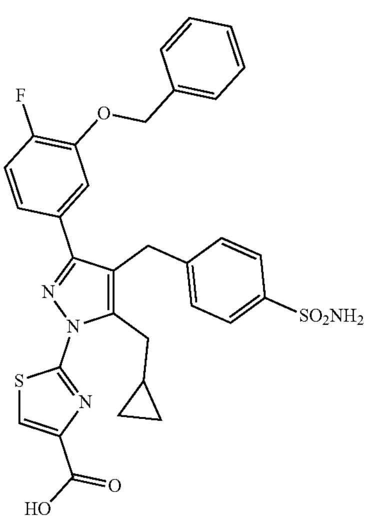 [SMILES: NS(=O)(=O)c1ccc(Cc2c(-c3ccc(F)c(OCc4ccccc4)c3)nn(-c3nc(C(=O)O)cs3)c2CC2CC2)cc1] | 2-(3-(3-(benzyloxy)-4-fluorophenyl)-5-(cyclopropylmethyl)-4-(4-sulfamoylbenzyl)-1H-pyrazol-1-yl)thiazole-4-carboxylic acid; $^1$H-NMR (CDCl$_3$) δ 8.11(s, 1H), 7.84(d, J = 8 Hz, 2H), 7.24-7.38(m, 8H), 7.15(d, J = 7.4 Hz, 1H) 7.08(d, J = 8 Hz, 2H), 5.01(s, 2H), 4.95(s, 3H), 4.02(s, 2H), 3.16(d, J = 6.7 Hz, 2H), 1.11-1.15(m, 1H), 0.42(d, J = 7 Hz, 2H), 0.21(d, J = 5.24 Hz, 2H); MS (ES) 619 (M + H)$^+$ LCMS RT = 1.28 min. | +++ | Example 127 |

TABLE 7-continued

| Cmpd ID | Structure | Compound name and physical data | Inhibitory activity IC$_{50}$ (μM) | Example Method |
|---|---|---|---|---|
| 481 | 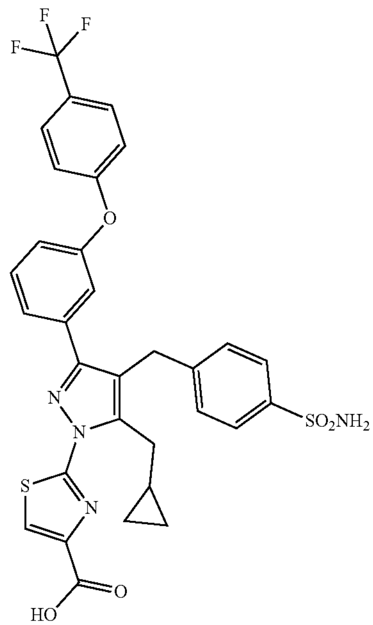 [SMILES: NS(=O)(=O)c1ccc(Cc2c(-c3cccc(Oc4ccc(C(F)(F)F)cc4)c3)nn(-c3nc(C(=O)O)cs3)c2CC2CC2)cc1] | 2-(5-(cyclopropylmethyl)-4-(4-sulfamoylbenzyl)-3-(3-(4-(trifluoromethyl)phenoxy)phenyl)-1H-pyrazol-1-yl)thiazole-4-carboxylic acid; $^{1}$H-NMR (CDCl$_3$) δ 8.11(s, 1H), 7.8(d, J = 8Hz, 2H), 7.6(d, J = 8 Hz, 2H), 7.21-7.40(m, 5H), 7.01-7.06(m, 3H), 5.04(s, 2H), 4.08(s, 2H), 3.16(d, J = 6 Hz, 2H), 1.09-1.15(m, 1H) 0.42(d, J = 8. Hz, 2H), 0.21 (d, J = 5 Hz, 2H), MS (ES) 655 (M + H)$^+$ LCMS RT = 1.38 min in 2 min method. | +++ | Example 128 |
| 482 | 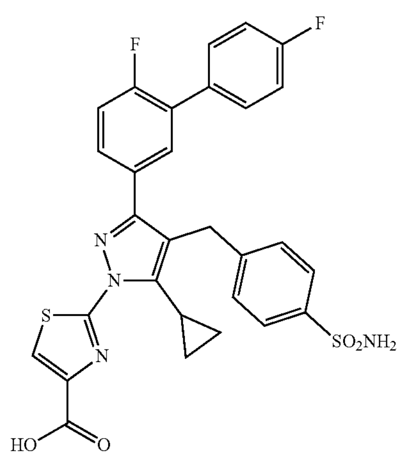 [SMILES: NS(=O)(=O)c1ccc(Cc2c(-c3ccc(F)c(-c4ccc(F)cc4)c3)nn(-c3nc(C(=O)O)cs3)c2C2CC2)cc1] | 2-(5-cyclopropyl-3-(4',6-difluoro-[1,1'-biphenyl]-3-yl)-4-(4-sulfamoylbenzyl)-1H-pyrazol-1-yl)thiazole-4-carboxylic acid; $^{1}$H-NMR (MeOD) δ 8.27(s, 1H) 7.85(d, J = 12 Hz, 2H),; 7.57-7.63(m, 1H), 7.5(d, J = 16 Hz, 1H), 7.29-7.42(m, 4H), 7.12-7.25(m, 4H), 4.25(s, 2H), 2.32-2.41(m, 1H), 1.15 (d, J = 12 Hz, 2H), 0.7(d, J = 9 Hz, 2H ); (ES) 593 (M + H)$^+$ LCMS RT = 1.28 min in 2 min method. | +++ | Example 112 |

TABLE 7-continued

| Cmpd ID | Structure | Compound name and physical data | Inhibitory activity IC$_{50}$ (μM) | Example Method |
|---|---|---|---|---|
| 483 | 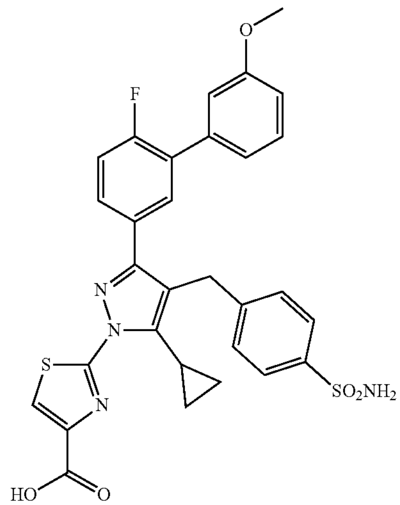 [SMILES: COc1cccc(-c2cc(-c3nn(-c4nc(C(=O)O)cs4)c(C4CC4)c3Cc3ccc(S(N)(=O)=O)cc3)ccc2F)c1] | 2-(5-cyclopropyl-3-(6-fluoro-3'-methoxy-[1,1'-biphenyl]-3-yl)-4-(4-sulfamoylbenzyl)-1H-pyrazol-1-yl)thiazole-4-carboxylic acid; $^1$H-NMR (CDCl$_3$) δ 8.13(s, 1H), 7.85 (d, J = 8 Hz, 2H), 7.55-7.59 (m, 1H), 7.35-7.39(m, 2H), 7.25-7.31 (m, 4H), 7.17(t, J = 18.84 Hz, 1H), 7.04 (d, J = 7.56 Hz, 1H), 6.91-6.94 (dd, J = 2, 2 Hz, 1H), 6.73 (s, 1H), 5.04 (s, Broad, 2H), 4.17 (s, 2H), 3.87(s, 3H), 2.23-2.27(m, 1H), 1.12 (d, J = 7 Hz, 2H), 0.73 (d, J = 5 Hz, 2H), MS (ES) 605 (M + H)$^+$ LCMS RT = 1.25 min in 2 min method. | +++ | Example 113 |
| 484 | 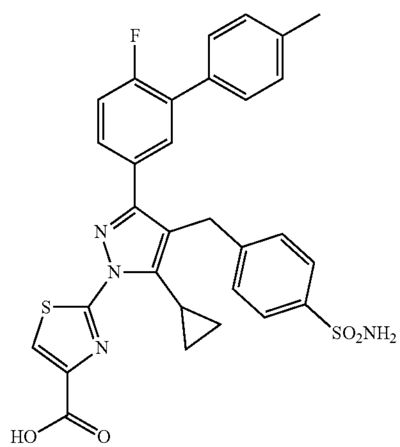 [SMILES: Cc1ccc(-c2cc(-c3nn(-c4nc(C(=O)O)cs4)c(C4CC4)c3Cc3ccc(S(N)(=O)=O)cc3)ccc2F)cc1] | 2-(5-cyclopropyl-3-(6-fluoro-4'-methyl-[1,1'-biphenyl]-3-yl)-4-(4-sulfamoylbenzyl)-1H-pyrazol-1-yl)thiazole-4-carboxylic acid; $^1$H-NMR (CDCl$_3$) δ 8.10(s, 1H), 7.82(d, J = 8.Hz, 2H), 7.5(dd, J1 = 2; J2 = 2 Hz, 1H), 7.41-7.45(m, 1H), 7.22-7.32(m, 7H), 7.13(t, J = 19 Hz, 1H), 5.06(s, 2H), 4.14(s, 2H), 2.40 (s, 3H), 2.17-2.23(m, 1H), 1.07(d, J = 8 Hz, 2H), 0.68(d, J = 5. Hz, 2H), MS (ES) 589 (M + H)$^+$ LCMS RT = 1.31 min in 2 min method. | +++ | Example 114 |
| 485 | 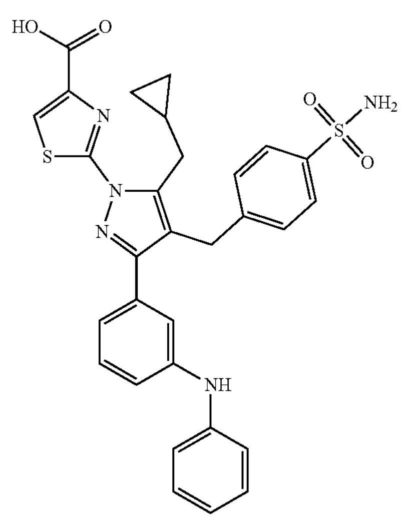 [SMILES: NS(=O)(=O)c1ccc(Cc2c(-c3cccc(Nc4ccccc4)c3)nn(-c3nc(C(=O)O)cs3)c2CC2CC2)cc1] | 2-(5-(cyclopropylmethyl)-3-(3-(phenylamino)phenyl)-4-(4-sulfamoylbenzyl)-1H-pyrazol-1-yl)thiazole-4-carboxylic acid; $^1$H-NMR (CDCl$_3$) δ 7.96 (1H, s), 7.72 (2H, d, J = 8.3 Hz), 7.23-7.18 (6H, m), 7.02-6.99 (4H, m), 6.88 (1H, t, J = 7.4 Hz), 4.02 (2H, s), 3.10 (2H, d, J = 6.8 Hz), 1.01 (1H, m), 0.33 (2H, dd, J = 13.8, 5.8 Hz), 0.14 (2H, dd, J = 10.2, 5.0 Hz); MS (ES) 587.7 (M + H)$^+$; LCMS RT = 1.06 min. | +++ | Example 115 |

TABLE 7-continued

| Cmpd ID | Structure | Compound name and physical data | Inhibitory activity IC$_{50}$ (μM) | Example Method |
|---|---|---|---|---|
| 486 | 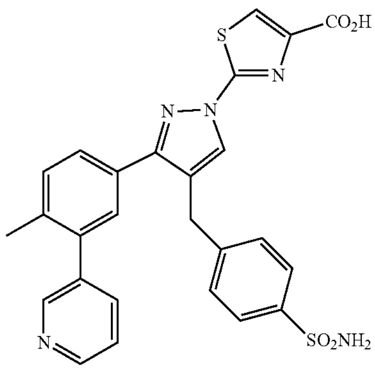 | 2-(3-(4-methyl-3-(pyridin-3-yl)phenyl)-4-(4-sulfamoylbenzyl)-1H-pyrazol-1-yl)thiazole-4-carboxylic acid; $^1$H-NMR (MeOD) δ 8.77 (s, 1H), 8.72 (s, 1H), 8.40 (s, 1H), 8.25 (d, J = 8.0 Hz, 1H), 8.16 (s, 1H), 7.92 (dd, J = 7.6, 5.6 Hz, 1H), 7.81 (d, J = 8.4 Hz, 2H), 7.74 (dd, J = 7.6, 1.6 Hz, 1H), 7.47 (d, J = 8.0 Hz, 2H), 7.39 (d, J = 8.0 Hz, 2H), 4.21 (s, 2H), 2.34 (s, 3H); MS (ES) 532.7 (M + H)$^+$, LCMS RT = 0.82 min. | +++ | Example 88 |
| 487 | 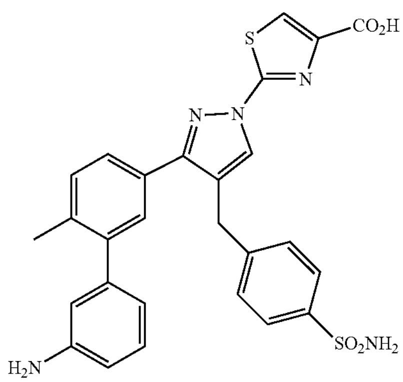 [SMILES: Cc1ccc(-c2nn(-c3nc(C(=O)O)cs3)cc2Cc2ccc(S(N)(=O)=O)cc2)cc1-c1cccc(N)c1] | 2-(3-(3'-amino-6-methyl-[1,1'-biphenyl]-3-yl)-4-(4-sulfamoylbenzyl)-1H-pyrazol-1-yl)thiazole-4-carboxylic acid; $^1$H-NMR (MeOD) δ 8.37 (s, 1H), 8.16 (s, 1H), 7.81 (d, J = 8.4 Hz, 2H), 7.63 (dd, J = 7.6, 6.6 Hz, 1H), 7.54 (t, J = 8.0 Hz, 1H), 7.42 (d, J = 1.6 Hz, 1H), 7.40 (s, 2H), 7.38 (s, 1H), 7.27-7.20 (m, 2H), 7.15 (s, 1H), 4.19 (s, 2H), 2.30 (s, 3H); MS (ES) 546.7 (M + H)$^+$; LCMS RT = 0.87 min. | +++ | Example 89 |
| 488 | 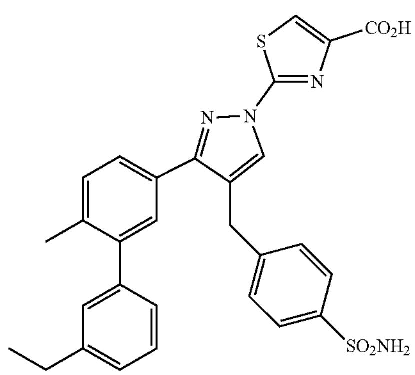 [SMILES: CCc1cccc(-c2cc(-c3nn(-c4nc(C(=O)O)cs4)cc3Cc3ccc(S(N)(=O)=O)cc3)ccc2C)c1] | 2-(3-(3'-ethyl-6-methyl-[1,1'-biphenyl]-3-yl)-4-(4-sulfamoylbenzyl)-1H-pyrazol-1-yl)thiazole-4-carboxylic acid; ; $^1$H-NMR (MeOD) δ 8.34 (s, 1H), 8.13 (s, 1H), 7.83 (d, J = 8.4 Hz, 2H), 7.59 (dd, J = 8.0, 2.0 Hz, 1H), 7.48 (d, J = 2.0 Hz, 1H), 7.41 (d, J = 8.0 Hz, 2H), 7.35 (d, J = 8.0 Hz, 2H), 7.23 (d, J = 8.0 Hz, 1H), 7.15 (s, 1H), 7.10 (d, J = 8.0 Hz, 1H), 4.20 (s, 2H), 2.73 (q, J = 8.0 Hz, 2H), 2.29 (s, 3H), 1.30 (t, J = 8.0 Hz, 3H); MS (ES) 559.4 (M + H)$^+$; LCMS RT = 1.28 min. | ++ | Example 90 |

TABLE 7-continued

| Cmpd ID | Structure | Compound name and physical data | Inhibitory activity IC$_{50}$ (μM) | Example Method |
|---|---|---|---|---|
| 489 | 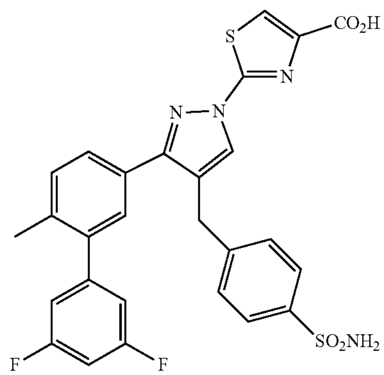 [SMILES: Cc1ccc(-c2nn(-c3nc(C(=O)O)cs3)cc2Cc2ccc(S(N)(=O)=O)cc2)cc1-c1cc(F)cc(F)c1] | 2-(3-(3',5'-difluoro-6-methyl-[1,1'-biphenyl]-3-yl)-4-(4-sulfamoylbenzyl)-1H-pyrazol-1-yl)thiazole-4-carboxylic acid; MS (ES) 569.6 (M + H)$^+$; LCMS RT = 1.24 min. | ++ | Example 91 |
| 490 | 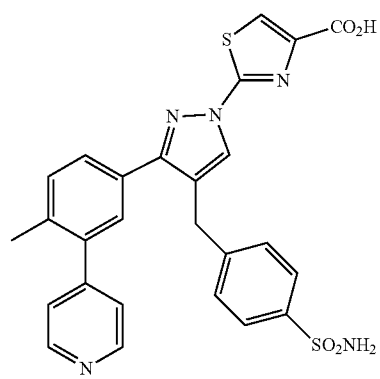 [SMILES: Cc1ccc(-c2nn(-c3nc(C(=O)O)cs3)cc2Cc2ccc(S(N)(=O)=O)cc2)cc1-c1ccncc1] | 2-(3-(4-methyl-3-(pyridin-4-yl)phenyl)-4-(4-sulfamoylbenzyl)-1H-pyrazol-1-yl)thiazole-4-carboxylic acid; ; $^1$H-NMR (MeOD) δ 8.80 (br s, 2H), 8.44 (s, 1H), 8.17 (s, 1H), 7.85-7.76 (m, 5H), 7.49 (d, J = 6.0 Hz, 1H), 7.41 (d, J = 2.0 Hz, 1H), 7.40 (s, 1H), 7.38 (s, 1H), 4.21 (s, 2H), 2.39 (s, 3H); MS (ES) 533.6 (M + H)$^+$; LCMS RT = 0.83 min. | ++ | Example 92 |
| 491 | 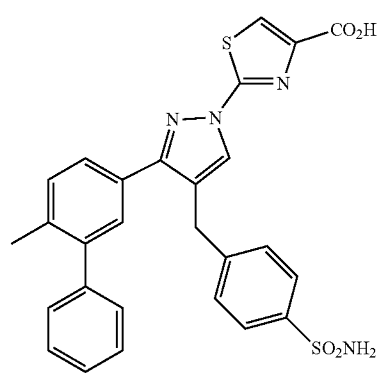 [SMILES: Cc1ccc(-c2nn(-c3nc(C(=O)O)cs3)cc2Cc2ccc(S(N)(=O)=O)cc2)cc1-c1ccccc1] | 2-(3-(6-methyl-[1,1'-biphenyl]-3-yl)-4-(4-sulfamoylbenzyl)-1H-pyrazol-1-yl)thiazole-4-carboxylic acid; ; $^1$H-NMR (MeOD) δ 8.34 (s, 1H), 8.14 (s, 1H), 7.89-7.82 (m, 2H), 7.83 (d, J = 8.4 Hz, 2H), 7.60 (dd, J = 8.0, 2.0 Hz, 1H), 7.54 (d, J = 8.0 Hz, 2H), 7.49-7.35 (m, 4H), 7.29 (d, J = 8.0 Hz, 2H), 4.20 (s, 2H), 2.30 (s, H); MS (ES) 531.6 (M + H)$^+$; LCMS RT = 1.18 min. | ++ | Example 93 |

TABLE 7-continued

| Cmpd ID | Structure | Compound name and physical data | Inhibitory activity IC$_{50}$ (μM) | Example Method |
|---|---|---|---|---|
| 492 | 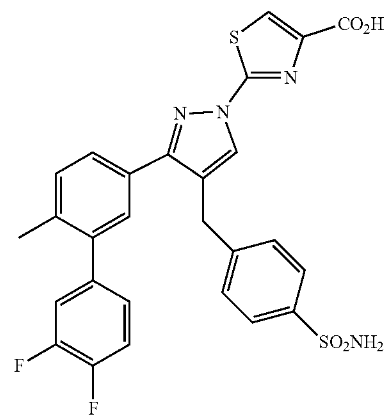 [SMILES: Cc1ccc(-c2nn(-c3nc(C(=O)O)cs3)cc2Cc2ccc(S(N)(=O)=O)cc2)cc1-c1ccc(F)c(F)c1] | 2-(3-(3',4'-difluoro-6-methyl-[1,1'-biphenyl]-3-yl)-4-(4-sulfamoylbenzyl)-1H-pyrazol-1-yl)thiazole-4-carboxylic acid; MS (ES) 567.9 (M + H)$^+$; LCMS RT = 1.20 min. | ++ | Example 94 |
| 493 | 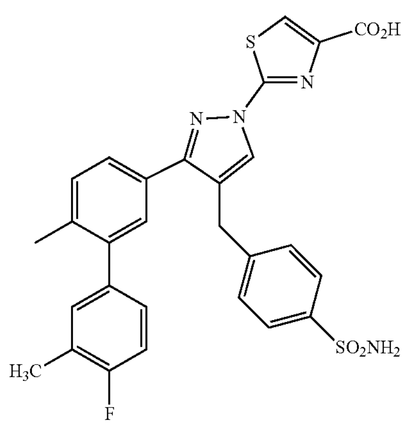 [SMILES: Cc1cc(-c2cc(-c3nn(-c4nc(C(=O)O)cs4)cc3Cc3ccc(S(N)(=O)=O)cc3)ccc2C)ccc1F] | 2-(3-(4'-fluoro-3',6-dimethyl-[1,1'-biphenyl]-3-yl)-4-(4-sulfamoylbenzyl)-1H-pyrazol-1-yl)thiazole-4-carboxylic acid; MS (ES) 563.9 (M + H)$^+$; LCMS RT = 1.25 min. | ++ | Example 95 |
| 494 | 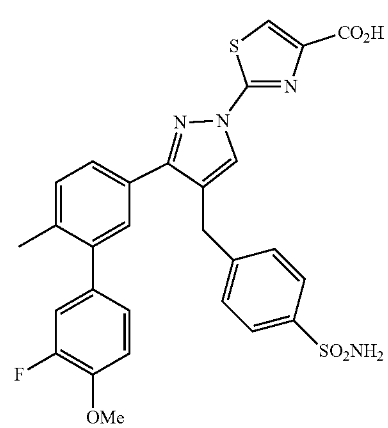 [SMILES: COc1ccc(-c2cc(-c3nn(-c4nc(C(=O)O)cs4)cc3Cc3ccc(S(N)(=O)=O)cc3)ccc2C)cc1F] | 2-(3-(3'-fluoro-4'-methoxy-6-methyl-[1,1'-biphenyl]-3-yl)-4-(4-sulfamoylbenzyl)-1H-pyrazol-1-yl)thiazole-4-carboxylic acid; MS (ES) 579.6 (M + H)$^+$; LCMS RT = 1.18 min. | ++ | Example 96 |

TABLE 7-continued

| Cmpd ID | Structure | Compound name and physical data | Inhibitory activity IC$_{50}$ (μM) | Example Method |
|---|---|---|---|---|
| 495 | 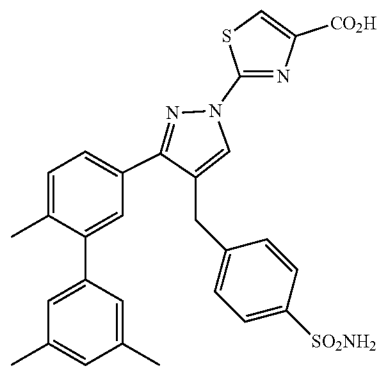 [SMILES: Cc1cc(C)cc(-c2cc(-c3nn(-c4nc(C(=O)O)cs4)cc3Cc3ccc(S(N)(=O)=O)cc3)ccc2C)c1] | 2-(4-(4-sulfamoylbenzyl)-3-(3',5',6-trimethyl-[1,1'-biphenyl]-3-yl)-1H-pyrazol-1-yl)thiazole-4-carboxylic acid; MS (ES) 559.9 (M + H)$^+$; LCMS RT = 1.29 min. | ++ | Example 97 |
| 496 | 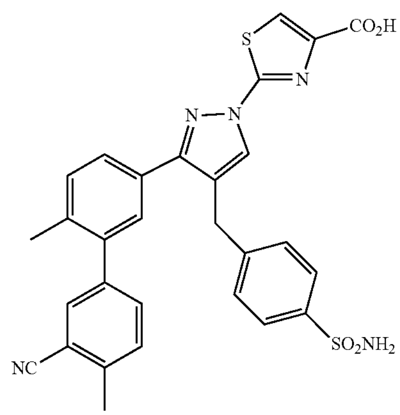 [SMILES: Cc1ccc(-c2cc(-c3nn(-c4nc(C(=O)O)cs4)cc3Cc3ccc(S(N)(=O)=O)cc3)ccc2C)cc1C#N] | 2-(3-(3'-cyano-4',6-dimethyl-[1,1'-biphenyl]-3-yl)-4-(4-sulfamoylbenzyl)-1H-pyrazol-1-yl)thiazole-4-carboxylic acid; MS (ES) 570.9 (M + H)$^+$; LCMS RT = 1.16 min. | ++ | Example 98 |
| 497 | 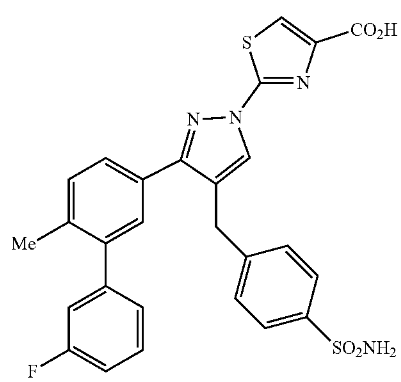 [SMILES: Cc1ccc(-c2nn(-c3nc(C(=O)O)cs3)cc2Cc2ccc(S(N)(=O)=O)cc2)cc1-c1cccc(F)c1] | 2-(3-(3'-fluoro-6-methyl-[1,1'-biphenyl]-3-yl)-4-(4-sulfamoylbenzyl)-1H-pyrazol-1-yl)thiazole-4-carboxylic acid; MS (ES) 549.6 (M + H)$^+$; LCMS RT = 1.18 min. | ++ | Example 99 |
| 498 | 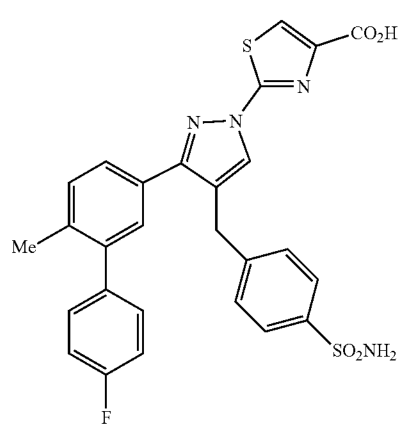 [SMILES: Cc1ccc(-c2nn(-c3nc(C(=O)O)cs3)cc2Cc2ccc(S(N)(=O)=O)cc2)cc1-c1ccc(F)cc1] | 2-(3-(4'-fluoro-6-methyl-[1,1'-biphenyl]-3-yl)-4-(4-sulfamoylbenzyl)-1H-pyrazol-1-yl)thiazole-4-carboxylic acid; MS (ES) 549.6 (M + H)$^+$; LCMS RT = 1.16 min. | ++ | Example 100 |

TABLE 7-continued

| Cmpd ID | Structure | Compound name and physical data | Inhibitory activity IC$_{50}$ (μM) | Example Method |
|---|---|---|---|---|
| 499 | 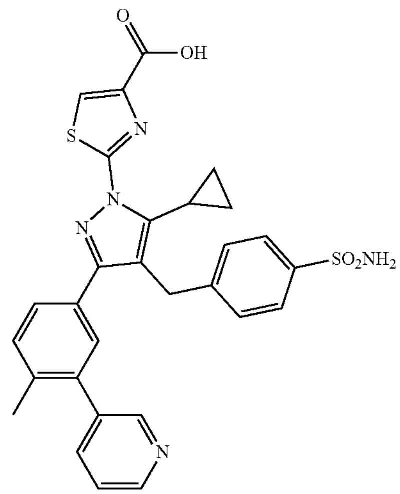 [SMILES: Cc1ccc(-c2nn(-c3nc(C(=O)O)cs3)c(C3CC3)c2Cc2ccc(S(N)(=O)=O)cc2)cc1-c1cccnc1] | 2-(5-cyclopropyl-3-(4-methyl-3-(pyridin-3-yl)phenyl)-4-(4-sulfamoylbenzyl)-1H-pyrazol-1-yl)thiazole-4-carboxylic acid; $^1$H-NMR (MeOD) δ 8.86 (d, J = 5.2 Hz, 1H), 8.83 (s, 1H), 8.45 (d, J = 8.4 Hz, 1H), 8.27 (s, 1H), 8.13 (dd, J = 8.0, 1.6 Hz, 1H), 7.76 (d, J = 8.4 Hz, 2H), 7.64 (dd, J = 8.0, 1.6 Hz, 1H), 7.43 (d, J = 8.0 Hz, 1H), 7.29 (s, 2H), 7.27 (s, 1H), 4.25 (s, 2H), 2.42-2.34 (m, 1H), 2.33 (s, 3H), 1.10 (dt, J = 8.4, 4.6 Hz, 2H), 0.69 (dt, J = 5.6, 4.6 Hz, 2H); MS (ES) 572.9 (M + H)$^+$; LCMS RT = 0.87 min. | +++ | Example 116 |
| 500 | 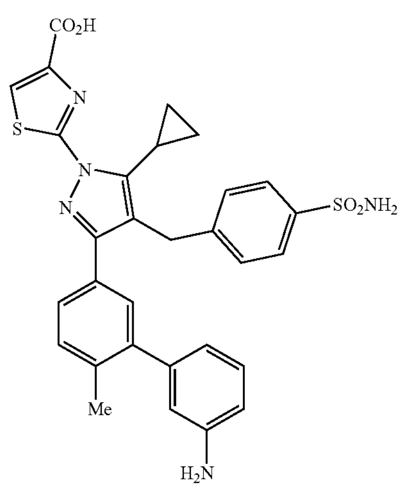 [SMILES: Cc1ccc(-c2nn(-c3nc(C(=O)O)cs3)c(C3CC3)c2Cc2ccc(S(N)(=O)=O)cc2)cc1-c1cccc(N)c1] | 2-(3-(3'-amino-6-methyl-[1,1'-biphenyl]-3-yl)-5-cyclopropyl-4-(4-sulfamoylbenzyl)-1H-pyrazol-1-yl)thiazole-4-carboxylic acid; ; $^1$H-NMR (MeOD) δ 8.26 (s, 1H), 7.78 (d, J = 8.4 Hz, 2H), 7.53 (t, J = 8.0 Hz, 1H), 7.49 (dd, J = 8.0, 1.6 Hz, 1H), 7.32 (d, J = 8.0 Hz, 1H), 7.29 (s, 1H), 7.27 (s, 3H), 7.18 (d, J = 8.0 Hz, 1H), 7.13 (s, 1H), 4.23 (s, 2H), 2.41-2.33 (m, 1H), 2.27 (s, 3H), 1.08 (dt, J = 8.4, 6.4 Hz, 2H), 0.67 (dt, J = 5.6, 4.6 Hz, 2H); MS (ES) 586.9 (M + H)$^+$; LCMS RT = 0.92 min. | +++ | Example 117 |

TABLE 7-continued

| Cmpd ID | Structure | Compound name and physical data | Inhibitory activity IC$_{50}$ (μM) | Example Method |
|---|---|---|---|---|
| 501 | 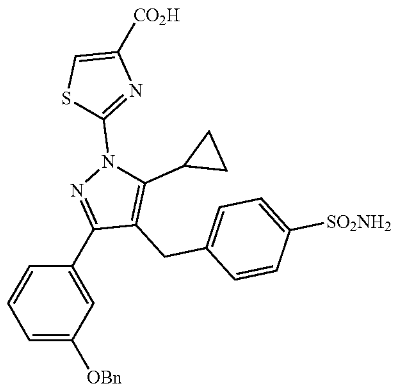 [SMILES: NS(=O)(=O)c1ccc(Cc2c(-c3cccc(OCc4ccccc4)c3)nn(-c3nc(C(=O)O)cs3)c2C2CC2)cc1] | 2-(3-(3-(benzyloxy)phenyl)-5-cyclopropyl-4-(4-sulfamoylbenzyl)-1H-pyrazol-1-yl)thiazole-4-carboxylic acid; $^1$H-NMR (MeOD) δ 8.24 (s, 1H), 7.81 (d, J = 8.4 Hz, 2H), 7.40-7.34 (m, 4H), 7.31-7.22 (m, 4H), 7.14-7.09 (m, 2H), 6.99 (dd, J = 8.0, 2.0 Hz, 1H), 4.96 (s, 2H), 4.16 (s, 2H), 2.37-2.28 (m, 1H), 1.04 (dt, J = 8.4, 6.4 Hz, 2H), 0.63 (dt, J = 5.6, 4.8 Hz, 2H); MS (ES) 586.9 (M + H)$^+$; LCMS RT = 0.92 min. | +++ | Example 118 |
| 502 | 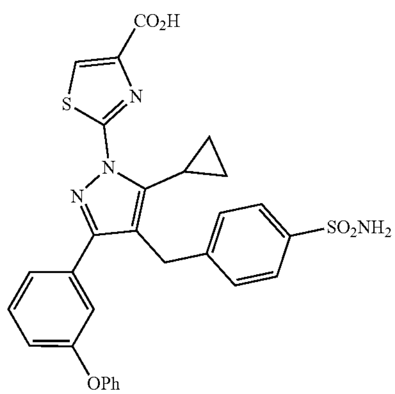 [SMILES: NS(=O)(=O)c1ccc(Cc2c(-c3cccc(Oc4ccccc4)c3)nn(-c3nc(C(=O)O)cs3)c2C2CC2)cc1] | 2-(5-cyclopropyl-3-(3-phenoxyphenyl)-4-(4-sulfamoylbenzyl)-1H-pyrazol-1-yl)thiazole-4-carboxylic acid; $^1$H-NMR (MeOD) δ 8.24 (s, 1H), 7.76 (d, J = 8.4 Hz, 2H), 7.40-7.31 (m, 4H), 7.19 (d, J = 8.4 Hz, 2H), 7.13 (t, J = 8.4 Hz, 1H), 7.07 (s, 1H), 7.00 (dd, J = 8.0, 1.6 Hz, 1H), 6.93 (d, J = 8.0 Hz, 2H), 4.15 (s, 2H), 2.37-2.29 (m, 1H), 1.03 (dt, J = 8.4, 6.4 Hz, 2H), 0.62 (dt, J = 5.6, 4.8 Hz, 2H); MS (ES) 573.6 (M + H)$^+$; LCMS RT = 0.94 min. | +++ | Example 119 |
| 503 | 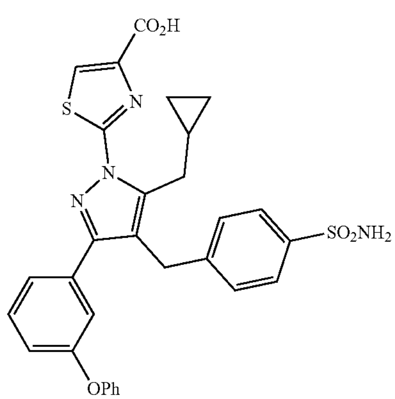 [SMILES: NS(=O)(=O)c1ccc(Cc2c(-c3cccc(Oc4ccccc4)c3)nn(-c3nc(C(=O)O)cs3)c2CC2CC2)cc1] | 2-(5-(cyclopropylmethyl)-3-(3-phenoxyphenyl)-4-(4-sulfamoylbenzyl)-1H-pyrazol-1-yl)thiazole-4-carboxylic acid; $^1$H-NMR (MeOD) δ 8.19 (s, 1H), 7.75 (d, J = 8.4 Hz, 2H), 7.38-7.31 (m, 4H), 7.20 (d, J = 8.4 Hz, 2H), 7.15-7.10 (m, 2H), 7.02-6.97 (m, 1H), 7.00 (dd, J = 8.0, 1.2 Hz, 2H), 4.10 (s, 2H), 3.22 (d, J = 6.8 Hz, 2H), 1.12-1.06 (m, 1H), 0.39-0.33 (m, 2H), 0.21 (dt, J = 6.0, 5.2 Hz, 2H); MS (ES) 587.7 (M + H)$^+$; LCMS RT = 1.00 min. | +++ | Example 129 |

TABLE 7-continued

| Cmpd ID | Structure | Compound name and physical data | Inhibitory activity IC$_{50}$ (μM) | Example Method |
|---|---|---|---|---|
| 504 | 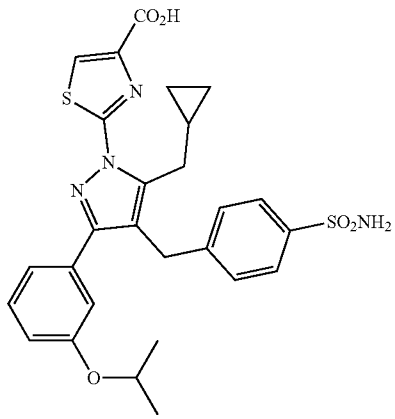 [SMILES: CC(C)Oc1cccc(-c2nn(-c3nc(C(=O)O)cs3)c(CC3CC3)c2Cc2ccc(S(N)(=O)=O)cc2)c1] | 2-(5-(cyclopropylmethyl)-3-(3-isopropoxyphenyl)-4-(4-sulfamoylbenzyl)-1H-pyrazol-1-yl)thiazole-4-carboxylic acid; MS (ES) 552.6 (M + H)$^+$; LCMS RT = 0.98 min. | +++ | Example 130 |
| 505 | 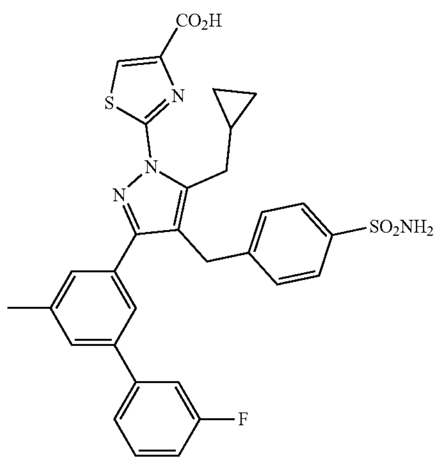 [SMILES: Cc1cc(-c2cccc(F)c2)cc(-c2nn(-c3nc(C(=O)O)cs3)c(CC3CC3)c2Cc2ccc(S(N)(=O)=O)cc2)c1] | 2-(5-(cyclopropylmethyl)-3-(3'-fluoro-5-methyl-[1,1'-biphenyl]-3-yl)-4-(4-sulfamoylbenzyl)-1H-pyrazol-1-yl)thiazole-4-carboxylic acid; MS (ES) 603.7 (M + H)$^+$; LCMS RT = 1.26 min. | +++ | Example 141 |
| 506 | 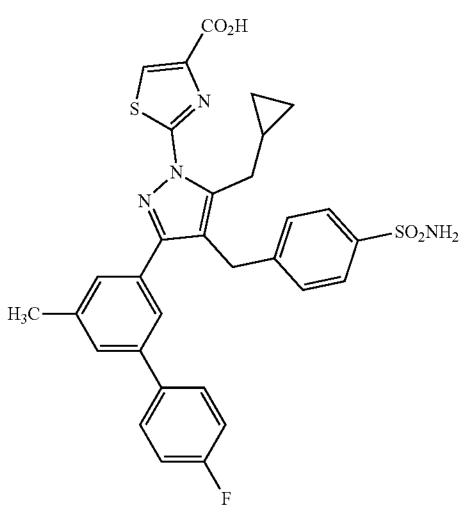 [SMILES: Cc1cc(-c2ccc(F)cc2)cc(-c2nn(-c3nc(C(=O)O)cs3)c(CC3CC3)c2Cc2ccc(S(N)(=O)=O)cc2)c1] | 2-(5-(cyclopropylmethyl)-3-(4'-fluoro-5-methyl-[1,1'-biphenyl]-3-yl)-4-(4-sulfamoylbenzyl)-1H-pyrazol-1-yl)thiazole-4-carboxylic acid; MS (ES) 603.4 (M + H)$^+$; LCMS RT = 1.26 min. | +++ | Example 142 |

TABLE 7-continued

| Cmpd ID | Structure | Compound name and physical data | Inhibitory activity IC$_{50}$ (μM) | Example Method |
|---|---|---|---|---|
| 507 | 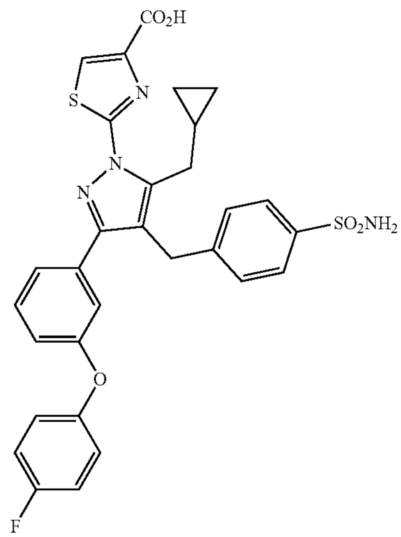 [SMILES: NS(=O)(=O)c1ccc(Cc2c(-c3cccc(Oc4ccc(F)cc4)c3)nn(-c3nc(C(=O)O)cs3)c2CC2CC2)cc1] | 2-(5-(cyclopropylmethyl)-3-(3-(4-fluorophenoxy)phenyl)-4-(4-sulfamoylbenzyl)-1H-pyrazol-1-yl)thiazole-4-carboxylic acid; $^1$H-NMR (MeOD) δ (ppm) 8.14 (s, 1H), 7.78 (d, J = 8.4 Hz, 2H), 7.40 (t, J = 8.0 Hz, 1H), 7.23 (d, J = 8.4 Hz, 2H), 7.10-7.04 (m, 2H), 7.01-6.96 (m, 4H), 6.84 (t, J = 2.0 Hz, 1H), 3.92 (s, 2H), 2.46 (d, J = 7.2 Hz, 2H), 1.00-0.90 (m, 1H), 0.44 (ddd, J = 8.4, 6.0, 4.4 Hz, 2H), 0.13 (dd, J = 10.0, 4.4 Hz, 2H); MS (ES) 605.2 (M + H)$^+$; LCMS RT = 1.20 min. | +++ | Example 134 |
| 508 | 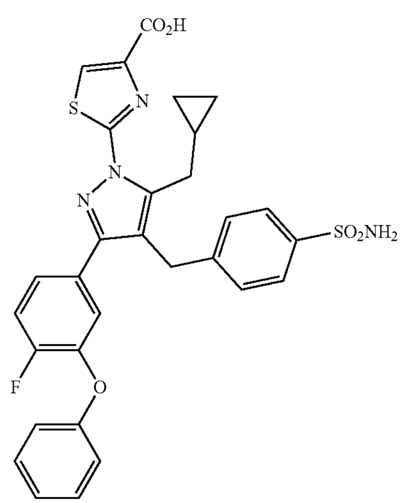 [SMILES: NS(=O)(=O)c1ccc(Cc2c(-c3ccc(F)c(Oc4ccccc4)c3)nn(-c3nc(C(=O)O)cs3)c2CC2CC2)cc1] | 2-(5-(cyclopropylmethyl)-3-(4-fluoro-3-phenoxyphenyl)-4-(4-sulfamoylbenzyl)-1H-pyrazol-1-yl)thiazole-4-carboxylic acid; $^1$H-NMR (d6-DMSO) δ 7.63 (d, J = 8.4 Hz, 2H), 7.42-7.33 (m, 4H), 7.23 (s, 2H), 7.25 (d, J = 8.8 Hz, 1H), 7.14 (d, J = 8.4 Hz, 2H), 6.90 (d, J = 7.6 Hz, 2H), 4.06 (s, 2H), 3.12 (d, J = 6.8 Hz, 2H), 0.87-0.80 (m, 1H), 0.30 (ddd, J = 10.0, 6.0, 4.4 Hz, 2H), 0.13 (dd, J = 10.0, 5.2 Hz, 2H); MS (ES) 605.2 (M + H)$^+$; LCMS RT = 1.18 min. | +++ | Example 135 |

TABLE 7-continued

| Cmpd ID | Structure | Compound name and physical data | Inhibitory activity IC$_{50}$ (μM) | Example Method |
|---|---|---|---|---|
| 509 | 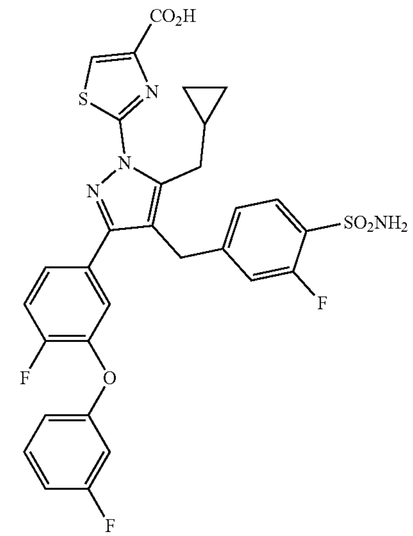 [SMILES: NS(=O)(=O)c1ccc(Cc2c(-c3ccc(F)c(Oc4cccc(F)c4)c3)nn(-c3nc(C(=O)O)cs3)c2CC2CC2)cc1F] | 2-(5-(cyclopropylmethyl)-3-(4-fluoro-3-(3-fluorophenoxy)phenyl)-4-(3-fluoro-4-sulfamoylbenzyl)-1H-pyrazol-1-yl)thiazole-4-carboxylic acid; ; $^1$H-NMR (MeOD) δ 8.20 (s, 1H), 7.72 (t, J = 8.0 Hz, 1H), 7.50-7.46 (m, 1H), 7.37-7.25 (m, 3H), 6.99 (s, 1H), 6.98 (d, J = 16.8 Hz, 1H), 6.88 (dt, J = 8.4, 2.0 Hz, 1H), 6.73 (dt, J = 10.0, 2.0 Hz, 1H), 6.66 (dd, J = 8.4, 2.4 Hz, 1H), 4.13 (s, 2H), 3.24 (d, J = 6.8 Hz, 2H), 1.13-1.05 (m, 1H), 0.44 (ddd, J = 8.0, 5.6, 4.0 Hz, 2H), 0.22 (dd, J = 10.4, 5.2 Hz, 2H); MS (ES) 640.9 (M + H)$^+$; LCMS RT = 1.19 min. | +++ | Example 136 |
| 510 | 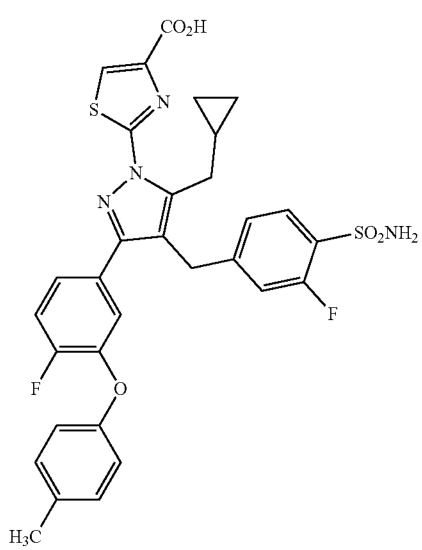 [SMILES: Cc1ccc(Oc2cc(-c3nn(-c4nc(C(=O)O)cs4)c(CC4CC4)c3Cc3ccc(S(N)(=O)=O)c(F)c3)ccc2F)cc1] | 2-(5-(cyclopropylmethyl)-3-(4-fluoro-3-(p-tolyloxy)phenyl)-4-(3-fluoro-4-sulfamoylbenzyl)-1H-pyrazol-1-yl)thiazole-4-carboxylic acid; $^1$H-NMR (MeOD) δ 8.19 (s, 1H), 7.70 (t, J = 8.4 Hz, 1H), 7.44-7.40 (m, 1H), 7.25 (dd, J = 10.8, 8.8 Hz, 1H), 7.17-7.12 (m, 3H), 6.93 (s, 1H), 6.92 (d, J = 17.6 Hz, 1H), 6.88 (d, J = 8.4 Hz, 2H), 4.07 (s, 2H), 3.22 (d, J = 6.8 Hz, 2H), 1.11-1.04 (m, 1H), 0.37 (ddd, J = 8.0, 6.0, 4.8 Hz, 2H), 0.21 (dd, J = 10.4, 5.2 Hz, 2H); MS (ES) 636.9 (M + H)$^+$; LCMS RT = 1.12 min. | +++ | Example 137 |

| Cmpd ID | Structure | Compound name and physical data | Inhibitory activity IC$_{50}$ (μM) | Example Method |
|---|---|---|---|---|
| 511 | 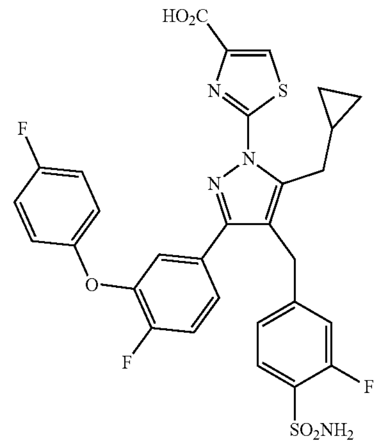 [SMILES: NS(=O)(=O)c1ccc(Cc2c(-c3ccc(F)c(Oc4ccc(F)cc4)c3)nn(-c3nc(C(=O)O)cs3)c2CC2CC2)cc1F] | 2-(5-(cyclopropylmethyl)-3-(4-fluoro-3-(4-fluorophenoxy)phenyl)-4-(3-fluoro-4-sulfamoylbenzyl)-1H-pyrazol-1-yl)thiazole-4-carboxylic acid; $^1$H-NMR (MeOD): δ 8.19 (s, 1H), 7.71 (t, J = 8.8 Hz, 1H), 7.45-7.41 (m, 1H), 7.26 (dd, J = 8.8, 11.0 Hz, 1H), 7.15 (dd, J = 2.2, 7.9 Hz, 1H), 7.09 (dd, J = 8.5, 9.0 Hz, 2H), 6.98-6.89 (m, 4H), 4.09 (s, 2H), 3.23 (d, J = 7.05 Hz, 2H), 1.13-1.04 (m, 1H), 0.40-0.35 (m, 2H), 0.23-0.19 (m, 2H); MS (ES) 641.0 (M + H)$^+$; LCMS RT = 1.18 min. | +++ | Example 138 |
| 512 | 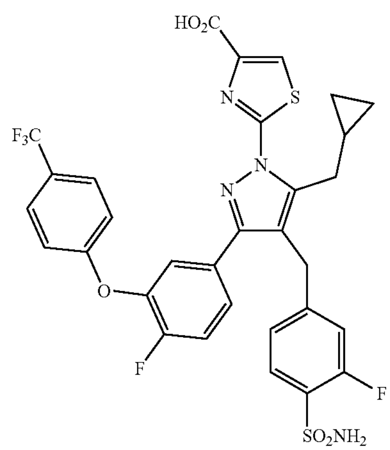 [SMILES: NS(=O)(=O)c1ccc(Cc2c(-c3ccc(F)c(Oc4ccc(C(F)(F)F)cc4)c3)nn(-c3nc(C(=O)O)cs3)c2CC2CC2)cc1F] | 2-(5-(cyclopropylmethyl)-3-(4-fluoro-3-(4-(trifluoromethyl)phenoxy)phenyl)-4-(3-fluoro-4-sulfamoylbenzyl)-1H-pyrazol-1-yl)thiazole-4-carboxylic acid; $^1$H-NMR (MeOD) δ 8.28 (s, 1H), 7.73-7.67 (m, 3H), 7.52-7.48 (m, 1H), 7.38 (dd, J = 2.1, 7.6 Hz, 1H), 7.30 (dd, J = 8.5, 10.5 Hz, 1H), 7.03-6.96 (m, 4H), 4.16 (s, 2H), 3.27 (d, J = 6.8 Hz, 2H), 1.18-1.08 (m, 1H), 0.42-0.38 (m, 2H), 0.26-0.23 (m, 2H); MS (ES) 691.0 (M + H)$^+$; LCMS RT = 1.24 min. | +++ | Example 139 |
| 513 | 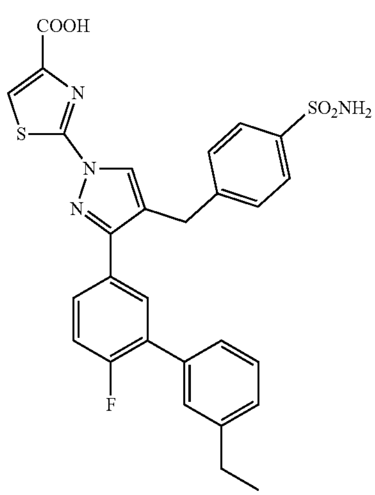 [SMILES: CCc1cccc(-c2cc(-c3nn(-c4nc(C(=O)O)cs4)cc3Cc3ccc(S(N)(=O)=O)cc3)ccc2F)c1] | 2-(3-(3'-ethyl-6-fluoro-[1,1'-biphenyl]-3-yl)-4-(4-sulfamoylbenzyl)-1H-pyrazol-1-yl)thiazole-4-carboxylic acid; $^1$H-NMR (MeOD) δ 8.37 (s, 1H), 8.17 (s, 1H), 7.86 (d, J = 8.24 Hz, 2H), 7.77 (d, J = 6.4 Hz, 2H), 7.44 (d, J = 8.2 Hz, 2H), 7.33 (t, J = 9.62 Hz, 1H), 7.16 (d, J = 7.79 Hz, 2H), 7.03 (m, 1H), 4.23 (s, 2H), 3.63 (q, J = 7.1, 14.2 Hz, 2H), 1.20 (t, J = 7.1 Hz, 3H); MS (ES) 562.9 (M + H)$^+$; LCMS RT = 1.24 min. | ++ | Example 101 |

TABLE 7-continued

| Cmpd ID | Structure | Compound name and physical data | Inhibitory activity IC$_{50}$ (μM) | Example Method |
|---|---|---|---|---|
| 514 | 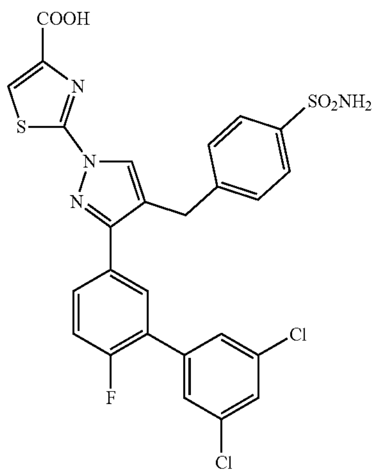 [SMILES: NS(=O)(=O)c1ccc(Cc2cn(-c3nc(C(=O)O)cs3)nc2-c2ccc(F)c(-c3cc(Cl)cc(Cl)c3)c2)cc1] | 2-(3-(3',5'-dichloro-6-fluoro-[1,1'-biphenyl]-3-yl)-4-(4-sulfamoylbenzyl)-1H-pyrazol-1-yl)thiazole-4-carboxylic acid; $^1$H-NMR (MeOD) δ 8.36 (s, 1H), 8.16 (s, 1H), 7.87 (d, J = 6.4 Hz, 2H), 7.81 (m, 2H), 7.75 (d, J = 8.1 Hz, 2H), 7.46 (M, 2H), 7.34 (m, 2H), 4.24 (s, 2H); MS (ES) 602.9 (M + H)$^+$; LCMS RT = 1.30 min. | + | Example 102 |
| 515 | 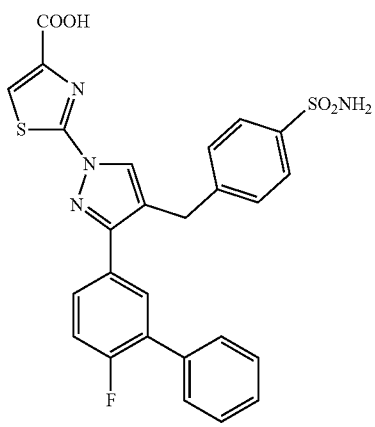 [SMILES: NS(=O)(=O)c1ccc(Cc2cn(-c3nc(C(=O)O)cs3)nc2-c2ccc(F)c(-c3ccccc3)c2)cc1] | 2-(3-(6-fluoro-[1,1'-biphenyl]-3-yl)-4-(4-sulfamoylbenzyl)-1H-pyrazol-1-yl)thiazole-4-carboxylic acid; MS (ES) 544.0 (M + H)$^+$; LCMS RT = 1.18 min. | +++ | Example 103 |
| 516 | 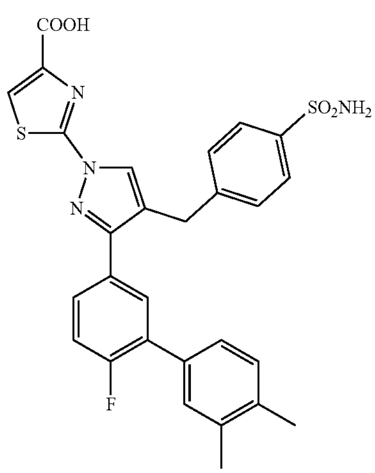 [SMILES: Cc1ccc(-c2cc(-c3nn(-c4nc(C(=O)O)cs4)cc3Cc3ccc(S(N)(=O)=O)cc3)ccc2F)cc1C] | 2-(3-(6-fluoro-3',4'-dimethyl-[1,1'-biphenyl]-3-yl)-4-(4-sulfamoylbenzyl)-1H-pyrazol-1-yl)thiazole-4-carboxylic acid; MS (ES) 562.9 (M + H)$^+$; LCMS RT = 1.23 min. | ++ | Example 104 |

TABLE 7-continued

| Cmpd ID | Structure | Compound name and physical data | Inhibitory activity IC$_{50}$ (μM) | Example Method |
|---|---|---|---|---|
| 517 | 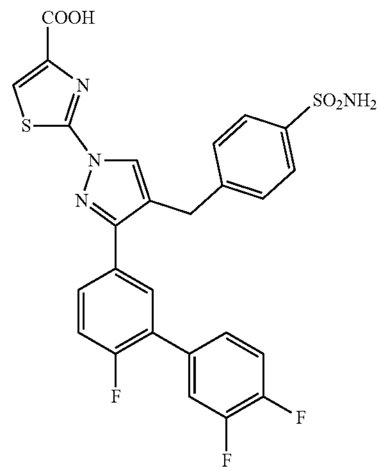 [SMILES: NS(=O)(=O)c1ccc(Cc2cn(-c3nc(C(=O)O)cs3)nc2-c2ccc(F)c(-c3ccc(F)c(F)c3)c2)cc1] | 2-(4-(4-sulfamoylbenzyl)-3-(3',4',6-trifluoro-[1,1'-biphenyl]-3-yl)-1H-pyrazol-1-yl)thiazole-4-carboxylic acid; MS (ES) 571.0 (M + H)$^+$; LCMS RT = 1.18 min. | ++ | Example 105 |
| 518 | 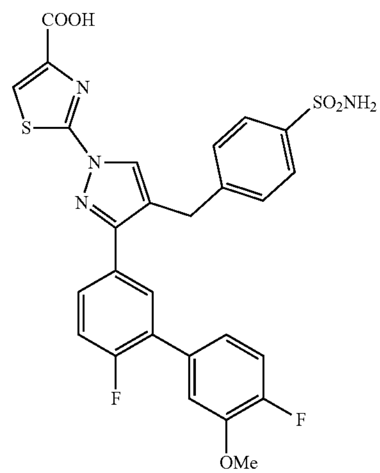 [SMILES: COc1cc(-c2cc(-c3nn(-c4nc(C(=O)O)cs4)cc3Cc3ccc(S(N)(=O)=O)cc3)ccc2F)ccc1F] | 2-(3-(4',6-difluoro-3'-methoxy-[1,1'-biphenyl]-3-yl)-4-(4-sulfamoylbenzyl)-1H-pyrazol-1-yl)thiazole-4-carboxylic acid; MS (ES) 582.9 (M + H)$^+$; LCMS RT = 1.14 min. | +++ | Example 106 |
| 519 | 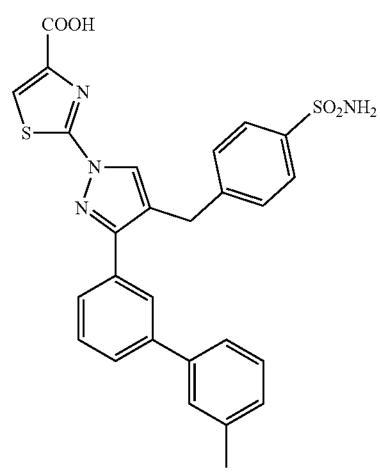 [SMILES: Cc1cccc(-c2cccc(-c3nn(-c4nc(C(=O)O)cs4)cc3Cc3ccc(S(N)(=O)=O)cc3)c2)c1] | 2-(3-(3'-methyl-[1,1'-biphenyl]-3-yl)-4-(4-sulfamoylbenzyl)-1H-pyrazol-1-yl)thiazole-4-carboxylic acid; MS (ES) 530.9 (M + H)$^+$; LCMS RT = 1.00 min. | +++ | Example 107 |

TABLE 7-continued

| Cmpd ID | Structure | Compound name and physical data | Inhibitory activity IC$_{50}$ (μM) | Example Method |
|---|---|---|---|---|
| 520 | 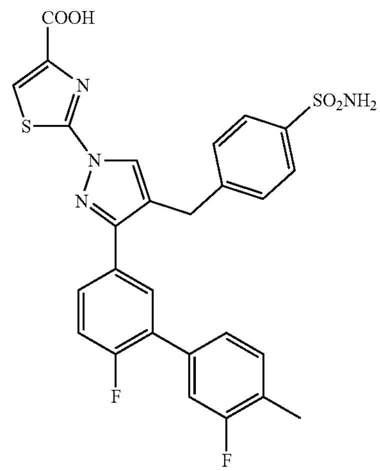 [SMILES: Cc1ccc(-c2cc(-c3nn(-c4nc(C(=O)O)cs4)cc3Cc3ccc(S(N)(=O)=O)cc3)ccc2F)cc1F] | 2-(3-(3',6-difluoro-4'-methyl-[1,1'-biphenyl]-3-yl)-4-(4-sulfamoylbenzyl)-1H-pyrazol-1-yl)thiazole-4-carboxylic acid; MS (ES) 566.9 (M + H)$^+$; LCMS RT = 1.22 min. | ++ | Example 108 |
| 521 | 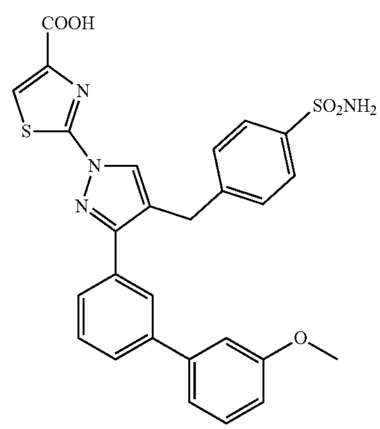 [SMILES: COc1cccc(-c2cccc(-c3nn(-c4nc(C(=O)O)cs4)cc3Cc3ccc(S(N)(=O)=O)cc3)c2)c1] | 2-(3-(3'-methoxy-[1,1'-biphenyl]-3-yl)-4-(4-sulfamoylbenzyl)-1H-pyrazol-1-yl)thiazole-4-carboxylic acid; MS (ES) 546.9 (M + H)$^+$; LCMS RT = 0.89 min. | +++ | Example 109 |
| 522 | 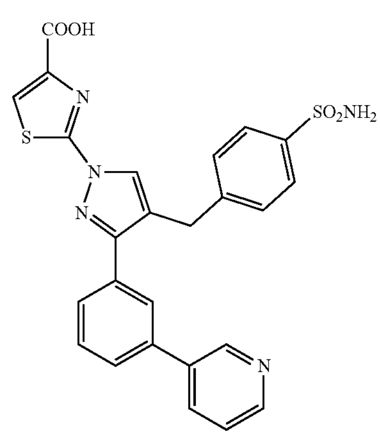 [SMILES: NS(=O)(=O)c1ccc(Cc2cn(-c3nc(C(=O)O)cs3)nc2-c2cccc(-c3cccnc3)c2)cc1] | 2-(3-(3-(pyridin-3-yl)phenyl)-4-(4-sulfamoylbenzyl)-1H-pyrazol-1-yl)thiazole-4-carboxylic acid; MS (ES) 517.9 (M + H)$^+$; LCMS RT = 0.82 min. | ++ | Example 110 |

TABLE 7-continued

| Cmpd ID | Structure | Compound name and physical data | Inhibitory activity IC$_{50}$ (μM) | Example Method |
|---|---|---|---|---|
| 523 | 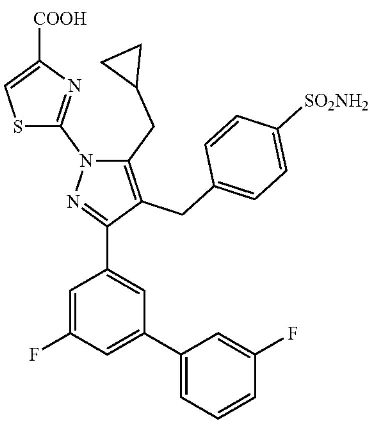 [SMILES: NS(=O)(=O)c1ccc(Cc2c(-c3cc(F)cc(-c4cccc(F)c4)c3)nn(-c3nc(C(=O)O)cs3)c2CC2CC2)cc1] | 2-(5-(cyclopropylmethyl)-3-(3',5-difluoro-[1,1'-biphenyl]-3-yl)-4-(4-sulfamoylbenzyl)-1H-pyrazol-1-yl)thiazole-4-carboxylic acid; MS (ES) 607.0 (M + H)$^+$; LCMS RT = 1.10 min. | ++ | |
| 524 | 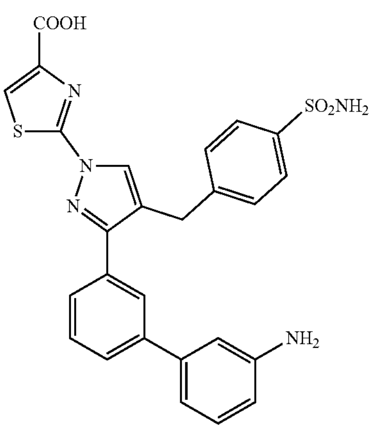 [SMILES: Nc1cccc(-c2cccc(-c3nn(-c4nc(C(=O)O)cs4)cc3Cc3ccc(S(N)(=O)=O)cc3)c2)c1] | 2-(3-(3'-amino-[1,1'-biphenyl]-3-yl)-4-(4-sulfamoylbenzyl)-1H-pyrazol-1-yl)thiazole-4-carboxylic acid; MS (ES) 532.0 (M + H)$^+$; LCMS RT = 0.70 min. | ++ | Example 111 |
| 525 | 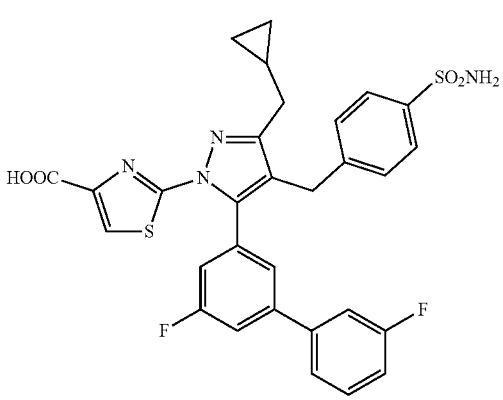 [SMILES: NS(=O)(=O)c1ccc(Cc2c(CC3CC3)nn(-c3nc(C(=O)O)cs3)c2-c2cc(F)cc(-c3cccc(F)c3)c2)cc1] | 4-((3-(cyclopropylmethyl)-5-(3',5-difluoro-[1,1'-biphenyl]-3-yl)-1-(4-((oxo-l3-methyl)-l3-oxidanyl)thiazol-2-yl)-1H-pyrazol-4-yl)methyl)benzenesulfonamide; $^1$H-NMR (CDCl$_3$) δ 7.96 (s, 1H), 7.84 (d, J = 8.4 Hz, 2H), 7.39 (m, 2H), 7.24 (m, 4H) 7.06 (m, 4H), 3.93 (s, 2H) 2.53 (d, J = 6.8 Hz, 2H), 1.05 (m, 1H), 0.55 (m, 2H), 0.22 (d, J = 5.8 Hz, 2H); MS (ES) 607.0 (M + H)$^+$; LCMS RT = 0.95 min. | + | Example 133 |

TABLE 7-continued

| Cmpd ID | Structure | Compound name and physical data | Inhibitory activity IC$_{50}$ (μM) | Example Method |
|---|---|---|---|---|
| 526 | 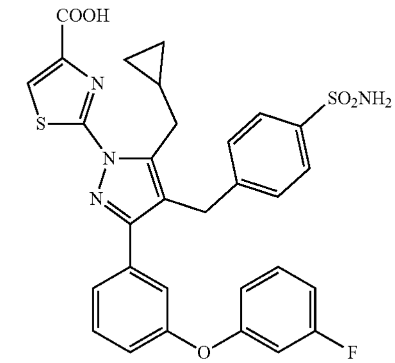 [SMILES: NS(=O)(=O)c1ccc(Cc2c(-c3cccc(Oc4cccc(F)c4)c3)nn(-c3nc(C(=O)O)cs3)c2CC2CC2)cc1] | 2-(5-(cyclopropylmethyl)-3-(3-(3-fluorophenoxy)phenyl)-4-(4-sulfamoylbenzyl)-1H-pyrazol-1-yl)thiazole-4-carboxylic acid; $^1$H-NMR (MeOD) δ 7.89 (s, 1H), 7.75 (d, J = 8.4 Hz, 2H), 7.42 (m, 2H), 7.34 (m, 2H), 7.23 (d, J = 8.4 Hz, 2H), 7.12 (m, 1H) 8.87 (m, 2H), 6.70 (m, 2H), 4.13 (s, 2H), 3.25 (d, J = 6.7 Hz, 2H), 0.32 (d, J = 8.2 Hz, 2H), 0.12 (d, J = 4.39 Hz, 2H); MS (ES) 605.2 (M + H)$^+$; LCMS RT = 1.21 min. | ++ | Example 140 |
| 527 | 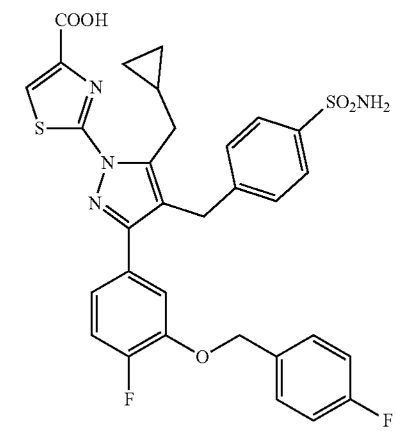 [SMILES: NS(=O)(=O)c1ccc(Cc2c(-c3ccc(F)c(OCc4ccc(F)cc4)c3)nn(-c3nc(C(=O)O)cs3)c2CC2CC2)cc1] | 2-(5-(cyclopropylmethyl)-3-(4-fluoro-3-((4-fluorobenzyl)oxy)phenyl)-4-(4-sulfamoylbenzyl)-1H-pyrazol-1-yl)thiazole-4-carboxylic acid; $^1$H-NMR (MeOD) δ 8.21 (s, 1H), 7.83 (d, J = 8.4 Hz, 2H), 7.40 (m, 2H), 7.31 (d, J = 8.3 Hz, 2H), 7.23 (m, 1H), 7.17 (m, 1H), 7.107 (m, 3H), 4.96 (s, 2H), 4.13 (s, 2H), 3.25 (d, J = 6.83 Hz, 2H), 1.12 (m, 1H), 0.38 (d, J = 8.1 Hz, 2H), 0.23 (d, J = 5.1 Hz, 2H); MS (ES) 636.9 (M + H)$^+$; LCMS RT = 1.12 min. | +++ | Example 131 |
| 528 | 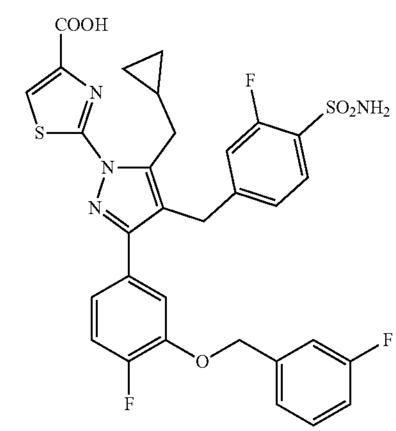 [SMILES: NS(=O)(=O)c1ccc(Cc2c(-c3ccc(F)c(OCc4cccc(F)c4)c3)nn(-c3nc(C(=O)O)cs3)c2CC2CC2)cc1F] | 2-(5-(cyclopropylmethyl)-3-(4-fluoro-3-((3-fluorobenzyl)oxy)phenyl)-4-(3-fluoro-4-sulfamoylbenzyl)-1H-pyrazol-1-yl)thiazole-4-carboxylic acid; $^1$H-NMR (MeOD) δ 8.19 (s, 1H), 7.77 (t, J = 7.7 Hz, 1H), 7.40 (m, 1H), 7.23 (m, 3H), 7.16 (m, 2H), 7.04 (m, 3H), 5.08 (s, 2H), 4.11 (s, 2H), 3.25 (d, J = 6.5 Hz), 1.11 (m, 1H), 0.39 (d, J = 7.8 Hz), 0.23 (d, J = 4.6 Hz); MS (ES) 655.0 (M + H)$^+$; LCMS RT = 1.19 min. | +++ | Example 132 |

TABLE 7-continued

| Cmpd ID | Structure | Compound name and physical data | Inhibitory activity IC$_{50}$ (μM) | Example Method |
|---|---|---|---|---|
| 529 | 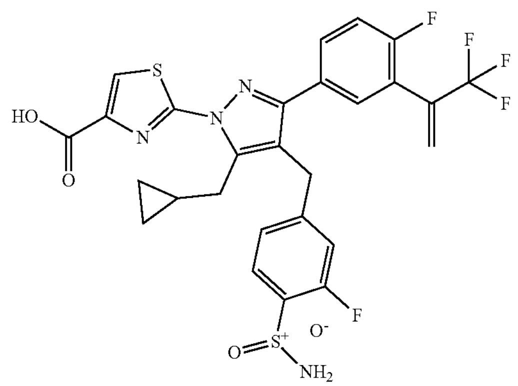 | 2-(3-(3,4-difluorophenyl)-1H-pyrazolo[3,4-b]pyridin-1-yl)thiazole-4-carboxylic acid, 1H NMR (400 MHz, DMSO-d6) δ 13.18 (s, 1H), 8.24 (s, 1H), 7.70-7.59 (m, 2H), 7.57 (s, 2H), 7.49 (dd, J = 7.2, 2.3 Hz, 1H), 7.37 (dd, J = 10.0, 8.6 Hz, 1H), 7.10 (dd, J = 11.3, 1.6 Hz, 1H), 7.01 (dd, J = 8.1, 1.6 Hz, 1H), 6.30 (dt, J = 2.1, 1.0 Hz, 1H), 5.95 (s, 1H), 4.12 (s, 2H), 3.15 (d, J = 6.9 Hz, 2H), 1.18-0.99 (m, 0H), 0.38-0.27 (m, 2H), 0.25-0.15 (m, 2H); MS (M + H)+ = 625 | +++ | 145 |
| 530 | 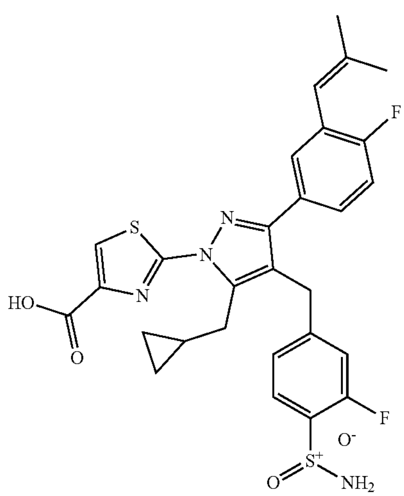 | 2-(5-(cyclopropylmethyl)-3-(4-fluoro-3-(2-methylprop-1-en-1-yl)phenyl)-4-(3-fluoro-4-sulfamoylbenzyl)-1H-pyrazol-1-yl)thiazole-4-carboxylic acid; 1H NMR (400 MHz, DMSO-d6) δ 13.14 (s, 1H), 8.26 (s, 1H), 7.64 (t, J = 7.9 Hz, 1H), 7.56 (s, 2H), 7.45 (ddd, J = 8.4, 5.0, 2.3 Hz, 1H), 7.34 (dd, J = 7.5, 2.2 Hz, 1H), 7.21 (dd, J = 10.0, 8.5 Hz, 1H), 7.14-6.99 (m, 2H), 6.23-6.09 (m, 1H), 4.11 (s, 2H), 3.13 (d, J = 6.9 Hz, 2H), 1.85 (d, J = 1.4 Hz, 3H), 1.54 (t, J = 1.1 Hz, 3H), 1.18-1.04 (m, 1H), 0.36-0.27 (m, 2H), 0.24-0.15 (m, 2H); MS (M + H)+ = 585 | +++ | 145 |

| Cmpd ID | Structure | Compound name and physical data | Inhibitory activity IC$_{50}$ (μM) | Example Method |
|---|---|---|---|---|
| 531 | 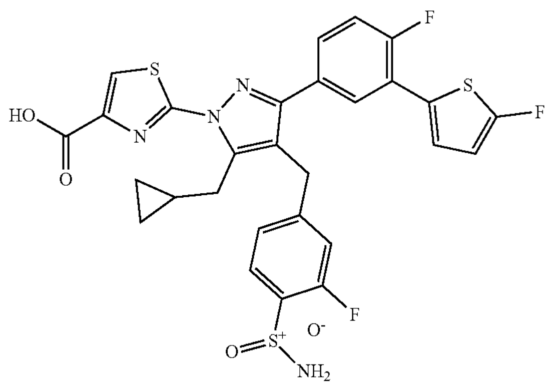 | 2-(5-(cyclopropylmethyl)-3-(4-fluoro-3-(prop-1-en-2-yl)phenyl)-4-(3-fluoro-4-sulfamoylbenzyl)-1H-pyrazol-1-yl)thiazole-4-carboxylic acid, 1H NMR (400 MHz, DMSO-d6) δ 13.17 (s, 1H), 8.28 (s, 1H), 7.73-7.61 (m, 2H), 7.61-7.49 (m, 3H), 7.37 (dd, J = 11.3, 8.6 Hz, 1H), 7.17 (dd, J = 11.3, 1.6 Hz, 1H), 7.07 (s, 1H), 7.10-7.02 (m, 1H), 6.79 (ddd, J = 4.2, 2.2, 1.1 Hz, 1H), 4.16 (s, 2H), 3.16 (d, J = 7.0 Hz, 2H), 1.24-1.06 (m, 1H), 0.38-0.28 (m, 2H), 0.32-0.17 (m, 2H); MS (M + H)+ = 632 | +++ | 145 |
| 532 | 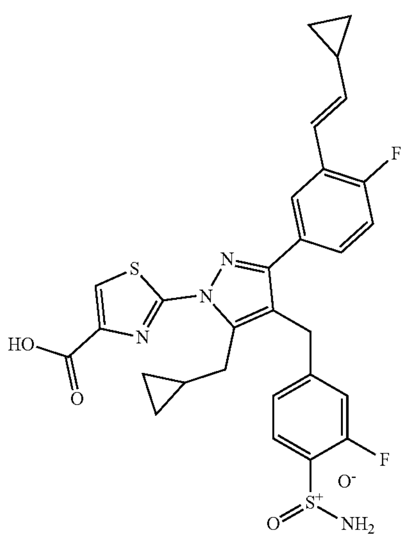 | (E)-2-(5-(cyclopropylmethyl)-3-(3-(2-cyclopropylvinyl)-4-fluorophenyl)-4-(3-fluoro-4-sulfamoylbenzyl)-1H-pyrazol-1-yl)thiazole-4-carboxylic acid, 1H NMR (400 MHz, DMSO-d6) δ 13.15 (s, 1H), 8.28 (s, 1H), 7.64 (t, J = 7.9 Hz, 1H), 7.57 (s, 2H), 7.51 (dd, J = 7.4, 2.3 Hz, 1H), 7.42 (ddd, J = 8.6, 5.0, 2.2 Hz, 1H), 7.23-7.10 (m, 2H), 7.03 (dd, J = 8.1, 1.6 Hz, 1H), 6.51 (d, J = 15.9 Hz, 1H), 5.64 (dd, J = 15.9, 9.4 Hz, 1H), 4.13 (s, 2H), 3.14 (d, J = 6.7 Hz, 2H), 1.59 (dddd, J = 12.8, 9.4, 8.1, 4.7 Hz, 1H), 1.24-0.96 (m, 1H), 0.84-0.74 (m, 2H), 0.55-0.46 (m, 2H), 0.37-0.16 (m, 4H); MS (M + H)+ = 597 | +++ | 145 |

TABLE 7-continued

| Cmpd ID | Structure | Compound name and physical data | Inhibitory activity IC$_{50}$ (μM) | Example Method |
|---|---|---|---|---|
| 533 | 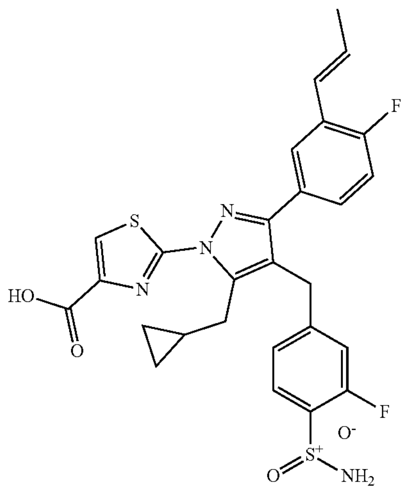 | (E)-2-(5-(cyclopropylmethyl)-3-(4-fluoro-3-(prop-1-en-1-yl)phenyl)-4-(3-fluoro-4-sulfamoylbenzyl)-1H-pyrazol-1-yl)thiazole-4-carboxylic acid, 1H NMR (400 MHz, DMSO-d6) δ 13.15 (s, 1H), 8.28 (s, 1H), 7.65 (t, J = 7.9 Hz, 1H), 7.60-7.49 (m, 3H), 7.43 (ddd, J = 8.5, 5.0, 2.3 Hz, 1H), 7.24-7.11 (m, 2H), 7.04 (dd, J = 8.1, 1.6 Hz, 1H), 6.45 (dq, J = 15.8, 1.6 Hz, 1H), 6.11 (dq, J = 16.0, 6.6 Hz, 1H), 4.12 (s, 2H), 3.16 (d, J = 7.0 Hz, 2H), 1.83 (dd, J = 6.6, 1.7 Hz, 3H), 1.20-1.06 (m, 1H), 0.38-0.28 (m, 2H), 0.25-0.17 (m, 2H); MS (M + H)+ = 571 | +++ | 145 |
| 534 | 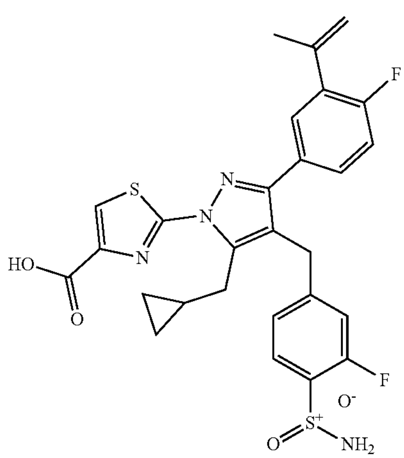 | 2-(5-(cyclopropylmethyl)-3-(4-fluoro-3-(prop-1-en-2-yl)phenyl)-4-(3-fluoro-4-sulfamoylbenzyl)-1H-pyrazol-1-yl)thiazole-4-carboxylic acid, 1H NMR (400 MHz, DMSO-d6) δ 13.15 (s, 1H), 8.28 (s, 1H), 7.64 (t, J = 7.9 Hz, 1H), 7.57 (s, 2H), 7.50 (ddd, J = 8.6, 4.8, 2.3 Hz, 1H), 7.40 (dd, J = 7.5, 2.3 Hz, 1H), 7.23 (dd, J = 11.1, 8.5 Hz, 1H), 7.13 (dd, J = 11.4, 1.6 Hz, 1H), 7.04 (dd, J = 8.1, 1.6 Hz, 1H), 5.24 (dp, J = 2.4, 1.2 Hz, 1H), 5.14 (dq, J = 1.8, 0.9 Hz, 1H), 4.12 (s, 2H), 3.15 (d, J = 6.9 Hz, 2H), 1.96 (q, J = 1.0 Hz, 3H), 1.24-0.93 (m, 1H), 0.37-0.28 (m, 2H), 0.25-0.16 (m, 2H); MS (M + H)+ = 571 | +++ | 145 |

TABLE 7-continued

| Cmpd ID | Structure | Compound name and physical data | Inhibitory activity IC$_{50}$ (μM) | Example Method |
|---|---|---|---|---|
| 535 | 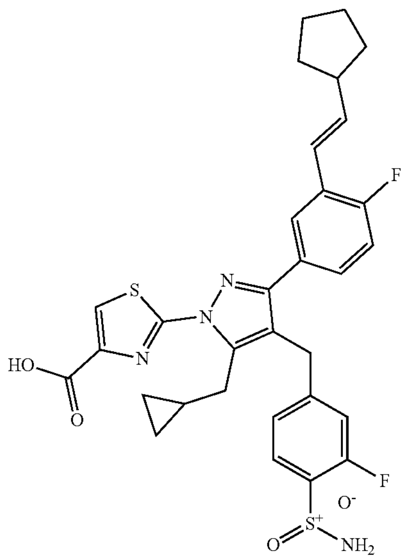 | (E)-2-(3-(3-(2-cyclopentylvinyl)-4-fluorophenyl)-5-(cyclopropylmethyl)-4-(3-fluoro-4-sulfamoylbenzyl)-1H-pyrazol-1-yl)thiazole-4-carboxylic acid, 1H NMR (400 MHz, DMSO-d6) δ 13.15 (s, 1H), 8.28 (s, 1H), 7.65 (t, J = 7.9 Hz, 1H), 7.59-7.43 (m, 4H), 7.25-7.12 (m, 2H), 7.05 (dd, J = 8.1, 1.6 Hz, 1H), 6.41 (dd, J = 16.0, 1.1 Hz, 1H), 6.08 (dd, J = 16.0, 8.0 Hz, 1H), 4.14 (s, 2H), 3.15 (d, J = 6.9 Hz, 2H), 2.63-2.49 (m, 1H), 1.83-1.62 (m, 2H), 1.66-1.48 (m, 2H), 1.31 (s, 1H), 1.39-1.24 (m, 1H), 1.20-1.05 (m, 1H), 0.37-0.28 (m, 2H), 0.29-0.16 (m, 2H); MS (M + H)+ = 625 | +++ | 145 |
| 536 | 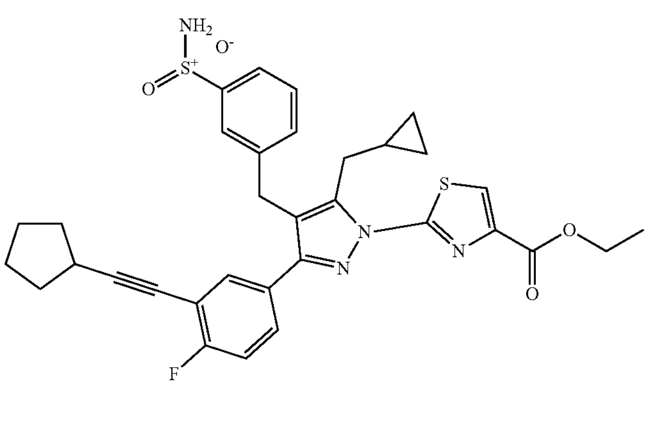 | ethyl 2-(3-(3-(cyclopentylethynyl)-4-fluorophenyl)-5-(cyclopropylmethyl)-4-(3-sulfamoylbenzyl)-1H-pyrazol-1-yl)thiazole-4-carboxylate, 1H NMR (400 MHz, DMSO-d6) δ 8.36 (s, 1H), 7.61 (dt, J = 7.9, 1.4 Hz, 1H), 7.53 (s, 1H), 7.56-7.49 (m, 1H), 7.53-7.38 (m, 2H), 7.36-7.21 (m, 2H), 7.28 (s, 2H), 4.30 (q, J = 7.1 Hz, 2H), 4.11 (s, 2H), 3.14 (d, J = 6.9 Hz, 2H), 2.87 (p, J = 7.3 Hz, 1H), 2.01-1.89 (m, 1H), 1.94 (s, 1H), 1.72-1.50 (m, 7H), 1.30 (t, J = 7.1 Hz, 3H), 1.12 (s, 1H), 0.37-0.17 (m, 4H); MS (M + H)+ = 633 | − | 145 |

TABLE 7-continued

| Cmpd ID | Structure | Compound name and physical data | Inhibitory activity IC$_{50}$ (μM) | Example Method |
|---|---|---|---|---|
| 537 | 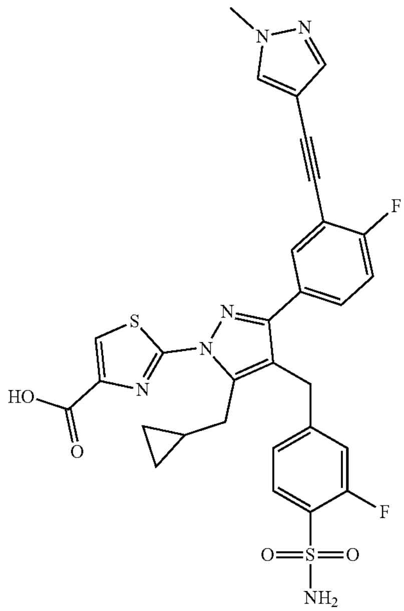 [SMILES: Cn1cc(C#Cc2cc(-c3nn(-c4nc(C(=O)O)cs4)c(CC4CC4)c3Cc3ccc(S(N)(=O)=O)c(F)c3)ccc2F)cn1] | 2-(5-(cyclopropylmethyl)-3-(4-fluoro-3-((1-methyl-1H-pyrazol-4-yl)ethynyl)phenyl)-4-(3-fluoro-4-sulfamoylbenzyl)-1H-pyrazol-1-yl)thiazole-4-carboxylic acid, MS (M + H)+ = 635 | | 145 |
| 538 | 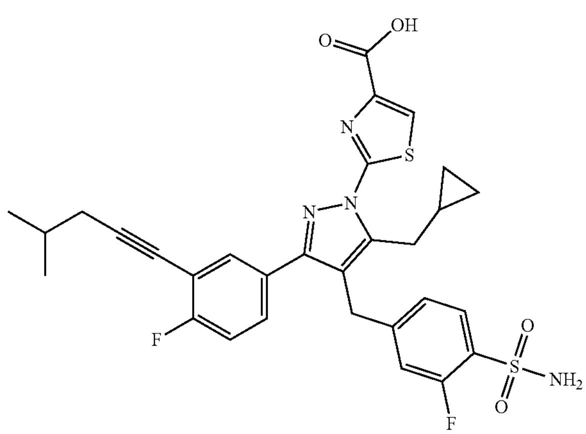 [SMILES: CC(C)CC#Cc1cc(-c2nn(-c3nc(C(=O)O)cs3)c(CC3CC3)c2Cc2ccc(S(N)(=O)=O)c(F)c2)ccc1F] | 2-(5-(cyclopropylmethyl)-3-(4-fluoro-3-(4-methylpent-1-yn-1-yl)phenyl)-4-(3-fluoro-4-sulfamoylbenzyl)-1H-pyrazol-1-yl)thiazole-4-carboxylic acid, 1H NMR (400 MHz, DMSO-d6) δ 13.16 (s, 1H), 8.28 (s, 1H), 7.64 (t, J = 7.9 Hz, 1H), 7.59-7.49 (m, 4H), 7.29 (ddd, J = 9.2, 8.0, 1.1 Hz, 1H), 7.13 (dd, J = 11.3, 1.6 Hz, 1H), 7.02 (dd, J = 8.1, 1.6 Hz, 1H), 4.12 (s, 2H), 3.14 (d, J = 6.8 Hz, 3H), 2.34 (d, J = 6.4 Hz, 2H), 1.83 (dp, J = 13.2, 6.6 Hz, 1H), 1.11 (dddd, J = 14.9, 8.0, 4.9, 1.9 Hz, 1H), 0.97 (d, J = 6.7 Hz, 6H), 0.37-0.25 (m, 2H), 0.26-0.15 (m, 2H); MS (M + H)+ = 611 | +++ | 145 |

TABLE 7-continued

| Cmpd ID | Structure | Compound name and physical data | Inhibitory activity IC$_{50}$ (μM) | Example Method |
|---|---|---|---|---|
| 539 | 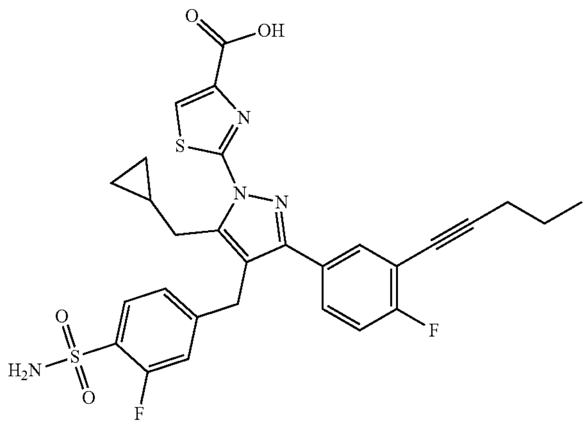 [SMILES: CCCC#Cc1cc(-c2nn(-c3nc(C(=O)O)cs3)c(CC3CC3)c2Cc2ccc(S(N)(=O)=O)c(F)c2)ccc1F] | 2-(5-(cyclopropylmethyl)-3-(4-fluoro-3-(pent-1-yn-1-yl)phenyl)-4-(3-fluoro-4-sulfamoylbenzyl)-1H-pyrazol-1-yl)thiazole-4-carboxylic acid, 1H NMR (400 MHz, DMSO-d6) δ 13.16 (s, 1H), 8.28 (s, 1H), 7.64 (t, J = 7.9 Hz, 1H), 7.57 (s, 2H), 7.58-7.49 (m, 2H), 7.33-7.24 (m, 1H), 7.13 (dd, J = 11.3, 1.6 Hz, 1H), 7.02 (dd, J = 8.1, 1.6 Hz, 1H), 4.12 (s, 2H), 3.17-3.11 (m, 3H), 2.42 (t, J = 6.9 Hz, 2H), 1.54 (q, J = 7.1 Hz, 2H), 1.18-1.03 (m, 1H), 0.97 (t, J = 7.4 Hz, 3H), 0.37-0.27 (m, 2H), 0.24-0.15 (m, 2H); MS (M + H)+ = 597 | +++ | 145 |
| 540 | 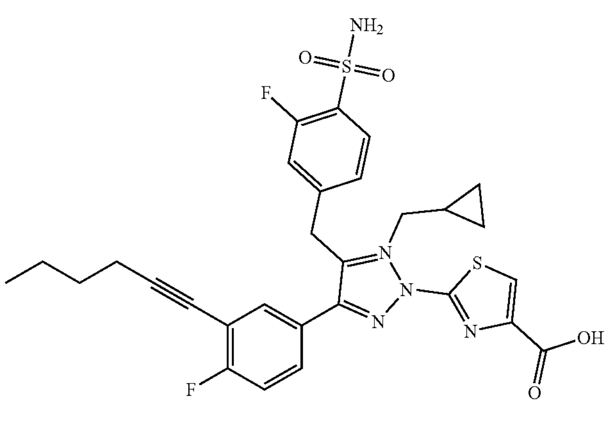 | 2-(5-(cyclopropylmethyl)-3-(4-fluoro-3-(hex-1-yn-1-yl)phenyl)-4-(3-fluoro-4-sulfamoylbenzyl)-1H-pyrazol-1-yl)thiazole-4-carboxylic acid, 1H NMR (400 MHz, DMSO-d6) δ 13.16 (s, 1H), 8.28 (s, 1H), 7.57 (s, 2H), 7.69-7.48 (m, 3H), 7.28 (dd, J = 9.4, 8.6 Hz, 1H), 7.13 (dd, J = 11.4, 1.6 Hz, 1H), 7.02 (dd, J = 8.1, 1.6 Hz, 1H), 4.12 (s, 2H), 3.18-3.11 (m, 3H), 2.44 (t, J = 6.9 Hz, 2H), 1.57-1.34 (m, 4H), 1.18-1.03 (m, 1H), 0.89 (t, J = 7.2 Hz, 3H), 0.37-0.27 (m, 2H), 0.24-0.16 (m, 2H); MS (M + H)+ = 611 | +++ | 145 |

TABLE 7-continued

| Cmpd ID | Structure | Compound name and physical data | Inhibitory activity IC$_{50}$ (μM) | Example Method |
|---|---|---|---|---|
| 541 | 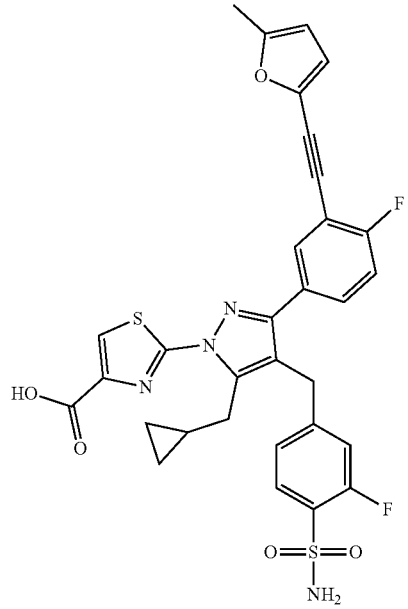 [SMILES: Cc1ccc(C#Cc2cc(-c3nn(-c4nc(C(=O)O)cs4)c(CC4CC4)c3Cc3ccc(S(N)(=O)=O)c(F)c3)ccc2F)o1] | 2-(5-(cyclopropylmethyl)-3-(4-fluoro-3-((5-methylfuran-2-yl)ethynyl)phenyl)-4-(3-fluoro-4-sulfamoylbenzyl)-1H-pyrazol-1-yl)thiazole-4-carboxylic acid, MS (M + H)+ = 635 | | 145 |
| 542 | 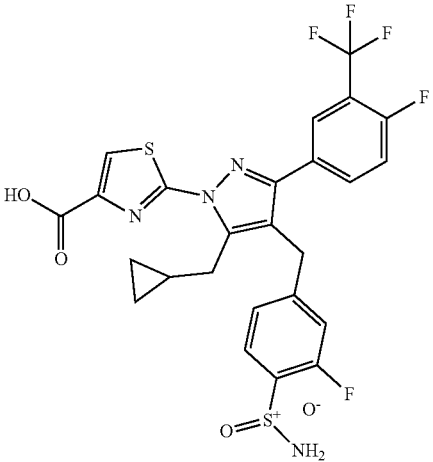 | 2-(5-(cyclopropylmethyl)-3-(4-fluoro-3-(trifluoromethyl)phenyl)-4-(3-fluoro-4-sulfamoylbenzyl)-1H-pyrazol-1-yl)thiazole-4-carboxylic acid (M + H)+ = 599 | +++ | 49 |
| 543 | 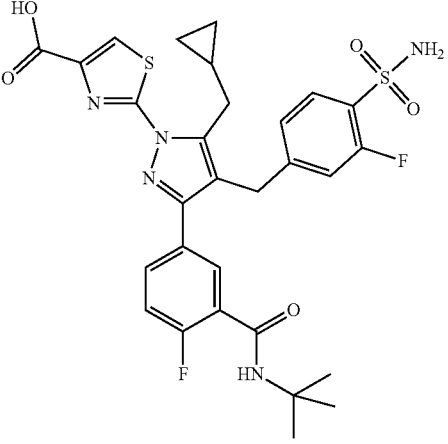 [SMILES: CC(C)(C)NC(=O)c1cc(-c2nn(-c3nc(C(=O)O)cs3)c(CC3CC3)c2Cc2ccc(S(N)(=O)=O)c(F)c2)ccc1F] | 2-(3-(3-(tert-butylcarbamoyl)-4-fluorophenyl)-5-(cyclopropylmethyl)-4-(3-fluoro-4-sulfamoylbenzyl)-1H-pyrazol-1-yl)thiazole-4-carboxylic acid: $^1$H-NMR (MeOD) δ: 8.21 (s, 1H), 7.79-7.69 (m, 3H), 7.19 (dd, J = 8.6, 10.0 Hz, 1H), 7.11-7.05 (m, 2H), 4.21 (s, 2H), 3.28 (d, J = 6.8 Hz, 2H), 1.44 (s, 9H), 1.18-1.10 (m, 1H), 0.43-0.39 (m, 2H), 0.28-0.24 (m, 2H); MS (ES) 630.1 (M + H)$^+$, LCMS RT = 1.048 min. | +++ | 162 |

TABLE 7-continued

| Cmpd ID | Structure | Compound name and physical data | Inhibitory activity IC$_{50}$ (μM) | Example Method |
|---|---|---|---|---|
| 544 | 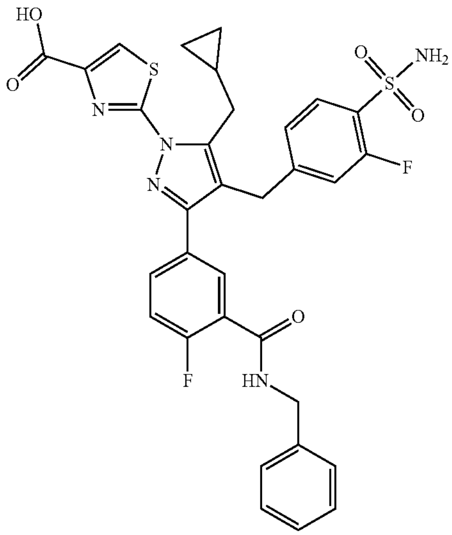 [SMILES: NS(=O)(=O)c1ccc(Cc2c(-c3ccc(F)c(C(=O)NCc4ccccc4)c3)nn(-c3nc(C(=O)O)cs3)c2CC2CC2)cc1F] | 2-(3-(3-(benzylcarbamoyl)-4-fluorophenyl)-5-(cyclopropylmethyl)-4-(3-fluoro-4-sulfamoylbenzyl)-1H-pyrazol-1-yl)thiazole-4-carboxylic acid: MS (ES) 664.0 (M + H)$^+$, LCMS RT = 1.052 min. | +++ | 162 |
| 545 | 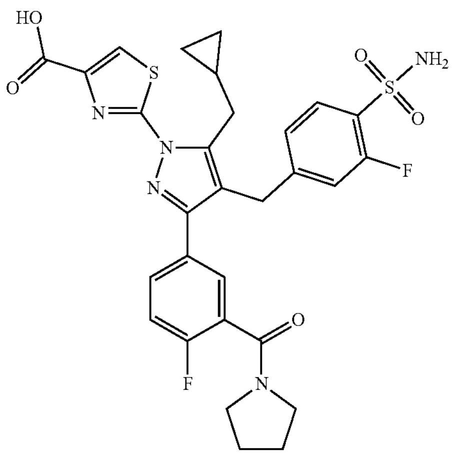 [SMILES: NS(=O)(=O)c1ccc(Cc2c(-c3ccc(F)c(C(=O)N4CCCC4)c3)nn(-c3nc(C(=O)O)cs3)c2CC2CC2)cc1F] | 2-(5-(cyclopropylmethyl)-3-(4-fluoro-3-(pyrrolidine-1-carbonyl)phenyl)-4-(3-fluoro-4-sulfamoylbenzyl)-1H-pyrazol-1-yl)thiazole-4-carboxylic acid: $^1$H-NMR (MeOD) δ: 8.22 (s, 1H), 7.75-7.71 (m, 2H), 7.54 (dd, J = 2.2, 6.4 Hz, 1H), 7.24 (t, J = 8.8 Hz, 1H), 7.07 (t, J = 7.4 Hz, 2H), 4.20 (s, 2H), 3.59 (t, J = 7.1 Hz, 2H), 3.30 (d, J = 6.9 Hz, 2H), 3.19 (t, J = 2H), 2.03-1.91 (m, 4H), 0.95-0.86 (m, 1H), 0.45-0.40 (m, 2H), 0.29-0.25 (m, 2H); MS (ES) 628.0 (M + H)$^+$, LCMS RT = 0.968 min. | +++ | 163 |
| 546 | 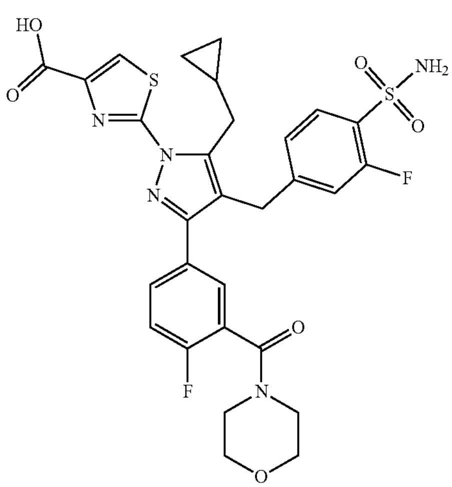 [SMILES: NS(=O)(=O)c1ccc(Cc2c(-c3ccc(F)c(C(=O)N4CCOCC4)c3)nn(-c3nc(C(=O)O)cs3)c2CC2CC2)cc1F] | 2-(5-(cyclopropylmethyl)-3-(4-fluoro-3-(morpholine-4-carbonyl)phenyl)-4-(3-fluoro-4-sulfamoylbenzyl)-1H-pyrazol-1-yl)thiazole-4-carboxylic acid: MS (ES) 644.0 [M + H]$^+$, LCMS RT = 0.977 min. | | 163 |

Example 165

This example describes the inhibition of lactate production, as measured by the assay set forth in Example 1, of exemplary compounds of formula (I) in an embodiment of the invention. See Table 8. The lactate activity in Table 8 is represented by 0 to 3 pluses as follows: ++++<1 μM; ++1-10 μM; +10-57 μM; and −>57 μM.

TABLE 8

| Cmpd ID | Lactate activity |
| --- | --- |
| 42 | ++ |
| 43 | + |
| 47 | − |
| 52 | ++ |
| 53 | − |
| 54 | − |
| 160 | ++ |
| 183 | +++ |
| 189 | ++ |
| 203 | +++ |
| 206 | ++ |
| 207 | ++ |
| 212 | − |
| 213 | − |
| 214 | ++ |
| 215 | + |
| 217 | ++ |
| 219 | ++ |
| 221 | +++ |
| 223 | +++ |
| 227 | +++ |
| 229 | − |
| 230 | +++ |
| 231 | +++ |
| 232 | +++ |
| 233 | +++ |
| 234 | +++ |
| 237 | ++ |
| 239 | +++ |
| 251 | ++ |
| 252 | ++ |
| 257 | +++ |
| 258 | +++ |
| 259 | + |
| 260 | ++ |
| 261 | ++ |
| 262 | +++ |
| 263 | + |
| 264 | +++ |
| 265 | ++ |
| 266 | − |
| 267 | + |
| 268 | − |
| 269 | +++ |
| 276 | +++ |
| 281 | +++ |
| 284 | +++ |
| 288 | +++ |
| 290 | +++ |
| 294 | +++ |
| 296 | ++ |
| 304 | + |
| 306 | +++ |
| 307 | +++ |
| 309 | +++ |
| 310 | +++ |
| 324 | +++ |
| 326 | +++ |
| 327 | + |
| 330 | +++ |
| 331 | +++ |
| 332 | +++ |
| 336 | +++ |
| 337 | +++ |
| 338 | +++ |
| 364 | +++ |
| 365 | +++ |
| 366 | +++ |
| 367 | +++ |
| 368 | + |
| 369 | + |
| 370 | ++ |
| 371 | +++ |
| 372 | ++ |
| 373 | +++ |
| 374 | +++ |
| 375 | ++ |
| 376 | +++ |
| 377 | − |
| 378 | +++ |
| 379 | +++ |
| 380 | ++ |
| 381 | +++ |
| 382 | +++ |
| 383 | +++ |
| 384 | +++ |
| 385 | +++ |
| 386 | +++ |
| 387 | ++ |
| 388 | ++ |
| 389 | ++ |
| 390 | − |
| 391 | +++ |
| 393 | − |
| 394 | + |
| 395 | + |
| 396 | ++ |
| 397 | ++ |
| 398 | + |
| 399 | − |
| 400 | +++ |
| 401 | +++ |
| 402 | +++ |
| 403 | +++ |
| 404 | +++ |
| 405 | +++ |
| 406 | ++ |
| 407 | +++ |
| 408 | +++ |
| 409 | ++ |
| 410 | +++ |
| 411 | +++ |
| 412 | ++ |
| 413 | +++ |
| 414 | ++ |
| 415 | ++ |
| 416 | ++ |
| 417 | ++ |
| 418 | ++ |
| 419 | +++ |
| 420 | − |
| 421 | ++ |
| 422 | + |
| 423 | +++ |
| 428 | − |
| 429 | − |
| 430 | +++ |
| 431 | +++ |
| 432 | +++ |
| 433 | +++ |
| 434 | − |
| 435 | − |
| 436 | +++ |
| 437 | +++ |
| 438 | ++ |
| 439 | − |
| 440 | ++ |
| 442 | ++ |
| 443 | +++ |
| 444 | +++ |
| 445 | +++ |
| 446 | +++ |
| 458 | ++ |
| 467 | +++ |
| 468 | ++ |

TABLE 8-continued

| Cmpd ID | Lactate activity |
|---|---|
| 469 | ++ |
| 470 | ++ |
| 471 | ++ |
| 472 | +++ |
| 473 | +++ |
| 477 | +++ |
| 478 | ++ |
| 479 | +++ |
| 480 | +++ |
| 481 | ++ |
| 485 | ++ |
| 501 | ++ |
| 502 | ++ |
| 503 | ++ |
| 504 | ++ |
| 505 | ++ |
| 506 | ++ |
| 507 | ++ |
| 508 | ++ |
| 509 | +++ |
| 510 | +++ |
| 511 | ++ |
| 512 | +++ |
| 523 | ++ |
| 526 | + |
| 527 | ++ |
| 528 | +++ |
| 542 | ++ |
| 543 | ++ |
| 544 | ++ |
| 545 | + |

Example 167

This example evaluates the pharmacokinetics (PK) of compound 42 when administered orally as the ethyl ester prodrug (compound 141) to in an embodiment of the invention.

Compound 141 is the ethyl ester prodrug of compound 42. A dose formulation was freshly prepared comprising either compound 42 or compound 141, in a solution of 10% N-methyl-2-pyrrolidone (NMP), 40% PEG400, and 50% of SOLUTOL™ (30%) in water to provide a concentration of 1 mg/mL of compound 42 or 141. The dose formulation was stirred at room temperature and used within 30 minutes after preparing.

Male CD1 mice obtained from Si Bei Fu Laboratory Animal Technology Co. Ltd were fed prior to dosing. On the first day of dosing, the mice ranged in age from about 7-9 weeks and weighed approximately 20-30 g. The mice were orally administered 10 mL/kg (10 mg/kg) of the formulation comprising either compound 42 or 141.

PK measurements were taken at 5 min, 15 min, 30 min, 1 h, 2 h, 4 h, 8 h, 12, h, and 24 h post dose. For sample collections, approximately 0.03 mL blood was collected by the dorsal metatarsal vein at each time point. All blood samples were transferred into plastic micro centrifuge tubes containing 2 microliters (μL) of 1,000 IU heparin as anticoagulant. Collection tubes with blood samples and anticoagulant were inverted several times for proper mixing of the tube contents and then placed on wet ice prior to centrifugation for plasma. Blood samples were centrifuged at 4,000 g for 5 minutes at 4° C. to obtain plasma. Plasma samples were stored in polypropylene tubes, quickly frozen in an ice box, and kept at −75±15° C. Plasma samples were analyzed using an LC/MS/MS method. The peak concentration ($C_{max}$), area under the curve ($AUC_{last}$), and the fraction of the dose that enters systemic circulation (F) of compounds 42 and 142 are set forth below in Table 9.

TABLE 9

| Compound | $C_{max}$ (ng/mL) | $AUC_{last}$ (h · ng/mL) | F (%) |
|---|---|---|---|
| 42 | 159 | 1214 | 34 |
| 141 | 851 | 2409 | 69 |

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A compound of formula (Ia):

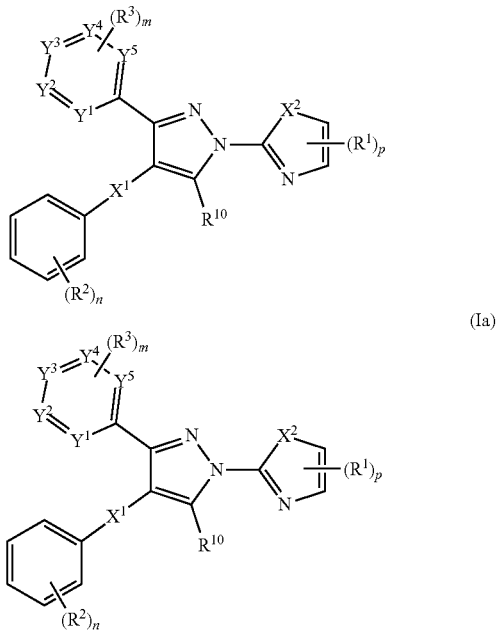

wherein
$Y^1$, $Y^2$, $Y^3$, $Y^4$, and $Y^5$ are each independently CH or N;
$R^1$ is independently chosen from halo, —$CO_2R^4$, —$CONH_2$, —C(O)NHOH, —P(O)(OH)$_2$, —B(OR$^{13}$)(OR$^{14}$), —SO$_2$(OH), —SO$_2$NR$^5$R$^6$, —($C_1$-$C_8$alkylene)OH, $C_1$-$C_4$alkyl, $C_1$-$C_4$alkoxy, d-$C_2$haloalkyl, $C_1$-$C_2$haloalkoxy, heteroaryl, and —C(O)O— heteroaryl, each of which $R^1$ except hydrogen, halo, —P(O)(OH)$_2$, —CONH$_2$, and —SO$_2$(OH), is substituted or unsubstituted;

$R^2$ is independently chosen from hydroxyl, halo, —CN, —NO$_2$ C$_1$-C$_8$alkyl, C$_2$-C$_8$ alkenyl, C$_3$-C$_6$ cycloalkyl, C$_1$-C$_8$ alkoxy, —O—C$_3$-C$_6$cycloalkyl, C$_6$-C$_{12}$aryl, —O—C$_6$-C$_{12}$aryloxy, —(CH$_2$)$_q$aryl, —(CH$_2$)$_q$heteroaryl, —(CH$_2$)$_q$heterocycloalkyl, —C(O)R$^4$, —CO$_2$R$^4$, —C(O)NR$^5$R$^6$, —NR$^5$C(O)R$^4$, —(CH$_2$)$_q$NR$^5$(SO$_2$)R$^4$, —(CH$_2$)$_q$NR$^5$C(O)R$^4$, —(CH$_2$)$_q$NR$^7$C(O)NR$^5$R$^6$, —(CH$_2$)$_q$NR$^5$R$^6$, —(CH$_2$)$_q$SO$_2$NR$^5$R$^6$, and —(CH$_2$)$_q$SO$_2$R$^4$, each of which R$^2$ except hydrogen, hydroxyl, halo, —CN, —NO$_2$, SF$_5$, is substituted or unsubstituted;

$R^3$ is independently chosen from hydroxyl, halo, —CN, —NO$_2$, SF$_5$, C$_1$-C$_8$ alkyl, C$_2$-C$_8$ alkenyl, C$_2$-C$_8$ alkynyl, C$_3$-C$_6$alkenynyl, C$_1$-C$_8$alkoxy, —(CH$_2$)$_q$C$_3$-C$_8$cycloalkyl, —O(CH$_2$)$_q$C$_3$-C$_8$cycloalkyl, —(CH$_2$)$_q$C$_3$-C$_8$cycloalkenyl, —(C$_2$-C$_4$alkynyl)(C$_3$-C$_6$cycloalkenyl), —(CH$_2$)$_q$C$_6$-C$_{12}$aryl, —O(CH$_2$)$_q$C$_6$-C$_{12}$aryl, —(CH$_2$)$_q$heteroaryl, —O(CH$_2$)$_q$heteroaryl, —(C$_2$-C$_4$alkenyl)heteroaryl, —(C$_2$-C$_4$alkynyl)heteroaryl, —(CH$_2$)$_q$heterocycloalkenyl, —O(CH$_2$)$_q$(heterocyloalkenyl, —(C$_2$-C$_4$alkenyl)heterocycloalkenyl, —(C$_2$-C$_4$alkynyl)heterocycloalkenyl, —(CH$_2$)$_q$heterocycloalkyl, —O(CH$_2$)$_q$heterocycloalkyl, —(C$_2$-C$_4$alkenyl)heterocycloalkyl, and —(C$_2$-C$_4$alkynyl)heterocycloalkyl, each of which R except hydrogen, hydroxyl, halo, —CN, —NO$_2$, and SF$_5$ is substituted or unsubstituted;

each $R^4$, $R^5$, and $R^6$ is the same or different and each is hydrogen, C$_1$-C$_8$ alkyl, C$_2$-C$_8$ alkenyl, C$_3$-C$_6$cycloalkyl, C$_6$-C$_{12}$aryl, heteroaryl, or heterocycloalkyl, each of which R$^4$, R$^5$, and R$^6$ except H is substituted or unsubstituted;

each $R^7$, $R^8$, and $R^9$ is the same or different and each is hydrogen, C$_1$-C$_8$alkyl, C$_2$-C$_8$alkenyl, C$_3$-C$_6$cycloalkyl, C$_6$-C$_{12}$aryl, C$_1$-C$_{12}$heteroaryl, or C$_1$-C$_{12}$heterocycloalkyl, each of which C$_1$-C$_8$alkyl, C$_2$-C$_8$ alkenyl, C$_3$-C$_6$cycloalkyl, C$_6$-C$_{12}$aryl, C$_1$-C$_{12}$heteroaryl, or C$_1$-C$_{12}$heterocycloalkyl is substituted or unsubstituted;

$R^{10}$ is hydrogen, —CN, hydroxyl, halo, C$_1$-C$_8$alkyl, C$_2$-C$_8$alkenyl, C$_2$-C$_8$alkynyl, C$_1$-C$_6$alkoxy, —(C$_0$-C$_2$alkyl)NR$^5$R$^6$, —(C$_0$-C$_2$alkyl)C$_3$-C$_6$cycloalkyl, —C≡C(C$_3$-C$_6$cycloalkyl) —(C$_0$-C$_2$alkyl)C$_6$-C$_{12}$ aryl, —(C$_0$-C$_2$alkyl)heterocycloalkyl, or —(C$_0$-C$_2$alkyl)heteroaryl, each of which R$^{10}$ except hydrogen, hydroxyl, and halo is substituted or unsubstituted;

or pharmaceutically acceptable salt thereof; and
    each $R^{13}$ and $R^{14}$ is the same or different and each is hydrogen, C$_1$-C$_8$ alkyl, C$_2$-C$_8$alkenyl, C$_3$-C$_6$cycloalkyl, C$_6$-C$_{12}$ aryl, wherein R$^{13}$ and R$^{14}$ are optionally connected to each other to form a ring;
$X^1$ is a bond, —CR$^8$R$^9$—, —NR$^5$—, —CR$^8$NR$^5$—, —NR$^5$CR$^8$—, —NR$^5$C(O)—, —O—, —CO—, —SO—, —SO$_2$—, or —S—;
$X^2$ is —NR$^5$—, —O—, —SO$_2$—, or —S—;
m, n, and q are the same or different and each is 0, 1, 2, 3, 4, or 5; and
p is 1 or 2;
or a pharmaceutically acceptable salt thereof.

2. The compound of claim 1, wherein:
$R^1$ is independently chosen from halo, hydroxyl, —CONH$_2$, C$_1$-C$_4$alkyl, C$_1$-C$_4$alkoxy, —CO$_2$R$^4$, —CH$_2$OH, —CHCF$_3$OH, —C(CF$_3$)$_2$OH, —C(O)NHOH, —P(O)(OH)$_2$, —B(OR$^{13}$)(OR$^{14}$), —SO$_2$(OH), —SO$_2$NR$^5$R$^6$, —C(O)O-2,3-dihydro-1H-indenyl, —C(O)O-(5-methyl-2-oxo-1,3-dioxol-4-yl) methyl, 1,3,4-oxadiazol-2(3H)-one, isoxazol-3(2H)-one, and tetrazolyl, each of which R$^1$ except hydrogen, halo is substituted or unsubstituted;

$R^2$ is independently chosen from halo, C$_1$-C$_4$alkyl C$_1$-C$_4$alkoxy and —(CH$_2$)$_q$SO$_2$NR$^5$R$^6$, where one of R$^2$ is —(CH$_2$)$_q$SO$_2$NR$^5$R$^6$;

$R^3$ is independently chosen from hydroxyl, halo, —CN, —NO$_2$, SF$_5$, C$_1$-C$_8$ alkyl, C$_2$-C$_8$ alkenyl, C$_2$-C$_8$ alkynyl, C$_3$-C$_6$ alkenynyl, C$_1$-C$_8$alkoxy, —(CH$_2$)$_q$C$_3$-C$_8$cycloalkyl, —O(CH$_2$)$_q$C$_3$-C$_6$cycloalkyl, —(CH$_2$)$_q$C$_3$-C$_6$cycloalkenyl, —(C$_2$-C$_4$alkynyl)(C$_3$-C$_6$cycloalkenyl), —(CH$_2$)$_q$C$_6$-C$_{12}$phenyl, —O(CH$_2$)$_q$C$_6$-C$_{12}$phenyl, —(CH$_2$)$_q$heteroaryl, —O(CH$_2$)$_q$heteroaryl, —(C$_2$-C$_4$alkenyl)heteroaryl, and —(C$_2$-C$_4$alkynyl)heteroaryl, where the heteroaryl group is a oxazolyl, thienyl, thiazolyl, furanyl, pyrazolyl, or imidazolyl group; —(CH$_2$)$_q$heterocycloalkenyl, —O(CH$_2$) (heterocyloalkenyl, —(C$_2$-C$_4$alkenyl) heterocycloalkenyl, —(C$_2$-C$_4$alkynyl) heterocycloalkenyl, where the heterocycloalkenyl is dihydropyranyl, dihydrofuranyl, dihydrothiopyranyl, or dihydropyridinyl, —(CH$_2$) heterocycloalkyl, —O(CH$_2$)$_q$heterocycloalkyl, —(C$_2$-C$_4$alkenyl)heterocycloalkyl, —(C$_2$-C$_4$alkynyl)heterocycloalkyl, where the heterocycloalkyl is tetrahydropyranyl, tetrahydrofuranyl, piperazinyl, piperidinyl, or pyrrolidinyl, each of which R except hydrogen, hydroxyl, halo, —CN, —NO$_2$, and SF$_5$ is substituted or unsubstituted;

each $R^4$, $R^5$, and $R^6$ is the same or different and each is H or C$_1$-C$_8$ alkyl, wherein C$_1$-C$_8$alkyl is substituted or unsubstituted;

$R^{10}$ is hydrogen, —OH, halo, —CH$_2$OH, —CN, —CH$_2$CN, —NH$_2$, C$_1$-C$_4$alkyl, C$_2$-C$_4$alkenyl, C$_1$-C$_4$alkoxy, C$_1$-C$_2$haloalkyl, C$_1$-C$_2$haloalkoxy, —(C$_0$-C$_3$ alkyl)-cyclopropyl, —(C$_0$-C$_3$ alkyl)-cyclobutyl, —C≡C-cyclopropyl, —C≡C-cyclobutyl phenyl, benzyl, or —CH$_2$-tetrazolyl, each of which cyclopropyl, —(C$_1$-C$_3$alkyl)-cyclopropyl, —CH═CH$_2$, —C≡C-cyclopropyl, phenyl, or benzyl is substituted or unsubstituted; and each $R^{13}$ and $R^{14}$ is the same or different and each is hydrogen, C$_1$-C$_8$ alkyl, C$_2$-C$_8$ alkenyl, C$_3$-C$_6$ cycloalkyl, C$_6$-C$_{12}$ aryl, wherein R$^{13}$ and R$^{14}$ are optionally connected to each other to form a ring.

3. The compound of claim 1, wherein n is 1.
4. The compound of claim 1, wherein m is 1 or 2.
5. The compound of claim 1, wherein X is —CR$^8$R$^9$—, —O—, or —NH—.
6. The compound of claim 1, wherein X is —S—.
7. The compound of claim 1, wherein the compound is a compound of formula (Ia-1)

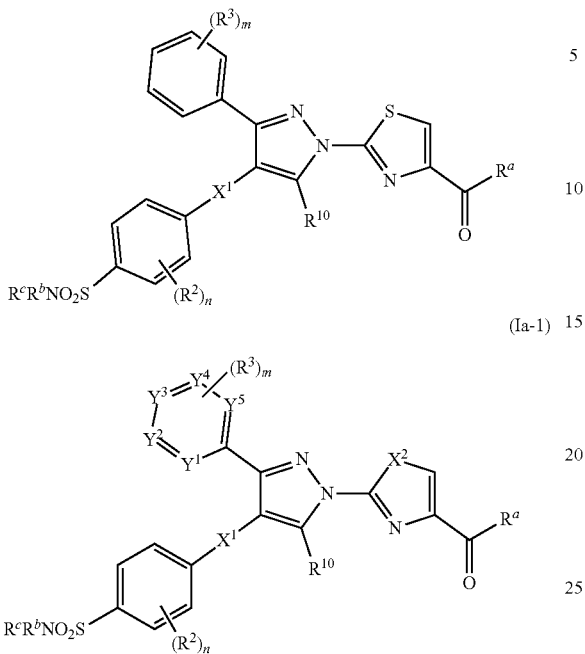

(Ia-1)

(Ia-1)

wherein:
R$^a$ is —R$^4$, —OR$^4$, or —NR$^5$R$^6$, each of which is substituted or unsubstituted;
R$^b$ and R$^c$ are the same or different and each is H or substituted or unsubstituted C$_1$-C$_8$ alkyl;
R$^2$ is independently chosen from hydroxyl, C$_1$-C$_8$ alkyl, C$_2$-C$_8$ alkenyl, C$_3$-C$_6$ cycloalkyl, C$_1$-C$_8$alkoxy, C$_3$-C$_6$cycloalkyloxy, aryloxy, halo, C$_1$-C$_8$ haloalkoxy, C$_1$-C$_8$ haloalkyl, haloaryl, haloaryloxy, —CN, —NO$_2$, —C(O)R$^4$, —CO$_2$R$^4$, —C(O)NR$^5$R$^6$, —NR$^5$C(O)R$^4$, —(CH$_2$)$_q$NR$^5$(SO$_2$)R$^4$, —(CH$_2$)$_q$NR$^5$C(O)R$^4$, —(CH$_2$)$_q$NR$^7$C(O)NR$^5$R$^6$, —(CH$_2$)$_q$NR$^5$R$^6$, —(CH$_2$)$_q$SO$_2$NR$^5$R$^6$, —(CH$_2$)$_q$SO$_2$R$^4$, —(CH$_2$)$_q$aryl, —(CH$_2$)$_q$heteroaryl, and —(CH$_2$)$_2$heterocycloalkyl, each of which R except hydroxyl and halo is substituted or unsubstituted;
one of R$^3$ is selected from C$_2$-C$_6$alkynyl, —(C$_0$-C$_2$alkyl)C$_3$-C$_6$cycloalkyl, —(C$_4$-C$_4$alkenyl)C$_3$-C$_6$cycloalkyl, —(C$_2$-C$_4$alkynyl)C$_3$-C$_6$cycloalkyl, —(C$_0$-C$_2$alkoxy)C$_3$-C$_6$cycloalkyl, dihydropyranyl, —(C$_0$-C$_4$alkoxy)phenyl, —(C$_0$-C$_4$alkyl)phenyl, —(C$_2$-C$_4$alkenyl)phenyl, —(C$_2$-C$_4$alkynyl)phenyl, —(C$_0$-C$_4$alkoxy)heteroaryl, —(C$_0$-C$_4$alkyl)heteroaryl, —(C$_2$-C$_4$alkenyl)heteroaryl, and —(C$_2$-C$_4$alkynyl)heteroaryl, where heteroaryl is chosen from thienyl, furanyl, thiazolyl, pyrazolyl, and imidazolyl; each of which one or more substituents selected from hydroxyl, halo, —CN, C$_1$-C$_4$ alkyl, C$_2$-C$_4$ alkenyl, C$_1$-C$_4$ alkynyl, C$_1$-C$_4$ alkoxy, (C$_3$-C$_6$ cycloalkyl)C$_0$-C$_2$alkyl, C$_1$-C$_2$ haloalkyl, and C$_1$-C$_2$haloalkoxy;
and 0 or 1 or more R$^3$ is selected from hydroxyl, halo, —CN, C$_1$-C$_4$alkyl, C$_1$-C$_4$alkoxy, C$_1$-C$_2$haloalkyl, and C$_1$-C$_2$haloalkoxy;
each R$^4$, R$^5$, R$^6$, R$^7$, R$^8$, and R$^9$ is the same or different and each is hydrogen, C$_1$-C$_8$alkyl, or C$_3$-C$_6$cycloalkyl, each of which C$_1$-C$_8$alkyl and C$_3$-C$_6$cycloalkyl is substituted or unsubstituted;
R$^{10}$ is hydrogen, C$_1$-C$_8$alkyl, C$_2$-C$_8$alkenyl, C$_2$-C$_8$alkynyl, C$_3$-C$_6$ cycloalkyl, C$_3$-C$_6$cycloalkylalkyl, hydroxyl, hydroxyalkyl, C$_1$-C$_8$ alkoxy, halo, C$_1$-C$_8$ haloalkyl, aryl, arylalkyl, heteroarylalkyl, —CN, —CO$_2$R$^4$, —NR$^5$R$^6$, or —SO$_2$R$^4$, each of which R$^{10}$ except hydrogen, hydroxyl and halo is substituted or unsubstituted;
X$^1$ is a bond, —CR$^8$R$^9$—, —NR$^5$—, —O—, —S(O)—, or —S(O)$_2$—, or —S—, each of which R$^8$ and R$^9$ is substituted or unsubstituted;
n is an integer from 0 to 4; and
m and q are the same or different and each is 0 or an integer from 1-5,
or a pharmaceutically acceptable salt thereof.

8. The compound of claim 7, wherein n is 1 and R$^2$ is halogen.

9. The compound of claim 7, wherein
R$^a$ is hydroxyl or substituted or unsubstituted —O(C$_1$-C$_8$ alkyl);
R$^b$ and R$^c$ are H;
n is 0;
R$^3$ is halo, C$_2$-C$_8$ alkenyl, C$_2$-C$_8$ alkynyl, —(C$_0$-C$_2$alkyl) heteroaryl, phenyl, or 3,4-dihalophenyl, each of which R except halo is substituted or unsubstituted; or
two R$^3$ moieties and the phenyl group to which they are attached form a naphthyl group that is optionally substituted;
R$^{10}$ is hydrogen, substituted or unsubstituted C$_1$-C$_8$ alkyl, substituted or unsubstituted cyclopropyl, substituted or unsubstituted —CH$_2$-cyclopropyl, —CH$_2$CH$_2$-cyclopropyl, substituted or unsubstituted —CH=CH$_2$, substituted or unsubstituted —C≡C-cyclopropyl, substituted or unsubstituted phenyl, substituted or unsubstituted benzyl, —I, —CF$_3$, —NH$_2$, or —CN;
X$^1$ is —CH$_2$— or —NH—; and
m is 0, 1, or 2.

10. The compound or salt of claim 7, wherein the compound is a compound of formula (Ia-3):

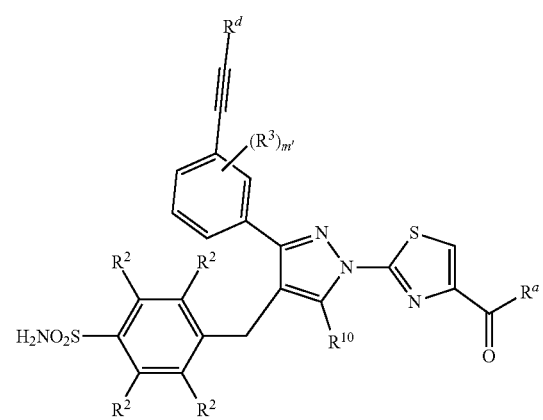

(Ia-3)

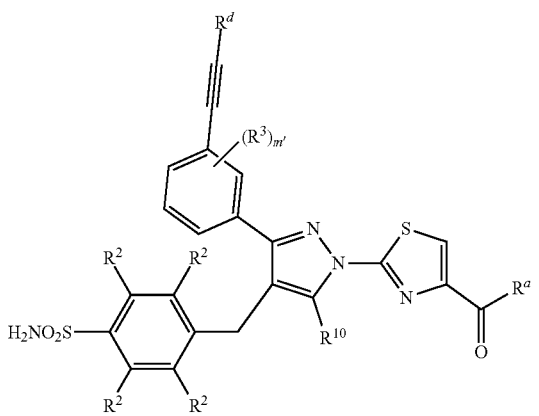

wherein
- $R^a$ is —$R^4$, —$OR^4$, or —$NR^5R^6$, each of which $R^4$, $R^5$, and $R^6$ is substituted or unsubstituted;
- each $R^2$ is the same or different and each is hydrogen, hydroxyl, $C_1$-$C_8$alkyl, $C_2$-$C_8$alkenyl, $C_3$-$C_6$cycloalkyl, $C_3$-$C_6$cycloalkylalkyl, $C_1$-$C_8$ alkoxy, $C_3$-$C_6$cycloalkyloxy, aryloxy, halo, $C_1$-$C_8$haloalkoxy, $C_1$-$C_8$haloalkyl, haloaryl, haloaryloxy, —CN, —$NO_2$, —C(O)$R^4$, —$CO_2R^4$, —C(O)$NR^5R^6$, —$NR^5$C(O)$R^4$, —$(CH_2)_qNR^5(SO_2)R^4$, —$(CH_2)_qNR^5$C(O)$R^4$, —$(CH_2)_qNR^7$C(O)$NR^5R^6$, —$(CH_2)_qNR^5R^6$, —$(CH_2)_qSO_2NR^5R^6$, —$(CH_2)_qSO_2R^4$, —$(CH_2)_q$aryl, —$(CH_2)_q$heteroaryl, or —$(CH_2)_q$heterocycloalkyl, each of which R except hydrogen, hydroxyl, and halo is substituted or unsubstituted;
- $R^3$ is hydroxyl, $C_1$-$C_8$alkyl, $C_2$-$C_8$alkenyl, $C_3$-$C_6$cycloalkyl, $C_3$-$C_6$cycloalkylalkyl, $C_1$-$C_8$ alkoxy, $C_3$-$C_6$cycloalkyloxy, aryloxy, halo, $C_1$-$C_8$haloalkoxy, $C_1$-$C_8$haloalkyl, haloaryl, haloaryloxy, —CN, —$NO_2$, —C(O)$R^4$, —$CO_2R^4$, —C(O)$NR^5R^6$, —$NR^5$C(O)$R^4$, —$(CH_2)_qNR^5(SO_2)R^4$, —$(CH_2)_qNR^5$C(O)$R^4$, —$(CH_2)_qNR^7$C(O)$NR^5R^6$, —$(CH_2)_qNR^5R^6$, —$(CH_2)$ $SO_2NR^5R^6$, —$(CH_2)_qSO_2R^4$, —$(CH_2)_q$aryl, —$(CH_2)_q$heteroaryl, or —$(CH_2)_q$heterocycloalkyl, each of which R except hydroxyl and halo is substituted or unsubstituted;
- $R^d$ is $C_3$-$C_6$cycloalkyl, $C_1$-$C_8$alkyl, $C_2$-$C_8$alkenyl, phenyl, thienyl, thiazolyl, furanyl, oxazolyl, isooxazolyl, pyrazolyl, oxadiazolyl, or imidazolyl, each of which is unsubstituted or substituted with 1 or more substituents independently chosen from hydroxyl, cyano, amino, $C_1$-$C_2$alkyl, $C_1$-$C_2$alkoxy, mono- or di-$C_1$-$C_2$alkylamino, $C_1$-$C_2$haloalkyl, and $C_1$-$C_2$haloalkoxy;
- each $R^4$, $R^5$, $R^6$, and $R^7$ is the same or different and each is hydrogen, $C_1$-$C_8$ alkyl, or $C_3$-$C_6$ cycloalkyl, each of which $C_1$-$C_8$ alkyl and $C_3$-$C_6$cycloalkyl are substituted or unsubstituted;
- q is 0 or and integer from 1-5;
- m' is 0 or an integer from 1-4; and
- $R^{10}$ is hydrogen, $C_1$-$C_8$ alkyl, $C_2$-$C_8$alkenyl, $C_2$-$C_8$alkynyl, $C_3$-$C_6$cycloalkyl, $C_3$-$C_6$ cycloalkylalkyl, hydroxyl, hydroxyalkyl, $C_1$-$C_8$ alkoxy, halo, $C_1$-$C_8$ haloalkyl, aryl, arylalkyl, heteroarylalkyl, —CN, —$CO_2R^4$, —$NR^5R^6$, or —$SO_2R^4$, each of which $R^{10}$ except hydrogen, hydroxy, and halo is substituted or unsubstituted.

11. The compound of claim 10, where $R^d$ is thienyl substituted with methyl.

12. The compound of claim 10, wherein:
- $R^a$ is hydroxyl or substituted or unsubstituted —O($C_1$-$C_8$ alkyl);
- R is hydrogen, substituted or unsubstituted $C_1$-$C_8$ alkyl, substituted or unsubstituted $C_1$-$C_8$alkoxy, or halo;
- $R^{11}$ and $R^{12}$ are each independently selected from substituted or unsubstituted $C_1$-$C_4$ alkyl, substituted or unsubstituted $C_1$-$C_8$ alkoxy, or halo;
- $R^{10}$ is hydrogen, substituted or unsubstituted $C_1$-$C_8$alkyl substituted or unsubstituted cyclopropyl, substituted or unsubstituted —$CH_2$-cyclopropyl, substituted or unsubstituted —CH=$CH_2$, substituted or unsubstituted —C≡C-cyclopropyl, substituted or unsubstituted phenyl, substituted or unsubstituted benzyl, —I, —$CF_3$, —$NH_2$, or —CN;
- m is 0, 1, or 2; and
- m' is 0.

13. The compound of claim 7, wherein the compound is a compound of formula (Ia-4):

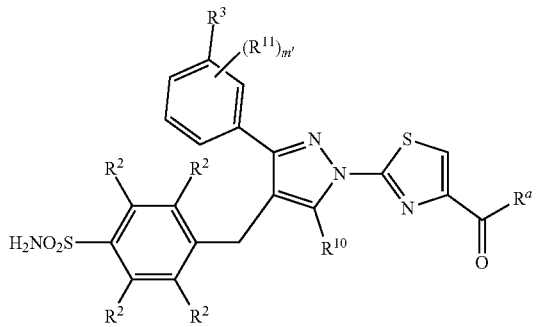

(Ia-4)

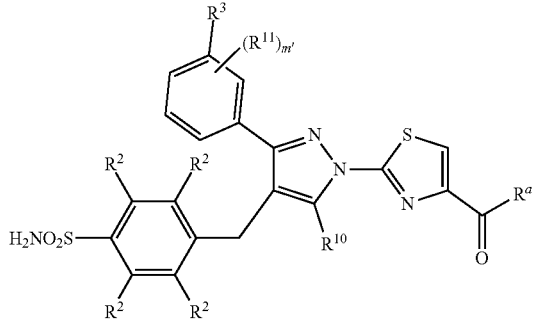

wherein
- $R^a$ is hydrogen, hydroxyl, amino, $C_1$-$C_2$alkyl, $C_1$-$C_2$alkoxy, and mono- or di-$C_1$-$C_2$alkylamino-;
- each $R^2$ is the same or different and is independently selected from hydrogen, halo, hydroxyl, —CN, —$NO_2$, amino, —C(O)$R^4$, —$CO_2R^4$, —C(O)$NR^5R^6$, —$NR^5$C(O)$R^4$, $C_1$-$C_2$alkyl, $C_1$-$C_2$ alkoxy, $C_1$-$C_2$haloalkyl, and $C_1$-$C_2$haloalkoxy;
- $R^3$ is selected from $C_2$-$C_6$alkynyl, —($C_0$-$C_2$alkyl)$C_3$-$C_6$cycloalkyl, —($C_2$-$C_4$alkenyl)$C_3$-Cecycloalkyl, —($C_2$-$C_4$alkynyl)$C_3$-$C_6$cycloalkyl, —($C_0$-$C_2$alkoxy)$C_3$-$C_6$cycloalkyl, dihydropyranyl, —($C_0$-$C_4$alkoxy) phenyl, —($C_2$-$C_4$alkenyl)phenyl, —($C_2$-$C_4$alkynyl) phenyl, —($C_0$-$C_4$alkoxy)heteroaryl, —($C_0$-$C_4$alkyl)

heteroaryl, —($C_2$-$C_4$alkenyl)heteroaryl, and —($C_2$-$C_4$alkynyl)heteroaryl, where heteroaryl is a 5- or 6-membered heteroaryl having 1, 2, 3, or 4 heteroatoms independently chosen from N, O, and S, and where each R is unsubstituted or substituted with one or more substituents selected from hydroxyl, halo, —CN, $C_1$-$C_4$ alkyl, $C_2$-$C_4$alkenyl, $C_1$-$C_4$alkynyl, $C_1$-$C_4$alkoxy, ($C_3$-$C_6$cycloalkyl)$C_0$-$C_2$alkyl, $C_1$-$C_2$haloalkyl, and $C_1$-$C_2$haloalkoxy;

each $R^{11}$ is independently selected from hydroxyl, halo, —CN, $C_1$-$C_4$ alkyl, $C_1$-$C_4$ alkoxy, $C_1$-$C_2$ haloalkyl, and $C_1$-$C_2$haloalkoxy;

each $R^4$, $R^5$, $R^6$, and $R^7$ is the same or different and each is hydrogen or $C_1$-$C_2$ alkyl;

$R^{10}$ is hydrogen, hydroxyl, halo, —CN, $C_1$-$C_4$ alkyl, hydroxyl$C_1$-$C_4$alkyl, $C_1$-$C_4$ alkoxy, $C_2$-$C_4$ alkenyl, ($C_3$-$C_6$cycloalkyl)$C_0$-$C_2$alkyl, $C_1$-$C_2$haloalkyl, $C_1$-$C_2$haloalkoxy, —$CO_2R^4$, —$NR^5R^6$, or —$SO_2R^4$;

m is 0 or 1, 2, 3, 4, or 5; and m' is 0 or an integer from 1-4.

14. The compound of claim 13, wherein:

$R^a$ is hydrogen, hydroxyl, $C_1$-$C_2$alkyl, or $C_1$-$C_2$alkoxy;

each $R^2$ is the same or different and is independently selected from hydrogen, halo, hydroxyl, $C_1$-$C_2$ alkyl, $C_1$-$C_2$ alkoxy, $C_1$-$C_2$ haloalkyl, and $C_1$-$C_2$haloalkoxy;

$R^3$ is selected from $C_2$-$C_6$alkynyl, —($C_0$-$C_2$alkyl)$C_3$-$C_6$cycloalkyl, —($C_4$-$C_4$alkenyl)$C_3$-$C_6$cycloalkyl, —($C_4$-$C_4$alkynyl)$C_3$-$C_6$cycloalkyl, —($C_0$-$C_2$alkoxy)$C_3$-$C_6$cycloalkyl, dihydropyranyl, —($C_0$-$C_4$alkoxy) phenyl, —($C_0$-$C_4$alkyl)phenyl, —($C_2$-$C_4$alkenyl)phenyl, —($C_2$-$C_4$alkynyl)phenyl, —($C_0$-$C_4$alkoxy) heteroaryl, —($C_0$-$C_4$alkyl)heteroaryl, —($C_2$-$C_4$alkenyl)heteroaryl, and —($C_2$-$C_4$alkynyl)heteroaryl, where heteroaryl is chosen from thienyl, furanyl, thiazolyl, pyrazolyl, imidazolyl; each of which one or more substituents selected from hydroxyl, halo, —CN, $C_1$-$C_4$ alkyl, $C_2$-$C_4$ alkenyl, $C_1$-$C_4$ alkynyl, $C_1$-$C_4$ alkoxy, ($C_3$-$C_6$ cycloalkyl)$C_0$-$C_2$alkyl, $C_1$-$C_2$ haloalkyl, and $C_1$-$C_2$haloalkoxy;

Each $R^{11}$ is independently selected from hydroxyl, halo, —CN, $C_1$-$C_4$ alkyl, $C_4$-$C_4$ alkoxy, $C_1$-$C_2$haloalkyl, and $C_1$-$C_2$haloalkoxy;

m' is 0 or an integer from 1-4; and $R^{10}$ is hydrogen, hydroxyl, halo, —CN, $C_1$-$C_4$ alkyl, hydroxyl$C_1$-$C_4$alkyl, $C_1$-$C_4$ alkoxy, $C_2$-$C_4$ alkenyl, ($C_3$-$C_6$ cycloalkyl)$C_0$-$C_2$alkyl, $C_1$-$C_2$haloalkyl, or $C_1$-$C_2$haloalkoxy.

15. The compound of claim 13, wherein $R^a$ is hydroxyl; and each $R^2$ is independently chosen from hydrogen and halogen.

16. A method of inhibiting lactate dehydrogenase A (LDHA) activity in a cell comprising contacting the cell with a compound of claim 1, whereby activity of LDHA in the cell is inhibited.

17. A method of treating fibrosis or cancer in a patient, comprising administering to the patient an effective amount of the compound of claim 1, or a pharmaceutically acceptable salt thereof.

* * * * *

UNITED STATES PATENT AND TRADEMARK OFFICE
CERTIFICATE OF CORRECTION

| | |
|---|---|
| PATENT NO. | : 11,247,971 B2 |
| APPLICATION NO. | : 17/160868 |
| DATED | : February 15, 2022 |
| INVENTOR(S) | : David J. Maloney et al. |

It is certified that error appears in the above-identified patent and that said Letters Patent is hereby corrected as shown below:

In the Specification

Column 1, Line 18, the following statement should be added:
FEDERAL RESEARCH STATEMENT
This invention was made with government support under HHSN261200800001E, and CA051497 awarded by the National Institutes of Health. The government has certain rights in the invention.

Signed and Sealed this
Twenty-first Day of October, 2025

John A. Squires
*Director of the United States Patent and Trademark Office*